(12) United States Patent  (10) Patent No.: US 8,207,176 B2
Callahan et al.  (45) Date of Patent: Jun. 26, 2012

(54) COMPOUNDS

(75) Inventors: James F. Callahan, King of Prussia, PA (US); Jeffrey C. Boehm, King of Prussia, PA (US); Anthony William James Cooper, Stevenage (GB); Stefano Livia, Stevenage (GB); Paul Bamborough, Stevenage (GB); Neysa Nevins, King of Prussia, PA (US); Zehong Wan, King of Prussia, PA (US); Beth A. Norton, Research Triangle Park, NC (US); Xichen Lin, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 392 days.

(21) Appl. No.: 11/908,440

(22) PCT Filed: Mar. 24, 2006

(86) PCT No.: PCT/US2006/010855
§ 371 (c)(1),
(2), (4) Date: Sep. 12, 2007

(87) PCT Pub. No.: WO2006/104915
PCT Pub. Date: Oct. 5, 2006

(65) Prior Publication Data
US 2009/0069318 A1 Mar. 12, 2009

Related U.S. Application Data

(60) Provisional application No. 60/665,315, filed on Mar. 25, 2005.

(51) Int. Cl.
C07D 471/04 (2006.01)
A61K 31/519 (2006.01)
A61P 29/00 (2006.01)
C07D 409/06 (2006.01)

(52) U.S. Cl. ........................ 514/264.1; 544/279; 546/125

(58) Field of Classification Search .................. 544/279; 514/264.1; 546/125
See application file for complete search history.

(56) References Cited

U.S. PATENT DOCUMENTS

| | | |
|---|---|---|
| 2,833,779 A | 5/1958 | Fields |
| 3,707,475 A | 12/1972 | Lombardino |
| 3,772,441 A | 11/1973 | Lombardino |
| 3,843,663 A | 10/1974 | Williams et al. |

(Continued)

FOREIGN PATENT DOCUMENTS

EP 0 278 686 2/1988

(Continued)

OTHER PUBLICATIONS

Griesser, Chapter 8, The Importance of Solvates (pp. 211-230), in the text, Polymorphism: In the Pharmaceutical Industry, Hilfiker, 2006.*

(Continued)

*Primary Examiner* — James O Wilson
*Assistant Examiner* — Cecilia M Jaisle
(74) *Attorney, Agent, or Firm* — James P. Riek

(57) ABSTRACT

The present invention is directed to novel substituted 2,4,8-trisubstituted 8H-pyrido[2,3-d]pyrimidin-7-one containing compounds, compositions, and use in therapy as CSBP/RK/p38 kinase inhibitors of Formulas (V) and (Va)

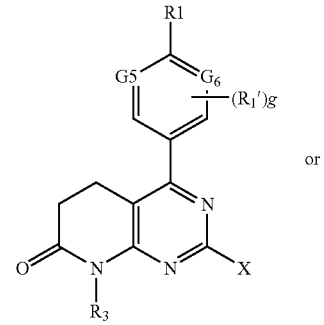

(V)

or

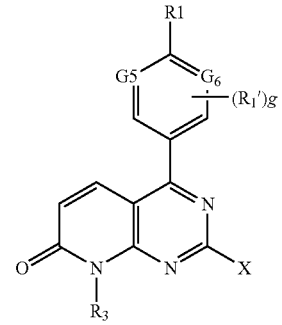

(Va)

wherein inter alia,
$G_5$ and $G_6$ are nitrogen and CH, provided that only one of G5 or G6 is nitrogen and the other is CH;
$R_1$ is $C(Z)N(R_{10'})(CR_{10}R_{20})_vR_b$, $C(Z)O(CR_{10}R_{20})_vR_b$, $N(R_{10'})C(Z)(CR_{10}R_{20})_vR_b$, $N(R_{10'})C(Z)N(R_{10'})(CR_{10}R_{20})_vR_b$, or $N(R_{10'})OC(Z)(CR_{10}R_{20})_vR_b$;
$R_{1'}$ is independently selected at each occurrence from halogen, $C_{1-4}$ alkyl, halo-substituted-$C_{1-4}$ alkyl, cyano, nitro, $(CR_{10}R_{20})_vNR_dR_{d'}$, $(CR_{10}R_{20})_vC(O)R_{12}$, $SR_5$, $S(O)R_5$, $S(O)_2R_5$, or $(CR_{10}R_{20})_vOR_{13}$;
$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;
X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_{2'})(R_{2''})$, or $N(R_{10'})R_nNH-C(=N-CN)NR_qR_{q'}$; and $R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted.

31 Claims, No Drawings

U.S. PATENT DOCUMENTS

| | | |
|---|---|---|
| 3,910,913 A | 10/1975 | Kim et al. |
| 3,929,807 A | 12/1975 | Fitzi |
| 3,940,486 A | 2/1976 | Fitzi |
| 4,058,614 A | 11/1977 | Baldwin |
| 4,199,592 A | 4/1980 | Cherkofsky |
| 4,447,431 A | 5/1984 | Sallmann |
| 4,503,065 A | 3/1985 | Wilkerson |
| 4,560,691 A | 12/1985 | Lesher et al. |
| 4,565,875 A | 1/1986 | Cavender |
| 4,686,231 A | 8/1987 | Bender et al. |
| 4,822,805 A | 4/1989 | Takasugi et al. |
| 4,886,807 A | 12/1989 | Kitamura et al. |
| 4,897,395 A | 1/1990 | Duch et al. |
| 5,304,560 A | 4/1994 | Shimazaki et al. |
| 5,409,930 A | 4/1995 | Spada et al. |
| 5,426,110 A | 6/1995 | Gossett et al. |
| 5,466,692 A | 11/1995 | Ellingboe |
| 5,545,669 A | 8/1996 | Adams et al. |
| 5,547,954 A | 8/1996 | Henrie, II et al. |
| 5,559,137 A | 9/1996 | Adams et al. |
| 5,591,992 A | 1/1997 | Leach |
| 5,593,991 A | 1/1997 | Adams et al. |
| 5,593,992 A | 1/1997 | Adams et al. |
| 5,597,776 A | 1/1997 | Bratz et al. |
| 5,620,981 A | 4/1997 | Blankley et al. |
| 5,656,644 A | 8/1997 | Adams et al. |
| 5,658,903 A | 8/1997 | Adams et al. |
| 5,663,334 A | 9/1997 | Sheldrake et al. |
| 5,670,527 A | 9/1997 | Adams et al. |
| 5,686,455 A | 11/1997 | Adams et al. |
| 5,716,955 A | 2/1998 | Adams et al. |
| 5,716,972 A | 2/1998 | Adams et al. |
| 5,733,913 A | 3/1998 | Blankley et al. |
| 5,733,914 A | 3/1998 | Blankley et al. |
| 5,739,143 A | 4/1998 | Adams et al. |
| 5,756,499 A | 5/1998 | Adams et al. |
| 5,760,220 A | 6/1998 | Giguere et al. |
| 5,767,097 A | 6/1998 | Tam |
| 5,777,097 A | 7/1998 | Lee et al. |
| 5,783,664 A | 7/1998 | Lee et al. |
| 5,817,670 A | 10/1998 | Takayama et al. |
| 5,864,036 A | 1/1999 | Adams et al. |
| 5,869,043 A | 2/1999 | McDonnell et al. |
| 5,869,660 A | 2/1999 | Adams et al. |
| 5,871,934 A | 2/1999 | Lee et al. |
| 5,916,891 A | 6/1999 | Adams et al. |
| 5,917,043 A | 6/1999 | Sisko |
| 5,929,076 A | 7/1999 | Adams et al. |
| 5,945,422 A | 8/1999 | Doherty et al. |
| 5,955,366 A | 9/1999 | Lee et al. |
| 5,969,184 A | 10/1999 | Adams et al. |
| 5,977,103 A | 11/1999 | Adams et al. |
| 5,977,372 A | 11/1999 | Giguere et al. |
| 5,998,425 A | 12/1999 | Adams et al. |
| 6,008,235 A | 12/1999 | Adams et al. |
| 6,063,772 A | 5/2000 | Tam |
| 6,083,948 A | 7/2000 | Wilde |
| 6,096,739 A | 8/2000 | Feuerstein |
| 6,150,337 A | 11/2000 | Tam |
| 6,150,373 A | 11/2000 | Harris et al. |
| 6,200,977 B1 | 3/2001 | Cushing et al. |
| 6,235,760 B1 | 5/2001 | Feuerstein |
| 6,248,225 B1 | 6/2001 | Palaika et al. |
| 6,277,989 B1 | 8/2001 | Chakravarty et al. |
| 6,288,062 B1 | 9/2001 | Adams et al. |
| 6,335,340 B1 | 1/2002 | Gallagher et al. |
| 6,362,193 B1 | 3/2002 | Adams et al. |
| 6,399,609 B1 | 6/2002 | Wilde |
| 6,423,425 B1 | 7/2002 | Faucher et al. |
| 6,423,695 B1 | 7/2002 | Tam et al. |
| 6,455,690 B1 | 9/2002 | Tam et al. |
| 6,476,031 B1 | 11/2002 | Chakravarty et al. |
| 6,479,463 B1 | 11/2002 | Wang et al. |
| 6,492,520 B1 | 12/2002 | Chen |
| 6,498,163 B1 | 12/2002 | Boschelli et al. |
| 6,509,320 B1 | 1/2003 | Wang et al. |
| 6,509,363 B2 | 1/2003 | Salituro et al. |
| 6,528,508 B2 | 3/2003 | Salituro et al. |
| 6,528,513 B2 | 3/2003 | Cushing et al. |
| 6,593,333 B1 | 7/2003 | Cumming |
| 6,800,626 B2 | 10/2004 | Salituro et al. |
| 6,809,199 B2 | 10/2004 | Doherty et al. |
| 6,838,559 B2 | 1/2005 | Vaccaro et al. |
| 6,869,955 B2 | 3/2005 | Wilde |
| 6,875,769 B2 | 4/2005 | Chen |
| 7,022,849 B2 | 4/2006 | Pitts et al. |
| 7,208,629 B2 | 4/2007 | Angell et al. |
| 7,235,551 B2 | 6/2007 | Adams et al. |
| 7,314,881 B2 | 1/2008 | Adams et al. |
| 7,314,934 B2 | 1/2008 | Adams et al. |
| 7,323,472 B2 | 1/2008 | Adams et al. |
| 7,423,042 B2 | 9/2008 | Boehm et al. |
| 2002/0058635 A1 | 5/2002 | Averett |
| 2002/0132784 A1 | 9/2002 | Tam et al. |
| 2002/0137696 A1 | 9/2002 | Tam |
| 2003/0064993 A1 | 4/2003 | Wilde |
| 2003/0092721 A1 | 5/2003 | Pitts et al. |
| 2003/0092908 A1 | 5/2003 | Pitts et al. |
| 2003/0100571 A1 | 5/2003 | Vaccaro et al. |
| 2003/0104974 A1 | 6/2003 | Pitts et al. |
| 2003/0114671 A1 | 6/2003 | Chen |
| 2003/0130264 A1 | 7/2003 | Jaen |
| 2003/0139434 A1 | 7/2003 | Balkan et al. |
| 2003/0162802 A1 | 8/2003 | Guo et al. |
| 2003/0191143 A1 | 10/2003 | Pitts et al. |
| 2003/0207826 A1 | 11/2003 | Tam et al. |
| 2003/0212015 A1 | 11/2003 | Tam |
| 2004/0009993 A1 | 1/2004 | Angiolini et al. |
| 2004/0044012 A1 | 3/2004 | Dobrusin et al. |
| 2004/0063658 A1 | 4/2004 | Roberts et al. |
| 2004/0065378 A1 | 4/2004 | Chini et al. |
| 2004/0077641 A1 | 4/2004 | Bretschneider et al. |
| 2004/0087600 A1 | 5/2004 | Cai et al. |
| 2004/0092402 A1 | 5/2004 | Kuragano et al. |
| 2004/0116697 A1 | 6/2004 | Adams et al. |
| 2004/0142945 A1 | 7/2004 | Barbosa et al. |
| 2004/0209901 A1 | 10/2004 | Adams et al. |
| 2004/0224958 A1 | 11/2004 | Booth et al. |
| 2004/0235847 A1 | 11/2004 | Quan et al. |
| 2004/0236084 A1 | 11/2004 | Biwersi et al. |
| 2004/0242604 A1 | 12/2004 | Bhattacharya et al. |
| 2005/0187217 A1 | 8/2005 | Wilson et al. |
| 2005/0203109 A1 | 9/2005 | Adams et al. |
| 2005/0272728 A1 | 12/2005 | Altenbach et al. |
| 2006/0116516 A1 | 6/2006 | Pitts et al. |
| 2006/0217401 A1 | 9/2006 | Boehm et al. |
| 2006/0235029 A1 | 10/2006 | Boehm et al. |
| 2006/0235030 A1 | 10/2006 | Callahan et al. |
| 2006/0258687 A1 | 11/2006 | Boehm et al. |
| 2007/0167467 A1 | 7/2007 | Adams et al. |
| 2007/0179118 A1 | 8/2007 | Barvian et al. |
| 2007/0238743 A1 | 10/2007 | Adams et al. |
| 2008/0032969 A1 | 2/2008 | Adams et al. |
| 2008/0033170 A1 | 2/2008 | Adams et al. |
| 2008/0096905 A1 | 4/2008 | Callahan et al. |
| 2008/0268044 A1 | 10/2008 | Appleby et al. |
| 2009/0048442 A1 | 2/2009 | Adams et al. |
| 2009/0048444 A1 | 2/2009 | Callahan et al. |
| 2009/0069318 A1 | 3/2009 | Callahan et al. |
| 2009/0074676 A1 | 3/2009 | Yang |
| 2009/0149492 A1* | 6/2009 | Fevig et al. .................... 514/300 |
| 2009/0156597 A1* | 6/2009 | Callahan et al. ........... 514/234.2 |
| 2009/0170834 A1* | 7/2009 | Venkat et al. ................. 514/218 |
| 2009/0176811 A1 | 7/2009 | Oberborsch |
| 2009/0221600 A1* | 9/2009 | Verma et al. ............. 514/252.16 |
| 2009/0233907 A1* | 9/2009 | Austin et al. ............. 514/217.04 |
| 2009/0270389 A1* | 10/2009 | Brookfield et al. ........ 514/234.2 |
| 2009/0270430 A1* | 10/2009 | Baik et al. ................ 514/264.11 |

FOREIGN PATENT DOCUMENTS

| | | |
|---|---|---|
| EP | 0 477 049 | 3/1992 |
| EP | 0 530 994 | 3/1993 |
| EP | 0477049 | 12/1999 |
| GB | 2 123 830 | 2/1984 |
| JP | 1-261306 | 10/1989 |
| JP | 20000038350 | 8/2000 |
| JP | 2003/127542 | 5/2003 |

| | | |
|---|---|---|
| JP | 2004-203751 | 7/2004 |
| WO | 91/19497 | 12/1991 |
| WO | 92/10190 | 6/1992 |
| WO | 92/10498 | 6/1992 |
| WO | WO 92/12154 | 7/1992 |
| WO | 93/14081 | 7/1993 |
| WO | 93/14082 | 7/1993 |
| WO | WO 94/19350 | 9/1994 |
| WO | 95/02591 | 1/1995 |
| WO | 95/03297 | 2/1995 |
| WO | 95/09847 | 4/1995 |
| WO | 95/09851 | 4/1995 |
| WO | 95/09852 | 4/1995 |
| WO | 95/09853 | 4/1995 |
| WO | 95/13067 | 5/1995 |
| WO | WO 95/15952 | 6/1995 |
| WO | WO 95/19774 | 7/1995 |
| WO | 95/31451 | 11/1995 |
| WO | 95/33461 | 12/1995 |
| WO | WO 95/33750 | 12/1995 |
| WO | 96/21452 | 7/1996 |
| WO | 96/21654 | 7/1996 |
| WO | 96/40143 | 12/1996 |
| WO | 97/05877 | 2/1997 |
| WO | 97/05878 | 2/1997 |
| WO | 97/12876 | 4/1997 |
| WO | 97/16426 | 5/1997 |
| WO | 97/16441 | 5/1997 |
| WO | 97/16442 | 5/1997 |
| WO | 97/23479 | 7/1997 |
| WO | 97/25045 | 7/1997 |
| WO | 97/25046 | 7/1997 |
| WO | 97/25047 | 7/1997 |
| WO | 97/25048 | 7/1997 |
| WO | 97/32583 | 9/1997 |
| WO | 97/33883 | 9/1997 |
| WO | 97/35855 | 10/1997 |
| WO | 97/35856 | 10/1997 |
| WO | 97/36587 | 10/1997 |
| WO | WO 97/38992 | 10/1997 |
| WO | 97/47618 | 12/1997 |
| WO | 98/03484 | 1/1998 |
| WO | 98/06715 | 2/1998 |
| WO | 98/07425 | 2/1998 |
| WO | WO 98/05661 | 2/1998 |
| WO | WO 98/08846 | 3/1998 |
| WO | 98/16230 | 4/1998 |
| WO | 98/22109 | 5/1998 |
| WO | 98/22457 | 5/1998 |
| WO | 98/24780 | 6/1998 |
| WO | 98/24782 | 6/1998 |
| WO | 98/25619 | 6/1998 |
| WO | WO 98/27098 | 6/1998 |
| WO | 98/28292 | 7/1998 |
| WO | WO 98/30223 | 7/1998 |
| WO | WO 98/33798 | 8/1998 |
| WO | 98/47892 | 10/1998 |
| WO | 98/48799 | 11/1998 |
| WO | 98/52558 | 11/1998 |
| WO | 98/52937 | 11/1998 |
| WO | 98/52940 | 11/1998 |
| WO | 98/52941 | 11/1998 |
| WO | 98/56377 | 12/1998 |
| WO | 98/56788 | 12/1998 |
| WO | 98/57966 | 12/1998 |
| WO | 99/00357 | 1/1999 |
| WO | 99/01130 | 1/1999 |
| WO | 99/01131 | 1/1999 |
| WO | 99/01136 | 1/1999 |
| WO | 99/01449 | 1/1999 |
| WO | 99/01452 | 1/1999 |
| WO | 99/03837 | 1/1999 |
| WO | 99/17776 | 4/1999 |
| WO | 99/18942 | 4/1999 |
| WO | 99/32110 | 7/1999 |
| WO | 99/32121 | 7/1999 |
| WO | WO 99/32121 | 7/1999 |
| WO | 99/42592 | 8/1999 |
| WO | WO 99/41253 | 8/1999 |
| WO | 99/57101 | 11/1999 |
| WO | 99/57253 | 11/1999 |
| WO | 99/58128 | 11/1999 |
| WO | 99/58502 | 11/1999 |
| WO | 99/58523 | 11/1999 |
| WO | 99/59959 | 11/1999 |
| WO | 99/59960 | 11/1999 |
| WO | 99/61426 | 12/1999 |
| WO | 99/61437 | 12/1999 |
| WO | 99/61440 | 12/1999 |
| WO | WO 99/61444 | 12/1999 |
| WO | WO 99/64400 | 12/1999 |
| WO | 00/01688 | 1/2000 |
| WO | 00/06563 | 2/2000 |
| WO | 00/07980 | 2/2000 |
| WO | 00/07991 | 2/2000 |
| WO | 00/10563 | 3/2000 |
| WO | 00/12074 | 3/2000 |
| WO | 00/12497 | 3/2000 |
| WO | 00/17175 | 3/2000 |
| WO | 00/18738 | 4/2000 |
| WO | 00/19824 | 4/2000 |
| WO | 00/20402 | 4/2000 |
| WO | 00/23072 | 4/2000 |
| WO | WO 00/23444 | 4/2000 |
| WO | 00/25791 | 5/2000 |
| WO | 00/26209 | 5/2000 |
| WO | 00/31063 | 6/2000 |
| WO | 00/31065 | 6/2000 |
| WO | 00/31072 | 6/2000 |
| WO | 00/35911 | 6/2000 |
| WO | 00/39116 | 7/2000 |
| WO | 00/40243 | 7/2000 |
| WO | 00/41698 | 7/2000 |
| WO | 00/43384 | 7/2000 |
| WO | WO 00/43374 | 7/2000 |
| WO | 00/59541 | 10/2000 |
| WO | 00/75131 | 12/2000 |
| WO | 01/00229 | 1/2001 |
| WO | 01/19322 | 3/2001 |
| WO | WO 01/19828 | 3/2001 |
| WO | 01/37835 | 5/2001 |
| WO | 01/38314 | 5/2001 |
| WO | WO 01/42243 | 6/2001 |
| WO | WO 01/55147 | 8/2001 |
| WO | WO 01/55148 | 8/2001 |
| WO | 01/64679 | 9/2001 |
| WO | WO 01/70741 | 9/2001 |
| WO | 02/32862 | 4/2002 |
| WO | 02/39954 | 5/2002 |
| WO | 02/007772 | 8/2002 |
| WO | WO 02/058695 | 8/2002 |
| WO | WO 02/059083 | 8/2002 |
| WO | WO02/060869 | 8/2002 |
| WO | WO 02/102315 | 12/2002 |
| WO | 03/088972 | 10/2003 |
| WO | WO 03/093290 | 11/2003 |
| WO | WO 2004/043367 | 5/2004 |
| WO | WO 2004/065378 | 8/2004 |
| WO | WO 2005/014558 | 2/2005 |
| WO | WO 2006/021547 | 3/2006 |
| WO | 2006/104889 | 10/2006 |
| WO | 2006/104917 | 10/2006 |
| WO | 2006/110298 | 10/2006 |
| WO | 2007/144390 | 12/2007 |
| WO | 2007/147103 | 12/2007 |
| WO | 2007/147104 | 12/2007 |
| WO | 2007/147109 | 12/2007 |

OTHER PUBLICATIONS

Wikipedia, Derivative, http://en.wikipedia.org/wiki/Derivative_(chemistry), last modified Aug. 5, 2009, downloaded Oct. 15, 2009.*
Anderson et al., *J. Org. Chem.*, 1977, vol. 42, p. 993.
Baker et al., *J. Heterocyclic Chem.*, 1964, vol. 1, pp. 263-270.
Boehm, et al., *Expert Opinion on Therapeutic Patents*, vol. 10(1), pp. 25-37 (2000).
Carboni et al., *Gazzetta Chimica Italiana*, vol. 97(8) pp. 1262-1273 (1967).

Carboni et al., *Gazzetta Chimica Italiana*, vol. 98(10) pp. 1174-1188 (1968).
Ferrarini et al., *Journal of Heterocyclic Chemistry*, vol. 21(2) pp. 417-419 (1984).
Ferrarini et al., *Journal of Heterocyclic Chemistry*, vol. 34(5) pp. 1501-1510 (1997).
Foster, et al., *Drug News Perspect.*, vol. 13(8) pp. 488-497 (2000).
Hanson, G., *Expert Opinion on Therapeutic Patents*, vol. 7(7) pp. 729-733 (1997).
Henry, et al., *Bioorganic & Medicinal Chemistry Letters*, vol. 8 pp. 3335-3340 (1998).
Herlaar, et al., *Molecular Medicine Today*, vol. 5 pp. 439-447 (1999).
Hurlbert, et al., *J. Med. Chem.*, 1968, vol. 11, pp. 703-707.
Khabar, Khalid, *Journal of Interferon & Cytokine Research*, vol. 25 pp. 1-10 (2005).
Lee, et al., *Immunopharmacology*, vol. 47(2-3) pp. 185-201 (2000).
Marin, et al., *Blood*, vol. 98(3) pp. 667-673 (2001).
Rewcastle, et al., . *Med Chem*, vol. 39 pp. 1823-1835 (1996).
Schoffstall, *J Org Chem*, vol. 36(16) pp. 2385-2387 (1971).
Underwood, et al., *Journal of Pharmacology and Experimental Therapeutics*, vol. 293 (1) pp. 281-288 (2000).
Victory, et al., *J Heterocyclic Chem*, vol. v 25 pp. 245-247 (1988).
Wadsworth, et al., *Journal of Pharmacology and Experimental Therapeutics*, vol. 291(2) pp. 680-687 (1999).
U.S. Appl. No. 11/871,039, filed Oct. 11, 2007, Adams, et al.
Adams et al., Progress in Medicinal Chemistry, vol. 38, pp. 2-61 (2001).
Armarego, W., Chem. Soc., Quinazolines, Part IV (JCSOA9) p. 561 (1962).
Votta et al., Bone, vol. 15 (5) pp. 533-538 (1994).
Bradlerova et al., Chem. Zvesti, vol. 29 (6), pp. 795-802 (1975).
de Silva et al., J. Chem. Soc., vol. 4, pp. 685-690 (1995).
Engel & Steglich, Liebigs Ann. Chem., p. 1916 (1978).
Ferles et al., Collect. Czech. Chem. Commun., vol. 5 (46), pp. 1167-1172 (1981).
Fischer et al., Rec. Trav. Chim. Pays. Bas., vol. 84, p. 439 (1965).
Fulmer et al., J. Heterocycl. Chem., vol. 17 (4), pp. 799-800 (1980).
Gilbert, E., Synthesis, pp. 30-32 (1972).
Han et al., Science, vol. 265, pp. 808-811 (1994).
Hunter et al., Academic Press, San Diego, vol. 200, p. 3 (1991).
Irwin et al., Archives of Internal Medicine, vol. 157 (17), pp. 1981-1987 (1997).
Ishibashi et al., Chem. Pharm. Bull., vol. 37(8), pp. 2214-2216 (1989).
Johnson et al., PG.A., J.Chem.Soc., Perkin Trans., vol. 1, pp. 895-905 (1996).
Jurkowska-Kowalczyk, R., Chem., vol. 51(6), pp. 1191-1199 (1977).
Katritzky et al., Synthesis, pp. 45-47 (Jan. 1993).
Kawasaki et al., J. Bio. Chem., vol. 272(30), pp. 18518-18521 (1997).
Mikailu et al., Zh. Obshch. Khim., vol. 56 (7), pp. 1513-1517 (1986).
Morton et al., Tetrahedron Letters, p. 4123 (1982).
Protecting Groups in Organic Synthesis, 2$^{nd}$ Edition, Greene TW and Wuts PSM, Wiley-Interscience, New York, pp. 10-174 (Hydroxyl and Phenolic) and pp. 309-403 (NH protection) (1991).
Santilli et al., J. Heterocycl Chem., vol. 8, pp. 445-453 (1971).
Sniekus, V., Tetrahedron Letters, vol. 29, p. 2135 (1988).
Stille et al., J. Amer. Chem. Soc., vol. 109, p. 5478 (1978).
Strzybny et al., J. Org. Chem., vol. 28, p. 3381 (1963).
Terashimia et al., M., Chem. Pharm. Bull., vol. 11, p. 4755 (1985).
Thompson et al., J. Org. Chem., vol. 49, p. 5237 (1984).
Uno et al., Bull. Chem. Soc. Japan., vol. 69, pp. 1763-1767 (1996).
Vartanyan et al., vol. 40, (9), pp. 552-560 (1987).
Borrel, et al., Coll. Czech. Chem. Commun., 1996, 61(6) pp. 901-909.
Victory et al., Heterocycles, 1985, 23(5), pp. 1135-1141.
Gallagher et al., Bioorganic and Med Chem, vol. 5(1), pp. 49-64 (1997).
Garigipati, R., Tetrahedron Letters, vol. 31,p. 190 (1989).
Kumada et al., Tetrahedron Letters, vol. 22, p. 5319 (1981).
Lamartina et al., Boll. Chim. Farm., vol. 129 (12), pp. 314-316 (1990).
Victory et al., Heterocycles, 1985, 23(8), pp. 1947-1950.

Victory et al., AFINIDAD, Mar. 1989, vol. 46, pp. 107-113 (Spanish).
Klotzer et al., Monatsh Chem., 1965, vol. 96, p. 1567.
Zavyalov, et al., Khim Farm Zh, vol. 26(3), p. 88 (1992) (With Translation).
Hunt, et al., *Bioorganic & Medicinal Chemistry Letters*, vol. 13 pp. 467-470 (2003).
Nishikawa et al., Chemical Pharm. Bull., 1976, vol. 24(9), pp. 2057-2077.
U.S. Appl. No. 11/839,830, filed Aug. 16, 2007, Adams, et al.
U.S. Appl. No. 11/839,833, filed Aug. 16, 2007, Adams, et al.
U.S. Appl. No. 11/839,834, filed Aug. 16, 2007, Adams, et al.
U.S. Appl. No. 12/305,077, Corsi et al.
U.S. Appl. No. 12/305,067, Corsi et al.
U.S. Appl. No. 12/305,079, Corsi et al.
U.S. Appl. No. 11/613,517, Adams, et al.
U.S. Appl. No. 11/613,598, Adams, et al.
U.S. Appl. No. 11/908,340, Boehm, et al.
U.S. Appl. No. 11/908,435, Callahan, et al.
U.S. Appl. No. 11/908,440, Callahan, et al.
U.S. Appl. No. 11/908,839, Callahan, et al.
Dinarello, J. Clinical Immunology, vol. 5(5) pp. 287-597 (1985).
Griswold et al., Drugs Exptl. Clin. Res., XIX(6), 1993, pp. 243-248.
Griswold et al., Arthritis and Rheumatism, vol. 31 No. 11, Nov. 1998, pp. 1406-1412.
Grunberg et al., Am. J. Respir. Crit. Care Med., vol. 156, (1997), p. 609.
Hanafusa, et al., J. Biol. CHem., vol. 274, pp. 27161-27167 (1999).
Jackson, et al., J. Pharmacol. Exp. Ther., vol. 284, pp. 687-692 (1998).
Kumar, et al., Nature Rev. Drug Discovery, vol. 2, p. 717 (2003).
Kyriakis, et al., J. Physiol. Rev., vol. 81, pp. 807-869 (2001).
Laping, et al., Molec. Pharmacol., vol. 62, pp. 58-64 (2002).
Lee, et al., Annals NY Acad. Sci., vol. 696, pp. 149 (1993).
Lee, et al., Pharmacol. Ther. vol. 82(2-3), pp. 389-397 (1999).
Marshall, et al., Cell, vol. 80, pp. 179-278 (1995).
Hare, et al., *J. Med Chem.*, vol. 47 pp. 4731-4740 (2004).
Morin, et al., Cancer Research, vol. 64, pp. 1893-1898 (2004).
Badger, et al., Circulatory Shock, vol. 27, pp. 51-61 (1991).
Badger, et al., Arthritis Rheum., vol. 43, pp. 175-183 (2000).
Badger, et al., J. Pharm. Exp. Therap., vol. 279(3) ,pp. 1453-1461 (1996).
Ono, et al., Cellular Signalling, vol. 12, pp. 1-13 (2000).
Platanias, Pharmacol. Therap vol. 98, pp. 129-142 (2003).
Saccini, Nature Immunology, vol. 3, pp. 69-75 (2002).
Subauste et al., J. Clin. Invest., vol. 96, 1995, p. 549.
Teren et al., Am. J. Respir. Crit. Care Med., vol. 155, 1997, p. 1362.
Turner et al. Clin. Infect. Dis., vol. 26, 1998, p. 840.
Votta et al., Int. J. Immunotherapy ,vol (1), pp. 1-12 (1990).
Witz, Fertility and Sterility, vol. 73, pp. 212-214 (2000).
Zhu et al., J. Clin. Invest., vol. 97, 1996, pp. 421.
Yoo et al., J. Biol. Chem., vol. 278, No. 44, pp. 43001-43007 (2003).
Tumkevicius, Liebigs Ann., pp. 1703-1705 (1995).
Tumkevicius, Chem. Hetero. Compounds, vol. 36(7), pp. 841-846 (2000).
Solberg, et al., Acta Chemica Scandinavica, vol. 43, pp. 62-68 (1989).
Ridker, P., Circulation, Jan. 2003, pp. 363-369.
Boschelli et al., J. Med Chem., vol. 41, pp. 4365-4377 (1998).
Jacobsen et al., Tetrahedron, vol. 50, No. 15, pp. 4323-4334 (1994).
Fleisher, et al., Advanced Drug Delivery Reviews (1996) 19(2) 115-130.
Tanji et al., Chem Pharm Bull. 351(12), pp. 4972-4976 (1987).
Griswold, et al., Pharm of Cytokine Supp. vol. 7, pp. 323-329 (1996).
Dinarello, C., Reviews of Infectious Diseases, vol. 6, No. 1, pp. 51-95 (1984).
Boehm, et al., Journal Med. Chem., vol. 39, pp. 3929-3937, (1996).
Still, et al., Tetrahedron Letters, vol. 24, No. 41, pp. 4405-4408 (1983).
Matyus, et al., Heterocycles, vol. 23, No. 8, pp. 2057-2064 (1985).
Bedaiwy, et al., Human Reproduction, vol. 17, pp. 426-431 (2002).
Cohen, P., Trends Cell Biol, pp. 353-361 (1997).
Carter, et al., J. Biological Chem., vol. 274, pp. 30858-30864 (1999).
Colotta et al., J. Immunol., vol. 132(2), p. 936 (1984).
Barvian et al., J. Med. Chem., (2000) vol. 43, pp. 4606-4616.

U.S. Appl. No. 11/915,008, filed Jun. 26, 2008.
U.S. Appl. No. 12/132,793, filed Jun. 4, 2008.
U.S. Appl. No. 12/253,327, filed Oct. 17, 2008.
Agarwal et al., Bioorganic & Medicinal Chemistry Letters, 10(8), 703-706, Apr. 2000.
Becker et al., J. Immunol., vol. 147, p. 4307 (1991).
Cohen et al., Cell Biology, vol. 7, pp. 353-361 (1997).
Courtney, S. et al., Bioorganic & Medicinal Chemistry Letters, vol. 14 pp. 3269-3273 (2004).
Damasio, Cecil Textbook of Medicine, 20th Edition, vol. 2, pp. 1992-1996 (1996).
El-Assiery et al., CAPLUS Abstract 132:151761, 1999.
El-Reedy et al., CAPLUS Abstract 112:35791, 1990.
Gartner et al., PubMed Abstract (Pathol. Biol. (Paris) 50(2): 118-26), Mar. 2002.
Kasparec, et al., Tetrahedron Letters, 44(24) 4567-70 (2003).
Layzer, Cecil Textbook of Medicine, 20th Edition, vol. 2, pp. 2050-2057, 1996.
Lee et al., Int. J. Immunopharmac., vol. 10(7), pp. 835-843 (1988).
Lee et al., Nature, vol. 372, 22/29, pp. 739-746 (1994).
Manhi et al., CAPLUS Abstract 121:83254, 1994.
Niimi et al., Euro. Resp. J., vol. 11(5), pp. 1064-1069 (1998).
Olivera et al., Circulatory Shock, vol. 37, pp. 301-306 (1992).
Poli et al., Proc. Nat'l Acad. Sci., vol. 87, pp. 782-784 (1990).
Pridgen, J. Org. Chem., vol. 47, p. 4319 (1982).
Ram, CAPLUS Abstract 112:77090, 1990.
Ram, CAPLUS Abstract 113:78321, 1990.
Ram, CAPLUS Abstract 113;97564, 1990.
Ram, CAPLUS Abstract 114:42726, 1991.
Ram et al., CAPLUS Abstract 115:256109, 1991.
Simon et al., J. Immunol. Methods, vol. 84, p. 85 (1985).
Soni, R. Aust. J. Chem., vol. 35, pp. 1493-1496 (1982).
Szucs et al., Chem. Zvesti, vol. 26 (4), pp. 354-359 (1972).
Szucs et al., Acta Fac. Pharm. Univ. Commenianae, vol. 30, pp. 127-146 (1977).
Upadhyay et al., CAPLUS Abstract 131:18977, 1999.
Upadhyay et al., Indian J. Chemistry, vol. 38B, pp. 173-177 (1999).
Van Leusen et al., J.O.C., vol. 42, p. 1153 (1977).
Warrior et al., Journal of Biomolecular Screening, vol. 4 (3), pp. 129-135 (1999).
Weinstein et al., J. Immunol., vol. 151, p. 3829 (1993).
Wilson et al., Chemistry & Biology, vol. 4, No. 6, pp. 423-431 (1997).
Douglas, Cecil Textbook of Medicine, 20th Edition, vol. 2, pp. 1739-1742 (1996).
Alves et al., Tetrahedron Letters, vol. 29, pp. 2135-2136, 1988.
Echavarren et al., J. Am. Chem. Soc., vol. 109(18), pp. 5478-5486, 1987.
Ishikura et al., Chem. Pharm. Bull., vol. 33(11), pp. 4755-4763, 1985.
Martinez-Teipel et al., J. Comb. Chem., vol. 7(3), pp. 436-448, 2005.
Minato et al., Tetrahedron Letters, vol. 22(52), pp. 5319-5322, 1981.
Puig et al., Sleep, vol. 28(10), pp. 1312-1316, 2005.

* cited by examiner

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Epidermal Growth Factor Receptor-Derived

```
                         Peptide

<400> SEQUENCE: 1

Lys Arg Glu Leu Val Glu Pro Leu Thr Pro Ser Gly Glu Ala Pro Asn
  1               5                  10                  15

Gln Ala Leu Leu Arg
             20
```

COMPOUNDS

This application is the §371 national stage entry of PCT/US2006/010855, filed 24 Mar. 2006, which claims the benefit of U.S. Provisional Application No. 60/665,315, filed 25 Mar. 2005.

SUMMARY OF THE INVENTION

This invention relates to novel compounds and their use as pharmaceuticals, particularly as p38 kinase inhibitors, for the treatment of certain diseases and conditions.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phospholipases are the essential machinery by which the signal is further transmitted within the cell [Marshall, J. C. *Cell*, 80, 179-278 (1995)]. Protein kinases can be categorized into five classes with the two major classes being tyrosine kinases and serine/threonine kinases, depending upon whether the enzyme phosphorylates its substrate(s) on specific tyrosine(s) or serine/threonine(s) residues [Hunter, T., *Methods in Enzymology* (*Protein Kinase Classification*) p. 3, Hunter, T.; Sefton, B. M.; eds. vol. 200, Academic Press; San Diego, 1991].

Three major related intracellular pathways, the mitogen-activated kinases, or MAPKs, are now understood to transduce signals from many extracellular stimuli such as environmental stress, infectious agents, cytokines and growth factors. The MAPKs modulate the activity of numerous cell functions such as translocation and activation of transcription factors that control transcription of effector molecules such as cytokines, COX-2, iNOS; the activity of downstream kinases that effect translation of mRNAs; and cell cycle pathways through transcription or modification of enzymes. One of these three major pathways is the p38 MAPK pathway, which refers in most cell types to the isoform p38α which is ubiquitously expressed. The role of p38 in a multitude of functions, particularly related to inflammatory response has been elucidated using selective p38 inhibitors in numerous in vitro and in vivo studies. These functions have been extensively reviewed and a summary can be found in Nature Reviews [Kumar, S. Nature Rev. Drug Discovery, 2:717 (2003)].

Extracellular stimuli such as those described above are generated in a number of chronic diseases which are now understood to have a common underlying pathophysiology termed inflammation. An environmental insult or local cell damage activates cellular response pathways, including but not limited to p38; local cells then generate cytokines and chemokines, in turn recruiting lymphocytes such as neutrophils and other granulocytes. In a secondary response, the consequences include recruitment of additional lymphocytes such as additional phagocytic cells or cytotoxic T cells, and ultimately the adaptive immune response is initiated through activation of T cells. It is not currently fully understood how this acute inflammatory response becomes a chronic response leading to diseases such as rheumatoid arthritis (RA), atherosclerosis, chronic obstructive pulmonary disease (COPD), inflammatory bowel disease (IBD), etc. Nevertheless, the features of inflammation are recognized to contribute to a large number of chronic diseases and pathways such as the p38 pathway are accepted to contribute to the initiation of inflammatory diseases.

For example, atherosclerosis is regarded as a chronic inflammatory disease, which develops in response to injury of the vessel wall and is characterized by the complex development of an occlusive and prothrombotic atheroma. The pathogenesis of this lesion generally involves endothelial dysfunction (reduced bioavailable NO), adhesion molecule expression, adhesion and infiltration of leukocytes, cytokine and growth factor generation, accumulation of foam cells, expansion of extracellular lipid and matrix, activation of matrix metalloproteases (MMPs) and proliferation of vascular smooth muscle cells.

The discovery of p38 (initially termed CSBP, now p38; the isoforms p38α and p38β are the targets of the compounds described) provided a mechanism of action of a class of anti-inflammatory compounds for which SK&F 86002 was the prototypic example. These compounds inhibited IL-1 and TNF synthesis in human monocytes at concentrations in the low uM range [Lee, et al., *Int. J. Immunopharmac.* 10(7), 835(1988)] and exhibited activity in animal models which are refractory to cyclooxygenase inhibitors [Lee; et al., *Annals N. Y. Acad. Sci.*, 696, 149(1993)].

The mechanism by which stress signals (including bacterial and viral infection, pro-inflammatory cytokines, oxidants, UV light and osmotic stress) activate p38 is through activation of kinases upstream from p38 which in turn phosphorylate p38 at threonine 180 and tyrosine 182 resulting in p38 activation. MAPKAP kinase-2 and MAPKAP kinase-3 have been identified as downstream substrates of CSBP/p38 which in turn phosphorylate heat shock protein Hsp27 and other substrates. Additional downstream substrates known to be phosphorylated by p38 include kinases (Mnk1/2, MSK1/2 and PRAK) and transcription factors (CHOP, MEF2, ATF2 and CREB). While many of the signaling pathways required for transduction of stress stimuli remain unknown it appears clear that many of the substrates for p38 listed above are involved. [Cohen, P. *Trends Cell Biol.*, 353-361(1997) and Lee, J. C. et al, Pharmacol. Ther. vol. 82, nos. 2-3, pp. 389-397, 1999]. There is also emerging evidence that p38 is involved in modulation of the activity of the NF-kB signaling pathway through a role in histone phosphorylation or acetylation, or through reduction of transcription competence of the NF-kB complex [Saccini, S. *Nature Immunol.*, 3: 69-75, (2002); Carter, A B et al *J Biol Chem* 274: 30858-63 (1999)]. Finally, a role for p38 in generation of response to IFNs through activation by the Type I IFN receptor has been described [Platanias, *Pharmacol. Therap.* 98:129-142 (2003)]. Activation of p38 is involved in the transcriptional regulation of IFN sensitive genes through modification of specific transcription factors binding to promotor elements in these genes. Direct phosphorylation of STATs by p38 has not been conclusively demonstrated.

In addition to inhibiting IL-1 and TNF upregulation in response to inflammatory stimuli, p38 kinase inhibitors (e.g., SK&F 86002 and SB-203580) are effective in a number of different cell types in decreasing the synthesis of a wide variety of pro-inflammatory proteins including, IL-6, IL-8, GM-CSF, RANTES and COX-2. Inhibitors of p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that p38 is involved not only cytokine synthesis in response to stress, but also in propagating the consequent cytokine signaling [CSBP/P38 kinase reviewed in Cohen, P. *Trends Cell Biol.*, 353-361(1997)].

Interleukin-1 (IL-1) and Tumor Necrosis Factor (TNF) are important inflammatory cytokines produced by a variety of cells, such as monocytes, macrophages, and smooth muscle cells. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Evidence also links IL-1 activity to diabetes and pancreatic β cells [review of the biological activities which have been attributed to IL-1 Dinarello, *J. Clinical Immunology*, 5 (5), 287-297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic obstructive pulmonary disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Inflammatory diseases are also marked by increases in IL-6 and C-reactive protein (CRP), both of which are sensitive to inhibition by p38 inhibitors. IL-6 stimulation of CRP production is directly inhibited by p38 inhibitors in human vascular endothelial cells, and CRP is produced by hepatocytes in response to IL-6. CRP is considered a major risk factor for cardiovascular disease [Circulation 2003. 107: 363-369] and may be a significant independent risk factor for chronic obstructive pulmonary disease [Circulation 2003. 107:1514-1519]. IL-6 is also upregulated in endometriosis [Bedaiwy et al., 2002, Human Reproduction 17:426-431; Witz, 2000, Fertility and Sterility 73: 212-214].

Interleukin-8 (IL-8) and RANTES are chemotactic factors produced by several cell types including mononuclear cells, fibroblasts, endothelial cells, epithelial cells, neutrophils and T cells. Chemokine production is induced by pro-inflammatory stimuli such as IL-1, TNF, or lipopolysachharide (LPS), or viral infection. IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, which may contribute to increased adhesion of the neutrophils to vascular endothelial cells. Many diseases are characterized by massive neutrophil infiltration. Conditions such as chronic obstructive pulmonary disease associated with an increase in IL-8 production would benefit by compounds which are suppressive of IL-8 production. RANTES is produced by cells such as epithelial cells and airway smooth muscle in response to infection or cytokine stimulation. Its main chemoattraction is for T cell subtypes and blood-borne monocytes.

IL-1, TNF and other cytokines affect a wide variety of cells and tissues and these cytokines as well as other leukocyte derived cytokines are important as critical inflammatory mediators of a wide variety of disease states and conditions. The inhibition of these cytokines is of benefit in controlling, reducing and alleviating many of these disease states.

In addition to the involvement of p38 signaling in the production of IL-1, TNF, IL-8, IL-6, GM-CSF, COX-2, collagenase and stromelysin, signal transduction via CSBP/p38 is required for the effector functions of several of these same pro-inflammatory proteins plus many others. For example, growth factors such as VEGF, PDGF, NGF signal through surface receptors which in turn activate cellular signaling pathways including p38 MAPK [Ono, K. and Han, J., *Cellular Signalling*, 121-13 (2000); Kyriakis, S M and Avruch, J. *Physiol Rev* 81: 807-869 (2001)]. $TGF_\chi$, a key molecule in the control of inflammatory response, also activates p38 as a consequence of engagement of the TGFβ receptor. The involvement of CSBP/p38 in multiple stress-induced signal transduction pathways provides additional rationale for the potential utility of CSBP/p38 in the treatment of diseases resulting from the excessive and destructive activation of the immune system, or chronic inflammation. This expectation is supported by the potent and diverse activities described for CSBP/p38 kinase inhibitors [Badger, et al., *J. Pharm. Exp. Thera.* 279 (3): 1453-1461, (1996); Griswold, et al, *Pharmacol. Comm.* 7, 323-229 (1996); Jackson, et al., J. Pharmacol. Exp. Ther. 284, 687-692 (1998); Underwood, et al., J. Pharmacol. Exp. Ther. 293, 281-288 (2000); Badger, et al., Arthritis Rheum. 43, 175-183 (2000)].

Chronic inflammation is also characterized by ongoing remodeling and repair of affected tissue, leading in some cases to excess fibrotic tissue. A role for p38 MAPK in fibrosis is supported by findings that this enzyme mediates signaling of transforming growth factor beta (TGF-β) on markers and proteins of fibrosis. For example, it has been shown that TGF-β increases the kinase activity of p38 MAPK through the TGF-β activated kinase TAK-1 (Hanafasa et al., 1999, J. Biol. Chem. 274:27161-27167). Furthermore, the p38 inhibitor SB-242235 inhibited the TGF-β-induced increases in fibronectin and thrombospondin (Laping et al., 2002, Molec. Pharmacol. 62:58-64). These results show that p38 MAPK is a key signaling intermediate for the effect of the pro-fibrotic cytokine TGF-β on components of the extracellular matrix and markers of fibrosis.

P38 also plays a role in directing survival and apoptosis of cells in response to various stimuli. Both survival and apoptosis can be p38 regulated depending on the stimulus and the cell type [Morin and Huot, *Cancer Research*. 64:1893-1898 (2004)]. For example, TGF-beta can stimulate apoptosis in murine hepatocytes through activation of gadd45b, a protein involved in cell-cycle control, in a p38 mediated process [Yoo et al, J. Biol. Chem. 278:43001-43007, (2003)]. In a different response pathway, UV-stress can activate p38 and trigger apoptosis of a damaged cell. P38 has also been shown to promote survival of lymphocytes in response to stress, including neutrophils and CD8+ T cells.

There remains a need for treatment, in this field, for compounds which are cytokine suppressive anti-inflammatory drugs, i.e. compounds which are capable of inhibiting the CSBP/p38/RK kinase. The present invention is directed to such novel compounds which are inhibitors of p38 kinase.

SUMMARY OF THE INVENTION

This invention relates to the novel compounds of Formula (I) and (Ia), (II) and (IIa), (III) and (IIa), (IV) and (IVa), (V) and (Va), (VI), (VIa-VIi), (VIII), (VIIIa), (IX), (IXa), (A), (A1), (B), and (B1), and pharmaceutically acceptable salts, solvates or physiologically functional derivatives thereof, and pharmaceutical compositions comprising a compound of (I) and (Ia), (II) and (Ia), (III) and (IIIa), (IV) and (IVa), (V) and (Va), (VI), (VIa-VIi), (VIII), (VIIIa), (IX), (IXa), (A), (A1), (B), and (B1), and pharmaceutically acceptable salts, solvates or physiologically functional derivatives thereof, and a pharmaceutically acceptable diluent or carrier.

This invention relates to a method of treating a CSBP/RK/p38 kinase mediated disease in a mammal in need thereof, which comprises administering to said mammal an effective amount of a compound of Formula (I) and (Ia), (II) and (IIa), (III) and (IIIa), (IV) and (IVa), (V) and (Va), (VI), (VIa-VIi), (VIII), (VIIIa), (IX), (IXa), (A), (A1), (B), and (B1).

This invention also relates to a method of inhibiting cytokines and the treatment of a cytokine mediated disease, in a mammal in need thereof, which comprises administering to said mammal an effective amount of a compound of Formula (I) and (Ia), (II) and (IIa), (III) and (IIIa), (IV) and (IVa), (V) and (Va), (VIa-VIi), (VIII), (VIIIa), (IX), (IXa), (A), (A1), (B), and (B1).

This invention also relates to a method of inhibiting the production of IL-1 in a mammal in need thereof which comprises administering to said mammal an effective amount of a compound of Formula (I) and (Ia), (II) and (IIa), (III) and (IIIa), (IV) and (IVa), (V) and (Va), (VIa-VIi), (VIII), (VIIIa), (IX), (IXa), (A), (A1), (B), and (B1).

This invention also relates to a method of inhibiting the production of IL-6 in a mammal in need thereof which comprises administering to said mammal an effective amount of a compound of Formula (I) and (Ia), (II) and (IIa), (III) and (IIIa), (IV) and (IVa), (V) and (Va), (VIa-VIi), (VIII), (VIIIa), (IX), (IXa), (A), (A1), (B), and (B1).

This invention also relates to a method of inhibiting the production of IL-8 in a mammal in need thereof which comprises administering to said mammal an effective amount of a compound of Formula (I) and (Ia), (II) and (Ia), (III) and (IIIa), (IV) and (IVa), (V) and (Va), (VIa-VIi), (VIII), (VIIIa), (IX), (IXa), (A), (A1), (B), and (B1).

This invention also relates to a method of inhibiting the production of TNF in a mammal in need thereof which comprises administering to said mammal an effective amount of a compound of Formula (I) and (Ia), (II) and (IIa), (III) and (IIa), (IV) and (IVa), (V) and (Va), (VIa-VIi), (VIII), (VIIIa), (IX), (IXa), (A), (A1), (B), and (B1).

Accordingly, the present invention provides for a compound of Formula (I) and (Ia) having the structure:

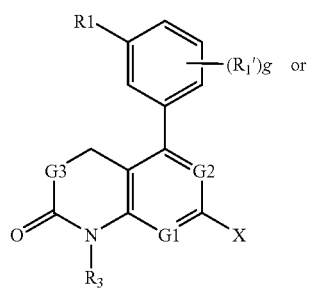

(I)

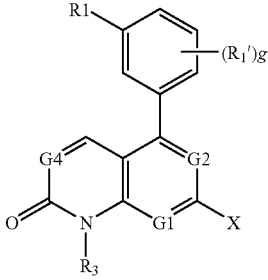

(Ia)

wherein $G_1$, and $G_2$ are independently nitrogen;

$G_3$ is $CH_2$;

$G_4$ is CH;

$R_1$ is $C(Z)N(R_{10'})(CR_{10}R_{20})_\nu R_b$, $C(Z)O(CR_{10}R_{20})_\nu R_b$, $N(R_{10'})C(Z)(CR_{10}R_{20})_\nu R_b$, $N(R_{10'})C(Z)N(R_{10})(CR_{10}R_{20})_\nu R_b$, or $N(R_{10'})OC(Z)(CR_{10}R_{20})_\nu R_b$;

$R_{1'}$ is independently selected at each occurrence from halogen, $C_{1-4}$ alkyl, halo-substituted-$C_{1-4}$ alkyl, cyano, nitro, $(CR_{10}R_{20})_\nu NR_d R_{d'}$, $(CR_{10}R_{20})_\nu C(O)R_{12}$, $SR_5$, $S(O)R_5$, $S(O)_2 R_5$, or $(CR_{10}R_{20})_\nu OR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl $C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_m R_{2'}$, $(CH_2)_n (R_{10'})S(O)_m R_{2'}$, $(CH_2)_n N(R_{10'})C(O)R_{2'}$, $(CH_2)_n NR_4 R_{14}$, $(CH_2)_n N(R_{2'})(R_{2''})$, or $N(R_{10'})R_h NH—C(=N—CN)NRqRq'$;

$X_1$ is $N(R_{11})$, O, $S(O)_m$, or $CR_{10}R_{20}$;

$R_h$ is selected from an optionally substituted $C_{1-10}$ alkyl, —$CH_2$—C(O)—$CH_2$—, —$CH_2$—$CH_2$—O—$CH_2$—$CH_2$—, —$CH_2$—C(O)N($R_{10'}$)$CH_2$—$CH_2$—, —$CH_2$—N($R_{10'}$)C(O)$CH_2$—, —$CH_2$—CH($OR_{10'}$)—$CH_2$—, —$CH_2$—C(O)O—$CH_2$—$CH_2$—, or —$CH_2$—$CH_2$—O—C(O)—$CH_2$—;

$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_q X_1 (CR_{10}R_{20})_q C(A_1)(A_2)(A_3)$, or $(CR_{10}R_{20})_q C(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally; or wherein $R_{2''}$ is the moiety $(CR_{10}R_{20})_{t}X_{1}(CR_{10}R_{20})_{q}C(A_{1})(A_{2})(A_{3})$;

$A_{1}$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_{2}$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_{3}$ is hydrogen or is an optionally substituted $C_{1-10}$ alkyl;

$R_{3}$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_{4}$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_{4}$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_{5}$ is independently selected at each occurrence from hydrogen, $C_{1-4}$ alkyl, $C_{2-4}$ alkenyl, $C_{2-4}$ alkynyl or $NR_{4}R_{14'}$, excluding the moieties $SR_{5}$ being $SNR_{4}R_{14'}$, $S(O)_{2}R_{5}$ being $SO_{2}H$ and $S(O)R_{5}$ being $SOH$;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{d}$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_{d}$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

DETAILED DESCRIPTION OF THE INVENTION

The present invention is directed to novel compounds of (I) and (Ia), (II) and (IIa), (III) and (IIIa), (IV) and (IVa), (V) and (Va), (VI), (VIa-VIi), (VIII), (VIIIa), (IX), (IXa), (A), (A1), (B), and (B1) and a pharmaceutically acceptable salt solvate or physiologically functional derivative thereof. As will be readily recognized, the difference between compounds of Formula (I) and (Ia) lies in the unsaturation of the ring system. The difference between compound of Formula (I) and (Ia) and compounds of Formula (II) and (IIa), (III) and (IIIa), (IV) and (IVa), (V) and (Va), (VI) and (VIa-VIi), etc., lies in ring substitution on the aryl or heteroaryl moiety of the $R_{1}$ substituent, and the ring position of the nitrogen(s) for the pyridyl or pyrimidine moiety where applicable.

The respective $R_{1}$, $R_{2}$, $R_{X}$, X and $R_{3}$, etc., terms are the same for both groups within the formulas themselves, for instance, in Formula (I) and (Ia), and except for the additional G5/G6/G7/G8 terms, applicable across all formulas herein. For purposes herein, everything applicable to Formula (I) is also applicable to Formula (Ia) unless otherwise indicated, and for the remaining compounds of Formula (II) and (IIa), etc. unless specified otherwise.

It is recognized that for compounds of Formula (I) and (Ia) wherein $G_{3}$ and $G_{4}$ are both carbon, and $G_{1}$ and $G_{2}$ are both nitrogen, the core ring system is considered a 2,4,8-trisubstituted-8H-pyrido[2,3-d]pyrimidin-7-one.

Compounds of Formula (I) and (Ia) are further represented by the structure:

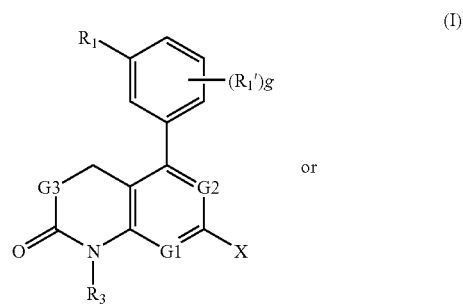

-continued

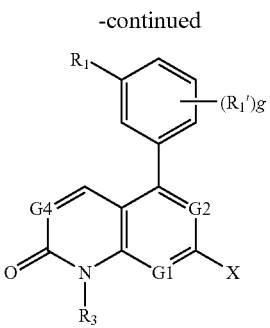

(Ia)

wherein
G$_1$, and G$_2$ are independently nitrogen;
G$_3$ is CH$_2$;
G$_4$ is CH;
R$_1$ is C(Z)N(R$_{10'}$)(CR$_{10}$R$_{20}$)$_v$R$_b$, C(Z)O(CR$_{10}$R$_{20}$)$_v$R$_b$, N(R$_{10'}$)C(Z)(CR$_{10}$R$_{20}$)$_v$R$_b$, N(R$_{10}$)C(Z)N(R$_{10'}$)(CR$_{10}$R$_{20}$)$_v$R$_b$, or N(R$_{10'}$)OC(Z)(CR$_{10}$R$_{20}$)$_v$R$_b$;
R$_{1'}$ is independently selected at each occurrence from halogen, C$_{1-4}$ alkyl, halo-substituted-C$_{1-4}$ alkyl, cyano, nitro, (CR$_{10}$R$_{20}$)$_v$NR$_d$R$_{d'}$, (CR$_{10}$R$_{20}$)$_v$C(O)R$_{12}$, SR$_5$, S(O)R$_5$, S(O)$_2$R$_5$, or (CR$_{10}$R$_{20}$)$_v$OR$_{13}$;
X is R$_2$, OR$_{2'}$, S(O)$_m$R$_{2'}$, (CH$_2$)$_n$N(R$_{10'}$)S(O)$_m$R$_{2'}$, (CH$_2$)$_n$N(R$_{10'}$)C(O)R$_{2'}$, (CH$_2$)$_n$NR$_4$R$_{14}$, (CH$_2$)$_n$N(R$_{2'}$)(R$_{2''}$), or N(R$_{10'}$)R$_n$NH—C(═N—CN)NR$_q$R$_{q'}$;
X$_1$ is N(R$_{11}$), O, S(O)$_m$, or CR$_{10}$R$_{20}$;
R$_h$ is selected from an optionally substituted C$_{1-10}$ alkyl, —CH$_2$—C(O)—CH$_2$—, —CH$_2$—CH$_2$—O—CH$_2$—CH$_2$—, —CH$_2$—C(O)N(R$_{10'}$)CH$_2$—CH$_2$—, —CH$_2$—N(R$_{10'}$)C(O)CH$_2$—, —CH$_2$—CH(OR$_{10'}$)—CH$_2$—, —CH$_2$—C(O)O—CH$_2$—CH$_2$—, or —CH$_2$—CH$_2$—O—C(O) CH$_2$—;
R$_q$ and R$_{q'}$ are independently selected at each occurrence from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, and wherein all of the moieties, excluding hydrogen, are optionally substituted, or R$_q$ and R$_{q'}$ together with the nitrogen to which they are attached form an optionally substituted heterocyclic ring of 5 to 7 members, which ring may contain an additional heteroatom selected from oxygen, nitrogen or sulfur;
A$_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A$_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A$_3$ is hydrogen or is an optionally C$_{1-10}$ alkyl;
R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and
wherein these moieties, excluding hydrogen, may be optionally substituted 1 to 4 times, independently, at each occurrence by C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$alkyl, C$_{5-7}$cycloalkenyl, C$_{5-7}$ cycloalkenyl C$_{1-10}$ alkyl, halogen, —C(O), cyano, nitro, aryl, aryl C$_{1-10}$ alkyl, heterocyclic, heterocyclylC$_{1-10}$ alkyl, hetero-arylC$_{1-10}$ alkyl, heteroaryl, heterocyclylC$_{1-10}$ alkyl, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$N(R$_{10'}$)S(O)$_2$R$_7$, (CR$_{10}$R$_{20}$)$_n$NR$_e$R$_{e'}$, (CR$_{10}$R$_{20}$)$_n$NR$_e$R$_{e'}$C$_{1-4}$alkylNR$_e$R$_{e'}$, (CR$_{10}$R$_{20}$)$_n$CN, (CR$_{10}$R$_{20}$)$_n$S(O)$_2$NR$_e$R$_{e'}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_e$R$_{e'}$, (CR$_{10}$R$_{20}$)$_n$N(R$_{10'}$)C(Z)R$_6$, (CR$_{10}$R$_{20}$)$_n$N(R$_{10}$)C(═N(R$_{10'}$))NR$_e$R$_{e'}$, (CR$_{10}$R$_{20}$)$_n$C(═NOR$_6$)NR$_e$R$_{e'}$, (CR$_{10}$R$_{20}$)$_n$OC(Z)NR$_e$R$_{e'}$, (CR$_{10}$R$_{20}$)$_n$N(R$_{10'}$)C(Z)NR$_e$R$_{e'}$, or (CR$_{10}$R$_{20}$)$_n$N(R$_{10'}$)C(Z)OR$_7$; or
wherein R$_2$ is the moiety (CR$_{10}$R$_{20}$)$_q$X$_1$(CR$_{10}$R$_{20}$)$_q$C(A$_1$)(A$_2$)(A$_3$), or (CR$_{10}$R$_{20}$)$_q$C(A$_1$)(A$_2$)(A$_3$);
R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and
wherein each of these moieties, excluding hydrogen, may be optionally substituted 1 to 4 times, independently, by C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$alkyl, C$_{5-7}$cycloalkenyl, C$_{5-7}$ cycloalkenyl C$_{1-10}$ alkyl, halogen, —C(O), cyano, nitro, aryl, aryl C$_{1-10}$ alkyl, heterocyclic, heterocyclic C$_{1-10}$ alkyl, heteroaryl, heteroaryl C$_{1-10}$ alkyl, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$N(R$_{10'}$)S(O)$_2$R$_7$, (CR$_{10}$R$_{20}$)$_n$NR$_e$R$_{e'}$, (CR$_{10}$R$_{20}$)$_n$NR$_e$R$_{e'}$C$_{1-4}$alkyl NR$_e$R$_{e'}$, (CR$_{10}$R$_{20}$)$_n$CN, (CR$_{10}$R$_{20}$)$_n$S(O)$_2$NR$_e$R$_{e'}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_e$R$_{e'}$, (CR$_{10}$R$_{20}$)$_n$N(R$_{10'}$)C(Z)R$_6$, (CR$_{10}$R$_{20}$)$_n$N(R$_{10'}$)C(═N(R$_{10'}$))NR$_e$R$_{e'}$, (CR$_{10}$R$_{20}$)$_n$C(═NOR$_6$)NR$_e$R$_{e'}$, (CR$_{10}$R$_{20}$)$_n$OC(Z) NR$_e$R$_{e'}$, (CR$_{10}$R$_{20}$)$_n$N(R$_{10'}$)C(Z)NR$_e$R$_{e'}$, or (CR$_{10}$R$_{20}$)$_n$N(R$_{10'}$)C(Z)OR$_7$;
R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and
wherein these moieties, excluding hydrogen, may be optionally substituted 1 to 4 times, independently at each occurrence by C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$alkyl, C$_{5-7}$cycloalkenyl, C$_{5-7}$ cycloalkenyl C$_{1-10}$ alkyl, halogen, —C(O), cyano, nitro, aryl, aryl C$_{1-10}$ alkyl, heterocyclic, heterocyclic C$_{1-10}$ alkyl, heteroaryl, heteroaryl C$_{1-10}$ alkyl, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$N(R$_{10'}$)S(O)$_2$R$_7$, (CR$_{10}$R$_{20}$)$_n$NR$_e$R$_{e'}$, (CR$_{10}$R$_{20}$)$_n$NR$_e$R$_{e'}$C$_{1-4}$alkylNR$_e$R$_{e'}$, (CR$_{10}$R$_{20}$)$_n$CN, (CR$_{10}$R$_{20}$)$_n$S(O)$_2$NR$_e$R$_{e'}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_e$R$_{e'}$, (CR$_{10}$R$_{20}$)$_n$N(R$_{10'}$)C(Z)R$_6$, (CR$_{10}$R$_{20}$)$_n$N(R$_{10}$)C('N(R$_{10'}$))NR$_e$R$_{e'}$, (CR$_{10}$R$_{20}$)$_n$C(═NOR$_6$)NR$_e$R$_{e'}$, (CR$_{10}$R$_{20}$)$_n$OC(Z)NR$_e$R$_{e'}$, (CR$_{10}$R$_{20}$)$_n$N(R$_{10'}$)C(Z) NR$_e$R$_{e'}$, or (CR$_{10}$R$_{20}$)$_n$N(R$_{10'}$)C(Z)OR$_7$; or
wherein R$_{2''}$ is the moiety (CR$_{10}$R$_{20}$)$_r$X$_1$(CR$_{10}$R$_{20}$)$_q$C(A$_1$)(A$_2$)(A$_3$);
R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic, or heterocyclylC$_{1-10}$ alkyl moiety, and
wherein these moieties are all optionally substituted one or more times, independently at each occurrence, by hydrogen, halogen, nitro, C$_{1-10}$ alkyl, halo-substituted C$_{1-10}$ alkyl, C$_{2-10}$ alkenyl, C$_{2-10}$ alkynyl, C$_{3-7}$cycloalkyl, C$_{3-7}$cycloalkylC$_{1-10}$ alkyl, C$_{5-7}$cycloalkenyl, C$_{5-7}$cycloalkenylC$_{1-10}$ alkyl, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$N(R$_{10'}$)S(O)$_2$R$_7$, (CR$_{10}$R$_{20}$)$_n$NR$_{16}$R$_{26}$, (CR$_{10}$R$_{20}$)$_n$CN, (CR$_{10}$R$_{20}$)$_n$S(O)$_2$NR$_{16}$R$_{26}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_{16}$R$_{26}$, $(CR_{10}R_{20})_nN(R_{10'})C(Z)R_6$, $(CR_{10}R_{20})_nN(R_{10'})C(=N(R_{10'}))NR_{16}R_{26}$, $(CR_{10}R_{20})_nOC(Z)NR_{16}R_{26}$, $(CR_{10}R_{20})_nN(R_{10'})C(Z)NR_{16}R_{26}$, or $(CR_{10}R_{20})_nN(R_{10'})C(Z)OR_7$;

$R_4$ and $R_{14}$ are each independently selected at each occurrence from hydrogen, $C_{1-10}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or heteroaryl $C_{1-4}$ alkyl; or the $R_4$ and $R_{14}$ together with the nitrogen which they are attached form an unsubstituted or substituted heterocyclic ring of 4 to 7 members which ring optionally contains an additional heteroatom selected from oxygen, sulfur or nitrogen; and wherein the $C_{1-4}$ alkyl, $C_{3-7}$cycloalkyl, $C_{3-7}$cycloalkyl$C_{1-4}$ alkyl, aryl, aryl-$C_{1-4}$ alkyl, heteroaryl and heteroaryl $C_{1-4}$ alkyl moieties, and the $R_4$ and $R_{14}$ cyclized ring are optionally substituted, 1 to 4 times, independently at each occurrence, by halogen; hydroxy; hydroxy substituted $C_{1-10}$alkyl; $C_{1-10}$ alkoxy; halo-substituted $C_{1-10}$ alkoxy; $C_{1-10}$ alkyl; halo-substituted $C_{1-10}$ alkyl; $SR_5$; $S(O)R_5$; $S(O)_2R_5$; $C(O)R_j$; $C(O)OR_j$; $C(O)NR_4R_{14'}$; $(CR_{10}R_{20})_nN(R_{10'})C(Z)OR_7$; $(CR_{10}R_{20})_nN(R_{10'})C(Z)NR_dR_{d'}$; $NR_4C(O)C_{1-10}$alkyl; $NR_4C(O)$aryl; $NR_4R_{14'}$; cyano; nitro; $C_{3-7}$cycloalkyl; $C_{3-7}$cycloalkyl $C_{1-10}$ alkyl; an unsubstituted or substituted aryl, or aryl$C_{1-4}$ alkyl; an unsubstituted or substituted heterocyclic, or heterocyclic $C_{1-4}$ alkyl; an unsubstituted or substituted heteroaryl, or hetero$C_{1-4}$ alkyl, and wherein these aryl, heterocyclic, and heteroaryl containing moieties are substituted one to two times independently at each occurrence by halogen; $C_{1-4}$ alkyl, hydroxy; hydroxy substituted $C_{1-4}$ alkyl; $C_{1-4}$ alkoxy; $S(O)_m$alkyl; amino, mono & di-substituted $C_{1-4}$ alkyl amino, or $CF_3$;

$R_{4'}$ and $R_{14'}$ are each independently selected at each occurrence from hydrogen or $C_{1-4}$ alkyl, or $R_{4'}$ and $R_{14'}$ can cyclize together with the nitrogen to which they are attached to form a 5 to 7 membered ring which optionally contains an additional heteroatom selected from oxygen, sulfur or $NR_{9'}$;

$R_{4''}$ and $R_{14''}$ are each independently selected at each occurrence from hydrogen or $C_{1-4}$ alkyl, or $R_{4''}$ and $R_{14''}$ together with the nitrogen to which they are attached, cyclize to form a heterocyclic 5 to 7 membered ring which optionally contains an additional heteroatom selected from oxygen, sulfur or $NR_{9'}$;

$R_5$ is independently selected at each occurrence from hydrogen, $C_{1-4}$ alkyl, $C_{2-4}$ alkenyl, $C_{2-4}$ alkynyl or $NR_4R_{14'}$, excluding the moieties $SR_5$ being $SNR_4R_{14'}$, $S(O)_2R_5$ being $SO_2H$ and $S(O)R_5$ being SOH;

$R_6$ is independently selected at each occurrence from hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein each of these moieties, excluding hydrogen are optionally substituted;

$R_7$ is independently selected at each occurrence from $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl moiety, and wherein each of these moieties may be optionally substituted;

$R_8$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein these moieties, excluding hydrogen, may be optionally substituted;

$R_9$ is independently selected at each occurrence from hydrogen, $C(Z)R_6$, optionally substituted $C_{1-10}$ alkyl, optionally substituted aryl, optionally substituted aryl-$C_{1-4}$ alkyl;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or heterocyclyl$C_{1-4}$ alkyl, and wherein these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{15}$ and $R_{25}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, or aryl-$C_{1-4}$ alkyl, heterocyclic, heterocyclic $C_{1-4}$ alkyl heteroaryl or heteroaryl $C_{1-4}$ alkyl moiety, and wherein these moieties, excluding hydrogen may be optionally substituted; or $R_5$ and $R_{25}$ together with the nitrogen which they are attached form an optionally substituted heterocyclic ring of 4 to 7 members, which ring optionally contains an additional heteroatom selected from oxygen, sulfur or $NR_9$; and wherein these moieties, excluding hydrogen, are optionally substituted 1 to 4 times, independently at each occurrence by halogen; hydroxy; hydroxy substituted $C_{1-10}$alkyl; $C_{1-10}$ alkoxy; halosubstituted $C_{1-10}$ alkoxy; $C_{1-4}$ alkyl; halosubstituted $C_{1-4}$ alkyl; $SR_5$, $S(O)R_5$, $S(O)_2R_5$; $C(O)R_j$; $C(O)OR_j$; $C(O)NR_4R_{14'}$; $NR_4C(O)C_{1-10}$alkyl; $NR_4C(O)$aryl; $NR_4R_{14'}$; cyano; nitro; $C_{1-10}$ alkyl; $C_{3-7}$cycloalkyl; $C_{3-7}$cycloalkyl $C_{1-10}$ alkyl; halo-substituted $C_{1-10}$ alkyl; aryl $C_{1-4}$ alkyl, heterocyclic, heterocyclic $C_{1-4}$ alkyl, heteroaryl, or hetero $C_{1-4}$ alkyl, and wherein these aryl, heterocyclic, and heteroaryl containing moieties may also be substituted one to two times independently at each occurrence by halogen, $C_{1-4}$ alkyl, hydroxy, hydroxy substituted $C_{1-4}$ alkyl, $C_{1-10}$ alkoxy, $S(O)_mC_{1-4}$ alkyl, amino, mono & di-substituted $C_{1-4}$ alkylamino, $C_{1-4}$ alkyl, or $CF_3$;

$R_{16}$ and $R_{26}$ are each independently selected at each occurrence from hydrogen, or $C_{1-4}$ alkyl; or the $R_{16}$ and $R_{26}$ together with the nitrogen which they are attached form an unsubstituted or substituted heterocyclic ring of 4 to 7 members, which ring optionally contains an additional heteroatom selected from oxygen, sulfur or $NR_{9'}$;

$R_{21'}$ and $R_{31'}$ are each independently selected at each occurrence from hydrogen or $C_{1-4}$ alkyl, or $R_{21'}$ and $R_{31'}$ together with the nitrogen to which they are attached cyclize to form a 5 to 7 membered ring which optionally contains an additional heteroatom selected from oxygen, sulfur or $NR_{9'}$;

$R_b$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety;

which moieties may all be optionally substituted 1 to 4 times independently at each occurrence by halogen; hydroxy; hydroxy substituted $C_{1-10}$alkyl; $C_{1-10}$ alkyl; $C_{1-10}$ alkoxy; halosubstituted $C_{1-10}$ alkoxy; $OR_8$, $SR_5$, $S(O)R_5$, $S(O)_2R_5$; $C(O)R_j$; $C(O)OR_j$; $C(O)NR_{15}R_{25}$; cyano; nitro; $NR_{15}R_{25}$; —Z'—$(CR_{10}R_{20})$s-Z'—, $C_{3-7}$cycloalkyl; $C_{3-7}$cycloalkyl $C_{1-10}$ alkyl; halosubstituted $C_{1-10}$ alkyl; an optionally substituted aryl or arylalkyl, an optionally substituted heteroaryl and heteroaryl$C_{1-10}$ alkyl, and an optionally substituted heterocyclic and heterocyclic$C_{1-10}$ alkyl, and wherein these aryl, heteroaryl and heterocyclic containing moieties may also be substituted one to two times independently at each occurrence by halogen, hydroxy, hydroxy substituted alkyl, $C_{1-10}$ alkoxy, $S(O)_mC_{1-4}$ alkyl, amino, mono & di-substituted $C_{1-4}$ alkyl amino, $C_{1-4}$ alkyl, or $CF_3$;

$R_d$ and $R_{d'}$ are each independently selected at each occurrence from hydrogen, $C_{1-4}$ alkyl, $C_{3-6}$cycloalkyl, $C_{3-6}$ cycloalkyl$C_{1-4}$alkyl, or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$; and wherein the $R_d$ and $R_{d'}$ moieties which are $C_{1-4}$ alkyl, $C_{3-6}$cycloalkyl, $C_{3-6}$cycloalkyl$C_{1-4}$alkyl, and the $R_d$ and $R_{d'}$ cyclized ring are substituted, 1 to 4 times, independently at each occurrence by halogen, halosubstituted $C_{1-4}$ alkyl, hydroxy, hydroxy substituted $C_{1-4}$alkyl, $C_{1-4}$ alkoxy, halosubstituted $C_{1-4}$ alkoxy, $S(O)mRf$, $C(O)Rj$, $C(O)ORj$, $C(O)NR_4R_{14'}$, $NR_4C(O)C_{1-4}$alkyl, $S(O)_2NR_4R_{14}C_{1-4}$ alkyl, $NR_4R_{14}S(O)_2C_{1-4}$ alkyl, or $NR_4R_{14'}$;

$R_e$ are $R_{e'}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heteroaryl or a heteroaryl $C_{1-4}$ alkyl moiety; or $R_e$ and $R_{e'}$ together with the nitrogen which they are attached form an optionally substituted heterocyclic ring of 4 to 7 members, which ring optionally contains an additional heteroatom selected from oxygen, sulfur or nitrogen; and wherein each of these moieties, excluding hydrogen, may be substituted 1 to 4 times, independently at each occurrence by halogen; hydroxy; hydroxy substituted $C_{1-10}$alkyl; $C_{1-10}$ alkoxy; halosubstituted $C_{1-10}$ alkoxy; amino, mono & di-substituted $C_{1-4}$ alkyl amino, $S(O)$ $mR_f$; $C(O)R_j$; $C(O)OR_j$; $(CR_{10}R_{20})_nN(R_{10'})C(Z)OR_7$; $(CR_{10}R_{20})_nN(R_{10'})C(Z)NR_dR_{d'}$; $C(O)NR_4R_{14'}$; $NR_4C(O)C_{1-10}$alkyl; $NR_4C(O)aryl$; cyano; nitro; $C_{1-10}$ alkyl; $C_{3-7}$cycloalkyl; $C_{3-7}$cycloalkyl $C_{1-10}$ alkyl; halosubstituted $C_{1-10}$ alkyl; aryl, aryl $C_{1-4}$ alkyl, heterocyclic, heterocyclic$C_{1-4}$ alkyl, heteroaryl, or hetero$C_{1-4}$alkyl, and wherein these aryl, heterocyclic, and heteroaryl containing moieties may be optionally substituted one to two times independently at each occurrence by halogen, $C_{1-4}$ alkyl, hydroxy, hydroxy substituted $C_{1-4}$ alkyl, $C_{1-10}$ alkoxy, $S(O)_m$alkyl, amino, mono & di-substituted $C_{1-4}$ alkyl amino, $C_{1-4}$ alkyl, or $CF_3$;

$R_f$ is independently selected at each occurrence from $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties may be optionally substituted;

$R_j$ is independently selected at each occurrence from hydrogen, $C_{1-4}$alkyl, aryl, aryl $C_{1-4}$alkyl, heteroaryl, heteroaryl $C_{1-4}$alkyl, heterocyclic, or a heterocyclic $C_{1-4}$alkyl moiety, and wherein these moieties, excluding hydrogen, may be optionally substituted;

g is 0, or integer having a value of 1, 2, 3, or 4;

n is independently selected at each occurrence from 0 or an integer having a value of 1 to 10;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

v is 0 or an integer having a value of 1 or 2;

v' is independently selected at each occurrence from 0 or an integer having a value of 1 or 2;

s is independently selected at each occurrence from an integer having a value of 1, 2, or 3;

t is an integer having a value of 2 to 6;

Z is independently selected at each occurrence from oxygen or sulfur;

Z' is independently selected at each occurrence from oxygen, nitrogen, or sulfur;

and a pharmaceutically acceptable salt thereof, solvate or physiologically functional derivative thereof.

Suitably, for compounds of Formula (I), and (Ia), and the remaining formulas described herein $R_1$ is $C(Z)N(R_{10'})$ $(CR_{10}R_{20})_vR_b$, $C(Z)O(CR_{10}R_{20})_vR_b$, $N(R_{10'})C(Z)(CR_{10}R_{20})_vR_b$, $N(R_{10'})C(Z)N(R_{10'})(CR_{10}R_{20})_vR_b$, or $N(R_{10'})OC(Z)(CR_{10}R_{20})_vR_b$.

In one embodiment of the invention, $R_1$ is $C(Z)N(R_{10'})$ $(CR_{10}R_{20})_vR_b$, or $N(R_{10'})C(Z)(CR_{10}R_{20})_vR_b$. In another embodiment of the invention, $R_1$ is $C(Z)N(R_{10'})(CR_{10}R_{20})_vR_b$.

Suitably, $R_{1'}$ is independently selected at each occurrence from halogen, $C_{1-4}$ alkyl, halo-substituted-$C_{1-4}$ alkyl, cyano, nitro, $(CR_{10}R_{20})_{v'}NR_dR_{d'}$, $(CR_{10}R_{20})_{v'}C(O)R_{12}$, $SR_5$, $S(O)R_5$, $S(O)_2R_5$, or $(CR_{10}R_{20})_{v'}OR_{13}$.

In one embodiment, $R_{1'}$ is independently selected at each occurrence from halogen, $C_{1-4}$ alkyl, or halo-substituted-$C_{1-4}$ alkyl. In another embodiment, $R_{1'}$ is independently selected at each occurrence from fluorine, chlorine, methyl, or $CF_3$.

Suitably, g is 0 or an integer having a value of 1, 2, 3, or 4. In one embodiment of the invention, g is 0, 1 or 2.

For compounds of Formula (I) and (Ia), when $R_{1'}$ is substituted on a phenyl ring in the ortho position, and a second $R_{1'}$ moiety is also substituted on the ring, then preferably the second substitution is not in the other ortho position. Suitably, the phenyl ring is substituted in the 2-position and if a second substituent is present, in the 3-position with the $R_1$ moiety in the 5-position. Alternatively, the $R_{1'}$ moiety may be in the other ortho 2-position and the $R_1$ moiety in the 3-position, which will change the ring position numbering.

Suitably, $R_d$ and $R_{d'}$ are each independently selected at each occurrence from hydrogen, $C_{1-4}$ alkyl, $C_{3-5}$ cycloalkyl, $C_{3-5}$ cycloalkyl$C_{1-4}$alkyl, or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$, and wherein the $R_d$ and $R_{d'}$ moieties which are $C_{1-4}$ alkyl, $C_{3-6}$cycloalkyl, $C_{3-6}$cycloalkyl$C_{1-4}$ alkyl, and the $R_d$ and $R_{d'}$ cyclized ring are optionally substituted, 1 to 4 times, independently at each occurrence by halogen; halosubstituted $C_{1-4}$ alkyl; hydroxy; hydroxy substituted $C_{1-4}$alkyl; $C_{1-4}$ alkoxy; $C_{1-4}$alkyl; halosubstituted $C_{1-4}$ alkoxy; $S(O)$ $mRf$; $C(O)Rj$; $C(O)ORj$; $C(O)NR_4R_{14'}$, $NR_4C(O)C_{1-4}$alkyl; $S(O)_2NR_4R_{14}C_{1-4}$ alkyl; $NR_4R_{14'}S(O)_2C_{1-4}$ alkyl; or $NR_4R_{14''}$.

Suitably $R_{9'}$ is independently selected at each occurrence from hydrogen, or $C_{1-4}$ alkyl.

Suitably, Z is independently selected at each occurrence from oxygen or sulfur.

Suitably, v is 0 or an integer having a value of 1 to 2.

Suitably, v' is 0 or an integer having a value of 1 or 2.

Suitably, $R_{10}$ and $R_{20}$ are independently selected at each occurrence from hydrogen or $C_{1-4}$ alkyl.

Suitably, $R_{10'}$ is independently selected at each occurrence from hydrogen or $C_{1-4}$ alkyl.

Suitably, $R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or heterocyclyl$C_{1-4}$ alkyl, and wherein these moieties, excluding hydrogen, may be optionally substituted.

Suitably, $R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted 1 to 4 times independently at each occurrence by halogen; halosubstituted $C_{1-4}$ alkyl; $C_{1-4}$ alkyl; hydroxy; hydroxy substituted $C_{1-4}$alkyl; $C_{1-4}$alkoxy; halosubstituted $C_{1-4}$ alkoxy; $S(O)mC_{1-4}$ alkyl; —C(O), $C(O)C_{1-4}$ alkyl; or $NR_{21'}R_{31'}$.

Suitably, $R_{21'}$ and $R_{31'}$ are each independently selected at each occurrence from hydrogen or $C_{1-4}$ alkyl, or $R_{21'}$ and $R_{31'}$ together with the nitrogen to which they are attached cyclize to form an optionally substituted heterocyclic 5 to 7 membered ring, which ring optionally contains an additional heteroatom selected from O/N/S.

Suitably $R_b$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety, which moieties, excluding hydrogen are all optionally substituted.

The $R_b$ moieties, excluding hydrogen, may be optionally substituted, one or more times, preferably 1 to 4 times independently at each occurrence by halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; $OR_8$, such as methoxy, ethoxy or phenoxy; $SR_5$, $S(O)R_5$, $S(O)_2R_5$, such as methylthio, methylsulfinyl or methyl sulfonyl; $C(O)R_j$; $C(O)OR_j$; $C(O)NR_{4''}R_{14''}$; cyano; nitro; $NR_{15}R_{25}$; —Z'—$(CR_{10}R_{20})$s-Z'—; $C_{1-10}$alkyl; $C_{3-7}$cycloalkyl or a $C_{3-7}$cycloalkyl$C_{1-10}$ alkyl group, such as cyclopropyl, or cyclopropyl methyl, or cyclopropylethyl, etc.; halosubstituted $C_{1-10}$ alkyl, such $CF_2CF_2H$, $CH_2CF_3$, or $CF_3$; an optionally substituted aryl, such as phenyl, or an optionally substituted aryl$C_{1-10}$alkyl, such as benzyl or phenethyl; an optionally substituted heterocyclic or heterocyclic$C_{1-10}$alkyl, or an optionally substituted heteroaryl or heteroaryl$C_{1-10}$alkyl, and wherein these aryl, heteroaryl, and heterocyclic containing moieties may also be substituted one to two times independently at each occurrence by halogen, hydroxy, hydroxy substituted alkyl, $C_{1-10}$ alkoxy, $S(O)_m$alkyl, amino, mono & di-substituted $C_{1-4}$ alkyl amino, $C_{1-4}$ alkyl, or $CF_3$.

The moiety —Z'—$(CR_{10}R_{20})$s-Z' forms a cyclic ring, such as a dioxalane ring.

Suitably Z' is independently at each occurrence selected from oxygen or sulfur.

Suitably, s is independently selected at each occurrence from an integer having a value of 1, 2, or 3.

Suitably, $R_5$ is independently selected at each occurrence from hydrogen, $C_{1-4}$ alkyl, $C_{2-4}$ alkenyl, $C_{2-4}$ alkynyl or $NR_{4'}R_{14'}$, excluding the moieties $SR_5$ being $SNR_{4'}R_{14'}$, $S(O)_2R_5$ being $SO_2H$ and $S(O)R_5$ being SOH.

Suitably, $R_{4'}$ and $R_{14'}$ are each independently selected at each occurrence from hydrogen or $C_{1-4}$ alkyl, or $R_{4'}$ and $R_{14'}$ can cyclize together with the nitrogen to which they are attached to form an optionally substituted 5 to 7 membered ring which optionally contains an additional heteroatom from oxygen, sulfur or $NR_{9'}$. Suitably, when $R_{4'}$ and $R_{14'}$ cyclize to form an optionally substituted ring, such rings include, but are not limited to pyrrolidine, piperidine, piperazine, morpholine, and thiomorpholine (including oxidizing the sulfur).

Suitably, $R_{4''}$ and $R_{14''}$ are each independently selected at each occurrence from hydrogen or $C_{1-10}$ alkyl, or $R_{4''}$ and $R_{14''}$ can cyclize together with the nitrogen to which they are attached to form an optionally substituted 5 to 7 membered ring which optionally contains an additional heteroatom selected from oxygen, sulfur or $NR_{9'}$. Suitably, when $R_{4''}$ and $R_{14''}$ cyclize to form an optionally substituted ring, such rings include, but are not limited to pyrrolidine, piperidine, piperazine, morpholine, and thiomorpholine (including oxidizing the sulfur).

Suitably, $R_f$ is independently selected at each occurrence from hydrogen, $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties, excluding hydrogen, may be optionally substituted.

Suitably, $R_j$ is independently selected at each occurrence from a $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein each of these moieties may be optionally substituted.

Suitably, when $R_b$ is an optionally substituted $C_{1-10}$alkyl, the moiety includes but is not limited to a methyl, ethyl, n-propyl, isopropyl, t-butyl, n-butyl, isobutyl, 1,2-dimethylpropyl, 2,2-dimethylpropyl, heptyl, 2-methylpropyl; a halosubstituted alkyl, such as 2,2,2-trifluroethyl, trifluoromethyl, 2-fluoroethyl; a cyano substituted alkyl, such as cyanomethyl, cyanoethyl; an alkoxy, thio or hydroxy substituted alkyl, such as 2-methoxy-ethyl, 2-hydroxy propyl or serinol, or an ethylthioethyl.

In an alternative embodiment, when $R_b$ is an optionally substituted $C_{1-10}$alkyl the moiety is a methyl, ethyl, n-propyl, isopropyl, t-butyl, n-butyl, or 2,2-dimethylpropyl or 2-hydroxy propyl group.

Suitably, when $R_b$ is an optionally substituted heteroaryl, or heteroarylalkyl, the heteroaryl containing moiety includes but is not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

In one embodiment, when $R_b$ is an optionally substituted heteroaryl it is a 1,3-thiazol-2-yl or 5-methyl-1,3-thiazol-2-yl, isoquinolinyl, thiophene, e.g. a 3-thiophene, indol-5-yl, pyridinyl, e.g. a pyridin3-yl, or pyridine-4-yl, indazolyl, benzothiazolyl, 2-methyl-1,3-benzothiazol-5-yl, 1H-imidazol-4-yl or 1H-imidazol-4-ylethyl. Further to this, the heteroaryl ring is an optionally substituted thiazolyl, pyridyl, or thiophene ring. Preferably, $R_b$ is an optionally substituted 1,3-thiazol-2-yl.

Suitably, when $R_b$ is an optionally substituted heterocyclic, or heterocyclicalkyl, the heterocyclic containing moiety includes but is not limited to tetrahydropyrrole, tetrahydropyran, tetrahydrofuran, tetrahydrothiophene (including oxidized versions of the sulfur moiety), azepine, diazepine, aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety). In one embodiment, the heterocyclic, heterocyclic alkyl group is pyrazol-3-yl, 4-morpholino, unsubstituted and substituted 2-furanyl, 2-furanylmethyl, 2-thienyl, 2-thienylmethyl, tetrahydro-2H-pyran-4yl, tetrahydro-2H-pyran-4yl methyl, tetrahydro-2-furanyl, or tetrahydro-2-furanylmethyl.

Suitably, when $R_b$ is an optionally substituted aryl or arylalkyl moiety, the aryl containing moiety is unsubstituted or substituted independently at each occurrence one or more times by halogen, alkyl, cyano, $OR_8$, $SR_5$, $S(O)_2R_5$, $C(O)R_j$, $C(O)OR_j$, —Z'—$(CR_{10}R_{20})$s-Z', halosubstituted $C_{1-10}$ alkyl, or an optionally substituted aryl.

In one embodiment, $R_b$ is a phenyl, or napthylene, 2-fluorophenyl, 3-fluorophenyl, 4-fluorophenyl, 2,3-difluorphenyl, 2,4-difluorophenyl, 3,4-difluorophenyl, 3,5-difluorophenyl, 3-chlorophenyl, 4-chlorophenyl, 3-chloro-4-fluorophenyl, 2-methyl phenyl, 3-methylphenyl, 4-methylphenyl, 6-methyl phenyl, 2-methyl phenyl, 3-amino phenyl, 3,4-dimethyl phenyl, 4-methyl-3-fluorophenyl, 4-trifluorophenyl, 4-ethoxyphenyl, 4-methoxyphenyl, 3-cyanophenyl, 4-cyanophenyl, 4-thiomethylphenyl, 4-acetylphenyl, 4-dimethylaminophenyl, benzyl, phenethyl, phenylpropyl, 2,3-difluoro-benzyl, 3,5-difluoro-benzyl, biphenyl, 4'-fluorobiphenyl, 4-sulfonamindo-2-methylphenyl, or 3-phenyloxyphenyl, 4-phenyloxyphenyl, 4-(1-piperidinylsulfonyl)-phenyl, or 3-(aminocarbonyl)phenyl.

In another embodiment, $R_b$ is a phenyl, 2-fluorophenyl, 3-fluorophenyl, 4-fluorophenyl, 2,4-difluorphenyl, 3,4-difluorophenyl, 3,5-difluorophenyl, 3-chlorophenyl, 4-chlorophenyl, 3-chloro-4-fluorophenyl, 4-methyl-3-fluorophenyl, 4-trifluorophenyl, 2-methylphenyl, 3-methylphenyl, 4-ethoxyphenyl, 4-methoxyphenyl, 3-cyanophenyl, 4-cyanophenyl, 4-thiomethylphenyl, 4-acetylphenyl, 4-dimethylaminophenyl, biphenyl, 4'-fluorobiphenyl, 4-sulfonamindo-2-methylphenyl, 3-phenyloxyphenyl, benzyl, or phenethyl. Further to this $R_b$ is a 4-fluorophenyl.

Suitably, when $R_b$ is an optionally substituted cycloalkyl or cycloalkyl alkyl moiety, the moiety is a cyclopropyl, cyclobutyl, cyclopentyl, cyclohexyl, cyclopropylmethyl, or a cyclopentylmethyl. In another embodiment, $R_b$ is a cyclopropyl or cyclopropylmethyl group.

In another embodiment, $R_b$ is $C_{1-10}$ alkyl, heteroaryl, or aryl, all optionally substituted.

In another embodiment, $R_b$ is hydrogen, or an optionally substituted alkyl.

In one embodiment of the invention $R_b$ is an alkyl, such as propyl or isopropyl; heteroaryl, such as a thiazolyl; an aryl, such phenyl, or 4-F phenyl; an arylalkyl, or a cycloalkylalkyl moiety, all optionally substituted. In another embodiment, $R_b$ is alkyl, heteroaryl, or aryl, all optionally substituted.

In another embodiment, $R_b$ is $C_{1-10}$ alkyl, heteroaryl, or aryl, all optionally substituted.

Suitably, m is independently selected at each occurrence from 0 or an integer having a value of 1 or 2.

For each of the integer variables where appropriate, e.g. n, n', m, q', s, t, or v', etc. they are independently chosen at each occurrence.

Suitably, $R_8$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein these moieties, excluding hydrogen, may be optionally substituted 1 to 4 times by halogen; halosubstituted $C_{1-4}$ alkyl; $C_{1-4}$ alkyl; $C_{3-5}$cycloalkyl; $C_{3-5}$cycloalkyl $C_{1-4}$alkyl; halosubstituted $C_{1-4}$ alkyl; hydroxy; hydroxy substituted $C_{1-4}$alkyl; $C_{1-4}$alkoxy; halosubstituted $C_{1-4}$ alkoxy; $S(O)mC_{1-4}$ alkyl; —C(O), $C(O)C_{1-4}$ alkyl; $NR_{21}R_{31}$; or an aryl or arylalkyl, and wherein these aryl containing moieties may also be substituted independently at each occurrence, one to two times by halogen, hydroxy, hydroxy substituted alkyl, $C_{1-4}$ alkoxy, $S(O)_mC_{1-4}$alkyl, amino, mono & di-substituted $C_{1-4}$ alkylamino, $C_{1-4}$ alkyl, or $CF_3$.

Suitably, $R_{15}$ and $R_{25}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, or aryl-$C_{1-4}$ alkyl, heteroaryl or heteroaryl $C_{1-4}$ alkyl moiety, and wherein these moieties, excluding hydrogen may be optionally substituted; or $R_{15}$ and $R_{25}$ together with the nitrogen which they are attached form an optionally substituted heterocyclic ring of 4 to 7 members, which ring optionally contains an additional heteroatom selected from oxygen, sulfur or $NR_9$; and wherein these moieties are optionally substituted 1 to 4 times, independently at each occurrence by halogen; hydroxy; hydroxy substituted $C_{1-10}$alkyl; $C_{1-10}$ alkoxy; halosubstituted $C_{1-10}$ alkoxy; $C_{1-4}$ alkyl; $SR_5$, $S(O)R_5$, $S(O)_2R_5$; $C(O)R_j$; $C(O)OR_j$; $C(O)NR_4R_{14}$; $NR_4C(O)C_{1-10}$alkyl; $NR_4C(O)$aryl; $NR_4R_{14}$; cyano; nitro; $C_{1-10}$ alkyl; $C_{3-7}$cycloalkyl; $C_{3-7}$cycloalkyl$C_{1-10}$ alkyl; halosubstituted$C_{1-10}$ alkyl; aryl, aryl$C_{1-4}$ alkyl, heterocyclic and heterocyclic$C_{1-4}$ alkyl, heteroaryl, or hetero$C_{1-4}$ alkyl, and wherein these aryl, heterocyclic and heteroaryl containing moieties may also be substituted one to two times independently at each occurrence by halogen, $C_{1-4}$ alkyl, hydroxy, hydroxy substituted $C_{1-4}$ alkyl, $C_{1-10}$ alkoxy, $S(O)_m$alkyl, amino, mono & di-substituted $C_{1-4}$ alkyl amino, $C_{1-4}$ alkyl, or $CF_3$.

Suitably, $R_4$ and $R_{14}$ are each independently selected at each occurrence from hydrogen, optionally substituted $C_{1-10}$ alkyl, optionally substituted $C_{3-7}$cycloalkyl, optionally substituted $C_{3-7}$cycloalkyl$C_{1-4}$ alkyl, optionally substituted aryl or optionally substituted aryl-$C_{1-4}$ alkyl, optionally substituted heteroaryl, optionally substituted heteroaryl $C_{1-4}$ alkyl, optionally substituted heterocyclic, or optionally substituted heterocyclic $C_{1-4}$ alkyl, or $R_4$ and $R_{14}$ together with the nitrogen to which they are attached may form an optionally substituted heterocyclic ring of 4 to 7 members which ring optionally contains an additional heteroatom selected from oxygen, sulfur or nitrogen.

The $R_4$ and $R_{14}$ moieties, excluding hydrogen, of $C_{1-10}$alkyl, $C_{3-7}$cycloalkyl, $C_{3-7}$cycloalkyl$C_{1-4}$ alkyl, aryl, aryl-$C_{1-4}$ alkyl, heteroaryl, heteroaryl $C_{1-4}$ alkyl, heterocyclic, or heterocyclic $C_{1-4}$ alkyl moieties, and the $R_4$ and $R_{14}$ cyclized ring, are all be optionally substituted, one or more times, preferably 1 to 4 times, independently at each occurrence, by halogen, such as fluorine, chlorine, bromine or iodine; hydroxy; hydroxy substituted $C_{1-10}$alkyl; $C_{1-10}$ alkoxy, such as methoxy or ethoxy; $C_{1-10}$alkyl, halosubstituted $C_{1-10}$ alkoxy; $SR_5$; $S(O)R_5$; $S(O)_2R_5$, such as methyl thio, methylsulfinyl or methyl sulfonyl; $C(O)Rj$; $C(O)ORj$; $C(O)NR_4R_{14}$; $(CR_{10}R_{20})_nN(R_{10'})C(Z)OR_7$; $(CR_{10}R_{20})_nN(R_{10'})C(Z)NR_dR_{d'}$; $NR_4C(O)C_{1-10}$alkyl; $NR_4C(O)$aryl; $NR_4R_{14}$; cyano; nitro; $C_{1-10}$ alkyl, such as methyl, ethyl, n-propyl, t-butyl, etc.; $C_{3-7}$cycloalkyl and $C_{3-7}$cycloalkyl $C_{1-10}$ alkyl, such as cyclopropyl, cyclopropyl methyl, or cyclopropyl ethyl, etc.; halosubstituted $C_{1-10}$ alkyl, such $CF_2CF_2H$, $CH_2CF_3$, or $CF_3$; $C_{1-10}$ alkyl substituted one or more times by an optionally substituted aryl; optionally substituted aryl, such as phenyl, or an optionally substituted aryl$C_{1-4}$ alkyl, such as benzyl or phenethyl; an unsubstituted or substituted heteroaryl, or hetero$C_{1-4}$ alkyl, an unsubstituted or substituted heterocyclic, or heterocyclic$C_{1-4}$ alkyl, and wherein these aryl, heteroaryl and heterocyclic containing moieties may also be substituted independently at each occurrence, one to two times, by halogen, $C_{1-4}$ alkyl, hydroxy, hydroxy substituted $C_{1-4}$ alkyl, $C_{1-4}$ alkoxy, $S(O)_m$alkyl, amino, mono & di-substituted $C_{1-4}$ alkyl amino, or $CF_3$.

Suitably, when $R_4$ and $R_{14}$ together with the nitrogen cyclize to form an optionally substituted ring, such as described above, such rings include, but are not limited to pyrrolidine, piperidine, piperazine, morpholine, and thiomorpholine (including oxidizing the sulfur).

Suitably, $R_6$ is independently selected at each occurrence from hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety, and wherein these moieties, excluding hydrogen may be optionally substituted independently at each occurrence, one or more times, suitably 1 to 2 times, by halogen; hydroxy; hydroxy substituted $C_{1-10}$alkyl; $C_{1-10}$alkoxy; halosubstituted $C_{1-10}$ alkoxy; S(O)m alkyl; C(O); $NR_4R_{14'}$; $C_{1-10}$ alkyl; $C_{3-7}$cycloalkyl; $C_{3-7}$cycloalkyl $C_{1-10}$ alkyl; halosubstituted $C_{1-10}$ alkyl; an unsubstituted aryl or aryl$C_{1-4}$ alkyl, an unsubstituted or substituted heteroaryl or heteroaryl$C_{1-4}$ alkyl, or a unsubstituted or substituted heterocyclic or heterocyclic $C_{1-4}$ alkyl; and wherein these aryl, heterocyclic, or heteroaryl containing moieties may be substituted independently at each occurrence, one or two times by halogen, hydroxy, hydroxy substituted alkyl, $C_{1-10}$ alkoxy, $S(O)_m$alkyl, amino, mono & di-substituted $C_{1-4}$ alkyl amino, $C_{1-4}$ alkyl, or $CF_3$.

Suitably, $R_9$ is independently selected at each occurrence from hydrogen, $C(Z)R_6$, optionally substituted $C_{1-10}$ alkyl, optionally substituted aryl or optionally substituted aryl-$C_{1-4}$ alkyl. These alkyl, aryl and arylalkyl moieties may be optionally substituted 1 or 2 times, independently at each occurrence by halogen; hydroxy; hydroxy substituted $C_{1-10}$alkyl; $C_{1-10}$ alkoxy; halosubstituted $C_{1-10}$ alkoxy; S(O)m alkyl; —C(O); $NR_4R_{14'}$; $C_{1-10}$ alkyl, $C_{3-7}$cycloalkyl; $C_{3-7}$cycloalkyl $C_{1-10}$ alkyl; halosubstituted $C_{1-10}$ alkyl; an aryl or aryl $C_{1-4}$ alkyl, and wherein these aryl containing moieties may also be substituted one or two times independently at each occurrence by halogen, hydroxy, hydroxy substituted alkyl, $C_{1-10}$ alkoxy, $S(O)_mC_{1-4}$ alkyl, amino, mono & di-substituted $C_{1-4}$ alkyl amino, $C_{1-4}$ alkyl, or $CF_3$.

Suitably, $R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic, or heterocyclyl$C_{1-10}$ alkyl moiety, which moieties may be optionally substituted one ore more times, suitably 1 to 4 times, independently at each occurrence by hydrogen, halogen, nitro, $C_{1-10}$ alkyl, halo-substituted $C_{1-10}$ alkyl, $C_{2-10}$ alkenyl, $C_{2-10}$alkynyl, $C_{3-7}$cycloalkyl, $C_{3-7}$cycloalkyl$C_{1-10}$ alkyl, $C_{5-7}$cycloalkenyl, $C_{5-7}$cycloalkenyl-$C_{1-10}$ alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_{16}R_{26}$, $(CR_{10}R_{20})_nCN$, $(CR_{10}R_{20})_nS(O)_2NR_{16}R_{26}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_{16}R_{26}$, $(CR_{10}R_{20})_nN(R_{10'})C(Z)R_6$, $(CR_{10}R_{20})_nN(R_{10'})C(=N(R_{10'}))NR_{16}R_{26}$, $(CR_{10}R_{20})_nOC(Z)NR_{16}R_{26}$, $(CR_{10}R_{20})_nN(R_{10'})C(Z)NR_{16}R_{26}$, or $(CR_{10}R_{20})_nN(R_{10'})C(Z)OR_7$.

In one embodiment, the $R_3$ moieties are optionally substituted 1 to 4 times, independently at each occurrence by halogen, nitro, $C_{1-4}$ alkyl, halo-substituted $C_{1-4}$ alkyl, $C_{2-4}$ alkenyl, $C_{2-4}$alkynyl, $C_{3-6}$cycloalkyl, $C_{3-6}$cycloalkyl$C_{1-4}$ alkyl, $C_{5-6}$cycloalkenyl, $C_{5-6}$cycloalkenyl$C_{1-4}$ alkyl, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nS(O)_2NR_{16}R_{26}$, $(CR_{10}R_{20})_nNR_{16}R_{26}$, $(CR_{10}R_{20})_nCN$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nN(R_{10'})C(Z)R_6$, or $(CR_{10}R_{20})_nC(Z)NR_{16}R_{26}$.

In one embodiment the $R_3$ moieties are optionally substituted independently, one or more times, suitably 1 to 4 times, independently at each occurrence by the $R_3$ optional substituent is independently selected from halogen, $C_{1-10}$ alkyl, $(CR_{10}R_{20})_nOR_6$, $(CR_{10}R_{20})_nNR_{16}R_{26}$, or halo-substituted $C_{1-10}$ alkyl.

In another embodiment the optional substituents are independently selected at each occurrence from halogen, $C_{1-10}$ alkyl, hydroxy, $C_{1-10}$ alkoxy, cyano, nitro, amino, or halosubstituted $C_{1-10}$ alkyl. In another embodiment, the $R_3$ substituents are selected independently from halogen, such as fluorine, chlorine, bromine or iodine, or $C_{1-10}$ alkyl, such as methyl.

In one embodiment the $R_3$ moieties are selected from an optionally substituted $C_{1-10}$ alkyl, optionally substituted $C_{3-7}$cycloalkyl, optionally substituted $C_{3-7}$cycloalkylalkyl, or an optionally substituted aryl. In another embodiment, the $R_3$ moiety is selected from an optionally substituted $C_{1-10}$ alkyl, or an optionally substituted aryl. In another embodiment, $R_3$ is an optionally substituted phenyl. Further to this embodiment, $R_3$ is a phenyl ring substituted one or more times by independently at each occurrence by fluorine, chlorine, hydroxy, methoxy, amino, methyl, or trifluoromethyl. Preferably, $R_3$ is a 2,6-difluorophenyl.

Suitably, in one embodiment when $R_3$ is an aryl moiety, it is a phenyl ring. The phenyl ring is optionally substituted, independently at each occurrence, one or more times, suitably 1 to 4 times by halogen, $C_{1-4}$ alkyl, or halo-substituted-$C_{1-4}$ alkyl. The phenyl ring may suitably be substituted in the 2, 4, or 6-position, or di-substituted in the 2,4-position, or 2,6-position, such as 2-fluoro, 4-fluoro, 2,4-difluoro, 2,6-difluoro, or 2-methyl-4-fluoro; or tri-substituted in the 2,4,6-position, such as 2,4,6-trifluoro.

Suitably, $R_7$ is independently selected at each occurrence from $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl; and wherein each of these moieties may be optionally substituted one or two times independently at each occurrence, by halogen; hydroxy; hydroxy substituted $C_{1-10}$alkyl; $C_{1-10}$ alkoxy; halosubstituted $C_{1-10}$ alkoxy; S(O)malkyl; C(O); $NR_4R_{14'}$; $C_{1-10}$ alkyl; $C_{3-7}$cycloalkyl; $C_{3-7}$cycloalkyl$C_{1-10}$ alkyl; halosubstituted $C_{1-10}$ alkyl; an aryl or aryl $C_{1-4}$ alkyl moiety, and wherein these aryl containing moieties may also be substituted one to two times by halogen, hydroxy, hydroxy substituted alkyl, $C_{1-10}$ alkoxy, $S(O)_m$alkyl, amino, mono & di-substituted $C_{1-4}$ alkyl amino, $C_{1-4}$ alkyl, or $CF_3$.

Suitably, $R_{16}$ and $R_{26}$ are each independently selected at each occurrence from hydrogen, or $C_{1-4}$ alkyl; or the $R_{16}$ and $R_{26}$ together with the nitrogen which they are attached form an unsubstituted or substituted heterocyclic ring, of 4 to 7 members, which ring optionally contains an additional heteroatom selected from oxygen, sulfur or $NR_9$.

Suitably, n is 0, or an integer having a value of 1 to 10.

Suitably, X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_4$, $(CH_2)_nN(R_{2'})(R_{2''})$, or $N(R_{10'})R_nNH—C(=N—CN)NRqRq'$.

In one embodiment of the invention X is $N(R_{10'})R_h NH-C(=N-CN)NR_qR_{q'}$.

Suitably, $X_1$ is $N(R_{11})$, O, $S(O)_m$, or $CR_{10}R_{20}$. In one embodiment of the invention, $X_1$ is $N(R_{11})$, or O.

Suitably, $R_h$ is selected from an optionally substituted $C_{1-10}$ alkyl, $-CH_2-C(O)-CH_2-$, $-CH_2-CH_2-O-CH_2-CH_2-$, $-CH_2-C(O)N(R_{10'})CH_2-CH_2-$, $-CH_2-N(R_{10'})C(O)CH_2-$, $-CH_2-CH(OR_{10'})-CH_2-$, $-CH_2-C(O)O-CH_2-CH_2-$, or $-CH_2-CH_2-O-C(O)CH_2-$.

Suitably, $R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein all of the moieties, excluding hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulphur.

Suitably, $R_{11}$ is independently selected at each occurrence from hydrogen, or $C_{1-4}$ alkyl.

Suitably, $R_2$ is independently selected from hydrogen, optionally substituted $C_{1-10}$ alkyl, optionally substituted $C_{3-7}$ cycloalkyl, optionally substituted $C_{3-7}$cycloalkylalkyl, optionally substituted aryl, optionally substituted aryl$C_{1-10}$alkyl, optionally substituted heteroaryl, optionally substituted heteroaryl$C_{1-10}$ alkyl, optionally substituted heterocyclic, optionally substituted heterocyclyl$C_{1-10}$alkyl moiety; or $R_2$ is the moiety $(CR_{10}R_{20})_q X_1(CR_{10}R_{20})_q C(A_1)(A_2)(A_3)$, or $(CR_{10}R_{20})_q C(A_1)(A_2)(A_3)$.

Suitably q' is 0, or an integer having a value of 1 to 6.

The $R_2$ moieties, excluding hydrogen, may be optionally substituted one or more times, preferably 1 to 4 times, independently at each occurrence by $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl $C_{1-10}$ alkyl, halogen, $-C(O)$, cyano, nitro, $(CR_{10}R_{20})_n OR_6$, $(CR_{10}R_{20})_n SH$, $(CR_{10}R_{20})_n S(O)_m R_7$, $(CR_{10}R_{20})_n N(R_{10'})S(O)_2 R_7$, $(CR_{10}R_{20})_n NR_e R_{e'}$, $(CR_{10}R_{20})_n NR_e R_{e'} C_{1-4}$alkyl$NR_e R_{e'}$, $(CR_{10}R_{20})_n CN$, $(CR_{10}R_{20})_n S(O)_2 NR_e R_{e'}$, $(CR_{10}R_{20})_n C(Z)R_6$, $(CR_{10}R_{20})_n OC(Z)R_6$, $(CR_{10}R_{20})_n C(Z)OR_6$, $(CR_{10}R_{20})_n C(Z)NR_e R_{e'}$, $(CR_{10}R_{20})_n N(R_{10'})C(Z)R_6$, $(CR_{10}R_{20})_n N(R_{10'})C(=N(R_{10'}))NR_e R_{e'}$, $(CR_{10}R_{20})_n C(=NOR_6)NR_e R_{e'}$, $(CR_{10}R_{20})_n OC(Z)NR_e R_{e'}$, $(CR_{10}R_{20})_n N(R_{10'})C(Z)NR_e R_{e'}$, or $(CR_{10}R_{20})_n N(R_{10'})C(Z)OR_7$.

Suitably, $R_e$ are $R_{e'}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heteroaryl or a heteroaryl $C_{1-4}$ alkyl moiety, which moieties may be optionally substituted; or $R_e$ and $R_{e'}$ together with the nitrogen which they are attached form an optionally substituted heterocyclic ring of 4 to 7 members, which ring optionally contains an additional heteroatom selected from oxygen, sulfur or $NR_9$; and wherein each of these moieties, including the cyclized ring, and excluding hydrogen, may be substituted 1 to 4 times, independently at each occurrence by halogen; hydroxy; hydroxy substituted $C_{1-10}$ alkyl; $C_{1-10}$ alkoxy; halosubstituted $C_{1-10}$ alkoxy; $C_{1-10}$alkyl; halosubstituted $C_{1-4}$ alkyl; $S(O)_m R_j$; $C(O)R_j$; $C(O)OR_j$; $(CR_{10}R_{20})_n N(R_{10'})C(Z)R_7$; $(CR_{10}R_{20})_n N(R_{10'})C(Z)NR_d R_{d'}$; $C(O)NR_4 R_{14}$; $NR_4 C(O)C_{1-10}$alkyl; $NR_4 C(O)$aryl; cyano; nitro; $NR_4 R_{14}$; $C_{1-10}$ alkyl; $C_{3-7}$ cycloalkyl; $C_{3-7}$ cycloalkyl $C_{1-10}$ alkyl; halosubstituted $C_{1-10}$ alkyl; aryl, aryl$C_{1-4}$alkyl, heterocyclic, heterocyclic $C_{1-4}$ alkyl, heteroaryl, or hetero $C_{1-4}$ alkyl, and wherein these aryl, heterocyclic or heteroaryl containing moieties may be optionally substituted one to two times independently at each occurrence by halogen, $C_{1-4}$ alkyl, hydroxy, hydroxy substituted $C_{1-4}$ alkyl, $C_{1-10}$ alkoxy, $S(O)_m$alkyl, amino, mono & di-substituted $C_{1-4}$ alkyl amino, $C_{1-4}$ alkyl, or $CF_3$.

Suitably, $R_{j'}$ is independently selected at each occurrence from hydrogen, $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties, excluding hydrogen, may be optionally substituted.

When X is $R_2$ and $R_2$ is an optionally substituted heterocyclic or heterocyclic alkyl, the heterocyclic containing moiety is suitably selected from tetrahydropyrrole, tetrahydropyran, tetrahydrofuran, tetrahydrothiophene (including oxidized versions of the sulfur moiety), aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety).

In one embodiment, $R_2$ is an optionally substituted piperidinyl or piperazinyl ring.

In another embodiment, when $R_2$ is an optionally substituted heterocyclic or heterocyclic alkyl ring the ring is substituted one or mores times independently by an optionally substituted heterocyclic, heterocyclic alkyl, aryl, arylalkyl, alkyl, $(CR_{10}R_{20})_n NR_e R_{e'}$, or $(CR_{10}R_{20})_n N(R_{10'})C(Z)OR_7$. The second heterocyclic ring is suitably selected from an optionally substituted tetrahydropyrrole, tetrahydropyran, tetrahydrofuran, tetrahydrothiophene (including oxidized versions of the sulfur moiety), aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, diazepine, morpholino or thiomorpholino (including oxidized versions of the sulfur moiety). Suitably, the second heterocyclic ring is selected from morpholino, piperidine, or pyrrolidinyl.

In one embodiment, $R_2$ is a 4-amino-1-piperidinyl, 1,1-dimethylethyl)oxy]-carbonyl}amino)-1-piperidinyl, 4-methyl-1-piperazinyl, 4-ethyl-1-piperazinyl, 4-propyl-1-piperazinyl, 4-butyl-1-piperazinyl, 4-(methylamino)-1-piperidinyl, 1,1-dimethylethyl-4-piperidinyl}methylcarbamate, 4-phenyl-1-piperazinyl, 1,4'-bipiperidin-1'-yl, 4-(1-pyrrolidinyl)-1-piperidinyl, 4-methyl-1,4'-bipiperidin-1'-yl, 4-(4-morpholinyl)-1-piperidinyl, 4-(diphenylmethyl)-1-piperazinyl, or 4-methylhexahydro-1H-1,4-diazepin-1-yl.

Suitably, $R_{2'}$ is independently selected at each occurrence from hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted 1 to 4 times, independently, at each occurrence, by $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl $C_{1-10}$ alkyl, halogen, $-C(O)$, cyano, nitro, aryl, aryl $C_{1-10}$ alkyl, heteroaryl, heteroaryl$C_{1-10}$ alkyl, heterocyclic, heterocyclyl$C_{1-10}$ alkyl, $(CR_{10}R_{20})_n OR_6$, $(CR_{10}R_{20})_n SH$, $(CR_{10}R_{20})_n S(O)_m R_7$, $(CR_{10}R_{20})_n N(R_{10'})S(O)_2 R_7$, $(CR_{10}R_{20})_n NR_e R_{e'}$, $(CR_{10}R_{20})_n NR_e R_{e'} C_{1-4}$alkyl$NR_e R_{e'}$, $(CR_{10}R_{20})_n CN$, $(CR_{10}R_{20})_n S(O)_2 NR_e R_{e'}$, $(CR_{10}R_{20})_n C(Z)R_6$, $(CR_{10}R_{20})_n OC(Z)R_6$, $(CR_{10}R_{20})_n C(Z)OR_6$, $(CR_{10}R_{20})_n C(Z)NR_e R_{e'}$, $(CR_{10}R_{20})_n N(R_{10'})C(Z)R_6$, $(CR_{10}R_{20})_n N(R_{10'})C(=N(R_{10'}))NR_e R_{e'}$, $(CR_{10}R_{20})_n C(=NOR_6)NR_e R_{e'}$, $(CR_{10}R_{20})_n OC(Z)NR_e R_{e'}$, $(CR_{10}R_{20})_n N(R_{10'})C(Z)NR_e R_{e'}$, or $(CR_{10}R_{20})_n N(R_{10'})C(Z)OR_7$.

In one embodiment, when X is $(CH_2)_nN(R_{2'})(R_{2''})$, one of $R_{2'}$, or $R_{2''}$, is hydrogen, or methyl.

In one embodiment, when $R_{2'}$ is an optionally substituted heterocyclic or heterocyclylC$_{1-10}$ alkyl the heterocyclic containing moiety is substituted one or more time independently by C$_{1-10}$ alkyl, aryl, heterocyclic, $(CR_{10}R_{20})_nNR_eR_{e'}$, $(CR_{10}R_{20})_nN(R_{10'})C(Z)OR_7$, or $(CR_{10}R_{20})_nC(Z)OR_6$. More specifically, methyl, ethyl, NHC(O)O—CCH$_3$, N(CH$_3$)C(O)O—CCH$_3$, amino, methylamino, dimethylamino, phenyl, piperidine, pyrrolidine, 1-ethylpropyl, 4-methyl-1,4'-bipiperidin-1'-yl, 1,4'-bipiperidin-1'-yl, morpholino, In one embodiment, when X is $(CH_2)_nN(R_{2'})(R_{2''})$, $R_{2'}$ is an optionally substituted C$_{1-10}$ alkyl, cycloalkyl, heterocyclic, heterocyclyl C$_{1-10}$ alkyl, heteroarylalkyl. Suitably, when $R_{2'}$ is an optionally substituted cycloalkyl it is a cyclohexyl ring. In one embodiment the cyclohexyl ring is optionally substituted one or more times by $(CR_{10}R_{20})_nNR_eR_{e'}$.

Suitably, when $R_{2'}$ is an optionally substituted heterocyclic, or a heterocyclylC$_{1-10}$ alkyl, the ring is selected from tetrahydropyrrole, tetrahydropyran, tetrahydrofuran, tetrahydrothiophene (including oxidized versions of the sulfur moiety), aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, diazepine, hexahydro-1-H-azepine, morpholino or thiomorpholino (including oxidized versions of the sulfur moiety). Preferably, the ring is a piperidine, piperazine, pyrrolidinyl, 2-oxo-1-pyrrolidinyl, morpholino, hexahydro-1-H-azepine ring. In one embodiment, the rings are substituted one or more times, suitably 1 to 4 times, independently by C$_{1-10}$ alkyl, aryl, arylalkyl, $(CR_{10}R_{20})_nNR_eR_{e'}$, or $(CR_{10}R_{20})_nN(R_{10'})C(Z)OR_7$.

In one embodiment, $(CH_2)_nN(R_{2'})(R_{2''})$ is 1-phenylmethyl)-4-piperidinamine, 2-[4-(phenylmethyl)-1-piperazinyl]ethylamine, 2-(1-piperidinyl)ethylamine, 2-(1-methyl-2-pyrrolidinyl)ethylamine, 1-[(phenylmethyl)-3-pyrrolidinyl]amine, 3-[(1-pyrrolidinyl)propyl]amine, 3-[(hexahydro-1H-azepin-1-yl)propyl]amine, (1-methyl-4-piperidinyl)amine, 3-[(4-morpholinyl)propyl]amine, 3-[(2-oxo-1-pyrrolidinyl)propyl]-amine, 2-[(4-morpholinyl)ethyl]amine, 2-[(1-pyrrolidinyl)ethyl]-amine, or [(1-ethyl-2-pyrrolidinyl)methyl]amino.

In one embodiment when X is $(CH_2)_nN(R_{2'})(R_{2''})$, and $R_{2'}$ is an optionally substituted C$_{1-10}$ alkyl, the alkyl is substituted one or more times independently by $(CR_{10}R_{20})_nNR_eR_{e'}$ or $(CR_{10}R_{20})_nNR_eR_{e'}C_{1-4}$alkylNR$_e$R$_{e'}$. In one embodiment R$_e$ and R$_{e'}$ are independently an optionally substituted C$_{1-4}$ alkyl, such as methyl, ethyl, isopropyl, n-butyl, or t-butyl. Preferably, $(CH_2)_nN(R_{2'})(R_{2''})$ is 3-(dimethylamino)propyl(methyl)amine, 3-(diethylamino)propylamine, propylamine, (2,2-dimethylpropyl)amine, (2-hydroxypropyl)amino, 2-(dimethylamino)ethylamine, 2-(dimethylamino)ethyl(methyl)amine, 3-(dimethylamino)propylamine, 2-(dimethylamino)ethyl(methyl)amine, 3-(diethylamino)propylamine, 2-(methylamino)ethylamine, [(1-methylethyl)amino]ethylamine, 3-(diethylamino)propylamine, 3-(dibutylamino)propylamine, 3-[(1-methylethyl)amino]propylamine, 3-(1,1-dimethylethyl)aminopropylamine, 3-(dimethylamino)-2,2-dimethylpropylamine, 4-(diethylamino)-1-methylbutylamine, or 3-[[3-(dimethylamino)propyl]-(methyl)amino]propyl(methyl)amine.

Suitably, $R_{2''}$ is selected from hydrogen, C$_{1-10}$ alkyl, C$_{3-7}$ cycloalkyl, C$_{3-7}$cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein the moieties, excluding hydrogen, may be optionally substituted 1 to 4 times, independently, at each occurrence by C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$alkyl, C$_{5-7}$cycloalkenyl, C$_{5-7}$ cycloalkenyl C$_{1-10}$ alkyl, halogen, —C(O), cyano, nitro, aryl, aryl C$_{1-10}$ alkyl, heteroaryl, heteroarylC$_{1-10}$ alkyl, heterocyclic, heterocyclylC$_{1-10}$ alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_eR_{e'}$, $(CR_{10}R_{20})_nNR_eR_{e'}C_{1-4}$alkylNR$_e$R$_{e'}$, $(CR_{10}R_{20})_nCN$, $(CR_{10}R_{20})_nS(O)_2NR_eR_{e'}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_eR_{e'}$, $(CR_{10}R_{20})_nN(R_{10'})C(Z)R_6$, $(CR_{10}R_{20})_nN(R_{10'})C(=N(R_{10'}))NR_eR_{e'}$, $(CR_{10}R_{20})_nC(=NOR_6)NR_eR_{e'}$, $(CR_{10}R_{20})_nOC(Z)NR_eR_{e'}$, $(CR_{10}R_{20})_nN(R_{10'})C(Z)NR_eR_{e'}$, or $(CR_{10}R_{20})_nN(R_{10'})C(Z)OR_7$; or wherein $R_{2''}$ is the moiety $(CR_{10}R_{20})_tX_1(CR_{10}R_{20})_qC(A_1)(A_2)(A_3)$.

Suitably, t is an integer having a value of 2 to 6.

Suitably, q is 0 or an integer having a value of 1 to 10.

Suitably, $A_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl.

Suitably, $A_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl.

Suitably, $A_3$ is hydrogen or is an optionally substituted C$_{1-10}$ alkyl.

The $A_1$, $A_2$, and $A_3$C$_{1-10}$ alkyl moieties may optionally substituted one or more times, independently, at each occurrence preferably from 1 to 4 times, with halogen, such as chlorine, fluorine, bromine, or iodine; halo-substituted C$_{1-10}$alkyl, such as CF$_3$, or CHF$_2$CF$_3$; C$_{2-10}$ alkenyl, C$_{2-10}$ alkynyl, C$_{3-7}$ cycloalkyl, C$_{3-7}$cycloalkylC$_{1-10}$alkyl, C$_{5-7}$cycloalkenyl, C$_{5-7}$ cycloalkenylC$_{1-10}$alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nN(R_{10'})C(Z)R_6$, $(CR_{10}R_{20})_nN(R_{10'})C(=N(R_{10'}))NR_4R_{14}$, $(CR_{10}R_{20})_nOC(Z)NR_4R_{14}$, $(CR_{10}R_{20})_nN(R_{10'})C(Z)NR_4R_{14}$, or $(CR_{10}R_{20})_nN(R_{10'})C(Z)OR_7$.

In another embodiment of the present invention, X is $R_2$, and $R_2$ is $(CR_{10}R_{20})_{q'}X_1(CR_{10}R_{20})_qC(A_1)(A_2)(A_3)$, or $(CR_{10}R_{20})_qC(A_1)(A_2)(A_3)$. In a further embodiment, q' is 0.

In another embodiment when $R_2$ is the moiety $(CR_{10}R_{20})_{q'}X_1(CR_{10}R_{20})_qC(A_1)(A_2)(A_3)$, q' is 0, $X_1$ is nitrogen, q is 0 or 1, $A_1$ is an optionally substituted heterocyclic or heterocyclic alkyl, and $A_2$ is an optionally substituted aryl. More specifically, $R_2$ is 2-phenyl-2-(1-pyrrolidinyl)ethyl]amino, or 1-phenyl-2-(1-pyrrolidinyl)ethyl]amino.

In one embodiment of the invention, one or more of the $A_1$, $A_2$ and $A_3$ moieties are substituted with $(CR_{10}R_{20})_nOR_6$. In another embodiment of the invention, the $R_6$ substituent in $(CR_{10}R_{20})_nOR_6$ is hydrogen.

In yet another embodiment of the present invention, X is $R_2$ and $R_2$ is $(CR_{10}R_{20})_qC(A_1)(A_2)(A_3)$, such as CH(CH$_2$OH)$_2$, or C(CH$_3$)(CH$_2$OH)$_2$; or wherein $R_2$ is $(CR_{10}R_{20})_{q'}X_1(CR_{10}R_{20})qC(A_1)(A_2)(A_3)$ and q' is 0, and the moiety is $X_1(CR_{10}R_{20})qCH(CH_2OH)_2$, or $X_1(CR_{10}R_{20})qC(CH_3)(CH_2OH)_2$; in another embodiment $X_1$ is oxygen or nitrogen.

In one embodiment of the present invention X is $R_2$, OR$_{2'}$, $(CH_2)_nNR_4R_{14}$, or $(CH_2)_nN(R_{2'})(R_{2''})$.

In another embodiment X is $S(O)_mR_{2'}$, $(CH_2)_nNR_4R_{14}$, or $(CH_2)_nN(R_{2'})(R_{2''})$.

In yet another embodiment, X is $(CH_2)_nNR_4R_{14}$, or $(CH_2)_nN(R_{2'})(R_{2''})$.

In yet another embodiment, X is $(CH_2)_nNR_4R_{14}$.

In yet another embodiment, X is $(CH_2)_nN(R_{2'})(R_{2''})$.

In one embodiment of the present invention X is $R_2$, OR$_{2'}$, $(CH_2)_nNR_4R_{14}$, or $(CH_2)_nN(R_{2'})(R_{2''})$.

Suitably, when X is $(CH_2)_nNR_4R_{14}$, then $R_4$ and $R_{14}$ are $C_{1-10}$ alkyl, aryl, aryl-$C_{1-4}$ alkyl, heterocyclic, heterocyclic $C_{1-4}$ alkyl, heteroaryl or heteroaryl $C_{1-4}$ alkyl. Suitably, the $C_{1-4}$ alkyl may be substituted one or more times, independently at each occurrence with $NR_{4'}R_{14'}$; halogen, hydroxy, alkoxy, $C(O)NR_{4'}R_{14'}$; or $NR_{4'}C(O)C_{1-10}$alkyl. Preferably, the $C_{1-4}$ alkyl is substituted with $NR_{4'}R_{14'}$.

In one embodiment at least one of $R_4$ and $R_{14}$ may be hydrogen when $R_4$ and $R_{14}$ are not cyclized. In another embodiment neither $R_4$ and $R_{14}$ is hydrogen.

In one embodiment when X is $(CH_2)_nNR_4R_{14}$, one of $R_4$ and $R_{14}$ are hydrogen, and the other is an optionally substituted heteroaryl $C_{1-4}$ alkyl. Suitably, the optionally substituted heteroaryl alkyl is an imidazolyl alkyl, such as a 1H-imidazol-2-yl-methyl group.

In another embodiment when X is $(CH_2)_nNR_4R_{14}$ and one of $R_4$ and $R_{14}$ is a heteroaryl $C_{1-4}$ alkyl moiety, the heteroaryl ring is selected from an optionally substituted thienyl, pyrrolyl, oxazolyl, thiazolyl, isoxazolyl, isothiazolyl, imidazolyl, pyrazolyl, triazolyl, pyridazinyl, pyrimidinyl, pyrazinyl, benzoxazolyl, benzimidazolyl, and benzothiazolyl. Suitably, the heteroaryl $C_{1-4}$ alkyl is selected from an optionally substituted pyrrolyl, oxazolyl, thiazolyl, isoxazolyl, imidazolyl, benzoxazolyl, benzimidazolyl, and benzothiazolyl.

In another embodiment when X is $(CH_2)_nNR_4R_{14}$ and one of $R_4$ and $R_{14}$ is a heterocyclic $C_{1-4}$ alkyl moiety, then the optionally substituted heterocyclic ring is selected from an optionally substituted tetrahydropyrrole, tetrahydropyran, tetrahydrofuran, pyrrolinyl, pyrrolidinyl, imidazolinyl, imidazolidinyl, indolinyl, pyrazolinyl, pyrazolidinyl, piperidinyl, piperazinyl, and morpholino. Suitably, the heterocyclic $C_{1-4}$ alkyl moiety is selected from optionally substituted pyrrolinyl, pyrrolidinyl, piperidinyl, piperazinyl, and morpholino.

In another embodiment when X is $(CH_2)_nNR_4R_{14}$ and $R_4$ and $R_{14}$ together with the nitrogen cyclize to form an optionally substituted ring, such as described above, such rings include, but are not limited to pyrrolidine, piperidine, piperazine, diazepine, and morpholine.

In one embodiment when X is $(CH_2)_nNR_4R_{14}$, the $R_4$ and $R_{14}$ substituents cyclize to form a heterocyclic 5 or 6 membered ring, which ring is optionally substituted as defined herein. When the $R_4$ and $R_{14}$ substituents cyclize to form a 4 to 7 membered ring, the optional substituents are suitably selected from an optionally substituted alkyl, an optionally substituted aryl, an optionally substituted heteroaryl, optionally substituted heterocyclic, $(CR_{10}R_{20})_nN(R_{10'})C(Z)OR_7$, $NR_{4'}R_{14'}$, or a $C_{1-10}$ alkyl substituted one or more times by an optionally substituted aryl. Such substituents more specifically include phenyl, pyrrolidinyl, morpholino, piperazinyl, 4-methyl-1-piperazinyl, piperidinyl, 2-oxo-2,3-dihydro-1H-benzimidazol-1-yl, 5-chloro-2-oxo-2,3-dihydro-1H-benzimidazol-1-yl, diphenylmethyl, methyl, ethyl, propyl, butyl, amino, methylamino, and dimethylamino.

In one embodiment the X substituent is a 1,4'-bipiperin-1-yl ring which may be optionally substituted such as in 4-methyl-1,4'-bipiperin-1-yl; 4-piperidinylamino, 4-amino-1-piperidinyl, 2,2,6,6-tetramethyl-4-piperidinyl)amino, 4-methyl-1-piperazinyl, (4-morpholinyl)-1-piperidinyl, (4-methyl-1-piperazinyl)-1-piperidinyl, 4-ethyl-1-piperazinyl, (2-oxo-2,3-dihydro-1H-benzimidazol-1-yl)-1-piperidinyl, 5-chloro-(2-oxo-2,3-dihydro-1H-benzimidazol-1-yl)-1-piperidinyl, 4-(1-pyrrolidinyl)-1-piperidinyl, 4-(diphenylmethyl)-1-piperazinyl, 4-methylhexahydro-1H-1,4-diazepin-1-yl, 4-propyl-1-piperazinyl, or 4-butyl-1-piperazinyl. In a further embodiment, the X substituent is an optionally substituted 1,4'-bipiperin-1'yl ring, a 4-amino-1-piperidinyl, or a 2,2,6,6-tetramethyl-4-piperidinyl)amino.

In another embodiment, when X is $(CH_2)_nN(R_{2'})(R_{2''})$, and $R_{2'}$ is an optionally substituted $C_{1-10}$ alkyl moiety, and the alkyl is substituted by $(CR_{10}R_{20})_nNR_eR_{e'}$, and $R_e$ and $R_{e'}$ are hydrogen, or an optionally substituted $C_{1-10}$ alkyl. Suitably, the X moiety is 3-(diethylamino)propylamino, 3-(dimethylamino)propyl(methyl)amino, 3-(dimethylamino)propyl (methyl)amino, 2-(dimethylamino)ethylamino, 1-(methylethyl)amino-propylamino, (1,1-dimethylethyl)aminopropylamino, (1-methylethyl)aminoethylamino, 2-(methylamino)ethylamino, 2-aminoethyl(methyl)amino, or a 2-(dimethylamino)ethyl(methyl)amino.

In another embodiment when X is $(CH_2)_nN(R_{2'})(R_{2''})$, and $R_{2'}$ moiety is an optionally substituted heteroaryl$C_{1-10}$ alkyl, the heteroaryl moiety is suitably an optionally substituted imidazole.

In one embodiment of the invention at least one of $R_4$ and $R_{14}$ may be hydrogen when $R_4$ and $R_{14}$ are not cyclized.

In one embodiment $R_3$ is a 2,6-difluoro phenyl, $R_{1'}$ is independently selected at each occurrence from hydrogen, fluorine, or methyl; g is 1 or 2; and $R_1$ is selected from $C(Z)N(R_{10'})(CR_{10}R_{20})_vR_b$, or $C(Z)O(CR_{10}R_{20})_vR_b$, or $N(R_{10'})C(Z)(CR_{10}R_{20})_vR_b$. Preferably, $R_1$ is selected from $C(Z)N(R_{10'})(CR_{10}R_{20})_vR_b$. In another embodiment, the $R_b$ moiety is selected from thiazolyl, $C_{1-10}$ alkyl or an optionally substituted aryl. In another embodiment the $R_b$ moiety is propyl or 4-fluorophenyl. In another embodiment, the $R_b$ moiety is thiazolyl.

In another embodiment, X is suitably selected from (1H-imidazol-2-ylmethyl)amino or 4-methyl-1,4'-bipiperidin-1'-yl, 2,2,6,6-tetramethyl-4-piperidinyl)amino, 4-amino-1-piperidinyl, 3-(diethylamino)propylamino, 3-(dimethylamino)propyl(methyl)amino, 3-(dimethylamino)propyl(methyl)amino, 2-(dimethylamino)ethylamino, 1-methylethyl)amino-propylamino, (1,1-dimethylethyl)aminopropylamino, (1-methylethyl)aminoethylamino, 2-(methylamino)ethylamino, 2-aminoethyl(methyl)amino, or 2-(dimethylamino)ethyl(methyl)amino.

In one embodiment, $R_3$ is a 2,6-difluoro phenyl, $R_{1'}$ is independently selected at each occurrence from hydrogen, fluorine, or methyl; g is 1 or 2; and $R_1$ is selected from $C(Z)N(R_{10'})(CR_{10}R_{20})_vR_b$, $R_b$ moiety is $C_{1-10}$ alkyl or an optionally substituted aryl, preferably propyl or 4-fluorophenyl, or optionally substituted heteroaryl, preferably thiazolyl; X is $(CH_2)_nN(R_{2'})(R_{2''})$, and n is 0. In another embodiment, X is $(CH_2)_nN(R_{2'})(R_{2''})$, $R_{2''}$ is hydrogen, n is 0, and $R_{2'}$ is an alkyl substituted by $(CR_{10}R_{20})_nNR_eR_{e'}$. In a further embodiment, $R_e$ and $R_{e'}$ are independently selected from an optionally substituted $C_{1-4}$ alkyl, such as methyl, ethyl, isopropyl, n-butyl, or t-butyl, preferably ethyl.

Another embodiment of the invention is the genus of compounds of formula (Ic), a subgenus of compounds of Formula (I) and (Ia) wherein $R_1$ is $C(Z)N(R_{10'})(CR_{10}R_{20})_vR_b$, and $R_b$ is an optionally substituted heteroaryl, an optionally substituted heteroaryl $C_{1-10}$ alkyl, optionally substituted heterocyclic and optionally substituted heterocyclic $C_{1-10}$ alkyl. The remaining groups are the same as enumerated above for Formula (I) and (Ia).

In another embodiment for compounds of Formula (Ic), $R_1$ is $C(Z)N(R_{10'})(CR_{10}R_{20})_vR_b$, and $R_b$ is an optionally substituted heteroaryl, or an optionally substituted heteroaryl $C_{1-10}$ alkyl.

Suitably, the heteroaryl, heteroarylalkyl, heterocyclic and heterocyclicalkyl moieties are as defined above for Formula (I) and (Ia). A preferred heteroaryl ring is an optionally substituted thiazolyl ring, pyridyl, or thiophene ring.

In one embodiment of this invention, for compounds of Formula (I), (Ia), and (Ic), as well as the remaining formulas herein, $R_{1'}$ is independently selected hydrogen, halogen, $C_{1-4}$ alkyl, or halo-substituted-$C_{1-4}$ alkyl. In another embodiment, $R_{1'}$ is independently selected from hydrogen, fluorine, chlorine, methyl, or $CF_3$. In one embodiment when $R_{1'}$ is substituted on the phenyl ring in the ortho position, and a second $R_{1'}$ moiety is also substituted on the ring, then preferably the second substitution is not in the other ortho position.

In one embodiment of the invention, g is 1 or 2.

Suitably, in one embodiment when $R_3$ is an aryl moiety, it is a phenyl ring, and the phenyl ring is optionally substituted, independently at each occurrence, one or more times, suitably 1 to 4 times by halogen, $C_{1-4}$ alkyl, or halo-substituted-$C_{1-4}$ alkyl. The phenyl ring may suitably be substituted in the 2, 4, or 6-position, or di-substituted in the 2,4-position, such as 2-fluoro, 4-fluoro, 2,4-difluoro, 2,6-difluoro, 6-difluoro, or 2-methyl-4-fluoro; or tri-substituted in the 2,4,6-position, such as 2,4,6-trifluoro. Preferably, $R_3$ is a 2,6-difluoro phenyl.

In one embodiment, $R_3$ is a 2,6-difluoro phenyl, $R_{1'}$ is independently selected at each occurrence from hydrogen, fluorine, or methyl; g is 1 or 2.

In another embodiment of the present invention the compounds of Formula(s) (I) and (Ia), (II) and (IIa), (III) and (IIIa), (IV) and (IVa), (V) and (Va), (VI), (VIa-VIi), (VIII), (VIIIa), (IX), (IXa), (A), (A1), (B), and (B1), may also include for the X term the B-Non-Ar-cyc moiety as disclosed in U.S. Pat. No. 6,809,199 whose disclosure is incorporated by reference herein.

As represented by the disclosure in U.S. Pat. No. 6,809,199, Non-Ar-Cyc is suitably selected from;

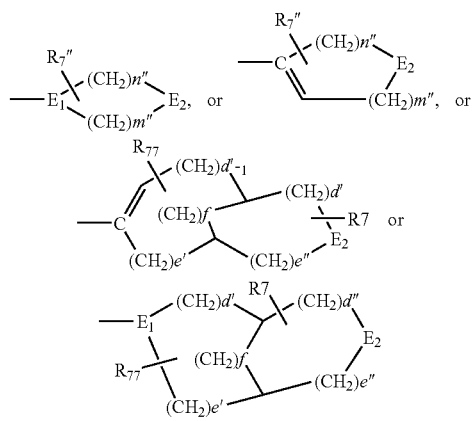

wherein
d is an integer having a value of 1, 2, 3, or 4;
d' is 0, or an integer having a value of 1, 2, or 3;
d" is 0, or an integer having a value of 1, 2, or 3;
e is 0, or is an integer having a value of 1, 2, 3, or 4;
e' is 0, or an integer having a value of 1, 2, or 3;
e" is 0, or an integer having a value of 1, 2, or 3;
f is 0, or is an integer having a value of 1, 2, or 3;
d+e is 2, 3, 4, 5, or 6;
d'+e"=d
e'+e"=m Suitably, $R_{7'}$, $R_{77}$ and $R_{77''}$ are each independently selected from hydrogen, $C_{1-6}$ alkyl-group, $C_{2-6}$ alkenyl-group, $C_{4-6}$ cycloalkyl-$C_{0-6}$ alkyl-group, $N(C_{0-4}$ alkyl)$(C_{0-4}$ alkyl)-C1-4 alkyl-N$(C_{0-4}$alkyl)-group, —N$(C_{0-4}$ alkyl)$(C_{0-4}$ alkyl) group, $C_{1-3}$ alkyl-CO—$C_{0-4}$ alkyl-group, $C_{0-6}$ alkyl-O—C(O)—$C_{0-4}$ alkyl-group, $C_{0-6}$ alkyl-C(O)—O—$C_{0-4}$alkyl-group, N$(C_{0-4}$ alkyl)$(C_{0-4}$ alkyl)-$(C_{0-4}$ alkyl)C(O)$(C_{0-4}$ alkyl)-group, phenyl-$C_{0-4}$ alkyl-group, pyridyl-$C_{0-4}$ alkyl-group, pyrimidinyl-$C_{0-4}$ alkyl-group, pyrazinyl-$C_{0-4}$ alkyl-group, thiophenyl-$C_{0-4}$ alkyl-group, pyrazolyl-$C_{0-4}$ alkyl-group, imidazolyl-$C_{0-4}$ alkyl-group, triazolyl-$C_{0-4}$ alkyl-group, azetidinyl-$C_{0-4}$ alkyl-group, pyrrolidinyl-$C_{0-4}$ alkyl-group, isoquinolinyl-$C_{0-4}$alkyl-group, indanyl-$C_{0-4}$ alkyl-group, benzothiazolyl-$C_{0-4}$ alkyl-group, any of the groups optionally substituted with 1-6 substituents, each substituent independently being —OH, —N$(C_{0-4}$ alkyl)$(C_{0-4}$alkyl), $C_{1-4}$alkyl, $C_{1-6}$ alkoxyl, $C_{1-6}$ alkyl-CO—$C_{0-4}$ alkyl-, pyrrolidinyl-$C_{0-4}$ alkyl-, or halogen; or $R_{7'}$ together with a bond from an absent ring hydrogen is =O.

Suitably, B is —$C_{1-6}$alkyl-, —$C_{0-3}$ alkyl-O—$C_{0-3}$alkyl-, —$C_{0-3}$ alkyl-NH—$C_{0-3}$alkyl-, —$C_{0-3}$alkyl-NH—$C_{3-7}$cycloalkyl-, —$C_{0-3}$alkyl-N$(C_{0-3}$alkyl)-C(O)—$C_{0-3}$ alkyl-, —$C_{0-3}$ alkyl-NH—$SO_2$—$C_{0-3}$ alkyl-, —$C_{0-3}$ alkyl-, —$C_{0-3}$alkyl-S—$C_{0-3}$ alkyl-, —$C_{0-3}$ alkyl-$SO_2$—$C_{0-3}$alkyl-, —$C_{0-3}$alkyl-PH—$C_{0-3}$ alkyl-, $C_{0-3}$ alkyl—C(O)—$C_{0-3}$ alkyl, or a direct bond.

Suitably, $E_1$ is CH, N, or $CR_{66}$; or B and $E_1$ together form a double bond, i.e., —CH=C.

Suitably, $E_2$ is $CH_2$, $CHR_{77}$, $C(OH)R_{77}$NH, $NR_{77}$, O, S, —S(O)—, or —S(O)$_2$—.

Suitably, $R_{66}$ is independently selected from at each occurrence from halogen, $C_{0-4}$ alkyl, —C(O)—O$(C_{0-4}$ alkyl), or —C(O)—N$(C_{0-4}$ alkyl)-$(C_{0-4}$ alkyl).

In an alternative embodiment of this invention, Non-Ary Cyc is:

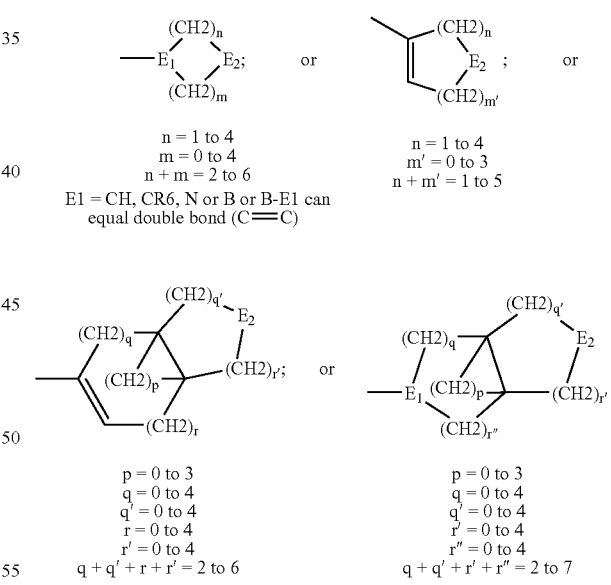

In another embodiment of the present invention, the compounds of Formula(s) (I) and (Ia), (II) and (IIa), (III) and (IIIa), (IV) and (IVa), (V) and (Va), (VI), (VIa-VIi), (VIII), (VIIIa), (IX), (IXa), (A), (A1), (B), and (B1), may also include for the X term, the X moieties as disclosed in WO 2004/073628, published September 2004, Boehm et al., whose disclosure is incorporated by reference herein.

In another embodiment of the present invention, compounds of Formula (II) and (IIa) are represented by the structure:

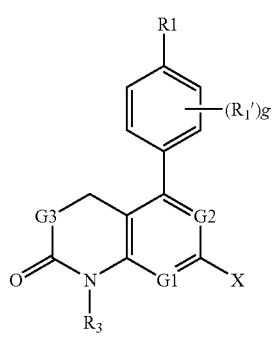

(II)

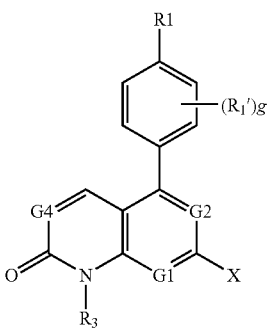

(IIa)

wherein
$G_1$ and $G_2$ are nitrogen:
$G_3$ is $CH_2$;
$G_4$ is CH;
$R_1$ is $C(Z)N(R_{10'})(CR_{10}R_{20})_vR_b$, $C(Z)O(CR_{10}R_{20})_vR_b$, $N(R_{10'})C(Z)(CR_{10}R_{20})_vR_b$, $N(R_{10'})C(Z)N(R_{10'})(CR_{10}R_{20})_vR_b$, or $N(R_{10'})OC(Z)(CR_{10}R_{20})_vR_b$;
$R_{1'}$ is independently selected at each occurrence from halogen, $C_{1-4}$ alkyl, halo-substituted-$C_{1-4}$ alkyl, cyano, nitro, $(CR_{10}R_{20})_vNR_dR_{d'}$, $(CR_{10}R_{20})_vC(O)R_{12}$, $SR_5$, $S(O)R_5$, $S(O)_2R_5$, or $(CR_{10}R_{20})_vOR_{13}$;
$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;
X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_{2'})(R_{2''})$, or $N(R_{10'})R_hNH—C(=N—CN)NRqRq'$;
$X_1$ is $N(R_{11})$, O, $S(O)_m$, or $CR_{10}R_{20}$;
$R_h$ is selected from an optionally substituted $C_{1-10}$ alkyl, $—CH_2—C(O)—CH_2—$, $—CH_2—CH_2—O—CH_2—CH_2—$, $—CH_2—C(O)N(R_{10'})CH_2—CH_2—$, $—CH_2—N(R_{10'})C(O)CH_2—$, $—CH_2—CH(OR_{10'})—CH_2—$, $—CH_2—C(O)O—CH_2—CH_2—$, or $—CH_2—CH_2—O—C(O)CH_2—$;
$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or
$R_2$ is the moiety $(CR_{10}R_{20})_qX_1(CR_{10}R_{20})_qC(A_1)(A_2)(A_3)$, or $(CR_{10}R_{20})_qC(A_1)(A_2)(A_3)$;
$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;
$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally; or wherein $R_{2''}$ is the moiety $(CR_{10}R_{20})_rX_1(CR_{10}R_{20})_qC(A_1)(A_2)(A_3)$;
$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;
$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;
$A_3$ is hydrogen or is an optionally substituted $C_{1-10}$ alkyl;
$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;
$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;
$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;
$R_5$ is independently selected at each occurrence from hydrogen, $C_{1-4}$ alkyl, $C_{2-4}$ alkenyl, $C_{2-4}$ alkynyl or $NR_4R_{14'}$, excluding the moieties $SR_5$ being $SNR_4R_{14'}$, $S(O)_2R_5$ being $SO_2H$ and $S(O)R_5$ being SOH;
$R_{9'}$ is independently selected at each occurrence from hydrogen, or $C_{1-4}$ alkyl;
$R_{10}$ and $R_{20}$ are independently selected at each occurrence from hydrogen or $C_{1-4}$alkyl;
$R_{10'}$ is independently selected at each occurrence from hydrogen or $C_{1-4}$alkyl;
$R_{11}$ is independently selected at each occurrence from hydrogen or $C_{1-4}$alkyl;
$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;
$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

Another aspect of the invention are compounds of the formula:

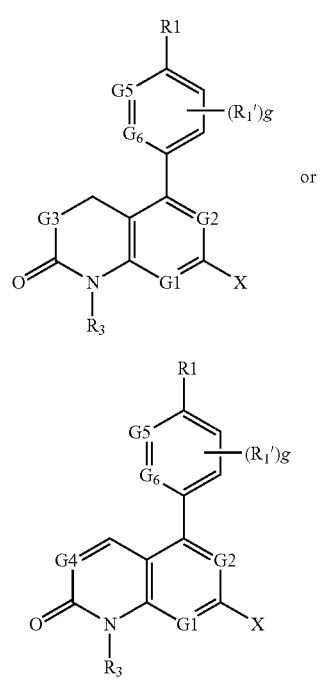

wherein
$G_1$ and $G_2$ are nitrogen:
$G_3$ is $CH_2$;
$G_4$ is CH;
$G_5$ and $G_6$ are independently selected from nitrogen or CH;
$R_1$ is $C(Z)N(R_{10'})(CR_{10}R_{20})_{v'}R_b$, $C(Z)O(CR_{10}R_{20})_{v'}R_b$, $N(R_{10'})C(Z)(CR_{10}R_{20})_{v'}R_b$, $N(R_{10'})C(Z)N(R_{10'})(CR_{10}R_{20})_{v'}R_b$, or $N(R_{10'})OC(Z)(CR_{10}R_{20})_{v'}R_b$;

$R_{1'}$ is independently selected at each occurrence from halogen, $C_{1-4}$ alkyl, halo-substituted-$C_{1-4}$ alkyl, cyano, nitro, $(CR_{10}R_{20})_{v'}NR_dR_{d'}$, $(CR_{10}R_{20})_{v'}C(O)R_{12}$, $SR_5$, $S(O)R_5$, $S(O)_2R_5$, or $(CR_{10}R_{20})_{v'}OR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_{2'})(R_{2''})$, or $N(R_{10'})R_hNH—C(=N—CN)NRqRq'$;

$X_1$ is $N(R_{11})$, O, $S(O)_m$, or $CR_{10}R_{20}$;

$R_h$ is selected from an optionally substituted $C_{1-10}$ alkyl, $—CH_2—C(O)—CH_2—$, $—CH_2—CH_2—O—CH_2—CH_2—$, $—CH_2—C(O)N(R_{10'})CH_2—CH_2—$, $—CH_2—N(R_{10'})C(O)CH_2—$, $—CH_2—CH(OR_{10'})—CH_2—$, $—CH_2—C(O)O—CH_2—CH_2—$, or $—CH_2—CH_2—O—C(O)CH_2—$;

$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_qX_1(CR_{10}R_{20})_qC(A_1)(A_2)(A_3)$, or $(CR_{10}R_{20})_qC(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally; or wherein $R_{2''}$ is the moiety $(CR_{10}R_{20})_rX_1(CR_{10}R_{20})_qC(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_5$ is independently selected at each occurrence from hydrogen, $C_{1-4}$ alkyl, $C_{2-4}$ alkenyl, $C_{2-4}$ alkynyl or $NR_{4'}R_{14'}$, excluding the moieties $SR_5$ being $SNR_{4'}R_{14'}$, $S(O)_2R_5$ being $SO_2H$ and $S(O)R_5$ being $SOH$;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$ alkyl;

$R_{10'}$ is independently selected at each occurrence from hydrogen or $C_{1-4}$ alkyl;

$R_{11}$ is independently selected at each occurrence from hydrogen or $C_{1-4}$ alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

It should be recognized that the difference between compounds of Formula (I) and (Ia), and Formula (II) and (IIa) and those of Formulas (III) and (IIIa) through Formula (V) and (Va) lie not only in the in the ring substitution of the $R_1$ group, but the ring positions of the nitrogen in the pyridyl ring, e.g. the G5 and G6 variables. All of the remaining variables have the same meaning for Formulas (III) and (IIIa) through Formula (V) and (Va) as those described herein for Formula (I) and (Ia), etc.

Another aspect of the invention are compounds of the formula:

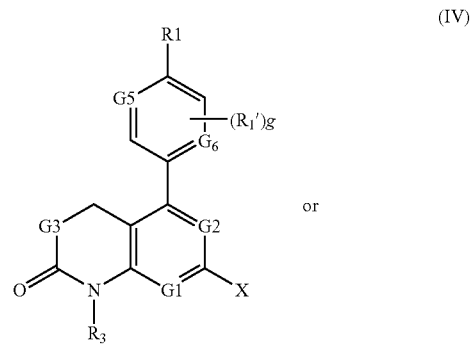

(IV)

or

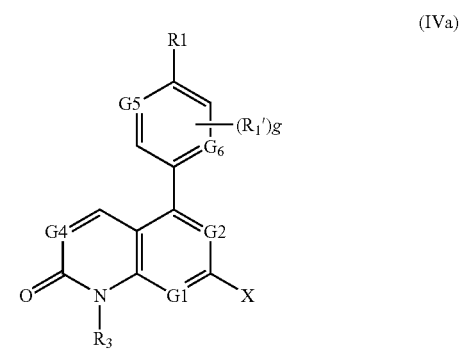

(IVa)

$G_1$ and $G_2$ are nitrogen:

$G_3$ is $CH_2$;

$G_4$ is CH;

$G_5$ and $G_6$ are independently selected from nitrogen or CH;

$R_1$ is $C(Z)N(R_{10'})(CR_{10}R_{20})_{v'}R_b$, $C(Z)O(CR_{10}R_{20})_{v'}R_b$, $N(R_{10'})C(Z)(CR_{10}R_{20})_{v'}R_b$, $N(R_{10'})C(Z)N(R_{10'})(CR_{10}R_{20})_{v'}R_b$, or $N(R_{10'})OC(Z)(CR_{10}R_{20})_{v'}R_b$;

$R_{1'}$ is independently selected at each occurrence from halogen, $C_{1-4}$ alkyl, halo-substituted-$C_{1-4}$ alkyl, cyano, nitro, $(CR_{10}R_{20})_{v'}NR_dR_{d'}$, $(CR_{10}R_{20})_{v'}C(O)R_{12}$, $SR_5$, $S(O)R_5$, $S(O)_2R_5$, or $(CR_{10}R_{20})_{v'}OR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_{2'})(R_{2''})$, or $N(R_{10'})R_hNH-C(=N-CN)NR_qR_{q'}$;

$X_1$ is $N(R_{11})$, O, $S(O)_m$, or $CR_{10}R_{20}$;

$R_h$ is selected from an optionally substituted $C_{1-10}$ alkyl, $-CH_2-C(O)-CH_2-$, $-CH_2-CH_2-O-CH_2-CH_2-$, $-CH_2-C(O)N(R_{10'})CH_2-CH_2-$, $-CH_2-N(R_{10'})C(O)CH_2-$, $-CH_2-CH(OR_{10'})-CH_2-$, $-CH_2-C(O)O-CH_2-CH_2-$, or $-CH_2-CH_2-O-C(O)CH_2-$;

$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_q X_1 (CR_{10}R_{20})_q C(A_1)(A_2)(A_3)$, or $(CR_{10}R_{20})_q C(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally; or wherein $R_{2''}$ is the moiety $(CR_{10}R_{20})_t X_1 (CR_{10}R_{20})_q C(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_4$ and $R_{14'}$ together with the nitrogen to which they are attached form a heterocyclic ring of 5 to 7 members, which ring optionally contains an additional heteroatom selected from $NR_9$;

$R_5$ is independently selected at each occurrence from hydrogen, $C_{1-4}$ alkyl, $C_{2-4}$ alkenyl, $C_{2-4}$ alkynyl or $NR_{4'}R_{14'}$, excluding the moieties $SR_5$ being $SNR_4R_{14'}$, $S(O)_2R_5$ being $SO_2H$ and $S(O)R_5$ being $SOH$;

$R_9$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

Representative examples of Formula (IV) and (IVa) are:

4-[2-{[3-(diethylamino)propyl]amino}-8-(2,6-difluorophenyl)-7-oxo-7,8-dihydropyrido[2,3-d]pyrimidin-4-yl]benzoic acid 4-[2-{[3-(diethylamino)propyl]amino}-8-(2,6-difluorophenyl)-7-oxo-7,8-dihydropyrido[2,3-d]pyrimidin-4-yl]-N-propylbenzamide 4-[2-{[3-(diethylamino)propyl]amino}-8-(2,6-difluorophenyl)-7-oxo-7,8-dihydropyrido[2,3-d]pyrimidin-4-yl]-N-(1-methylethyl)benzamide N-cyclopropyl-4-[2-{[3-(diethylamino)propyl]amino}-8-(2,6-difluorophenyl)-7-oxo-7,8-dihydropyrido[2,3-d]pyrimidin-4-yl]benzamide 4-[2-{[3-(diethylamino)propyl]amino}-8-(2,6-difluorophenyl)-7-oxo-7,8-dihydropyrido[2,3-d]pyrimidin-4-yl]-N-(4-fluorophenyl)benzamide 4-[2-{[3-(diethylamino)propyl]amino}-8-(2,6-difluorophenyl)-7-oxo-7,8-dihydropyrido[2,3-d]pyrimidin-4-yl]-N-1,3-thiazol-2-ylbenzamide Another aspect of the invention are compounds of the formula:

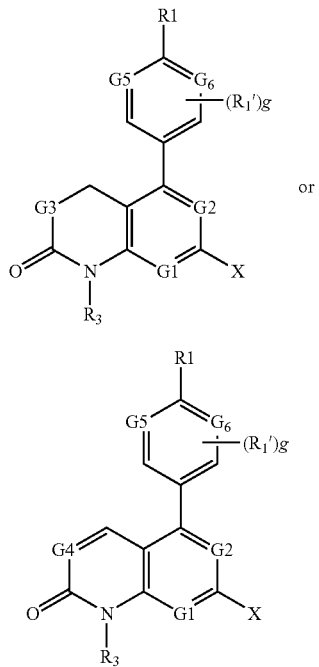

(V)

(Va)

wherein
G$_1$ and G$_2$ are independently selected from nitrogen or carbon:
G$_3$ is CH$_2$;
G$_4$ is CH;
G$_5$ and G$_6$ are nitrogen and CH, provided that only one of G5 or G6 is nitrogen and the other is CH;
R$_1$ is C(Z)N(R$_{10'}$)(CR$_{10}$R$_{20}$)$_v$R$_b$, C(Z)O(CR$_{10}$R$_{20}$)$_v$R$_b$, N(R$_{10'}$)C(Z)(CR$_{10}$R$_{20}$)$_v$R$_b$, N(R$_{10}$)C(Z)N(R$_{10}$) (CR$_{10}$R$_{20}$)$_v$R$_b$, or N(R$_{10'}$)OC(Z)(CR$_{10}$R$_{20}$)$_v$R$_b$;
R$_{1'}$ is independently selected at each occurrence from halogen, C$_{1-4}$ alkyl, halo-substituted-C$_{1-4}$ alkyl, cyano, nitro, (CR$_{10}$R$_{20}$)$_v$NR$_d$R$_{d'}$, (CR$_{10}$R$_{20}$)$_v$C(O)R$_{12}$, SR$_5$, S(O)R$_5$, S(O)$_2$R$_5$, or (CR$_{10}$R$_{20}$)$_v$OR$_{13}$;
R$_b$ is hydrogen, C$_{1-10}$ alkyl, C$_{3-7}$ cycloalkyl, C$_{3-7}$ cycloalkyl C$_{1-10}$, aryl, arylC$_{1-10}$alkyl, heteroaryl, heteroarylC$_{1-10}$ alkyl, heterocyclic, or heterocyclylC$_{1-10}$ alkyl moiety, which moieties, excluding hydrogen, may all be optionally substituted;
X is R$_2$, OR$_{2'}$, S(O)$_m$R$_{2'}$, (CH$_2$)$_n$N(R$_{10'}$)S(O)$_m$R$_{2'}$, (CH$_2$)$_n$N (R$_{10'}$)C(O)R$_{2'}$, (CH$_2$)$_n$NR$_4$R$_{14}$, (CH$_2$)$_n$N(R$_{2'}$)(R$_{2''}$), or N(R$_{10'}$)R$_h$NH—C(=N—CN)NRqRq';
X$_1$ is N(R$_{11}$), O, S(O)$_m$, or CR$_{10}$R$_{20}$;
R$_h$ is selected from an optionally substituted C$_{1-10}$ alkyl, —CH$_2$—C(O)—CH$_2$—, —CH$_2$—CH$_2$—O—CH$_2$—CH$_2$—, —CH$_2$—C(O)N(R$_{10'}$)CH$_2$—CH$_2$—, —CH$_2$—N(R$_{10'}$)C(O)CH$_2$—, —CH$_2$—CH(OR$_{10'}$)—CH$_2$—, —CH$_2$—C(O)O—CH$_2$—CH$_2$—, or —CH$_2$—CH$_2$—O—C(O)CH$_2$—;
R$_q$ and R$_{q'}$ are independently selected at each occurrence from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, wherein all of the moieties except for hydrogen, are optionally substituted, or R$_q$ and R$_{q'}$ together with the nitrogen to which they are attached form an optionally substituted heterocyclic ring of 5 to 7 members, which ring may contain an additional heteroatom selected from oxygen, nitrogen or sulfur;
R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted; or
R$_2$ is the moiety (CR$_{10}$R$_{20}$)$_q$X$_1$(CR$_{10}$R$_{20}$)$_q$C(A$_1$)(A$_2$) (A$_3$), or (CR$_{10}$R$_{20}$)$_q$C(A$_1$)(A$_2$)(A$_3$);
R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted;
R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein these moieties, excluding hydrogen, may be optionally; or wherein R$_{2''}$ is the moiety (CR$_{10}$R$_{20}$)$_r$X$_1$ (CR$_{10}$R$_{20}$)$_q$C(A$_1$)(A$_2$)(A$_3$);
A$_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A$_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A$_3$ is hydrogen or is an optionally substituted C$_{1-10}$ alkyl;
R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;
R$_4$ and R$_{14}$ are each independently selected at each occurrence from hydrogen, C$_{1-4}$ alkyl, C$_{3-7}$ cycloalkyl, C$_{3-7}$ cycloalkylC$_{1-4}$alkyl, aryl, aryl-C$_{1-4}$ alkyl, heterocyclic, heterocyclic C$_{1-4}$ alkyl, heteroaryl or a heteroaryl C$_{1-4}$ alkyl moiety, and wherein each of these moieties, excluding hydrogen, may be optionally substituted; or the R$_4$ and R$_{14}$ together with the nitrogen which they are attached form an optionally substituted heterocyclic ring of 4 to 7 members, which ring optionally contains an additional heteroatom selected from oxygen, sulfur or nitrogen;
R$_{4'}$ and R$_{14'}$ are each independently selected at each occurrence from hydrogen or C$_{1-4}$ alkyl, or R$_{4'}$ and R$_{14'}$ together with the nitrogen to which they are attached form a heterocyclic ring of 5 to 7 members, which ring optionally contains an additional heteroatom selected from NR$_{9'}$;
R$_5$ is independently selected at each occurrence from hydrogen, C$_{1-4}$ alkyl, C$_{2-4}$ alkenyl, C$_{2-4}$ alkynyl or NR$_{4'}$R$_{14'}$, excluding the moieties SR$_5$ being SNR$_{4'}$R$_{14'}$, S(O)$_2$R$_5$ being SO$_2$H and S(O)R$_5$ being SOH;
R$_{9'}$ is independently selected at each occurrence from hydrogen, or C$_{1-4}$ alkyl;
R$_{10}$ and R$_{20}$ are independently selected at each occurrence from hydrogen or C$_{1-4}$alkyl;
R$_{10'}$ is independently selected at each occurrence from hydrogen or C$_{1-4}$alkyl;
R$_{11}$ is independently selected at each occurrence from hydrogen or C$_{1-4}$alkyl;
R$_{12}$ is independently selected at each occurrence from hydrogen, C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{3-7}$cycloalkylC$_{1-4}$ alkyl, C$_{5-7}$ cycloalkenyl, C$_{5-7}$cycloalkenyl C$_{1-4}$ alkyl, aryl, arylC$_{1-4}$ alkyl, heteroaryl, heteroarylC$_{1-4}$ alkyl, heterocyclyl, or a heterocyclylC$_{1-4}$ alkyl moiety, and wherein each of these moieties, excluding hydrogen, may be optionally substituted;

R$_{13}$ is independently selected at each occurrence from hydrogen, C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{3-7}$cycloalkylC$_{1-4}$ alkyl, C$_{5-7}$ cycloalkenyl, C$_{5-7}$cycloalkenyl C$_{1-4}$ alkyl, aryl, arylC$_{1-4}$ alkyl, heteroaryl, heteroarylC$_{1-4}$ alkyl, heterocyclyl, or a heterocyclylC$_{1-4}$ alkyl moiety, and wherein each of these moieties, excluding hydrogen, may be optionally substituted;

R$_d$ and R$_{d'}$ are each independently selected from hydrogen, C$_{1-4}$ alkyl, C$_{3-6}$ cycloalkyl, C$_{3-6}$ cycloalkylC$_{1-4}$alkyl moiety, and wherein each of these moieties, excluding hydrogen, may be optionally substituted; or R$_d$ and R$_{d'}$ together with the nitrogen which they are attached form an optionally substituted heterocyclic ring of 5 to 6 members, which ring optionally contains an additional heteroatom selected from oxygen, sulfur or NR$_9$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

Another aspect of the invention are compounds of the formula:

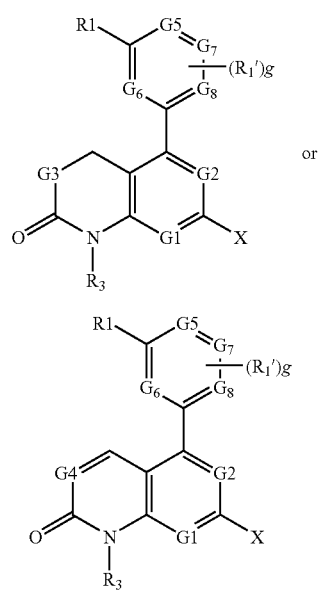

wherein
G$_1$ and G$_2$ are independently selected from nitrogen or CH:
G$_3$ is CH$_2$;
G$_4$ is CH;
one of G5, G6, G7 and G8 is nitrogen and the others are CH;

R$_1$ is C(Z)N(R$_{10'}$)(CR$_{10}$R$_{20}$)$_v$R$_b$, C(Z)O(CR$_{10}$R$_{20}$)$_v$R$_b$, N(R$_{10'}$)C(Z)(CR$_{10}$R$_{20}$)$_v$R$_b$, N(R$_{10'}$)C(Z)N(R$_{10'}$)(CR$_{10}$R$_{20}$)$_v$R$_b$, or N(R$_{10'}$)OC(Z)(CR$_{10}$R$_{20}$)$_v$R$_b$;

R$_{1'}$ is independently selected at each occurrence from halogen, C$_{1-4}$ alkyl, halo-substituted-C$_{1-4}$ alkyl, cyano, nitro, (CR$_{10}$R$_{20}$)$_{v'}$NR$_d$R$_{d'}$, (CR$_{10}$R$_{20}$)$_{v'}$C(O)R$_{12}$, SR$_5$, S(O)R$_5$, S(O)$_2$R$_5$, or (CR$_{10}$R$_{20}$)$_{v'}$OR$_{13}$;

R$_b$ is hydrogen, C$_{1-10}$ alkyl, C$_{3-7}$ cycloalkyl, C$_{3-7}$ cycloalkyl C$_{1-10}$ alkyl, aryl, arylC$_{1-10}$alkyl, heteroaryl, heteroarylC$_{1-10}$ alkyl, heterocyclic, or heterocyclylC$_{1-10}$ alkyl moiety, which moieties, excluding hydrogen, may all be optionally substituted;

X is R$_2$, OR$_{2'}$, S(O)$_m$R$_{2'}$, (CH$_2$)$_n$N(R$_{10'}$)S(O)$_m$R$_{2'}$, (CH$_2$)$_n$N(R$_{10'}$)C(O)R$_{2'}$, (CH$_2$)$_n$NR$_4$R$_{14}$, (CH$_2$)$_n$N(R$_{2'}$)(R$_{2''}$), or N(R$_{10'}$)R$_h$NH—C(=N—CN)NRqRq';

X$_1$ is N(R$_{11}$) O, S(O)$_m$, or CR$_{10}$R$_{20}$;

R$_h$ is selected from an optionally substituted C$_{1-10}$ alkyl, —CH$_2$—C(O)—CH$_2$—, —CH$_2$—CH$_2$—O—CH$_2$—CH$_2$—, —CH$_2$—C(O)N(R$_{10'}$)CH$_2$—CH$_2$—, —CH$_2$—N(R$_{10'}$)C(O)CH$_2$—, —CH$_2$—CH(OR$_{10'}$)—CH$_2$—, —CH$_2$—C(O)O—CH$_2$—CH$_2$—, or —CH$_2$—CH$_2$—O—C(O)CH$_2$—;

R$_q$ and R$_{q'}$ are independently selected at each occurrence from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, wherein all of the moieties except for hydrogen, are optionally substituted, or R$_q$ and R$_{q'}$ together with the nitrogen to which they are attached form an optionally substituted heterocyclic ring of 5 to 7 members, which ring may contain an additional heteroatom selected from oxygen, nitrogen or sulfur;

R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted; or
R$_2$ is the moiety (CR$_{10}$R$_{20}$)$_q$X$_1$(CR$_{10}$R$_{20}$)$_q$C(A$_1$)(A$_2$)(A$_3$), or (CR$_{10}$R$_{20}$)$_q$C(A$_1$)(A$_2$)(A$_3$);

R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted;

R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein these moieties, excluding hydrogen, may be optionally; or wherein R$_{2''}$ is the moiety (CR$_{10}$R$_{20}$)$_t$X$_1$(CR$_{10}$R$_{20}$)$_q$C(A$_1$)(A$_2$)(A$_3$);

A$_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;

A$_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;

A$_3$ is hydrogen or is an optionally substituted C$_{1-10}$ alkyl;

R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;

R$_4$ and R$_{14}$ are each independently selected at each occurrence from hydrogen, C$_{1-4}$ alkyl, C$_{3-7}$ cycloalkyl, C$_{3-7}$ cycloalkylC$_{1-4}$alkyl, aryl, aryl-C$_{1-4}$ alkyl, heterocyclic, heterocyclic C$_{1-4}$ alkyl, heteroaryl or a heteroaryl C$_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_5$ is independently selected at each occurrence from hydrogen, $C_{1-4}$ alkyl, $C_{2-4}$ alkenyl, $C_{2-4}$ alkynyl or $NR_{4'}R_{14'}$, excluding the moieties $SR_5$ being $SNR_{4'}R_{14'}$, $S(O)_2R_5$ being $SO_2H$ and $S(O)R_5$ being SOH;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is 0 or an integer having a value of 1 or 2;

Z is independently selected at each occurrence from oxygen or sulfur; and a pharmaceutically acceptable salt, solvate or physiologically functional derivative thereof.

It should be recognized that the difference between compounds of Formula (I) and (Ia), and Formula (II) and (IIa) and those of Formulas (VII) through Formula (VIi) lie not only in the in the ring substitution of the RI group, but that the ring position of the two nitrogen's in the pyrimidine ring. All of the remaining variables have the same meaning for Formulas (VI) through Formula (VIi) as those described herein for Formula (I) and (Ia), etc.

Another aspect of the invention are compounds of the formula:

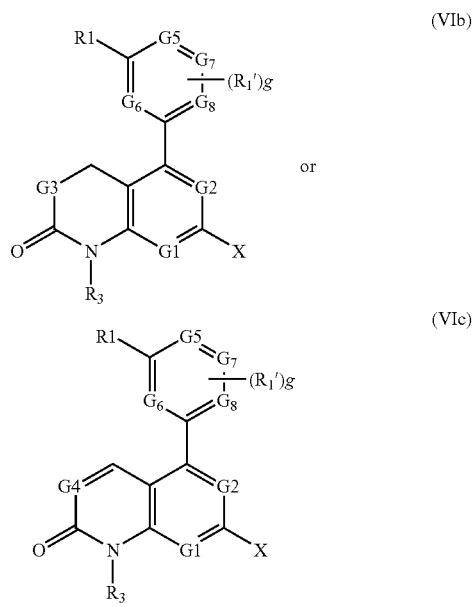

wherein $G_1$ and $G_2$ are nitrogen:

$G_3$ is $CH_2$;

$G_4$ is CH;

G5 and G6 are nitrogen; and

G7 and G8 are CH;

$R_1$ is $C(Z)N(R_{10'})(CR_{10}R_{20})_v R_b$, $C(Z)O(CR_{10}R_{20})_v R_b$, $N(R_{10'})C(Z)(CR_{10}R_{20})_v R_b$, $N(R_{10'})C(Z)N(R_{10'})(CR_{10}R_{20})_v R_b$, or $N(R_{10'})OC(Z)(CR_{10}R_{20})_v R_b$;

$R_{1'}$ is independently selected at each occurrence from halogen, $C_{1-4}$ alkyl, halo-substituted-$C_{1-4}$ alkyl, cyano, nitro, $(CR_{10}R_{20})_v NR_d R_{d'}$, $(CR_{10}R_{20})_v C(O)R_{12}$, $SR_5$, $S(O)R_5$, $S(O)_2R_5$, or $(CR_{10}R_{20})_v OR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_m R_{2'}$, $(CH_2)_n N(R_{10'})S(O)_m R_{2'}$, $(CH_2)_n N(R_{10'})C(O)R_{2'}$, $(CH_2)_n NR_4R_{14}$, $(CH_2)_n N(R_{2'})(R_{2''})$, or $N(R_{10'})R_h NH-C(=N-CN)NRqRq'$;

$X_1$ is $N(R_{11})$, O, $S(O)_m$, or $CR_{10}R_{20}$;

$R_h$ is selected from an optionally substituted $C_{1-10}$ alkyl, $-CH_2-C(O)-CH_2-$, $-CH_2-CH_2-O-CH_2-CH_2-$, $-CH_2-C(O)N(R_{10'})CH_2-CH_2-$, $-CH_2-N(R_{10'})C(O)CH_2-$, $-CH_2-CH(OR_{10'})-CH_2-$, $-CH_2-C(O)O-CH_2-CH_2-$, or $-CH_2-CH_2-O-C(O)CH_2-$;

$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_q X_1 (CR_{10}R_{20})_q C(A_1)(A_2)(A_3)$, or $(CR_{10}R_{20})_q C(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally; or wherein $R_{2''}$ is the moiety $(CR_{10}R_{20})_t X_1 (CR_{10}R_{20})_q C(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_5$ is independently selected at each occurrence from hydrogen, $C_{1-4}$ alkyl, $C_{2-4}$ alkenyl, $C_{2-4}$ alkynyl or $NR_4R_{14'}$, excluding the moieties $SR_5$ being $SNR_4R_{14'}$, $S(O)_2R_5$ being $SO_2H$ and $S(O)R_5$ being SOH;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

Another aspect of the invention are compounds of the formula:

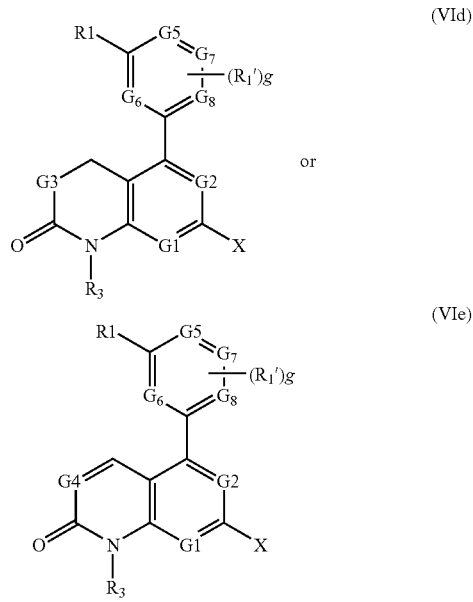

wherein
G$_1$ and G$_2$ are independently selected from nitrogen or CH:
G$_3$ is CH$_2$;
G$_4$ is CH;
G6 and G8 are nitrogen; and G5 and G7 are CH;

$R_1$ is $C(Z)N(R_{10'})(CR_{10}R_{20})_vR_b$, $C(Z)O(CR_{10}R_{20})_vR_b$, $N(R_{10'})C(Z)(CR_{10}R_{20})_vR_b$, $N(R_{10'})C(Z)N(R_{10'})(CR_{10}R_{20})_vR_b$, or $N(R_{10'})OC(Z)(CR_{10}R_{20})_vR_b$;

$R_{1'}$ is independently selected at each occurrence from halogen, $C_{1-4}$ alkyl, halo-substituted-$C_{1-4}$ alkyl, cyano, nitro, $(CR_{10}R_{20})_vNR_dR_{d'}$, $(CR_{10}R_{20})_vC(O)R_{12}$, $SR_5$, $S(O)R_5$, $S(O)_2R_5$, or $(CR_{10}R_{20})_vOR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_2)(R_{2''})$, or $N(R_{10'})R_hNH-C(=N-CN)NRqRq'$;

$X_1$ is $N(R_{11})$, O, $S(O)_m$, or $CR_{10}R_{20}$;

$R_h$ is selected from an optionally substituted $C_{1-10}$ alkyl, $-CH_2-C(O)-CH_2-$, $-CH_2-CH_2-O-CH_2-CH_2-$, $-CH_2-C(O)N(R_{10'})CH_2-CH_2-$, $-CH_2-N(R_{10'})C(O)CH_2-$, $-CH_2-CH(OR_{10'})-CH_2-$, $-CH_2-C(O)O-CH_2-CH_2-$, or $-CH_2-CH_2-O-C(O)CH_2-$;

$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_qX_1(CR_{10}R_{20})_qC(A_1)(A_2)(A_3)$, or $(CR_{10}R_{20})_qC(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally; or wherein $R_{2''}$ is the moiety $(CR_{10}R_{20})_tX_1(CR_{10}R_{20})_qC(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_5$ is independently selected at each occurrence from hydrogen, $C_{1-4}$ alkyl, $C_{2-4}$ alkenyl, $C_{2-4}$ alkynyl or $NR_4R_{14'}$, excluding the moieties $SR_5$ being $SNR_4R_{14'}$, $S(O)_2R_5$ being $SO_2H$ and $S(O)R_5$ being SOH;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

Another aspect of the invention are compounds of the formula:

(VIf)

(VIg)

wherein
G$_1$ and G$_2$ are nitrogen;
G$_3$ is CH$_2$;
G$_4$ is CH;
G5 and G8 are nitrogen;
G6 and G7 are CH;
R$_1$ is C(Z)N(R$_{10'}$)(CR$_{10}$R$_{20}$)$_v$R$_b$, C(Z)O(CR$_{10}$R$_{20}$)$_v$R$_b$, N(R$_{10'}$)C(Z)(CR$_{10}$R$_{20}$)$_v$R$_b$, N(R$_{10'}$)C(Z)N(R$_{10'}$)(CR$_{10}$R$_{20}$)$_v$R$_b$, or N(R$_{10'}$)OC(Z)(CR$_{10}$R$_{20}$)$_v$R$_b$;
R$_{1'}$ is independently selected at each occurrence from halogen, C$_{1-4}$ alkyl, halo-substituted-C$_{1-4}$ alkyl, cyano, nitro, (CR$_{10}$R$_{20}$)$_v$NR$_d$R$_{d'}$, (CR$_{10}$R$_{20}$)$_v$C(O)R$_{12}$, SR$_5$, S(O)R$_5$, S(O)$_2$R$_5$, or (CR$_{10}$R$_{20}$)$_v$OR$_{13}$;
R$_b$ is hydrogen, C$_{1-10}$ alkyl, C$_{3-7}$ cycloalkyl, C$_{3-7}$ cycloalkyl C$_{1-10}$ alkyl, aryl, arylC$_{1-10}$alkyl, heteroaryl, heteroarylC$_{1-10}$ alkyl, heterocyclic, or heterocyclylC$_{1-10}$ alkyl moiety, which moieties, excluding hydrogen, may all be optionally substituted;
X is R$_2$, OR$_{2'}$, S(O)$_m$R$_{2'}$, (CH$_2$)$_n$N(R$_{10'}$)S(O)$_m$R$_{2'}$, (CH$_2$)$_n$N(R$_{10'}$)C(O)R$_{2'}$, (CH$_2$)$_n$NR$_4$R$_{14}$, (CH$_2$)$_n$N(R$_{2'}$)(R$_{2''}$), or N(R$_{10'}$)R$_n$NH—C(=N—CN)NR$_q$R$_{q'}$;
X$_1$ is N(R$_{11}$), O, S(O)$_m$, or CR$_{10}$R$_{20}$;
R$_n$ is selected from an optionally substituted C$_{1-10}$ alkyl, —CH$_2$—C(O)—CH$_2$—, —CH$_2$—CH$_2$—O—CH$_2$—CH$_2$—, —CH$_2$—C(O)N(R$_{10'}$)CH$_2$—CH$_2$—, —CH$_2$—N(R$_{10'}$)C(O)CH$_2$—, —CH$_2$—CH(OR$_{10'}$)—CH$_2$—, —CH$_2$—C(O)O—CH$_2$—CH$_2$—, or —CH$_2$—CH$_2$—O—C(O)CH$_2$—;
R$_q$ and R$_{q'}$ are independently selected at each occurrence from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, wherein all of the moieties except for hydrogen, are optionally substituted, or R$_q$ and R$_{q'}$ together with the nitrogen to which they are attached form an optionally substituted heterocyclic ring of 5 to 7 members, which ring may contain an additional heteroatom selected from oxygen, nitrogen or sulfur;

R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted; or
R$_2$ is the moiety (CR$_{10}$R$_{20}$)$_q$X$_1$(CR$_{10}$R$_{20}$)$_q$C(A$_1$)(A$_2$)(A$_3$), or (CR$_{10}$R$_{20}$)$_q$C(A$_1$)(A$_2$)(A$_3$);
R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted;
R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein these moieties, excluding hydrogen, may be optionally; or wherein R$_{2''}$, is the moiety (CR$_{10}$R$_{20}$)$_r$X$_1$(CR$_{10}$R$_{20}$)$_q$C(A$_1$)(A$_2$)(A$_3$);
A$_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A$_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A$_3$ is hydrogen or is an optionally substituted C$_{1-10}$ alkyl;
R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;
R$_4$ and R$_{14}$ are each independently selected at each occurrence from hydrogen, C$_{1-4}$ alkyl, C$_{3-7}$ cycloalkyl, C$_{3-7}$ cycloalkylC$_{1-4}$alkyl, aryl, aryl-C$_{1-4}$ alkyl, heterocyclic, heterocyclic C$_{1-4}$ alkyl, heteroaryl or a heteroaryl C$_{1-4}$ alkyl moiety, and wherein each of these moieties, excluding hydrogen, may be optionally substituted; or the R$_4$ and R$_{14}$ together with the nitrogen which they are attached form an optionally substituted heterocyclic ring of 4 to 7 members, which ring optionally contains an additional heteroatom selected from oxygen, sulfur or nitrogen;
R$_{4'}$ and R$_{14'}$ are each independently selected at each occurrence from hydrogen or C$_{1-4}$ alkyl, or R$_{4'}$ and R$_{14'}$ together with the nitrogen to which they are attached form a heterocyclic ring of 5 to 7 members, which ring optionally contains an additional heteroatom selected from NR$_9$;
R$_5$ is independently selected at each occurrence from hydrogen, C$_{1-4}$ alkyl, C$_{2-4}$ alkenyl, C$_{2-4}$ alkynyl or NR$_4$R$_{14'}$, excluding the moieties SR$_5$ being SNR$_4$R$_{14'}$, S(O)$_2$R$_5$ being SO$_2$H and S(O)R$_5$ being SOH;
R$_9$ is independently selected at each occurrence from hydrogen, or C$_{1-4}$ alkyl;
R$_{10}$ and R$_{20}$ are independently selected at each occurrence from hydrogen or C$_{1-4}$alkyl;
R$_{10'}$ is independently selected at each occurrence from hydrogen or C$_{1-4}$alkyl;
R$_{11}$ is independently selected at each occurrence from hydrogen or C$_{1-4}$alkyl;
R$_{12}$ is independently selected at each occurrence from hydrogen, C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{3-7}$cycloalkylC$_{1-4}$ alkyl, C$_{5-7}$ cycloalkenyl, C$_{5-7}$cycloalkenyl C$_{1-4}$ alkyl, aryl, arylC$_{1-4}$ alkyl, heteroaryl, heteroarylC$_{1-4}$ alkyl, heterocyclyl, or a heterocyclylC$_{1-4}$ alkyl moiety, and wherein each of these moieties, excluding hydrogen, may be optionally substituted;
R$_{13}$ is independently selected at each occurrence from hydrogen, C$_{1-4}$ alkyl, halo-substituted C$_{1-4}$ alkyl, C$_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

Another aspect of the invention are compounds of the formula:

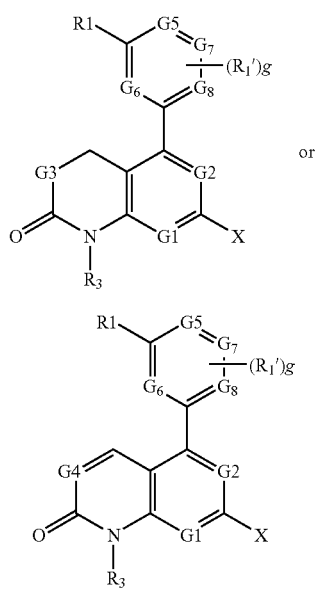

wherein
$G_1$ and $G_2$ are nitrogen;
$G_3$ is $CH_2$;
$G_4$ is CH;
G6 and G7 are nitrogen;
G5 and G8 are CH;
$R_1$ is $C(Z)N(R_{10'})(CR_{10}R_{20})_vR_b$, $C(Z)O(CR_{10}R_{20})_vR_b$, $N(R_{10'})C(Z)(CR_{10}R_{20})_vR_b$, $N(R_{10'})C(Z)N(R_{10'})(CR_{10}R_{20})_vR_b$, or $N(R_{10'})OC(Z)(CR_{10}R_{20})_vR_b$;

$R_{1'}$ is independently selected at each occurrence from halogen, $C_{1-4}$ alkyl, halo-substituted-$C_{1-4}$ alkyl, cyano, nitro, $(CR_{10}R_{20})_{v'}NR_dR_{d'}$, $(CR_{10}R_{20})_{v'}C(O)R_{12}$, $SR_5$, $S(O)R_5$, $S(O)_2R_5$, or $(CR_{10}R_{20})_{v'}OR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_{2'})(R_{2''})$, or $N(R_{10'})R_hNH—C(=N—CN)NRqRq'$;

$X_1$ is $N(R_{11})$, O, $S(O)_m$, or $CR_{10}R_{20}$;

$R_h$ is selected from an optionally substituted $C_{1-10}$ alkyl, $—CH_2—C(O)—CH_2—$, $—CH_2—CH_2—O—CH_2—CH_2—$, $—CH_2—C(O)N(R_{10'})CH_2—CH_2—$, $—CH_2—N(R_{10'})C(O)CH_2—$, $—CH_2—CH(OR_{10'})—CH_2—$, $—CH_2—C(O)O—CH_2—CH_2—$, or $—CH_2—CH_2—O—C(O)CH_2—$;

$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_qX_1(CR_{10}R_{20})_qC(A_1)(A_2)(A_3)$, or $(CR_{10}R_{20})_qC(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally; or wherein $R_{2''}$, is the moiety $(CR_{10}R_{20})_tX_1(CR_{10}R_{20})_qC(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_5$ is independently selected at each occurrence from hydrogen, $C_{1-4}$ alkyl, $C_{2-4}$ alkenyl, $C_{2-4}$ alkynyl or $NR_{4'}R_{14'}$, excluding the moieties $SR_5$ being $SNR_{4'}R_{14'}$, $S(O)_2R_5$ being $SO_2H$ and $S(O)R_5$ being $SOH$;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$ alkyl;

$R_{10'}$ is independently selected at each occurrence from hydrogen or $C_{1-4}$ alkyl;

$R_{11}$ is independently selected at each occurrence from hydrogen or $C_{1-4}$ alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is 0 or an integer having a value of 0 or an integer having a value of 1 or 2;

Z is independently selected at each occurrence from oxygen or sulfur; and a pharmaceutically acceptable salt, solvate or physiologically functional derivative thereof.

Another aspect of the invention are compounds of Formula (A) and (A1):

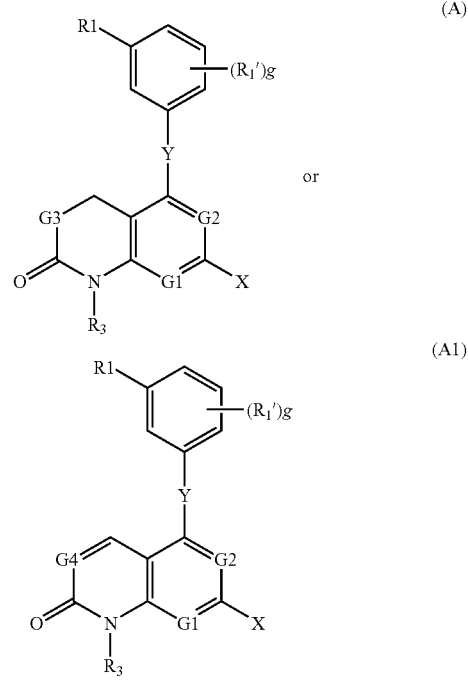

wherein $G_1$, and $G_2$ are independently nitrogen;

$G_3$ is $CH_2$;

$G_4$ is CH;

Y is $C(R_x)(R_z)$, $C(O)$, $N(R_z)$, $N(R_w)C(R_y)(R_z)$, oxygen, $OC(R_y)(R_z)$, $S(O)m$, or $S(O)_mC(R_y)(R_z)$;

$R_x$ is hydrogen, $C_{1-2}$ alkyl, $N(R_v)_2$, hydroxy, thio, $C_{1-2}$ alkoxy, or $S(O)_mC_{1-2}$alkyl;

$R_y$ is hydrogen or $C_{1-2}$ alkyl;

$R_{z'}$ is hydrogen or $C_{1-2}$ alkyl;

$R_w$ is hydrogen or $C_{1-2}$ alkyl;

$R_v$ is independently selected from hydrogen or $C_{1-2}$ alkyl;

$R_1$ is $C(Z)N(R_{10'})(CR_{10}R_{20})_vR_b$, $C(Z)O(CR_{10}R_{20})_vR_b$, $N(R_{10'})C(Z)(CR_{10}R_{20})_vR_b$, $N(R_{10'})C(Z)N(R_{10})(CR_{10}R_{20})_vR_b$, or $N(R_{10'})OC(Z)(CR_{10}R_{20})_vR_b$;

$R_{1'}$ is independently selected at each occurrence from halogen, $C_{1-4}$ alkyl, halo-substituted-$C_{1-4}$ alkyl, cyano, nitro, $(CR_{10}R_{20})_vNR_dR_{d'}$, $(CR_{10}R_{20})_vC(O)R_{12}$, $SR_5$, $S(O)R_5$, $S(O)_2R_5$, or $(CR_{10}R_{20})_vOR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_{2'})(R_{2''})$, or $N(R_{10'})R_hNH—C(=N—CN)NR_qR_{q'}$;

$X_1$ is $N(R_{11})$, O, $S(O)_m$, or $CR_{10}R_{20}$;

$R_h$ is selected from an optionally substituted $C_{1-10}$ alkyl, $—CH_2—C(O)—CH_2—$, $—CH_2—CH_2—O—CH_2—CH_2—$, $—CH_2—C(O)N(R_{10'})CH_2—CH_2—$, $—CH_2—N(R_{10'})C(O)CH_2—$, $—CH_2—CH(OR_{10'})—CH_2—$, $—CH_2—C(O)O—CH_2—CH_2—$, or $—CH_2—CH_2—O—C(O)CH_2—$;

$R_q$ and $R_{q'}$ are independently selected at each occurrence from hydrogen, $C_{1-10}$ alkyl, $C_{3-7}$cycloalkyl, $C_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, wherein all of the moieties except for hydrogen, are optionally substituted, or R$_q$ and R$_{q'}$ together with the nitrogen to which they are attached form an optionally substituted heterocyclic ring of 5 to 7 members, which ring may contain an additional heteroatom selected from oxygen, nitrogen or sulfur;

R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted; or R$_2$ is the moiety (CR$_{10}$R$_{20}$)$_q$X$_1$(CR$_{10}$R$_{20}$)$_q$C(A$_1$)(A$_2$)(A$_3$), or (CR$_{10}$R$_{20}$)$_q$C(A$_1$)(A$_2$)(A$_3$);

R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted;

R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein these moieties, excluding hydrogen, may be optionally; or wherein R$_{2''}$ is the moiety (CR$_{10}$R$_{20}$)$_t$X$_1$(CR$_{10}$R$_{20}$)$_q$C(A$_1$)(A$_2$)(A$_3$);

A$_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;

A$_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;

A$_3$ is hydrogen or is an optionally substituted C$_{1-10}$ alkyl;

R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;

R$_4$ and R$_{14}$ are each independently selected at each occurrence from hydrogen, C$_{1-4}$ alkyl, C$_{3-7}$ cycloalkyl, C$_{3-7}$ cycloalkylC$_{1-4}$alkyl, aryl, aryl-C$_{1-4}$ alkyl, heterocyclic, heterocyclic C$_{1-4}$ alkyl, heteroaryl or a heteroaryl C$_{1-4}$ alkyl moiety, and wherein each of these moieties, excluding hydrogen, may be optionally substituted; or the R$_4$ and R$_{14}$ together with the nitrogen which they are attached form an optionally substituted heterocyclic ring of 4 to 7 members, which ring optionally contains an additional heteroatom selected from oxygen, sulfur or nitrogen;

R$_{4'}$ and R$_{14'}$ are each independently selected at each occurrence from hydrogen or C$_{1-4}$ alkyl, or R$_{4'}$ and R$_{14'}$ together with the nitrogen to which they are attached form a heterocyclic ring of 5 to 7 members, which ring optionally contains an additional heteroatom selected from NR$_9$;

R$_5$ is independently selected at each occurrence from hydrogen, C$_{1-4}$ alkyl, C$_{2-4}$ alkenyl, C$_{2-4}$ alkynyl or NR$_{4'}$R$_{14'}$, excluding the moieties SR$_5$ being SNR$_{4'}$R$_{14'}$, S(O)$_2$R$_5$ being SO$_2$H and S(O)R$_5$ being SOH;

R$_{9'}$ is independently selected at each occurrence from hydrogen, or C$_{1-4}$ alkyl;

R$_{10}$ and R$_{20}$ are independently selected at each occurrence from hydrogen or C$_{1-4}$alkyl;

R$_{10'}$ is independently selected at each occurrence from hydrogen or C$_{1-4}$alkyl;

R$_{11}$ is independently selected at each occurrence from hydrogen or C$_{1-4}$alkyl;

R$_{12}$ is independently selected at each occurrence from hydrogen, C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{3-7}$cycloalkylC$_{1-4}$ alkyl, C$_{5-7}$ cycloalkenyl, C$_{5-7}$cycloalkenyl C$_{1-4}$ alkyl, aryl, arylC$_{1-4}$ alkyl, heteroaryl, heteroarylC$_{1-4}$ alkyl, heterocyclyl, or a heterocyclylC$_{1-4}$ alkyl moiety, and wherein each of these moieties, excluding hydrogen, may be optionally substituted;

R$_{13}$ is independently selected at each occurrence from hydrogen, C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{3-7}$cycloalkylC$_{1-4}$ alkyl, C$_{5-7}$ cycloalkenyl, C$_{5-7}$cycloalkenyl C$_{1-4}$ alkyl, aryl, arylC$_{1-4}$ alkyl, heteroaryl, heteroarylC$_{1-4}$ alkyl, heterocyclyl, or a heterocyclylC$_{1-4}$ alkyl moiety, and wherein each of these moieties, excluding hydrogen, may be optionally substituted;

R$_d$ and R$_{d'}$ are each independently selected from hydrogen, C$_{1-4}$ alkyl, C$_{3-6}$ cycloalkyl, C$_{3-6}$ cycloalkylC$_{1-4}$alkyl moiety, and wherein each of these moieties, excluding hydrogen, may be optionally substituted; or R$_d$ and R$_{d'}$ together with the nitrogen which they are attached form an optionally substituted heterocyclic ring of 5 to 6 members, which ring optionally contains an additional heteroatom selected from oxygen, sulfur or NR$_9$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

The present invention is directed to novel compounds of Formula (A) and Formula (A1), or a pharmaceutically acceptable derivative thereof. As will be readily recognized, the difference between compounds of Formula (A) and Formula (A1), and that of Formula (I) and (Ia) lies in the linker Y. The respective R$_1$, R$_2$, and R$_3$, etc. terms are the same for both groups. For purposes herein, everything applicable to Formula (I) is also applicable to Formula (A) unless otherwise indicated.

Another aspect of the invention are compounds of Formula (B) and (B1):

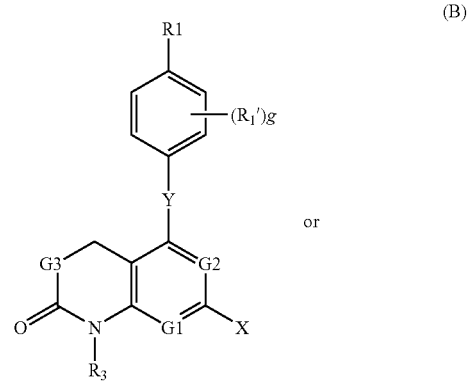

-continued (B1)

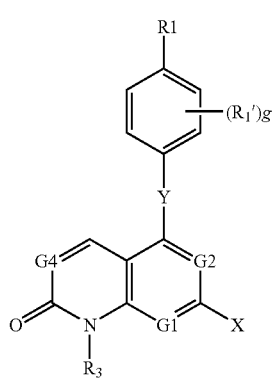

wherein
G₁, and G₂ are independently nitrogen;
G₃ is CH₂;
G₄ is CH;
Y is C(R$_x$)(R$_z$), C(O), N(R$_z$), N(R$_w$)C(R$_y$)(R$_z$), oxygen, OC(R$_y$)(R$_z$), S(O)m, or S(O)$_m$C(R$_y$)(R$_z$);
R$_x$ is hydrogen, C$_{1-2}$ alkyl, N(R$_v$)$_2$, hydroxy, thio, C$_{1-2}$ alkoxy, or S(O)$_m$C$_{1-2}$ alkyl;
R$_y$ is hydrogen or C$_{1-2}$ alkyl;
R$_{z'}$ is hydrogen or C$_{1-2}$ alkyl;
R$_w$ is hydrogen or C$_{1-2}$ alkyl;
R$_v$ is independently selected from hydrogen or C$_{1-2}$ alkyl;
R₁ is C(Z)N(R$_{10'}$)(CR$_{10}$R$_{20}$)$_v$R$_b$, C(Z)O(CR$_{10}$R$_{20}$)$_v$R$_b$, N(R$_{10}$)C(Z)(CR$_{10}$R$_{20}$)$_v$R$_b$, N(R$_{10}$)C(Z)N(R$_{10'}$)(CR$_{10}$R$_{20}$)$_v$R$_b$, or N(R$_{10'}$)OC(Z)(CR$_{10}$R$_{20}$)$_v$R$_b$;
R$_{1'}$ is independently selected at each occurrence from halogen, C$_{1-4}$ alkyl, halo-substituted-C$_{1-4}$ alkyl, cyano, nitro, (CR$_{10}$R$_{20}$)$_v$NR$_d$R$_d$, (CR$_{10}$R$_{20}$)$_v$C(O)R$_{12}$, SR$_5$, S(O)R$_5$, S(O)$_2$R$_5$, or (CR$_{10}$R$_{20}$)$_v$OR$_{13}$;
R$_b$ is hydrogen, C$_{1-10}$ alkyl, C$_{3-7}$ cycloalkyl, C$_{3-7}$ cycloalkyl C$_{1-10}$ alkyl, aryl, arylC$_{1-10}$alkyl, heteroaryl, heteroarylC$_{1-10}$ alkyl, heterocyclic, or heterocyclylC$_{1-10}$ alkyl moiety, which moieties, excluding hydrogen, may all be optionally substituted;
X is R$_2$, OR$_{2'}$, S(O)$_m$R$_{2'}$, (CH$_2$)$_n$N(R$_{10'}$)S(O)$_m$R$_{2'}$, (CH$_2$)$_n$N(R$_{10'}$)C(O)R$_{2'}$, (CH$_2$)$_n$NR$_4$R$_{14}$, (CH$_2$)$_n$N(R$_{2'}$)(R$_{2''}$), or N(R$_{10'}$)R$_h$NH—C(=N—CN)NRqRq';
X₁ is N(R$_{11}$)) O, S(O)$_m$, or CR$_{10}$R$_{20}$;
R$_h$ is selected from an optionally substituted C$_{1-10}$ alkyl, —CH$_2$—C(O)—CH$_2$—, —CH$_2$—CH$_2$—O—CH$_2$—CH$_2$—, —CH$_2$—C(O)N(R$_{10'}$)CH$_2$—CH$_2$—, —CH$_2$—N(R$_{10'}$)C(O)CH$_2$—, —CH$_2$—CH(OR$_{10'}$)—CH$_2$—, —CH$_2$—C(O)O—CH$_2$—CH$_2$—, or —CH$_2$—CH$_2$—O—C(O)CH$_2$—;
R$_q$ and R$_{q'}$ are independently selected at each occurrence from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, wherein all of the moieties except for hydrogen, are optionally substituted, or R$_q$ and R$_{q'}$ together with the nitrogen to which they are attached form an optionally substituted heterocyclic ring of 5 to 7 members, which ring may contain an additional heteroatom selected from oxygen, nitrogen or sulfur;
R₂ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted; or R₂ is the moiety (CR$_{10}$R$_{20}$)$_q$X$_1$(CR$_{10}$R$_{20}$)$_q$C(A$_1$)(A$_2$)(A$_3$), or (CR$_{10}$R$_{20}$)$_q$C(A$_1$)(A$_2$)(A$_3$);
R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted;
R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein these moieties, excluding hydrogen, may be optionally; or wherein R$_{2''}$ is the moiety (CR$_{10}$R$_{20}$)$_t$X$_1$(CR$_{10}$R$_{20}$)$_q$C(A$_1$)(A$_2$)(A$_3$);
A₁ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A₂ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A₃ is hydrogen or is an optionally substituted C$_{1-10}$ alkyl;
R₃ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;
R₄ and R₁₄ are each independently selected at each occurrence from hydrogen, C$_{1-4}$ alkyl, C$_{3-7}$ cycloalkyl, C$_{3-7}$ cycloalkylC$_{1-4}$alkyl, aryl, aryl-C$_{1-4}$ alkyl, heterocyclic, heterocyclic C$_{1-4}$ alkyl, heteroaryl or a heteroaryl C$_{1-4}$ alkyl moiety, and wherein each of these moieties, excluding hydrogen, may be optionally substituted; or the R₄ and R₁₄ together with the nitrogen which they are attached form an optionally substituted heterocyclic ring of 4 to 7 members, which ring optionally contains an additional heteroatom selected from oxygen, sulfur or nitrogen;
R$_{4'}$ and R$_{14'}$ are each independently selected at each occurrence from hydrogen or C$_{1-4}$ alkyl, or R$_{4'}$ and R$_{14'}$ together with the nitrogen to which they are attached form a heterocyclic ring of 5 to 7 members, which ring optionally contains an additional heteroatom selected from NR$_{9'}$;
R₅ is independently selected at each occurrence from hydrogen, C$_{1-4}$ alkyl, C$_{2-4}$ alkenyl, C$_{2-4}$ alkynyl or NR$_4$R$_{14'}$, excluding the moieties SR$_5$ being SNR$_4$R$_{14'}$, S(O)$_2$R$_5$ being SO$_2$H and S(O)R$_5$ being SOH;
R$_{9'}$ is independently selected at each occurrence from hydrogen, or C$_{1-4}$ alkyl;
R₁₀ and R₂₀ are independently selected at each occurrence from hydrogen or C$_{1-4}$alkyl;
R$_{10'}$ is independently selected at each occurrence from hydrogen or C$_{1-4}$alkyl;
R₁₁ is independently selected at each occurrence from hydrogen or C$_{1-4}$alkyl;
R₁₂ is independently selected at each occurrence from hydrogen, C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{3-7}$cycloalkylC$_{1-4}$ alkyl, C$_{5-7}$ cycloalkenyl, C$_{5-7}$cycloalkenyl C$_{1-4}$ alkyl, aryl, arylC$_{1-4}$ alkyl, heteroaryl, heteroarylC$_{1-4}$ alkyl, heterocyclyl, or a heterocyclylC$_{1-4}$ alkyl moiety, and wherein each of these moieties, excluding hydrogen, may be optionally substituted;
R₁₃ is independently selected at each occurrence from hydrogen, C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{3-7}$cycloalkylC$_{1-4}$ alkyl, C$_{5-7}$ cycloalkenyl, C$_{5-7}$cycloalkenyl C$_{1-4}$ alkyl, aryl, arylC$_{1-4}$ alkyl, heteroaryl, heteroarylC$_{1-4}$ alkyl, heterocyclyl, or a heterocyclylC$_{1-4}$ alkyl moiety, and wherein each of these moieties, excluding hydrogen, may be optionally substituted;

R$_d$ and R$_{d'}$ are each independently selected from hydrogen, C$_{1-4}$ alkyl, C$_{3-6}$ cycloalkyl, C$_{3-6}$ cycloalkylC$_{1-4}$alkyl moiety, and wherein each of these moieties, excluding hydrogen, may be optionally substituted; or R$_d$ and R$_{d'}$ together with the nitrogen which they are attached form an optionally substituted heterocyclic ring of 5 to 6 members, which ring optionally contains an additional heteroatom selected from oxygen, sulfur or NR$_9$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

As will be readily recognized, the differences between compounds of Formula (B) and Formula (B1), and that of Formula (II) and (IIa) lie in the linker Y. The respective R$_1$, R$_2$, and R$_3$, etc. terms are the same for both groups. For purposes herein, everything applicable to Formula (II) is also applicable to Formula (B) unless otherwise indicated.

In another aspect of the invention, it is the linker Y may be present in a similar manner in the same position for all of the remaining formulas, Formula's (III) and (IIIa), (IV) and (IVa), (V) and (Va), (VI), (VIa-VIi), etc., herein. The respective R$_1$, R$_2$, and R$_3$, etc. terms will be the same for all the groups.

Another aspect of the invention are compounds of Formula (VIII) and (VIIIa):

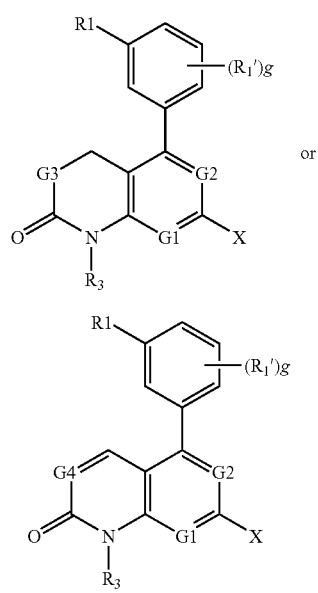

wherein

G$_1$, G$_2$ are independently nitrogen or CH, but G$_1$, and G$_2$ are not both nitrogen;

G$_3$ is CH$_2$;

G$_4$ is CH;

R$_1$ is C(Z)N(R$_{10'}$)(CR$_{10}$R$_{20}$)$_v$R$_b$, C(Z)O(CR$_{10}$R$_{20}$)$_v$R$_b$, N(R$_{10'}$)C(Z)(CR$_{10}$R$_{20}$)$_v$R$_b$, N(R$_{10'}$)C(Z)N(R$_{10'}$)(CR$_{10}$R$_{20}$)$_v$R$_b$, or N(R$_{10'}$)OC(Z)(CR$_{10}$R$_{20}$)$_v$R$_b$;

R$_{1'}$ is independently selected at each occurrence from halogen, C$_{1-4}$ alkyl, halo-substituted-C$_{1-4}$ alkyl, cyano, nitro, (CR$_{10}$R$_{20}$)$_{v'}$NR$_d$R$_{d'}$, (CR$_{10}$R$_{20}$)$_{v'}$C(O)R$_{12}$, SR$_5$, S(O)R$_5$, S(O)$_2$R$_5$, or (CR$_{10}$R$_{20}$)$_{v'}$OR$_{13}$;

R$_b$ is hydrogen, C$_{1-10}$ alkyl, C$_{3-7}$ cycloalkyl, C$_{3-7}$ cycloalkyl C$_{1-10}$ alkyl, aryl, arylC$_{1-10}$alkyl, heteroaryl, heteroarylC$_{1-10}$ alkyl, heterocyclic, or heterocyclylC$_{1-10}$ alkyl moiety, which moieties, excluding hydrogen, may all be optionally substituted;

X is R$_2$, OR$_{2'}$, S(O)$_m$R$_{2'}$, (CH$_2$)$_n$N(R$_{10'}$)S(O)$_m$R$_{2''}$, (CH$_2$)$_n$N (R$_{10'}$)C(O)R$_{2'}$, (CH$_2$)$_n$NR$_4$R$_{14}$, (CH$_2$)$_n$N(R$_{2'}$)(R$_{2''}$), or N(R$_{10'}$)R$_n$NH—C(=N—CN)NRqRq';

X$_1$ is N(R$_{11}$), O, S(O)$_m$, or CR$_{10}$R$_{20}$;

R$_h$ is selected from an optionally substituted C$_{1-10}$ alkyl, —CH$_2$—C(O)—CH$_2$—, —CH$_2$—CH$_2$—O—CH$_2$—CH$_2$—, —CH$_2$—C(O)N(R$_{10'}$)CH$_2$—CH$_2$—, —CH$_2$—N (R$_{10'}$)C(O)CH$_2$—, —CH$_2$—CH(OR$_{10'}$)—CH$_2$—, —CH$_2$—C(O)O—CH$_2$—CH$_2$—, or —CH$_2$—CH$_2$—O—C(O) CH$_2$—;

R$_q$ and R$_{q'}$ are independently selected at each occurrence from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, wherein all of the moieties except for hydrogen, are optionally substituted, or R$_q$ and R$_{q'}$ together with the nitrogen to which they are attached form an optionally substituted heterocyclic ring of 5 to 7 members, which ring may contain an additional heteroatom selected from oxygen, nitrogen or sulfur;

R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted; or R$_2$ is the moiety (CR$_{10}$R$_{20}$)$_q$X$_1$(CR$_{10}$R$_{20}$)$_q$C(A$_1$)(A$_2$) (A$_3$), or (CR$_{10}$R$_{20}$)$_q$C(A$_1$)(A$_2$)(A$_3$);

R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted;

R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein these moieties, excluding hydrogen, may be optionally; or wherein R$_{2''}$ is the moiety (CR$_{10}$R$_{20}$)$_t$X$_1$ (CR$_{10}$R$_{20}$)$_q$C(A$_1$)(A$_2$)(A$_3$);

A$_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;

A$_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;

A$_3$ is hydrogen or is an optionally substituted C$_{1-10}$ alkyl;

R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;

$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_5$ is independently selected at each occurrence from hydrogen, $C_{1-4}$ alkyl, $C_{2-4}$ alkenyl, $C_{2-4}$ alkynyl or $NR_4 R_{14'}$, excluding the moieties $SR_5$ being $SNR_4 R_{14'}$, $S(O)_2 R_5$ being $SO_2H$ and $S(O)R_5$ being SOH;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

In another embodiment of the present invention, for compounds of Formula (VIII) and (VIIIa) the X term may also be the B-Non-Ar-cyc moiety as disclosed above.

In another embodiment of the present invention, for compound of Formula (VIII) and (VIIIa), and the remaining formulas, the X term may also be the X moiety as disclosed in WO 2004/073628, published September 2004, Boehm et al., whose disclosure is incorporated by reference herein.

For purposes herein the template containing the $G_1$ and $G_2$ moieties will have a numbering system that allows for different ($R_1$ and $R_{1'}$) substituents on the phenyl, the pyridyl and pyrimidine ring at the $C_4$ position of the pharmacophore; the X term at the $C_2$ position and the $R_3$ substituent in the $N_8$ position.

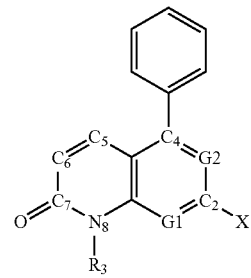

The respective $R_1$, $R_2$, $R_x$, X and $R_3$, etc., terms are the same for both groups within the formulas themselves, for instance, in Formula (VIII) and (VIIIa). For purposes herein, everything applicable to Formula (VIII) is also applicable to Formula (VIIIa) unless otherwise indicated.

It is recognized that for compounds of Formula (I) and (Ia), etc. and those of Formula (VIII) and (VIIIa) the difference is in the allowance of the $G_1$ and $G_2$ moieties to be carbon or nitrogen, independently. For purposes of brevity herein, the remaining compounds of Formulas (II) and (IIa), (III) and (IIIa), (IV) and (IVa), (V) and (Va), (VI) and (VIa-VIi), may also have the same pharmacophore template of:

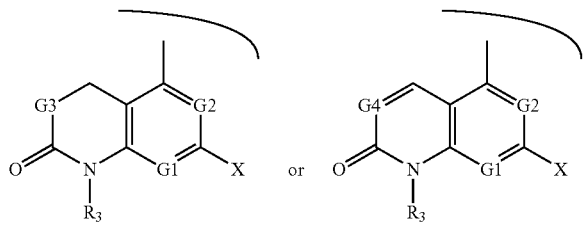

Illustrative of this would be the C4 substitution from compounds of formula (II) and (IIa) on this pharmacophore template, represented by the structure:

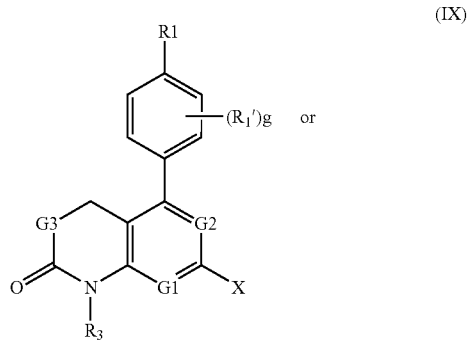

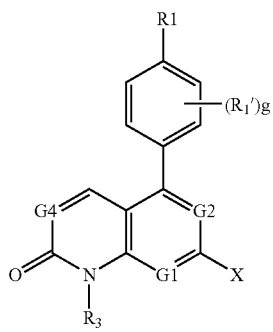

(IXa)

wherein

G₁, G₂ are independently nitrogen or CH, but G₁, and G₂ are not both nitrogen;

$G_3$ is $CH_2$;

$G_4$ is CH;

$R_1$ is $C(Z)N(R_{10'})(CR_{10}R_{20})_vR_b$, $C(Z)O(CR_{10}R_{20})_vR_b$, $N(R_{10'})C(Z)(CR_{10}R_{20})_vR_b$, $N(R_{10'})C(Z)N(R_{10})(CR_{10}R_{20})_vR_b$, or $N(R_{10'})OC(Z)(CR_{10}R_{20})_vR_b$;

$R_{1'}$ is independently selected at each occurrence from halogen, $C_{1-4}$ alkyl, halo-substituted-$C_{1-4}$ alkyl, cyano, nitro, $(CR_{10}R_{20})_v NR_dR_{d'}$, $(CR_{10}R_{20})_v C(O)R_{12}$, $SR_5$, $S(O)R_5$, $S(O)_2R_5$, or $(CR_{10}R_{20})_v OR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_mR_{2'}$, $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_{2'})(R_{2''})$, or $N(R_{10'})R_hNH-C(=N-CN)NR_qR_{q'}$;

$X_1$ is $N(R_{11})$, O, $S(O)_m$, or $CR_{10}R_{20}$;

$R_h$ is selected from an optionally substituted $C_{1-10}$ alkyl, $-CH_2-C(O)-CH_2-$, $-CH_2-CH_2-O-CH_2-CH_2-$, $-CH_2-C(O)N(R_{10'})CH_2-CH_2-$, $-CH_2-N(R_{10'})C(O)CH_2-$, $-CH_2-CH(OR_{10'})-CH_2-$, $-CH_2-C(O)O-CH_2-CH_2-$, or $-CH_2-CH_2-O-C(O)CH_2-$;

$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or
  $R_2$ is the moiety $(CR_{10}R_{20})_qX_1(CR_{10}R_{20})_qC(A_1)(A_2)(A_3)$, or $(CR_{10}R_{20})_qC(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally; or wherein $R_{2''}$ is the moiety $(CR_{10}R_{20})_rX_1(CR_{10}R_{20})_qC(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_5$ is independently selected at each occurrence from hydrogen, $C_{1-4}$ alkyl, $C_{2-4}$ alkenyl, $C_{2-4}$ alkynyl or $NR_{4'}R_{14'}$, excluding the moieties $SR_5$ being $SNR_{4'}R_{14'}$, $S(O)_2R_5$ being $SO_2H$ and $S(O)R_5$ being SOH;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$;

g is 0 or an integer having a value of 1, 2, 3, or 4;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt, solvate or physiologically functional derivative thereof.

Therefore, compounds having the C4 position substitution from Formula (III) and (IIIa) with the G1/G2 pharmacophore template of carbon or nitrogen, would be considered compounds of Formula (X) and (Xa), etc.

It is to be understood that the present invention covers all combinations of particular and preferred groups described hereinabove. It is also to be understood that the present invention encompasses compounds of formula (I) in which a particular group or parameter, for example $R_5$, $R_6$, $R_9$, $R_{10}$, $R_{11}$, $R_{12}$, $R_{13}$, p, n, or q, etc. may occur more than once. In such compounds it will be appreciated that each group or parameter is independently selected from the values listed. When any variable occurs more than one time in a Formula (as described herein), its definition on each occurrence is independent of its definition at every other occurrence.

Particular compounds according to the invention include those mentioned in the examples and their pharmaceutically derivatives.

As used herein, the term "pharmaceutically acceptable" means a compound which is suitable for pharmaceutical and veterinary usage. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate or prodrug e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol. 1: Principles and Practice, which is incorporated herein by reference to the extent of teaching such derivatives. In one embodiment pharmaceutically acceptable derivatives are salts, solvates, esters, carbamates and phosphate esters. In another embodiment pharmaceutically acceptable derivatives are salts, solvates and esters. In yet another embodiment of the invention pharmaceutically acceptable derivatives are salts and esters, in particular salts.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Salts of the compounds of the present invention may, for example, comprise acid addition salts resulting from reaction of an acid with a nitrogen atom present in a compound of formula (I). Salts encompassed within the term "pharmaceutically acceptable salts" refer to non-toxic salts of the compounds of this invention. Suitable addition salts are formed from acids which form non-toxic salts and examples are acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanesulphonate, formate, fumarate, gluceptate, gluconate, glutamate, glycollylarsanilate, hexylresorcinate, hydrabamine, hydrobromide, hydrochloride, hydrogen phosphate, hydroiodide, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmitate, pantothenate, phosphate/diphosphate, piruvate, polygalacturonate, saccharate, salicylate, stearate, subacetate, succinate, sulphate, tannate, tartrate, teoclate, tosylate, triethiodide, trifluoroacetate and valerate.

Pharmaceutically acceptable base salts include ammonium salts such as a trimethylammonium salt, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Those skilled in the art of organic chemistry will appreciate that many organic compounds can form complexes with solvents in which they are reacted or from which they are precipitated or crystallized. These complexes are known as "solvates". As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water. A complex with water is known as a "hydrate". Solvates of the compound of the invention are within the scope of the invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series; Edward B. Roche, ed., Bioreversible Carriers in Drug Design, American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy or amine groups are bonded to any group that, when administered to a patient, cleaves to form the hydroxy or amine groups. Thus, representative examples of prodrugs include (but are not limited to) acetate, formate and benzoate derivatives of alcohol and amine functional groups of the compounds of formula (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halo-substituted $C_{1-10}$ alkoxy; S(O)m alkyl, such as methyl thio, methylsulfinyl or methyl sulfonyl; a ketone (—C(O)), or an aldehyde (—C(O)$R_{6'}$), such as C(O)$C_{1-10}$ alkyl or C(O)aryl, wherein $R_{6'}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, (and wherein the $R_{6'}$ moieties, excluding hydrogen, may themselves be optionally substituted 1 or 2 times, independently at each occurrence by halogen; hydroxy; hydroxy substituted alkyl; $C_{1-4}$ alkoxy; S(O)$_m$ $C_{1-4}$ alkyl; amino, mono & di-substituted $C_{1-4}$ alkyl amino; $C_{1-4}$ alkyl, or $CF_3$); C(O)O$R_{6'}$; $NR_{4'}R_{14'}$, wherein $R_{4'}$ and $R_{14'}$ are each independently hydrogen or $C_{1-4}$ alkyl, such as amino or mono or -disubstituted $C_{1-4}$ alkyl or wherein the $R_{4'}R_{14'}$ can cyclize together with the nitrogen to which they are attached to form a 5 to 7 membered ring which optionally contains an additional heteroatom selected from O/N/S; $C_{1-10}$ alkyl, such as methyl, ethyl, propyl, isopropyl, t-butyl, etc.; $C_{3-7}$cycloalkyl, or $C_{3-7}$cycloalkyl $C_{1-10}$ alkyl group, such as cyclopropyl, cyclobutyl, or cyclopropyl methyl; halosubstituted $C_{1-10}$ alkyl, such $CF_2CF_2H$, or $CF_3$; an optionally substituted aryl, such as phenyl, or an optionally substituted aryl$C_{1-4}$ alkyl, such as benzyl or phenethyl, wherein these aryl containing moieties may also be substituted one to two times independently at each occurrence by halogen; hydroxy; hydroxy substituted alkyl; $C_{1-4}$ alkoxy; S(O)$_m$$C_{1-4}$ alkyl; amino, mono & di-substituted $C_{1-4}$ alkyl amino; $C_{1-4}$ alkyl, or $CF_3$.

Suitable pharmaceutically acceptable salts are well known to those skilled in the art and include salts formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, alkyl sulphonic acid derivatives, such as methanesulphonic, or ethanesulphonic, arylsulphonic acid derivatives, such as p-toluenesulphonic, m-toluenesulphonic, benzenesulphonic, camphor sulphonic, 4-chlorobenzenesulphonic, 4-bromobenzenesulphonic, 4-phenylbenzenesulphonic, naphthalenesulphonic or naphthalenedisulphonic), phenylacetic, mandelic, salicylic, glutaric, gluconic, tricarballylic, cinnamic, substituted cinnamic (for example, phenyl, methyl, cynao, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids.

Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The term "halo" or "halogens" is used herein to mean the halogens, chloro, fluoro, bromo and iodo.

As used herein, the term "$C_{1-10}$alkyl" or "alkyl" or "alkyl$_{1-10}$" is used herein to mean both straight and branched hydrocarbon chain containing the specified number of carbon atoms, e.g. $C_{1-10}$alkyl means a straight of branched alkyl chain of at least 1, and at most 10, carbon atoms, unless the chain length is otherwise limited. Examples of "alkyl" as used herein include, but are not limited to, methyl, ethyl, n-propyl, n-butyl, n-pentyl, isobutyl, isopropyl, sec-butyl, tert-butyl or t-butyl and hexyl and the like.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond. Examples of "alkenyl" as used herein include, but are not limited to ethenyl, 2-propenyl, 3-butenyl, 2-butenyl, 2-pentenyl, 3-pentenyl, 3-methyl-2-butenyl, 3-methylbut-2-enyl, 3-hexenyl, 1,1-dimethylbut-2-enyl and the like.

As used herein, the term "alkoxy" refers to straight or branched chain alkoxy groups containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy.

As used herein, the term "cycloalkyl" refers to cyclic radicals, such as a non-aromatic hydrocarbon ring containing a specified number of carbon atoms. For example, $C_{3-7}$cycloalkyl means a non-aromatic ring containing at least three, and at most seven, ring carbon atoms. Representative examples of "cycloalkyl" as used herein include, but are not limited to, cyclopropyl, cyclobutyl, cyclopentyl, cyclohexyl and cycloheptyl and the like.

The term "cycloalkenyl" is used herein to mean cyclic radicals, such as a non-aromatic hydrocarbon ring containing a specified number of carbon atoms preferably of 5 to 7 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl, naphthyl, and indene.

The terms "heteroaryl ring", "heteroaryl moiety", and "heteroaryl" are used herein to mean a monocyclic five- to seven-membered unsaturated hydrocarbon ring containing at least one heteroatom selected from oxygen, nitrogen and sulfur. Examples of heteroaryl rings include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil. The terms "heteroaryl ring", "heteroaryl moiety", and "heteroaryl" shall also used herein to refer to fused aromatic rings comprising at least one heteroatom selected from oxygen, nitrogen and sulfur. Each of the fused rings may contain five or six ring atoms. Examples of fused aromatic rings include, but are not limited to, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

The terms "heterocyclic rings", "heterocyclic moieties", and "heterocyclyl" is used herein to mean a monocyclic three- to seven-membered saturated or non-aromatic, unsaturated hydrocarbon ring containing at least one heteroatom selected from nitrogen, oxygen, sulphur or oxidized sulphur moieties, such as S(O)m, and m is 0 or an integer having a value of 1 or 2. The terms "heterocyclic rings", "heterocyclic moieties", and "heterocyclyl" shall also refer to fused rings, saturated or partially unsaturated, and wherein one of the rings may be aromatic, or heteroaromatic. Each of the fused rings may have from four to seven ring atoms. Examples of heterocyclyl groups include, but are not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), azepine, diazepine, aziridinyl, pyrrolinyl, pyrrolidinyl, 2-oxo-1-pyrrolidinyl, 3-oxo-1-pyrrolidinyl, pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety).

The term "arylalkyl" or "heteroarylalkyl" or "heterocyclicalkyl" is used herein to mean a $C_{1-4}$ alkyl (as defined above) attached to an aryl, heteroaryl or heterocyclic moiety (as also defined above) unless otherwise indicated.

The term "sulfinyl" is used herein to mean the oxide S(O) of the corresponding sulfide, the term "thio" refers to the sulfide, and the term "sulfonyl" refers to the fully oxidized $S(O)_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean $C(O)C_{1-10}$ alkyl wherein the alkyl is as defined above.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

It is to be understood that the present invention covers all combinations of particular and preferred groups described hereinabove. It is also to be understood that the present invention encompasses compounds of formula (I) in which a particular group or parameter, for example $R_5$, $R_6$, $R_9$, $R_{10}$, $R_{11}$, $R_{12}$, $R_{13}$, n, m, or t, etc. may occur more than once. In such compounds it will be appreciated that each group or parameter is independently selected from the values listed. When any variable occurs more than one time in a Formula (as described herein), its definition on each occurrence is independent of its definition at every other occurrence.

With regard to stereoisomers, the compounds of the Formulas herein may have one or more asymmetric carbon atom and may occur as racemates, racemic mixtures and as individual enantiomers or diastereomers. All such isomeric forms are included within the present invention, including mixtures thereof.

Cis (E) and trans (Z) isomerism may also occur. The present invention includes the individual stereoisomers of the compounds of the invention and where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. A stereoisomeric mixture of the agent may also be prepared from a corresponding optically pure intermediate or by resolution, such as H.P.L.C. of the corresponding racemate using a suitable chiral support or by fractional crystallisation of the diastereoisomeric salts formed by reaction of the corresponding racemate with a suitable optically active acid or base, as appropriate.

Furthermore, some of the crystalline forms of the compounds of the Formulas herein may exist as polymorphs, which are included in the present invention.

Exemplified compounds of the compounds of this invention include the racemates, or optically active forms of the compounds of the working examples herein, and pharmaceutically acceptable salts thereof.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Methods of Manufacture

The compounds of Formula (I) and (Ia), (II) and (IIa), (III) and (IIIa), (IV) and (IVa), (V) and (Va), (VI), (VIa-VIi), (VIII), (VIIIa), (IX), (IXa), (A), (A1), (B), and (B1), may be obtained by applying the synthetic procedures described herein. The synthesis provided for is applicable to producing compounds of the Formulas herein having a variety of different $R_1$, $R_2$, X, and $R_3$ groups which are reacted, employing optional substituents which are suitably protected, to achieve compatibility with the reactions outlined herein. Subsequent deprotection, in those cases, then affords compounds of the nature generally disclosed. While a particular formula with particular substituent groups is shown herein, the synthesis is applicable to all formulas and all substituent groups herein.

Once the nucleus has been established, further compounds of Formula (I) and (Ia), (II) and (IIa), (III) and (IIIa), (IV) and (IVa), (V) and (Va), (VI), (VIa-VIi), (VIII), (VIIIa), (IX), (IXa), (A), (A1), (B), and (B1) may be prepared by applying standard techniques for functional group inter-conversion, well known in the art. For instance: $C(O)NR_4R_{14}$ from $CO_2CH_3$ by heating with $HNR_4R_{14}$ in $CH_3OH$ with or without catalytic or stoichiometric metal cyanide or Aluminum trimethyl, e.g. NaCN; $OC(O)R_6$ from OH with e.g., ClC(O)$R_6$ in bases such as triethylamine and pyridine; $NR_{10}$—C(S)$NR_4R_{14}$ from $NHR_{10}$ with an alkylisothiocyanate, or thiocyanic acid and $ClC(S)NR_4R_{14}$; $NR_{10}C(O)OR_6$ from $NHR_{10}$ with an alkyl or aryl chloroformate; $NR_{10}C(O)NR_4H$ from $NHR_{10}$ by treatment with an isocyanate, e.g. $R_4N$=C=O; $NR_{10}$—$C(O)R_6$ from $NHR_{10}$ by treatment with Cl—$C(O)R_6$ in pyridine; $C$(=$NR_{10}$)$NR_4R_{14}$ from $C(NR_4R_{14})S$ with $H_3NR_{10}^+OAc^-$ by heating in alcohol; $C(NR_4R_{14})SR_6$ from C(S)NR$_4$R$_{14}$ with R$_6$—I in an inert solvent, e.g. acetone; NR$_{10}$SO$_2$R$_7$ from NHR$_{10}$ by treatment with ClSO$_2$R$_7$ by heating in bases such as pyridine; NR$_{10}$C(S)R$_6$ from NR$_{10}$C(O)R$_6$ by treatment with Lawesson's reagent [2,4-bis(4-methoxyphenyl)-1,3,2,4-dithiadiphosphetane-2,4-disulfide]; NR$_{10}$SO$_2$CF$_3$ from NHR$_{10}$ with triflic anhydride and base wherein R$_6$, R$_{10}$, R$_4$ and R$_{14}$ are as defined in Formula (I) herein.

Precursors of the groups R$_1$, R$_2$ and R$_3$, can be other R$_1$, R$_2$ and R$_3$, etc. groups that may be interconverted by applying standard techniques for functional group interconversion. For example, wherein a moiety is a halo substituted C$_{1-10}$ alkyl can be converted to the corresponding C$_{1-10}$ alkylN$_3$ derivative by reacting with a suitable azide salt, and thereafter if desired can be reduced to the corresponding C$_{1-10}$alkylNH$_2$ compound, which in turn can be reacted with R$_7$S(O)$_2$X' wherein X' is halo (e.g., chloro) to yield the corresponding C$_{1-10}$alkylNHS(O)$_2$R$_7$ compound.

Alternatively wherein the moiety is a halo-substituted C$_{1-10}$-alkyl it can be reacted with an amine R$_4$R$_{14}$NH to yield the corresponding C$_{1-10}$-alkylNR$_4$R$_{14}$ compound, or can be reacted with an alkali metal salt of R$_7$SH to yield the corresponding C$_{1-10}$alkylSR$_7$ compound.

As noted above, it may be desirable during the synthesis of the compounds of this invention, to derivatize reactive functional groups in the molecule undergoing reaction so as to avoid unwanted side reactions. Functional groups such as hydroxy, amino, and acid groups are typically protected with suitable groups that can be readily removed when desired. Suitable common protecting groups for use with hydroxyl groups and nitrogen groups are well known in the art and described in many references, for instance, Protecting Groups in Organic Synthesis, Greene et al., John Wiley & Sons, New York, N.Y., (2nd edition, 1991 or the earlier 1981 version). Suitable examples of hydroxyl protecting groups include ether forming groups such as benzyl, and aryl groups such as tert-butoxycarbonyl (Boc), silyl ethers, such as t-butyldimethyl or t-butyldiphenyl, and alkyl ethers, such as methyl connected by an alkyl chain of variable link, (CR$_{10}$R$_{20}$)$_n$. Amino protecting groups may include benzyl, aryl such as acetyl and trialkylsilyl groups. Carboxylic acid groups are typically protected by conversion to an ester that can easily be hydrolyzed, for example, trichloethyl, tert-butyl, benzyl and the like.

Pharmaceutically acid addition salts of compounds of the various Formulas described herein may be obtained in known manner, for example by treatment thereof with an appropriate amount of acid in the presence of a suitable solvent.

An illustration of the preparation of compounds of the present invention is shown in the scheme below. For purposes herein, the compounds in Schemes I and II are shown with an S-methyl, or S(O)$_2$-methyl group which is deemed representative of the S(O)m-Rg group, as described in the formulas below.

Preparation of compounds with Formula (Ia) can be achieved through compound 2, which in turn may be constructed from aldehyde I as shown in Scheme 1. Leaving groups (LG, described as Leaving group 1 (LG1) & LG2) in Scheme 1, and elsewhere can be independently selected from —Cl, —Br, —I, or —OTf and these groups can be installed through the transformation of another functional group (e.g. —OH) by following the methods well known in the art (e.g., treatment of the —OH compound with POCl$_3$).

Method A is for conversion of 1 to 2. Treatment of 1 with an amine R$_3$NH$_2$ in the presence of an olefin forming agent, such as bis(2,2,2-trifluoroethyl)-(methoxycarbonylmethyl)-phosphonate or an acylating agent, such as acetic acid anhydride, meldrums acid or acetyl chloride affords compound 2. While the olefin forming reagent bis(2,2,2-trifluoroethyl)(methoxycarbonylmethyl)phosphonate is used, alternative cyclization reagents, include, but are not limited to bis(2,2,2-trifluoroethyl)-(ethoxycarbonylmethyl)phosphonate, bis(2,2,2-trifluoroethyl)-(isopropoxycarbonyl-methyl)phosphonate, (diethoxy-phosphoryl)-acetic acid methyl ester, (diisopropoxy-phosphoryl)-acetic acid methyl ester, (diphenyloxy-phosphoryl)-acetic acid methyl ester, (diethoxy-phosphoryl)-acetic acid ethyl ester, (diisopropoxy-phosphoryl)-acetic acid ethyl ester, or (diphenyloxy-phosphoryl)-acetic acid ethyl ester. Elevated temperatures (reflux or microwave irradiations), longer reaction times (over night or 24 hours) and presence of triethyl amine or diisopropyl ethyl amine or NaH (or Na) may be necessary for reaction completion. The reaction solvents can be various organic solvents, such as chloroform, methylene chloride, acetonitrile, toluene, DMF, or n-methylpyrrolidine, DCM, THF, toluene, DMSO, or combinations thereof. While the reaction shows triethylamine as a base, suitable alternative bases can include, but are not limited to pyridine, diisopropyl ethyl amine, or pyrrolidone, or combinations thereof.

The reaction temperature of this particular step in the reaction scheme can be varied from room temperature to >100° C., i.e. reflux temperature of the solvent. Alternatively, this reaction process step may be performed under suitable microwave conditions.

Method B is for the installation of group —X [e.g., 2 to 3, 6 to (Ia), or 5 to 4]. This may or may not require first conversion of sulfide (—SMe) to sulfoxide (—SOMe) or sulfone (—SO$_2$Me). This conversion can be achieved using meta-chloroperoxybenzoic acid (mCPBA) in high yield and purity. Suitable oxidation methods for use herein include use of one or two equivalents of meta-chloroperoxybenzoic acid (mCPBA) or Oxone to afford either the sulfoxides or sulfones or a mixture of both. Oxidation of the sulfides to sulfoxides or sulfones can also be effected by OsO$_4$ and catalytic tertiary amine N-oxide, hydrogen peroxide, hydrogen peroxide/NaWO4, and other peracids, oxygen, ozone, organic peroxides, potassium and zinc permanganate, potassium persulfate, and sodium hypochlorite. The subsequent displacement of sulfone group —SO$_2$Me (likewise, all displacement reactions mentioned below may be achieved using the sulfide —SMe or sulfoxide —SOMe) requires a suitable nucleophile (e.g., amine, alcohol) containing the unit —X. Displacements with amines were usually done with an excess of amine in N-methylpyrrolidine (Barvian et al., *J. Med. Chem.* (2000), 4606-4616). A wide range of primary amines underwent this reaction with excellent yields. In some cases (e.g., in O-displacement) an anion of the nucleophile was prepared with base (usually sodium hydride) in DMF (or DMSO) and then added to the sulfone. Yields for these reactions were usually lower. The sulfone may be displaced by primary and secondary alkylamines without additional base catalysis, preferably in a polar aprotic solvent, such as but not limited to, N-methyl pyrrolidin-2-one (NMP), and at varying temperatures depending upon the nucleophilicity of the amine. For instance displacement of the sulfone with ethanolamine, in NMP, occurred in 30 min. at 65° C., while a more hindered amine such as tris(hydroxymethyl)-aminomethane may require elevated temperatures and extended reaction times (80° C. over a 24 hour reaction time). The sulfone can also be displaced by a primary or secondary amine with an additional non-nucleophilic base (e.g. DIPEA) in aprotic solvents like DCM, CH$_3$CN, NMP, and at varying temperatures depending upon the nucleophilicity of the amine.

The sulfone may also be displaced with a substituted arylamine, or heteroarylamine at elevated temperatures, sometimes requiring formation of the aryl or heteroarylamine anion with sodium hydride, or other suitable base, in DMSO. In addition, the sulfone may be readily displaced with aluminum salts of aryl or heteroaryl amines as previously described in the patent literature (WO 99/32121, whose disclosure is incorporated by reference herein). Likewise, sulfone may be displaced with aryl or heteroaryl or alkyl thiols or alkyl or aryl or heteroaryl alcohols. Analogs containing sulfones as the X substituents may be displaced with sodium alkoxide in the alcohol, or alternatively reactive alkoxide or phenoxide nucleophiles that may be generated from the alcohol or phenol with a suitable base such as sodium, NaH or sodium bistrimethylsilyl amide in a polar aprotic solvent such as DMSO, or run as a neat reaction. Similarly the sulfone may be displaced with carbon nucleophiles. Suitable carbon nucleophiles include, but not limited to aryl Grignard reagents, alkyl Grignard reagents or related organometallics such as organo lithium, zinc, tin, copper or boron. These reactions may, in some cases, require transition metal catalysis such as with Pd or Ni catalysts.

Method C is for coupling with appropriate aryl groups to convert 3 to compounds with Formula (Ia) (or 2 to 6). This transformation may be achieved using, but not limited to boronic acids (e.g., C1A) under Suzuki cross-coupling conditions, employing a palladium catalyst, such as tetrakis(triphenylphosphine) palladium(0).

Alternatively, the cross-coupling may be performed using aryl or heteroaryl organozinc, (e.g., aryl/heteroaryl-ZnBr, aryl/heteroaryl-ZnCl, aryl/heteroaryl-Zn—R1), organocopper, [e.g., (aryl/heteroaryl)$_2$-CuLi], organotin [e.g., aryl/heteroaryl-Sn(CH$_3$)$_3$, aryl/heteroaryl —Sn(CH$_2$CH$_2$CH$_2$CH$_3$)$_3$], (e.g., C1C), or other organometallic reagents (e.g., C1B) known in the art [see for example Solberg, J.; Undheim, K. *Acta Chemica Scandinavia* 1989, 62-68].

Method D is for coupling of 2 (or 3 or 7) with an aryl group whose structure has a suitable precursor (e.g., acidic group —CO$_2$H, ester group —CO$_2$Me) to the final substituent R$_1$ in Formula (Ia). This transformation may be achieved using, but not limited to boronic acids (e.g., D1A) or protected acids (e.g., D1C, D1E) under Suzuki coupling conditions, (THF/H$_2$O, and K$_2$CO$_3$) employing a palladium catalyst, such as tetrakis(triphenylphosphine) palladium(0). If desired, these Suzuki coupling reactions may be run under microwave conditions. The boronic acid (D1A or D1E) or ester can be synthesized either by the palladium catalyzed coupling of an aryl halide and 4,4,4',4',5,5,5',5'-octamethyl-2,2'-bi-1,3,2-dioxaborolane or the transmetalation of an aryl halide with a Grignard reagent, e.g., isopropylmagnesium bromide followed by a trialkylborate (e.g., triethylborate) in a suitable solvent like THF.

Suitably the arylboronic acids, or their corresponding boronic acid esters are Aryl-boronic acid or an Aryl-boronic acid ester; e.g. Aryl B(OH)$_2$, Aryl —B(O—C$_{1-4}$ alkyl)$_2$, or

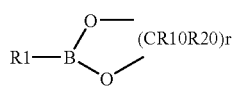

wherein R$_1$, R$_{10}$, and R$_{20}$ is as defined for compounds of Formula (I) herein; and r is an integer having a value of 2 to 6.

The coupling conditions include the use of appropriate solvents. These solvents include, but are not limited to dioxane, THF, DMF, DMSO, NMP, acetone, water, or a combination or a mixture thereof. Preferably, the solvent is THF/H$_2$O, or dioxane/H$_2$O.

The coupling conditions also include the presence of catalytic amount of catalysts and these catalysts include, but not limited to tetrakis(triphenylphosphine)-palladium (0), PdCl2, Pd(OAc)2, (CH3CN)2PdCl2, Pd(dppf)2, or [1,1'-bis(diphenylphosphino)-ferrocene]-dichloropalladium(II).

The coupling reaction may or may not require the presence of a base. Suitable bases include, but are not limited to NaHCO$_3$, KHCO$_3$, Na$_2$CO$_3$, K$_2$CO$_3$, KOAc or combination or mixture thereof. Preferably, the base is K$_2$CO$_3$ and KOAc.

The coupling reaction may or may not require heating. The heating can be carried out with a regular oil bath or microwave irradiations and the temperature can be varied from room temperature to >100° C., i.e. reflux temperature of the solvent. The coupling reaction may or may not require a sealed reaction vessel and the internal pressure can be varied from one atmosphere to 100 atmospheres.

The aryl or heteroaryl boronic acid or ester intermediates containing the RI moiety, used in the Suzuki coupling reactions may or may not be commercially available and they can be prepared by utilizing proper methods in the literature known to those with appropriate training. Examples of these methods include, but not limited to palladium catalyzed coupling of an aryl halide and 4,4,4',4',5,5,5',5'-octamethyl-2,2'-bi-1,3,2-dioxaborolane or the transmetalation of an aryl halide with a Grignard reagent, e.g., isopropylmagnesium bromide followed by a trialkylborate (e.g., triethylborate) in a suitable solvent. These solvents include, but not limited to CH2Cl2, chloroform, CH3CN, benzene, THF, hexane, ethyl ether, tert-butyl methyl ether, DMSO, DMF, toluene, n-methyl-pyrrolidine, dioxane. The reaction temperature can be varied from −78° C. to >100° C., i.e. reflux temperature of the solvent. Alternatively, this reaction process step may or may not be performed under suitable microwave irradiation conditions. This reaction may or may not require a sealed reaction vessel and the internal pressure can be varied from one atmosphere to 100 atmospheres.

Alternatively, the cross-coupling may be performed using aryl or heteroaryl organozinc, organocopper, organotin (e.g., D1B), or other organometallic reagents (e.g., D1D) known in the art [see for example Solberg, J.; Undheim, K. *Acta Chemica Scandinavia* 1989, 62-68]. Suitable de-protection is followed if a protected precursor (e.g., D1C, D1D, D1E) is used.

This coupling reaction may be performed utilizing aryl or heteroaryl organozinc (e.g., Aryl-ZnBr, R$_1$—ZnCl, Aryl-Zn-Aryl), organocopper [e.g., (Aryl)$_2$-CuLi], organotin (e.g., Aryl-Sn(CH$_3$)$_3$, Aryl-Sn(CH$_2$CH$_2$CH$_2$CH$_3$)$_3$], or other organometallic reagents to afford the cross-coupling product. If the desired aryl organozinc (e.g., Aryl-ZnBr, R$_1$—ZnCl, Aryl-Zn-Aryl), organocopper [e.g., (Aryl)$_2$-CuLi], organotin (e.g., Aryl-Sn(CH$_3$)$_3$, Aryl-Sn(CH$_2$CH$_2$CH$_2$CH$_3$)$_3$], or other organometallic reagent is not commercially available, they can readily be prepared by utilizing proper methods, known in the literature.

These types of coupling reactions require the use of appropriate solvents. Such solvents include, but are not limited to dioxane, THF, methylene chloride, chloroform, benzene, hexane, ethyl ether, tert-butyl methyl ether or a combination or a mixture thereof. The coupling reaction may, or may not, require the presence of catalytic amount of a catalyst. Such catalysts include, but are not limited to tetrakis(triphenylphosphine)palladium (0), $PdCl_2$, $Pd(OAc)_2$, $(CH_3CN)_2PdCl_2$, $Pd(dppf)_2$.

The reaction temperature can be varied from −78° C. to >100° C., i.e. reflux temperature of the solvent. Alternatively, this reaction process step may be performed under suitable microwave irradiation conditions, if needed. This reaction may, or may not, require a sealed reaction vessel and the internal pressure can be varied from one atmosphere to 100 atmospheres.

Method E is for the transformation of the suitable precursor (e.g., acidic group —COOH in 4, 5, 9, 11, 15, 16, 17, or 18) to the final substituent $R_1$. This type of transformations can be achieved by utilizing well-established strategies in the art. The transformation may be done in one step (such as coupling with amines $HN(R_{10'})R_b$ under standard coupling conditions e.g. EDC/HOBT/$ET_3N$ in $CH_3CN$; coupling with alcohol, $HOR_b$ under standard coupling conditions, e.g. DCC, DMAP in DCM to form esters or reduction to alcohol) or in more than one step (e.g., Curtuis rearrangement to form isocyanates followed by urea formation with amines or acid chloride formation followed by addition of an amine, $HN(R_{10'})R_b$ or an alcohol, $HOR_b$ plus a non-nucleophilic base, e.g. DIPEA in an aprotic solvent like DCM. This conversion may require a deprotection step to install the precursor at first (e.g., hydrolysis of —$CO_2Me$ with LiOH/THF/water to prepare —COOH).

Scheme 1

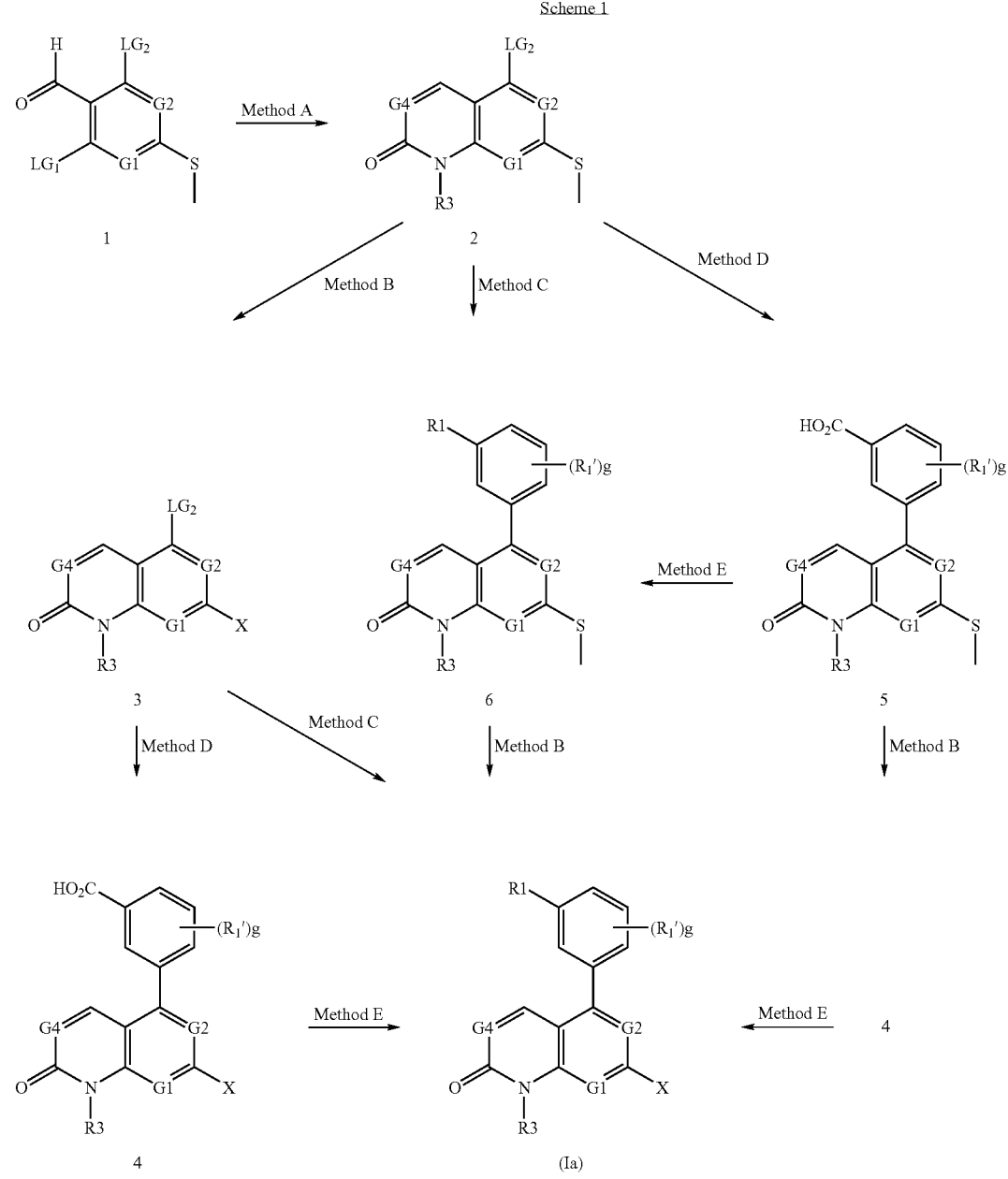

Examples of Reagents for methods C & D

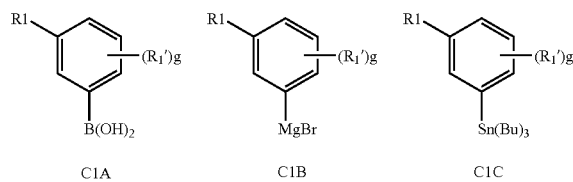

C1A     C1B     C1C

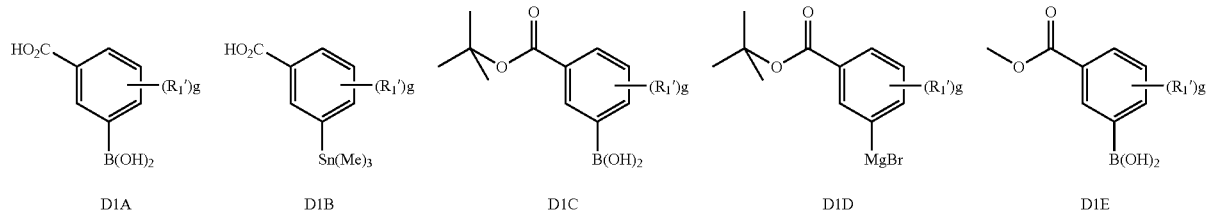

D1A     D1B     D1C     D1D     D1E

Preparation of compounds with Formula (Ia) can also be achieved through compound 7, which in turn may be constructed from aldehyde 1 as shown in Scheme 2. Suitable methods from Methods A-E can be utilized to furnish appropriate conversions in Scheme 2.

Method F is for selective displacement of suitable aldehyde 1 with an amine ($R_3$—$NH_2$). This type of displacement may be achieved using triethylamine and the desired amine $R_3NH_2$ in chloroform at room temperature for 10 minutes. The reaction was very effective for a range of alkyl amines (78-95% yield). For aryl or heteroaryl amines, elevated temperatures (reflux or microwave irradiations), longer reaction times (overnight or 24 hours) and presence of NaH (or Na) may be necessary for reaction completion. Use of the base could be omitted when 3 or more equivalent of desired amine were used. Other suitable bases include but are not limited to pyridine, diisopropyl ethylamine or pyrrolidine, which may also be used in an appropriate organic solvent, including but not limited to THF, diethyl ether, DCM, DMF, DMSO, toluene or dioxane.

Method G is for cyclization of 8 to 9. It may be achieved by mixing compound 8 with an olefin forming agent (e.g., Wittig reagents) or amide forming agent (e.g., acid, acid chloride, ester) or an agent with both potential reactivities such as bis(2,2,2-trifluoroethyl)-(methoxycarbonylmethyl)-phosphonate, bis(2,2,2-trifluoroethyl)-(ethoxycarbonylmethyl) phosphonate, bis(2,2,2-trifluoroethyl)-(isopropoxycarbonyl-methyl)phosphonate, (diethoxy-phosphoryl)-acetic acid methyl ester, (diisopropoxy-phosphoryl)-acetic acid methyl ester, (diphenyloxy-phosphoryl)-acetic acid methyl ester, (diethoxy-phosphoryl)-acetic acid ethyl ester, (diisopropoxy-phosphoryl)-acetic acid ethyl ester, (diphenyloxy-phosphoryl)-acetic acid ethyl ester, acetic acid, thioacetic acid, acetic acid anhydride, meldrums acid, or acetyl chloride. Elevated temperatures (reflux or microwave irradiations), longer reaction times (over night or 24 hours) and presence of triethyl amine, diisopropyl ethyl amine, NaOAc, or NaH (or Na) may be necessary for reaction completion. Reaction solvent can be DCM, THF, toluene, DMSO or DMF. During the cyclization, the protected group (—$CO_2Me$ in 8) may or may not be hydrolyzed. Either output may be utilized to the advantage of expanding structure-activity-relationship (SAR) studies. If necessary, the hydrolysis can be achieved by mixing with LiOH in THF/water. A different protecting group at this position (e.g., tert-butyl) may require a different de-protection method (e.g., treatment with TFA).

Scheme 2

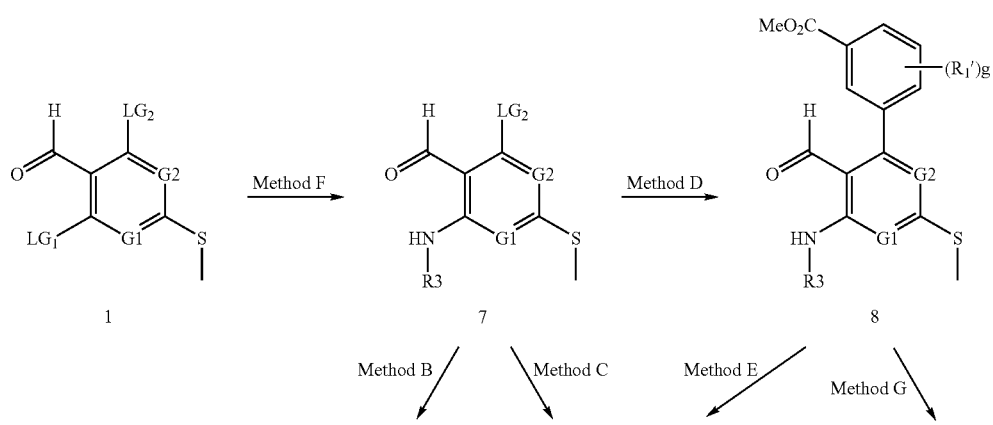

-continued

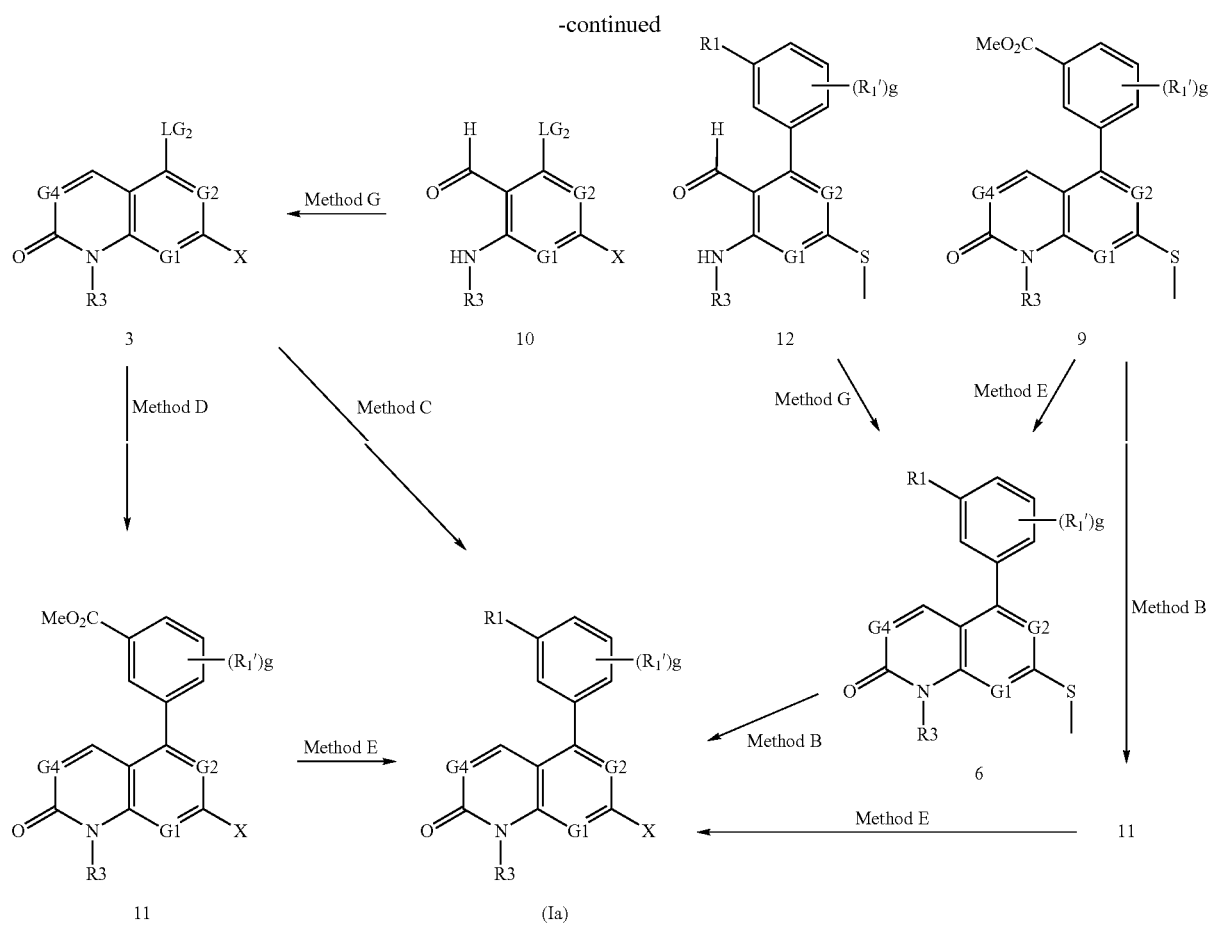

Preparation of compounds with Formula (I) can be achieved through compound 14, which in turn may be constructed from aldehyde 1 as shown in Scheme 3. Suitable methods from Methods A-G can be utilized to furnish appropriate conversions in Scheme 3.

Method H is for the reduction of a double bond that is directly connected to a carbonyl group [—C(=O)—]. This type of conversion can be achieved by utilizing suitable methods well documented in the literature for the 1,4-reduction of an enone system [e.g., —CH=CH—C(=O)—]. These methods include, but not limited to, Li/NH$_3$, H$_2$ (catalyst Rh—Al$_2$O$_3$), NaBH$_4$/CoCl$_2$.6H$_2$O, NaBH$_3$CN/ZnCl$_2$, LiHCu(n-Bu), or Et$_3$SiH.

Scheme 3

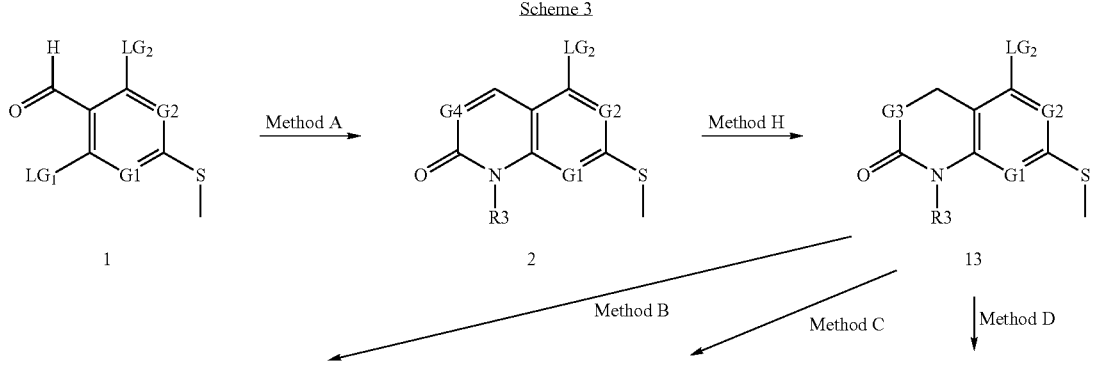

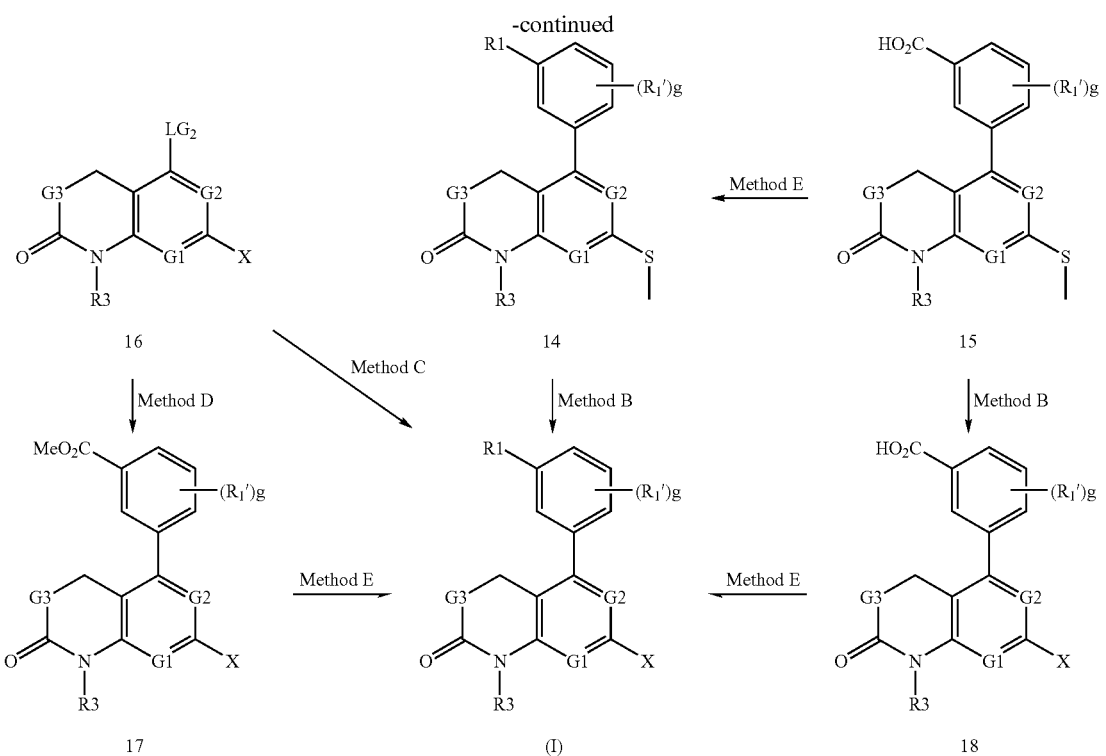
Preparation of compounds with Formula (I) may also be achieved through compound 2, which in turn may be constructed from aldehyde 1 as shown in Scheme 4. Suitable methods from Methods A-H can be utilized to furnish appropriate conversions in Scheme 4.
Scheme 4
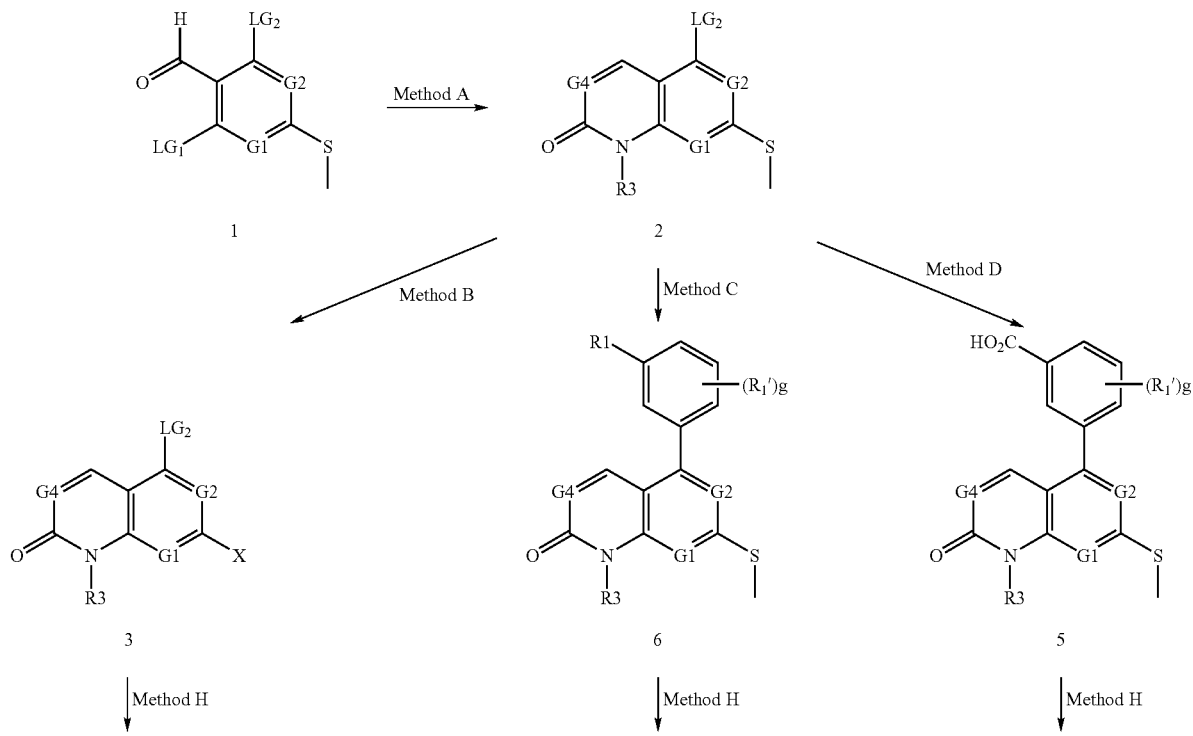

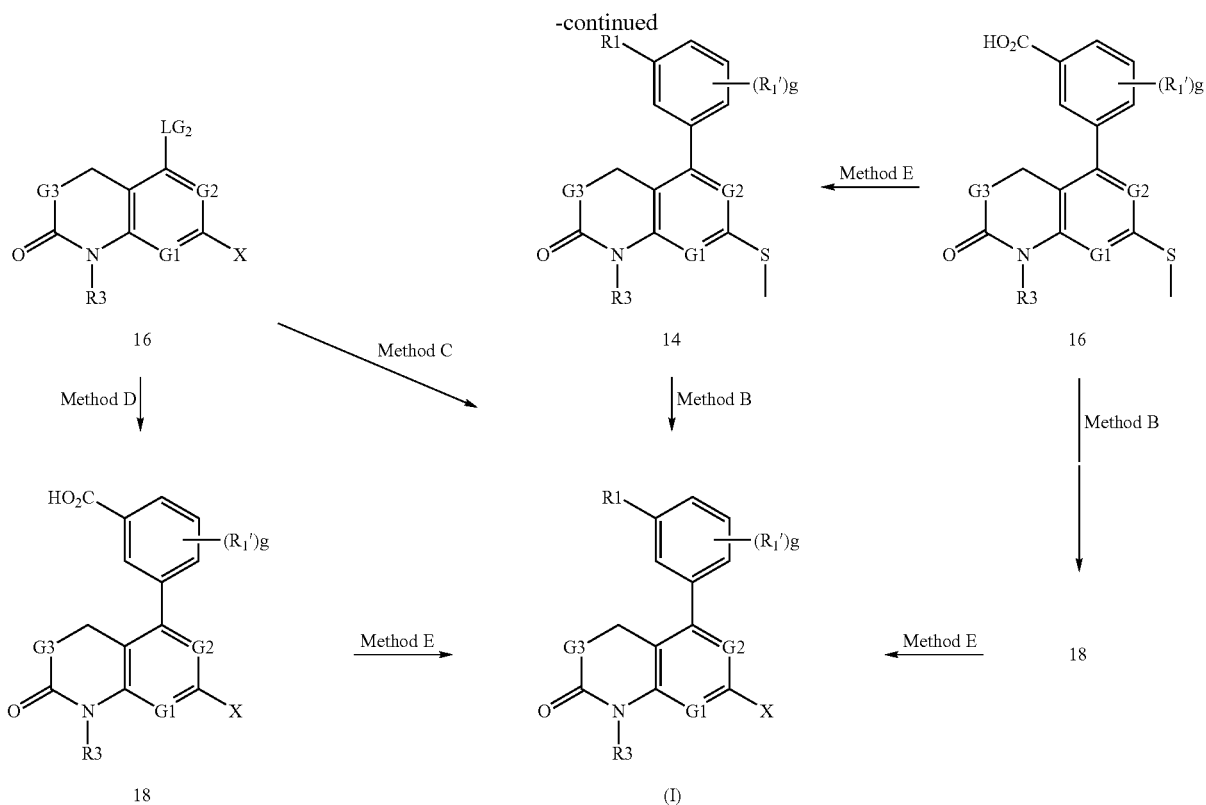
Preparation of compounds with Formula (I) may also be achieved through compound 2, which in turn may be constructed from aldehyde 1 as shown in Scheme 5. Suitable methods from Methods A-H can be utilized to furnish appropriate conversions in Scheme 5.
Scheme 5
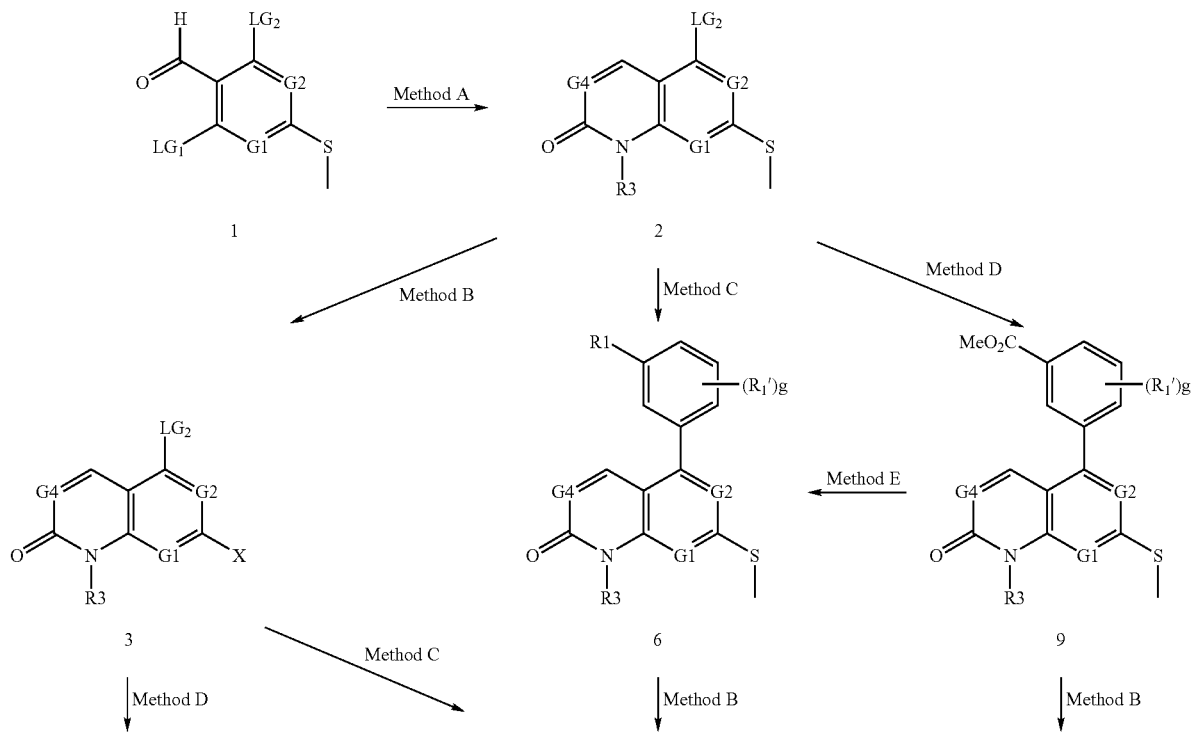

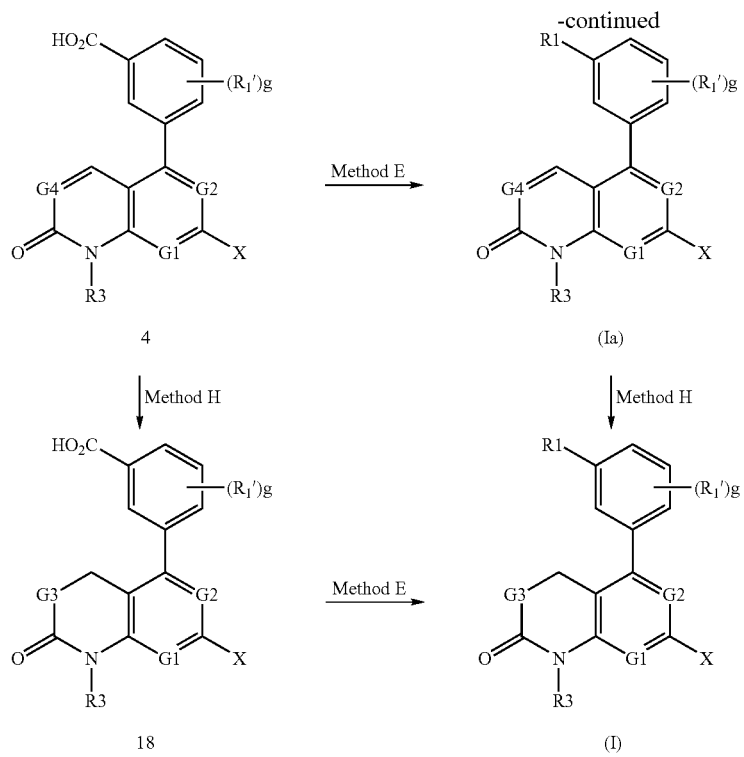

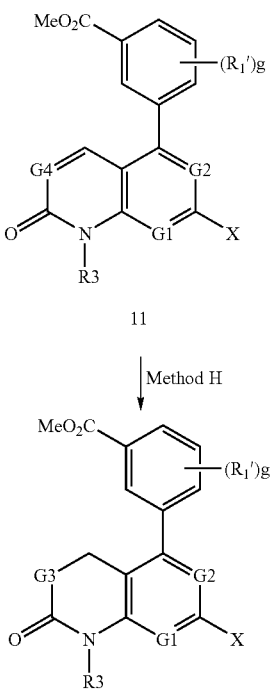

The compounds of Formula (II) and (IIa), (III) and (IIIa), (IV) and (IVa), (V) and (Va), (VI) and (VIa-VIi) may be obtained by applying the synthetic procedures described above in Schemes 1 to 5 except suitable reagents in Method C & D should be utilized. Examples of these reagents include, but not limited to those shown in Scheme 6. Suitable reagents in Method C & D for the preparation of compounds with Formula (VIb-VIi) require the presence of G5-8 in appropriate position.

Scheme 6

Examples of Reagents in Method C & D for the Preparation of Compounds with Formula (II) & (IIa)

C2A

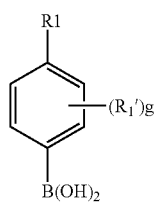

C2B

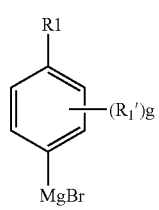

-continued

C2C

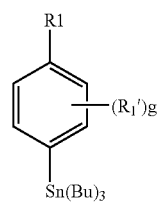

D2A

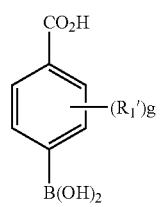

D2B

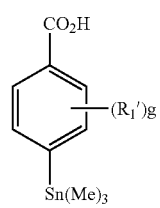

D2C

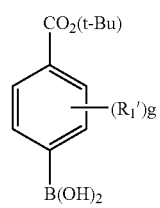

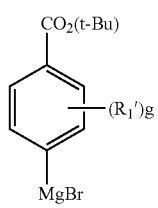
D2D
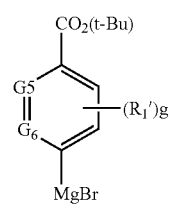
D3D
Examples of Reagents in Method C & D for the Preparation of Compounds with Formula (III) & (IIIa)
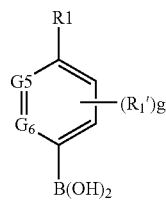
C3A
C4A
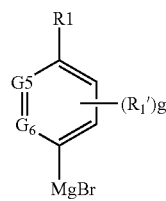
C3B
C4B
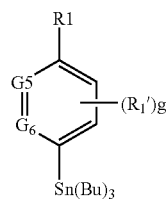
C3C
C4C
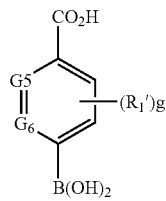
D3A
D4A
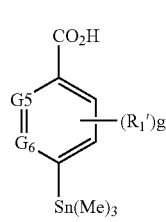
D3B
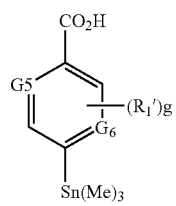
D4B
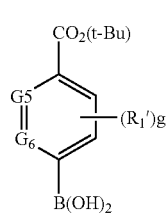
D3C
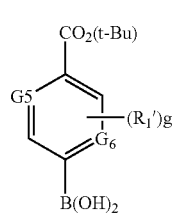
D4C
Examples of Reagents in Method C & D for the Preparation of Compounds with Formula (IV) & (IVa)

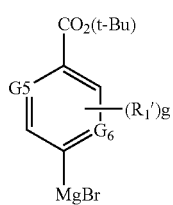
D4D

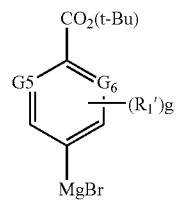
D5D

Examples of Reagents in Method C & D for the Preparation of Compounds with Formula (V) & (Va)

Examples of Reagents in Method C & D for the Preparation of Compounds with Formula (VI) & (VIa)

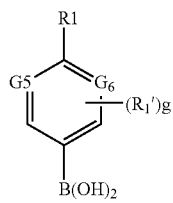
C5A

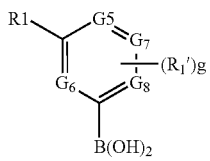
C6A

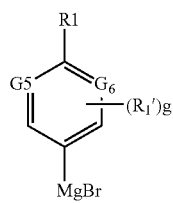
C5B

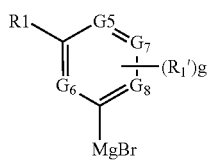
C6B

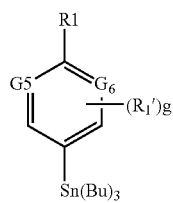
C5C

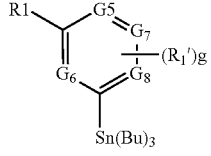
C6C

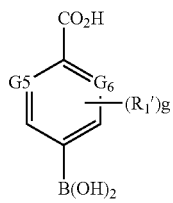
D5A

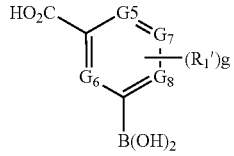
D6A

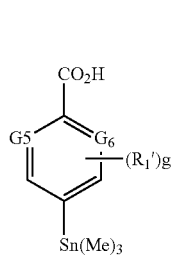
D5B

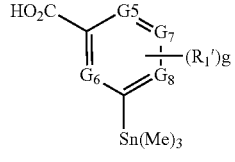
D6B

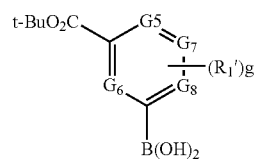
D6C

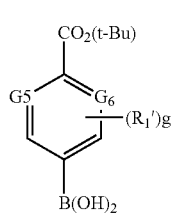
D5C

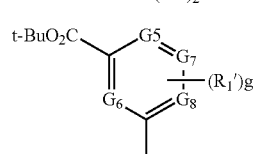
D6D

The starting material 1-Scheme 7 may be obtained from the commercially available 4,6-dihydroxy-2-methylmercapto-pyrimidine by known literature procedures, such as those noted in Santilli et al., *J. Heterocycl. Chem.* (1971), 445-53, wherein $POCl_3$ and DMF are used.

The intermediate 2-Scheme 7 was produced by two different routes. In the first route, coupling of dichloro aldehyde 1-Scheme 7 with aryl amines in the presence of NaH in DMSO (Santilli et al., *J. Heterocycl. Chem.* (1971), 445-53) afforded the desired compound 2-Scheme 7 along with imine 13-Scheme 7. The imine was converted to aldehyde 2-Scheme 7 by treatment with aqueous HCl in THF. Conversion of 1-Scheme 7 to 2-Scheme 7 may also be achieved using triethylamine and the desired amine in chloroform at room temperature for 10 minutes. The reaction was very effective for a range of alkyl amines (78-95% yield). For aryl amines, elevated temperatures (reflux) and longer reaction time (24 hours) were necessary for reaction completion. Use of the base could be omitted when 3 or more equivalent of amine were used. Other suitable bases, include but are not limited to pyridine, diisopropyl ethylamine or pyrrolidine, which may also be used in an appropriate organic solvent, including but not limited to THF, diethyl ether or dioxane.

In the second route, the nitrile 9-Scheme 7 was prepared in three steps from the aldehyde 1-Scheme 7 (Santilli et al., *J. Heterocycl. Chem.* (1971), 445-53). Coupling of dichloro nitrile 9-Scheme 7 with aryl amines in the presence of NaH in DMSO afforded the desired compound 10-Scheme 7. Other suitable bases such as pyridine, diisopropyl ethylamine, or sodium may also be used in an appropriate organic solvent such as THF, DMF or dioxane. Production and use of the nitrile 9-Scheme-I may also be found in PCT/US01/06688, filed Mar. 2, 2001 whose disclosure is incorporated herein by reference in its entirety.

The nitrile 10-Scheme 7 was easily reduced with DIBAL in dichloromethane at room temperature (Boschelliat et al., *J. Med. Chem.* (1998), 4365-4377) to afford desired 2-Scheme 7 along with the unsubstituted imine 13-Scheme 7 (R=H). The latter was hydrolyzed to 2-Scheme 7 in situ with HCl. Other reduction agents, such as lithium aluminum hydride, Raney Ni, or $SnCl_2$, may be utilized in an appropriate organic solvent such as THF, diethyl ether or dioxane to perform the conversion of 10-Scheme 7 to 2-Scheme 7.

Aldehyde 2-Scheme 7 was coupled to arylboronic acids under Suzuki coupling conditions, using a palladium catalyst, such as tetrakis(triphenylphosphine) palladium(0), to afford good to excellent yields of 3-Scheme 7. Alternatively, the bi-aryl coupling reaction of 2-Scheme 7 may be performed using aryl or heteroaryl organozinc, organocopper, organotin, or other organometallic reagents known to afford bi-aryl cross-coupling products such as 3-Scheme 7 [see for example Solberg, J.; Undheim, K. *Acta Chemica Scandinavia* 1989, 62-68]. Displacement of the chlorine in 2-Scheme 7 may also be achieved with nitrogen nucleophiles [for related aminations see U.S. Pat. Nos. 3,631,045 and 3,910,913], sulphur nucleophiles, [see Tumkevicius, S. *Liebigs Ann.* 1995, 1703-1705], oxygen nucleophiles, or alkyl nucleophiles.

3-Scheme 7 was then converted to pyridopyrimidinone 5-Scheme 7 by one of three procedures. The first procedure used the Wittig reaction, as modified by Homer-Emmons, converting 3-Scheme 7 to 4-Scheme 7. In this reaction, the aldehyde 3-Scheme 7 was treated with a suitable phosphorus ylide, such as triethyl phosphonoacetate or methyl diethylphosphonoacetate, to give the olefin intermediate 4-Scheme 7. The reaction was performed under reflux, in a suitable base, such as sodium hydride, sodium methoxide, or sodium hydroxide, and in a suitable organic solvent such as diethyl ether, dioxane or ethanol. The conversion of 3-Scheme, 7 to 4-Scheme 7 may also be performed using the Peterson olefination reaction, or an aldol-based olefination reaction that utilizes acetic anhydride, malonic acid and its monoalkyl esters, or ethyl acetate.

Heating of 4-Scheme 7 in toluene at 220° C. in a sealed tube (Matyus et al. *Heterocycles* (1985), 2057-64), followed by solvent removal, afforded the desired product 5-Scheme 7. This reaction may be run in the presence of a suitable base, such as DBU or diisopropylethyl amine, pyridine, lithium bi(trimethylsilyl)amide, or LDA and in an appropriate organic solvent such as an organic hydrocarbon, cresol, dioxane, DMF, pyridine, or xylene.

The second procedure used a Homer-Emmons reaction with Still modification (Still et al., *Tetrahedron Lett.* (1983), 4405-8; Jacobsen et al., *Tetrahedron* (1994), 4323-34) to produce a mixture of desired product 5-Scheme 7 and trans isomer 4-Scheme 7. Trans isomer 4-Scheme 7 was isolated and converted to the desired product 5-Scheme 7 by heating to 220° C. in toluene in a sealed tube as described above.

The third procedure involved acetylation of 3-Scheme 7, followed by the intramolecular aldol condensation, promoted by an acetylating agent (such as acetic anhydride, acetyl chloride, or a ketene) and a suitable base (such as pyridine, diisopropyl ethylamine, or pyrrolidine), to generate 5-Scheme 7 in a very good yield. The third procedure is optimal when $R_3$ is an optionally substituted aryl, or heteroaryl. When $R_3$ is an arylalkyl, or heteroarylalkyl substituent it is not clear that the reaction will form the key intermediate of Formula (VII), as shown below (3a-Scheme 8), which may optionally be isolated, as shown in Scheme 8 below. Compounds of Formula (VII) are preferably not isolated but further reacted with a base or with heat to cyclize into 5-Scheme-7. The first and second procedures should be utilized for all other $R_3$ moieties.

Oxidation of the sulfide 5-Scheme 7 to the sulfone 6-Scheme 7 was performed using meta-chloroperoxybenzoic acid (mCPBA) in high yield and purity. Suitable oxidation methods for use herein include use of one or two equivalents of meta-chloroperoxybenzoic acid (mCPBA) or Oxone® to afford either the sulfoxides or sulfones. Oxidation of the sulfides to sulfoxides or sulfones can also be effected by $OsO_4$ and catalytic tertiary amine N-oxide, hydrogen peroxide, other peracids, oxygen, ozone, organic peroxides, potassium and zinc permanganate, potassium persulfate, and sodium hypochlorite.

Displacements of the sulfones 6-Scheme 7 to the final products 7-Scheme-7 were usually done with an excess of amine in N-methylpyrrolidine (Barvian et al., *J. Med. Chem.* (2000), 4606-4616). A wide range of primary amines underwent this reaction with excellent yields. In some cases (in O-displacement or sulfonamide formation) an anion of the nucleophile was prepared with base (usually sodium hydride) in dimethylformamide and then added to the sulfone. Yields for these reactions were usually lower. Similarly related sulfones and sulfoxides of the compounds herein wherein X is SO-alkyl or $SO_2$-alkyl have been reported in the literature to be displaced by a wide variety of nucleophiles. Thus the analogs of the compounds herein wherein X is an alkyl sulfone or sulfoxide may be displaced by primary and secondary alkylamines with or without additional base catalysis, preferably in a polar aprotic solvent, such as but not limited to, N-methyl pyrrolidin-2-one (NMP), and at varying temperatures depending upon the nucleophilicity of the amine. For instance displacement of the sulfone of analogs of Formula (I) compounds with ethanolamine, in NMP, occurred in 30 min. at 65° C., while a more hindered amine such as tris(hydroxymethyl)-aminomethane may require elevated temperatures and extended reaction times (80° C. over a 24 hour reaction time). The sulfone can also be displaced by a primary or secondary amine with an additional non-nucleophilic base (e.g. DIPEA) in aprotic solvents like DCM, $CH_3CN$, NMP, and at varying temperatures depending upon the nucleophilicity of the amine.

The sulfone may also be displaced with a substituted arylamine, or heteroarylamine at elevated temperatures, sometimes requiring formation of the aryl or heteroarylamine anion with sodium hydride, or other suitable base, in DMSO. In addition, the sulfoxide analogs of Formula (I) compounds may be readily displaced with aluminum salts of aryl or heteroaryl amines as previously described in the patent literature (WO 99/32121). Likewise, sulfone and sulfoxide analogs of Formula (I) and (Ia) may be displaced with aryl or heteroaryl or alkyl thiols or alkyl or aryl or heteroaryl alcohols. For instance analogs of (I) containing sulfones as the X substituents may be displaced with sodium alkoxide in the alcohol, or alternatively reactive alkoxide or phenoxide nucleophiles may be generated from the alcohol or phenol with a suitable base such as sodium, NaH or sodium bistrimethylsilyl amide in a polar aprotic solvent such as DMSO, or run as a neat reaction. Similarly sulfones related to Formula (I) and (Ia), for instance, may be displaced with carbon nucleophiles such as aryl or alkyl Grignard reagents or related organometallics such as organo lithium, zinc, tin or boron. These reactions may, in some cases, require transition metal catalysis such as with Pd or Ni catalysts. Displacement of related 2-pyrimidine sulfones with cyanide, malonate anions, unactivated enolates, or heterocyclic C nucleophiles such as 1-methylimidazole anion, by the generation of the anion with NaH or other suitable base in THF also has precedent (see for example, Chem Pharm Bull. 1987, 4972-4976.). For example, analogs of Formula (I) and (Ia) compounds wherein X is an alkyl sulfone may be displaced with the anion of 1-methyl imidazole, generated by treatment of 1-methyl imidazole with n-butyl lithium in a solvent such as THF at temperatures of about −70°, to afford the C-alkylated product substituted on the imidazole C-2.

For the purposes herein, compounds of Formulas (I), (Ia), (II) and (IIa) wherein X is $R_2$ or $NHS(O)mR_2$ may be obtained from compounds of 6-Scheme 7 by displacement of the sulfone using the appropriate "X" functionality as defined in Formula (I) and (Ia). To obtain compounds of Formulas (I), (Ia), (II) and (Ia) wherein X is $S(O)_m R_2$ and $R_2$ is other than methyl, displacement of the sulfone on the corresponding compound 6-Scheme 7 by thiol ($R_2SH$) and then followed by oxidation, if desired, with an appropriate oxidating agent, such as MCPBA, or $KMnO_4$. Suitable oxidation methods for use herein include use of an oxidant such as one or two equivalents of meta-chloroperoxybenzoic acid or Oxone® to afford either the sulfoxides or sulfones. Oxidation of the sulfides to sulfones may also be effected by $OsO_4$ and catalytic tertiary amine N-oxide. Other methods for sulfide oxidation include the use of hydrogen peroxide, other peracids, oxygen, ozone, organic peroxides, potassium and zinc permanganate, potassium persulfate, and sodium hypochlorite.

8-Scheme 7 can be also prepared by heating the trans ester 4-Scheme 7 in alcohol in the presence of the corresponding sodium alkoxide. The yield of this reaction was very high for primary alcohols, but longer reaction times were required for secondary alcohols. Sodium alkoxides may be easily prepared from corresponding alcohol and base, such as sodium or sodium hydride.

Reduction of trans ester 4-Scheme 7 with $SmI_2$ gives the reduced analogue 11-Scheme 7. This reduction can be also done in the presence of other reducing agents such as hydrogen gas, lithium in liquid ammonia, magnesium or sodium borohydride in the appropriate organic solvent such as THF, ethanol or diethyl ether.

Cyclization of the ester 11-Scheme 7 can be done utilizing sodium methoxide in methanol to give reduced analogue 12-Scheme 7. Other organic bases, such as sodium, sodium ethoxide or TEA can be used in an appropriate organic solvent such as methanol, ethanol or dioxane. The product 12-Scheme 7 can be also obtained by heating ester 11-Scheme 7 to 150° C. in an appropriate organic solvent, such as toluene, xylene or isopropanol.

Scheme 7

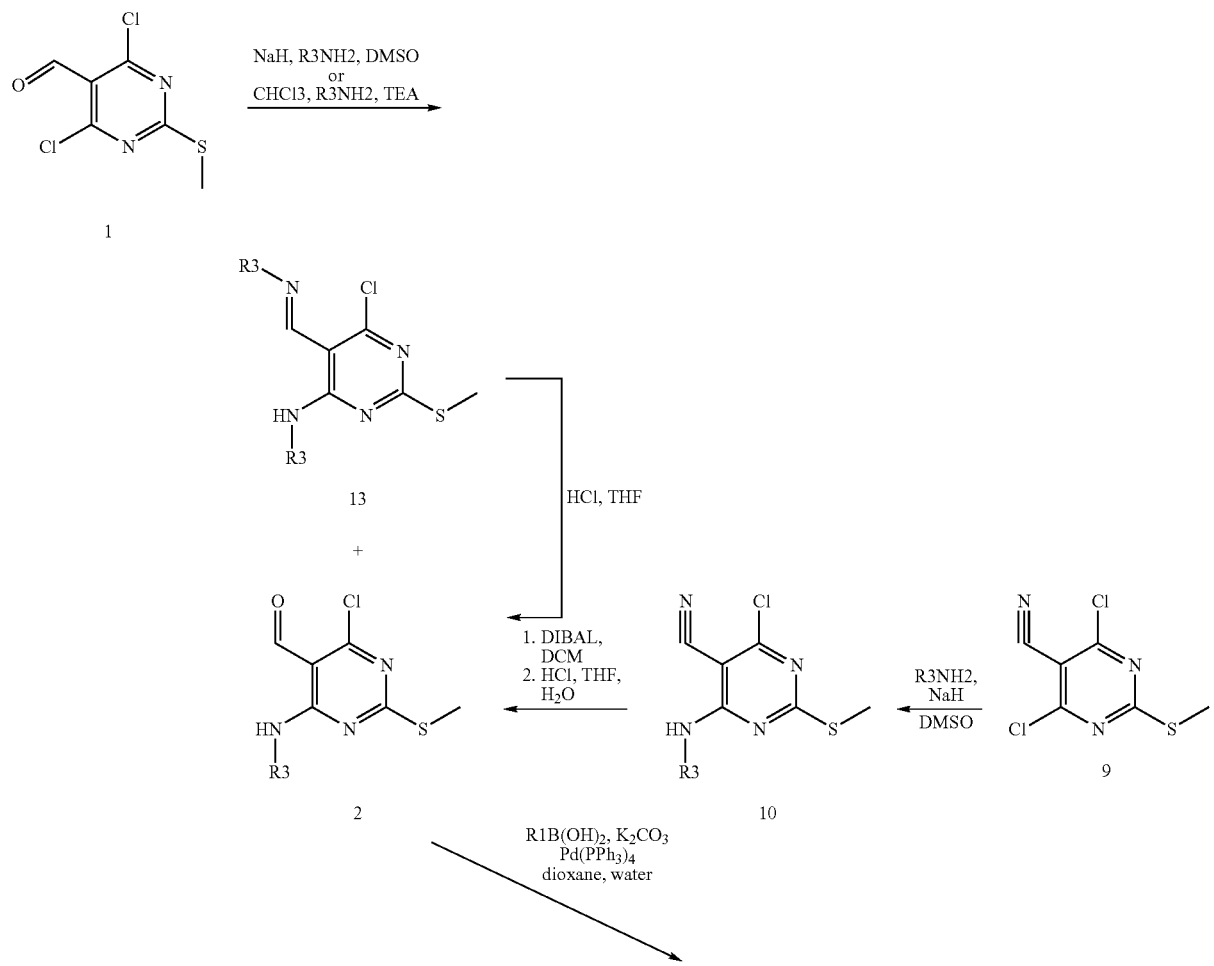

-continued
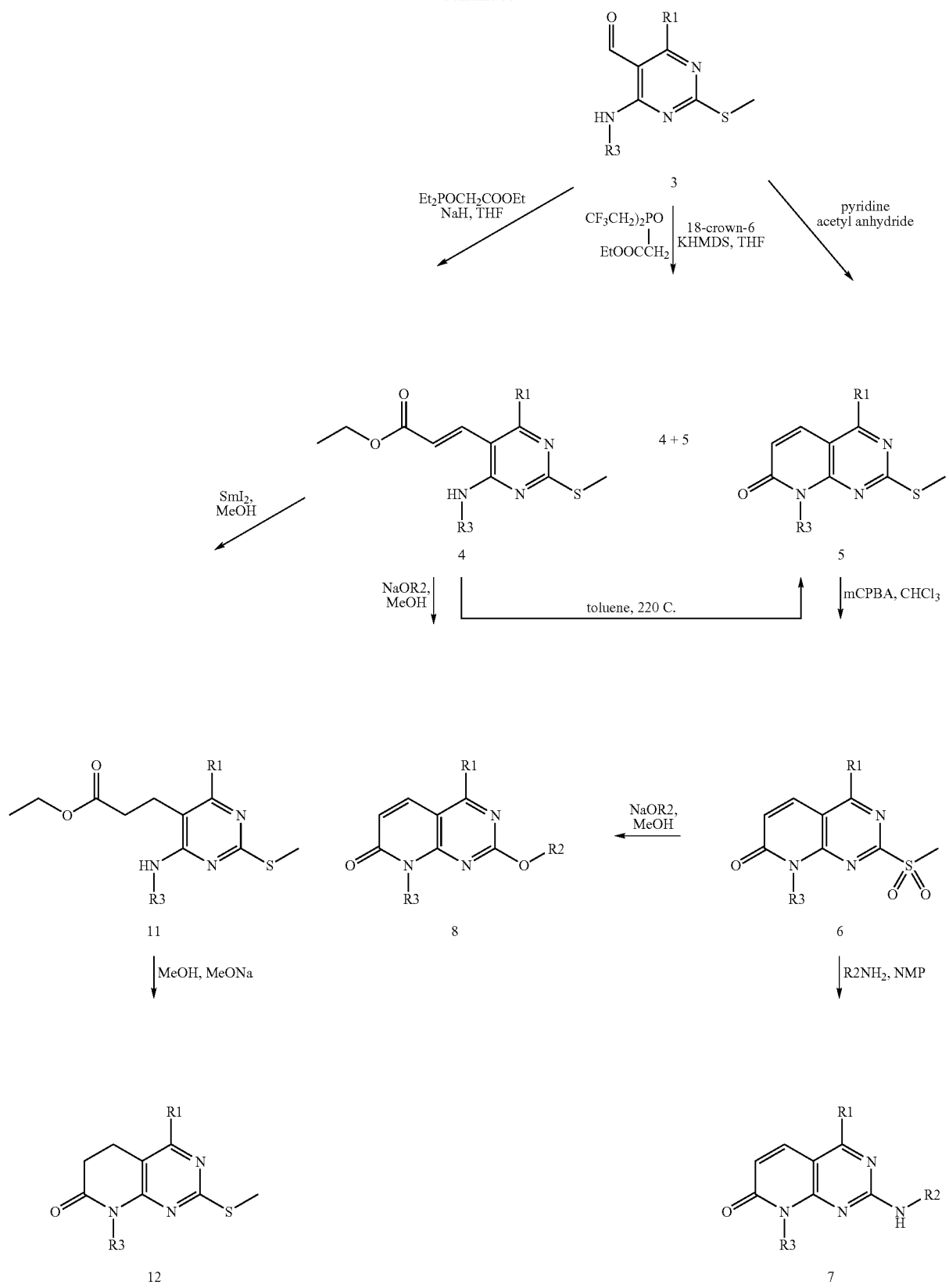

Additional procedures for producing similar intermediates to those herein, which the skilled artisan may find may be found in WO 99/41253, now U.S. Pat. No. 6,200,977; U.S. Pat. No. 6,153,619; U.S. Pat. No. 6,268,310; U.S. Pat. No. 5,468,751; U.S. Pat. No. 5,474,996; and EP 1 040 831.

An illustration for an alternative preparation of compounds of Formula (VII) is shown in Scheme 8 below.

Scheme 8

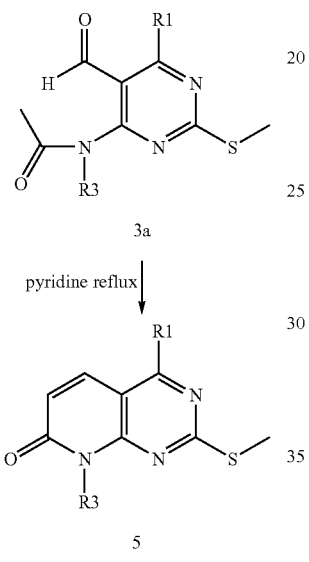

Preparation of compounds with Formula (A), (A1), (B) or (B1) can be achieved from appropriate intermediates in Scheme 1 through Scheme 5 using proper synthetic methods known to the scientists with appropriate training in the literature. An example of these types of preparations is demonstrated, but not limited to, in Scheme 9. The preparation can be achieved by reacting compound 16 (for A or B) or 3 (for A1 or B1) with another reagent with appropriate structures as shown in Scheme 9 employing Method I.

Method I is for the substitution of $-LG_2$ with appropriate compound containing the structural unit of —Y—H. This can be achieved by heating the reaction mixtures in appropriate solvents. The heating method can be selected from either a regular oil bath or microwave irradiations. Solvents can be $CH_2Cl_2$, DMSO, DMF, toluene, benzene, $CH_3CN$ or NMP. The reaction may or may not require the presence of bases. An example of the base can be selected from, but not limited to triethyl amine, diisopropyl ethyl amine, NaH, n-BuLi, tert-BuLi, tert-BuOK, $Li_2CO3$, $Cs_2CO_3$ and pyridine. This transformation may also require the presence of catalytic amount of catalysts containing transition metals (e.g., Pd, Cu, Ni, or W). These catalysts include, but not limited to Pd/C, $Pd(PPh_3)_4$ and $PdCl_2$. Compounds that have $Y=S(O)_m$ or $S(O)_mC(R_y)(R_z)$ may also be prepared by the oxidation of their corresponding compounds with $Y=S$ or $SC(R_y)(R_z)$. Suitable oxidation methods for use herein include, but not limited to mCPBA, Oxone, $OsO_4$, $H_2O_2$, potassium and zinc permanganate.

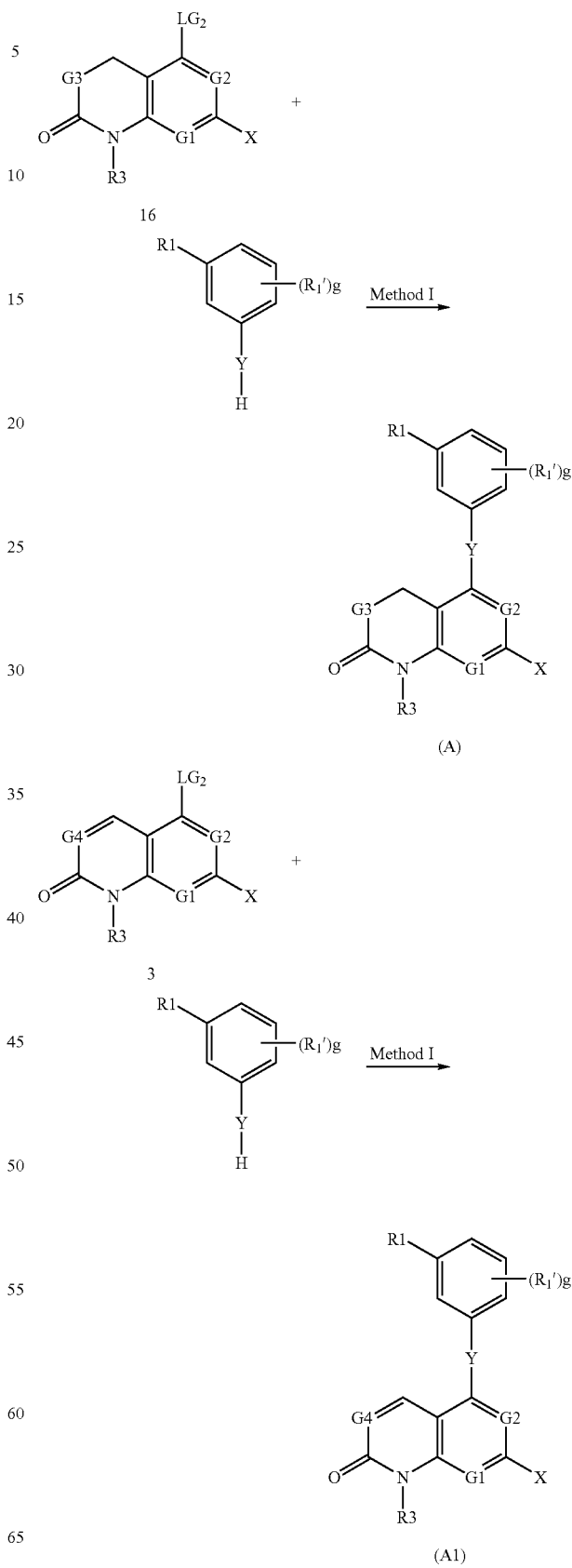

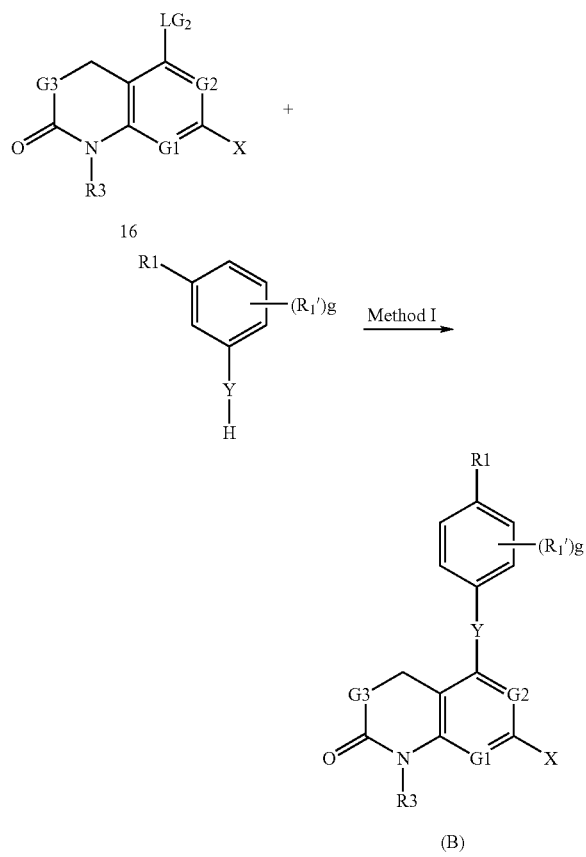

(B)

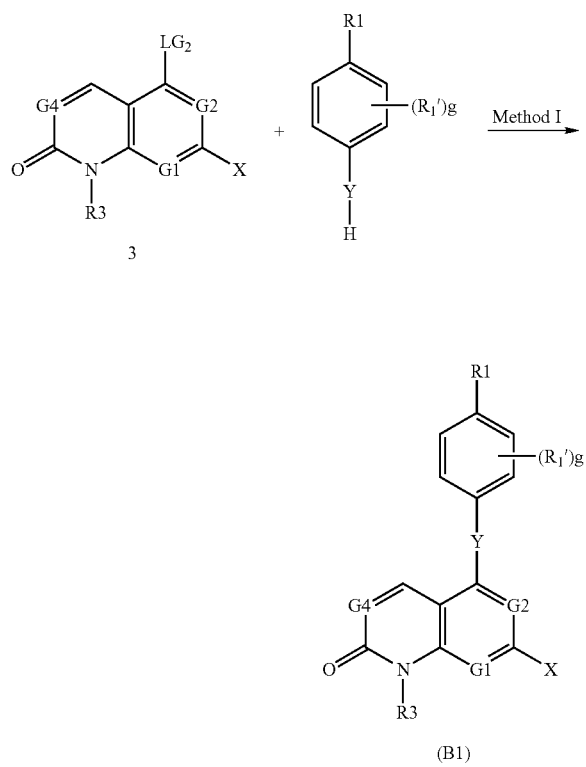

(B1)

Another aspect of the invention are the novel intermediates of the formula (X)

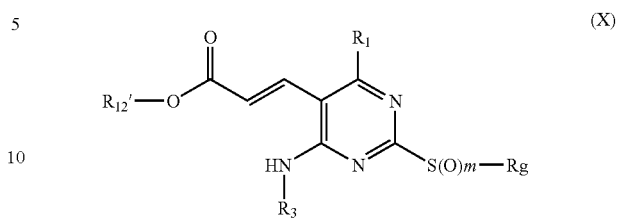

wherein $R_1$ is an aryl ring substituted as defined in compounds of Formula (I) and (II) inclusive;

$R_3$ is an $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted;

$R_{12'}$ is a $C_{1-10}$ alkyl, aryl, heteroaryl, or arylalkyl;

m is 0 or an integer having a value of 1 or 2; and

Rg is a $C_{1-4}$ alkyl.

Preferably, Rg is a $C_{1-4}$ alkyl, and more preferably methyl.

Preferably, m is 0 or an integer having a value of 1 or 2. More preferably m is 0 or 2.

Another aspect of the invention are the novel intermediates of the formula (XI)

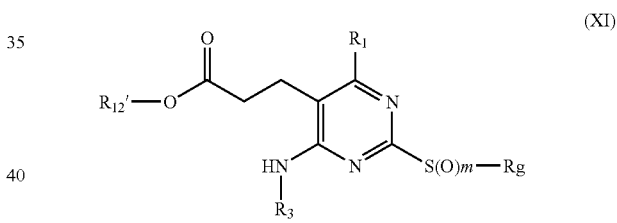

wherein $R_3$, $R_{12'}$, m and $R_g$ are as defined for Formula (VII) above; and $R_1$ is a ring substituted as defined in compounds of Formula (III).

Another aspect of the invention are the novel intermediates of the formula (XII)

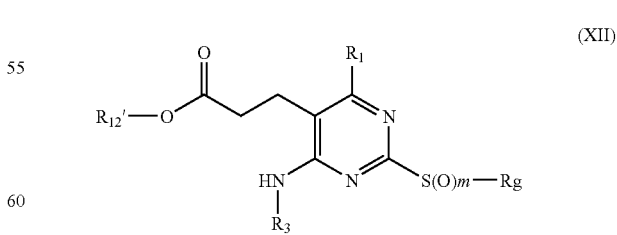

$R_3$, $R_{12'}$, m and $R_g$ are as defined for Formula (VII) above; and $R_1$ is a ring substituted as defined in compounds of Formula (IV).

Another aspect of the present invention are novel intermediates of the formula (XIII)

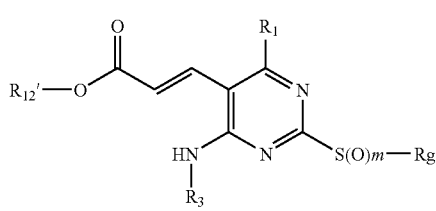

(XIII)

wherein $R_3$, $R_{12'}$, m and $R_g$ are as defined for Formula (VII) above; and $R_1$ is a ring substituted as defined in compounds of Formula (V).

Another aspect of the invention are the novel intermediates of the formula (XIV)

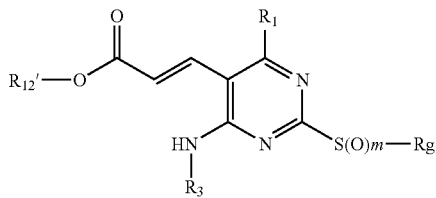

(XIV)

wherein $R_3$, $R_{12'}$, m and $R_g$ are as defined for Formula (VII) above; and $R_1$ is a ring substituted as defined in compounds of Formula (VI).

Another aspect of the present invention are the novel intermediates of the formula

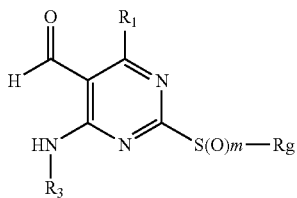

(XV)

wherein $R_1$ is a phenyl ring substituted as defined in Formula (I) or (II);

$R_3$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted; provided that when $R_3$ is hydrogen, then $R_1$ is other than chlorine;

m is 0 or an integer having a value of 1 or 2; and

Rg is a $C_{1-4}$ alkyl.

In one embodiment, $R_3$ is an optionally substituted $C_{1-10}$ alkyl, $C_{3-7}$ cycloalkyl, $C_{3-7}$ cycloalkylalkyl, or aryl.

In another embodiment the $R_3$ optional substituents are independently selected from halogen, alkyl, hydroxy, alkoxy, amino, or halosubstituted alkyl.

Another aspect of the invention are the novel intermediates of Formula (XVI)

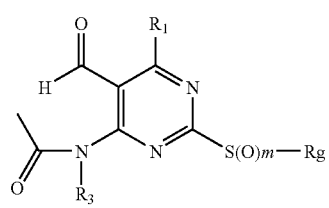

(XVI)

wherein $R_1$ is as defined above for Formula (I) and (II) compounds, and $R_3$, Rg, and m is an optionally substituted aryl or heteroaryl moiety, as defined for Formula (VII) compounds.

Another aspect of the invention are the novel intermediates of Formula (XVII)

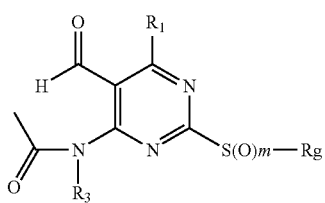

(XVII)

wherein $R_1$ is defined above for Formula (III) to (VI) compounds, and $R_3$, Rg, and m is an optionally substituted aryl or heteroaryl moiety, as defined for Formula (VII) compounds.

Another aspect of the invention are compounds of Formula (C) and (C1):

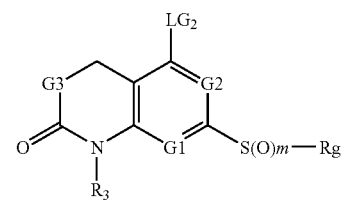

(C)

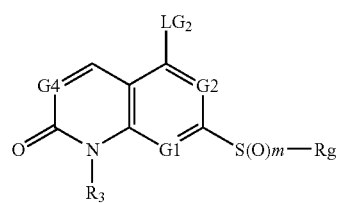

(C1)

wherein,

G1, G2, G3, and G4 are as described for Formula (I) and (Ia) herein;

m is 0 or an integer having a value of 1 or 2;

Rg is a $C_{1-10}$alkyl;

$LG_2$ is chlorine, bromine, iodine, or O—$S(O)_2CF_3$;

$R_3$ is a $C_{1-10}$ alkyl, $C_{3-7}$ cycloalkyl, $C_{3-7}$ cycloalkyl $C_{1-10}$ alkyl, aryl, aryl $C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted, and is as defined for compound of Formula (I) and (Ia) herein.

In one embodiment, Rg is methyl. In another embodiment, m is 0 or 1.

Another aspect of the invention are compounds of Formula (D) and (D1) represented by the structure:

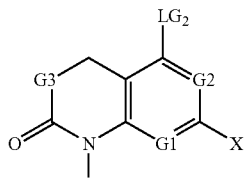
(D)

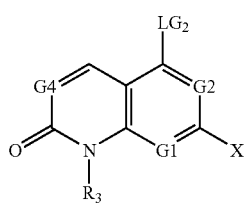
(D1)

wherein,
G1, G2, G3, G4 and X are as described for compounds Formula (I) and (Ia) herein;
$LG_2$ is chlorine, bromine, iodine, or O—S(O)$_2$CF$_3$;
$R_3$ is a $C_{1-10}$ alkyl, $C_{3-7}$ cycloalkyl, $C_{3-7}$ cycloalkyl $C_{1-10}$ alkyl, aryl, aryl $C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted (and are as defined for compounds of Formula (I) and (Ia) herein).

Another aspect of the invention compounds of Formula (E) and (E1) represented by the structure:

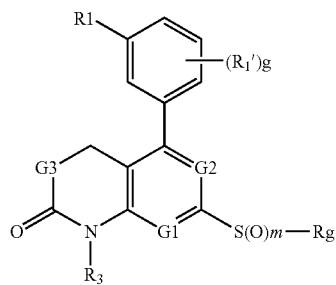
(E)

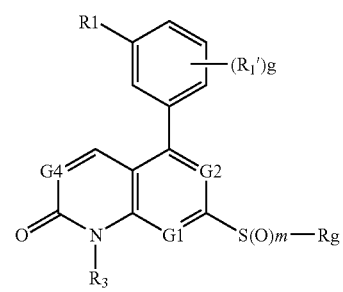
(E1)

wherein,
G1, G2, G3, G4, $R_1$ and $(R_1)_g$ are as described for compounds of Formula (I) and (Ia) herein;
m is 0 or an integer having a value of 1 or 2;
Rg is a $C_{1-10}$alkyl;
$LG_2$ is chlorine, bromine, iodine, or O—S(O)$_2$CF$_3$;
$R_3$ is a $C_{1-10}$ alkyl, $C_{3-7}$ cycloalkyl, $C_{3-7}$ cycloalkyl $C_{1-10}$ alkyl, aryl, aryl $C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted (as defined for compounds of Formula (I) and (Ia) herein).

It is also recognized that a similar set of Formulas (F) and (F1) are contemplated when the $R_1$ moiety is substituted in the 3-position of the phenyl ring, as shown in compounds of Formula (II) and (IIa). Similar intermediates are also contemplated for the remaining Formulas herein wherein the C4 position of the pharmacophore is substituted with the various heteroaryl rings, e.g. G5/G6, etc. of the formulas described herein as Formula (III) and (IIIa), (IV) and (IVa), etc.

Another aspect of the invention are compounds of Formula (XVIII):

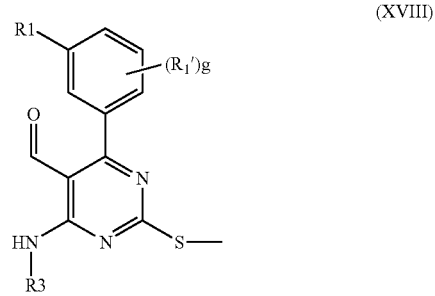
(XVIII)

wherein
$R_1$, $R_1'$, g, and $R_3$ are as defined for Formula (I) herein.

Another aspect of the invention are compounds of Formula (XIX):

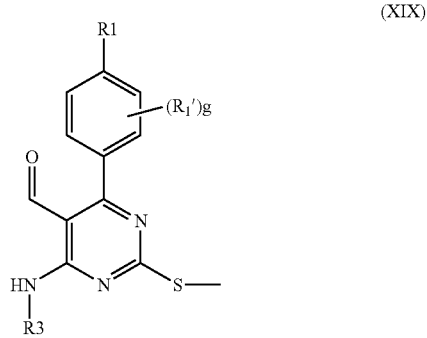
(XIX)

wherein
$R_1$, $R_1'$, g, and $R_3$ are as defined for Formula (II) herein.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an Ar atmosphere where necessary.

List of Abbreviations

| | |
|---|---|
| EDC: 1-(3-Dimethylaminopropyl)-3-ethylcarbodiimide hydrochloride | dppf: 1,1'-Bis(diphenylphosphino)ferrocene |
| DMAP: 4-(Dimethylamino)pyridine | DMSO: Dimethylsulfoxide |
| m-CPBA: 3-Chlorobenzene-carboperoxoic acid | EtOAc: Ethyl acetate |
| HPLC: High Pressure Liquid Chromatography | DIPEA or DIEA: N,N-Diisopropylethylamine |
| DCM: Dichloromethane | SPE: Solid phase extraction |
| TFA: Trifluoroacetic anhydride | MDAP: Mass directed auto preparation |
| HATU: O-(7-Azabenzotriazol-1-yl)-N,N,N',N'-tetramethyluronium hexafluorophosphate | HBTU: O-Benzotriazol-1-yl-N,N,N',N'-tetramethyluronium hexafluorophosphate |
| NIS: N-Iodosuccinimide | HOBT: 1-Hydoxybenzotriazole hydrate |
| DMF: N,N-Dimethylformamide | THF: Tetrahydrofuran |
| IPA: isopropyl alcohol | M: molar |
| DSC: differential scanning calorimetry | mmol: millimoles |
| mL: milliliters | aq: aqueous |
| mg: milligrams | eq: equivalents |
| rt: room temperature | mp: melting point |
| min: minutes | g: grams |
| L: liters | h: hours |
| mol: moles | satd: saturated |
| NMP = 1-methyl-2-pyrrolidinone | mEq: miliequivalents |

Other abbreviations as used herein are described in the ACS Style Guide (American Chemical Society, Washington, D.C., 1986), whose disclosure is incorporated by reference herein.

LC-MS Experimental Conditions:

Liquid Chromatograph

| | |
|---|---|
| System: | Shimadzu LC system with SCL-10A Controller and dual UV detector |
| Autosampler: | Leap CTC with a Valco six port injector |
| Column: | Aquasil/Aquasil (C18 40 × 1 mm) |
| Inj. Vol.(uL): | 2.0 |
| Solvent A: | $H_2O$, 0.02% TFA |
| Solvent B: | MeCN, 0.018% TFA |
| Gradient: | linear |
| Channel A: | UV 214 nm |
| Channel B: | ELS |

| Step | Time (min) | Dura. (min) | Flow (μL/min) | Sol. A | Sol. B |
|---|---|---|---|---|---|
| 0 | 0.00 | 0.00 | 300.00 | 95.00 | 5.00 |
| 1 | 0.00 | 0.01 | 300.00 | 95.00 | 5.00 |
| 2 | 0.01 | 3.20 | 300.00 | 10.00 | 90.00 |
| 3 | 3.21 | 1.00 | 300.00 | 10.00 | 90.00 |
| 4 | 4.21 | 0.10 | 300.00 | 95.00 | 5.00 |
| 5 | 4.31 | 0.40 | 300.00 | 95.00 | 5.00 |

| | |
|---|---|
| Mass Spectrometer: | PE Sciex Single Quadrupole LC/MS API-150 |
| Polarity: | Positive |
| Acquisition mode: | Profile |

General Procedures

Nuclear magnetic resonance spectra were recorded at 400 MHz using on a Bruker AC 400 spectrometer. $CDCl_3$ is deuteriochloroform, DMSO-$d_6$ is hexadeuteriodimethylsulfoxide, and $CD_3OD$ (or MeOD) is tetradeuteriomethanol. Chemical shifts are reported in parts per million (δ) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on a instruments, using electrospray (ES) ionization techniques. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative hplc were performed using a Gilson Preparative System using a Luna 5u C18(2) 100A reverse phase column eluting with a 10-80 gradient (0.1% TFA in acetonitrile/0.1% aqueous TFA) or a 10-80 gradient (acetonitrile/water). The CombiFlash system used for purification in this application was purchased from Isco, Inc. CombiFlash purification was carried out using a prepacked $SiO_2$ column, a detector with UV wavelength at 254 nm and mixed solvents.

Heating of reaction mixtures with microwave irradiations was carried out on a Smith Creator (purchased from Personal Chemistry, Forboro/MA, now owned by Biotage), a Emrys Optimizer purchased from Personal Chemistry) or an Explorer (provided by CEM Discover, Matthews/NC) microwave.

General Procedure for EDC Couplings

The acid is dissolved in $CHCl_3$ and EDC (1.1 equivalents (hereinafter "eq") is added. The amine (2 eq.) is added dropwise followed by DMAP (cat.) and allowed to stir until the reaction is judged to be complete. The reaction mixture is washed with water. The aqueous portion is extracted with ethyl acetate. The ethyl acetate portion is washed with brine and combined with the other organic portion, dried ($MgSO_4$) and concentrated.

General Procedure for Sulfide Oxidations

The sulfide is dissolved in $CHCl_3$ and mCPBA (1.5 eq.) is added. The mixture is allowed to stir for 30 minutes (hereinafter "min") then quenched with $NaHCO_3$. The organic portion is washed with brine and dried ($MgSO_4$).

General Procedure for Sulfoxide/Sulfone Displacement

The sulfoxide/sulfone is dissolved in THF and the amine (5 eq.) is added and allowed to stir for 1 h. The mixture is concentrated in vacuo.

Example 1

N-(cyclopropylmethyl)-3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-benzamide 1a) 4-chloro-8-(2,6-difuorophenyl)-2-(methylthio)pyrido[2,3-d]pyrimidin-7(8H)-one

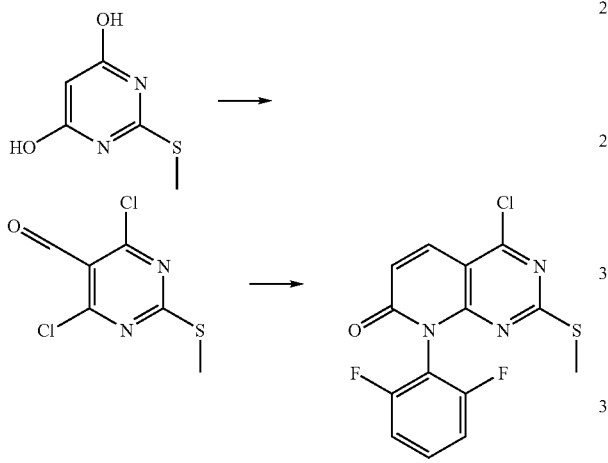

To the solution of phosphorus oxychloride (65 mL, 0.70 mol) in trichloroethylene (46.5 mL) was added DMF (25 mL, 0.32 mol) slowly to keep the temperature between 5° C. to 10° C. The solution was then warmed up to room temperature before 6-hydroxy-2-(methylthio)-4(1H)-pyrimidinone (25 g, 0.16 mol) was added in portions. The resultant reaction mixture was heated at 80° C. overnight followed by concentration under vacuum. The resulting slurry like residue was poured into ice, stirred for 2 hours then filtered to afford the crude product. The crude product was further purified by recrystalization with hexane to afford 4,6-dichloro-2-(methylthio)-5-pyrimidinecarbaldehyde (21.3 g, 61%). $^1$H-NMR (CDCl$_3$) δ 2.66 (s, 3H), 10.4 (s, 1H).

To a solution of 4,6-dichloro-2-(methylthio)-5-pyrimidinecarbaldehyde (10.0 g, 44.8 mmol) in THF (250 mL) was added 2,6-difluoroaniline (5.35 mL, 49.3 mmol, 1.1 eq) followed by Et$_3$N (12.6 mL, 89.6 mmol, 2 eq). The reaction mixture was heated to 55° C. for about 22 h before concentrated. The slurry was re-dissolved in DCM (250 mL) and washed with H$_2$O (2×100 mL), then concentrated and further washed with acetone (2×10 mL) to give 9.87 g (70%) of pure 4-chloro-6-[(2,6-difluorophenyl)amino]-2-(methylthio)-5-pyrimidinecarbaldehyde. LC-MS m/z 316 (M+H)$^+$.

A solution of 4-chloro-6-[(2,6-difluorophenyl)amino]-2-(methylthio)-5-pyrimidinecarbaldehyde (200 mg, 0.63 mmol) in DMF (4.0 mL) and acetic anhydride (2.0 mL) was heated with a microwave (160° C.) for about 30 minutes. The resultant mixture was then concentrated. Flash chromatography (EtOAc/Hexane, 1:5) provided the title compound (109 mg, 51%): LC-MS m/z 340 (M+H)$^+$.

1b) 3-[8-(2,6-difluorophenyl)-2-(methylthio)-7-oxo-7,8-dihydropyrido[2,3-d]pyrimidin-4-yl]-4-methyl-benzoic acid

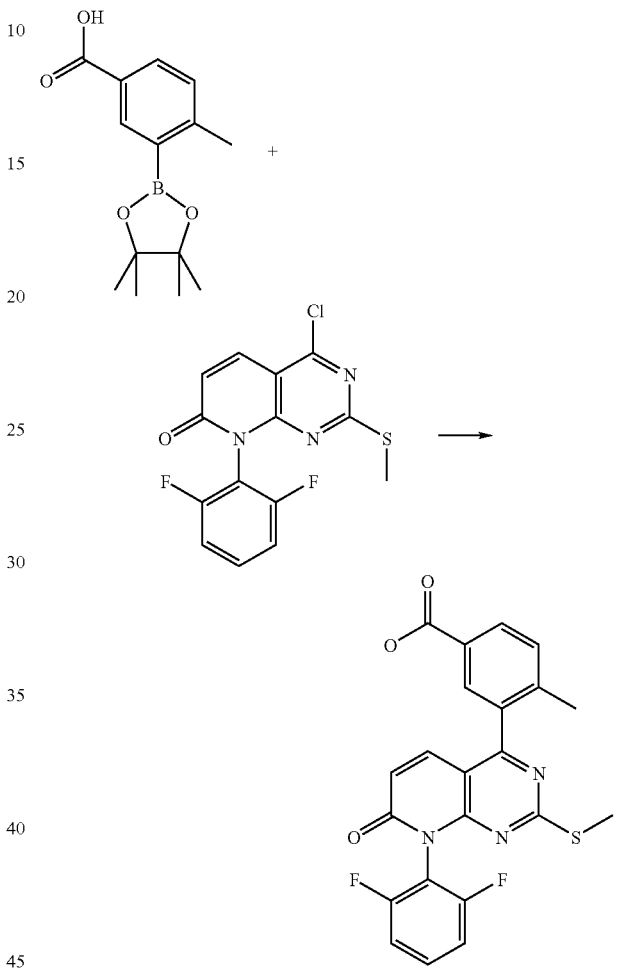

To a stirring solution of 3-iodo-4-methylbenzoic acid (60 g, 0.22 mol, 1 eq) in degassed DMF (1400 mL, 23.3 vol.) was charged 4,4,4',4',5,5,5',5'-octamethyl-2,2'-bi-1,3,2-dioxaborolane (81.4 g, 0.32 mol, 1.4 eq) followed by potassium acetate (112 g, 1.14 mole, 5 eq) and [1,1'-bis(diphenylphosphino)ferrocene]-dichloropalladium(II) (18.7 g, 0.02 mole, 0.1 eq). The resulting mixture was placed under a nitrogen atmosphere and was heated to 80° C. with the exclusion of light overnight. The mixture was then concentrated under high vacuum and the residue partitioned between EtOAc and 2M HCl. The mixture was then filtered and the layers separated. The aqueous phase was re-extracted with EtOAc. The combined organics were then washed with brine, dried and evaporated to yield a brown solid that was applied to a silica plug then eluted with 2:1 cyclohexane:ethyl acetate. Fractions were then combined and evaporated to yield a brown foam that was triturated with cyclohexane, collected by filtration then dried in vacuo to yield 4-methyl-3-(4,4,5,5-tetramethyl-1,3,2-dioxaborolan-2-yl)benzoic acid. δ (CDCl$_3$) 8.50-8.49 (1H, d), 8.04-8.02 (1H, dd), 7.27-7.25 (1H, d), 2.61 (3H, s), 1.36 (12H, s).

The solution of 4-chloro-8-(2,6-difluorophenyl)-2-(methylthio) pyrido[2,3-d]pyrimidin-7(8H)-one (1.70 g, 5.00 mmol) in DME (150 mL) and H₂O (50 mL), in a pressure flask (500 mL, Chemglass), was added 4-methyl-3-(4,4,5,5-tetramethyl-1,3,2-dioxaborolan-2-yl) benzoic acid (1.97 g, 7.50 mmol) and K₂CO₃ (4.15 g, 30.0 mmol). The resulting mixture was degassed with Argon for 5 minutes, mixed with Pd(PPh₃)₄ (0.232 g, 0.20 mmol) and heated with a preheated oil bath (160° C.) under vigorous stirring for 30 minutes. The reaction mixture was filtered through celite, concentrated under vaccum to remove DME. It was then mixed with EtOAc (200 mL) and AcOH (2.5 mL), and shaked. The layers were separated. The organic layer was collected, further washed with brine (70 mL), dried over Na₂SO₄, filtered, concentrated and purified via a flash chromatography (load column with DCM, mobile phase EtOAc/Hexane) to afford the title compound as a white solid 2.15 g (98%). LC-MS (ES) m/z 440 (M+H)⁺; ¹H-NMR (MeOD) δ 2.27 (s, 3H), 2.31 (s, 3H), 6.71 (d, J=9.6 Hz, 1H), 7.28 (t, J=8.2 Hz, 2H), 7.57 (d, J=8.4 Hz, 1H), 7.64 (m, 2H), 8.00 (d, J=1.6 Hz, 1H), 8.14 (dd, J₁=7.6 Hz, J₂=1.6 Hz, 1H).

1c) N-(cyclopropylmethyl)-3-[8-(2,6-difluorophenyl)-2-(methylsulfonyl)-7-oxo-7,8-dihydropyrido[2,3-d]pyrimidin-4-yl]-4-methylbenzamide To a solution of 3-[8-(2,6-difluorophenyl)-2-(methylthio)-7-oxo-7,8-dihydropyrido[2,3-d]pyrimidin-4-yl]-4-methylbenzoic acid (246.0 mg, 0.5 mmol) in CH₂Cl₂ (10.0 ml) was added DMAP (122.0 mg, 1.0 mmol), EDC (115.0 mg, 0.6 mmol), HOBT (81.0 mg, 0.6 mmol), and 1-cyclopropylmethanamine (71.0 mg, 1.0 mmol). The reaction mixture was stirred for about 14 h at room temperature and concentrated. It was then diluted with H₂O (5.0 mL) and EtOAc (10.0 mL). The organic layer was separated and the aqueous layer was extracted with EtOAc (3×10 mL). The combined organic layers were washed with saturated aq. NaCl, dried over Na₂SO₄, filtered, and concentrated. Purification via the CombiFlash system (hexane:ethylacetate=3:1) then afforded N-(cyclopropylmethyl)-3-[8-(2,6-difluorophenyl)-2-(methylthio)-7-oxo-7,8-dihydropyrido[2,3-d]pyrimidin-4-yl]-4-methylbenzamide (210.0 mg, 85%): LC-MS m/z 493 (M+H)⁺, 2.33 min (ret. time).

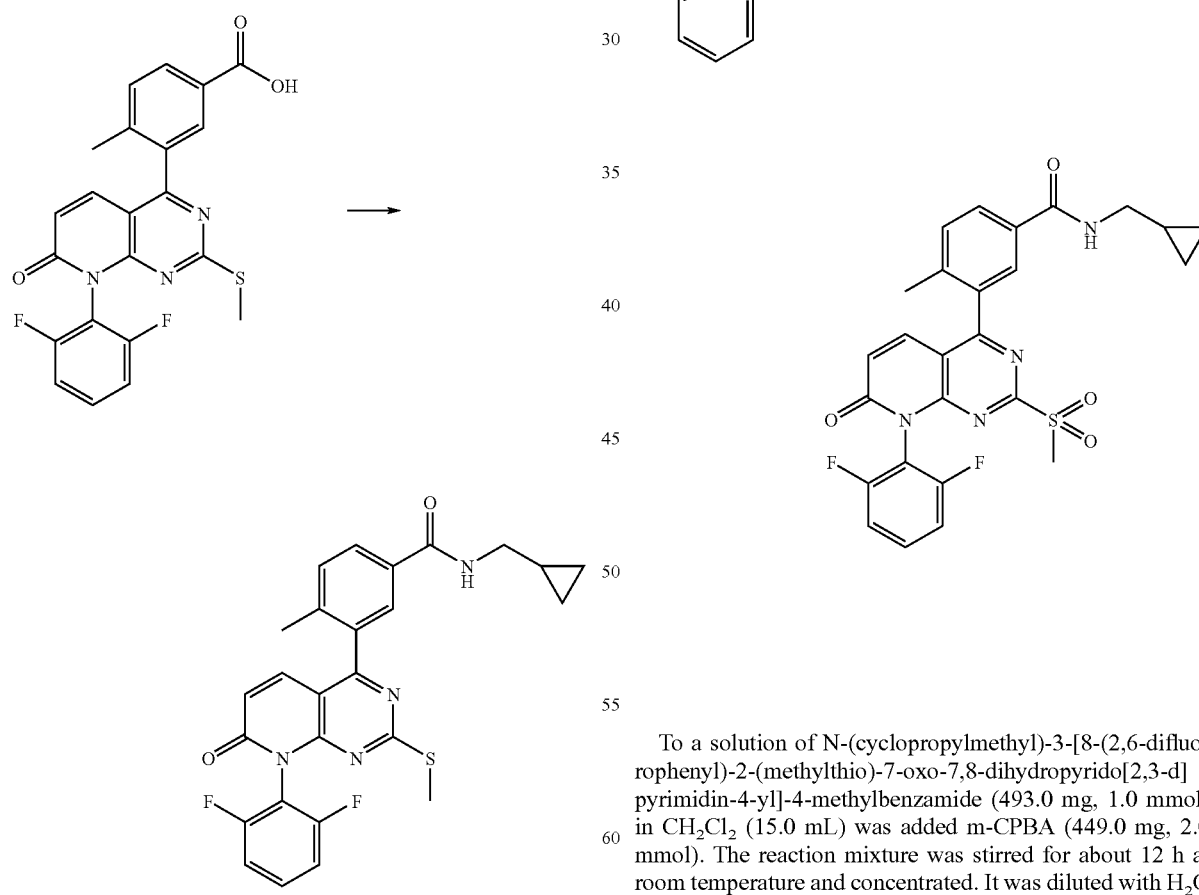

To a solution of N-(cyclopropylmethyl)-3-[8-(2,6-difluorophenyl)-2-(methylthio)-7-oxo-7,8-dihydropyrido[2,3-d]pyrimidin-4-yl]-4-methylbenzamide (493.0 mg, 1.0 mmol) in CH₂Cl₂ (15.0 mL) was added m-CPBA (449.0 mg, 2.0 mmol). The reaction mixture was stirred for about 12 h at room temperature and concentrated. It was diluted with H₂O (5.0 mL) and EtOAc (20.0 mL). The organic layer was separated and the aqueous layer was extracted with EtOAc (3×20 mL). The combined organic layers were washed with saturated aq. NaCl, dried over Na₂SO₄, filtered, and concentrated. Purification via the CombiFlash system (hexane:EtOAc=4:1)

the afforded the title sulfone compound (490.0 mg, 93%): LC-MS m/z 526 (M+H)+, 2.00 min (ret. time)

1d) N-(cyclopropylmethyl)-3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylbenzamide

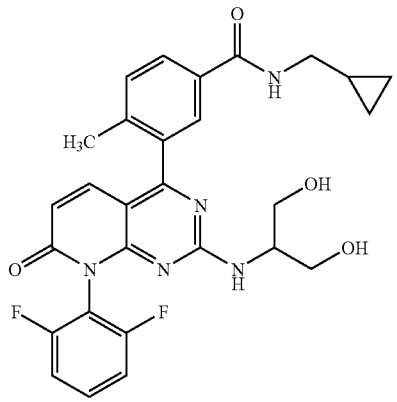

To a solution of N-(cyclopropylmethyl)-3-(8-(2,6-difluorophenyl)-2-methyl sulfone-7-oxo-7,8-dihydropyrido[2,3-d]pyrimidin-4-yl)-4-methylbenzamide (50.0 milligrams (hereinafter "mg"), 0.095 millimoles (hereinafter "mmol")) in THF (5.0 milliliters (hereinafter "mL")) was added 2-amino-3-propanediol (10.0 mg, 0.105 mmol, 1.1 eq). The reaction mixture was stirred for about 4 hours (hereinafter "h") at room temperature and concentrated. Purification via a CombiFlash system (DCM:MeOH=1:10) then afforded the title compound: LC-MS m/z 536 (M+H)+, 1.70 min (ret time).

Example 2

N-(cyclopropylmethyl)-3-[8-(2,6-difluorophenyl)-7-oxo-2-(4-piperidinylamino)-7,8-dihydropyrido[2,3-d]pyrimidin-4-yl]-4-methylbenzamide 2a) 1,1-dimethylethyl 4-{[4-(5-{[(cyclopropylmethyl)amino]carbonyl}-2-methylphenyl)-8-(2,6-difluorophenyl)-7-oxo-7,8-dihydropyrido[2,3-d]pyrimidin-2-yl]amino}-1-piperidinecarboxylate

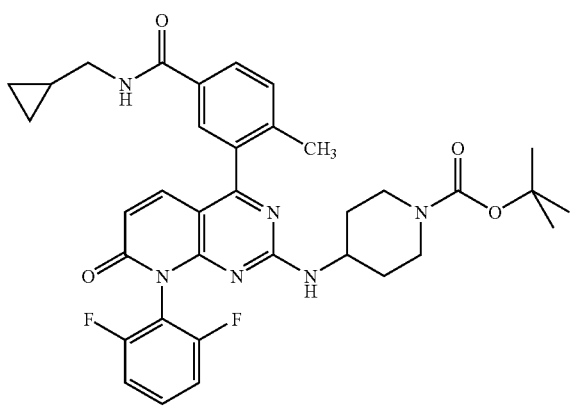

The title compound was prepared by following the procedure in Example 1d from N-(cyclopropylmethyl)-3-(8-(2,6-difluorophenyl)-2-methyl sulfone-7-oxo-7,8-dihydropyrido[2,3-d]pyrimidin-4-yl)-4-methylbenzamide and 1,1-dimethylethyl 4-amino-1-piperidinecarboxylate.

2b) N-(cyclopropylmethyl)-3-[8-(2,6-difluorophenyl)-7-oxo-2-(4-piperidinylamino)-7,8-dihydropyrido[2,3-d]pyrimidin-4-yl]-4-methylbenzamide

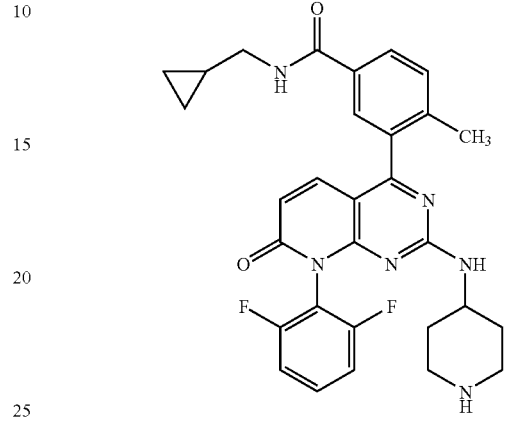

To a solution of 1,1-dimethylethyl 4-{[4-(5-{[(cyclopropylmethyl)amino]carbonyl}-2-methylphenyl)-8-(2,6-difluorophenyl)-7-oxo-7,8-dihydropyrido[2,3-d]pyrimidin-2-yl]amino}-1-piperidinecarboxylate in THF (2 mL) was added TFA (3.0 mL). The reaction mixture was stirred for about 12 h and concentrated. The residue was mixed with H₂O (5.0 mL) and EtOAc (20.0 mL) and the resultant mixture was basified with 2.5 N NaOH aqueous (hereinafter "aq") solution. The organic layer was separated and the aqueous layer was extracted with EtOAc (3×15 mL). The combined organic phases were washed with saturated aq. NaCl, dried over Na₂SO₄, filtered, and concentrated. Purification via a CombiFlash system (DCM:MeOH=10:1) then afforded the title compound: LC-MS m/z 545 (M+H)+, 1.65 min (ret. time).

Example 3

N-(cyclopropylmethyl)-3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylbenzamide

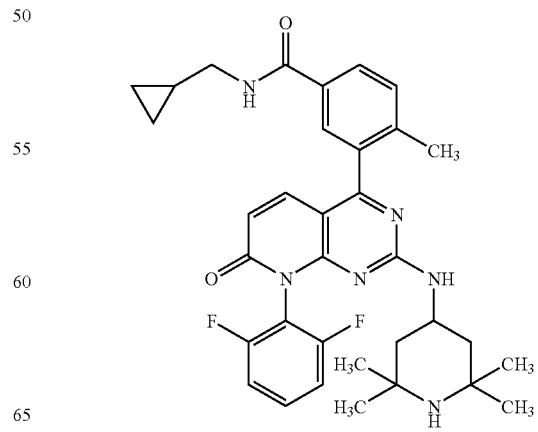

The title compound was prepared as described in Example 1d from N-(cyclopropylmethyl)-3-(8-(2,6-difluorophenyl)-2-methyl sulfone-7-oxo-7,8-dihydropyrido[2,3-d]pyrimidin-4-yl)-4-methylbenzamide and 2,2,6,6-tetramethyl-4-piperidinamine: LC-MS m/z 601 (M+H)+, 1.75 min (ret. time)

Example 4

N-(cyclopropylmethyl)-3-{8-(2,6-difuorophenyl)-7-oxo-2-[(2,2,6,6-tetramethyl-4-piperidinyl)amino]-7,8-dihydropyrido[2,3-d]pyrimidin-4-yl}-4-methylbenzamide

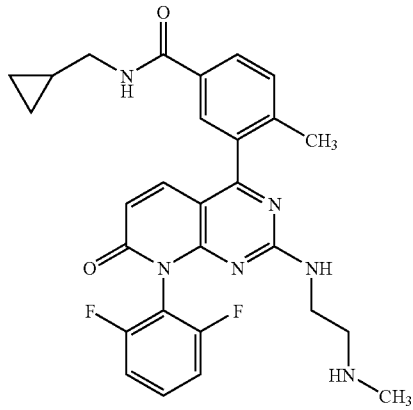

The title compound was prepared as described in Example 1d from N-(cyclopropylmethyl)-3-(8-(2,6-difluorophenyl)-2-methyl sulfone-7-oxo-7,8-dihydropyrido[2,3-d]pyrimidin-4-yl)-4-methylbenzamide and N-methyl-1,2-ethanediamine: LC-MS m/z 519 (M+H)+, 1.60 min (ret. time).

Example 5

N-(cyclopropylmethyl)-3-{8-(2,6-difluorophenyl)-2-[(1H-imidazol-2-ylmethyl)amino]-7-oxo-7,8-dihydropyrido[2,3-d]pyrimidin-4-yl}-4-methylbenzamide

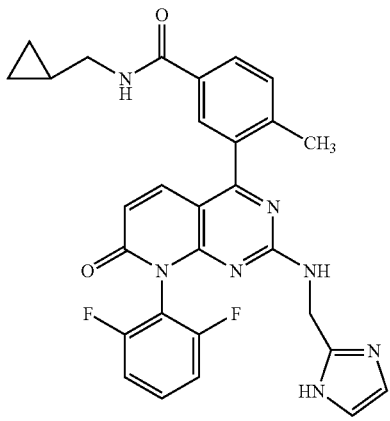

The title compound was prepared as described in Example 1d from N-(cyclopropylmethyl)-3-(8-(2,6-difluorophenyl)-2-methyl sulfone-7-oxo-7,8-dihydropyrido[2,3-d]pyrimidin-4-yl)-4-methylbenzamide and (1H-imidazol-2-ylmethyl)amine dihydrochloride: LC-MS m/z 542 (M+H)+, 1.61 min (ret. time).

Example 6

3-[2-[(2-aminoethyl)(methyl)amino]-8-(2,6-difluorophenyl)-7-oxo-7,8-dihydropyrido[2,3-d]pyrimidin-4-yl]-N-(cyclopropylmethyl)-4-methylbenzamide

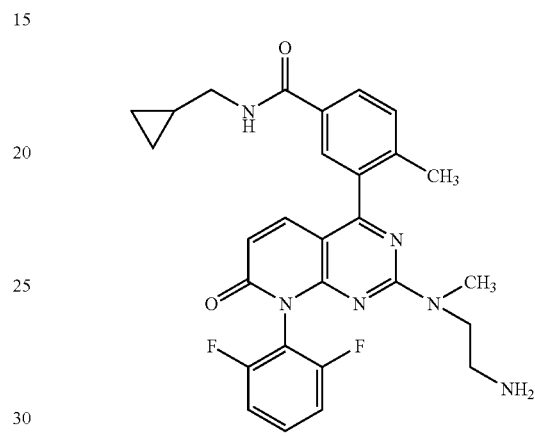

The title compound was prepared as described in Example 2 from N-(cyclopropylmethyl)-3-(8-(2,6-difluorophenyl)-2-methyl sulfone-7-oxo-7,8-dihydropyrido[2,3-d]pyrimidin-4-yl)-4-methylbenzamide and 1,1-dimethylethyl [2-(methylamino)ethyl]carbamate: LC-MS m/z 519 (M+H)+, 1.62 min (ret. time).

Example 7

N-{3-[8-(2,6-difluorophenyl)-7-oxo-2-(4-piperidinylamino)-7,8-dihydropyrido[2,3-d]pyrimidin-4-yl]-4-methylphenyl}-2-thiophenecarboxamide 7a) 4-(5-amino-2-methylphenyl)-8-(2,6-difluorophenyl)-2-(methylthio)pyrido[2,3-d]pyrimidin-7(8H)-one

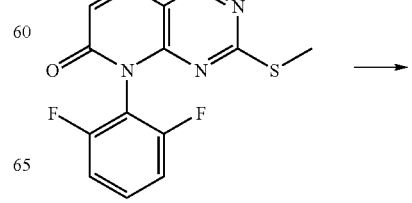

-continued

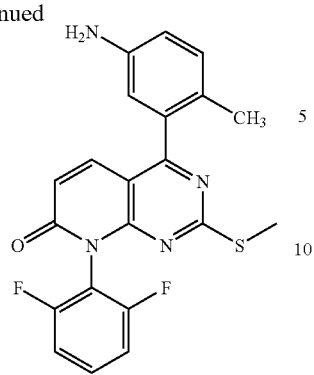

To a solution of 3-iodo-4-methylaniline (110.0 mg, 0.47 mmol) in dioxane (1.0 mL) was added (under argon) triethylamine (0.26 mL, 1.86 mmol), palladium diacetate (5.2 mg, 0.023 mmol), 2-(dicyclohexyl phosphino) biphenyl (33.0 mg, 0.093 mmol), and pinacolborane (0.20 mL, 1.40 mmol). The mixture was stirred at about 80° C. for about 1 hour, cooled to room temperature (rt), and added with water (0.2 mL), barium hydroxide octahydrate (440.0 mg, 1.40 mmol) and 4-chloro-8-(2,6-difluorophenyl)-2-(methylthio)pyrido[2,3-d]pyrimidin-7(8H)-one (180.0 mg, 0.47 mmol). The mixture was heated at about 100° C. under stirring for about 1 hour, cooled to room temperature, filtered through celite, and diluted with brine (5.0 mL). The mixture was then extracted with $CH_2Cl_2$ (3×10 mL). The combined organic phases were dried over $Na_2SO_4$, filtered, and concentrated. Purification via the CombiFlash system then afforded the title compound (155.0 mg, 75%): LC-MS m/z 411 (M+H)$^+$, 2.60 min (ret. time).

7b) N-{3-[8-(2,6-difluorophenyl)-2-(methylthio)-7-oxo-7,8-dihydropyrido[2,3-d]pyrimidin-4-yl]-4-methylphenyl}-2-thiophenecarboxamide

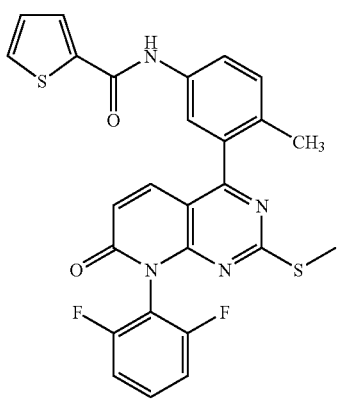

To a solution of 4-(5-amino-2-methylphenyl)-8-(2,6-difluorophenyl)-2-(methylthio)pyrido[2,3-d]pyrimidin-7(8H)-one (411.0 mg, 1.0 mmol) in $CH_2Cl_2$ (10 mL) at 0° C. was added $Et_3N$ (200.0 mg, 2.0 mmol, 2.0 eq), DMAP (5.0 mg, 0.2 mmol, 0.2 eq) and 2-thiophenecarbonyl chloride (292.0 mg, 2.0 mmol, 2.0 eq). After addition the reaction mixture was stirred for about 14 h at ambient temperature. The mixture was concentrated and mixed with $H_2O$ (5.0 mL) and EtOAc (20.0 mL). The organic layer was separated and the aqueous layer was extracted with EtOAc (3×15 mL). The combined organic phases were washed with saturated aq. NaCl solution, dried over $Na_2SO_4$, filtered, and concentrated. Purification via a CombiFlash system (hexane:EtOAc; 4:1) then afforded the title compound: LC-MS m/z 521 (M+H)$^+$, 2.57 min (ret time).

7c) N-{3-[8-(2,6-difluorophenyl)-2-(methylsulfonyl)-7-oxo-7,8-dihydropyrido[2,3-d]pyrimidin-4-yl]-4-methylphenyl}-2-thiophenecarboxamide

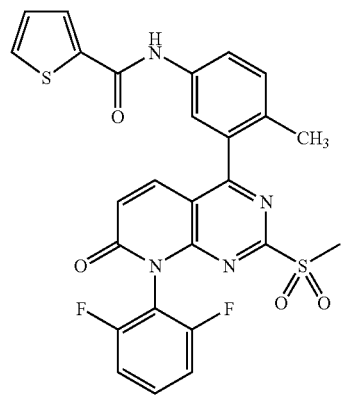

To a solution of N-{3-[8-(2,6-difluorophenyl)-2-(methylthio)-7-oxo-7,8-dihydropyrido[2,3-d]pyrimidin-4-yl]-4-methylphenyl}-2-thiophenecarboxamide (521.0 mg, 1.0 mmol) in $CH_2Cl_2$ (15.0 mL) was added m-CPBA (449.0 mg, 2.0 mmol, 2.0 eq). The reaction mixture was stirred for about 14 h at room temperature, concentrated, and mixed with $H_2O$ (5.0 mL) and EtOAc (20.0 mL). The organic layer was separated and the aqueous layer was extracted with EtOAc (3×15 mL). The combined organic phases were washed with saturated aq. NaCl solution, dried over $Na_2SO_4$, filtered, and concentrated. Purification via a CombiFlash system (hexane:EtOAc; 4:1) then afforded the title compound: LC-MS m/z 553 (M+H)$^+$, 2.30 min (ret time).

7d) N-{3-[8-(2,6-difluorophenyl)-7-oxo-2-(4-piperidinylamino)-7,8-dihydropyrido[2,3-d]pyrimidin-4-yl]-4-methylphenyl}-2-thiophenecarboxamide

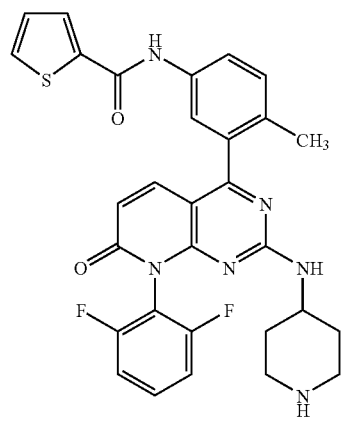

The title compound was prepared as described in Example 2 from N-{3-[8-(2,6-difluorophenyl)-2-(methylsulfonyl)-7- oxo-7,8-dihydropyrido[2,3-d]pyrimidin-4-yl]-4-methylphenyl}-2-thiophenecarboxamide and 1,1-dimethylethyl 4-amino-1-piperidinecarboxylate. LC-MS m/z 573 (M+H)$^+$, 1.90 min (ret time).

Example 8

N-{3-[2-(4-amino-1-piperidinyl)-8-(2,6-difluorophenyl)-7-oxo-7,8-dihydropyrido[2,3-d]pyrimidin-4-yl]-4-methylphenyl}-2-thiophenecarboxamide

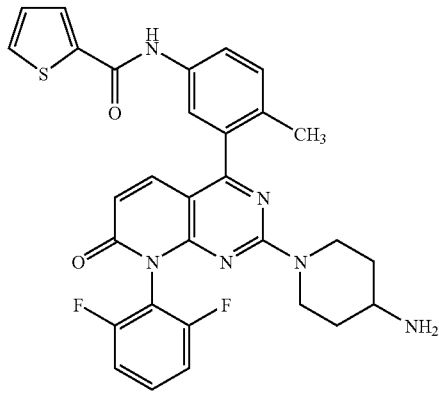

The title compound was prepared as described in Example 2 from N-{3-[8-(2,6-difluorophenyl)-2-(methylsulfonyl)-7-oxo-7,8-dihydropyrido[2,3-d]pyrimidin-4-yl]-4-methylphenyl}-2-thiophenecarboxamide and 1,1-dimethylethyl 4-piperidinylcarbamate: LC-MS m/z 573 (M+H)$^+$, 1.90 min (ret time).

Example 9

N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-2-thiophenecarboxamide

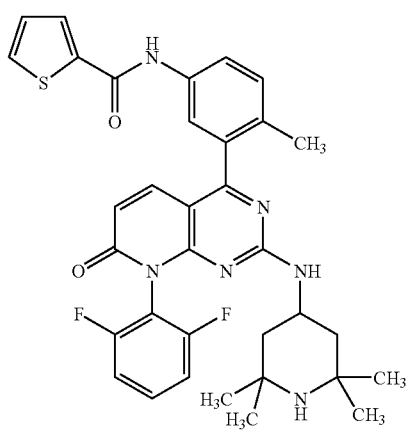

The title compound was prepared as described in Example 1d from N-{3-[8-(2,6-difluorophenyl)-2-(methylsulfonyl)-7-oxo-7,8-dihydropyrido[2,3-d]pyrimidin-4-yl]-4-methylphenyl}-2-thiophenecarboxamide and 2,2,6,6-tetramethyl-4-piperidinamine: LC-MS m/z 629 (M+H)$^+$, 2.0 min (ret time).

Example 10

N-(3-{8-(2,6-difluorophenyl)-2-[(1H-imidazol-2-ylmethyl)amino]-7-oxo-7,8-dihydropyrido[2,3-d]pyrimidin-4-yl}-4-methylphenyl)-2-thiophenecarboxamide

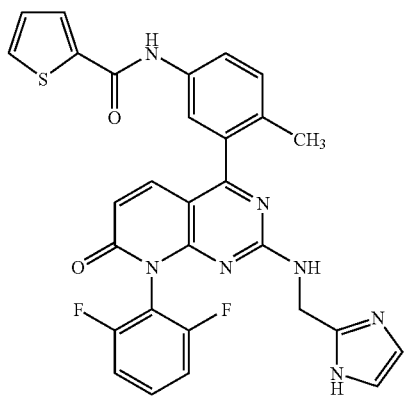

The title compound was prepared as described in Example 1d from N-{3-[8-(2,6-difluorophenyl)-2-(methylsulfonyl)-7-oxo-7,8-dihydropyrido[2,3-d]pyrimidin-4-yl]-4-methylphenyl}-2-thiophenecarboxamide and (1H-imidazol-2-ylmethyl)amine dihydrochloride: LC-MS m/z 570 (M+H)$^+$, 1.70 min (ret time).

Example 11

N-[3-(8-(2,6-difluorophenyl)-2-{[2-(methylamino)ethyl]amino}-7-oxo-7,8-dihydropyrido[2,3-d]pyrimidin-4-yl)-4-methylphenyl]-2-thiophenecarboxamide

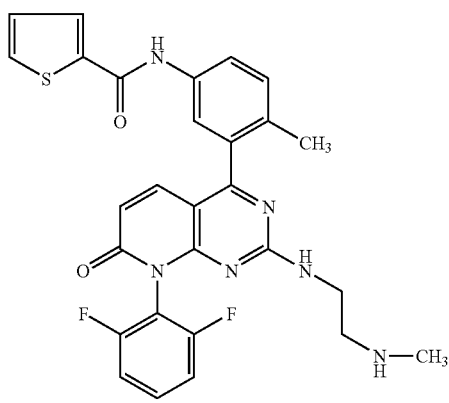

The title compound was prepared as described in Example 2 from N-{3-[8-(2,6-difluorophenyl)-2-(methylsulfonyl)-7-oxo-7,8-dihydropyrido[2,3-d]pyrimidin-4-yl]-4-methylphenyl}-2-thiophenecarboxamide and 1,1-dimethylethyl (2-aminoethyl)methylcarbamate: LC-MS m/z 547 (M+H)+, 1.80 min (ret time).

Example 12

N-{3-[8-(2,6-difluorophenyl)-7-oxo-2-(4-piperidinylamino)-7,8-dihydropyrido[2,3-d]pyrimidin-4-yl]-4-methylphenyl}-4-fluoro-3-methylbenzamide 12a) N-{3-[8-(2,6-difluorophenyl)-2-(methylthio)-7-oxo-7,8-dihydropyrido[2,3-d]pyrimidin-4-yl]-4-methylphenyl}-4-fluoro-3-methylbenzamide

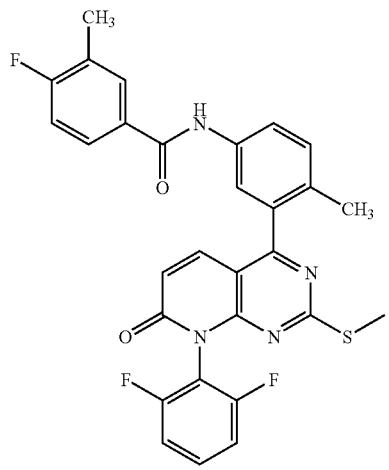

The title compound was prepared as described in Example 7b from 4-(5-amino-2-methylphenyl)-8-(2,6-difluorophenyl)-2-(methylthio)pyrido[2,3-d]pyrimidin-7(8H)-one and 4-fluoro-3-methylbenzoyl chloride: LC-MS m/z 547(M+H)+, 2.70 min (ret time).

12b) N-{3-[8-(2,6-difluorophenyl)-2-(methylsulfonyl)-7-oxo-7,8-dihydropyrido[2,3-d]pyrimidin-4-yl]-4-methylphenyl}-4-fluoro-3-methylbenzamide

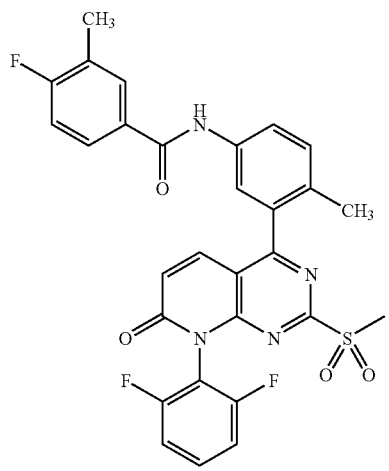

The title compound was prepared as described in Example 7c from N-{3-[8-(2,6-difluorophenyl)-2-(methylthio)-7-oxo-7,8-dihydropyrido[2,3-d]pyrimidin-4-yl]-4-methylphenyl}-4-fluoro-3-methylbenzamide and m-CPBA: LC-MS m/z 580 (M+H)+, 2.40 min (ret time).

12c) N-{3-[8-(2,6-difluorophenyl)-7-oxo-2-(4-piperidinylamino)-7,8-dihydropyrido[2,3-d]pyrimidin-4-yl]-4-methylphenyl}-4-fluoro-3-methylbenzamide

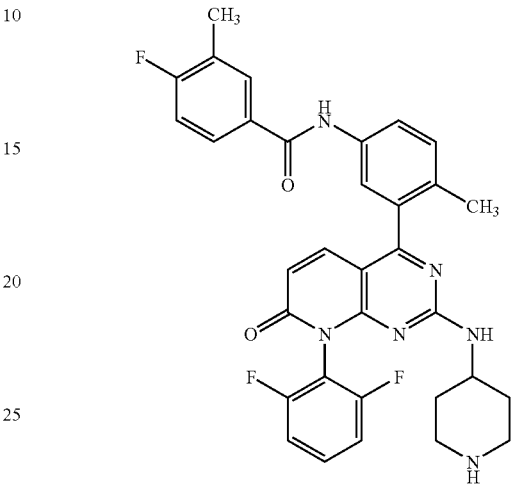

The title compound was prepared as described in Example 2 from N-{3-[8-(2,6-difluorophenyl)-2-(methylsulfonyl)-7-oxo-7,8-dihydropyrido[2,3-d]pyrimidin-4-yl]-4-methylphenyl}-4-fluoro-3-methylbenzamide and 1,1-dimethylethyl 4-amino-1-piperidinecarboxylate: LC-MS m/z 599 (M+H)+, 1.98 min (ret time).

Example 13

N-{3-[2-(4-amino-1-piperidinyl)-8-(2,6-difluorophenyl)-7-oxo-7,8-dihydropyrido[2,3-d]pyrimidin-4-yl]-4-methylphenyl}-4-fluoro-3-methylbenzamide

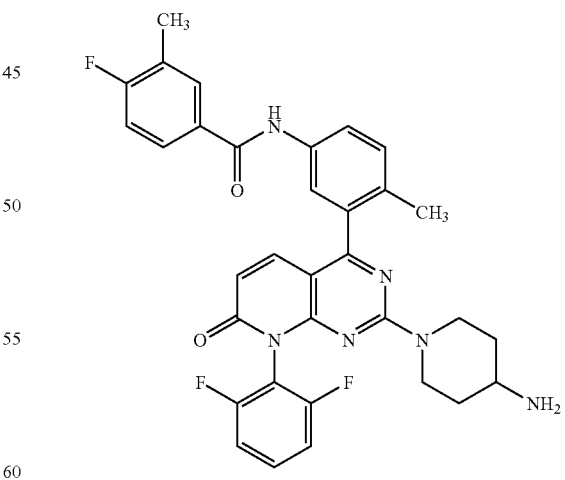

The title compound was prepared as described in Example 2 from N-{3-[8-(2,6-difluorophenyl)-2-(methylsulfonyl)-7-oxo-7,8-dihydropyrido[2,3-d]pyrimidin-4-yl]-4-methylphenyl}-4-fluoro-3-methylbenzamide and 1,1-dimethylethyl 4-piperidinylcarbamate: LC-MS m/z 599 (M+H)+, 1.99 min (ret time).

Example 14

6-chloro-N-{3-[8-(2,6-difluorophenyl)-7-oxo-2-(4-piperidinylamino)-7,8-dihydropyrido[2,3-d]pyrimidin-4-yl]-4-methylphenyl}-3-pyridinecarboxamide 14a) 6-chloro-N-{3-[8-(2,6-difluorophenyl)-2-(methylthio)-7-oxo-7,8-dihydropyrido[2,3-d]pyrimidin-4-yl]-4-methylphenyl}-3-pyridinecarboxamide

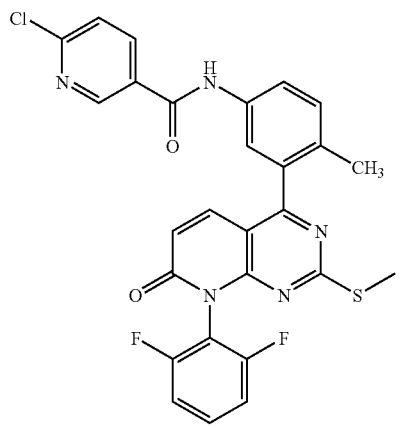

The title compound was prepared as described in Example 7b from 4-(5-amino-2-methylphenyl)-8-(2,6-difluorophenyl)-2-(methylthio)pyrido[2,3-d]pyrimidin-7(8H)-one and 6-chloro-3-pyridinecarbonyl chloride: LC-MS m/z 550 (M+H)$^+$, 2.63 min (ret time).

14b) 6-chloro-N-{3-[8-(2,6-difluorophenyl)-2-(methylsulfonyl)-7-oxo-7,8-dihydropyrido[2,3-d]pyrimidin-4-yl]-4-methylphenyl}-3-pyridinecarboxamide

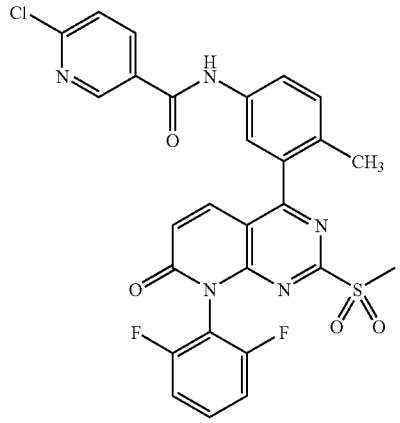

The title compound was prepared as described in Example 7c from 6-chloro-N-{3-[8-(2,6-difluorophenyl)-2-(methylthio)-7-oxo-7,8-dihydropyrido[2,3-d]pyrimidin-4-yl]-4-methylphenyl}-3-pyridinecarboxamide and m-CPBA: LC-MS m/z 582 (M+H)$^+$, 2.30 min (ret time).

14c) 6-chloro-N-{3-[8-(2,6-difluorophenyl)-7-oxo-2-(4-piperidinylamino)-7,8-dihydropyrido[2,3-d]pyrimidin-4-yl]-4-methylphenyl}-3-pyridinecarboxamide

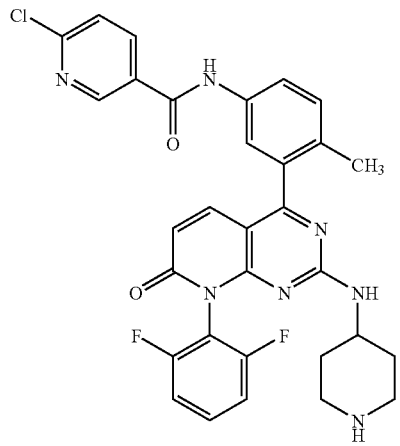

The title compound was prepared as described in Example 2 from 6-chloro-N-{3-[8-(2,6-difluorophenyl)-2-(methylsulfonyl)-7-oxo-7,8-dihydropyrido[2,3-d]pyrimidin-4-yl]-4-methylphenyl}-3-pyridinecarboxamide and 1,1-dimethylethyl 4-amino-1-piperidinecarboxylate: LC-MS m/z 602 (M+H)$^+$, 1.75 min (ret time).

Example 15

N-{3-[2-(4-amino-1-piperidinyl)-8-(2,6-difluorophenyl)-7-oxo-7,8-dihydropyrido[2,3-d]pyrimidin-4-yl]-4-methylphenyl}-6-chloro-3-pyridinecarboxamide

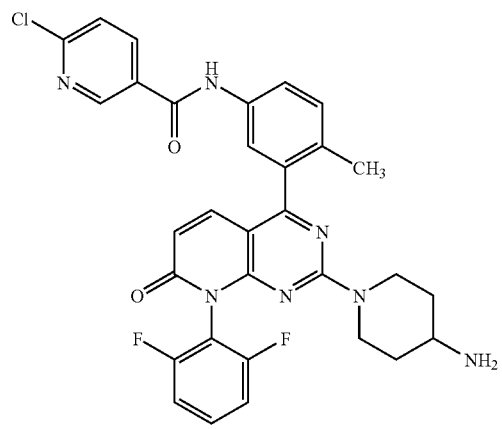

The title compound was prepared as described in Example 2 from 6-chloro-N-{3-[8-(2,6-difluorophenyl)-2-(methylsulfonyl)-7-oxo-7,8-dihydropyrido[2,3-d]pyrimidin-4-yl]-4-methylphenyl}-3-pyridinecarboxamide and 1,1-dimethylethyl 4-piperidinylcarbamate: LC-MS m/z 602 (M+H)$^+$, 1.75 min (ret time).

Example 16

6-chloro-N-(3-{8-(2,6-difuorophenyl)-7-oxo-2-[(2,2,6,6-tetramethyl-4-piperidinyl)amino]-7,8-dihydropyrido[2,3-d]pyrimidin-4-yl}-4-methylphenyl)-3-pyridinecarboxamide

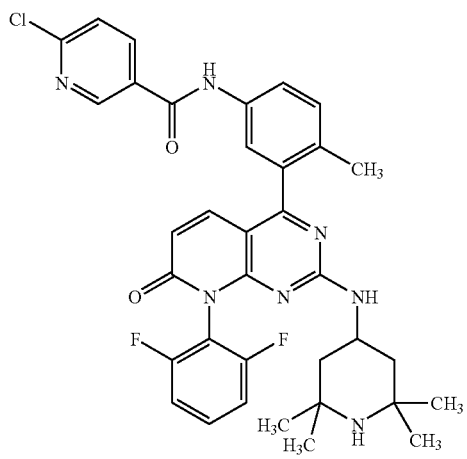

The title compound was prepared as described in Example 1d from 6-chloro-N-{3-[8-(2,6-difluorophenyl)-2-(methylsulfonyl)-7-oxo-7,8-dihydropyrido[2,3-d]pyrimidin-4-yl]-4-methylphenyl}-3-pyridinecarboxamide and 2,2,6,6-tetramethyl-4-piperidinamine: LC-MS m/z 658 (M+H)$^+$, 1.92 min (ret time).

Example 17

6-chloro-N-(3-{8-(2,6-difluorophenyl)-2-[(1H-imidazol-2-ylmethyl)amino]-7-oxo-7,8-dihydropyrido[2,3-d]pyrimidin-4-yl}-4-methylphenyl)-3-pyridinecarboxamide

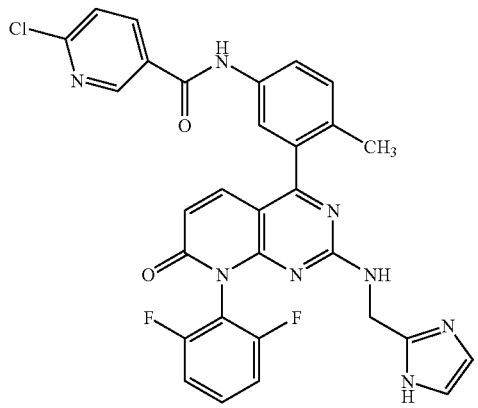

The title compound was prepared as described in Example 1d from 6-chloro-N-{3-[8-(2,6-difluorophenyl)-2-(methylsulfonyl)-7-oxo-7,8-dihydropyrido[2,3-d]pyrimidin-4-yl]-4-methylphenyl}-3-pyridinecarboxamide and (1H-imidazol-2-ylmethyl)amine dihydrochloride: LC-MS m/z 599 (M+H)$^+$, 1.92 min (ret time).

Example 18

N-cyclopropyl-3-(8-(2,6-difluorophenyl)-2-{[2-hydroxy-1-(hydroxymethyl)ethyl]amino}-7-oxo-7,8-dihydropyrido[2,3-d]pyrimidin-4-yl)-5-fluoro-4-methylbenzamide

18a) 3-fluoro-5-iodo-4-methylbenzoic acid

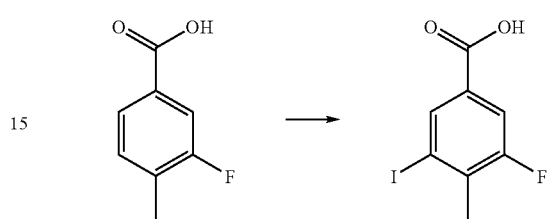

The benzoic acid (1.54 g, 0.01 mol) is dissolved in trifluoromethanesulfonic acid (10 mL) and cooled to about 0° C. NIS (2.25 g. 0.01 mol) is added in several portions over a 6 h period while maintaining the reaction temperature at about 0° C. The mixture is allowed to warm to rt. overnight. The reaction mixture is then poured over ice and extracted with ethyl acetate (3×). The organic layers are washed (Na$_2$S$_2$O$_5$) and concentrated. The material is carried on crude.

18b) N-cyclopropyl-3-fluoro-5-iodo-4-methylbenzamide

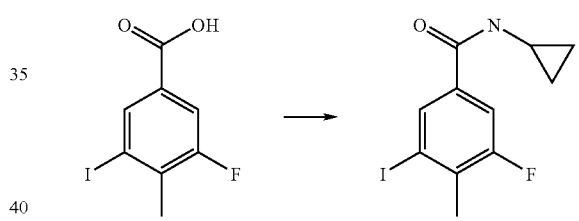

The crude acid from Example 18a (~1.5 g) is dissolved in thionyl chloride (75 mL) and heated to 80° C. for about 2 h. The mixture is then cooled to room temperature and stirred under N$_2$ overnight. The mixture is concentrated in vacuo and dissolved in 15 mL DCM. Na$_2$CO$_3$ (3 g) is added along with the cyclopropyl amine (0.69 mL, 0.01 moles (hereinafter "mol")). The mixture is allowed to stir overnight and purified via flash chromatography (5% MeOH/CH$_2$Cl$_2$) to afford 0.904 g of the title compound.

18c) N-cyclopropyl-3-fluoro-4-methyl-5-(4,4,5,5-tetramethyl-1,3,2-dioxaborolan-2-yl)benzamide

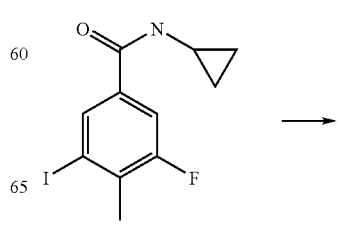

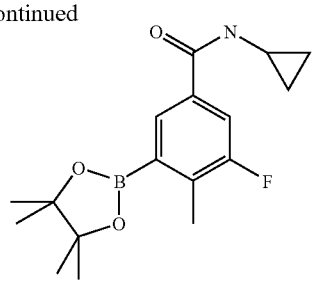

The iodo compound from Example 18b (0.904 g, 2.83 mmol) is dissolved in DMF (30 mL). Bis-pinicalato-diborane (1.44 g, 2.83 mmol) is added followed by PdCl$_2$.dppf (55 mg) and potassium acetate (1.38 g, 14.15 mmol). The mixture are stirred for about 18 h, concentrated in vacuo and purified via flash chromatography to afford the title compound (60 mg).

18d) 4-chloro-8-(2,6-difluorophenyl)-2-{[2-hydroxy-1-(hydroxymethyl)ethyl]amino}pyrido[2,3-d]-pyrimidin-7(8H)-one

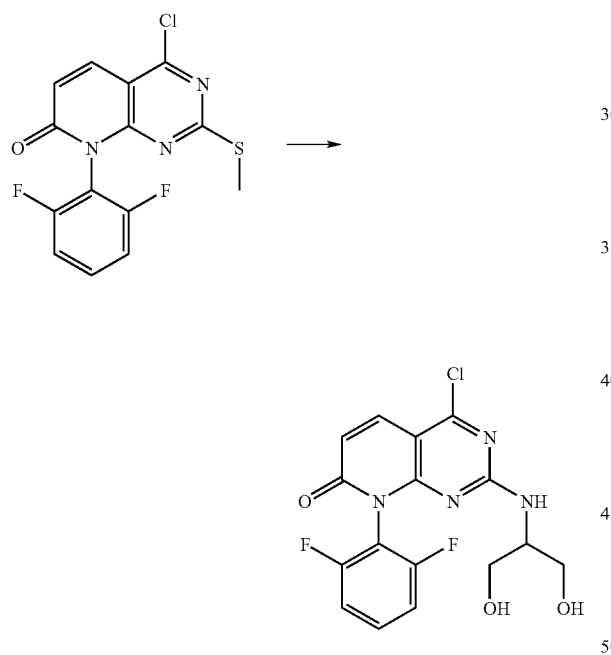

To a solution of 4-chloro-8-(2,6-difluorophenyl)-2-(methylthio)pyrido[2,3-d]pyrimidin-7(8H)-one (2.7 mmol) in dichloromethane (50 mL) was added m-cPBA (0.63 g, 4.0 mmol). The resultant mixture was stirred at room temperature for 10 minutes, then concentrated under vaco. Flash chromatography (EtOAc/Hexane, 1:3) afforded 4-chloro-2-methylsulfinyl-8-(2,6-difluoro-phenyl)-8H-pyrido[2,3-d]pyrimidin-7-one (88%): LC-MS m/z 356 (due to solventlysis with methanol, M+H)$^+$; $^1$H-NMR (CDCl$_3$) δ 2.85 (s, 3H), 7.03 (d, J=9.6 Hz, 1H), 7.15 (m, 2H), 7.53 (m, 1H), 8.18 (d, J=9.6 Hz, 1H).

A solution of 4-chloro-2-methylsulfinyl-8-(2,6-difluorophenyl)-8H-pyrido[2,3-d]pyrimidin-7-one (0.75 mmol) in dichloromethane (30 mL) was mixed with a solution of serinol (0.075 g, 0.82 mmol) and Et$_3$N (0.21 mL, 1.5 mmol) in DMF (0.75 mL). The resultant mixture was stirred at room temperature for about 1 hour, then concentrated under vaccum. Flash chromatography (EtOAc:Hexane, 3:1) provided the title compound 4-chloro-8-(2,6-difluorophenyl)-2-{[2-hydroxy-1-(hydroxy-methyl)ethyl]amino}pyrido[2,3-d]pyrimidin-7(8H)-one (42%): LC-MS m/z 383 (M+H)$^+$; $^1$H-NMR(CDCl$_3$) δ 1.95 (s, br, 2H), 3.90 (m, br, 5H), 6.05 (m, br, 1H), 6.56 (d, J=9.6 Hz, 1H), 7.10 (m, 2H), 7.48 (d, J=8.1 Hz, 2H), 7.94 (d, J=9.6 Hz, 1H).

18e) N-cyclopropyl-3-(8-(2,6-difluorophenyl)-2-{[2-hydroxy-1-(hydroxymethyl)ethyl]amino}-7-oxo-7,8-dihydropyrido[2,3-d]pyrimidin-4-yl)-5-fluoro-4-methylbenzamide

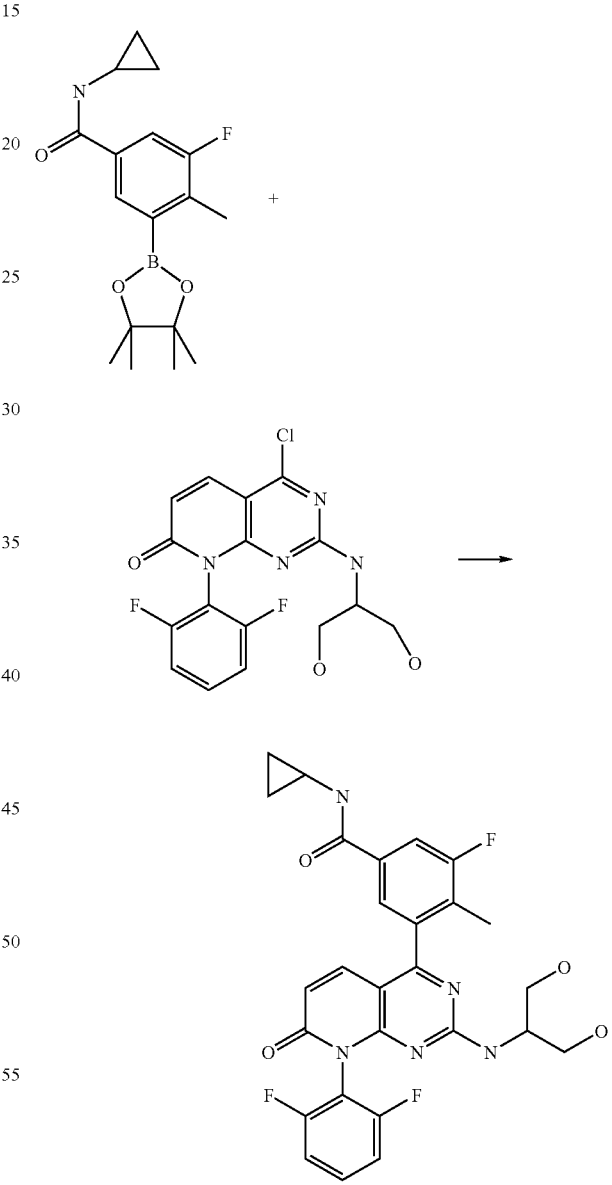

The chloride (0.056 g, 0.17 mmol), borate ester (0.065 g, 0.17 mmol), K$_2$CO$_3$ (0.07 g, 0.51 mmol) and tetrakis triphenyl phosphine palladium (10 mg, 0.05 eq) are dissolved in dioxane/water (3:1, 10 mL) and heated to about 100° C. for about 3 h. The mixture is concentrated and purified via reverse phase HPLC to afford the title compound (9 mg, yellow powder, mp 214.2-217.5): LC-MS in/z 540 (M+H)$^+$, 1.69 min (ret time). HPLC indicates 96% pure.

Example 19

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-N-(4-fluorophenyl)-4-methylbenzamide

19a) 3-[8-(2,6-difluorophenyl)-2-(methylthio)-7-oxo-7,8-dihydropyrido[2,3-d]pyrimidin-4-yl]-N-(4-fluorophenyl)-4-methylbenzamide

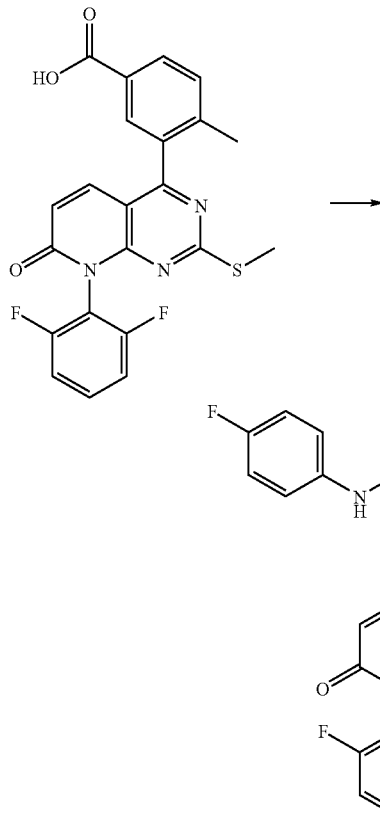

The title compound was prepared from 3-[8-(2,6-difluorophenyl)-2-(methylthio)-7-oxo-7,8-dihydropyrido[2,3-d]pyrimidin-4-yl]-4-methylbenzoic acid and 4-fluoroaniline by following the General Procedure for EDC couplings as disclosed in the general experimental section above. Crude reaction mixture was purified via flash chromatography (EtOAc:Hexanes, 2:1) to afford the title compound (0.125 g, 34%).

19b) 3-[8-(2,6-difluorophenyl)-2-(methylsulfinyl)-7-oxo-7,8-dihydropyrido[2,3-d]pyrimidin-4-yl]-N-(4-fluorophenyl)-4-methylbenzamide

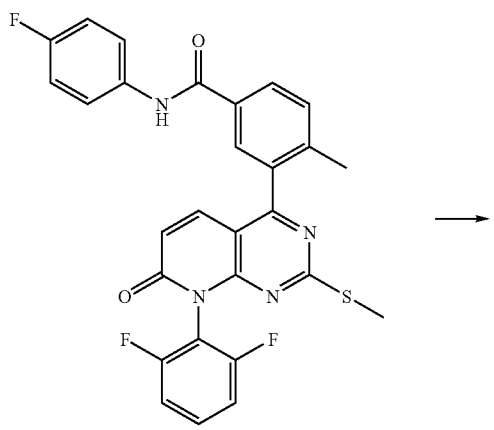

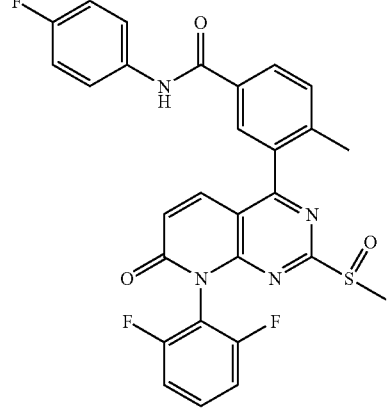

The title compound (0.105 g, 79%) was prepared by following the General Procedure for sulfide oxidations, as disclosed above.

19c) 3-(8-(2,6-difluorophenyl)-2-{[2-hydroxy-1-(hydroxymethyl)ethyl]amino}-7-oxo-7,8-dihydropyrido[2,3-d]pyrimidin-4-yl)-N-(4-fluorophenyl)-4-methylbenzamide

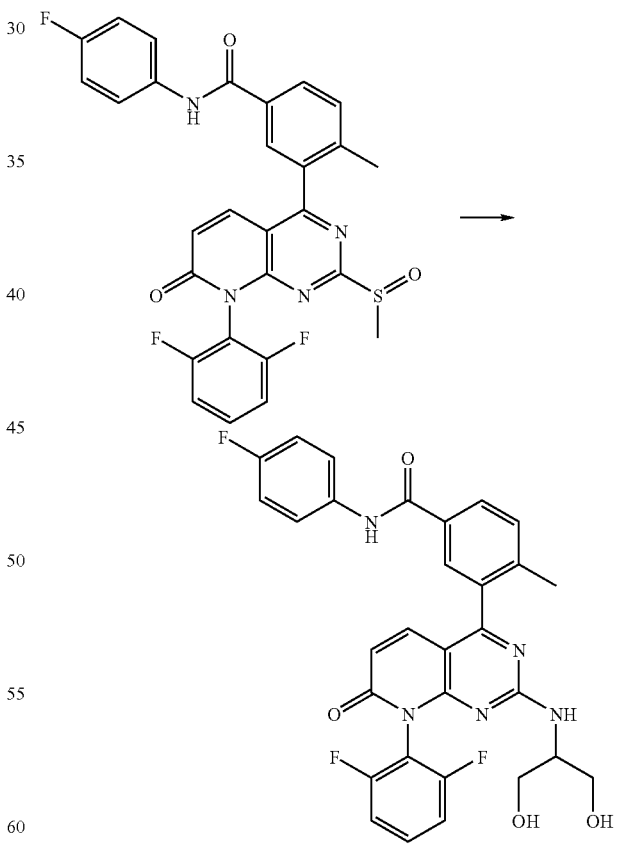

The title compound is prepared by following the General Procedure for Sulfoxide/Sulfone/sulfone displacement as disclosed above. Concentrated reaction mixture is purified via reversed-phase HPLC to give the desired compound as a white solid (43 mg, 39%): LC-MS m/z 576 (M+H)$^+$, 1.89 min (ret time). HPLC (254 nm) indicates 90% pure.

Example 20

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-(2-phenylethyl)benzamide

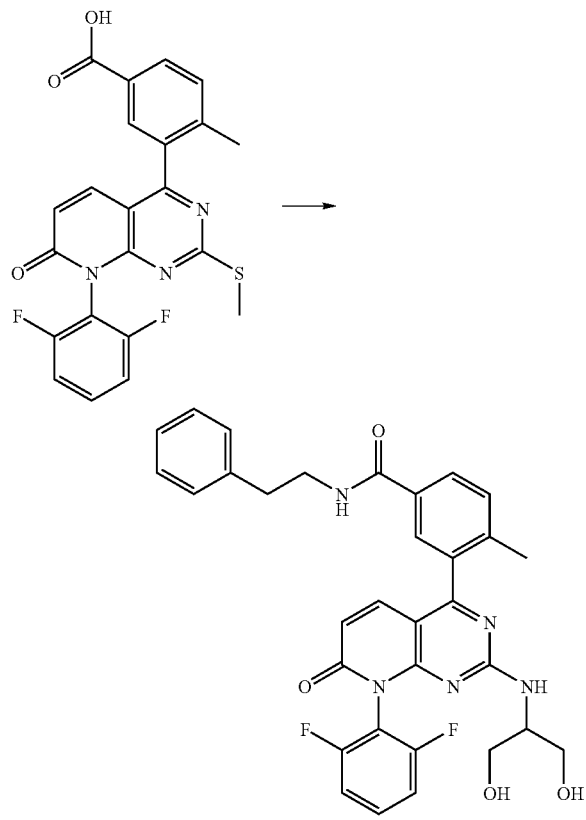

The title compound was prepared by following the procedures as described in Example 19 using 2-phenylethanamine for the amide formation: LC-MS m/z 586 (M+H)$^+$, 1.82 min (ret time).

Example 21

3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methyl-N-(1-methylpropyl)benzamide 21a) N-cyclopropyl-3-[8-(2,6-difluorophenyl)-2-(methylthio)-7-oxo-7,8-dihydropyrido[2,3-d]pyrimidin-4-yl]-4-methylbenzamide

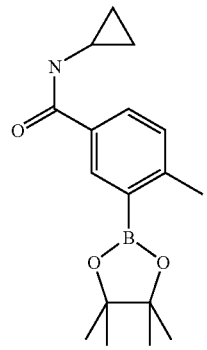

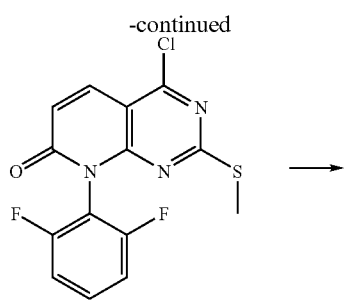

The borate ester (0.683 g, 2.27 mmol), chloride (0.768 g, 2.27 mmol), K$_2$CO$_3$ (0.941 g, 6.81 mmol) and tetrakistriphenylphosphine palladium (131 mg, 0.11 mmol) are dissolved in dioxane/water (3:1) and heated at reflux for about 4 h. The reaction mixture is then taken up in ethyl acetate and washed with water, brine and dried with Na$_2$SO$_4$. The concentrated mixture was purified via flash chromatography to give the desired product (0.6 g, 55%).

21b) N-cyclopropyl-3-[8-(2,6-difluorophenyl)-2-(methylsulfonyl)-7-oxo-7,8-dihydropyrido[2,3-d]pyrimidin-4-yl]-4-methylbenzamide

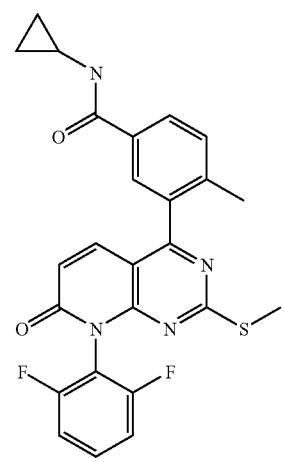

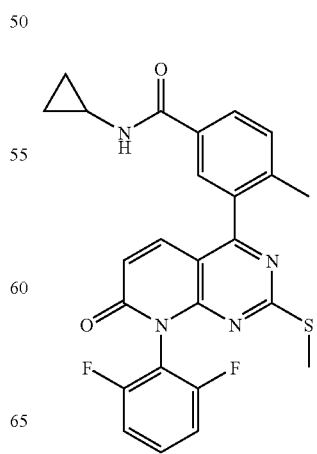

-continued

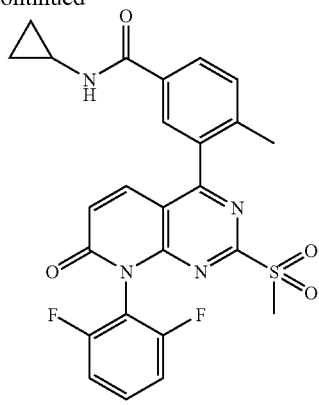

The title compound is prepared according to the General Procedure for sulfide oxidation, as disclosed above. It is concentrated to give the desired product as a yellow powder (0.3 g, 49%).

21c) 3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methyl-N-(1-methylpropyl)benzamide

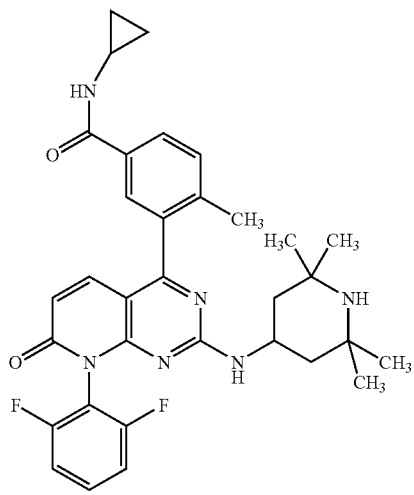

The title compound is prepared according to the General Procedure for Sulfoxide/Sulfone/Sulfone Displacement, as disclosed above. The concentrated reaction mixture is precipitated with DMSO/water, and filtered. The desired product is obtained as a white solid (m.p. 326.3-327.9) 95% pure by HPLC (55 mg, 45%): LC-MS m/z 587 (M+H)$^+$, 1.74 min (ret time).

Example 22

3-[2-(4-amino-1-piperidinyl)-8-(2,6-difluorophenyl)-7-oxo-7,8-dihydropyrido[2,3-d]pyrimidin-4-yl]-N-cyclopropyl-4-methylbenzamide

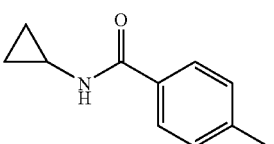
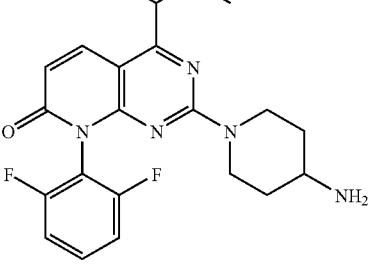

The title compound is prepared from compound N-cyclopropyl-3-[8-(2,6-difluorophenyl)-2-(methylsulfonyl)-7-oxo-7,8-dihydropyrido[2,3-d]pyrimidin-4-yl]-4-methylbenzamide and 4-piperidinamine by following the General Procedure for Sulfoxide/Sulfone/Sulfone Displacement, as disclosed above. The concentrated reaction mixture is precipitated with ethyl acetate/hexanes, and filtered. The desired product is obtained as a yellow solid (75 mg, 100%) 94% pure by HPLC: LC-MS m/z 531 (M+H)$^+$, 1.65 min (ret time).

Example 23

N-cyclopropyl-3-{8-(2,6-difluorophenyl)-2-[(1H-imidazol-2-ylmethyl)amino]-7-oxo-7,8-dihydropyrido[2,3-d]pyrimidin-4-yl}-4-methylbenzamide

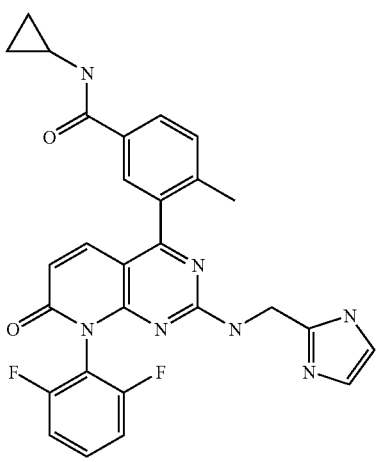

N-cyclopropyl-3-[8-(2,6-difluorophenyl)-2-(methylsulfonyl)-7-oxo-7,8-dihydropyrido[2,3-d]pyrimidin-4-yl]-4-methylbenzamide (0.1 g, 0.2 mmol) is dissolved in DMF (10 mL) and (1H-imidazol-2-ylmethyl)amine dihydrochloride (0.053 g, 0.4 mmol) is added followed by triethylamine (0.167 mL, 1.2 mmol). The mixture is heated to about 60° C. for about 3 h. The reaction is judged to be complete by LCMS and the crude mixture is purified via reversed-phase HPLC. HPLC indicates 95% pure (254 nm) and the desired product is obtained as a white powder (54 mg, 50%): LC-MS m/z 528 (M+H)+, 1.45 min (ret time).

Example 24

N-cyclopropyl-3-(8-(2,6-difluorophenyl)-7-oxo-2-{[2-(propylamino)ethyl]amino}-7,8-dihydropyrido[2,3-d]pyrimidin-4-yl)-4-methylbenzamide

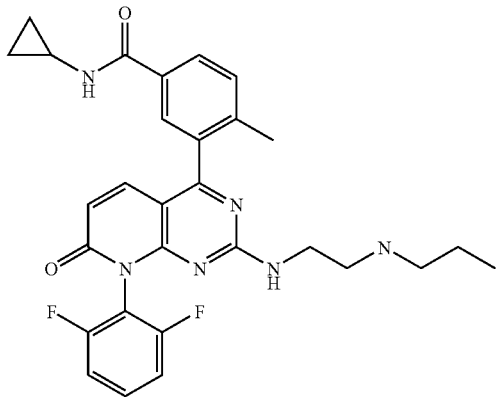

The title compound is prepared from N-cyclopropyl-3-[8-(2,6-difluorophenyl)-2-(methylsulfonyl)-7-oxo-7,8-dihydropyrido[2,3-d]pyrimidin-4-yl]-4-methylbenzamide and N-propyl-1,2-ethanediamine following the General Procedure for Sulfoxide/Sulfone Displacement, disclosed above. The concentrated reaction mixture is purified via reversed-phase HPLC. The desired product is obtained as a yellow solid (m.p. 120-134) >95% pure by HPLC (65 mg, 61%): LC-MS m/z 533 (M+H)+, 1.84 min (ret time).

Example 25

3-(8-(2,6-difluorophenyl)-2-{[2-(dimethylamino)ethyl]amino}-7-oxo-7,8-dihydropyrido[2,3-d]pyrimidin-4-yl)-4-methyl-N-(1-methylpropyl)benzamide

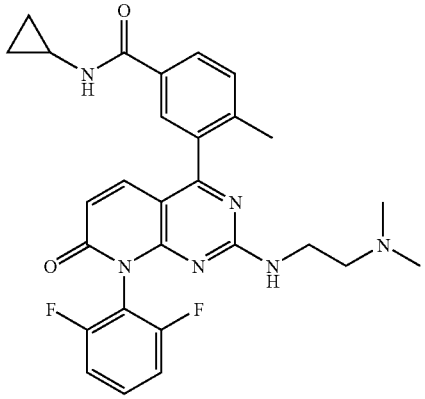

The title compound is prepared from the compound from N-cyclopropyl-3-[8-(2,6-difluorophenyl)-2-(methylsulfonyl)-7-oxo-7,8-dihydropyrido[2,3-d]pyrimidin-4-yl]-4-methylbenzamide and N,N'-dimethyl-1,2-ethanediamine by following the General Procedure for Sulfoxide/Sulfone Displacement, disclosed above. The concentrated reaction mixture is purified via reversed-phase HPLC. The desired product is obtained as an off-white solid (m.p. 214.7-217.5° C.) >95% pure by HPLC (69 mg, 67%): LC-MS m/z 519 (M+H)+, 1.54 min (ret time).

Example 26

3-{8-(2,6-difluorophenyl)-7-oxo-2-[(2,2,6,6-tetramethyl-4-piperidinyl)amino]-7,8-dihydropyrido[2,3-d]pyrimidin-4-yl}-N-[2-(4-fluorophenyl)ethyl]-4-methylbenzamide

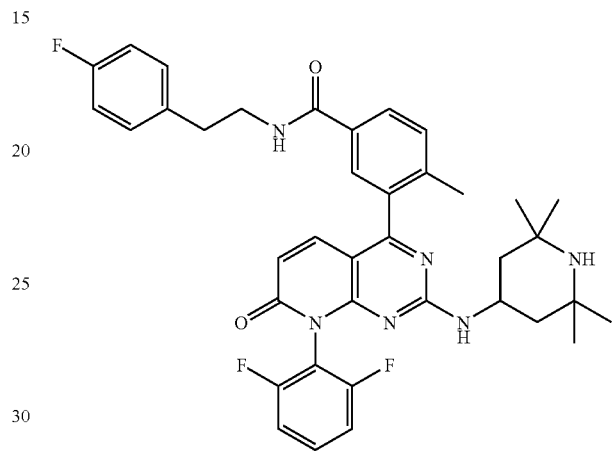

The title compound is prepared from the acid from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using 2-(4-fluorophenyl)ethanamine for the amide formation and 2,2,6,6-tetramethyl-4-piperidinamine for the displacement reaction: LC-MS m/z 669 (M+H)+, 2.03 min (ret time).

Example 27

3-[2-(4-amino-1-piperidinyl)-8-(2,6-difluorophenyl)-7-oxo-7,8-dihydropyrido[2,3-d]pyrimidin-4-yl]-N-(cyclopropylmethyl)-4-methylbenzamide

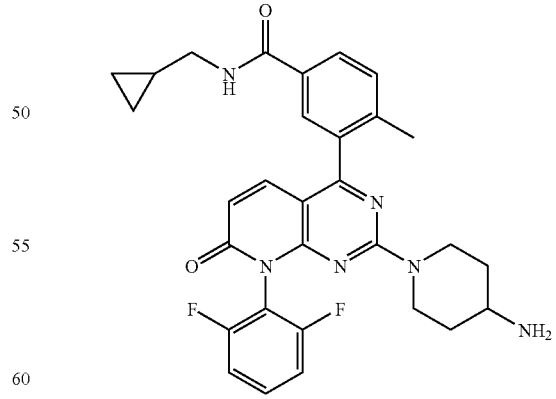

The title compound is prepared from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using (cyclopropylmethyl)amine for the amide formation and 4-piperidinamine for the displacement reaction: LC-MS m/z 545 (M+H)+, 1.63 min (ret time).

Example 28

3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methyl-N-(2-phenylethyl)benzamide

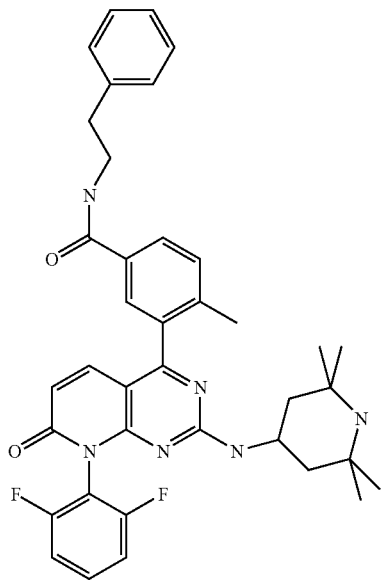

The title compound is prepared from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using 2-phenylethanamine for the amide formation and 2,2,6,6-tetramethyl-4-piperidinamine for the displacement reaction: LC-MS m/z 651 (M+H)$^+$, 1.87 min (ret time).

Example 29

3-(8-(2,6-difluorophenyl)-2-{[2-(methylamino)ethyl]amino}-7-oxo-7,8-dihydropyrido[2,3-d]pyrimidin-4-yl)-4-methyl-N-(2-phenylethyl)benzamide

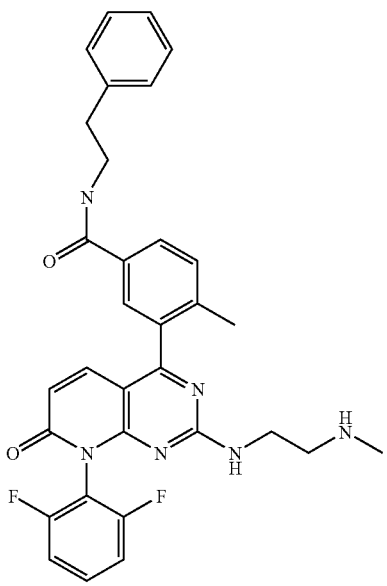

The title compound is prepared from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using 2-phenylethanamine for the amide formation and (2-aminoethyl)methylamine for the displacement reaction: LC-MS m/z 569 (M+H)$^+$, 1.69 min (ret time).

Example 30

3-{8-(2,6-difluorophenyl)-2-[(1H-imidazol-2-ylmethyl)amino]-7-oxo-7,8-dihydropyrido[2,3-d]pyrimidin-4-yl}-4-methyl-N-(2-phenylethyl)benzamide

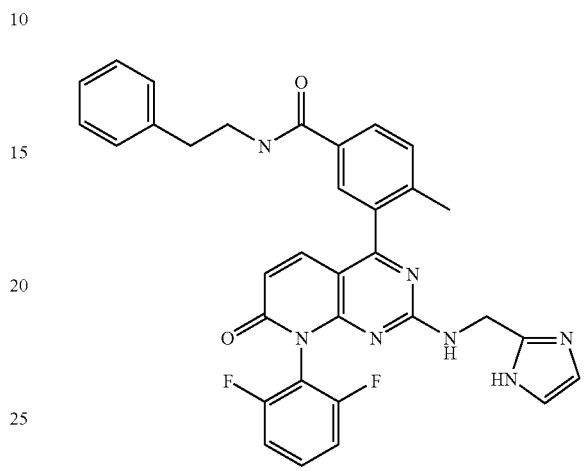

The title compound is prepared from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using 2-phenylethanamine for the amide formation and (1H-imidazol-2-ylmethyl)amine dihydrochloride for the displacement reaction: LC-MS m/z 592 (M+H)$^+$, 1.77 min (ret time).

Example 31

N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide 31a)
N-(3-iodo-4-methylphenyl)-3-thiophenecarboxamide

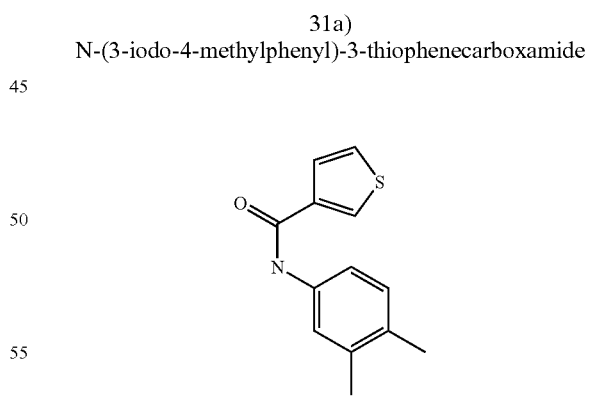

3-Thiophenecarboxylic acid (2.0 g, 15.6 mmol) was dissolved in methylene chloride (100 mL) and 2 drops of DMF were added. The mixture was cooled to about 0° C. and oxalyl chloride (1.5 mL, 17.1 mmol) was added slowly and allowed to warm to room temperature. Gas evolution was observed during warming. 3-Methyl-4-iodoaniline (5.45 g, 23.5 mmol), 4 drops of pyridine and K$_2$CO$_3$ (2.58 g, 18.7 mmol) are dissolved in CH$_2$Cl$_2$ (10 mL) and cooled to about 0° C. After about 1 h, the acid chloride mixture is slowly added to the cooled aniline mixture and allowed to warm to room temperature and stirred for about 18 h. The resulting mixture is filtered, washed with ethyl acetate and the filtrate is concentrated to a brown oil. The crude material was purified via flash chromatography (10-30% ethyl acetate in hexanes) to afford the desired product (1.56 g, 29%) as an off-white solid.

31b) N-[4-methyl-3-(4,4,5,5-tetramethyl-1,3,2-dioxaborolan-2-yl)phenyl]-3-thiophenecarboxamide

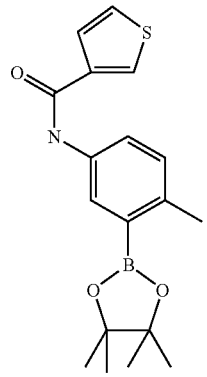

The iodide from Example 31a (1.56 g, 4.5 mmol), bis(pinacolato)diboran (2.3 g, 9.0 mmol), potassium acetate (2.21 g, 22.5 mmol) and PdCl₂.dppf (0.15 g, 0.225 mmol) are dissolved in DMF (50 mL) and heated to about 85° C. for about 24 h. The mixture was then concentrated to an oil and ethyl acetate and water were added. The organic portion was washed with brine and dried (Na₂SO₄). The concentrated organic layer was purified via flash chromatography to give the desired product (0.212 g, 13%).

31c) N-{3-[8-(2,6-difluorophenyl)-2-(methylthio)-7-oxo-7,8-dihydropyrido[2,3-d]pyrimidin-4-yl]-4-methylphenyl}-3-thiophenecarboxamide

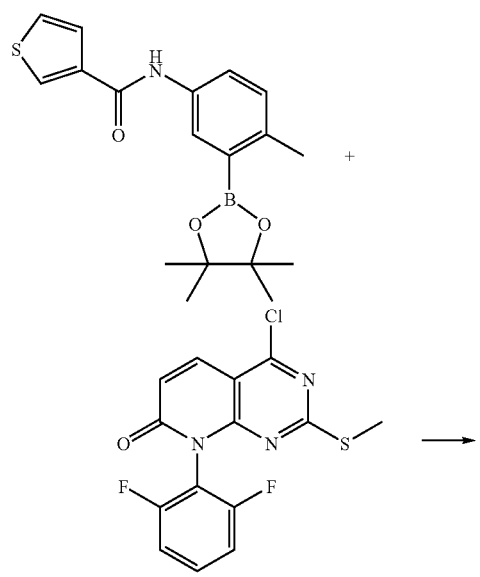

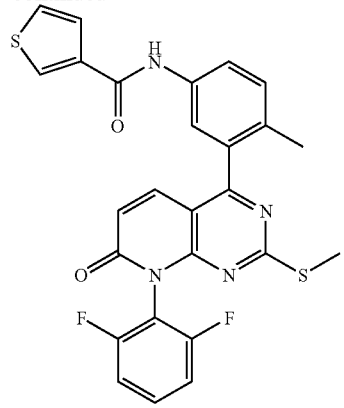

The title compound was prepared from the compound from Example 31b according to the procedures in Example 1b. Flash chromatography followed by recrystallization (ethyl acetate) afforded the desired compound (0.292 g, 90%).

31d) N-{3-[8-(2,6-difluorophenyl)-2-(methylsulfonyl)-7-oxo-7,8-dihydropyrido[2,3-d]pyrimidin-4-yl]-4-methylphenyl}-3-thiophenecarboxamide

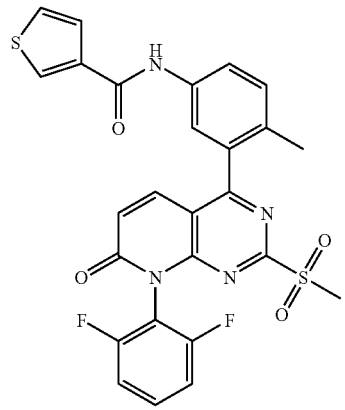

The title compound was prepared from the compound from Example 31c according to General Procedure for Sulfide Oxidation. The desired compound was obtained without need for purification (0.08 g, 63%).

31e) N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide

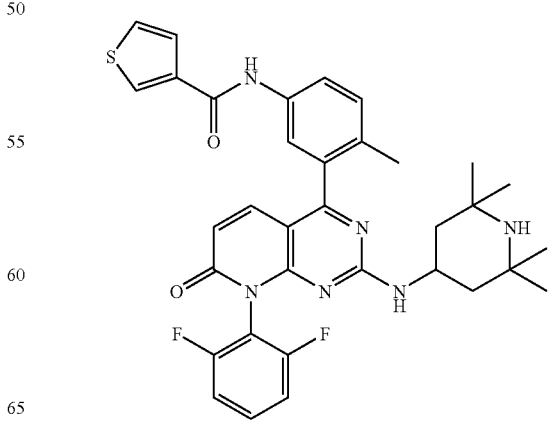

The title compound was prepared from N-{3-[8-(2,6-difluorophenyl)-2-(methylsulfonyl)-7-oxo-7,8-dihydropyrido[2,3-d]pyrimidin-4-yl]-4-methylphenyl}-3-thiophenecarboxamide and 2,2,6,6-tetramethyl-4-piperidinamine according to General Procedure for Sulfoxide/Sulfone Displacement, described above. The concentrated reaction mixture was slurried with acetonitrile and filtered. The solid was recrystallized from methanol/water to afford the desired product as a crystalline solid (0.2 g, 16%). HPLC indicated >99% pure: LC-MS m/z 629 (M+H)$^+$, 1.86 min (ret time).

31f) N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide hydrochloride Added IPA (5 mL) to N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide (196.5 mg) and heated to about 60° C. Added hydrochloric acid (1.1 eq; 1M in water), and solution mostly clarified. After a few minutes at about 60° C., crystallization had already begun, then cooled to RT. Stirred for about 3 hrs at rt, then filtered, washed with IPA, and dried to provide the title compound (160.9 mg).

31g) N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide 4-methylbenzenesulfonate Added IPA (5 mL) to N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide (203.2 mg) and heated to 60° C. Added p-toluenesulfonic acid (1.1 eq; 1M in water), and solution clarified. After a few minutes at about 60° C., cooled to rt. Stirred for about 3 hrs at rt, then filtered, washed with IPA, and dried in vacuum oven at 50° C. to provide the title compound (123.9 mg). Melting point (tested with DSC) is 335° C.

31h) N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide methanesulfonate Added 320 uL of CH$_3$CN to N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide (16.0 mg) and heated to about 60° C. Added methanesulfonic acid (1.1 eq; 1M in IPA), and solution clarified except for tiny amount stuck to bottom. After a few minutes at about 60° C., cooled to rt. Got lots of white precipitate. Stirred overnight at rt. Next day, filtered and dried to provide the title compound (3.5 mg). Melting point (tested with DSC) is 331° C.

31i) N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide hydrobromide Added 400 uL of acetone to N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide (9.8 mg), mostly dissolved. Added hydrobromic acid (1.1 eq; 1M in water). After about 2.5 weeks, small amounts of crystals were seen. The cap was loosened and let to evaporate overnight. This resulted in more crystals the next day. To this was added back 50 uL of acetone, filtered and dried to provide the title compound.

31j) N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide sulfate Added 400 uL of acetone to N-(3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylphenyl)-3-thiophenecarboxamide (9.1 mg), mostly dissolved. Added sulfuric acid (1.1 eq; 1M in water). After about 2.5 weeks, a lot of crystals were seen, and this was filtered and dried to provide the title compound.

Example 32

N-{3-[2-(4-amino-1-piperidinyl)-8-(2,6-difluorophenyl)-7-oxo-7,8-dihydropyrido[2,3-d]pyrimidin-4-yl]-4-methylphenyl}-3-thiophenecarboxamide

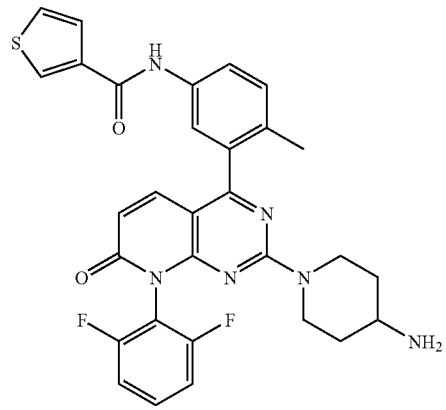

The title compound was prepared from N-{3-[8-(2,6-difluorophenyl)-2-(methylsulfonyl)-7-oxo-7,8-dihydropyrido[2,3-d]pyrimidin-4-yl]-4-methylphenyl}-3-thiophenecarboxamide and 4-piperidinamine according to General Procedure for Sulfoxide/Sulfone Displacement, described above. The concentrated reaction mixture was purified via reversed-phase HPLC to give the desired compound as a light tan powder (0.041 g, 32%). HPLC indicated the material to be >95% pure (m.p. 183.8-187.9): LC-MS m/z 573 (M+H)$^+$, 1.79 min (ret time).

Example 33

3-[2-[(2-aminoethyl)(methyl)amino]-8-(2,6-difluorophenyl)-7-oxo-7,8-dihydropyrido[2,3-d]pyrimidin-4-yl]-N-(4-fluorophenyl)-4-methylbenzamide

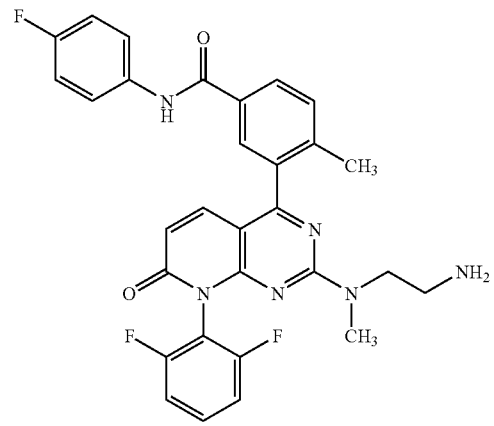

To a solution of 3-[8-(2,6-difluorophenyl)-2-(methylsulfinyl)-7-oxo-7,8-dihydropyrido[2,3-d]pyrimidin-4-yl]-N-(4-fluorophenyl)-4-methylbenzamide (50 mg, 0.09 mmol) in THF (5 mL) was added N-methyl-1,2-ethanediamine (0.044 mL, 0.5 mmol). The resultant mixture was stirred at room temperature overnight. The mixture was concentrated under vacuo. Flash chromatography (90% CH$_2$Cl$_2$/7% MeOH/3% NH$_4$OH) then provide the title compound (8.0 mg, 16%). LC-MS (ES) m/z 559 (M+H)$^+$; $^1$H-NMR(MeOD) δ 2.35 (s, 3H), 2.65 (m, 1H), 2.86 (m, 1H), 2.92 (m, 1H), 3.26 (m, 1H), 3.35 (m, 1H), 3.40 (m, 1H), 3.77 (m, 1H), 6.36 (d, 1H), 7.14 (m, 2H), 7.25 (m, 2H), 7.52 (d, 1H), 7.59 (d, 1H), 7.62 (m, 1H), 7.71 (m, 2H), 7.92 (s, 1H), 8.06 (d, 1H).

Example 34

3-{8-(2,6-difluorophenyl)-2-[[3-(dimethylamino) propyl](methyl)amino]-7-oxo-7,8-dihydropyrido[2, 3-d]pyrimidin-4-yl}-4-methyl-N-(1-methylethyl) benzamide

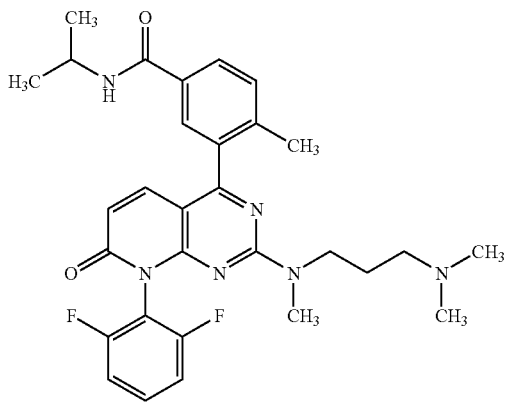

The title compound was prepared from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using 2-propanamine for the amide formation and N,N,N'-trimethyl-1,3-propanediamine for the displacement reaction (88%). LC-MS (ES) m/z 549 (M+H)$^+$; $^1$H-NMR(MeOD) δ 1.27 (d, 6H), 1.60 (m, 1H), 1.80 (m, 1H), 2.06 (m, 1H), 2.22 (m, 6H), 2.33 (m, 4H), 2.86 (m, 1H), 3.19 (m, 2H), 3.40 (m, 1H), 3.70 (m, 1H), 4.30 (m, 1H), 6.00 (m, 1H), 6.33 (d, 1H), 7.10 (t, 2H), 7.30 (m, 2H), 7.42 (d, 1H), 7.48 (m, 1H), 7.66 (s, 1H), 7.85 (d, 1H).

Example 35

N-[3-(8-(2,6-difluorophenyl)-2-{[2-hydroxy-1-(hydroxymethyl)ethyl]amino}-7-oxo-7,8-dihydropyrido [2,3-d]pyrimidin-4-yl)-4-methylphenyl]-3-thiophenecarboxamide

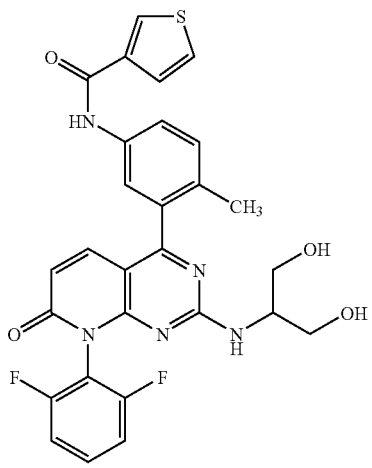

To a solution of 4-chloro-2-(2-hydroxy-1-hydroxymethyl-ethylamino)-8-(2,4-difluoro-phenyl)-8H-pyrido[2,3-d]pyrimidin-7-one (40.0 mg, 0.105 mmol) in dioxane/H$_2$O (3:1, 4.8 mL) was added N-[4-methyl-3-(4,4,5,5-tetramethyl-1,3,2-dioxaborolan-2-yl)phenyl]-3-thiophene carboxamide (53.9 mg, 0.157 mmol) and K$_2$CO$_3$ (58.0 mg, 0.420 mmol). The resultant mixture was bubbled with argon for 5 minutes, then added by Pd(PPh$_3$)$_4$ (2.4 mg, 0.0021 mmol). The reaction tube was sealed and heated in "Smith Creator" (microwave, 150° C.) for about 15 minutes. The mixture was concentrated under vacuo. Flash chromatography (EtOAc/Hexane, 3:1) then provided the title compound (50.0 mg, 85%): LC-MS (ES) m/z 564 (M+H)$^+$, $^1$H-NMR(MeOD) δ 2.24 (s, 3H), 3.63 (m, 5H), 6.38 (m, 1H), 7.22 (m, 2H), 7.39 (d, 1H), 7.65 (m, 6H), 8.24 (s, 1H).

Example 36

N-cyclopropyl-3-(8-(2,6-difluorophenyl)-2-{[2-hydroxy-1-(hydroxymethyl)ethyl]-amino}-7-oxo-7,8-dihydropyrido[2,3-d]pyrimidin-4-yl)-4-methylbenzamide

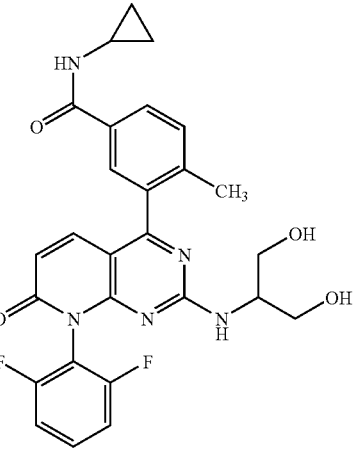

The title compound was prepared from 4-chloro-8-(2,6-difluorophenyl)-2-{[2-hydroxy-1-(hydroxymethyl)ethyl] amino}pyrido[2,3-d]pyrimidin-7(8H)-one by following the procedures of Example 35 using 3-N-cyclopropyl-4-methyl-3-(4,4,5,5-tetramethyl-1,3,2-dioxaborolan-2-yl) benzamide for the Suzuki cross-coupling reaction (29.6 mg, 55%): LC-MS (ES) m/z 522 (M+H)$^+$, $^1$H-NMR(MeOD) δ 0.65 (m, 2H), 0.81 (m, 2H), 2.31 (s, 3H), 2.87 (m, 1H), 3.64 (m, 5H), 6.39 (m, 1H), 7.25 (m, 2H), 7.45 (d, 1H), 7.51 (d, 1H), 7.59 (m, 1H), 7.78 (m, 1H), 7.91 (m, 1H).

Example 37

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-3-isoquinolinecarboxamide trifluoroacetate 37a) 4-(5-amino-2-methyl-phenyl)-8-(2,6-difluorophenyl)-2-(2-hydroxy-1-hydroxymethyl-ethylamino)-8H-pyrido[2,3-d]pyrimidin-7-one

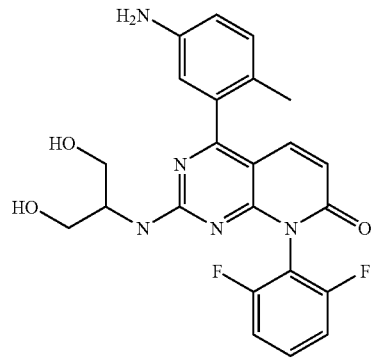

The title compound was prepared from 4-methyl-3-(4,4,5,5-tetramethyl-1,3,2-dioxaborolan-2-yl)aniline by following the procedures in Example 18e.

37b) N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-3-isoquinolinecarboxamide trifluoroacetate

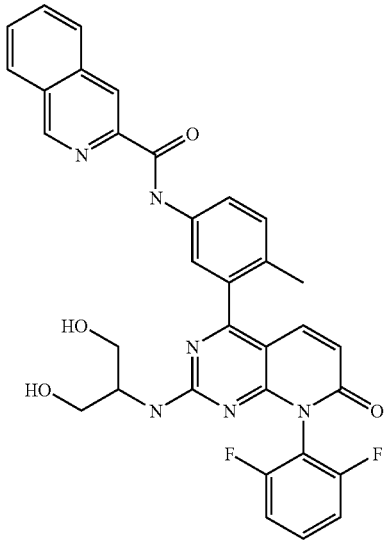

To isoquinoline-3-carboxylic acid (11.5 mg, 0.066 mmol, 1 eq) was added HATU (38.02 mg, 0.1 mmol, 1.5 eq) in DMF (250 uL). DIPEA (34.84 uL, 0.2 mmol, 3 eq) was then added. The resulting mixture was then allowed to stand for about 5 minutes before 4-(5-amino-2-methyl-phenyl)-8-(2,6-difluoro-phenyl)-2-(2-hydroxy-1-hydroxymethyl-ethylamino)-8H-pyrido[2,3-d]pyrimidin-7-one (30.23 mg, 0.066 mmol, 1 eq) was added. The resulting mixture was shaken to ensure efficient mixing of the reagents then was left to stand overnight. The solvent was then removed in vacuo. The residue was dissolved in methanol and was then placed down an aminopropyl SPE flushing the column with methanol. The elute from the SPE was then treated with NaOH (2 M, 200 uL) and the mixture was allowed to stand for about 1 hr. This was followed by HCl (2M, 200 uL) then the solvent was removed in vacuo. The residue was purified by MDAP. LC-MS m/z 609 (M+H)$^+$, 3.31 min (ret time).

Example 38

6-chloro-N-[3-(8-(2,6-difluorophenyl)-2-{[2-hydroxy-1-(hydroxymethyl)ethyl]-amino}-7-oxo-7,8-dihydropyrido[2,3-d]pyrimidin-4-yl)-4-methylphenyl]-3-pyridinecarboxamide trifluoroacetate

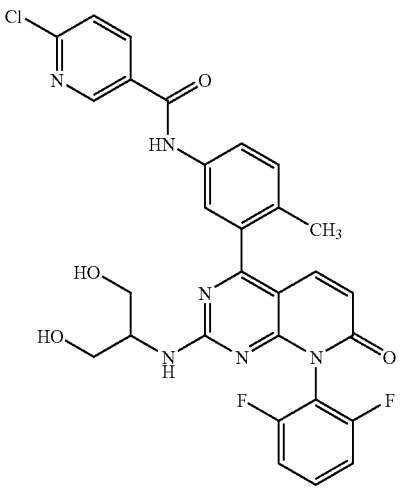

The title compound was prepared from 6-chloro-3-pyridinecarboxylic acid by following the procedures in Example 37b: LC-MS m/z 593 (M+H)$^+$, 2.99 min (ret time).

Example 39

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-2-hydroxy-1-naphthalenecarboxamide trifluoroacetate

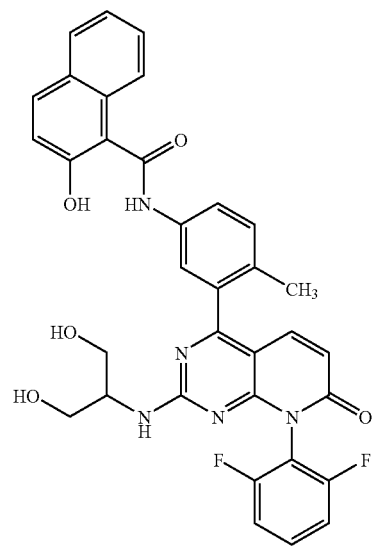

The title compound was prepared from 2-hydroxy-1-naphthalenecarboxylic acid by following the procedures in Example 37b: LC-MS m/z 624 (M+H)+, 3.37 min (ret time).

Example 40

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-4-fluoro-1-naphthalenecarboxamide trifluoroacetate

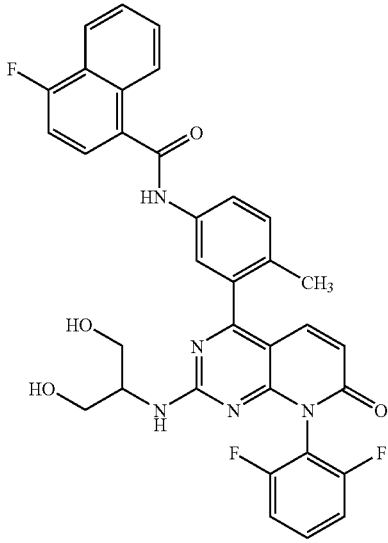

The title compound was prepared from 4-fluoro-1-naphthalenecarboxylic acid by following the procedures in Example 37b: LC-MS m/z 626 (M+H)+, 3.32 min (ret time).

Example 41

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-5-methyl-2-pyrazinecarboxamide trifluoroacetate

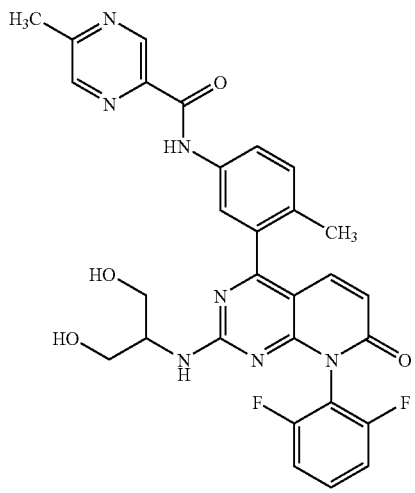

The title compound was prepared from 5-methyl-2-pyrazinecarboxylic acid by following the procedures in Example 37b: LC-MS m/z 574 (M+H)+, 2.86 min (ret time).

Example 42

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-1H-indole-5-carboxamide trifluoroacetate

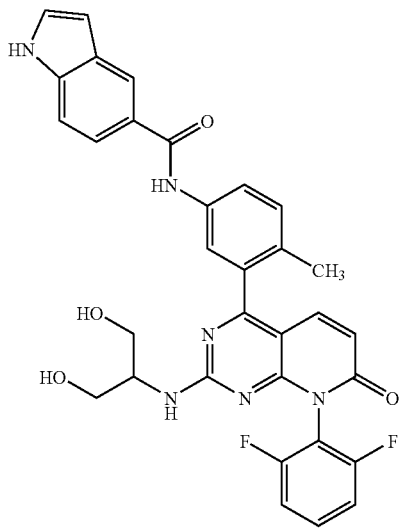

The title compound was prepared from 1H-indole-5-carboxylic acid by following the procedures in Example 37b: LC-MS m/z 597 (M+H)+, 3.06 min (ret time).

Example 43

3-amino-N-[3-(8-(2,6-difluorophenyl)-2-{[2-hydroxy-1-(hydroxymethyl)ethyl]-amino}-7-oxo-7,8-dihydropyrido[2,3-d]pyrimidin-4-yl)-4-methylphenyl]benzamide trifluoroacetate

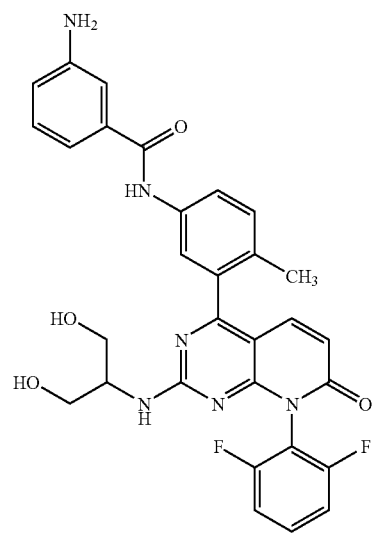

The title compound was prepared from 3-aminobenzoic acid by following the procedures in Example 37b: LC-MS m/z 573 (M+H)+, 2.77 min (ret time).

Example 44

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-1H-indole-7-carboxamide trifluoroacetate

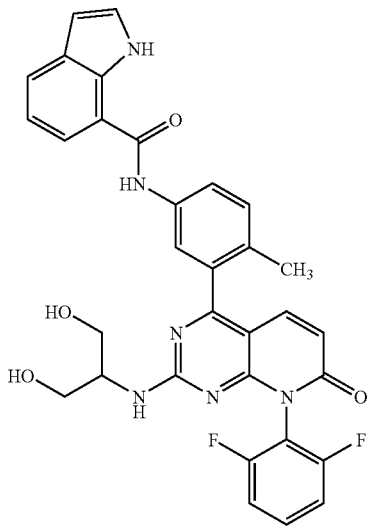

The title compound was prepared from 1H-indole-7-carboxylic acid by following the procedures in Example 37b: LC-MS m/z 597 (M+H)+, 3.27 min (ret time).

Example 45

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-2-(3-methylphenyl)acetamide trifluoroacetate

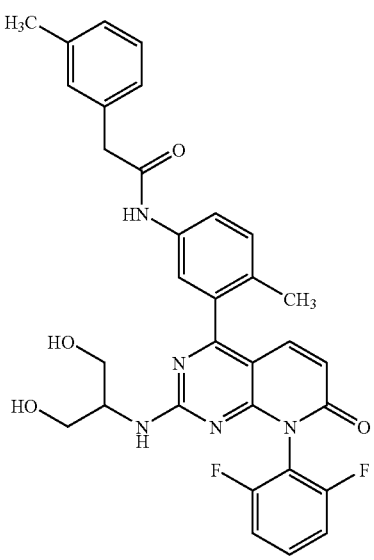

The title compound was prepared from (3-methylphenyl)acetic acid by following the procedures in Example 37b: LC-MS m/z 586 (M+H)+, 3.15 min (ret time).

Example 46

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-3,4-dimethylbenzamide trifluoroacetate

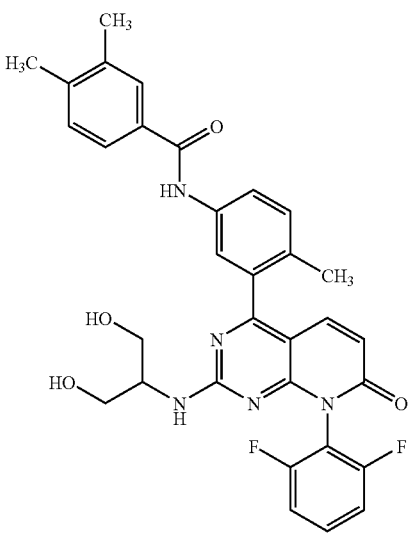

The title compound was prepared from 3,4-dimethylbenzoic acid by following the procedures in Example 37b: LC-MS m/z 586 (M+H)+, 3.25 min (ret time).

Example 47

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-3-fluoro-4-methylbenzamide trifluoroacetate

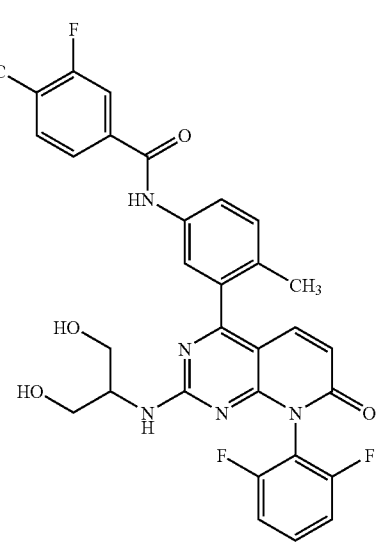

The title compound was prepared from 3-fluoro-4-methyl-benzoic acid by following the procedures in Example 37b: LC-MS m/z 590 (M+H)+, 3.23 min (ret time).

Example 48

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-3,5-dihydroxy-4-methylbenzamide trifluoroacetate

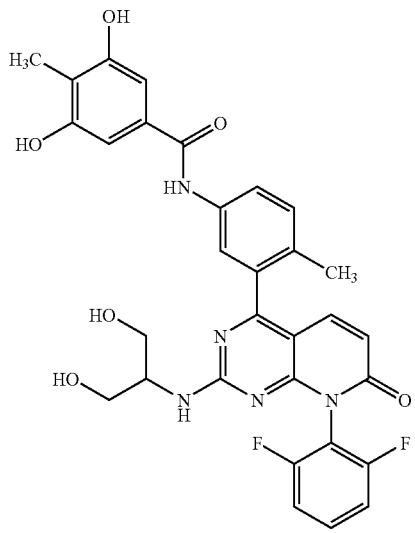

The title compound was prepared from 3,5-dihydroxy-4-methylbenzoic acid by following the procedures in Example 37b: LC-MS m/z 604 (M+H)+, 2.88 min (ret time).

Example 49

2-(2,3-difluorophenyl)-N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]acetamide trifluoroacetate

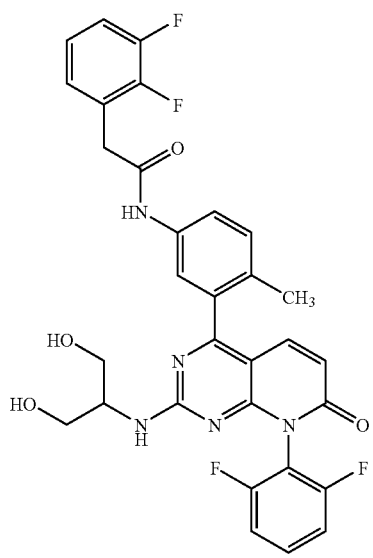

The title compound was prepared from (2,3-difluorophenyl)acetic acid by following the procedures in Example 37b: LC-MS m/z 608 (M+H)+, 3.12 min (ret time).

Example 50

2-(3,5-difluorophenyl)-N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]acetamide trifluoroacetate

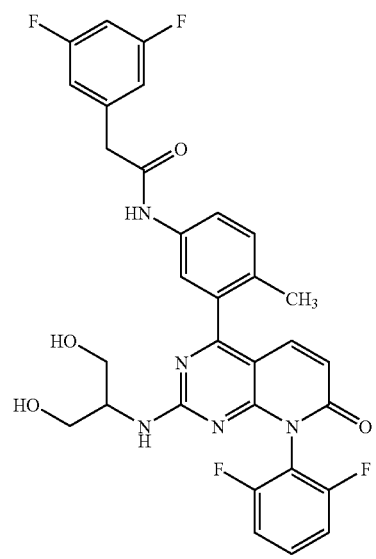

The title compound was prepared from (3,5-difluorophenyl)acetic acid by following the procedures in Example 37b: LC-MS m/z 608 (M+H)+, 3.17 min (ret time).

Example 51

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-1-methyl-1H-imidazole-4-carboxamide trifluoroacetate

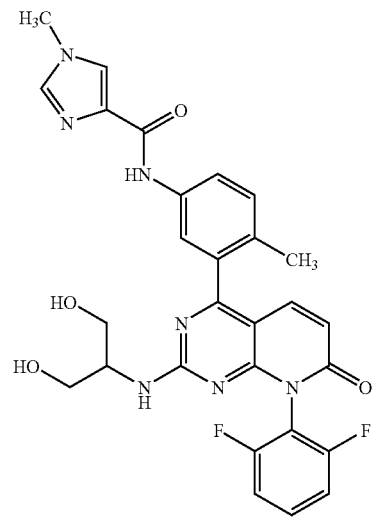

The title compound was prepared from 1-methyl-1H-imidazole-4-carboxylic acid by following the procedures in Example 37b: LC-MS m/z 562 (M+H)+, 2.65 min (ret time).

Example 52

4-[(3-{[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]amino}-3-oxopropyl)amino]-4-oxobutanoic acid trifluoroacetate

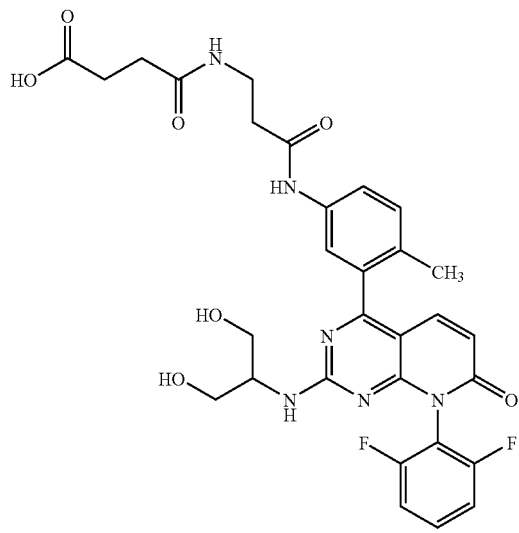

The title compound was prepared from 3-(2,5-dioxo-1-pyrrolidinyl)-propanoic acid by following the procedures in Example 37b: LC-MS m/z 607 (M+H)+, 2.56 min (ret time).

Example 53

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-1H-pyrazole-3-carboxamide trifluoroacetate

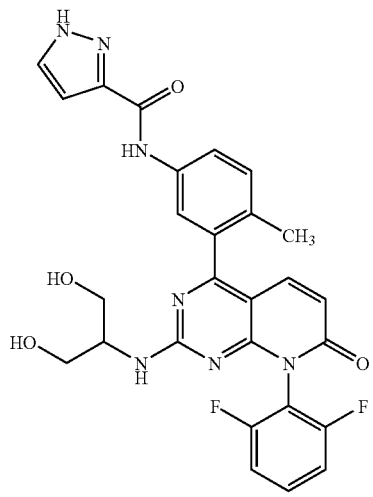

The title compound was prepared from 1H-pyrazole-3-carboxylic acid by following the procedures in Example 37b: LC-MS m/z 548 (M+H)+, 2.74 min (ret time).

Example 54

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-2-thiophenecarboxamide trifluoroacetate

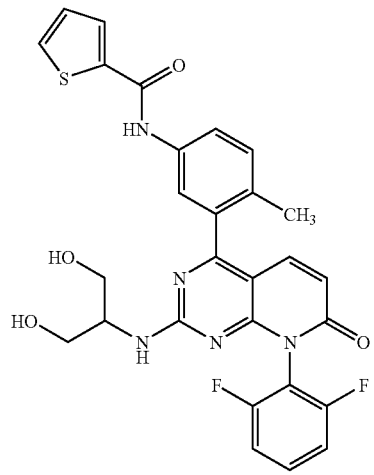

The title compound was prepared from 2-thiophenecarboxylic acid by following the procedures in Example 37b: LC-MS m/z 564 (M+H)+, 3.03 min (ret time).

Example 55

N-[3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylphenyl]-2-[(2,2,2-trifluoroethyl)oxy]acetamide trifluoroacetate

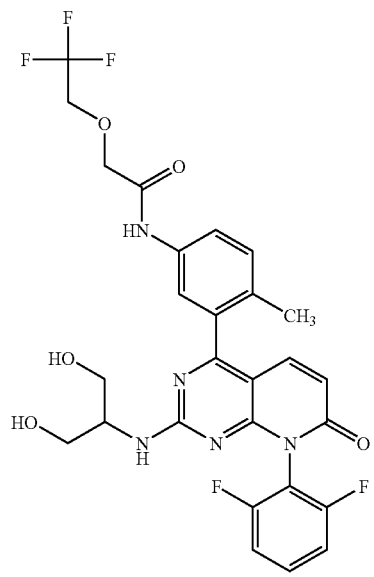

The title compound was prepared from [(2,2,2-trifluoroethyl)oxy]acetic acid by following the procedures in Example 37b: LC-MS m/z 594 (M+H)+, 2.96 min (ret time).

Example 56

3-(8-(2,6-difluorophenyl)-2-{[2-(methylamino)ethyl]amino}-7-oxo-7,8-dihydropyrido[2,3-d]pyrimidin-4-yl)-4-methyl-N-propylbenzamide 56a) 4-Methyl-N-propyl-3-(4,4,5,5-tetramethyl-[1,3,2]dioxaborolan-2-yl)-benzamide

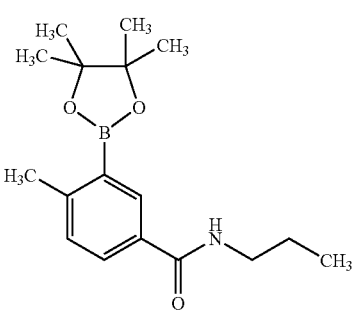

To 4-methyl-3-(4,4,5,5-tetramethyl-[1,3,2]dioxaborolan-2-yl)-benzoic acid (524 mg, 2 mmol, 1 eq) was added HBTU (642 mg, 2 mmol, 1 eq) in DMF (5 mL). DIPEA (700 uL, 4 mmol, 2 eq) was then added in 100 uL portions. After 10 min propylamine (328 uL, 4 mmol, 2 eq) was then added and the mixture was stirred overnight at room temperature. The solvent was then removed in vacuo. The residue was then dissolved in chloroform and purified by aminopropyl SPE: LC-MS m/z 304 (M+H)+, 3.37 min (ret time).

56b) 3-[8-(2,6-Difluoro-phenyl)-2-methylsulfanyl-7-oxo-7,8-dihydro-pyrido[2,3-d]pyrimidin-4-yl]-4-methyl-N-propyl-benzamide

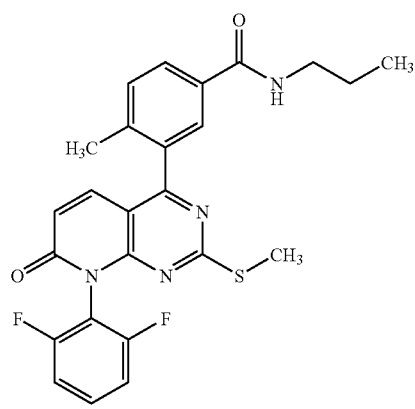

To 4-chloro-8-(2,6-difluoro-phenyl)-2-methylsulfanyl-8H-pyrido[2,3-d]pyrimidin-7 one (200 mg, 0.589 mmol, 1 eq) and 4-methyl-N-propyl-3-(4,4,5,5-tetramethyl-[1,3,2]dioxaborolan-2-yl)-benzamide (268 mg, 0.883 mmol, 1.5 eq) in isopropanol (6 mL) was added sodium bicarbonate (148 mg, 1.76 mmol, 3 eq) in water (1.5 mL). The reaction mixture was then purged with nitrogen followed by addition of tetrakis(triphenylphosphine)-palladium(0) (34 mg, 0.029 mmol, 5 mol %). The mixture was then heated to about 80° C. overnight. The mixture was then allowed to cool to room temperature before the solvent was removed in vacuo. The residue was then purified on the Flashmaster 2™: LC-MS m/z 481 (M+H)+, 3.34 min (ret time).

56c) 3-[8-(2,6-Difluoro-phenyl)-2-methanesulfonyl-7-oxo-7,8-dihydro-pyrido[2,3-d]pyrimidin-4-yl]-4-methyl-N-propyl-benzamide

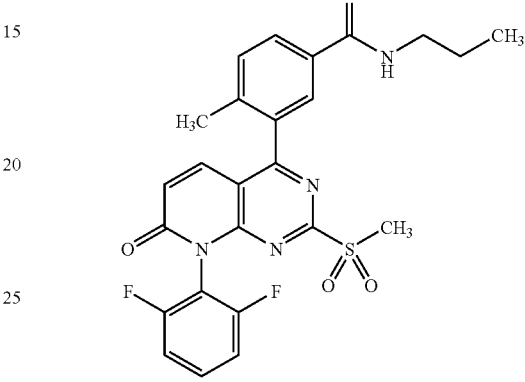

3-[8-(2,6-Difluoro-phenyl)-2-methylsulfanyl-7-oxo-7,8-dihydro-pyrido[2,3-d]pyrimidin-4-yl]-4-methyl-N-propyl-benzamide (204 mg, 0.426 mmol, 1 eq) was suspended in acetonitrile (6 mL). The suspension was added to a stirring suspension of Oxone® (786 mg, 1.28 mmol, 3 eq) in water (3 mL). The resulting mixture was stirred overnight at about 40° C. The reaction mixture was then partitioned between dichloromethane and sodium metabisulfite (10% aq solution). The layers were separated then the organic was dried over magnesium sulfate, filtered then evaporated to furnish the title compound: LC-MS m/z 513 (M+H)+, 2.9 min (ret time).

56d) 3-(8-(2,6-difluorophenyl)-2-{[2-(methylamino)ethyl]amino}-7-oxo-7,8-dihydropyrido[2,3-d]pyrimidin-4-yl)-4-methyl-N-propylbenzamide

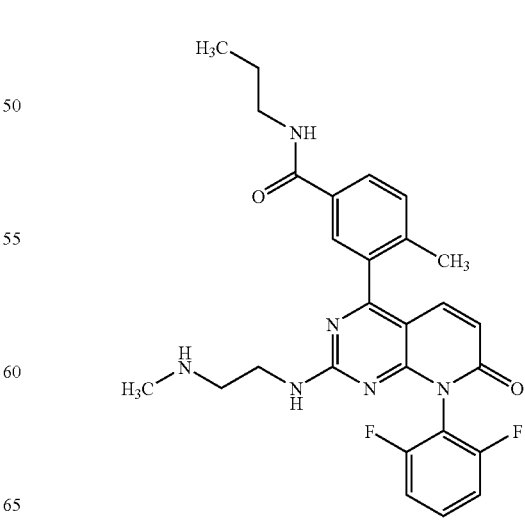

The title compound was prepared from the compound from Example 56c and (2-aminoethyl)methylamine by following the procedures in Example 31 e: LC-MS m/z 507 (M+H)$^+$, 2.31 min (ret time).

Example 57

3-(8-(2,6-difluorophenyl)-2-{[2-(methylamino)ethyl]amino}-7-oxo-7,8-dihydropyrido[2,3-d]pyrimidin-4-yl)-4-methyl-N-(1-methylethyl)benzamide

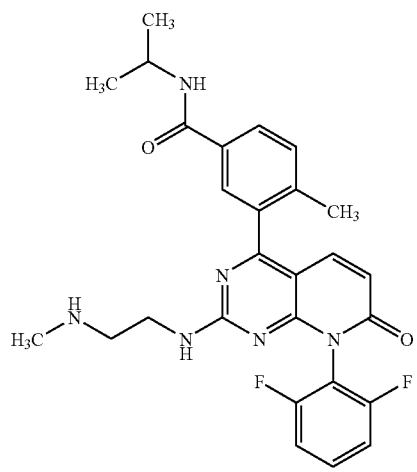

The title compound was prepared by following the procedures in Example 56 using 2-propanamine for amide formation and (2-aminoethyl)methylamine for the displacement: LC-MS m/z 507 (M+H)$^+$, 2.3 min (ret time).

Example 58

N-cyclopentyl-3-(8-(2,6-difluorophenyl)-2-{[2-(methylamino)ethyl]amino}-7-oxo-7,8-dihydropyrido[2,3-d]pyrimidin-4-yl)-4-methylbenzamide

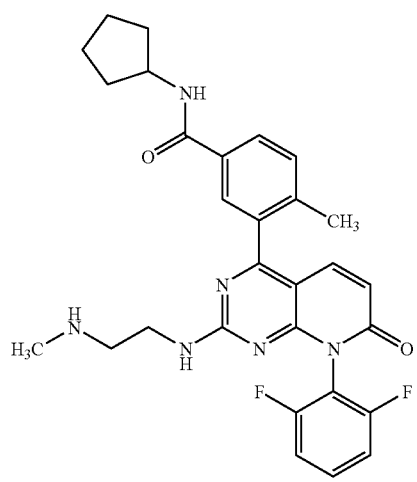

The title compound was prepared by following the procedures in Example 56 using cyclopentylamine for amide formation and (2-aminoethyl)methylamine for the displacement: LC-MS m/z 533 (M+H)$^+$, 2.43 min (ret time).

Example 59

3-(8-(2,6-difluorophenyl)-2-{[2-(methylamino)ethyl]amino}-7-oxo-7,8-dihydropyrido[2,3-d]pyrimidin-4-yl)-4-methyl-N-(phenylmethyl)benzamide

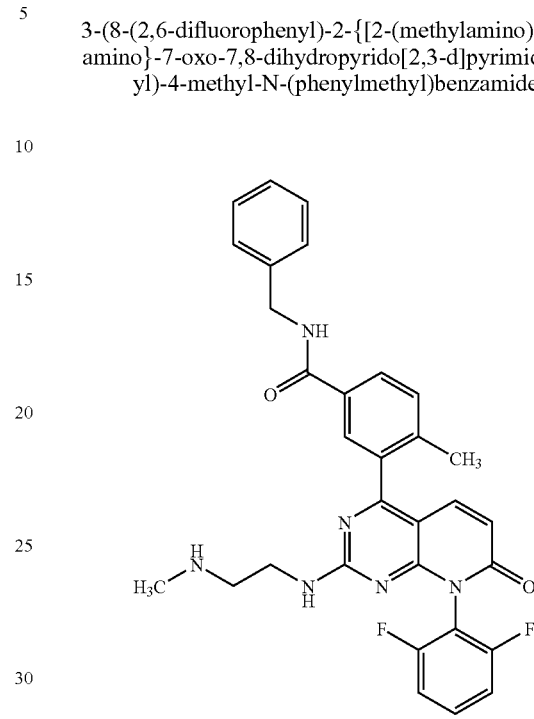

The title compound was prepared by following the procedures in Example 56 using benzylamine for the amide formation and (2-aminoethyl)methylamine for the displacement: LC-MS m/z 555 (M+H)$^+$, 2.48 min (ret time).

Example 60

3-(8-(2,6-difluorophenyl)-2-{[2-(methylamino)ethyl]amino}-7-oxo-7,8-dihydropyrido[2,3-d]pyrimidin-4-yl)-N-(4-fluorophenyl)-4-methylbenzamide

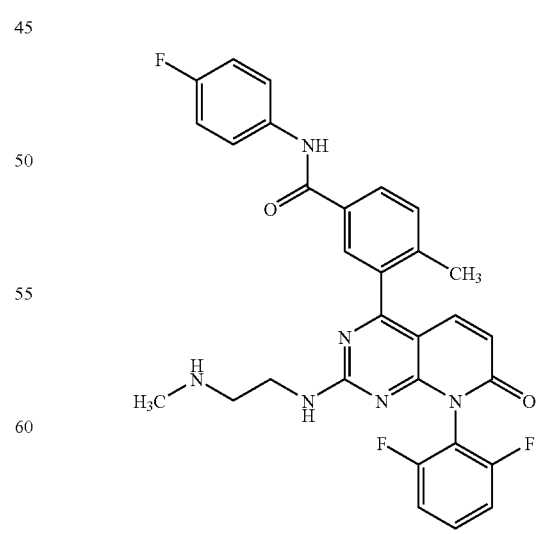

The title compound was prepared by following the procedures in example 56 using 4-fluoroaniline for the amide formation and (2-aminoethyl)methylamine for the displacement: LC-MS m/z 559 (M+H)+, 2.55 min (ret time).

Example 61

3-(8-(2,6-difluorophenyl)-2-{[2-(methylamino)ethyl]amino}-7-oxo-7,8-dihydropyrido[2,3-d]pyrimidin-4-yl)-4-methyl-N-1,3-thiazol-2-ylbenzamide

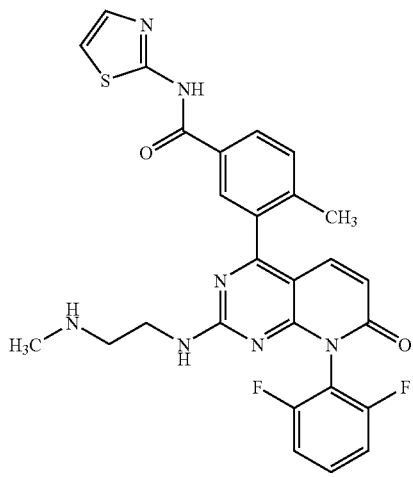

The title compound was prepared by following the procedures in Example 56 using 1,3-thiazole-2-amine for the amide formation and (2-aminoethyl)methylamine for the displacement: LC-MS m/z 548 (M+H)+, 2.41 min (ret time).

Example 62

3-{8-(2,6-difluorophenyl-7-oxo-2-[(2,2,6,6-tetramethyl-4-piperidinyl)amino]-7,8-dihydropyrido[2,3-d]pyrimidin-4-yl}-4-methyl-N-(1-methylethyl)benzamide

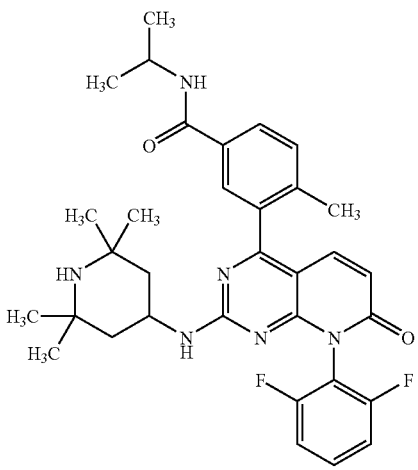

The title compound was prepared by following the procedures in Example 56 using 2-propanamine for the amide formation and 2,2,6,6-tetramethyl-4-piperidinamine for the displacement: LC-MS m/z 589 (M+H)+, 2.46 min (ret time).

Example 63

3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methyl-N-propylbenzamide

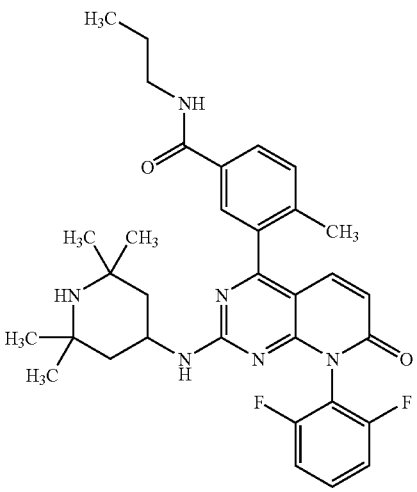

The title compound was prepared by following the procedures in Example 56 using propanamine for the amide formation and 2,2,6,6-tetramethyl-4-piperidinamine for the displacement: LC-MS m/z 589 (M+H)+, 2.47 min (ret time).

Example 64

N-cyclopentyl-3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methylbenzamide

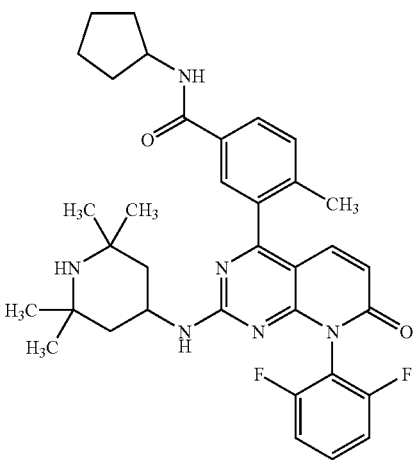

The title compound was prepared by following the procedures in Example 56 using cyclopentylamine for the amide formation and 2,2,6,6-tetramethyl-4-piperidinamine for the displacement: LC-MS m/z 615 (M+H)+, 2.58 min (ret time).

Example 65

3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methyl-N-(phenylmethyl)benzamide

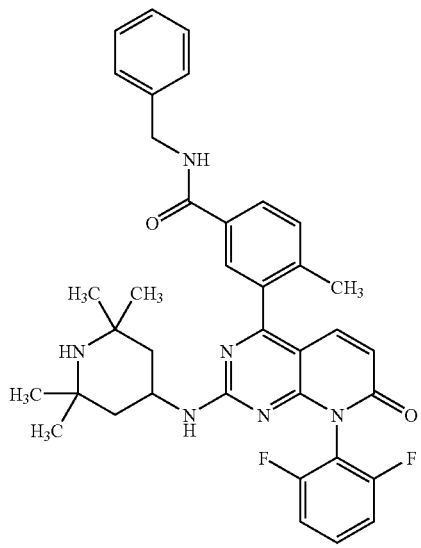

The title compound was prepared by following the procedures in Example 56 using benzylamine for the amide formation and 2,2,6,6-tetramethyl-4-piperidinamine for the displacement: LC-MS m/z 637 (M+H)⁺, 2.63 min (ret time).

Example 66

3-{8-(2,6-difluorophenyl)-7-oxo-2-[(2,2,6,6-tetramethyl-4-piperidinyl)amino]-7,8-dihydropyrido[2,3-d]pyrimidin-4-yl}-N-(4-fluorophenyl)-4-methylbenzamide

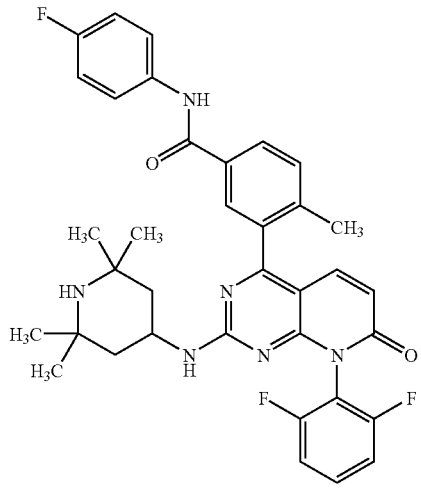

The title compound was prepared by following the procedures in Example 56 using 4-fluoroaniline for the amide formation and 2,2,6,6-tetramethyl-4-piperidinamine for the displacement: LC-MS m/z 641 (M+H)⁺, 2.71 min (ret time).

Example 67

3-{8-(2,6-difluorophenyl)-7-oxo-2-[(2,2,6,6-tetramethyl-4-piperidinyl)amino]-7,8-dihydropyrido[2,3-d]pyrimidin-4-yl}-4-methyl-N-1,3-thiazol-2-ylbenzamide

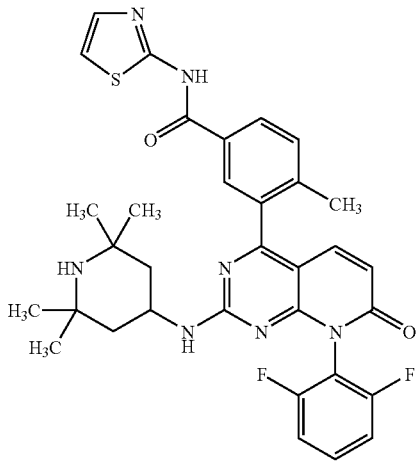

The title compound was prepared by following the procedures in Example 56 using 1,3-thiazole-2-amine for the amide formation and 2,2,6,6-tetramethyl-4-piperidinamine for the displacement: LC-MS m/z 630 (M+H)⁺, 2.57 min (ret time).

Example 68

3-[2-(4-amino-1-piperidinyl)-8-(2,6-difluorophenyl)-7-oxo-7,8-dihydropyrido[2,3-d]pyrimidin-4-yl]-4-methyl-N-(1-methylethyl)benzamide

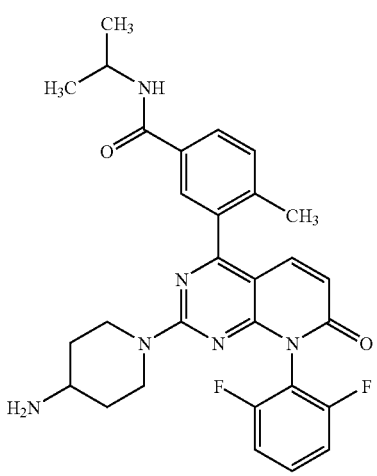

The title compound was prepared by following the procedures in Example 56 using 2-propanamine for the amide formation and 4-piperidinamine for the displacement: LC-MS m/z 533 (M+H)+, 2.42 min (ret time).

Example 69

3-[2-(4-amino-1-piperidinyl)-8-(2,6-difluorophenyl)-7-oxo-7,8-dihydropyrido[2,3-d]pyrimidin-4-yl]-4-methyl-N-propylbenzamide

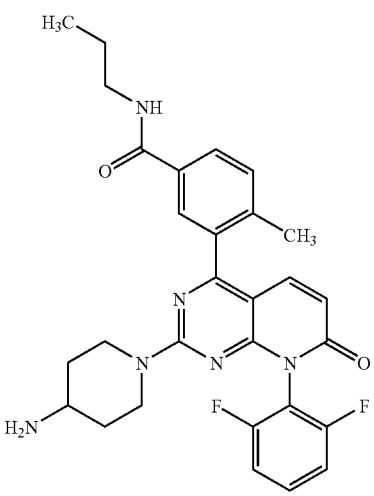

The title compound was prepared by following the procedures in Example 56 using propanamine for the amide formation and 4-piperidinamine for the displacement: LC-MS m/z 533 (M+H)+, 2.43 min (ret time).

Example 70

3-[2-(4-amino-1-piperidinyl)-8-(2,6-difluorophenyl)-7-oxo-7,8-dihydropyrido[2,3-d]pyrimidin-4-yl]-N-cyclopentyl-4-methylbenzamide

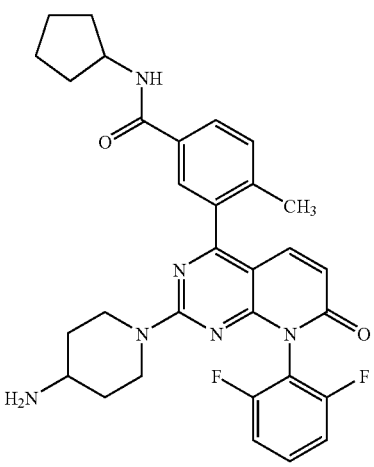

The title compound was prepared by following the procedures in Example 56 using cyclopentylamine for the amide formation and 4-piperidinamine for the displacement: LC-MS m/z 559 (M+H)+, 2.53 min (ret time).

Example 71

3-[2-(4-amino-1-piperidinyl)-8-(2,6-difluorophenyl)-7-oxo-7,8-dihydropyrido[2,3-d]pyrimidin-4-yl]-4-methyl-N-(phenylmethyl)benzamide

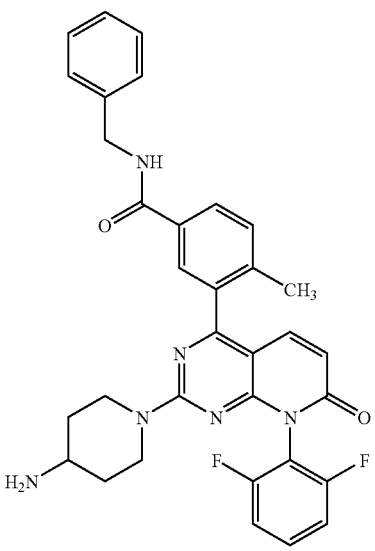

The title compound was prepared by following the procedures in Example 56 using benzylamine for the amide formation and 4-piperidinamine for the displacement: LC-MS m/z 581 (M+H)+, 2.59 min (ret time).

Example 72

3-[2-(4-amino-1-piperidinyl)-8-(2,6-difluorophenyl)-7-oxo-7,8-dihydropyrido[2,3-d]pyrimidin-4-yl]-N-(4-fluorophenyl-4-methylbenzamide

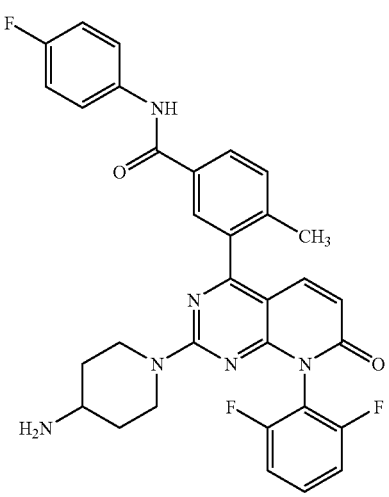

The title compound was prepared by following the procedures in Example 56 using 4-fluoroaniline for the amide formation and 4-piperidinamine for the displacement: LC-MS m/z 585 (M+H)+, 2.67 min (ret time).

Example 73

3-[2-(4-amino-1-piperidinyl)-8-(2,6-difluorophenyl)-7-oxo-7,8-dihydropyrido[2,3-d]pyrimidin-4-yl]-4-methyl-N-1,3-thiazol-2-ylbenzamide

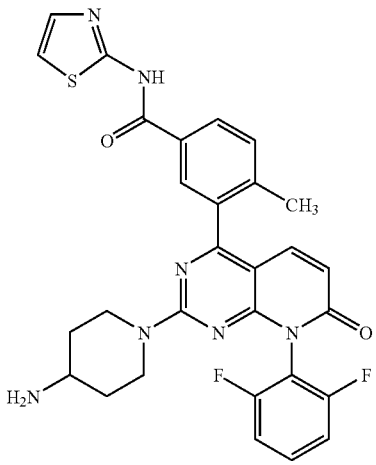

The title compound was prepared by following the procedures in Example 56 using 1,3-thiazole-2-amine for the amide formation and 4-piperidinamine for the displacement: LC-MS m/z 574 (M+H)+, 2.53 min (ret time).

Example 74

3-{8-(2,6-difluorophenyl)-2-[(1H-imidazol-2-ylmethyl)amino]-7-oxo-7,8-dihydropyrido[2,3-d]pyrimidin-4-yl}-4-methyl-N-(1-methylethyl)benzamide

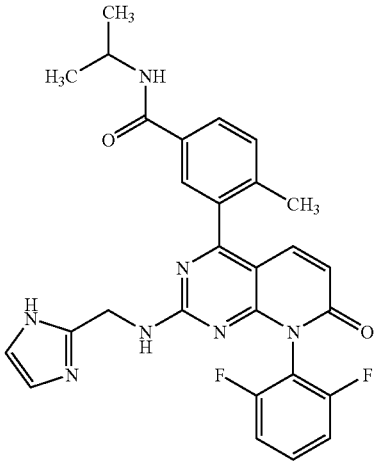

The title compound was prepared by following the procedures in Example 56 using 2-propanamine for the amide formation and (1H-imidazol-2-ylmethyl)amine hydrochloride for the displacement: LC-MS m/z 530 (M+H)+, 2.25 min (ret time).

Example 75

3-{8-(2,6-difluorophenyl)-2-[(1H-imidazol-2-ylmethyl)amino]-7-oxo-7,8-dihydropyrido[2,3-d]pyrimidin-4-yl}-4-methyl-N-propylbenzamide

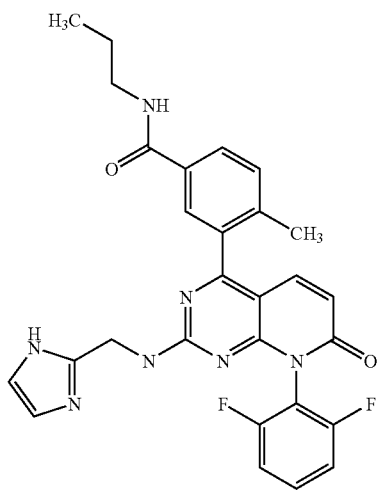

The title compound was prepared by following the procedures in Example 56 using propanamine for the amide formation and (1H-imidazol-2-ylmethyl)amine hydrochloride for the displacement: LC-MS m/z 530 (M+H)+, 2.26 min (ret time).

Example 76

N-cyclopentyl-3-{8-(2,6-difluorophenyl)-2-[(1H-imidazol-2-ylmethyl)amino]-7-oxo-7,8-dihydropyrido[2,3-d]pyrimidin-4-yl}-4-methylbenzamide

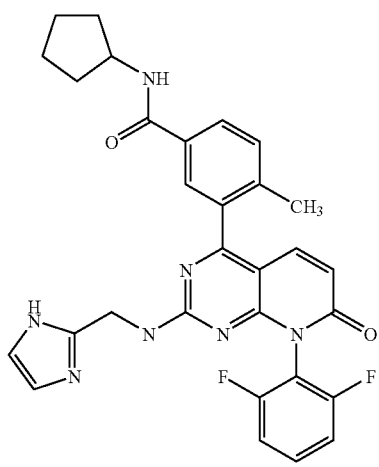

The title compound was prepared by following the procedures in Example 56 using cyclopentylamine for the amide formation and (1H-imidazol-2-ylmethyl)amine hydrochloride for the displacement: LC-MS m/z 556 (M+H)+, 2.38 min (ret time).

Example 77

3-{8-(2,6-difluorophenyl)-2-[(1H-imidazol-2-ylmethyl)amino]-7-oxo-7,8-dihydropyrido[2,3-d]pyrimidin-4-yl}-4-methyl-N-(phenylmethyl)benzamide

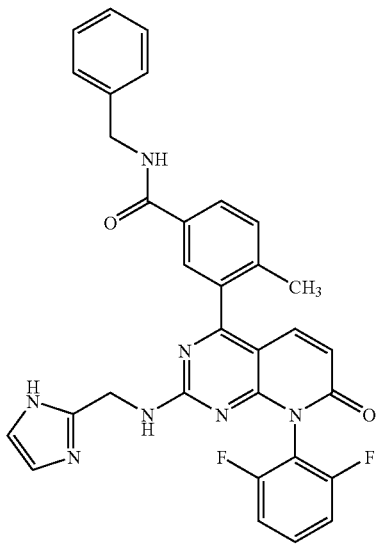

The title compound was prepared by following the procedures in Example 56 using benzylamine for the amide formation and (1H-imidazol-2-ylmethyl)amine hydrochloride for the displacement: LC-MS m/z 578 (M+H)$^+$, 2.44 min (ret time).

Example 78

3-{8-(2,6-difluorophenyl)-2-[(1H-imidazol-2-ylmethyl)amino]-7-oxo-7,8-dihydropyrido[2,3-d]pyrimidin-4-yl}-N-(4-fluorophenyl-4-methylbenzamide

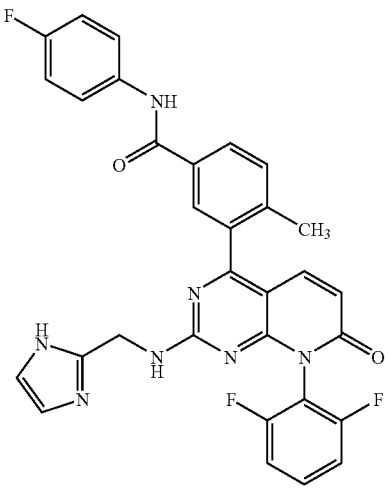

The title compound was prepared by following the procedures in Example 56 using 4-fluoroaniline for the amide formation and (1H-imidazol-2-ylmethyl)amine hydrochloride for the displacement: LC-MS m/z 582 (M+H)$^+$, 2.52 min (ret time).

Example 79

3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide 79a) 3-[8-(2,6-difluorophenyl)-2-(methylthio)-7-oxo-7,8-dihydropyrido[2,3-d]pyrimidin-4-yl]-4-methyl-N-1,3-thiazol-2-ylbenzamide

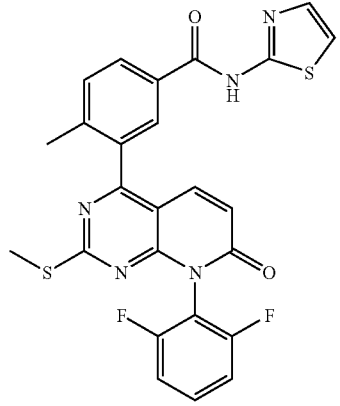

A solution of 3-[8-(2,6-difluorophenyl)-2-(methylthio)-7-oxo-7,8-dihydropyrido[2,3-d]pyrimidin-4-yl]-4-methylbenzoic acid (440 mg, 1.00 mmol) in DMF (15 mL) was mixed with DIEA (0.697 mL, 4.0 mmol), HATU (418 mg, 1.1 mmol) and 2-aminothiazole (150 mg, 1.5 mmol). The reaction mixture was stirred over night, diluted with H$_2$O (0.5 mL), and concentrated under vaccum to remove DMF. Flash chromatography (load column with DCM, mobile phase EtOAc/Hexane) then provided the title compound as a white solid 425 mg (81%). MS (ES) m/z 522 (M+H)$^+$; $^1$H-NMR (MeOD) δ 2.25 (s, 3H), 2.37 (s, 3H), 6.65 (d, J=6.0 Hz, 1H), 6.95 (d, J=3.6 Hz, 1H), 7.15 (t, J=8.4 Hz, 2H), 7.20 (d, J=3.6 Hz, 1H), 7.46 (d, J=9.6 Hz, 1H), 7.54 (m, 2H), 7.96 (d, J=1.6 Hz, 1H), 8.11 (dd, J$_1$=8.0 Hz, J$_2$=1.6 Hz, 1H).

79b) 3-[8-(2,6-difluorophenyl)-2-methylsulfinyl)-7-oxo-7,8-dihydropyrido[2,3-d]pyrimidin-4-yl]-4-methyl-N-1,3-thiazol-2-ylbenzamide

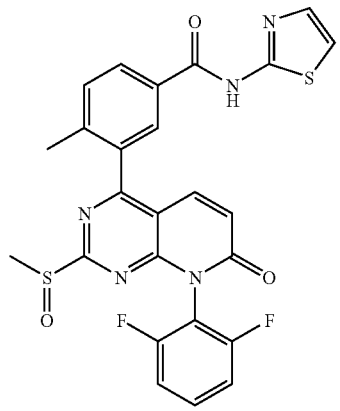

A solution of 3-[8-(2,6-difluorophenyl)-2-(methylthio)-7-oxo-7,8-dihydropyrido[2,3-d]pyrimidin-4-yl]-4-methyl-N-1,3-thiazol-2-ylbenzamide (1.65 g, 3.16 mmol) in DCM (53 mL) was mixed with mCPBA (0.736 g, 4.75 mmol). The mixture was stirred at room temperature for about 10 minutes before directly loaded onto a column. Flash chromatography (mobile phase EtOAc/Hexane) then provided the title compound as a white solid 1.38 g (81%). MS (ES) m/z 538 (M+H)$^+$; $^1$H-NMR (MeOD) δ 2.35 (s, 3H), 2.81 (s, 3H), 6.98 (d, J=10.0 Hz, 1H), 7.30 (d, J=3.6 Hz, 1H), 7.46 (t, J=8.6 Hz, 2H), 7.57 (d, J=3.6 Hz, 1H), 7.66 (d, J=8.0 Hz, 1H), 7.72 (m, 1H), 7.85 (d, J=10.0 Hz, 1H), 8.25 (d, J=8.0 Hz, 2H).

79c) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide

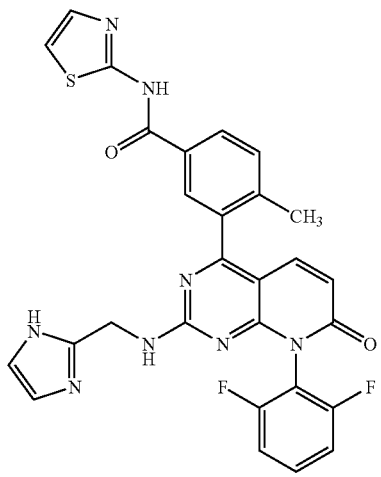

To the solution of 3-[8-(2,6-difluorophenyl)-2-(methylsulfinyl)-7-oxo-7,8-dihydropyrido[2,3-d]pyrimidin-4-yl]-4-methyl-N-1,3-thiazol-2-ylbenzamide (1.37 g, 2.54 mmol) in DCM (127 mL) were added Et$_3$N (1.78 mL, 12.7 mmol) and (1H-imidazol-2-yl)-methylamine dihydrochloride (0.625 g, 3.81 mmol). The mixture was stirred at room temperature over night and concentrated under vacuum. Flash chromatography [mobile phase DCM/DCM (90)+MeOH(7)+NH$_4$OH (3)] then provided the title compound as a white solid 1.23 g (85%). MS (ES) m/z 571 (M+H)$^+$; $^1$H-NMR (MeOD) δ 2.16 (s, 1.5H), 2.32 (s, 1.5H), 3.18 (d, J=4.4 Hz, 0.75H), 4.11 (d, J=5.2 Hz, 0.25H), 4.21 (d, J=5.0 Hz, 1H), 4.50 (m, 1H), 6.37 (d, J=9.6 Hz, 1H), 6.85 (s, 2H), 7.29 (s, 2H), 7.43 (m, 2H), 7.57 (m, 3H), 8.18 (m, 3 H), 11.60 (s, br, 1H), 12.64 (s, br, 2H).

79d) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide methanesulfonate Using material as made above in Example 79c, a reaction vessel is charged with the amorphous free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide (11.0 mg) and acetonitrile (250 μL) at room temperature (RT). The mixture is warmed to about 50° C. To the warmed mixture is added 1 eq of methanesulfonic acid solution (1N in water). The temperature is maintained for a few minutes until the solution clarifies. Heating is discontinued and the mixture is allowed to cool to room temperature while shaking. Shaking is continued at room temperature overnight. The product is filtered and washed with THF. Place cake in crystallization dish and dry for several hrs in vacuo (house vacuum, 50° C., N$_2$ bleed). The yield is 70.8% (9.1 mg) of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide methanesulfonate salt with a melting onset at 320° C. (determined by DSC).

Alternatively, using material as made above in Example 79c, a reaction vessel is charged with the free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide (10.05 g) and acetone (201 mL) at room temperature (RT). The mixture is warmed to about 50° C. and the temperature maintained for about 15 minutes. To the warm mixture is added 1 eq of methanesulfonic acid solution (1N in water). Maintain the temperature for about 5 min until the solution clarifies. To the warm mixture is added a small amount of seed material and the temperature is maintained at about 50° C. for an additional 30 min. Heating is discontinued and the mixture is allowed to cool to room temperature while stirring. Continue stirring at room temperature for at least two hours.

Filter using a Büchner funnel, collect the solid on Whatman No. 1 filter. Wash cake with 3×1 vol of acetone and suction dry. Place cake in crystallization dish and dry at least 8 hrs in vacuo (house vacuum, 50° C., N$_2$ bleed) to provide the title compound (11.14 g, 94.9%).

In the following examples, alternative embodiments of salts of the title compound were made: hydrochloric, hydrobromic, sulfuric (sulfonate), benzoic, p-toluenesulfonic (methylbenzenesulfonate), citrate, ethane sulphonic acid (ethanesulphonate), benzenesulphonic acid (benzenesulfonate), fumaric acid (fumarate). Additional salts include the camphor sulphonic acid, 1.2-dichlorobenzensulphonic acid and 1,2-napthalenesulphonic acid. Single equivalents of the acid were introduced to ensure protonation of the most basic nitrogen and reduce the likelihood of protonating the other less basic nitrogens.

79e) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide 4-methylbenzenesulfonate THF (17.5 mL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example 79c (762.2 mg) at room temperature resulting in a clear solution. P-toluenesulfonic acid was added (0.4 equivalent; 1N in water), and the mixture stirred for several hours. The product was filtered, washed with THF, and dried overnight in a vacuum oven at 50° C. with a slow nitrogen bleed. The yield was 32.9% (327.0 mg) of the title compound with a melting onset at 259° C. (determined by DSC).

79f) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide hydrochloride Acetone (250 uL) was added to amorphous free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example 79c (12.3 mg), and the resulting mixture was heated to about 50° C. Hydrochloric acid was added (1.0 equivalent; 1N in 1,4 dioxane). The mixture was cooled to room temperature and shook for several hours. The product was filtered, washed with acetone, and dried for several hours in a vacuum oven at 50° C. with a slow nitrogen bleed. The yield was 58.1% (7.6 mg) of title compound (melt begins at <50° C. by DSC).

Alternatively, acetone (535 uL) was added to amorphous free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example 79c (26.6 mg), and the resulting mixture was heated to about 50° C. Hydrochloric acid was added (1.0 equivalent; 1N in water) resulting in a clear solution. Seed crystals were added, and the mixture was cooled to room temperature and stirred for several hours. The product was filtered, washed with acetone, and dried overnight in a vacuum oven at 50° C. with a slow nitrogen bleed. The yield was 73.2% (20.7 mg).

79g) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide sulfate Acetonitrile (250 uL) was added to amorphous free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example 79c (11.2 mg), and the resulting mixture was heated to about 50° C. Sulfuric acid was added (1.0 equivalent; 1N in water). The mixture was cooled to room temperature and shook for several hours. The product was filtered, washed with acetonitrile, and dried for several hours in a vacuum oven at about 50° C. with a slow nitrogen bleed. The yield was 72.5% (9.5 mg) of title compound (melt begins around 50° C. by DSC).

Alternatively, THF (550 uL) was added to amorphous free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example 79c (27.4 mg) at room temperature resulting in a clear solution. Sulfuric acid was added (1.0 equivalent; 1N in water). Seed crystals were added, and the mixture stirred for several hours. The product was filtered, washed with THF, and dried overnight in a vacuum oven at about 50° C. with a slow nitrogen bleed. The yield was 88.9% (28.5 mg).

79h) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide hydrobromide Acetonitrile (300 uL) was added to amorphous free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example 79c (16.0 mg) at room temperature resulting in a mixture. Hydrobromic acid was added (1.0 equivalent; 1N in water) resulting in a clear solution. The following day, a white precipitate was observed. The product was filtered, washed with acetonitrile, and dried overnight in a vacuum oven at about 50° C. with a slow nitrogen bleed. The yield was 52.0% (9.5 mg) of title compound (melt begins at <50° C. by DSC).

79i) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide citrate Isopropanol (200 uL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from (10.6 mg), and the resulting mixture was heated to 50° C. Citric acid was added (1.0 equivalent; 1N in THF). The mixture was cooled to room temperature and shook for several days. The product was filtered, washed with isopropanol, and dried for several hours in a vacuum oven at 50° C. with a slow nitrogen bleed. The yield was 61.4% (8.7 mg) of title compound with a melting onset at 179° C. (determined by DSC).

Alternatively, Isopropanol (502 uL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from (25.1 mg), and the resulting mixture was heated to 50° C. Citric acid was added (1.0 equivalent; 1N in THF) resulting in an immediate precipitate. Seed crystals were added, and the mixture stirred for several hours. The product was filtered, washed with isopropanol, and dried overnight in a vacuum oven at 50° C. with a slow nitrogen bleed. The yield was 71.4% (24.0 mg).

79j) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide ethanesulfonate Acetone (200 uL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide (25.1 mg), and the resulting mixture was heated to 50° C. Ethanesulfonic acid was added (1.0 equivalent; 1N in THF), and the mixture stirred for several days. The product was filtered, washed with acetone, and dried overnight in a vacuum oven at 50° C. with a slow nitrogen bleed. The yield was 70.6% (9.1 mg) of title compound with a melting onset at 296° C. (determined by DSC).

Alternatively, acetone (501 uL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide (25.1 mg), and the resulting mixture was heated to 50° C. Ethanesulfonic acid was added (1.0 equivalent; 1N in THF). Seed crystals were added, and the mixture stirred for several days. The product was filtered, washed with acetone, and dried overnight in a vacuum oven at 50° C. with a slow nitrogen bleed. The yield was 78.1% (23.3 mg).

79k) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide benzenesulfonate Acetone (200 uL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide (10.4 mg), and the resulting mixture was heated to 50° C. Benzenesulfonic acid was added (1.0 equivalent; 1N in water) resulting in a clear solution. The mixture was cooled to room temperature and shook overnight. The product was filtered, washed with acetone, and dried for several hours in a vacuum oven at 50° C. with a slow nitrogen bleed. The yield was 83.2% (5.8 mg) of title compound with a melting onset at 317° C. (determined by DSC).

Alternatively, acetone (494 uL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example (24.7 mg) at room temperature resulting in a mixture. Benzenesulfonic acid was added (1.0 equivalent; 1N in water) resulting in a clear solution. Seed crystals were added, and the mixture stirred for several hours. The product was filtered, washed with acetone, and dried overnight in a vacuum oven at 50° C. with a slow nitrogen bleed. The yield was 83.2% (26.3 mg).

79l) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide fumarate Isopropanol (200 uL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example 79c (10.5 mg), and the resulting mixture was heated to 50° C. Fumaric acid was added (1.0 equivalent; 0.2 N in ethanol). The mixture was cooled to room temperature and shook for several days. The product was filtered, washed with isopropanol, and dried overnight in a vacuum oven at 50° C. with a slow nitrogen bleed. The yield was 61.4% (6.0 mg) of title compound with a melting onset at 251° C. (determined by DSC).

Alternatively, isopropanol (488 uL) was added to free-base version of 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide from Example 79c (24.4 mg), and the resulting mixture was heated to 50° C. Fumaric acid was added (1.0 equivalent; 0.2 N in ethanol) resulting in an immediate precipitate. Seed crystals were added, and the mixture stirred for several hours. The product was filtered, washed with isopropanol, and dried overnight in a vacuum oven at 50° C. with a slow nitrogen bleed. The yield was 63.0% (18.5 mg).

Example 80

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-propylbenzamide trifluoroacetate 80a) 3-(8-(2,6-difluorophenyl)-2-{[2-hydroxy-1-(hydroxymethyl)-ethyl]amino}-7-oxo-7,8-dihydropyrido[2,3-d]pyrimidin-4-yl)-4-methylbenzoic acid

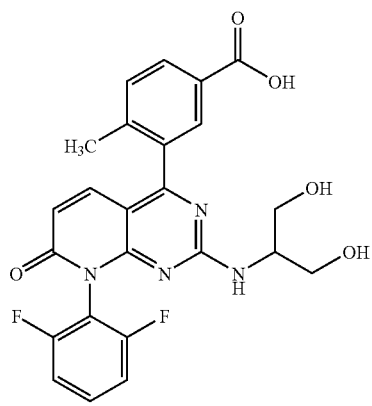

The title compound was prepared by following the procedures in Example 1b using 4-chloro-8-(2,6-difluorophenyl)-2-{[2-hydroxy-1-(hydroxymethyl)ethyl]-amino}pyrido[2,3-d]pyrimidin-7(8H)-one for the Suzuki cross-coupling reaction.

80b) 3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-propylbenzamide trifluoroacetate

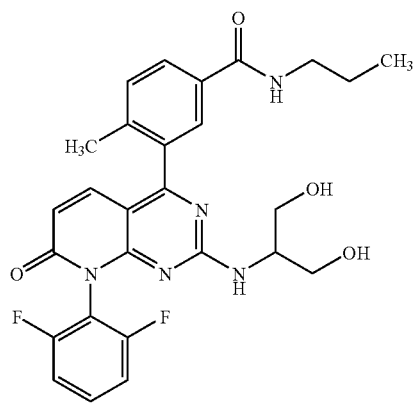

To the acid from Example 80a (32.3 mg, 0.066 mmol, 1 eq) was added HATU (28.5 mg, 0.075 mmol) in DMF (500 uL). DIPEA (34 μL, 0.2 mmol, 3 eq) was then added. The resulting mixture was then allowed to stand for about 5 minutes before adding to propylamine (6 mg, 0.1 mmol) in DMF (250 uL). The resulting mixture was shaken to ensure efficient mixing of the reagents then was left to stand overnight. The solvent was then removed in vacuo. The residue dissolved in methanol and was then placed down an aminopropyl SPE flushing the column with methanol. The residue was purified by MDAP to give the above named compound (7.4 mg): LC-MS m/z 524 (M+H)$^+$, 2.63 min (ret time).

Example 81

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-(1-methylethyl)benzamide trifluoroacetate

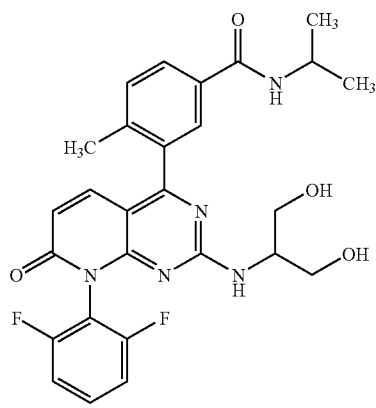

The title compound was prepared by following the procedures in Example 80b except using 1-methylethylamine: LC-MS m/z 524 (M+H)+, 2.62 min (ret time).

Example 82

N-cyclobutyl-3-(8-(2,6-difluorophenyl)-2-{[2-hydroxy-1-(hydroxymethyl)ethyl]-amino}-7-oxo-7,8-dihydropyrido[2,3-d]pyrimidin-4-yl)-4-methylbenzamide trifluoroacetate

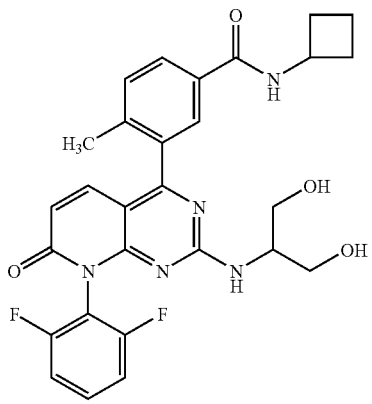

The title compound was prepared by following the procedures in Example 80b except using cyclobutanamine: LC-MS m/z 536 (M+H)+, 2.7 min (ret time).

Example 83

N-cyclopentyl-3-(8-(2,6-difluorophenyl)-2-{[2-hydroxy-1-(hydroxymethyl)ethyl]-amino}-7-oxo-7,8-dihydropyrido[2,3-d]pyrimidin-4-yl)-4-methylbenzamide trifluoroacetate

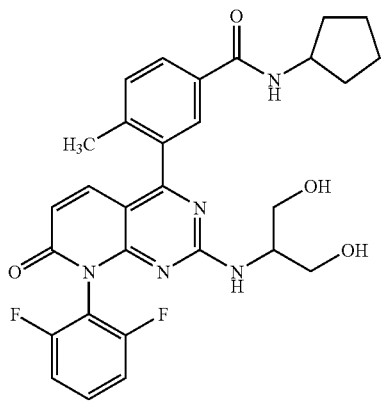

The title compound was prepared by following the procedures in Example 80b except using cyclopentylamine: LC-MS m/z 550 (M+H)+, 2.78 min (ret time).

Example 84

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-N-(4-fluorophenyl)-4-methylbenzamide trifluoroacetate

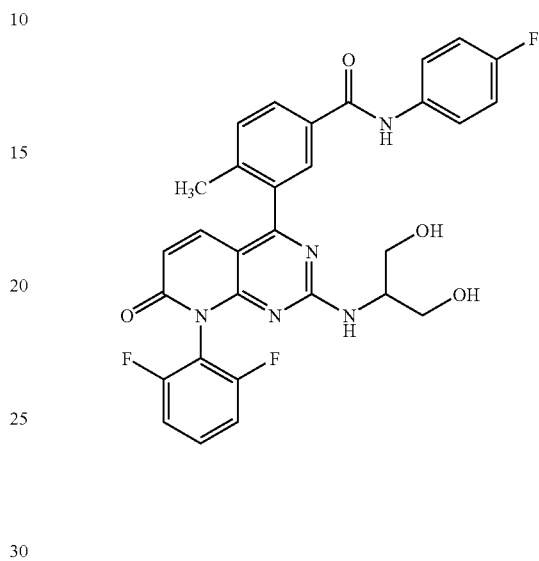

The title compound was prepared by following the procedures in Example 80b except using 4-fluoroaniline: LC-MS m/z 576 (M+H)+, 2.95 min (ret time).

Example 85

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-1,3-thiazol-2-ylbenzamide trifluoroacetate

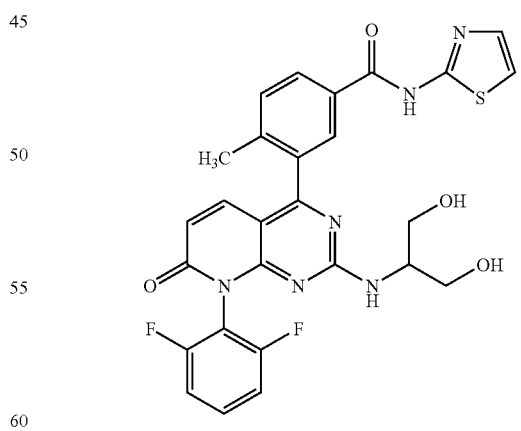

The title compound was prepared by following the procedures in Example 80b except using 1,3-thiazol-2-amine: LC-MS m/z 565 (M+H)+, 2.75 min (ret time).

Example 86

N-cyclopropyl-3-(8-(2,6-difluorophenyl)-2-{[2-hydroxy-1-(hydroxymethyl)ethyl]-amino}-7-oxo-7,8-dihydropyrido[2,3-d]pyrimidin-4-yl)-4-methylbenzamide trifluoroacetate

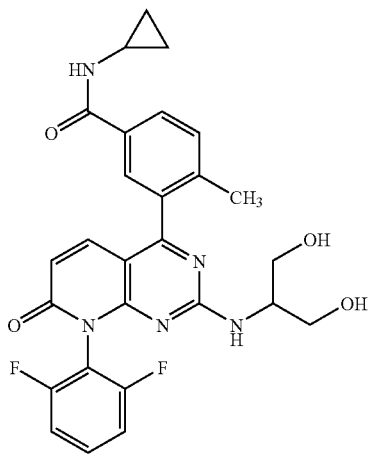

The title compound was prepared by following the procedures in Example 80b except using cyclopropylamine: LC-MS m/z 522 (M+H)+, 2.55 min (ret time).

Example 87

N-(cyclopropylmethyl)-3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methylbenzamide trifluoroacetate

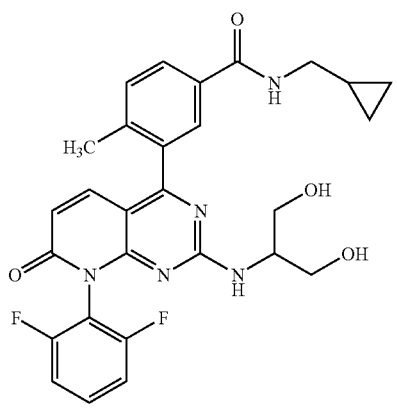

The title compound was prepared by following the procedures in Example 80b except using cyclopropylmethylamine: LC-MS m/z 536 (M+H)+, 2.67 min (ret time).

Example 88

8-(2,6-difluorophenyl)-2-{[2-hydroxy-1-(hydroxymethyl)ethyl]amino}-4-[2-methyl-5-(4-morpholinylcarbonyl)phenyl]pyrido[2,3-d]pyrimidin-7(8H)-one trifluoroacetate

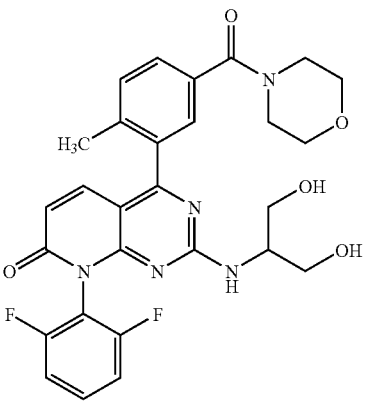

The title compound was prepared by following the procedures in Example 80b except using morpholine: LC-MS m/z 552 (M+H)+, 2.44 min (ret time).

Example 89

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-N-heptyl-4-methylbenzamide trifluoroacetate

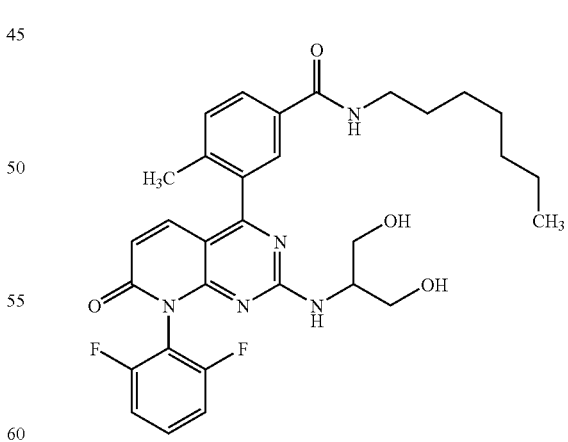

The title compound was prepared by following the procedures in Example 80b except using heptylamine: LC-MS m/z 580 (M+H)+, 3.16 min (ret time).

Example 90

N-(cyclopropylmethyl)-3-[8-(2,6-difluorophenyl)-7-oxo-7,8-dihydropyrido[2,3-d]pyrimidin-4-yl]-4-methylbenzamide

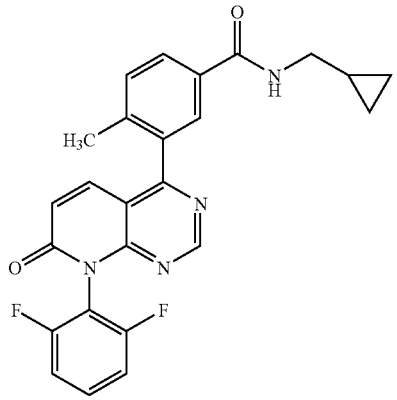

N-(cyclopropylmethyl)-3-[8-(2,6-difluorophenyl)-2-(methylthio)-7-oxo-7,8-dihydropyrido[2,3-d]pyrimidin-4-yl]-4-methylbenzamide (13.5 mg, 0.027 mmol), was dissolved in anhydrous methanol (2 mL) and was added to a tube containing nickel chloride hexahydrate (2 mg). The tube was placed under an atmosphere of nitrogen and cooled using a dry-ice/acetone bath to about −15° C. Sodium borohydride (2 mg) was then added (nitrogen removed during addition and then replaced) and the solution turned black. The solution was stirred in the dry ice/acetone bath for 1.5 h. 1 N HCl (4 mL) was added and the solution was allowed to warm to room temperature and stirred under an air atmosphere for about 2 hours. Dichloromethane (2 mL) was added to the solution and it was stirred vigorously for 10 min. The solution was filtered through a hydrophobic frit packed with celite and was washed with further dichloromethane (2 mL×2). The filtrate was concentrated and purified by HPLC to give the title product (1 mg, 8.2%). LC-MS m/z 447 (M+H)$^+$, 2.98 min (ret time). $^1$H-NMR (d$_6$-DMSO) δ 0.22 (m, 2H), 0.42 (m, 2H), 1.01 (br s, 1H), 2.23 (s, 3H), 3.14 (br s, 2H), 6.87 (m, 1H), 7.43 (m, 2H), 7.65 (m, 2H), 7.95 (m, 2H), 8.60 (m, 1H), 9.07 (s, 1H).

Example 91

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-(3-pyridinylmethyl)benzamide trifluoroacetate

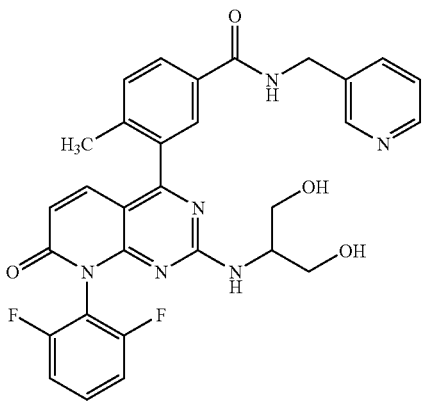

The title compound was prepared by following the procedures in Example 80b except using (3-pyridinylmethyl)amine: LC-MS m/z 573 (M+H)$^+$, 2.03 min (ret time).

Example 92

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-(3-phenylpropyl)benzamide trifluoroacetate

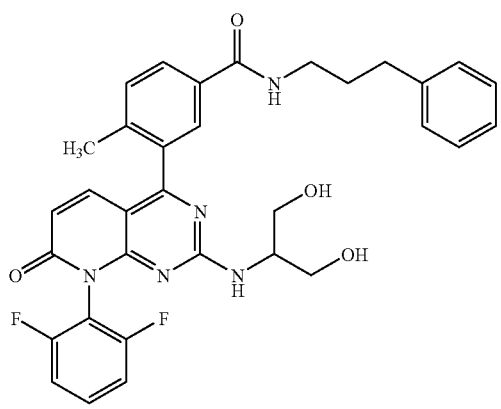

The title compound was prepared by following the procedures in Example 80b except using 3-phenyl-1-propanamine: LC-MS m/z 600 (M+H)$^+$, 2.97 min (ret time).

Example 93

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-(2-phenylethyl)benzamide trifluoroacetate

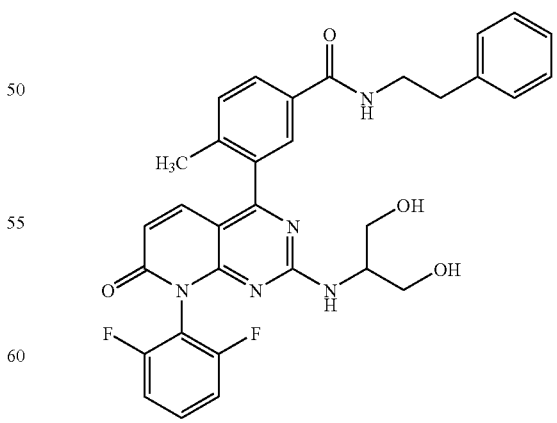

The title compound was prepared by following the procedures in Example 80b except using (2-phenylethyl)amine: LC-MS m/z 586 (M+H)$^+$, 2.88 min (ret time).

Example 94

3-(8-(2,6-difluorophenyl)-2-{[2-hydroxy-1-(hydroxymethyl)ethyl]amino}-7-oxo-7,8-dihydropyrido[2,3-d]pyrimidin-4-yl)-4-methyl-N-(phenylmethyl)benzamide trifluoroacetate

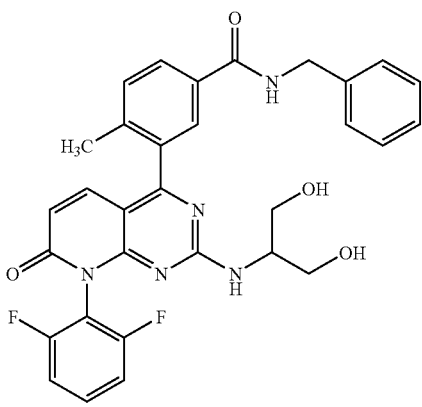

The title compound was prepared by following the procedures in Example 80b except using (phenylmethyl)amine: LC-MS m/z 572 (M+H)+, 2.83 min (ret time).

Example 95

1,1-dimethylethyl (2-{[8-(2,6-difluorophenyl)-4-(5-{[(4-fluorophenyl)amino]carbonyl}-2-methylphenyl)-7-oxo-7,8-dihydropyrido[2,3-d]pyrimidin-2-yl]amino}ethyl)methylcarbamate

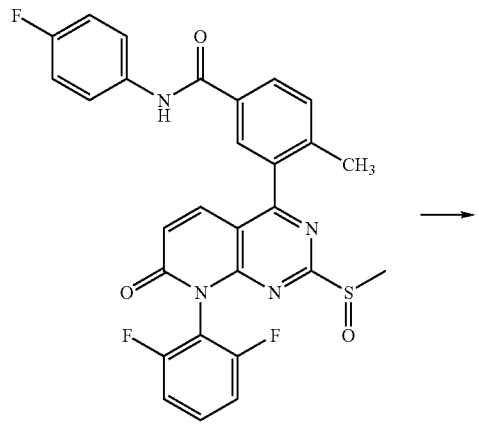

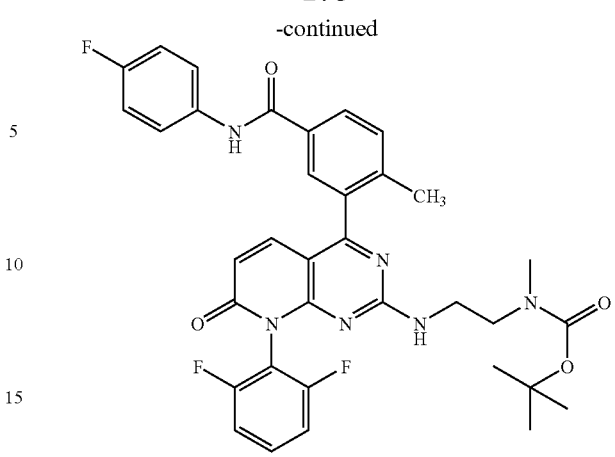

To a solution of 3-[8-(2,6-difluorophenyl)-2-(methylsulfinyl)-7-oxo-7,8-dihydropyrido[2,3-d]pyrimidin-4-yl]-N-(4-fluorophenyl)-4-methylbenzamide (50 mg, 0.09 mmol) in DCM (5 mL) was added 1,1-dimethylethyl (2-aminoethyl)methylcarbamate (0.09 mL, 0.5 mmol). The resultant mixture was stirred at room temperature overnight. The mixture was concentrated under vacuo. Flash chromatography (90% CH$_2$Cl$_2$/7% MeOH/3% NH$_4$OH) then provide the title compound (61 mg, 100%). LC-MS (ES) m/z 659 (M+H)+; $^1$H-NMR(CDCl$_3$) δ 1.39 (s, 9H), 1.70 (br, 1H), 2.32 (s, 3H), 2.65 (s, 2H), 2.82 (s, 2H), 3.22 (s, 3H), 3.60 (br, 1H), 6.34 (d, 1H), 7.03 (m, 4H), 7.34 (m, 1H), 7.48 (m, 2H), 7.64 (m, 1H), 7.84 (m, 2H), 8.14 (d, 1H).

Example 96

3-(8-(2,4-difluorophenyl)-2-{[2-hydroxy-1-(hydroxymethyl)ethyl]amino}-7-oxo-7,8-dihydropyrido[2,3-d]pyrimidin-4-yl)benzoic acid 96a) 4-chloro-8-(2,4-difluorophenyl)-2-(methylthio)pyrido[2,3-d]pyrimidin-7(8H)-one

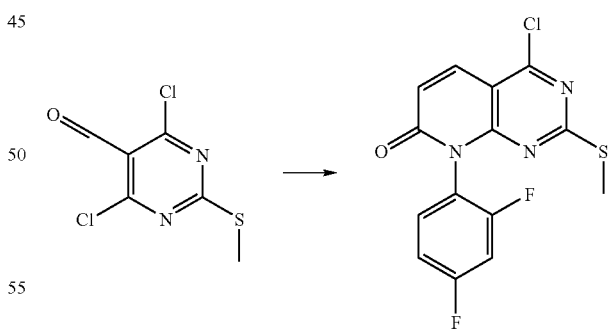

To a solution of 4,6-dichloro-2-methylsulfanyl-pyrimidine-5-carbaldehyde (4.2 g, 18.95 mmol) and triethylamine (5.3 ml, 38 mmol) in THF (100 ml) was added 2,4-difluoroaniline (2.1 ml, 20.58 mmol). The mixture was stirred for 2 h, and methyl {bis[(2,2,2-trifluoroethyl)oxy]phosphoryl}acetate (6.0 g, 18.95 mmol) was added. The mixture was stirred for 18 h, diluted with DCM (200 ml) and washed with water (2×100 ml). The dried (Na2SO4) organic phase was filtered and evaporated. Flash chromatography (EtOAc/Hexane, 1:5) provided the title compound as a cream solid (2.5 g, 40%): LC-MS m/z 340 (M+H)⁺ retention 3.24 min.

96b) 4-chloro-8-(2,4-difluorophenyl)-2-(methylsulfinyl)pyrido[2,3-d]pyrimidin-7(8H)-one

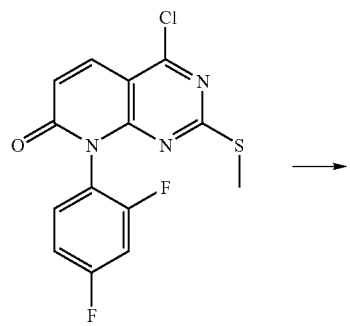

To a solution of 4-chloro-8-(2,4-difluorophenyl)-2-(methylthio)pyrido[2,3-d]pyrimidin-7(8H)-one (2.5 g, 7.6 mmol) in DCM (100 ml) was added m-CPBA (2.2 g, 10.2 mmol). The mixture was stirred for 10 min and evaporated. Flash chromatography (EtOAc) provided the title compound as a yellow solid (2.1 g, 80%): LC-MS m/z 356 (M+H)⁺ retention 2.43 min.

96c) 4-chloro-8-(2,4-difluorophenyl)-2-{[2-hydroxy-1-(hydroxymethyl)ethyl]amino}pyrido[2,3-d]pyrimidin-7(8H)-one

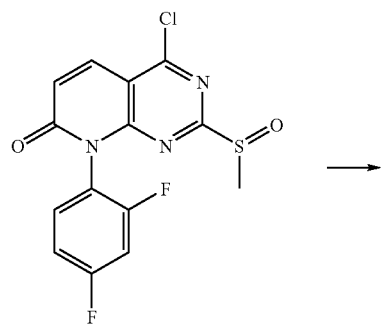

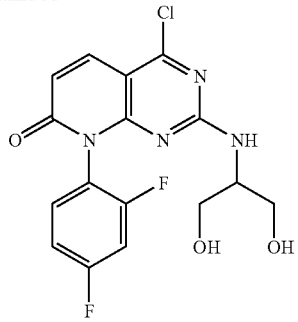

To a solution of 4-chloro-8-(2,4-difluorophenyl)-2-(methylsulfinyl)-pyrido[2,3-d]pyrimidin-7(8H)-one (2.0 g, 5.6 mmol) in DCM (100 ml) was added a solution of serinol (650 mg, 7.1 mmol) in DMF (5 ml). The mixture was stirred for 2 h, washed with water (2×50 ml), dried (Na2SO4), and evaporated. Flash chromatography (EtOAc/Hexane, 3:1) provided the title compound as a white solid (1.1 g, 50%): LC-MS m/z 383 (M+H)⁺ retention 2.45 min.

96d) 3-(8-(2,4-difluorophenyl)-2-{[2-hydroxy-1-(hydroxymethyl)ethyl]amino}-7-oxo-7,8-dihydropyrido[2,3-d]pyrimidin-4-yl)benzoic acid

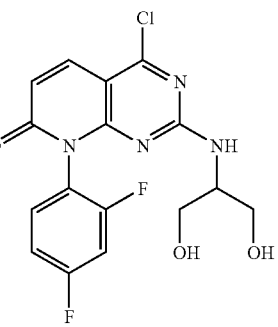

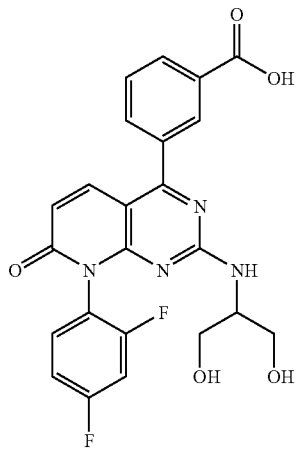

A mixture of 4-chloro-8-(2,4-difluorophenyl)-2-{[2-hydroxy-1-(hydroxymethyl)ethyl]amino}pyrido[2,3-d]pyrimidin-7(8H)-one (20 mg, 0.047 mmol), 3-(dihydroxyboranyl)benzoic acid (11.8 mg, 0.07 mmol), K2CO3 (20 mg, 0.14 mmol), tetrakis(triphenylphosphine)palladium (2 mg, 0.00177 mmol), dioxane (1.2 ml), and water (0.4 ml) was heated in a sealed microwave vessel at 150 degrees for 10 min. The cooled solution was treated with DCM (3 ml), passed through a hydrophobic frit directly onto a silica cartridge (2 g). The cartridge was eluted with EtOAc followed by EtOAc/MeOH (9:1) to provide the title compound as a brown solid (20 mg, 80%) LC-MS m/z 469 (M+H)+ retention 2.73 min.

Example 97

3-[2-[2-(aminomethyl)-1H-imidazol-1-yl]-8-(2,6-difluorophenyl)-7-oxo-7,8-dihydropyrido[2,3-d]pyrimidin-4-yl]-4-methylbenzoic acid trifluoroacetate 97a) 3-[8-(2,6-difluorophenyl)-2-(methylsulfinyl)-7-oxo-7,8-dihydropyrido[2,3-d]pyrimidin-4-yl]-4-methylbenzoic acid

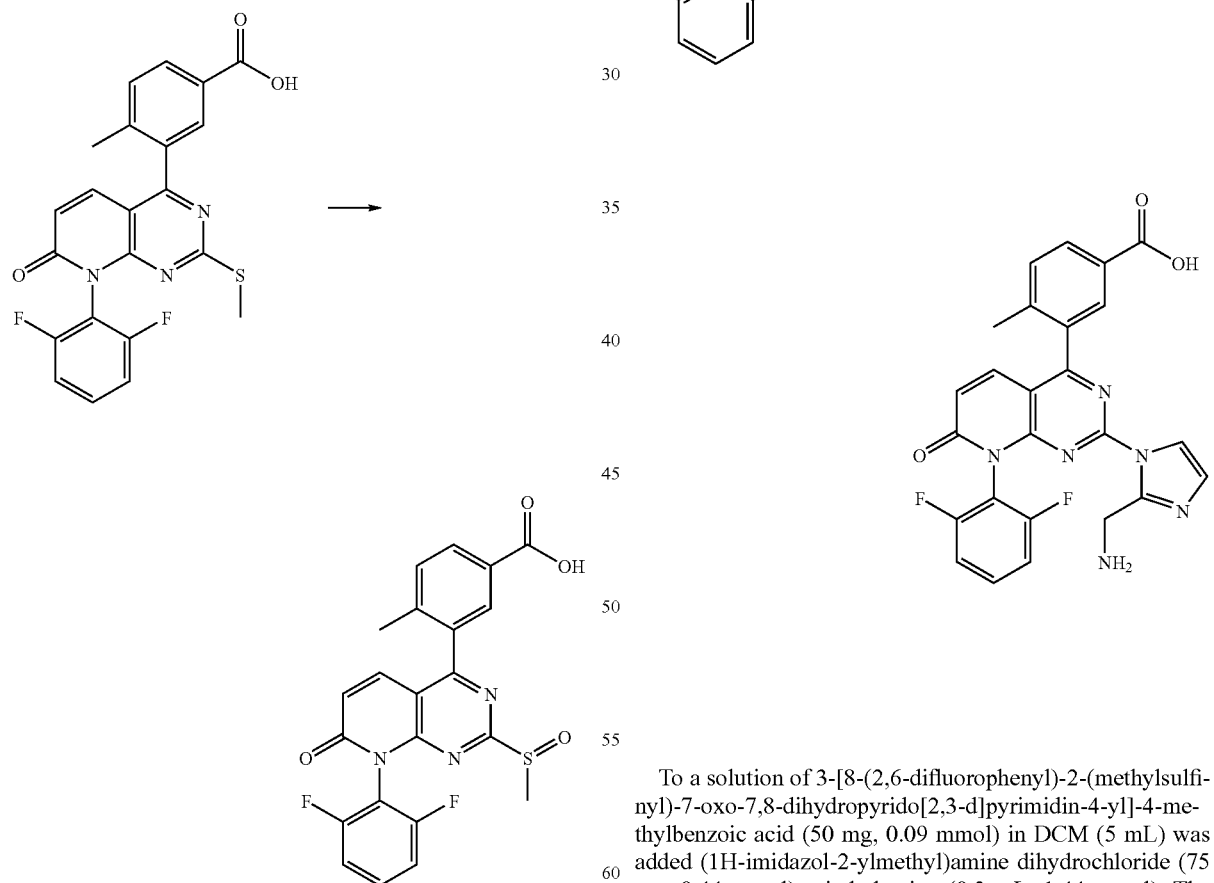

To a solution of 3-[8-(2,6-difluorophenyl)-2-(methylthio)-7-oxo-7,8-dihydropyrido[2,3-d]pyrimidin-4-yl]-4-methylbenzoic acid (30.0 mg, 0.068 mmol) in CH2Cl2 (5.0 ml) was added 3-chlorobenzenecarboperoxoic acid (23 mg, 0.103 mmol). The resultant mixture was stirred at room temperature 10 mins. Flash chromatography (EtOAc/Hex=1:1) then provided the title compound (20 mg, 64%). LC-MS (ES) m/z 456 (M+H)+.

97b) 3-[2-[2-(aminomethyl)-1H-imidazol-1-yl]-8-(2,6-difluorophenyl)-7-oxo-7,8-dihydropyrido[2,3-d]pyrimidin-4-yl]-4-methylbenzoic acid trifluoroacetate To a solution of 3-[8-(2,6-difluorophenyl)-2-(methylsulfinyl)-7-oxo-7,8-dihydropyrido[2,3-d]pyrimidin-4-yl]-4-methylbenzoic acid (50 mg, 0.09 mmol) in DCM (5 mL) was added (1H-imidazol-2-ylmethyl)amine dihydrochloride (75 mg, 0.44 mmol), triethylamine (0.2 mL, 1.44 mmol). The resultant mixture was stirred at room temperature overnight. The mixture was concentrated and purified by HPLC to give the title product as the minor component (8 mg, 15%). LC-MS (ES) m/z 489 (M+H)+; 1H-NMR(MeOD) δ 2.39 (s, 3H), 4.26 (s, 2H), 6.86 (d, 1H), 7.08 (s, 1H), 7.38 (t, 2H), 7.64 (d, 1H), 7.77 (m, 2H), 7.82 (s, 1H), 8.11 (s, 1H), 8.20 (d, 1H).

Example 98

3-{8-(2,6-difluorophenyl)-2-[(1H-imidazol-2-ylmethyl)amino]-7-oxo-7,8-dihydropyrido[2,3-d]pyrimidin-4-yl}-4-methylbenzoic acid trifluoroacetate

Example 99

3-{8-(2,6-difluorophenyl)-2-[[2-(dimethylamino)ethyl](methyl)amino]-7-oxo-7,8-dihydropyrido[2,3-d]pyrimidin-4-yl}-N-(4-fluorphenyl)-4-methylbenzamide

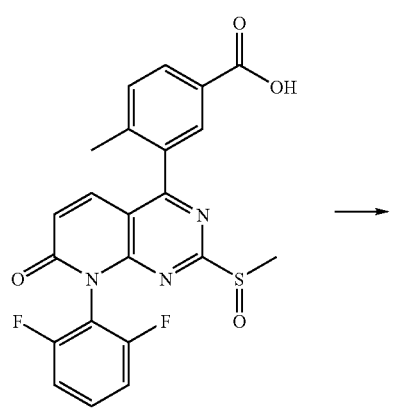

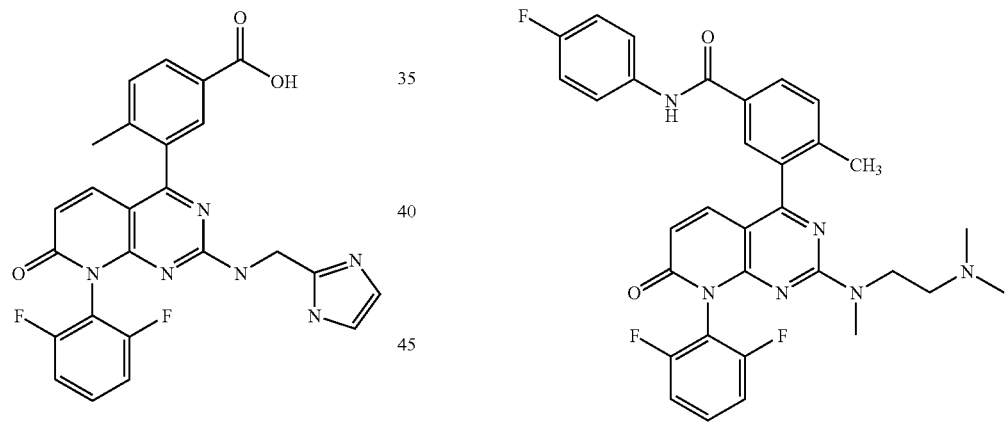

To a solution of 3-[8-(2,6-difluorophenyl)-2-(methylsulfinyl)-7-oxo-7,8-dihydropyrido[2,3-d]pyrimidin-4-yl]-4-methylbenzoic acid (50 mg, 0.09 mmol) in DCM (5 mL) was added (1H-imidazol-2-ylmethyl)amine dihydrochloride (75 mg, 0.44 mmol), triethylamine (0.2 mL, 1.44 mmol). The resultant mixture was stirred at room temperature overnight. The mixture was concentrated and purified by HPLC to give the title product as the major component (20 mg, 37%). LC-MS (ES) m/z 489 (M+H)$^+$; $^1$H-NMR(MeOD) δ 2.36 (s, 3H), 4.58 (s, 2H), 6.48 (d, 1H), 7.12 (m, 1H), 7.21 (m, 1H), 7.39 (s, 2H), 7.56 (m, 3H), 8.00 (s, 1H), 8.14 (d, 1H).

To a solution of 3-[8-(2,6-difluorophenyl)-2-(methylsulfinyl)-7-oxo-7,8-dihydropyrido[2,3-d]pyrimidin-4-yl]-N-(4-fluorophenyl)-4-methylbenzamide (50 mg, 0.09 mmol) in DCM (10 mL) was added N,N,N'-trimethyl-1,2-ethanediamine (0.057 mL, 0.44 mmol). The resultant mixture was stirred at room temperature overnight. The mixture was concentrated under vacuo. Flash chromatography (90% CH$_2$Cl$_2$/7% MeOH/3% NH$_4$OH) then provided the title compound (13 mg, 25%). LC-MS (ES) m/z 587 (M+H)$^+$; $^1$H-NMR (MeOD) δ 2.09 (s, 3H), 2.24 (s, 3H), 2.38 (s, 3H), 2.41 (m, 1H), 2.59 (m, 1H), 2.91 (s, 1H), 3.22 (s, 2H), 3.52 (m, 1H), 3.88 (m, 1H), 6.38 (d, 1H), 7.13 (m, 2H), 7.25 (m, 2H), 7.52 (d, 1H), 7.62 (m, 2H), 7.71 (m, 2H), 7.92 (s, 1H), 8.06 (d, 1H).

Example 100

3-{8-(2,6-difluorophenyl)-2-[[2-(dimethylamino)ethyl](methyl)amino]-7-oxo-7,8-dihydropyrido[2,3-d]-pyrimidin-4-yl}-4-methyl-N-(1-methylethyl)benzamide

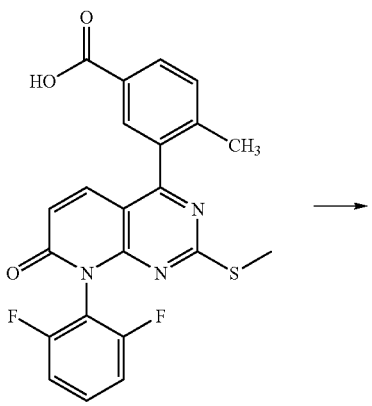

The title compound was prepared from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using 2-propanamine for the amide formation and N,N,N'-trimethyl-1,2-ethanediamine for the displacement reaction. LC-MS (ES) m/z 534 (M+H)+; $^1$H-NMR(MeOD) δ 1.27 (d, 6H), 2.08 (m, 3H), 2.23 (m, 3H), 2.32 (s, 3H), 2.38 (m, 1H), 2.52 (m, 1H), 2.90 (s, 1H), 3.21 (s, 2H), 3.50 (m, 1H), 3.83 (m, 1H), 4.23 (m, 1H), 6.36 (d, 1H), 7.27 (t, 2H), 7.48 (d, 1H), 7.52 (d, 1H), 7.62 (m, 1H), 7.79 (s, 1H), 7.93 (d, 1H).

Example 101

3-[8-(2,6-difluorophenyl)-2-({3-[(1-methylethyl)amino]propyl}amino)-7-oxo-7,8-dihydropyrido[2,3-d]pyrimidin-4-yl]-4-methyl-N-1,3-thiazol-2-ylbenzamide

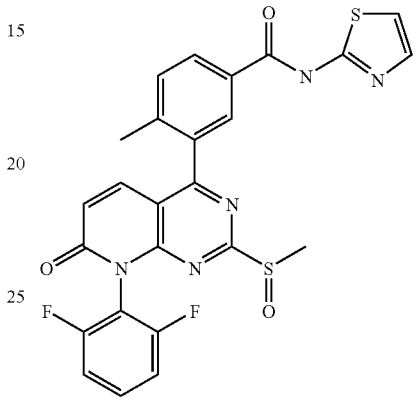

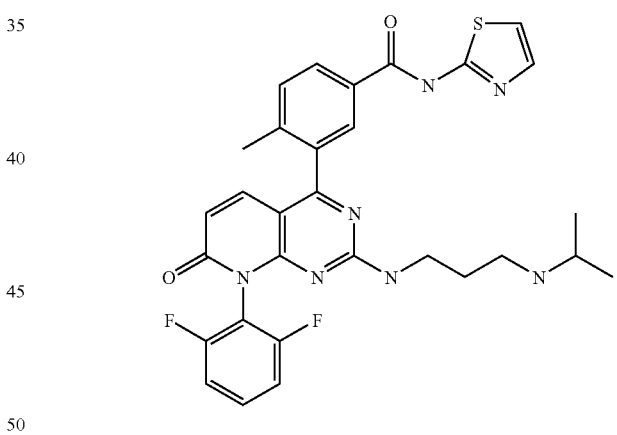

The title compound was prepared from 3-[8-(2,6-difluorophenyl)-2-(methylsulfinyl)-7-oxo-7,8-dihydropyrido[2,3-d]pyrimidin-4-yl]-4-methyl-N-1,3-thiazol-2-ylbenzamide and N-(1-methylethyl)-1,3-propanediamine by following the procedures in Example 79c. LC-MS m/z 590 (M+H)+; $^1$H-NMR (MeOD) 1.02 (m, 6H), 1.68 (m, 2H), 2.32 (m, 3H), 2.46 (m, 1H), 2.66 (m, 1H), 2.82 (m, 1H), 3.11 (m, 1H), 3.46 (m, 1H), 6.35 (d, J=8.8 Hz, 1H), 7.11 (m, 1H), 7.24 (m, 2H), 7.46 (m, 2H), 7.55 (m, 2H), 8.02 (m, 1H), 8.11 (d, J=7.6 Hz, 1H).

Example 102

3-[8-(2,6-difluorophenyl)-2-({3-[(1,1-dimethylethyl)amino]propyl}amino)-7-oxo-7,8-dihydropyrido[2,3-d]pyrimidin-4-yl]-4-methyl-N-1,3-thiazol-2-ylbenzamide

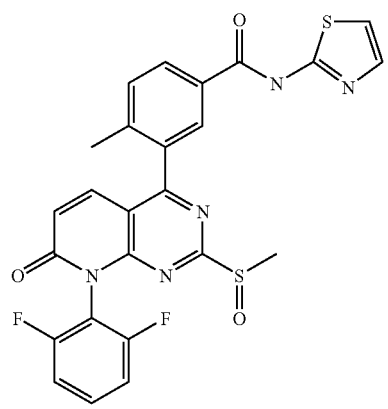

→

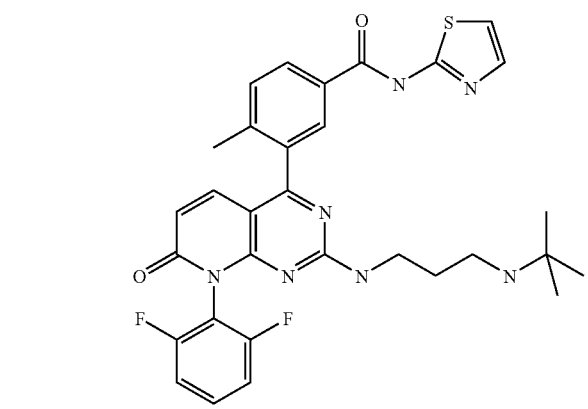

The title compound was prepared from 3-[8-(2,6-difluorophenyl)-2-(methylsulfinyl)-7-oxo-7,8-dihydropyrido[2,3-d]pyrimidin-4-yl]-4-methyl-N-1,3-thiazol-2-ylbenzamide and N-(1,1-dimethylethyl)-1,3-propanediamine by following the procedures in Example 79c. LC-MS m/z 604 (M+H)$^+$; $^1$H-NMR (MeOD) 1.09 (m, 9H), 1.70 (m, 2H), 2.33 (m, 3H), 2.47 (m, 1H), 2.66 (m, 1H), 3.13 (m, 1H), 3.47 (m, 1H), 6.36 (d, J=8.8 Hz, 1H), 7.10 (m, 1H), 7.23 (m, 2H), 7.47 (m, 2H), 7.58 (m, 2H), 8.04 (m, 1H), 8.13 (d, J=7.6 Hz, 1H).

Example 103

3-[8-(2,6-difluorophenyl)-2-({2-[(1-methylethyl)amino]ethyl}amino)-7-oxo-7,8-dihydropyrido[2,3-d]pyrimidin-4-yl]-4-methyl-N-1,3-thiazol-2-ylbenzamide

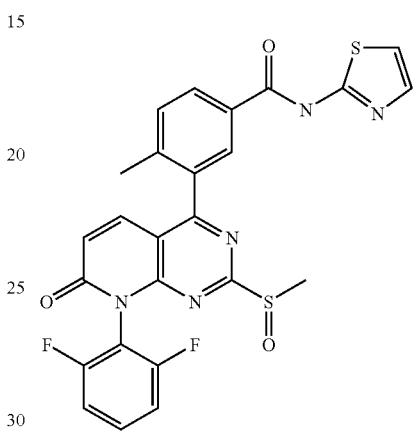

→

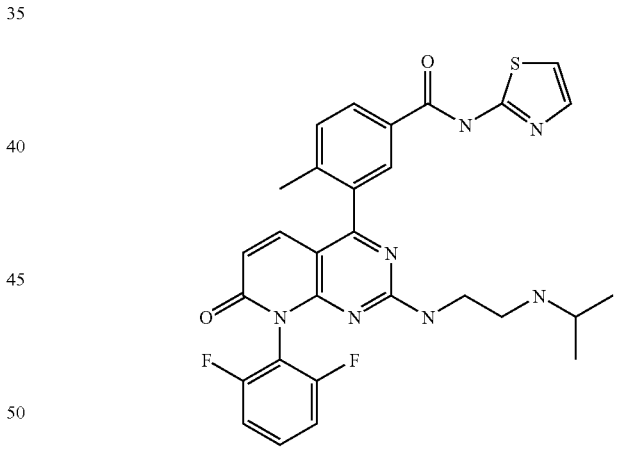

The title compound was prepared from 3-[8-(2,6-difluorophenyl)-2-(methylsulfinyl)-7-oxo-7,8-dihydropyrido[2,3-d]pyrimidin-4-yl]-4-methyl-N-1,3-thiazol-2-ylbenzamide and N-(1-methylethyl)-1,2-ethanediamine by following the procedures in Example 79c. LC-MS m/z 576 (M+H)$^+$; $^1$H-NMR (MeOD) 1.02 (d, J=6.0 Hz, 6H), 2.31 (m, 3H), 2.72 (m, 3H), 3.23 (m, 1H), 3.55 (m, 1H), 6.36 (d, J=8.8 Hz, 1H), 7.13 (m, 1H), 7.24 (m, 2H), 7.47 (m, 2H), 7.56 (m, 2H), 8.00 (s, 1H), 8.10 (d, J=7.6 Hz, 1H).

Example 104

3-{8-(2,6-difluorophenyl)-2-[[3-(dimethylamino)propyl](methyl)amino]-7-oxo-7,8-dihydropyrido[2,3-d]pyrimidin-4-yl}-4-methyl-N-propylbenzamide

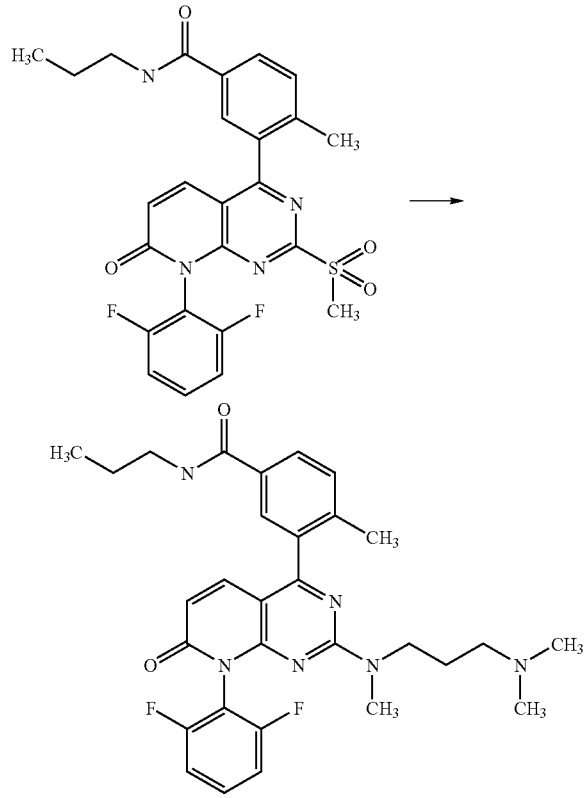

3-[8-(2,6-difluorophenyl)-2-(methylsulfonyl)-7-oxo-7,8-dihydropyrido[2,3-d]pyrimidin-4-yl]-4-methyl-N-propylbenzamide (0.04 g, 0.078 mmol), N,N,N'-trimethyl-1,3-propanediamine (0.134 g, 0.115 mmol), and TEA (0.016 g, 0.156 mmol) were combined in CH$_2$Cl$_2$ (5 mL) and stirred under argon at room temperature. The solvents were pumped off in vacuo. The residue was flash chromatographed on silica gel (10 g) eluted with CH$_2$Cl$_2$ to 6:1:0.1, CH$_2$Cl$_2$: ethanol: NH$_4$OH. The compound had an impurity which was removed by filtering through a silica gel plug with 3% MeOH/CH$_2$Cl$_2$ to give the title compound as an off-white amorphous solid. mp 104-109° C. LC-MS m/z 549 (M+H)$^+$, 1.65 min (ret time).

Example 105

3-(8-(2,6-difluorophenyl)-2-{[2-(dimethylamino)ethyl]amino}-7-oxo-7,8-dihydropyrido[2,3-d]pyrimidin-4-yl)-4-methyl-N-propylbenzamide

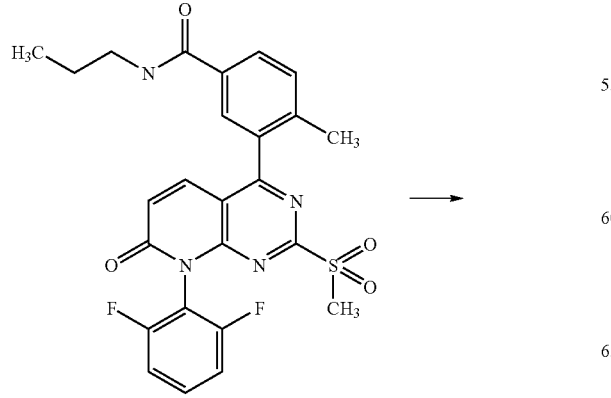

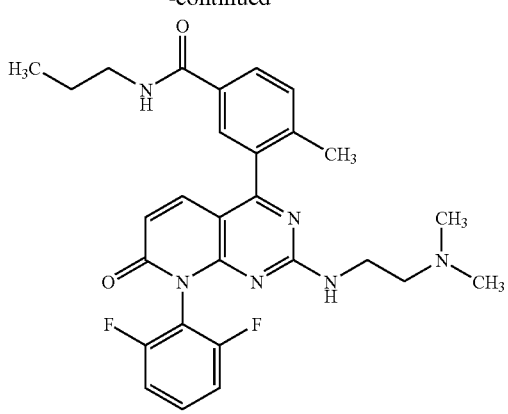

3-[8-(2,6-difluorophenyl)-2-(methylsulfonyl)-7-oxo-7,8-dihydropyrido[2,3-d]pyrimidin-4-yl]-4-methyl-N-propyl-benzamide (0.07 g, 0.13 mmol), N,N-dimethylethylenediamine (0.0173 g, 0.15 mmol), and TEA (0.026 g, 0.26 mmol) were combined in CH$_2$Cl$_2$ (5 mL) and stirred under argon at room temperature for 1 h. The solvents were pumped off in vacuo. The residue was flash chromatographed on silica gel (10 g) eluted with CH$_2$Cl$_2$ to 6:1:0.1, CH$_2$Cl$_2$:ethanol:NH$_4$OH to give the title compound as a white amorphous solid. mp 139-142° C. LC-MS m/z 521 (M+H)$^+$, 1.61 min (ret time).

Example 106

1,1-dimethylethyl {2-[(8-(2,6-difluorophenyl)-4-{2-methyl-5-[(propylamino)carbonyl]phenyl}-7-oxo-7,8-dihydro-pyrido[2,3-d]pyrimidin-2-yl)amino]ethyl}methylcarbamate

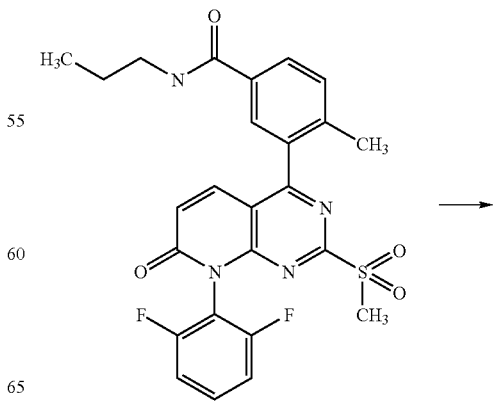

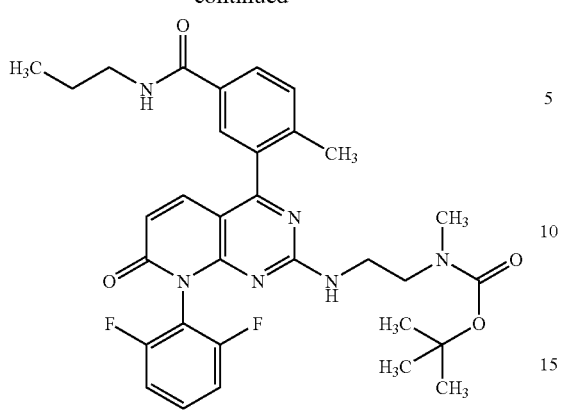

3-[8-(2,6-difluorophenyl)-2-(methylsulfonyl)-7-oxo-7,8-dihydropyrido[2,3-d]pyrimidin-4-yl]-4-methyl-N-propylbenzamide (1.59 g, 3.1 mmol), was dissolved in CH₂Cl₂ (140 mL) and stirred under argon at room temperature. 1,1-dimethylethyl (2-aminoethyl)methylcarbamate (0.806 g, 4.65 mmol), and TEA (0.87 mL, 6.2 mmol) were combined in CH₂Cl₂ (10 mL) and added to the solution of the sulfone. The resulting reaction mixture was stirred under argon overnight. The solvents were pumped off in vacuo. The residue was flash chromatographed on silica gel (150 g) eluted with 0-40% EtOAc/CH₂Cl₂ to give the title compound as a white amorphous solid. mp 115-118° C. LC-MS m/z 607 (M+H)⁺, 2.27 min (ret time).

Example 107

3-{8-(2,6-difluorophenyl)-2-[[3-(dimethylamino)propyl](methyl)amino]-7-oxo-7,8-dihydropyrido[2,3-d]pyrimidin-4-yl}-4-methyl-N-1,3-thiazol-2-ylbenzamide

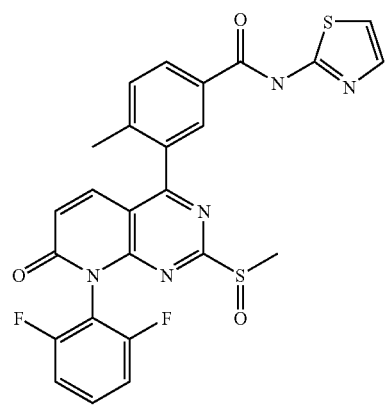

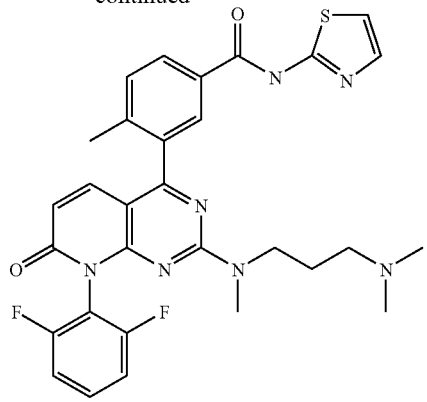

The title compound was prepared from 3-[8-(2,6-difluorophenyl)-2-(methylsulfinyl)-7-oxo-7,8-dihydropyrido[2,3-d]pyrimidin-4-yl]-4-methyl-N-1,3-thiazol-2-ylbenzamide and N,N,N'-trimethyl-1,3-propanediamine by following the procedures in Example 79c. LC-MS m/z 590 (M+H)⁺; ¹H-NMR (MeOD) 1.70 (m, 2H), 2.04 (m, 2H), 2.20 (s, 6H), 2.36 (s, 3H), 2.89-3.21 (m, 3H), 3.36-3.70 (m, 2 H), 6.36 (d, J=8.4 Hz, 1H), 7.16 (m, 1H), 7.27 (m, 2H), 7.50 (m, 2H), 7.59 (m, 2 H), 8.01 (s, 1H), 8.13 (m, 1H).

Example 108

N-[3-(8-(2,4-difluorophenyl)-2-{[2-hydroxy-1-(hydroxymethyl)ethyl]amino}-7-oxo-7,8-dihydropyrido[2,3-d]pyrimidin-4-yl)phenyl]acetamide

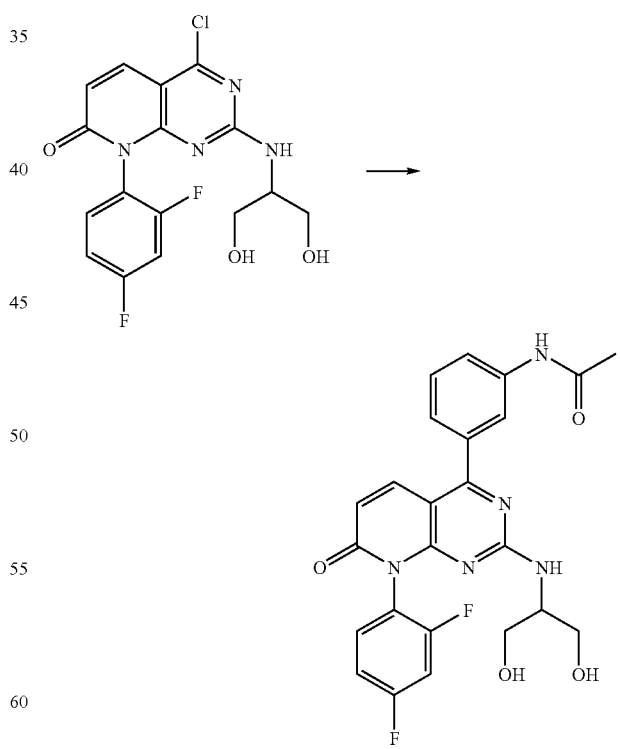

The title compound was prepared by following the procedure in example 96d from 4-chloro-8-(2,4-difluorophenyl)-2-{[2-hydroxy-1-(hydroxymethyl)ethyl]amino}pyrido[2,3-d]pyrimidin-7(8H)-one and [3-(acetylamino)phenyl]boronic acid: LC-MS m/z 482 (M+H)⁺, retention 2.69 min.

Example 109

3-(8-(2,6-difluorophenyl)-2-{[2-(dimethylamino)ethyl]amino}-7-oxo-7,8-dihydropyrido[2,3-d]pyrimidin-4-yl)-4-methyl-N-1,3-thiazol-2-ylbenzamide

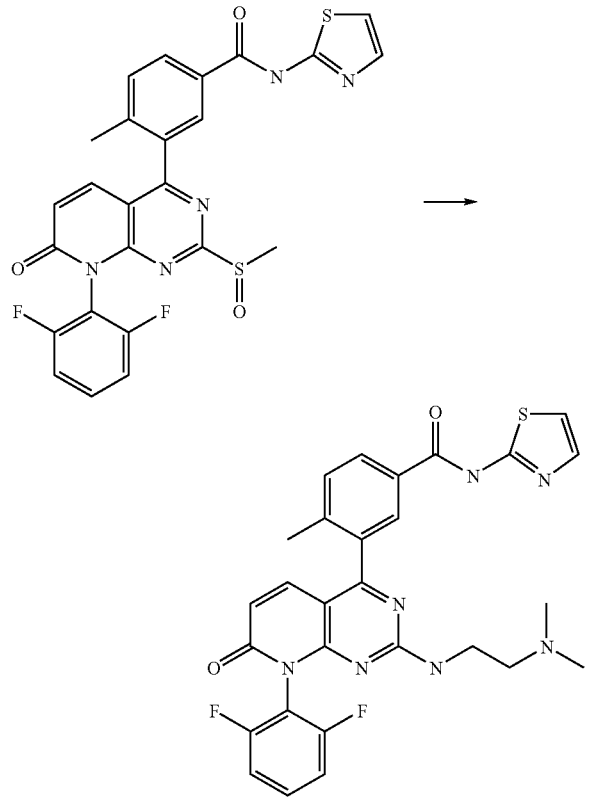

The title compound was prepared from 3-[8-(2,6-difluorophenyl)-2-(methylsulfinyl)-7-oxo-7,8-dihydropyrido[2,3-d]pyrimidin-4-yl]-4-methyl-N-1,3-thiazol-2-ylbenzamide and N,N-dimethyl-1,2-ethanediamine by following the procedures in Example 79c. LC-MS m/z 562 (M+H)+; $^1$H-NMR (MeOD) 2.15 (m, 6H), 2.36 (m, 4H), 2.65 (m, 1H), 3.27 (m, 2H), 6.38 (d, J=8.4 Hz, 1H), 7.17 (m, 1H), 7.25 (m, 2H), 7.49 (m, 2H), 7.59 (m, 2H), 8.00 (s, 1H), 8.11 (d, J=8.0 Hz, 1H).

Example 110

4-(5-amino-2-methylphenyl)-8-(2,6-difluorophenyl)-2-[(2,2,6,6-tetramethyl-4-piperidinyl)amino]pyrido[2,3-d]pyrimidin-7(8H)-one 110a) 4-(5-amino-2-methylphenyl)-8-(2,6-difluorophenyl)-2-(methylsulfonyl)pyrido[2,3-d]pyrimidin-7(8H)-one

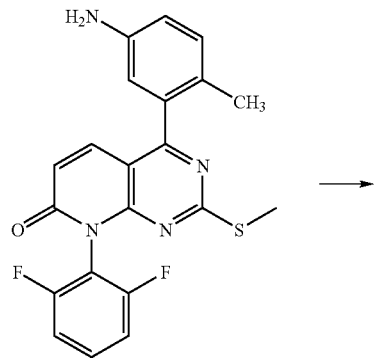

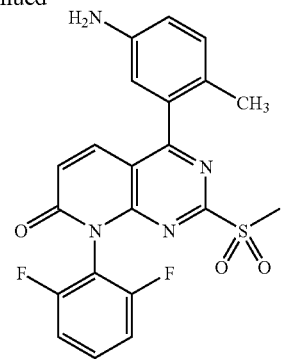

To a solution of 4-(5-amino-2-methylphenyl)-8-(2,6-difluorophenyl)-2-(methylthio)pyrido[2,3-d]pyrimidin-7(8H)-one (170.0 mg, 0.41 mmol) in CH$_2$Cl$_2$ (20.0 mL) was added m-CPBA (224.0 mg, 1.0 mmol). The reaction mixture was stirred for 12 h at room temperature and concentrated. It was diluted with H$_2$O (5.0 mL) and EtOAc (25.0 mL). The organic layer was separated and the aqueous layer was extracted with EtOAc (3×10 mL). The combined organic layers were washed with saturated aq. NaCl, dried over Na$_2$SO$_4$, filtered, and concentrated. Purification via the CombiFlash system (hexane:EtOAc=4:1) then afforded the title compound (190.0 mg, 94%): LC-MS m/z 443 (M+H)+, 2.12 min (ret. time)

110b) 4-(5-amino-2-methylphenyl)-8-(2,6-difluorophenyl)-2-[(2,2,6,6-tetramethyl-4-piperidinyl)amino]-pyrido[2,3-d]pyrimidin-7(8H)-one

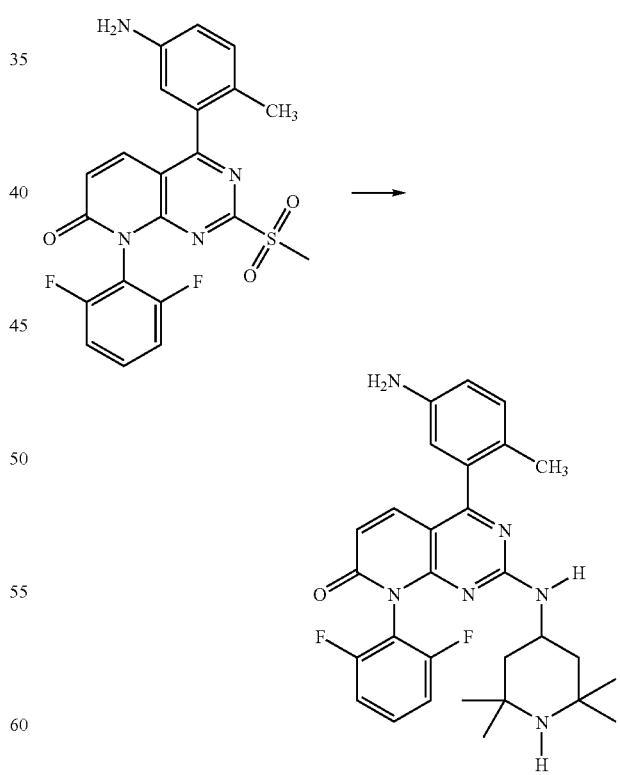

The title compound was prepared as described in Example 1d from 4-(5-amino-2-methylphenyl)-8-(2,6-difluorophenyl)-2-(methylsulfonyl)pyrido[2,3-d]pyrimidin-7(8H)-one and 2,2,6,6-tetramethyl-4-piperidinamine: LC-MS m/z 519 (M+H)+, 1.8 min (ret time).

Example 111

4-(5-amino-methylphenyl)-8-(2,6-difluorophenyl)-2-(4-piperidinylamino)-pyrido[2,3-d]pyrimidin-7(8H)-one

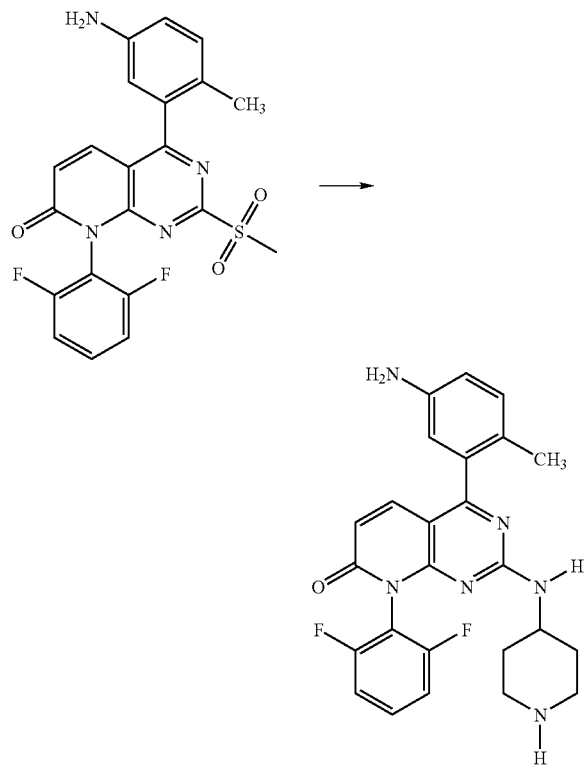

The title compound was prepared as described in Example 2 from 4-(5-amino-2-methylphenyl)-8-(2,6-difluorophenyl)-2-(methylsulfonyl)pyrido[2,3-d]pyrimidin-7(8H)-one and 1,1-dimethylethyl 4-amino-1-piperidinecarboxylate. LC-MS m/z 463 (M+H)$^+$, 1.73 min (ret time).

Example 112

3-(8-(2,6-difluorophenyl)-2-{[2-(dimethylamino)ethyl]amino}-7-oxo-7,8-dihydropyrido[2,3-d]pyrimidin-4-yl)-N-(4-fluorophenyl)-4-methylbenzamide

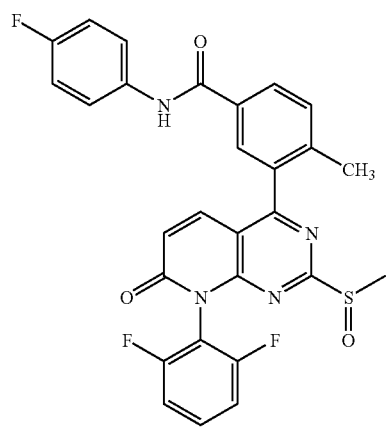

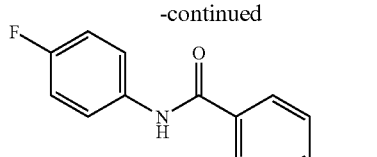

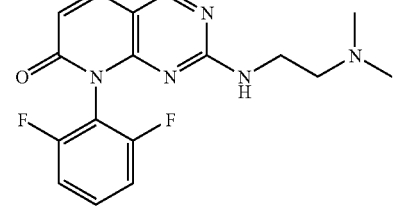

To a solution of 3-[8-(2,6-difluorophenyl)-2-(methylsulfinyl)-7-oxo-7,8-dihydropyrido[2,3-d]pyrimidin-4-yl]-N-(4-fluorophenyl)-4-methylbenzamide (15 mg, 0.027 mmol) in DCM (5 mL) was added N,N-dimethyl-1,2-ethanediamine (0.009 mL, 0.083 mmol). The resultant mixture was stirred at room temperature overnight. The mixture was concentrated under vacuo. Flash chromatography (90% CH$_2$Cl$_2$/7% MeOH/3% NH$_4$OH) then provide the title compound (11 mg, 72%). LC-MS (ES) m/z 573 (M+H)$^+$; $^1$H-NMR(CDCl$_3$) δ 2.21 (s, 6H), 2.30 (s, 3H), 2.40 (br, 1H), 2.43 (m, 2H), 3.17 (m, 2H), 3.55 (br, 1H), 6.23 (d, 1H), 6.89 (m, 1H), 7.04 (m, 3H), 7.29 (m, 1H), 7.36 (m, 1H), 7.47 (d, 1H), 7.61 (m, 2H), 7.84 (s, 1H), 8.05 (d, 1H).

Example 113

3-{8-(2,6-difluorophenyl)-2-[4-(methylamino)-1-piperidinyl]-7-oxo-7,8-dihydropyrido[2,3-d]pyrimidin-4-yl}-4-methyl-N-(1-methylethyl)benzamide 113a) 1,1-dimethylethyl {1-[8-(2,6-difluorophenyl)-4-(2-methyl-5-{[(1-methylethyl)amino]carbonyl}phenyl)-7-oxo-7,8-dihydropyrido[2,3-d]pyrimidin-2-yl]-4-piperidinyl}methylcarbamate

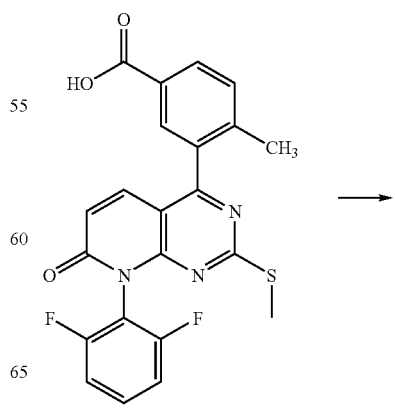

-continued

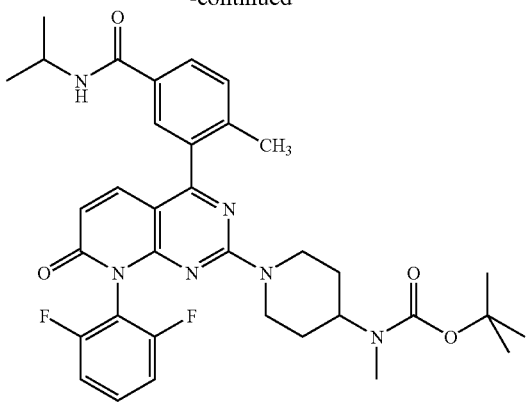

The title compound was prepared from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using 2-propanamine for the amide formation and 1,1-dimethylethyl methyl(4-piperidinyl)carbamate for the displacement reaction. LC-MS (ES) m/z 647 (M+H)+.

113b) 3-{8-(2,6-difluorophenyl)-2-[4-(methylamino)-1-piperidinyl]-7-oxo-7,8-dihydropyrido[2,3-d]pyrimidin-4-yl}-4-methyl-N-(1-methylethyl)benzamide

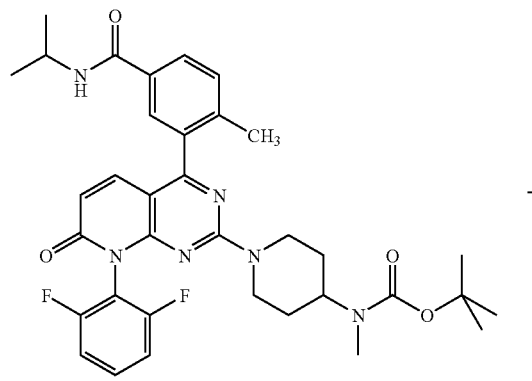

To a solution of 1,1-dimethylethyl {1-[8-(2,6-difluorophenyl)-4-(2-methyl-5-{[(1-methylethyl)amino]carbonyl}phenyl)-7-oxo-7,8-dihydropyrido[2,3-d]pyrimidin-2-yl]-4-piperidinyl}methylcarbamate in DCM (2 mL) was added TFA (0.03 mL). The reaction mixture was stirred at room temperature overnight, quenched with triethylamine (0.5 mL) at −78° C. The residue was mixed with H₂O (5.0 mL). The organic layer was separated and the aqueous layer was extracted with DCM (3×15 mL). The combined organic phases were washed with saturated aq. NaCl, dried over Na₂SO₄, filtered, and concentrated. Purification via a CombiFlash system (90% CH₂Cl₂/7% MeOH/3% NH₄OH) then afforded the title compound. LC-MS (ES) m/z 547 (M+H)+; ¹H-NMR(MeOD) δ 1.20 (m, 2H), 1.26 (d, 6H), 1.90 (m, 2H), 2.31 (s, 3H), 2.38 (s, 3H), 2.65 (m, 1H), 2.95 (m, 2H), 3.23 (m, 1H), 4.23 (m, 2H), 6.35 (d, 1H), 7.25 (t, 2H), 7.50 (d, 1H), 7.52 (d, 1H), 7.62 (m, 1H), 7.78 (s, 1H), 7.93 (d, 1H).

Example 114

3-{8-(2,6-difluorophenyl)-2-[4-(methylamino)-1-piperidinyl]-7-oxo-7,8-dihydropyrido[2,3-d]pyrimidin-4-yl}-N-(4-fluorophenyl)-4-methylbenzamide 114a) 1,1-dimethylethyl {1-[8-(2,6-difluorophenyl)-4-(5-{[(4-fluorophenyl)amino]carbonyl}-2-methylphenyl)-7-oxo-7,8-dihydropyrido[2,3-d]pyrimidin-2-yl]-4-piperidinyl}methylcarbamate

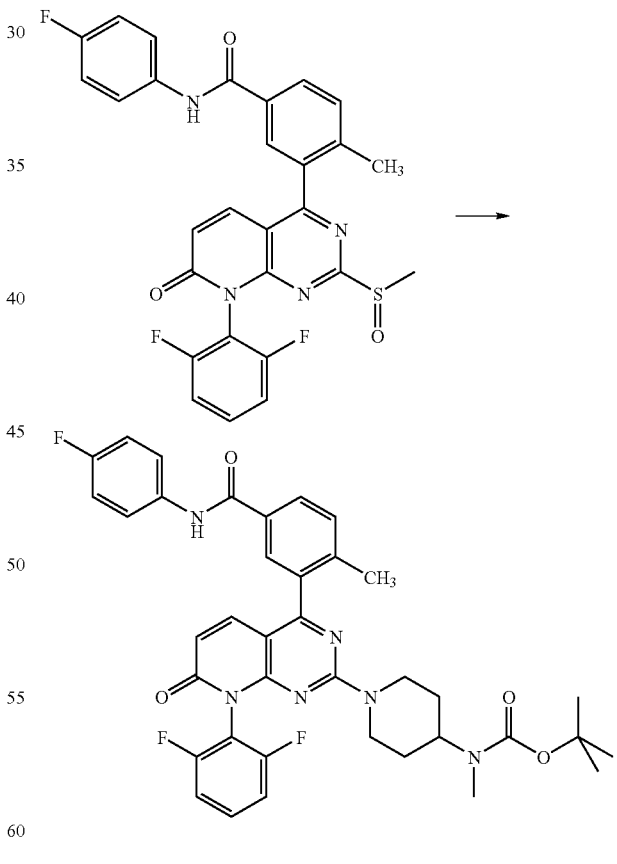

To a solution of 3-[8-(2,6-difluorophenyl)-2-(methylsulfinyl)-7-oxo-7,8-dihydropyrido[2,3-d]pyrimidin-4-yl]-N-(4-fluorophenyl)-4-methylbenzamide (Example 19b, 10 mg, 0.018 mmol) in DCM (5 mL) was added 1,1-dimethylethyl methyl(4-piperidinyl)carbamate (19 mg, 0.089 mmol). The resultant mixture was stirred at room temperature overnight.

114b) 3-{8-(2,6-difluorophenyl)-2-[4-(methylamino)-1-piperidinyl]-7-oxo-7,8-dihydropyrido[2,3-d]pyrimidin-4-yl}-N-(4-fluorophenyl)-4-methylbenzamide

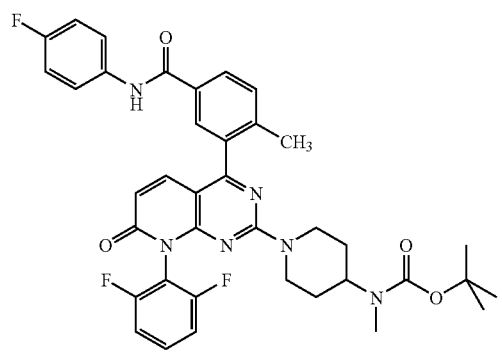

Example 115

3-{8-(2,6-difluorophenyl)-2-[[3-(dimethylamino)propyl](methyl)amino]-7-oxo-7,8-dihydropyrido[2,3-d]pyrimidin-4-yl}-N-(4-fluorophenyl)-4-methylbenzamide

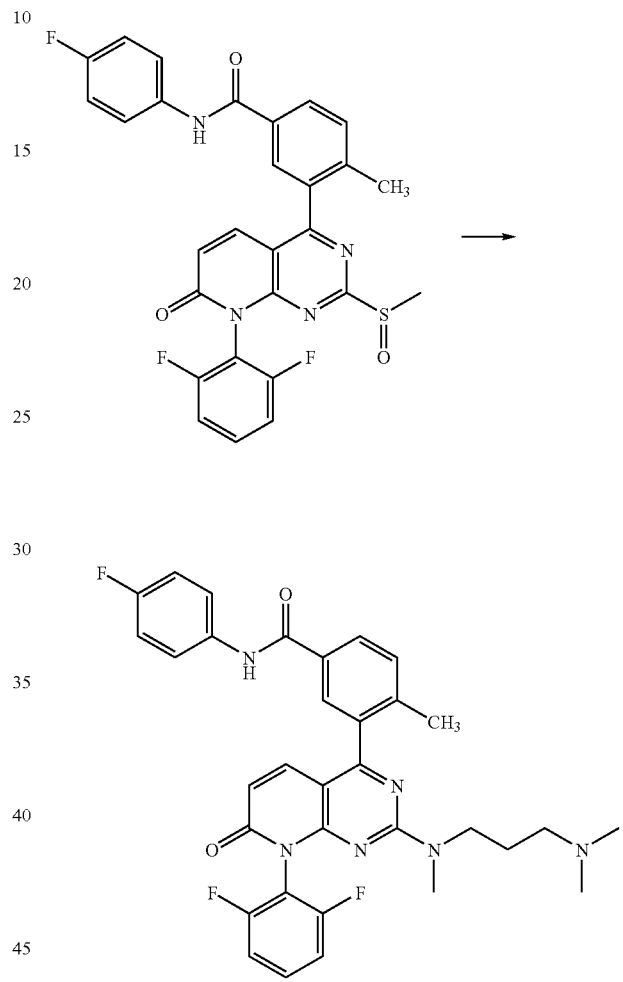

To a solution of 1,1-dimethylethyl {1-[8-(2,6-difluorophenyl)-4-(5-{[(4-fluorophenyl)amino]carbonyl}-2-methylphenyl)-7-oxo-7,8-dihydropyrido[2,3-d]pyrimidin-2-yl]-4-piperidinyl}methylcarbamate in DCM (2 mL) was added TFA (0.03 mL). The reaction mixture was stirred at room temperature overnight, quenched with triethylamine (0.5 mL) at −78° C. The residue was mixed with H$_2$O (5.0 mL). The organic layer was separated and the aqueous layer was extracted with DCM (3×15 mL). The combined organic phases were washed with saturated aq. NaCl, dried over Na$_2$SO$_4$, filtered, and concentrated. Purification via a CombiFlash system (90% CH$_2$Cl$_2$/7% MeOH/3% NH$_4$OH) then afforded the title compound (6 mg, 57%, 2 steps). LC-MS (ES) m/z 599 (M+H)$^+$; $^1$H-NMR(MeOD) δ 1.29 (m, 2H), 1.37 (m, 1H), 1.95 (m, 2H), 2.39 (s, 3H), 2.45 (s, 3H), 2.77 (m, 1H), 2.95 (m, 2H), 3.50 (m, 1H), 6.38 (d, 1H), 7.14 (m, 2H), 7.25 (m, 2H), 7.52 (d, 1H), 7.62 (m, 2H), 7.71 (m, 2H), 7.92 (s, 1H), 8.06 (d, 1H).

To a solution of 3-[8-(2,6-difluorophenyl)-2-(methylsulfinyl)-7-oxo-7,8-dihydropyrido[2,3-d]pyrimidin-4-yl]-N-(4-fluorophenyl)-4-methylbenzamide (15 mg, 0.027 mmol) in DCM (5 mL) was added N,N,N'-trimethyl-1,3-propanediamine (0.021 mL, 0.14 mmol). The resultant mixture was stirred at room temperature overnight. The mixture was concentrated under vacuo. Flash chromatography (90% CH$_2$Cl$_2$/7% MeOH/3% NH$_4$OH) then provide the title compound (10 mg, 63%). LC-MS (ES) m/z 601 (M+H)$^+$; $^1$H-NMR(MeOD) δ 1.62 (m, 1H), 1.80 (m, 1H), 2.05 (m, 2H), 2.20 (s, 6H), 2.32 (m, 4H), 2.89 (m, 2H), 3.32 (s, 2H), 6.36 (d, 1H), 7.14 (m, 2H), 7.28 (m, 2H), 7.52 (d, 1H), 7.59 (d, 1H), 7.65 (m, 1H), 7.71 (m, 2H), 7.92 (s, 1H), 8.06 (d, 1H).

Example 116

3-{8-(2,6-difluorophenyl)-2-[(1H-imidazol-2-ylmethyl)amino]-7-oxo-7,8-dihydropyrido[2,3-d]pyrimidin-4-yl}-4-methyl-N-(phenylmethyl)benzamide 116a) 3-[8-(2,6-difluorophenyl)-2-(methylthio)-7-oxo-7,8-dihydropyrido[2,3-d]pyrimidin-4-yl]-4-methyl-N-(phenylmethyl)benzamide

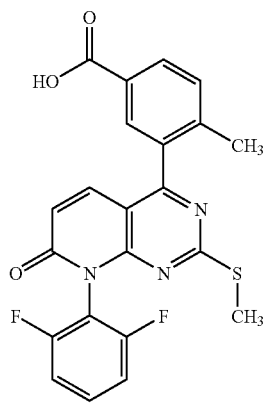 

116b) 3-[8-(2,6-difluorophenyl)-2-(methylsulfinyl)-7-oxo-7,8-dihydropyrido[2,3-d]pyrimidin-4-yl]-4-methyl-N-(phenylmethyl)benzamide

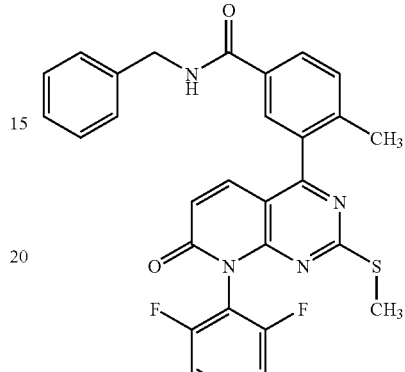 

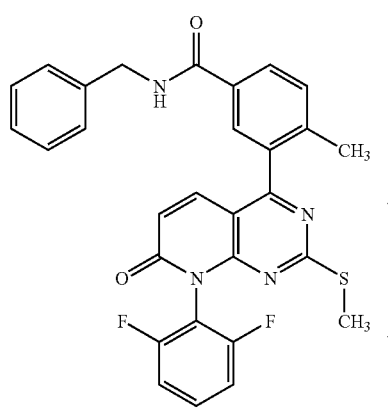

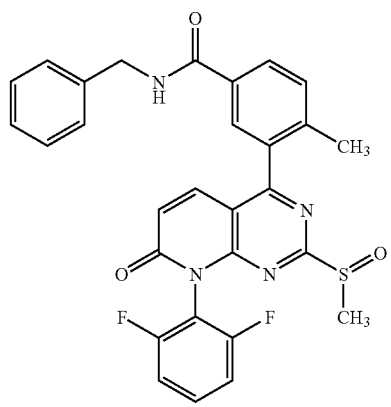

3-[8-(2,6-difluorophenyl)-2-(methylthio)-7-oxo-7,8-dihydropyrido[2,3-d]pyrimidin-4-yl]-4-methylbenzoic acid (0.15 g, 0.342 mmol) was dissolved in CH$_2$Cl$_2$ (10 mL) and stirred under argon at room temperature. N-Benzylamine (0.11 g, 1.03 mmol) was added followed by EDC (0.082 g, 0.41 mmol) and HOBT (0.055 g, 0.41 mmol). The reaction was stirred overnight. The solvents were pumped off in vacuo, and the residue taken up in EtOAc and washed twice with H$_2$O, once with brine, dried over anhydrous Na$_2$SO$_4$ filtered and evaporated. The residue was flash chromatographed on silica gel (20 g) eluted with 0-1.5% MeOH/CH$_2$Cl$_2$ to give the title compound. mp (dec) 124-130° C. LC-MS m/z 529 (M+H)$^+$, 2.36 min (ret time).

3-[8-(2,6-difluorophenyl)-2-(methylthio)-7-oxo-7,8-dihydropyrido[2,3-d]pyrimidin-4-yl]-4-methyl-N-(phenylmethyl)benzamide (0.12 g 0.227 mmol) was dissolved in CH$_2$Cl$_2$ (5 mL) and 50-60% 3-chloroperoxybenzoic acid (0.106 g, 0.34 mmol) was added and the mixture stirred for 10 min. The solvents were pumped off, and the residue taken up in EtOAc and washed with H$_2$O, brine, dried over anhydrous Na$_2$SO$_4$ filtered and evaporated. The crude product which contained a small amount of sulfone, was flashed on silica gel (20 g) eluted with a hexane to EtOAc gradient to isolate the title compound. mp (dec) 268-270° C. LC-MS m/z 545 (M+H)$^+$, 1.87 min (ret time).

203

116c) 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-(phenylmethyl)benzamide

204

Example 117

3-(8-(2,6-difluorophenyl)-2-{[2-(dimethylamino)ethyl]amino}-7-oxo-7,8-dihydropyrido[2,3-d]pyrimidin-4-yl)-4-methyl-N-(1-methylethyl)benzamide

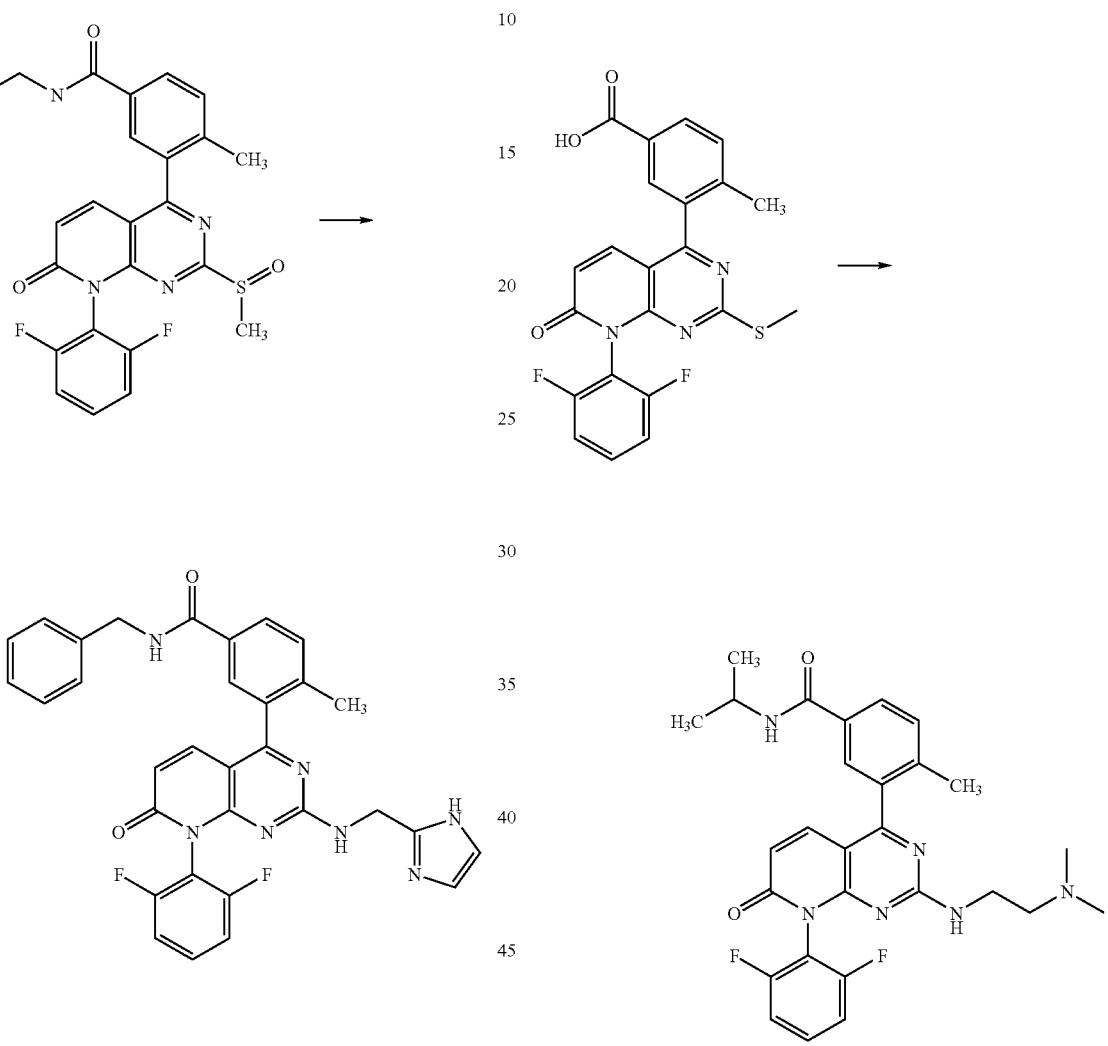

3-[8-(2,6-Difluorophenyl)-2-(methylsulfinyl)-7-oxo-7,8-dihydropyrido[2,3-d]pyrimidin-4-yl]-4-methyl-N-(phenylmethyl)benzamide (0.084 g, 0.154 mmol) and (1H-imidazol-2-ylmethyl)amine dihydrochloride (0.039 g, 0.23 mmol) were dissolved in $CH_2Cl_2$ (5 mL) and triethylamine (0.7 mL). The resulting mixture was stirred under argon at room temperature overnight. The solvents were pumped off in vacuo, and the residue taken up in EtOAc and 1 N NaOH. The organic phase was washed with brine, dried over anhydrous $Na_2SO_4$ filtered and evaporated. The residue was flash chromatographed on silica gel (20 g) eluted with 6:1:0.05 $CH_2Cl_2$:isopropanol:$NH_4OH$. The material isolated was not pure, and was rechromatographed on silica gel (20 g) eluted with 0-5% MeOH/$CH_2Cl_2$ to give the title compound as a white amorphous solid. mp (dec) 185-190° C. LC-MS m/z 578 (M+H)$^+$, 1.76 min (ret time).

The title compound was prepared from 3-[8-(2,6-difluorophenyl)-2-(methylthio)-7-oxo-7,8-dihydropyrido[2,3-d]pyrimidin-4-yl]-4-methylbenzoic acid by following the procedures in Example 19 using 2-propanamine for the amide formation and N,N-dimethyl-1,2-ethanediamine for the displacement reaction. LC-MS (ES) m/z 521 (M+H)$^+$; $^1$H-NMR (MeOD) δ 1.26 (d, 6H), 2.12 (s, 6H), 2.30 (m, 2H), 2.36 (m, 5H), 3.27 (m, 2H), 4.23 (m, 1H), 6.38 (d, 1H), 7.25 (m, 2H), 7.44 (d, 1H), 7.49 (d, 1H), 7.59 (m, 1H), 7.79 (s, 1H), 7.93 (d, 1H).

Example 118

3-[2-{[3-(diethylamino)propyl]amino}-8-(2,6-difluorophenyl)-7-oxo-7,8-dihydropyrido[2,3-d]pyrimidin-4-yl]-4-methyl-N-(1-methylethyl)benzamide 118a)
3-[2-{[3-(diethylamino)propyl]amino}-8-(2,6-difluorophenyl)-7-oxo-7,8-dihydropyrido[2,3-d]-pyrimidin-4-yl]-4-methylbenzoic acid

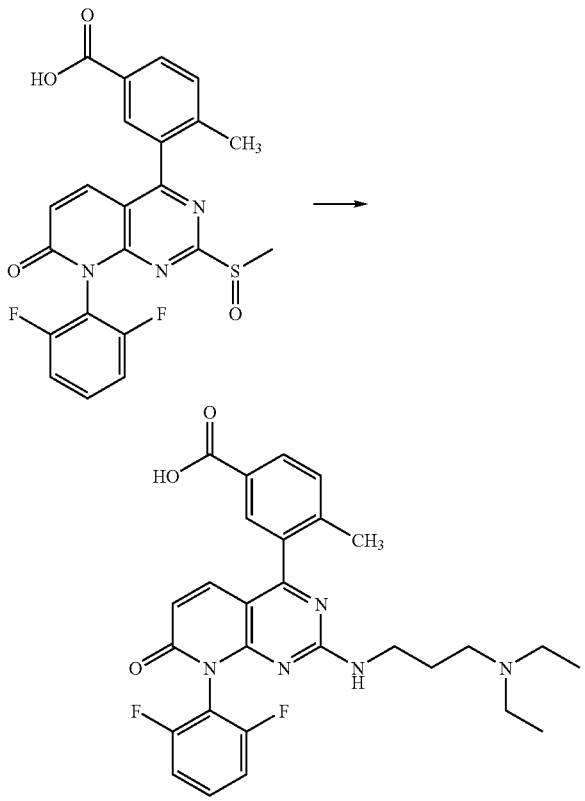

To the compound 3-[8-(2,6-difluorophenyl)-2-(methylsulfinyl)-7-oxo-7,8-dihydropyrido[2,3-d]pyrimidin-4-yl]-4-methylbenzoic acid (600 mg, 1.32 mmol) in dichloromethane (30 mL) was added N,N-diethyl-1,3-propanediamine (0.624 mL, 4.0 mol). The mixture was stirred at room temperature overnight. Solvent was removed by rotovap. Separation by HPLC with TFA afforded the title compound (695 mg, 85%). LC-MS m/z 522 (M+H)+.

118b) 3-[2-{[3-(diethylamino)propyl]amino}-8-(2,6-difluorophenyl)-7-oxo-7,8-dihydropyrido[2,3-d]pyrimidin-4-yl]-4-methyl-N-(1-methylethyl)benzamide

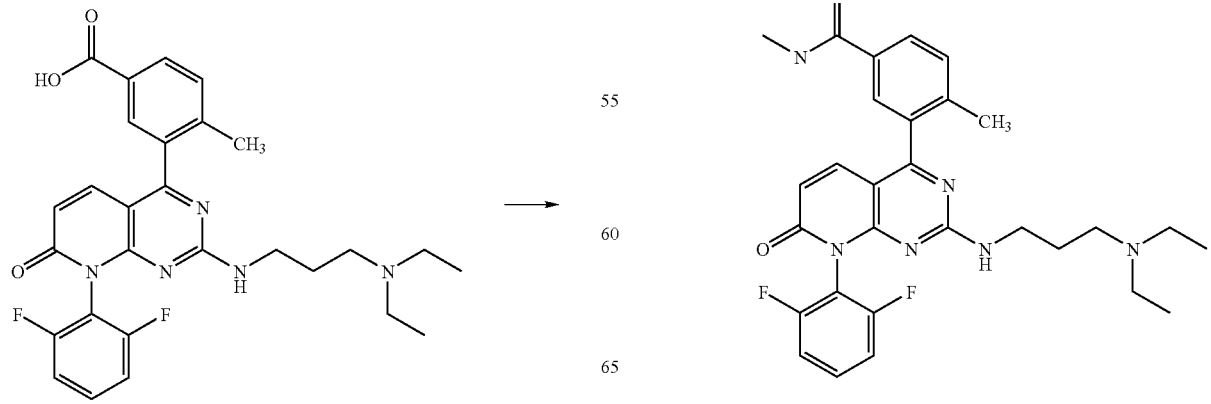

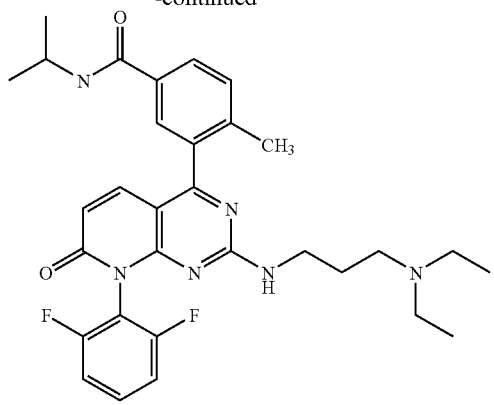

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in dichloromethane (2 mL) were added HBTU (30 mg, 0.079 mmol) and isopropylamine (0.032 mL, 0.37 mmol). The mixture was stirred at r.t. overnight. Solvent was removed by rotovap. Separation by chromatography (90% methylene chloride/7% MeOH/3% ammonia) afforded the title compound (22 mg, 51%). LC-MS m/z 563 (M+H)+.

Example 119

3-[2-{[3-(diethylamino)propyl]amino}-8-(2,6-difluorophenyl)-7-oxo-7,8-dihydropyrido[2,3-d]pyrimidin-4-yl]-N,4-dimethylbenzamide

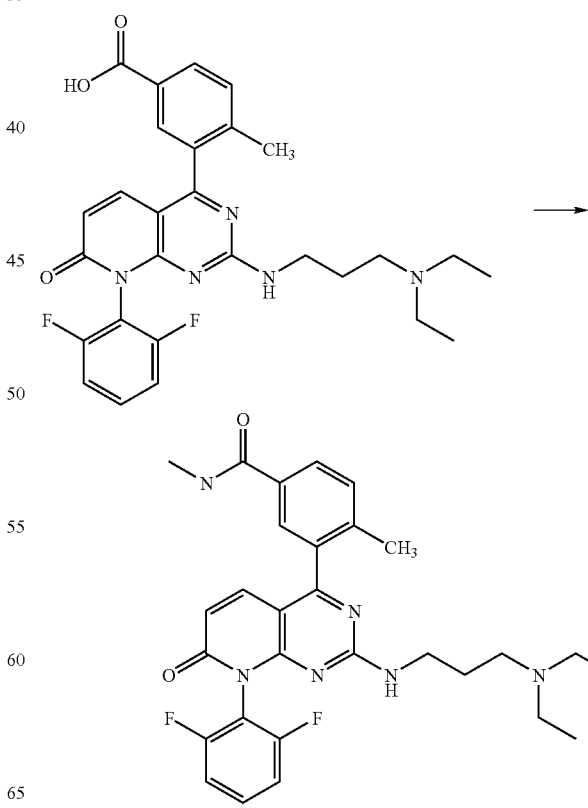

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in dichloromethane (2 mL) were added HBTU (30 mg, 0.079 mmol) and methylamine (0.185 mL, 0.37 mmol, 2.0M soln in THF). The mixture was stirred at rt overnight. Solvent was removed by rotovap. Separation by chromatography (90% methylene chloride/7% MeOH/3% ammonia) afforded the title compound (32 mg, 78%). LC-MS m/z 535 (M+H)⁺.

Example 120

3-[2-{[3-(diethylamino)-propyl]amino}-8-(2,6-difluorophenyl)-7-oxo-7,8-dihydropyrido[2,3-d]-pyrimidin-4-yl]-N,N,4-trimethylbenzamide

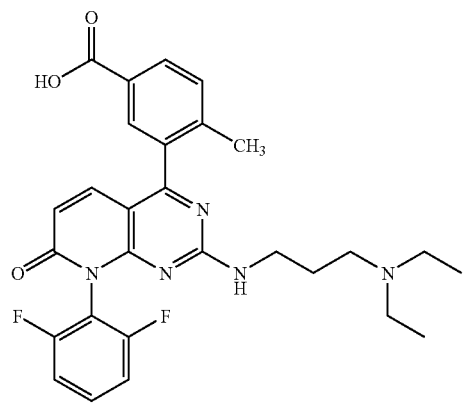

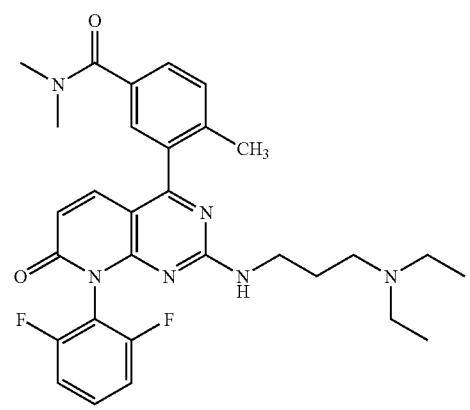

Example 121

3-[2-{[3-(diethylamino)propyl]amino}-8-(2,6-difluorophenyl)-7-oxo-7,8-dihydropyrido[2,3-d]pyrimidin-4-yl]-N-[2-hydroxy-1-(hydroxymethyl)ethyl]-4-methylbenzamide

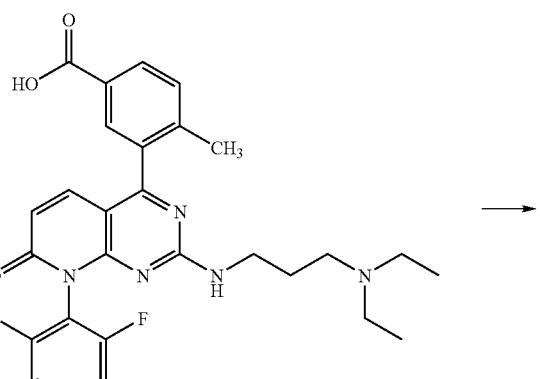

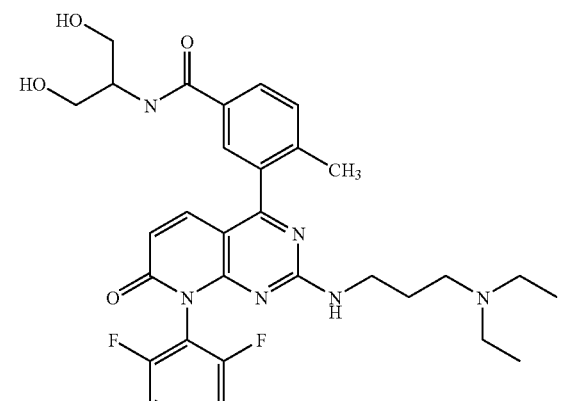

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in dichloromethane (2 mL) were added HBTU (30 mg, 0.079 mmol) and dimethylamine (0.185 mL, 0.37 mmol, 2.0M soln in THF). The mixture was stirred at rt overnight. Solvent was removed by rotovap. Separation by chromatography (90% methylene chloride/7% MeOH/3% ammonia) afforded the title compound (42 mg, 99%). LC-MS m/z 549 (M+H)⁺.

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in THF (2 mL) were added HBTU (30 mg, 0.079 mmol) and serinol (35 mg, 0.37 mmol). The mixture was stirred at rt overnight. Solvent was removed by rotovap. Separation by HPLC with TFA, followed by neutralization with SPE amine cartridge afforded the title compound (40 mg, 88%). LC-MS m/z 595 (M+H)⁺.

Example 122

3-[2-{[3-(diethylamino)propyl]amino}-8-(2,6-difluorophenyl)-7-oxo-7,8-dihydropyrido[2,3-d]pyrimidin-4-yl]-4-methyl-N-propylbenzamide

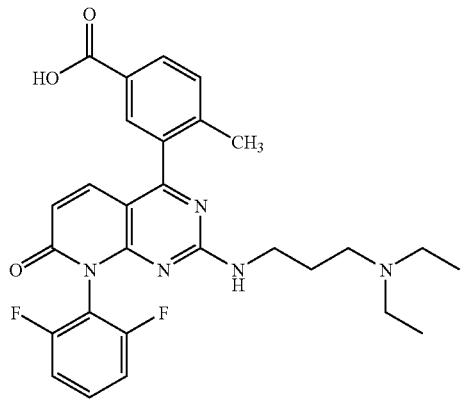

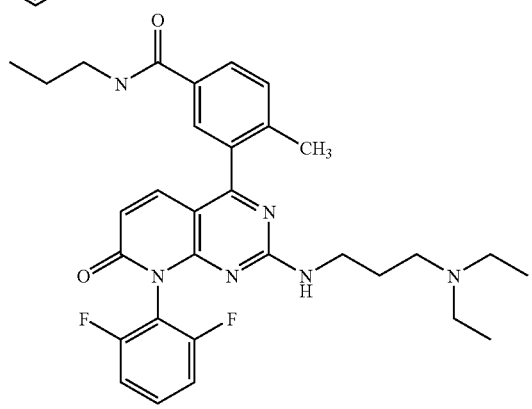

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in THF (2 mL) were added HBTU (30 mg, 0.079 mmol) and propylamine (0.031 mL, 0.37 mmol). The mixture was stirred at rt overnight. Solvent was removed by rotovap. Separation by HPLC with TFA, followed by neutralization with SPE amine cartridge afforded the title compound (16 mg, 37%). LC-MS m/z 563 (M+H)+.

Example 123

N-butyl-3-[2-{[3-(diethylamino)propyl]amino}-8-(2,6-difluorophenyl)-7-oxo-7,8-dihydropyrido[2,3-d]pyrimidin-4-yl]-4-methylbenzamide

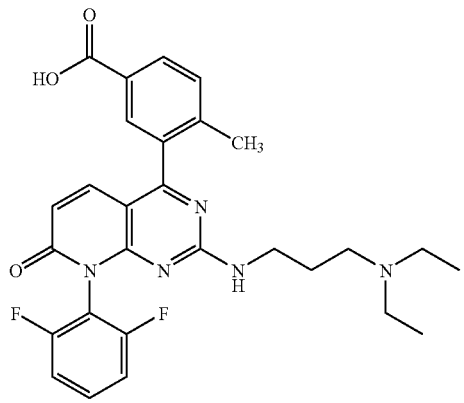

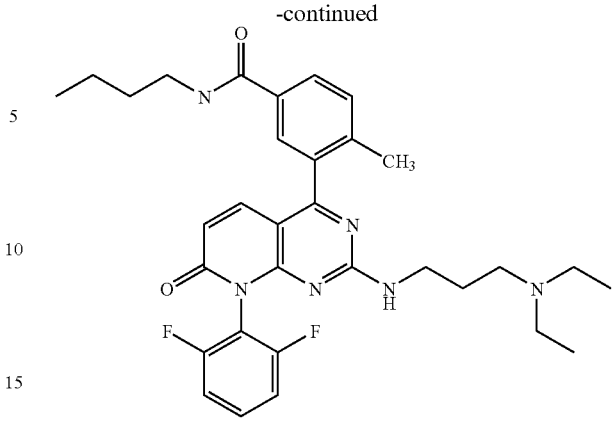

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in methylene chloride (2 mL) were added HBTU (30 mg, 0.079 mmol) and butylamine (0.038 mL, 0.37 mmol). The mixture was stirred at rt overnight. Solvent was removed by rotovap. Separation by HPLC with TFA, followed by neutralization with SPE amine cartridge afforded the title compound (29 mg, 66%). LC-MS m/z 577 (M+H)+.

Example 124

3-[2-{[3-(diethylamino)propyl]amino}-8-(2,6-difluorophenyl)-7-oxo-7,8-dihydropyrido[2,3-d]pyrimidin-4-yl]-4-methyl-N-(2-methylpropyl)benzamide

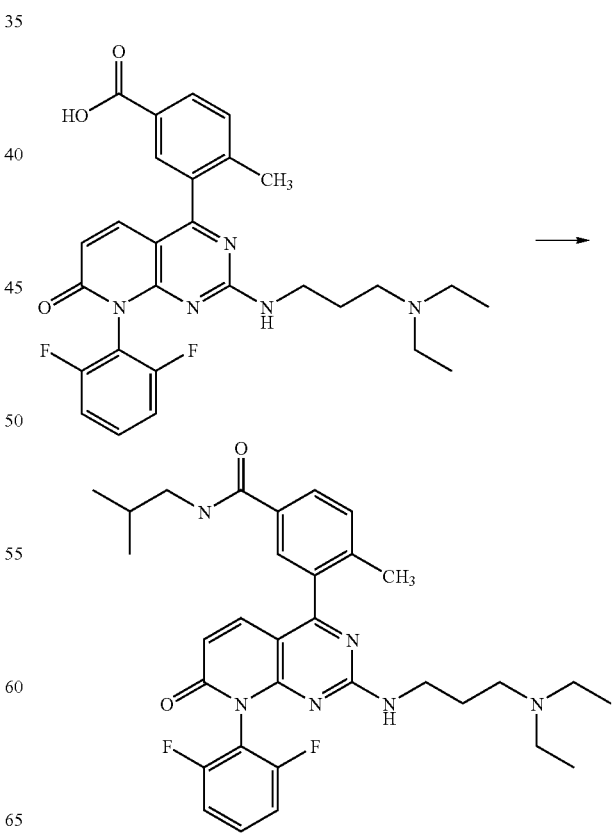

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in methylene chloride (2 mL) were added HBTU (30 mg, 0.079 mmol) and isobutylamine (0.038 mL, 0.37 mmol). The mixture was stirred at rt overnight. Solvent was removed by rotovap. Separation by HPLC with TFA, followed by neutralization with SPE amine cartridge afforded the title compound (19 mg, 43%). LC-MS m/z 577 (M+H)$^+$.

Example 125

N-cyclopentyl-3-[2-{[3-(diethylamino)propyl]amino}-8-(2,6-difluorophenyl)-7-oxo-7,8-dihydropyrido[2,3-d]pyrimidin-4-yl]-4-methylbenzamide

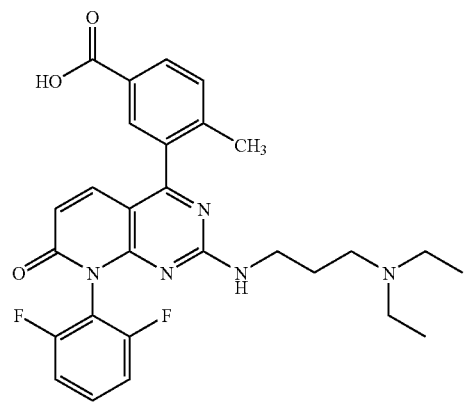

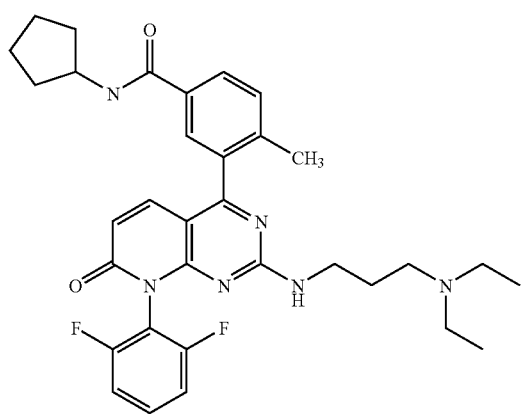

Example 126

3-[2-{[3-(diethylamino)propyl]amino}-8-(2,6-difluorophenyl)-7-oxo-7,8-dihydropyrido[2,3-d]pyrimidin-4-yl]-N-(1,1-dimethylethyl)-4-methylbenzamide

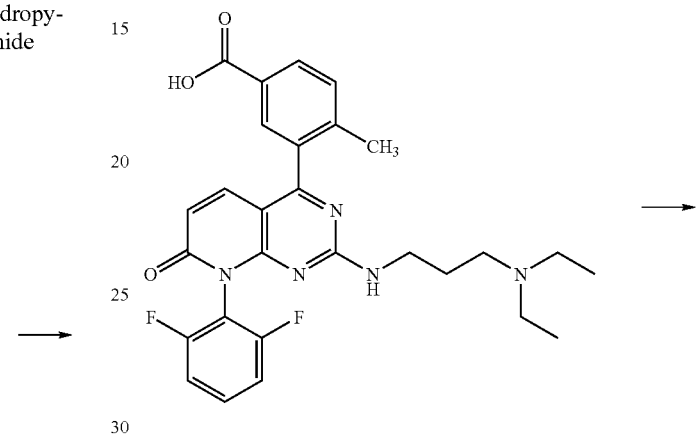

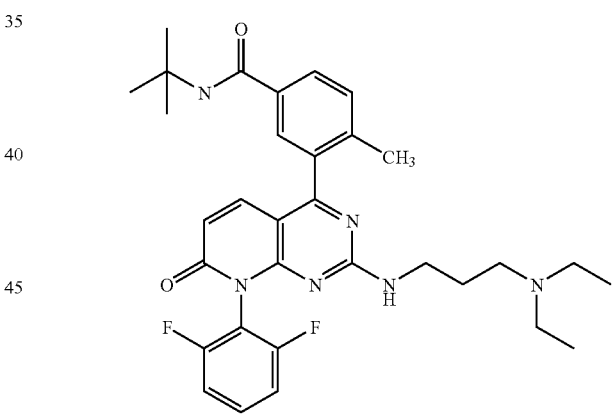

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in methylene chloride (2 mL) was bubbled with nitrogen for 5 min, then it was added HBTU (30 mg, 0.079 mmol) and cyclopentylamine (0.038 mL, 0.37 mmol). The mixture was stirred at rt overnight. Solvent was removed by rotovap. Separation by HPLC with TFA, followed by neutralization with SPE amine cartridge afforded the title compound (21 mg, 47%). LC-MS m/z 589 (M+H)$^+$.

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in methylene chloride (2 mL) were added HBTU (30 mg, 0.079 mmol) and t-butylamine (0.040 mL, 0.37 mmol). The mixture was stirred at rt overnight. Solvent was removed by rotovap. Separation by HPLC with TFA, followed by neutralization with SPE amine cartridge afforded the title compound (39 mg, 88%). LC-MS m/z 577 (M+H)$^+$.

Example 127

3-[2-{[3-(diethylamino)propyl]amino}-8-(2,6-difluorophenyl)-7-oxo-7,8-dihydropyrido[2,3-d]pyrimidin-4-yl]-N-(2,2-dimethylpropyl)-4-methylbenzamide

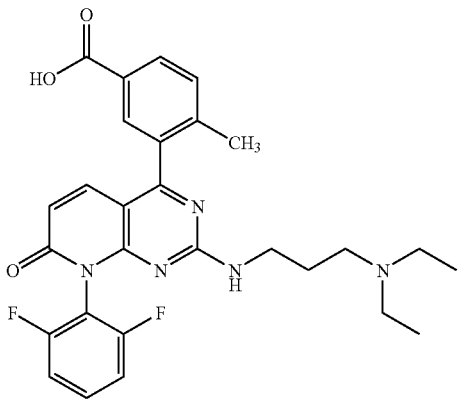

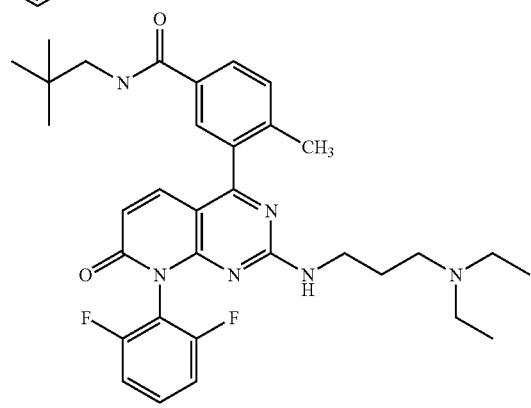

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in methylene chloride (2 mL) were added HBTU (30 mg, 0.079 mmol) and (2,2-dimethylpropyl)amine (0.045 mL, 0.37 mmol). The mixture was stirred at rt overnight. Solvent was removed by rotovap. Separation by HPLC with TFA, followed by neutralization with SPE amine cartridge afforded the title compound (39 mg, 86%). LC-MS m/z 591 (M+H)+.

Example 128

3-[2-{[3-(diethylamino)propyl]amino}-8-(2,6-difluorophenyl)-7-oxo-7,8-dihydropyrido[2,3-d]-pyrimidin-4-yl]-4-methyl-N-(2,2,2-trifluoroethyl)benzamide

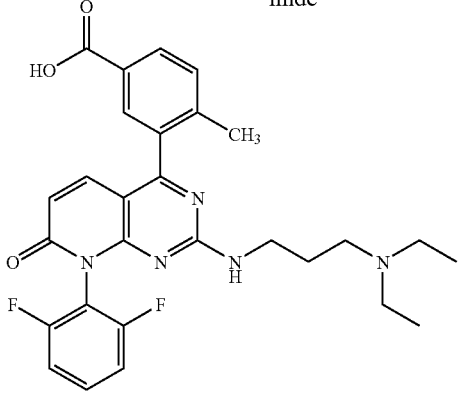

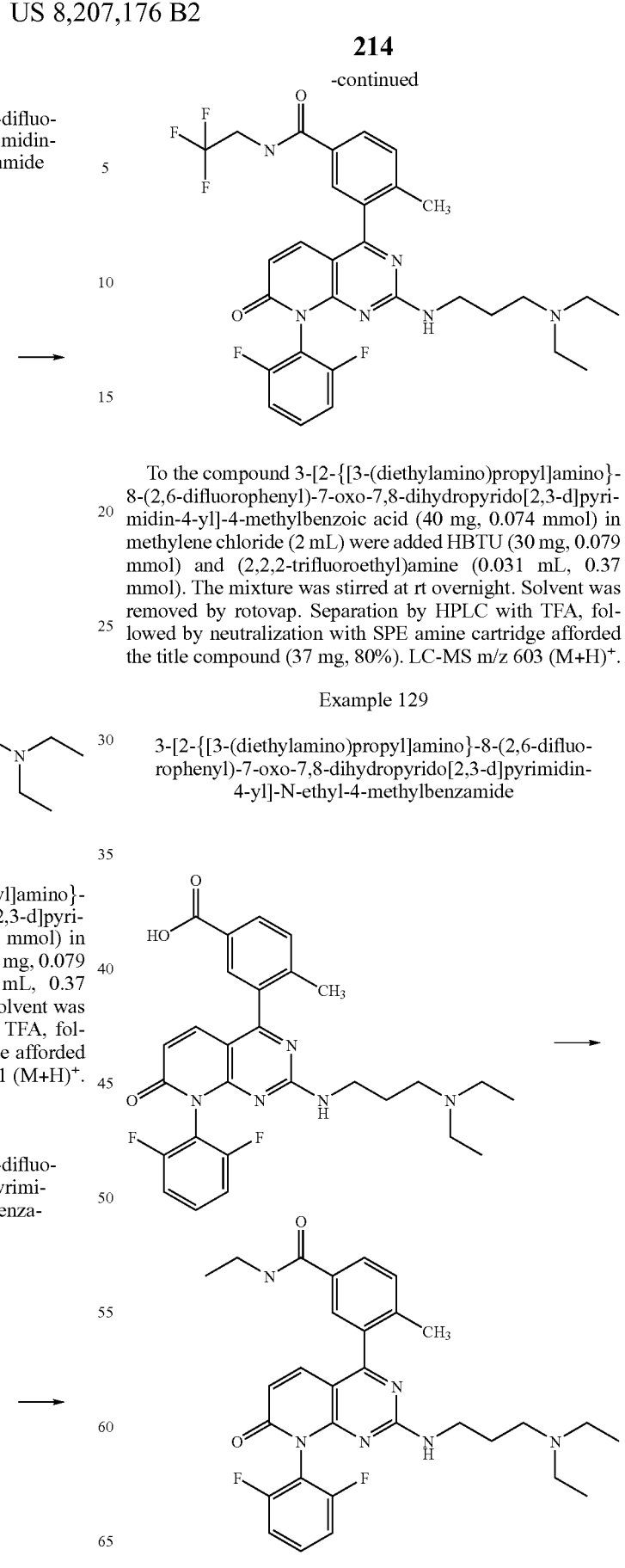

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in methylene chloride (2 mL) were added HBTU (30 mg, 0.079 mmol) and (2,2,2-trifluoroethyl)amine (0.031 mL, 0.37 mmol). The mixture was stirred at rt overnight. Solvent was removed by rotovap. Separation by HPLC with TFA, followed by neutralization with SPE amine cartridge afforded the title compound (37 mg, 80%). LC-MS m/z 603 (M+H)+.

Example 129

3-[2-{[3-(diethylamino)propyl]amino}-8-(2,6-difluorophenyl)-7-oxo-7,8-dihydropyrido[2,3-d]pyrimidin-4-yl]-N-ethyl-4-methylbenzamide To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (40 mg, 0.074 mmol) in methylene chloride (2 mL) were added HBTU (30 mg, 0.079 mmol) and ethylamine (0.19 mL, 0.37 mmol, 2.0M soln in THF). The mixture was stirred at rt overnight. Solvent was removed by rotovap. Separation by chromatography (90% methylene chloride/7% MeOH/3% ammonia) afforded the title compound (17 mg, 40%). LC-MS m/z 549 (M+H)+.

Example 130

3-[2-{[3-(diethylamino)propyl]amino}-8-(2,6-difluorophenyl-7-oxo-7,8-dihydropyrido[2,3-d]pyrimidin-4-yl]-N-[(1R)-1,2-dimethylpropyl]-4-methylbenzamide

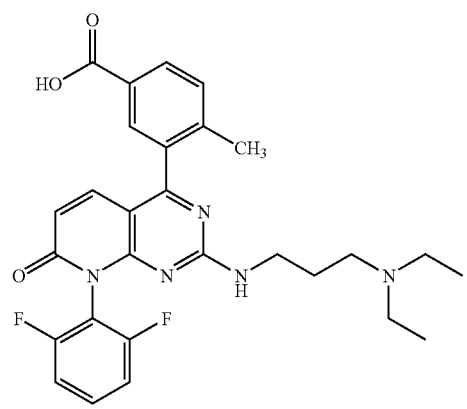

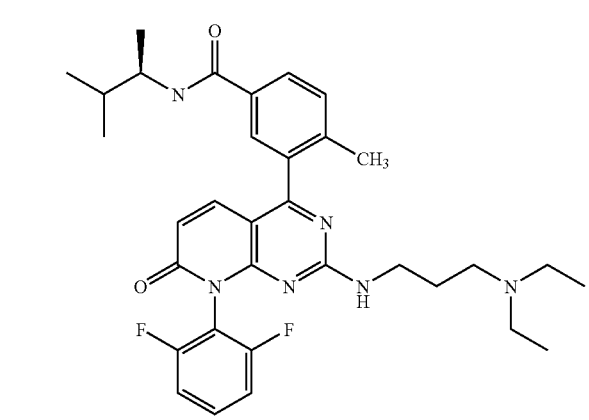

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (31 mg, 0.06 mmol) in DMF (0.5 mL) were added HBTU (27 mg, 0.072 mmol), triethylamine (16.9 uL, 0.12 mmol) and (2R)-3-methyl-2-butanamine (10.5 uL, 0.09 mmol). The mixture was stirred at rt overnight. Separation by HPLC with TFA, followed by neutralization with SPE amine cartridge afforded the title compound (14 mg, 40%). LC-MS m/z 591 (M+H)+.

Example 131

3-[2-{[3-(diethylamino)propyl]amino}-8-(2,6-difluorophenyl)-7-oxo-7,8-dihydropyrido[2,3-d]pyrimidin-4-yl]-N-[(1S)-1,2-dimethylpropyl]-4-methylbenzamide

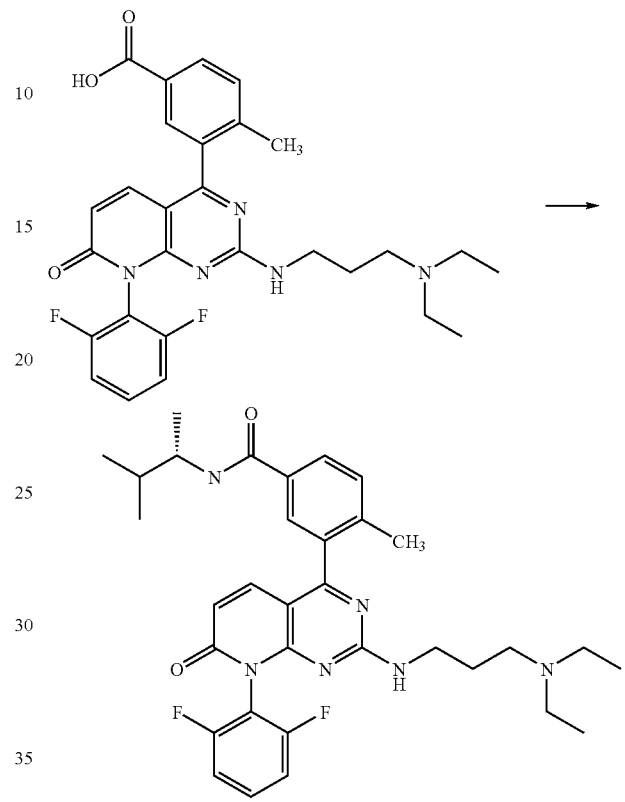

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (31 mg, 0.06 mmol) in DMF (0.5 mL) were added HBTU (27 mg, 0.072 mmol), triethylamine (16.9 uL, 0.12 mmol) and (2S)-3-methyl-2-butanamine (10.5 uL, 0.09 mmol). The mixture was stirred at rt overnight. Separation by HPLC with TFA, followed by neutralization with SPE amine cartridge afforded the title compound (14 mg, 40%). LC-MS m/z 591 (M+H)+.

Example 132

N-(cyclopentylmethyl)-3-[2-{[3-(diethylamino)propyl]amino}-8-(2,6-difluorophenyl)-7-oxo-7,8-dihydropyrido[2,3-d]pyrimidin-4-yl]-4-methylbenzamidetrifluoroacetate

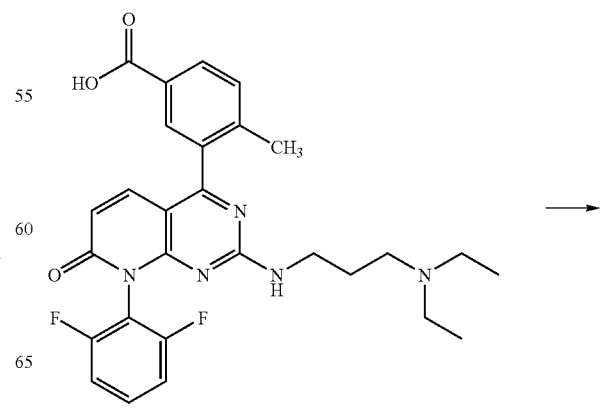

-continued

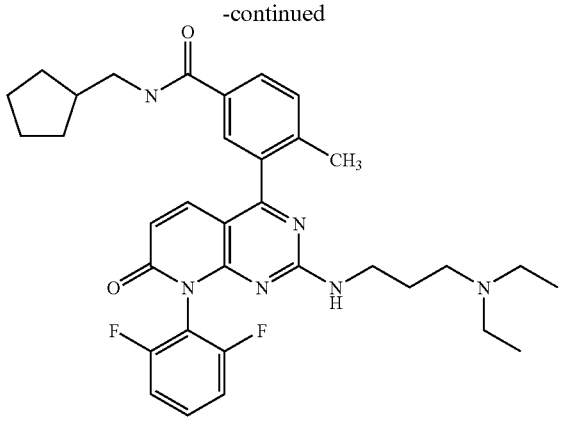

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and 1-cyclopentylmethanamine (9.9 mg, 0.1 mmol). The mixture was stirred at rt overnight. Separation by HPLC with TFA, afforded the title compound (10 mg, 33%). LC-MS m/z 603 (M+H)+.

Example 133

3-[2-{[3-(diethylamino)propyl]amino}-8-(2,6-difluorophenyl)-7-oxo-7,8-dihydropyrido[2,3-d]pyrimidin-4-yl]-N-(2-fluoroethyl)-4-methylbenzamidetrifluoroacetate

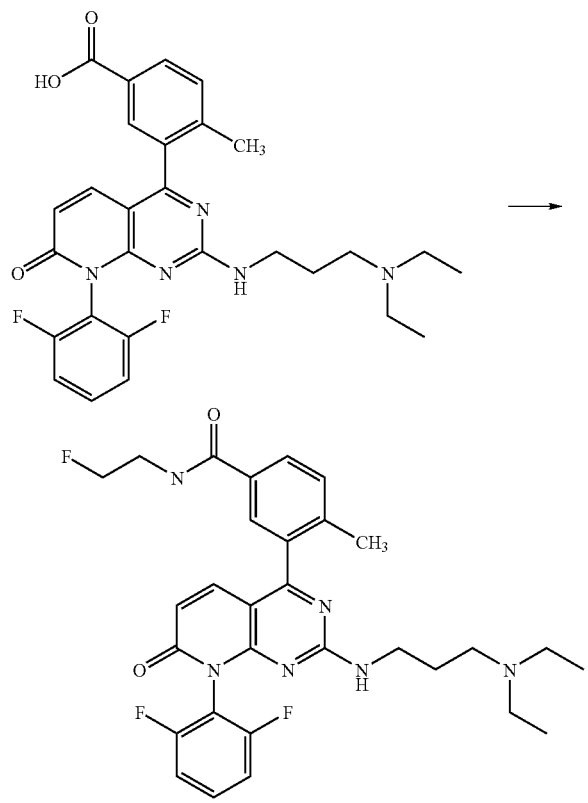

To the compound 3-[2-{[3-(diethylamino)propyl]amino}-8-(2,6-difluorophenyl)-7-oxo-7,8-dihydropyrido [2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and 2-fluoroethanamine hydrochloride (10 mg, 0.1 mmol). The mixture was stirred at rt overnight. Separation by HPLC with TFA, afforded the title compound (9 mg, 32%). LC-MS m/z 567 (M+H)+.

Example 134

3-[2-{[3-(diethylamino)propyl]amino-}8(2,6-difluorophenyl)-7-oxo-7,8-dihydropyrido[2,3-d]pyrimidin-4-yl]-4-methyl-N-[2-(methyloxy)ethyl]benzamidetrifluoroacetate

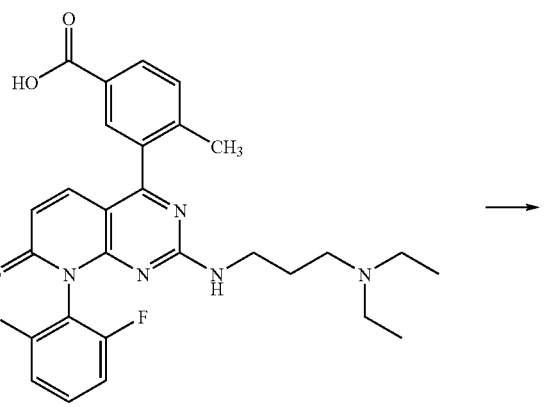

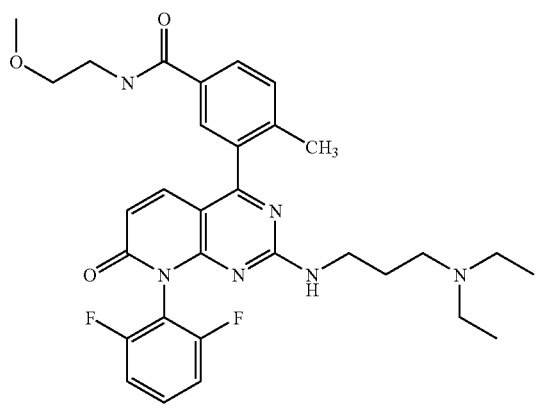

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and 2-(methyloxy)ethanamine (8.6 uL, 0.1 mmol). The mixture was stirred at rt overnight. Separation by HPLC with TFA, afforded the title compound (11 mg, 38%). LC-MS m/z 579 (M+H)+.

Example 135

N-(cyclohexylmethyl)-3-[2-{[3-(diethylamino)propyl]amino}-8-(2,6-difluorophenyl)-7-oxo-7,8-dihydropyrido[2,3-d]pyrimidin-4-yl]-4-methylbenzamide trifluoroacetate

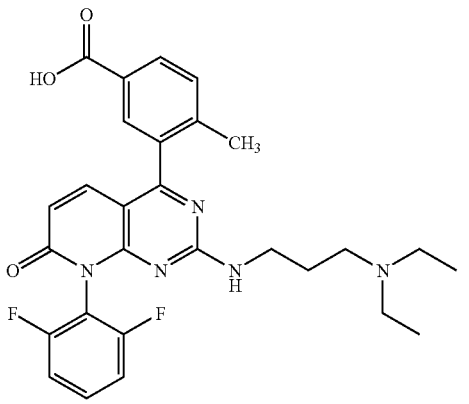

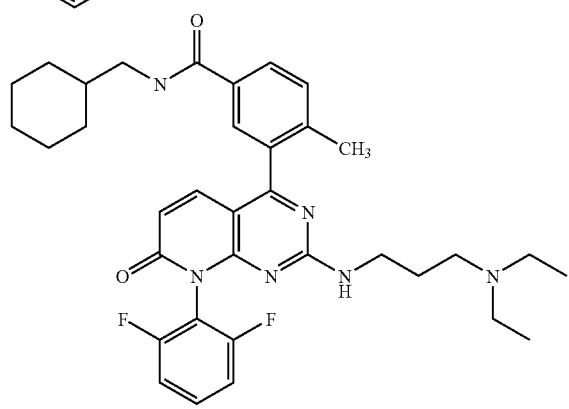

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and (cyclohexylmethyl)amine (13.0 uL, 0.1 mmol). The mixture was stirred at rt overnight. Separation by HPLC with TFA, afforded the title compound (10 mg, 32%). LC-MS m/z 617 (M+H)+.

Example 136

3-[2-{[3-(diethylamino)propyl]amino}-8-(2,6-difluorophenyl)-7-oxo-7,8-dihydropyrido[2,3-d]pyrimidin-4-yl]-4-methyl-N-[(5-methyl-2-furanyl)methyl]benzamide trifluoroacetate

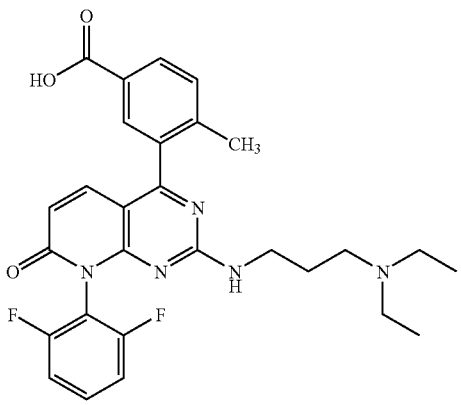

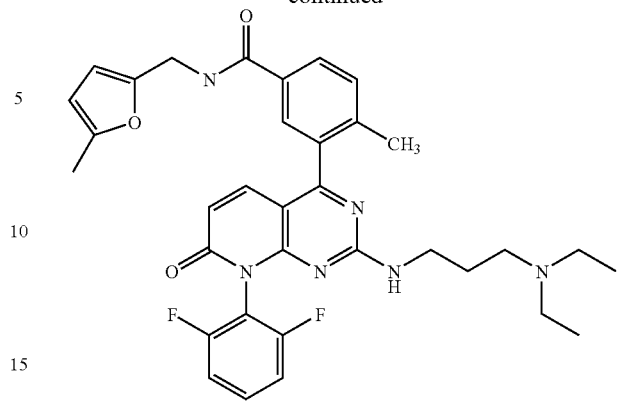

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) was added HBTU (28 mg, 0.075 mmol), triethylamine (21.1 uL, 0.15 mmol) and [(5-methyl-2-furanyl)methyl]amine (11.2 uL, 0.1 mmol). The mixture was stirred at rt overnight. Separation by HPLC with TFA, afforded the title compound (13 mg, 42%). LC-MS m/z 615 (M+H)+.

Example 137

N-cyclobutyl-3-[2-{[3-(diethylamino)propyl]amino}-8-(2,6-difluorophenyl)-7-oxo-7,8-dihydropyrido[2,3-d]pyrimidin-4-yl]-4-methylbenzamide trifluoroacetate

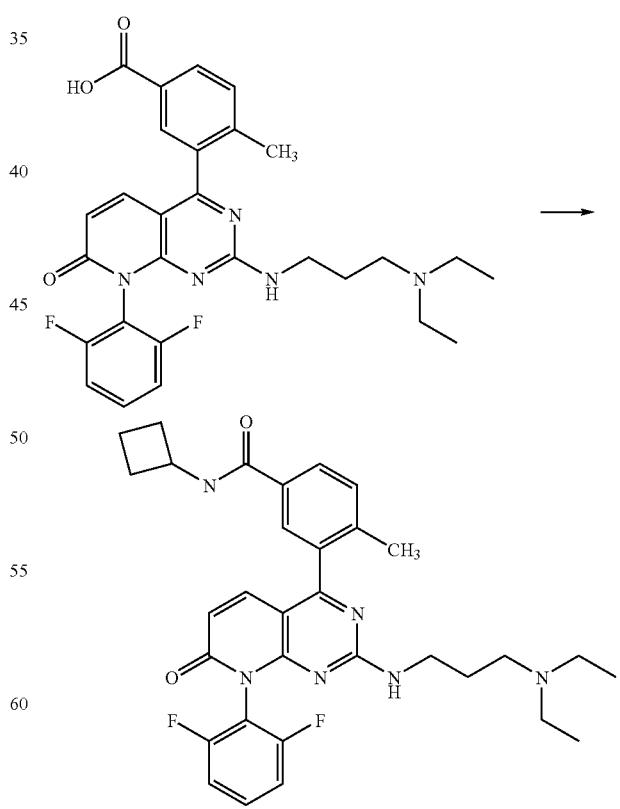

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and cyclobutylamine (8.5 uL, 0.1 mmol). The mixture was stirred at rt overnight. Separation by HPLC with TFA, afforded the title compound (10 mg, 35%). LC-MS m/z 575 (M+H)⁺.

Example 138

N-(cyclopropylmethyl)-3-[2-{[3-(diethylamino)propyl]amino}-8-(2,6-difluorophenyl)-7-oxo-7,8-dihydropyrido[2,3-d]pyridin-4-yl]-4-methylbenzamide trifluoroacetate

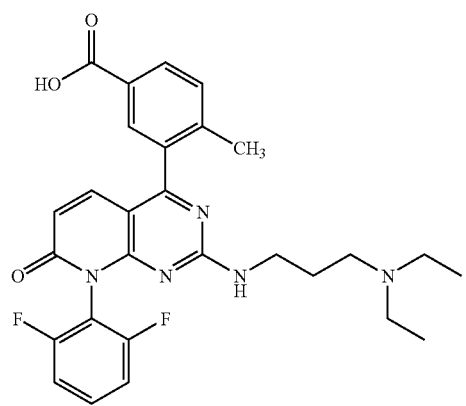

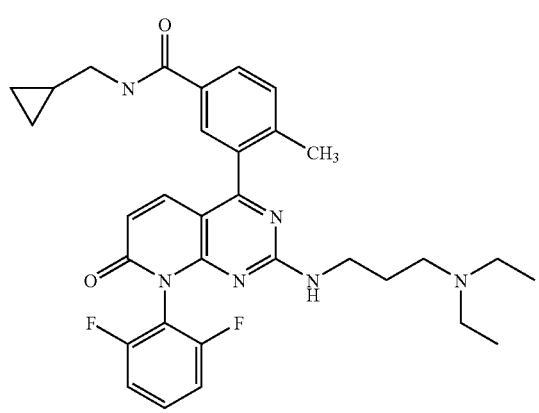

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and (cyclopropylmethyl)amine (10.3 uL, 0.1 mmol). The mixture was stirred at rt overnight. Separation by HPLC with TFA, afforded the title compound (9 mg, 31%). LC-MS m/z 575 (M+H)⁺.

Example 139

3-[2-{[3-(diethylamino)propyl]amino}-8-(2,6-difluorophenyl)-7-oxo-7,8-dihydropyrido[2,3-d]pyrimidin-4-yl]-4-methyl-N-(2-thienylmethyl)benzamide trifluoroacetate

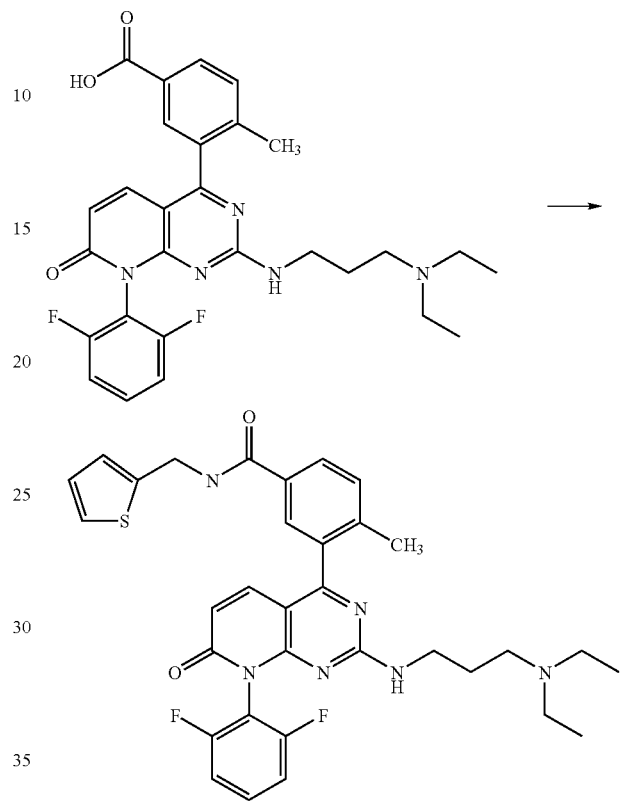

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and (2-thienylmethyl)amine (15.1 uL, 0.1 mmol). The mixture was stirred at rt overnight. Separation by HPLC with TFA, afforded the title compound (11 mg, 36%). LC-MS m/z 617 (M+H)⁺.

Example 140

3-[2-{[3-(diethylamino)propyl]amino}-8-(2,6-difluorophenyl)-7-oxo-7,8-dihydropyrido[2,3-d]pyrimidin-4-yl]-N,N-diethyl-4-methylbenzamide trifluoroacetate

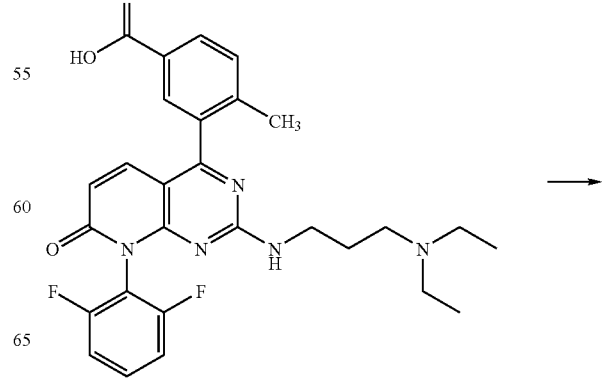

223

-continued

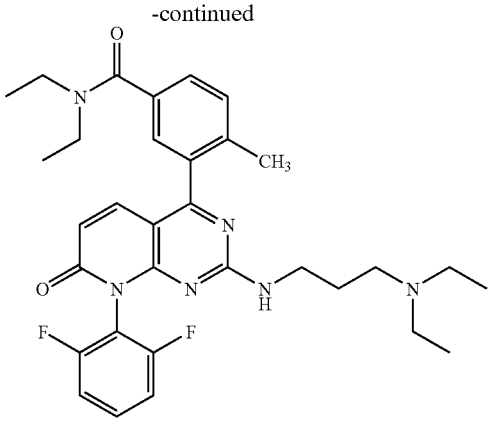

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and diethyl amine (7.4 uL, 0.1 mmol). The mixture was stirred at rt overnight. Separation by HPLC with TFA, afforded the title compound (7 mg, 24%). LC-MS m/z 577 (M+H)$^+$.

Example 141

3-[2-{[3-(diethylamino)propyl]amino}-8-(2,6-difluorophenyl)-7-oxo-7,8-dihydropyrido[2,3-d]pyrimidin-4-yl]-4-methyl-N-(tetrahydro-2H-pyran-4-ylmethyl)benzamide trifluoroacetate

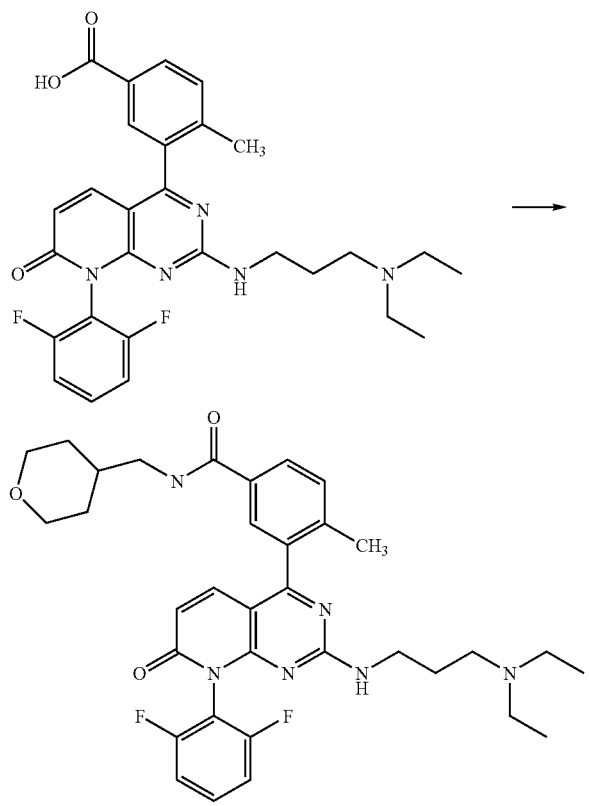

224

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and (tetrahydro-2H-pyran-4-ylmethyl)amine (15.4 uL, 0.1 mmol). The mixture was stirred at rt overnight. Separation by HPLC with TFA, afforded the title compound (8 mg, 26%). LC-MS m/z 617 (M+H)$^+$.

Example 142

3-[2-{[3-(diethylamino)propyl]amino}-8-(2,6-difluorophenyl-7-oxo-7,8-dihydropyrido[2,3-d]pyrimidin-4-yl]-4-methyl-N-(tetrahydro-2-furanylmethyl)benzamide trifluoroacetate

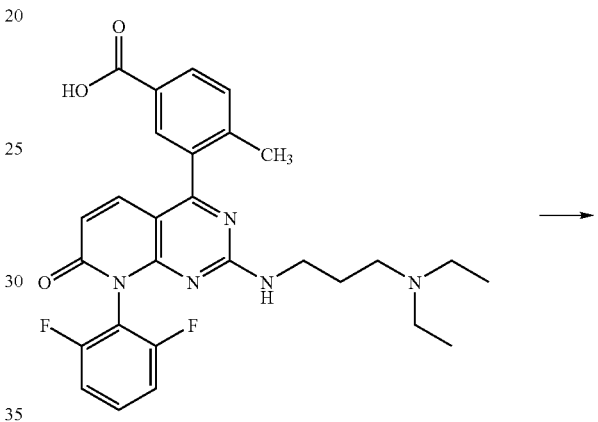

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and (tetrahydro-2-furanylmethyl)amine (10.3 uL, 0.1 mmol). The mixture was stirred at rt overnight. Separation by HPLC with TFA afforded the title compound (9 mg, 30%). LC-MS m/z 605 (M+H)$^+$.

Example 143

N-cyclohexyl-3-[2-{[3-(diethylamino)propyl]amino}-8-(2,6-difluorophenyl)-7-oxo-7,8-dihydropyrido[2,3-d]pyrimidin-4-yl]-4-methylbenzamide

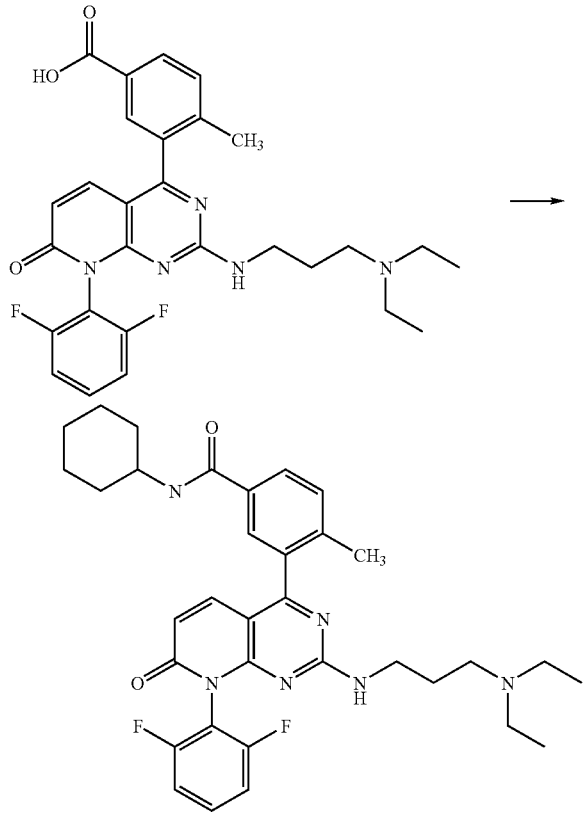

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and cyclohexanamine (11.5 uL, 0.1 mmol). The mixture was stirred at rt overnight. Separation by HPLC with TFA, followed by neutralization with SPE amine cartridge afforded the title compound (9 mg, 30%). LC-MS m/z 603 (M+H)+.

Example 144

3-[2-{[3-(diethylamino)propyl]amino}-8-(2,6-difluorophenyl)-7-oxo-7,8-dihydropyrido[2,3-d]pyrimidin-4-yl]-N-[2-(ethylthio)ethyl]-4-methylbenzamide

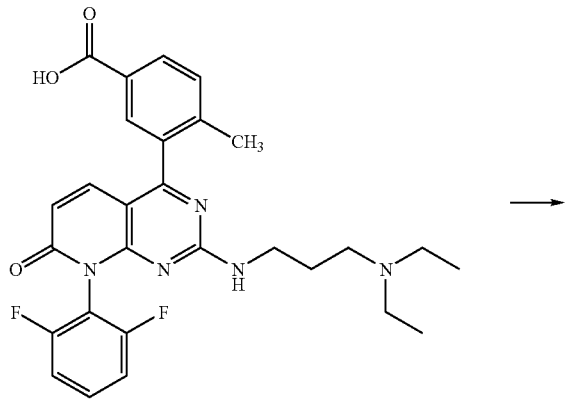

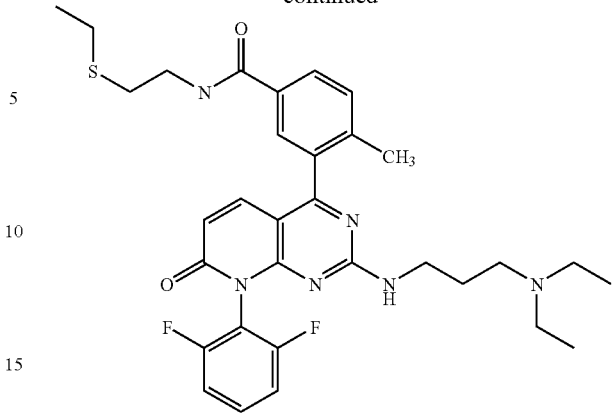

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and [2-(ethylthio)ethyl]amine hydrochloride (14.2 mg, 0.1 mmol). The mixture was stirred at rt overnight. Separation by HPLC with TFA, followed by neutralization with SPE amine cartridge afforded the title compound (7 mg, 23%). LC-MS m/z 607 (M+H)+.

Example 145

N-(2-cyanoethyl)-3-[2-{[3-(diethylamino)propyl]amino}-8-(2,6-difluorophenyl)-7-oxo-7,8-dihydropyrido[2,3-d]pyrimidin-4-yl]-4-methylbenzamide

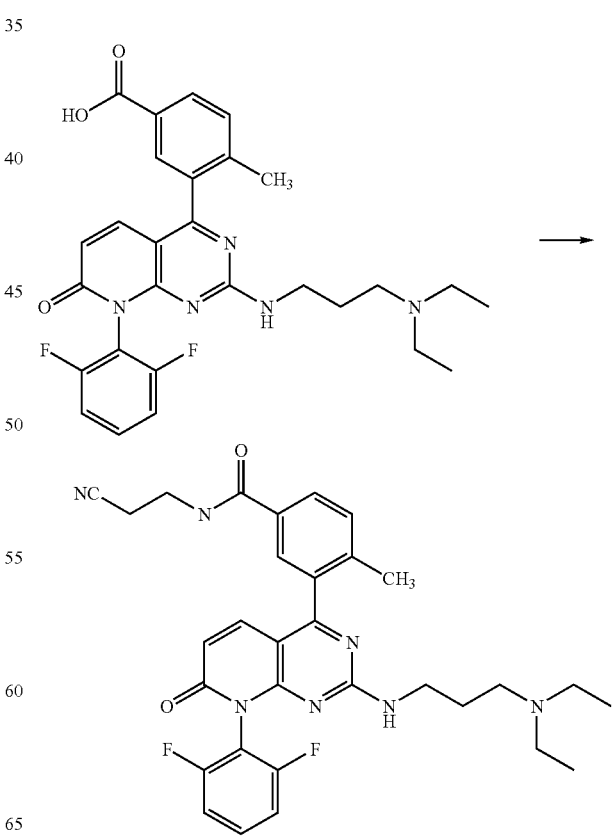

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and 3-aminopropanenitrile hydrochloride (9.3 mg, 0.1 mmol). The mixture was stirred at rt overnight. Separation by HPLC with TFA, followed by neutralization with SPE amine cartridge afforded the title compound (6 mg, 21%). LC-MS m/z 560 (M+H)$^+$.

Example 146

3-[2-{[3-(diethylamino)propyl]amino}-8-(2,6-difluorophenyl)-7-oxo-7,8-dihydropyrido[2,3-d]pyrimidin-4-yl]-N-[2-(1H-imidazol-4-yl)ethyl]-4-methylbenzamide

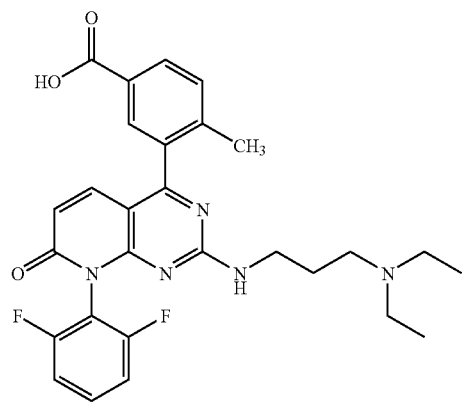

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and [2-(1H-imidazol-4-yl)ethyl]amine (22.2 mg, 0.2 mmol). The mixture was stirred at rt overnight. Separation by HPLC with TFA, followed by neutralization with SPE amine cartridge afforded the title compound (26 mg, 85%). LC-MS m/z 615 (M+H)$^+$.

Example 147

3-[2-{[3-(diethylamino)propyl]amino}-8-(2,6-difluorophenyl)-7-oxo-7,8-dihydropyrido[2,3-d]pyrimidin-4-yl]-4-methyl-N-phenylbenzamide

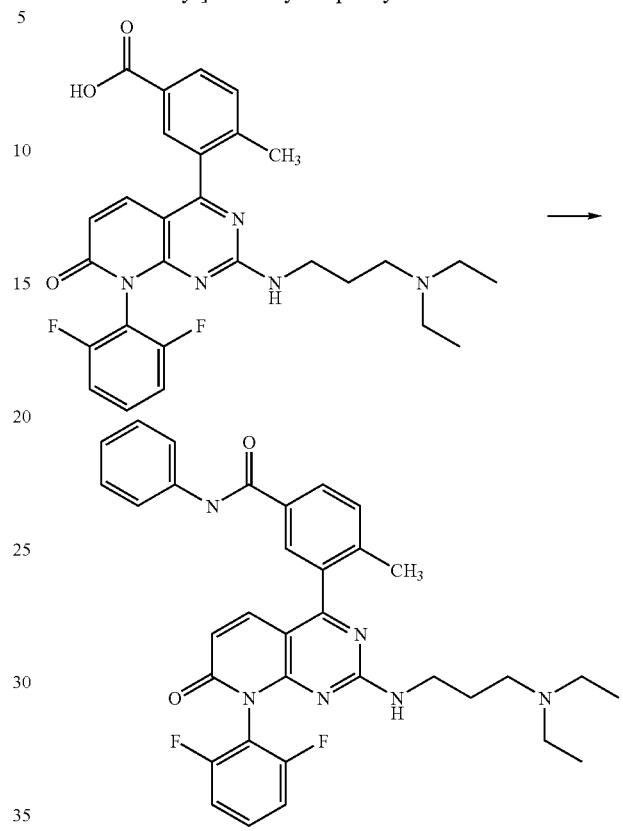

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and aniline (9.1 uL, 0.1 mmol). The mixture was stirred at rt overnight. To the mixture was added 5 mL dichloromethane and 2 mL water, stirred for 3 min. The organic layer was loaded onto the silica gel column. Chromatography (90% methylene chloride/7% MeOH/3% ammonia) afforded the title compound (9 mg, 30%). LC-MS m/z 597 (M+H)$^+$.

Example 148

3-[2-{[3-(diethylamino)propyl]amino}-8-(2,6-difluorophenyl)-7-oxo-7,8-dihydropyrido[2,3-d]pyrimidin-4-yl]-4-methyl-N-[(1R)-1-phenylethyl]benzamide

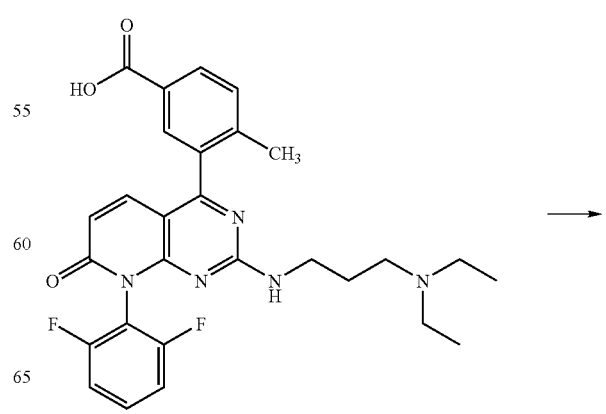

-continued

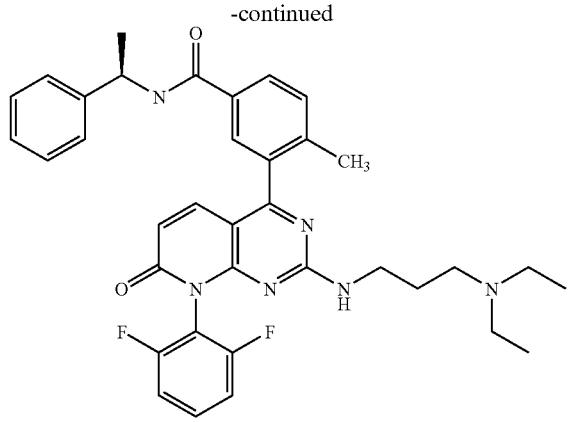

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and [(1R)-1-phenylethyl]amine (12.9 uL, 0.1 mmol). The mixture was stirred at rt overnight. Separation by HPLC with TFA, followed by neutralization with SPE amine cartridge afforded the title compound (14 mg, 45%). LC-MS m/z 625 (M+H)$^+$.

Example 149

3-[2-{[3-(diethylamino)propyl]amino}-8-(2,6-difluorophenyl)-7-oxo-7,8-dihydropyrido[2,3-d]pyrimidin-4-yl]-4-methyl-N-[(1S)-1-phenylethyl]benzamide

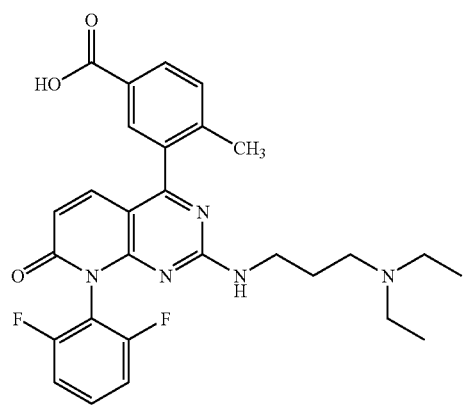

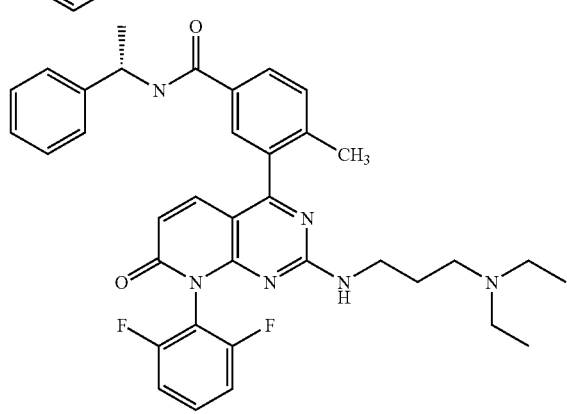

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and [(1S)-1-phenylethyl]amine (12.9 uL, 0.1 mmol). The mixture was stirred at rt overnight. Separation by HPLC with TFA, followed by neutralization with SPE amine cartridge afforded the title compound (14 mg, 45%). LC-MS m/z 625 (M+H)$^+$.

Example 150

3-[2-{[3-(diethylamino)propyl]amino}-8-(2,6-difluorophenyl)-7-oxo-7,8-dihydropyrido[2,3-d]pyrimidin-4-yl]-2-methyl-N-1,3-thiazol-2-ylbenzamide 150a) 4-chloro-8-(2,6-difluorophenyl)-2-(methylsulfinyl)pyrido[2,3-d]pyrimidin-7(8H)-one

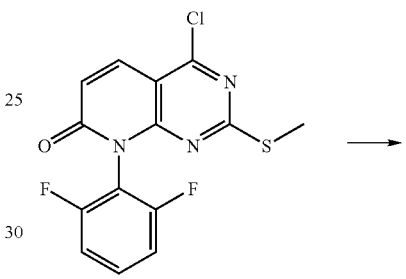

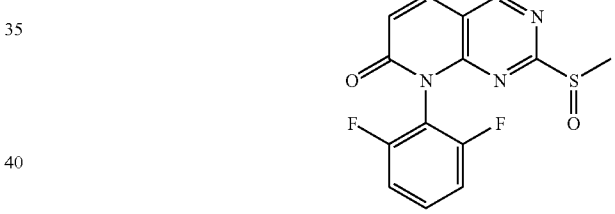

To the compound 4-chloro-8-(2,6-difluorophenyl)-2-(methylthio)pyrido[2,3-d]pyrimidin-7(8H)-one (1.70 g, 5.0 mmol) in dichloromethane (100 mL) was added mCPBA (1.16 g, 7.5 mmol). The mixture was stirred at rt for 10 min. Chromatography with hexane/ethyl acetate afforded the title compound (1.59 g, 89%). LC-MS m/z 356 (M+H)$^+$.

150b) 4-chloro-2-{[3-(diethylamino)propyl]amino}-8-(2,6-difluorophenyl)pyrido[2,3-d]pyrimidin-7(8H)-one

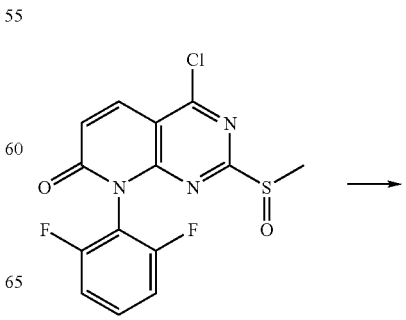

-continued

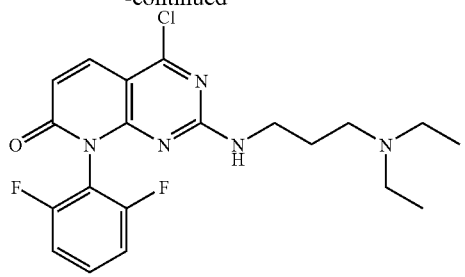

To the compound 4-chloro-8-(2,6-difluorophenyl)-2-(methylsulfinyl)-pyrido[2,3-d]pyrimidin-7(8H)-one (1.59 g, 4.47 mmol) in dichloromethane (89.4 mL) were added N,N-diethyl-1,3-propanediamine (0.845 mL, 5.36 mol) and triethylamine (1.26 uL, 8.94 mmol). The mixture was stirred at rt overnight. Some white precipitate was formed during the reaction. Filtration followed by wash with ethyl acetate/dichloromethane/methanol afforded the title compound (1.028 g, 60%). LC-MS m/z 383 (M+H)⁺.

150c) 3-[2-{[3-(diethylamino)propyl]amino}-8-(2,6-difluorophenyl)-7-oxo-7,8-dihydropyrido[2,3-d]pyrimidin-4-yl]-2-methylbenzoic acid

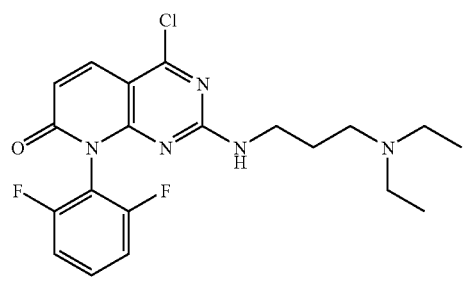

To the compound 4-chloro-2-{[3-(diethylamino)propyl]amino}-8-(2,6-difluorophenyl)pyrido[2,3-d]pyrimidin-7(8H)-one (176 mg, 0.418 mmol) in dioxane (4.5 mL) and water (1.5 mL) was added 2-methyl-3-(4,4,5,5-tetramethyl-1,3,2-dioxaborolan-2-yl)benzoic acid (173 mg, 0.626 mol), potassium carbonate (289 mg, 2.09 mmol) and tetrakis(triphenylphosphine)palladium(0) (24.2 mg, 0.0259 mmol). The mixture was heated with microwave at 150° C. for 15 min. The mixture was filtered. Separation by HPLC with TFA afforded the title compound (238 mg, 99%). LC-MS m/z 522 (M+H)⁺.

150d) 3-[2-{[3-(diethylamino)propyl]amino}-8-(2,6-difluorophenyl)-7-oxo-7,8-dihydropyrido[2,3-d]pyrimidin-4-yl]-2-methyl-N-1,3-thiazol-2-ylbenzamide

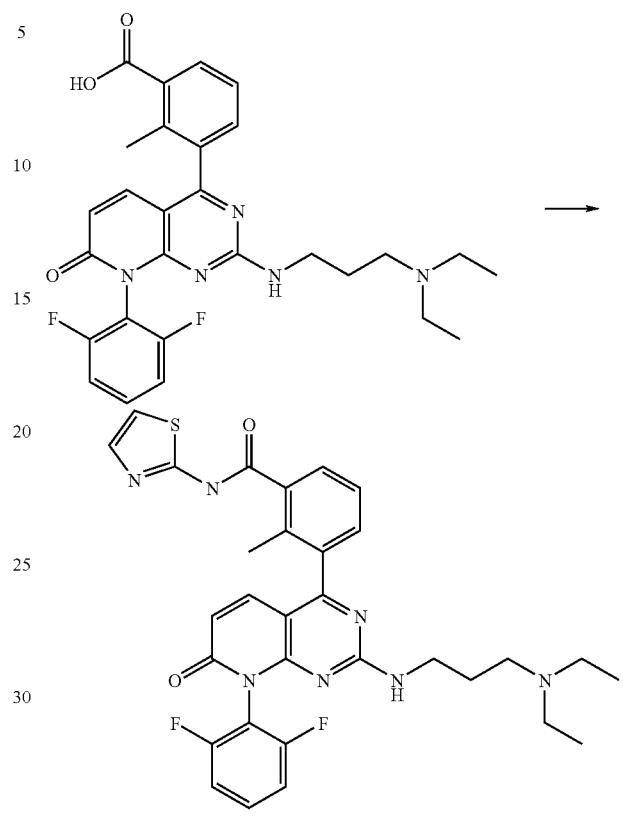

To the compound 3-[2-{[3-(diethylamino)propyl]amino}-8-(2,6-difluorophenyl)-7-oxo-7,8-dihydropyrido[2,3-d]pyrimidin-4-yl]-2-methylbenzoic acid (26 mg, 0.05 mmol) in DMF (0.5 mL) were added HBTU (28 mg, 0.075 mmol), triethylamine (21.1 uL, 0.15 mmol) and 1,3-thiazol-2-amine (10.0 mg, 0.1 mmol). The mixture was stirred at rt overnight. Separation by HPLC with TFA, followed by neutralization with SPE amine cartridge afforded the title compound (9 mg, 30%). LC-MS m/z 604 (M+H)⁺.

Example 151

3-[2-{[3-(diethylamino)propyl]amino}-8-(2,6-difluorophenyl)-7-oxo-7,8-dihydropyrido[2,3-d]pyrimidin-4-yl]-2-methyl-N-phenylbenzamide

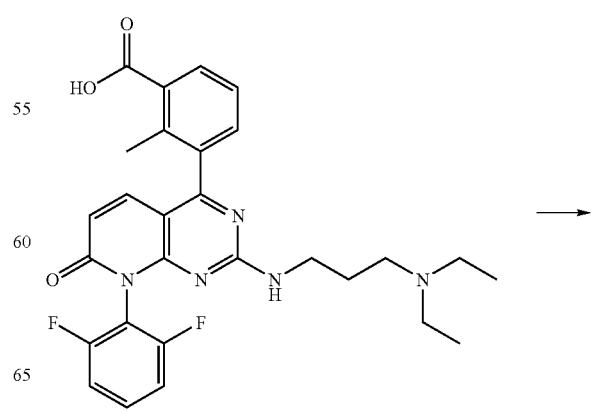

-continued

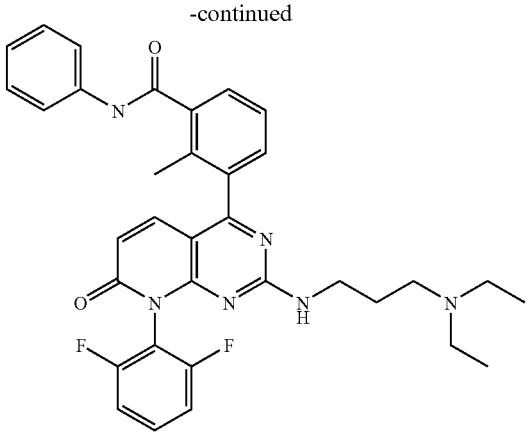

To the compound 3-[2-{[3-(diethylamino)propyl]amino}-8-(2,6-difluorophenyl)-7-oxo-7,8-dihydropyrido[2,3-d]pyrimidin-4-yl]-2-methylbenzoic acid (26 mg, 0.05 mmol) in DMF (0.5 mL) were added HBTU (28 mg, 0.075 mmol), triethylamine (21.1 uL, 0.15 mmol) and aniline (9.1 uL, 0.1 mmol). The mixture was stirred at rt overnight. Separation by HPLC with TFA, followed by neutralization with SPE amine cartridge afforded the title compound (18 mg, 60%). LC-MS m/z 597 (M+H)$^+$.

Example 152

3-[2-{[3-(diethylamino)propyl]amino}-8-(2,6-difluorophenyl)-7-oxo-7,8-dihydropyrido[2,3-d]-pyrimidin-4-yl]-N-(4-fluorophenyl)-2-methylbenzamide

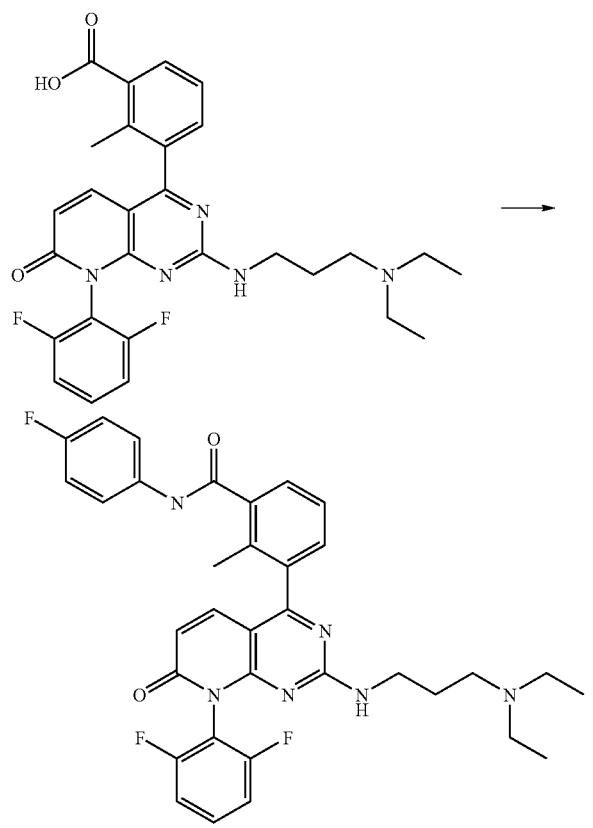

To the compound 3-[2-{[3-(diethylamino)propyl]amino}-8-(2,6-difluorophenyl)-7-oxo-7,8-dihydropyrido[2,3-d]pyrimidin-4-yl]-2-methylbenzoic acid (26 mg, 0.05 mmol) in DMF (0.5 mL) were added HBTU (28 mg, 0.075 mmol), triethylamine (21.1 uL, 0.15 mmol) and 4-fluoroaniline (9.6 uL, 0.1 mmol). The mixture was stirred at rt overnight. Separation by HPLC with TFA, followed by neutralization with SPE amine cartridge afforded the title compound (14 mg, 46%). LC-MS m/z 615 (M+H)$^+$.

Example 153

3-[2-{[3-(diethylamino)propyl]amino}-8-(2,6-difluorophenyl)-7-oxo-7,8-dihydropyrido[2,3-d]pyrimidin-4-yl]-2-methyl-N-propylbenzamide

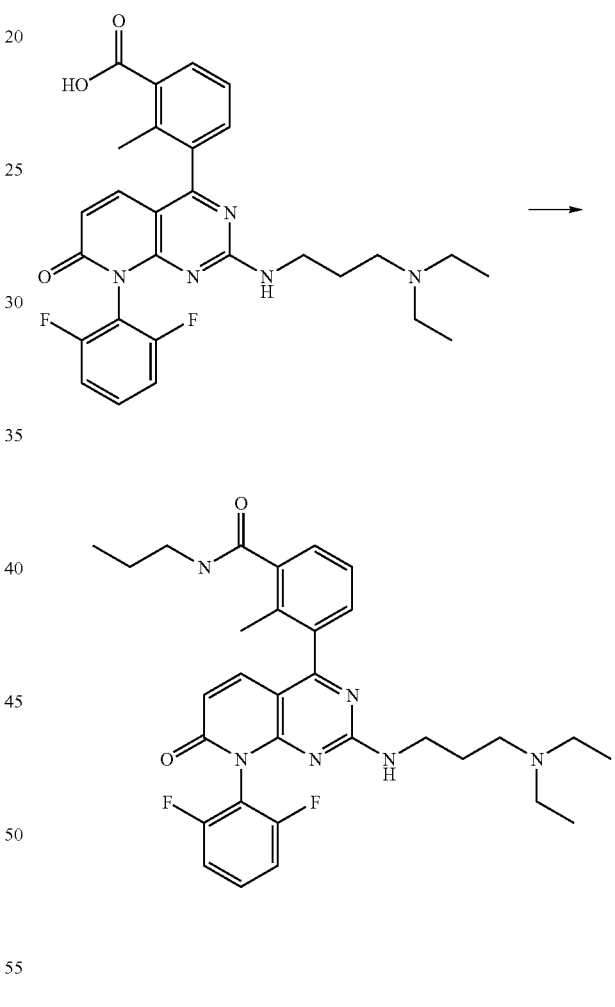

To the compound 3-[2-{[3-(diethylamino)propyl]amino}-8-(2,6-difluorophenyl)-7-oxo-7,8-dihydropyrido[2,3-d]pyrimidin-4-yl]-2-methylbenzoic acid (26 mg, 0.05 mmol) in DMF (0.5 mL) were added HBTU (28 mg, 0.075 mmol), triethylamine (21.1 uL, 0.15 mmol) and propylamine (8.2 uL, 0.1 mmol). The mixture was stirred at rt overnight. Separation by HPLC with TFA, followed by neutralization with SPE amine cartridge afforded the title compound (15 mg, 53%). LC-MS m/z 563 (M+H)$^+$.

Example 154

3-[2-{[3-(diethylamino)propyl]amino}-8-(2,6-difluorophenyl)-7-oxo-7,8-dihydropyrido[2,3-d]pyrimidin-4-yl]-2-methyl-N-(2-methylpropyl)benzamide

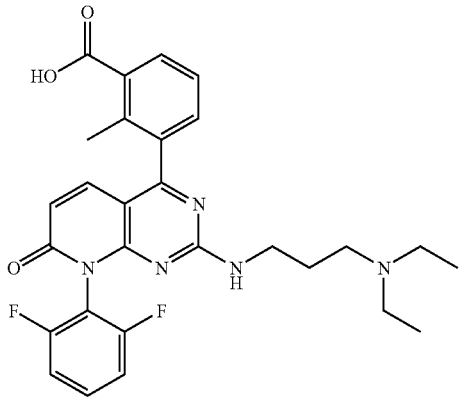

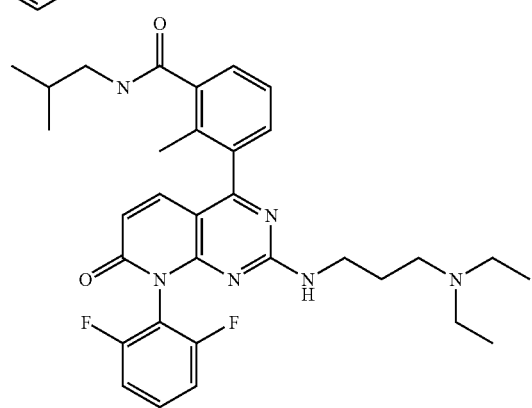

To the compound 3-[2-{[3-(diethylamino)propyl]amino}-8-(2,6-difluorophenyl)-7-oxo-7,8-dihydropyrido[2,3-d]pyrimidin-4-yl]-2-methylbenzoic acid (26 mg, 0.05 mmol) in DMF (0.5 mL) were added HBTU (28 mg, 0.075 mmol), triethylamine (21.1 uL, 0.15 mmol) and isobutylamine (10.0 uL, 0.1 mmol). The mixture was stirred at rt overnight. Separation by HPLC with TFA, followed by neutralization with SPE amine cartridge afforded the title compound (12.6 mg, 44%). LC-MS m/z 577 (M+H)+.

Example 155

N-cyclopropyl-3-[2-{[3-(diethylamino)propyl]amino}-8-(2,6-difluorophenyl)-7-oxo-7,8-dihydropyrido[2,3-d]-pyrimidin-4-yl]-2-methylbenzamide

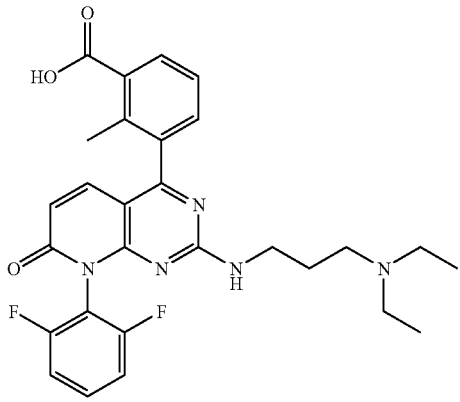

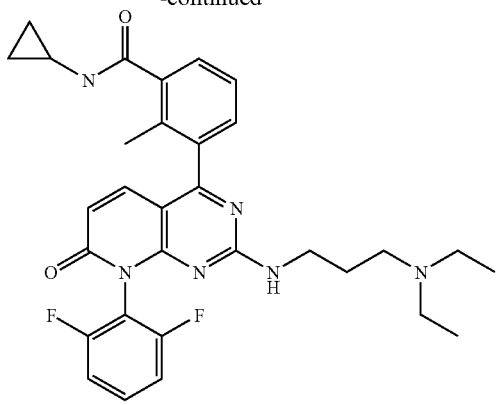

To the compound 3-[2-{[3-(diethylamino)propyl]amino}-8-(2,6-difluorophenyl)-7-oxo-7,8-dihydropyrido[2,3-d]pyrimidin-4-yl]-2-methylbenzoic acid (26 mg, 0.05 mmol) in DMF (0.5 mL) were added HBTU (28 mg, 0.075 mmol), triethylamine (21.1 uL, 0.15 mmol) and cyclopropylamine (6.9 uL, 0.1 mmol). The mixture was stirred at rt overnight. Separation by HPLC with TFA, followed by neutralization with SPE amine cartridge afforded the title compound (13.5 mg, 48%). LC-MS m/z 561 (M+H)+.

Example 156

N-(cyanomethyl)-3-[2-{[3-(diethylamino)propyl]amino}-8-(2,6-difluorophenyl)-7-oxo-7,8-dihydropyrido[2,3-d]pyrimidin-4-yl]-2-methylbenzamide

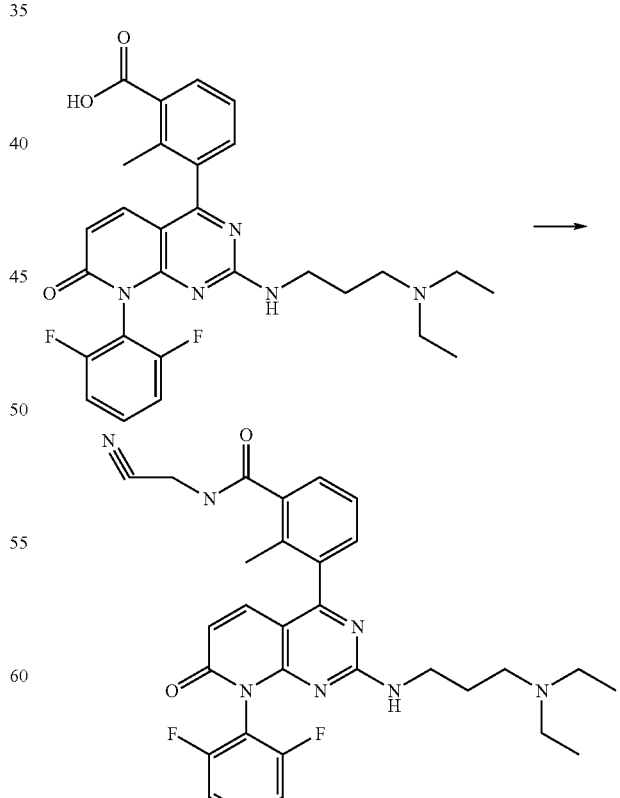

To the compound 3-[2-{[3-(diethylamino)propyl]amino}-8-(2,6-difluorophenyl)-7-oxo-7,8-dihydropyrido[2,3-d]pyrimidin-4-yl]-2-methylbenzoic acid (26 mg, 0.05 mmol) in DMF (0.5 mL) were added HBTU (28 mg, 0.075 mmol), triethylamine (21.1 uL, 0.15 mmol) and aminoacetonitrile (9.3 mg, 0.1 mmol). The mixture was stirred at rt overnight. Separation by HPLC with TFA, followed by neutralization with SPE amine cartridge afforded the title compound (9.1 mg, 33%). LC-MS m/z 560 (M+H)$^+$.

Example 157

N-(2-amino-2-oxoethyl)-3-[2-{[3-(diethylamino)propyl]amino}-8-(2,6-difluorophenyl)-7-oxo-7,8-dihydropyrido[2,3-d]pyrimidin-4-yl]-4-methylbenzamide

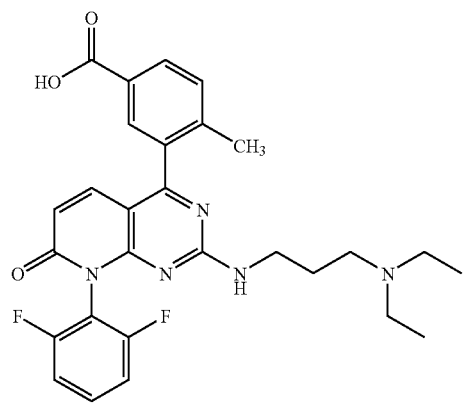

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and glycinamide (11.1 mg, 0.1 mmol). The mixture was stirred at rt overnight. Separation by HPLC with TFA, followed by neutralization with SPE amine cartridge afforded the title compound (9 mg, 31%). LC-MS m/z 578 (M+H)$^+$.

Example 158

3-[2-{[3-(diethylamino)propyl]amino}-8-(2,6-difluorophenyl)-7-oxo-7,8-dihydropyrido[2,3-d]pyrimidin-4-yl]-4-methyl-N-[2-(methylamino)-2-oxoethyl]benzamide

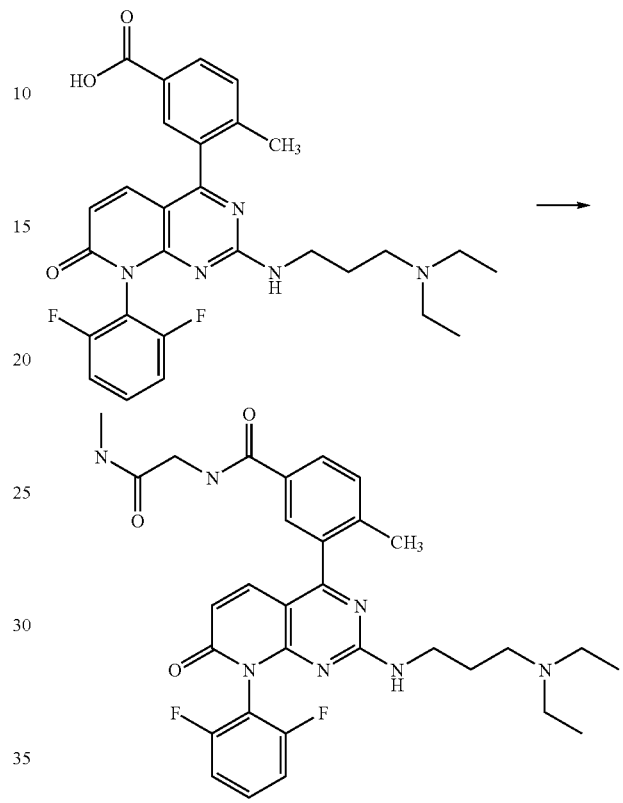

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (26 mg, 0.05 mmol) in DMF (0.5 mL) were added HBTU (28 mg, 0.075 mmol), triethylamine (21.1 uL, 0.15 mmol) and N$^1$-methylglycinamide (12.5 mg, 0.1 mmol). The mixture was stirred at rt overnight. Separation by HPLC with TFA, followed by neutralization with SPE amine cartridge afforded the title compound (9 mg, 30%). LC-MS m/z 592 (M+H)$^+$.

Example 159

3-[2-{[3-(diethylamino)propyl]amino}-8-(2,6-difluorophenyl)-7-oxo-7,8-dihydropyrido[2,3-d]pyrimidin-4-yl]-4-methyl-N-3-pyridinylbenzamide

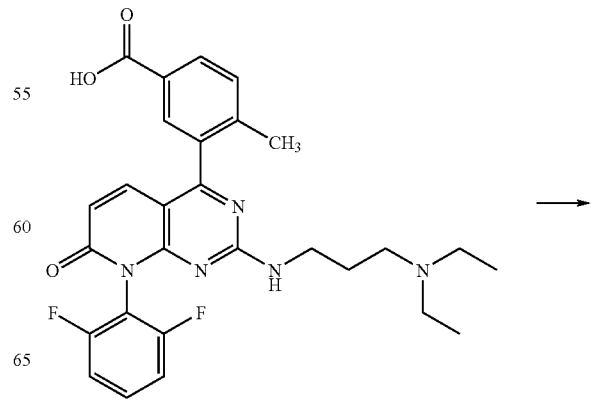

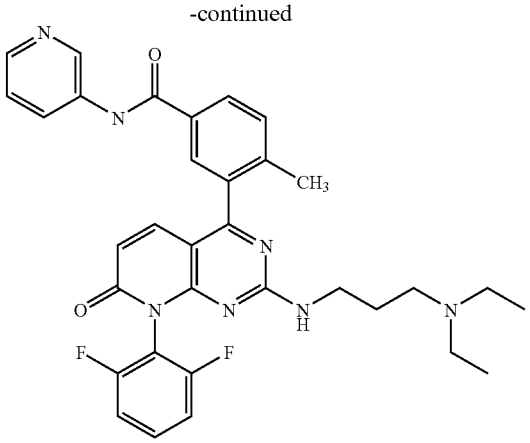

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (31.3 mg, 0.06 mmol) in DMF (0.5 mL) were added HBTU (27.3 mg, 0.072 mmol), triethylamine (16.9 uL, 0.12 mmol) and 3-aminopyridine (11.3 mg, 0.08 mmol). The mixture was stirred at rt overnight. Separation by HPLC with TFA, followed by neutralization with SPE amine cartridge afforded the title compound (3.3 mg, 9%). LC-MS m/z 598 (M+H)$^+$.

Example 160

3-[2-{[3-(diethylamino)propyl]amino}-8-(2,6-difluorophenyl)-7-oxo-7,8-dihydropyrido[2,3-d]pyrimidin-4-yl]-N-(4-fluorophenyl)-4-methylbenzamide

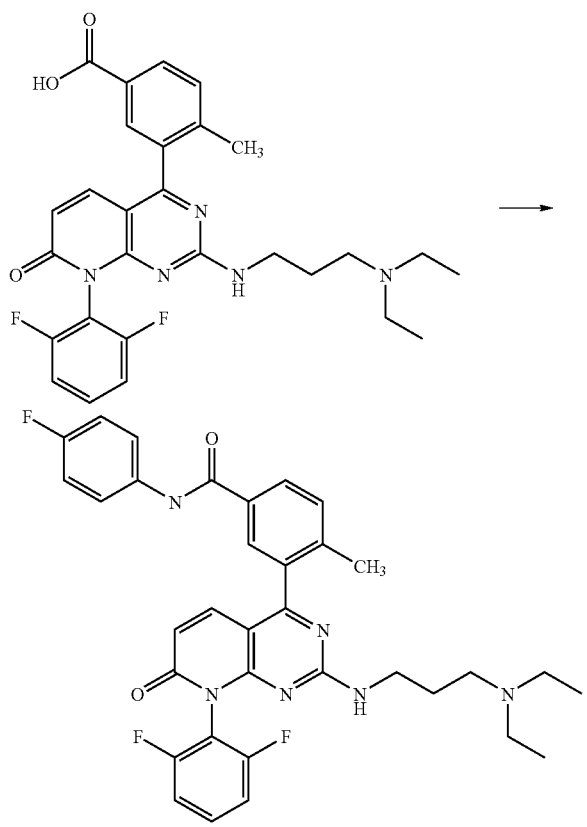

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (31.3 mg, 0.06 mmol) in DMF (0.5 mL) were added HBTU (27.3 mg, 0.072 mmol), triethylamine (16.9 uL, 0.12 mmol) and 4-fluoroaniline (8.64 uL, 0.08 mmol). The mixture was stirred at rt overnight. Separation by HPLC with TFA, followed by neutralization with SPE amine cartridge afforded the title compound (10 mg, 27%). LC-MS m/z 615 (M+H)$^+$.

Example 161

N-cyclopropyl-3-[2-{[3-(diethylamino)propyl]amino}-8-(2,6-difluorophenyl)-7-oxo-7,8-dihydropyrido[2,3-d]pyrimidin-4-yl]-4-methylbenzamide

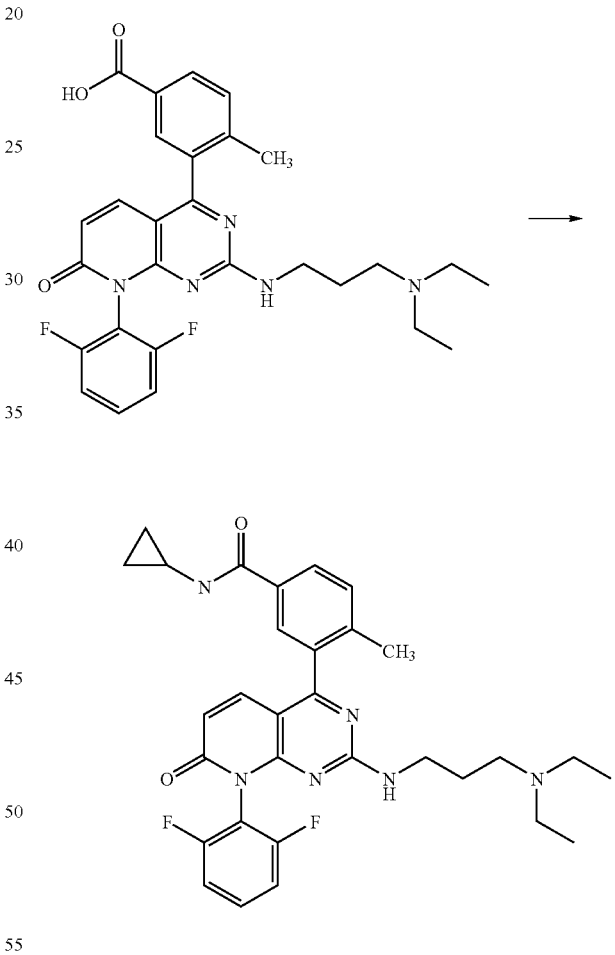

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (31.3 mg, 0.06 mmol) in DMF (0.5 mL) were added HBTU (27.3 mg, 0.072 mmol), triethylamine (16.9 uL, 0.12 mmol) and cyclopropylamine (6.24 uL, 0.08 mmol). The mixture was stirred at rt overnight. Separation by HPLC with TFA, followed by neutralization with SPE amine cartridge afforded the title compound (10 mg, 30%). LC-MS m/z 562 (M+H)$^+$.

Example 162

3-[2-{[3-(diethylamino)propyl]amino}-8-(2,6-difluorophenyl)-7-oxo-7,8-dihydropyrido[2,3-d]pyrimidin-4-yl]-4-methyl-N-(1-methylpropyl)benzamide

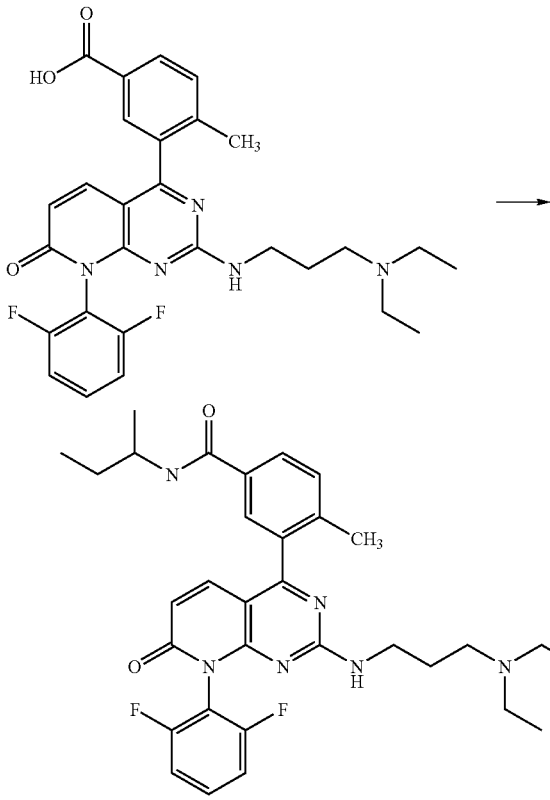

To the compound 3-[2-{[3-(diethylamino)propyl]amino}-8-(2,6-difluorophenyl)-7-oxo-7,8-dihydropyrido[2,3-d]pyrimidin-4-yl]-4-methylbenzoic acid (31.3 mg, 0.06 mmol) in DMF (0.5 mL) were added HBTU (27.3 mg, 0.072 mmol), triethylamine (16.9 uL, 0.12 mmol) and sec-butylamine (12.12 uL, 0.08 mmol). The mixture was stirred at rt overnight. Separation by HPLC with TFA, followed by neutralization with SPE amine cartridge afforded the title compound (3.2 mg, 9%). LC-MS m/z 577 (M+H)+.

Example 163

3-[8-(2,6-difluorophenyl)-2-(4-methyl-1,4'-bipiperidin-1'-yl)-7-oxo-7,8-dihydropyrido[2,3-d]pyrimidin-4-yl]-4-methyl-N-(1-methylethyl)benzamide 163a) 4-chloro-8-(2,6-difluorophenyl)-2-(4-methyl-1,4'-bipiperidin-1'-yl)pyrido[2,3-d]pyrimidin-7(8H)-one

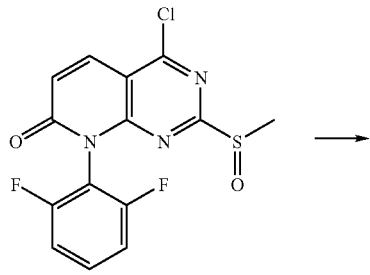

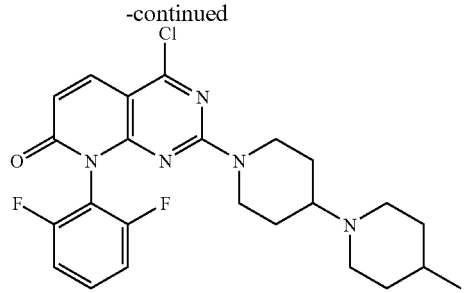

To the compound 4-chloro-8-(2,6-difluorophenyl)-2-(methylsulfinyl)pyrido[2,3-d]pyrimidin-7(8H)-one (1.39 g, 3.9 mmol) in dichloromethane (80 mL) were added 4-methyl-1,4'-bipiperidine (0.75 g, 5.85 mol) and triethylamine (1.03 mL, 11.7 mmol). The mixture was stirred at −20° C. overnight. Filtration followed by concentration, the crude was purified with flash chromatography to afford the title compound (0.904 g, 51%). LC-MS m/z 474 (M+H)+.

163b) 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (GSK1080365A)

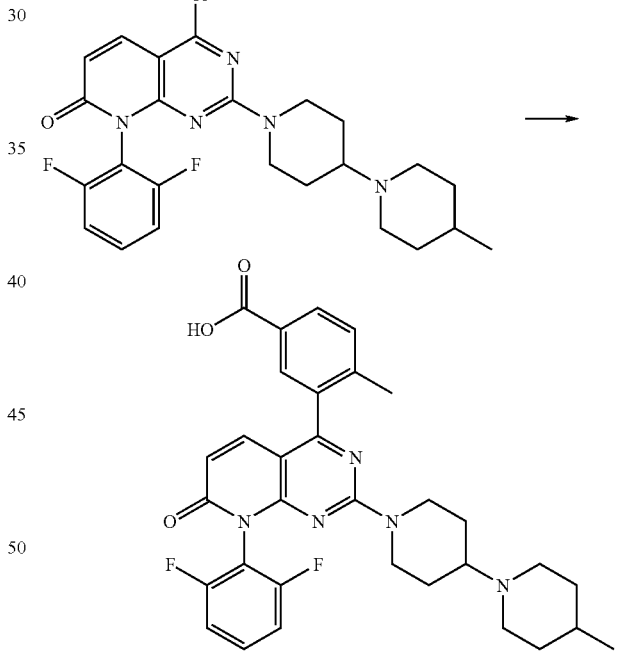

To the compound 4-chloro-8-(2,6-difluorophenyl)-2-(4-methyl-1,4'-bipiperidin-1'-yl)pyrido[2,3-d]pyrimidin-7(8H)-one (47.5 mg, 0.1 mmol) in dioxane (3 mL) and water (1 mL) were added 6-methyl-3-(4,4,5,5-tetramethyl-1,3,2-dioxaborolan-2-yl)benzoic acid (38.4 mg, 0.15 mol), potassium carbonate (83 mg, 0.6 mmol) and tetrakis(triphenylphosphine)palladium(0) (4.6 mL, 0.005 mmol). The mixture was heated with microwave at 150° C. for 15 min. The mixture was concentrated, & then added was DMSO (0.75 mL) and water (0.25 mL). Separation by HPLC afforded the title compound (39 mg, 68%). LC-MS m/z 574 (M+H)+.

163c) 3-[8-(2,6-difluorophenyl)-2-(4-methyl-1,4'-bipiperidin-1'-yl)-7-oxo-7,8-dihydropyrido[2,3-d]pyrimidin-4-yl]-4-methyl-N-(1-methylethyl)benzamide

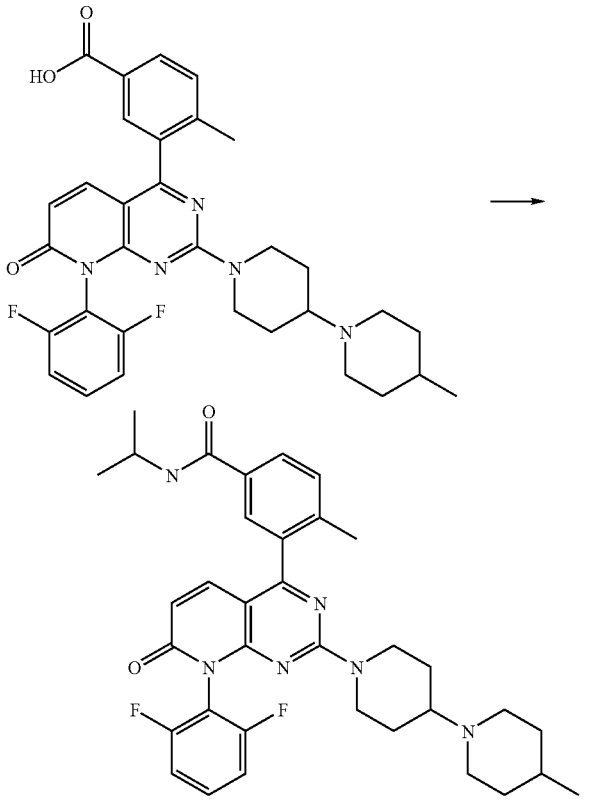

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and isopropylamine (7.03 uL, 0.0825 mmol). The mixture was stirred at rt overnight. Separation by HPLC with TFA, followed by neutralization with SPE amine cartridge afforded the title compound (16.4 mg, 48.5%). LC-MS m/z 615 (M+H)⁺.

Example 164

3-[8-(2,6-difluorophenyl)-2-(4-methyl-1,4'-bipiperidin-1'-yl)-7-oxo-7,8-dihydropyrido[2,3-d]pyrimidin-4-yl]-N,4-dimethylbenzamide

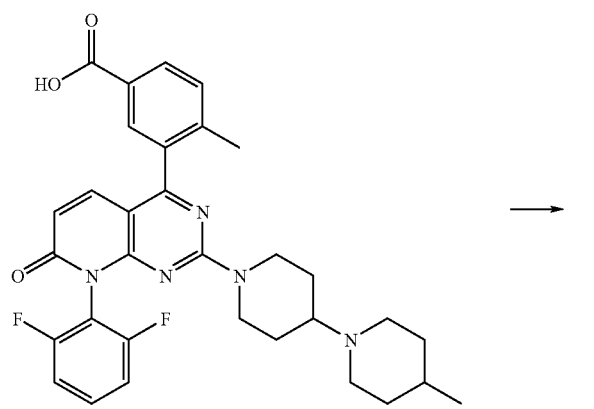

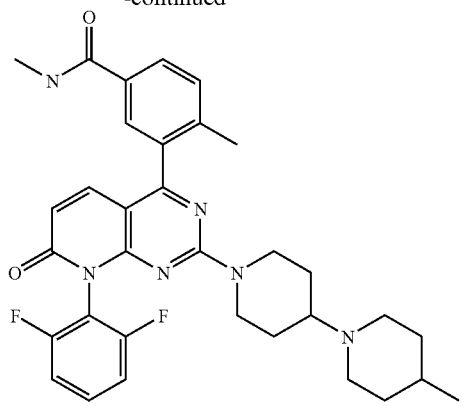

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and methylamine (41.3 uL, 0.0825 mmol, 2M soln in THF). The mixture was stirred at rt overnight. Separation by HPLC with TFA, followed by neutralization with SPE amine cartridge afforded the title compound (7.2 mg, 22%). LC-MS m/z 587 (M+H)⁺.

Example 165

3-[8-(2,6-difluorophenyl-2-(4-methyl-1,4'-bipiperidin-1'-yl)-7-oxo-7,8-dihydropyrido[2,3-d]pyrimidin-4-yl]-N,N,4-trimethylbenzamide

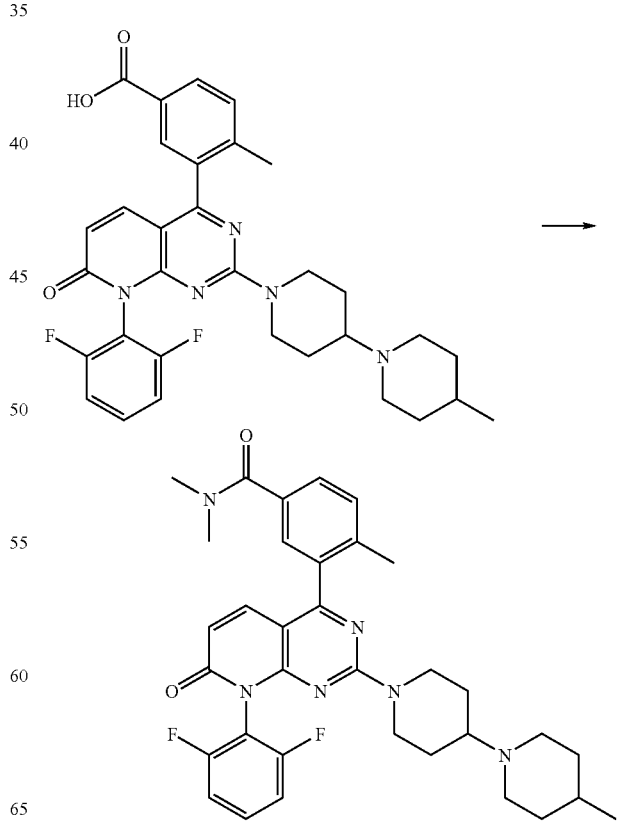

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and dimethylamine (41.3 uL, 0.0825 mmol, 2M soln in THF). The mixture was stirred at rt overnight. Separation by HPLC with TFA, followed by neutralization with SPE amine cartridge afforded the title compound (11.5 mg, 35%). LC-MS m/z 601 (M+H)+.

Example 166

3-[8-(2,6-difluorophenyl)-2-(4-methyl-1,4'-bipiperidin-1'-yl)-7-oxo-7,8-dihydropyrido[2,3-d]pyrimidin-4-yl]-4-methyl-N-propylbenzamide

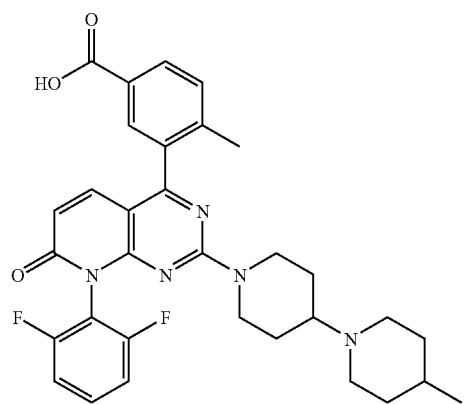

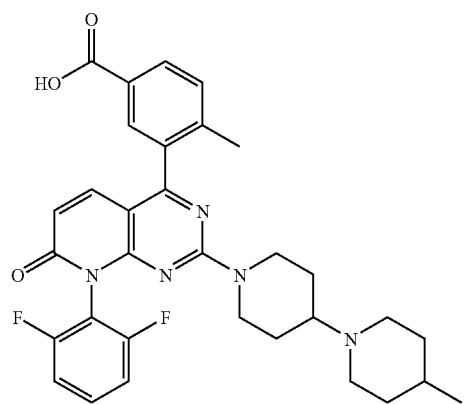

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and propylamine (6.78 uL, 0.0825 mmol). The mixture was stirred at rt overnight. Separation by HPLC with TFA, followed by neutralization with SPE amine cartridge afforded the title compound (18.6 mg, 55%). LC-MS m/z 615 (M+H)+.

Example 167

N-butyl-3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzamide

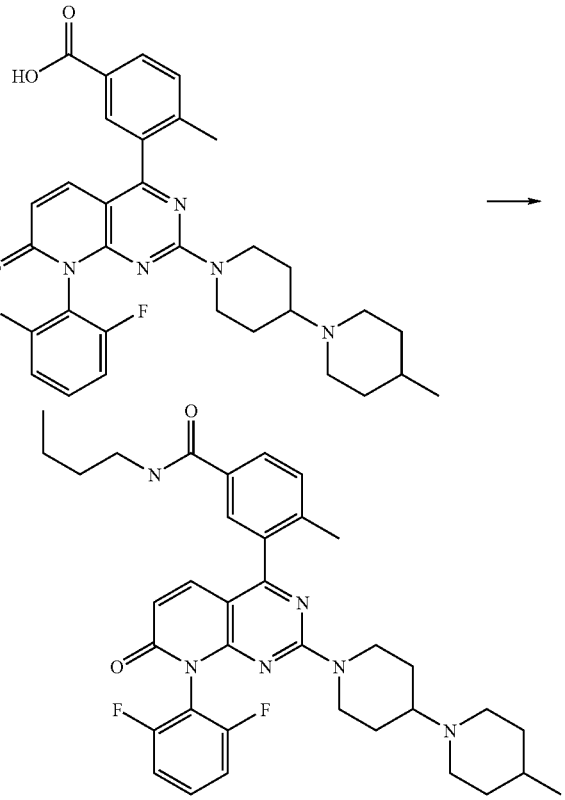

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and butylamine (8.19 uL, 0.0825 mmol). The mixture was stirred at rt overnight. Separation by HPLC with TFA, followed by neutralization with SPE amine cartridge afforded the title compound (18.7 mg, 55%). LC-MS m/z 629 (M+H)+.

Example 168

3-[8-(2,6-difluorophenyl)-2-(4-methyl-1,4'-bipiperidin-1'-yl)-7-oxo-7,8-dihydropyrido[2,3-d]pyrimidin-4-yl]-4-methyl-N-(2-methylpropyl)benzamide

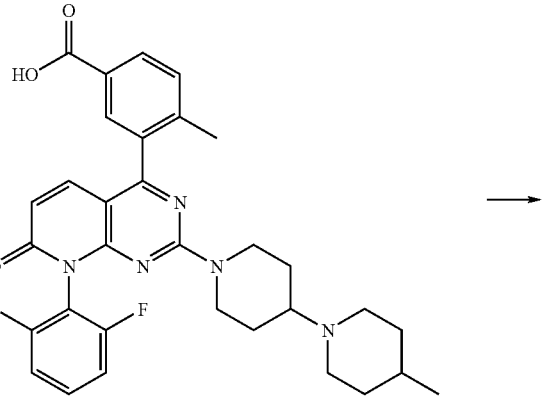

-continued

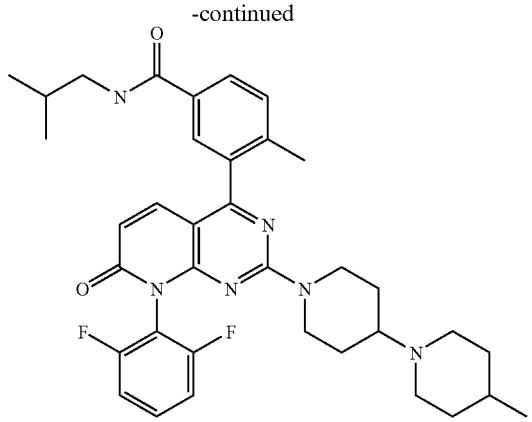

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and isobutylamine (8.28 uL, 0.0825 mmol). The mixture was stirred at rt overnight. Separation by HPLC with TFA, followed by neutralization with SPE amine cartridge afforded the title compound (18.4 mg, 53%). LC-MS m/z 629 (M+H)$^+$.

Example 169

N-cyclopentyl-3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzamide To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and cyclopentanamine (8.15 uL, 0.0825 mmol). The mixture was stirred at rt overnight. Separation by HPLC with TFA, followed by neutralization with SPE amine cartridge afforded the title compound (16.9 mg, 48%). LC-MS m/z 641 (M+H)$^+$.

Example 170

3-[8-(2,6-difluorophenyl)-2-(4-methyl-1,4'-bipiperidin-1'-yl)-7-oxo-7,8-dihydropyrido[2,3-d]pyrimidin-4-yl]-N-(1-dimethylethyl)-4-methylbenzamide

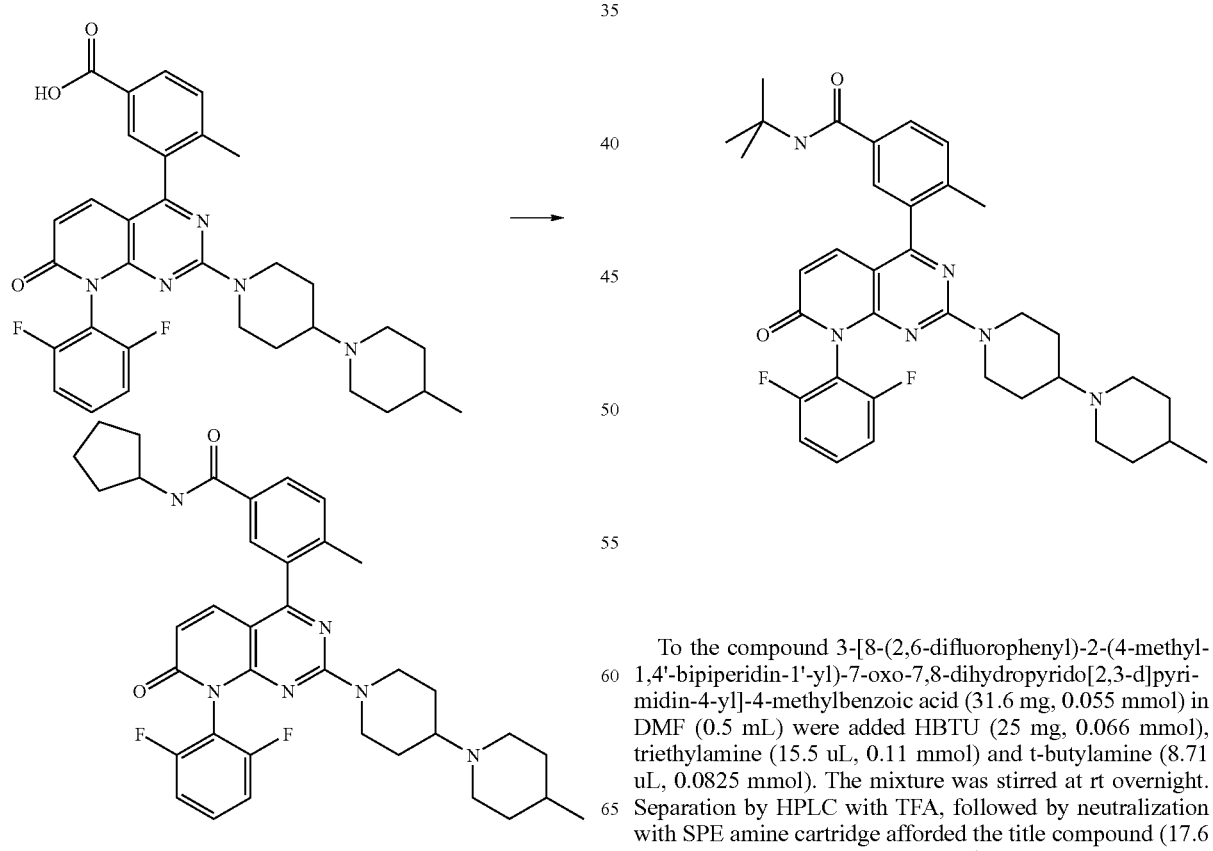

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and t-butylamine (8.71 uL, 0.0825 mmol). The mixture was stirred at rt overnight. Separation by HPLC with TFA, followed by neutralization with SPE amine cartridge afforded the title compound (17.6 mg, 51%). LC-MS m/z 629 (M+H)$^+$.

Example 171

3-[8-(2,6-difluorophenyl)-2-(4-methyl-1,4'-bipiperidin-1'-yl)-7-oxo-7,8-dihydropyrido[2,3-d]pyrimidin-4-yl]-N-(2,2-dimethylpropyl)-4-methylbenzamide

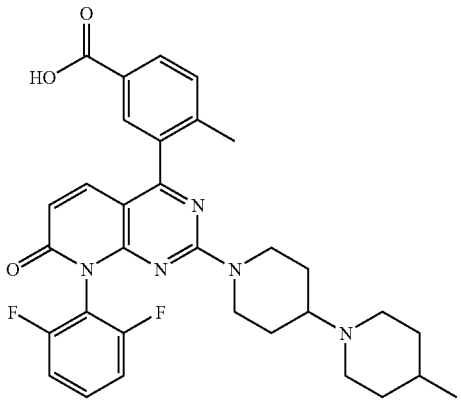

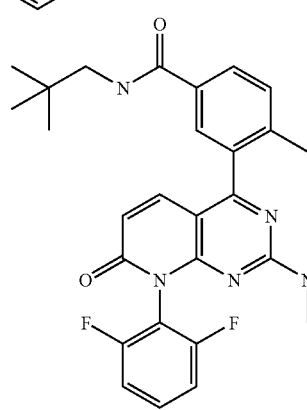

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and 2,2-dimethyl-1-propanamine (8.65 uL, 0.0825 mmol). The mixture was stirred at rt overnight. Separation by HPLC with TFA, followed by neutralization with SPE amine cartridge afforded the title compound (17.8 mg, 50%). LC-MS m/z 643 (M+H)+.

Example 172

3-[8-(2,6-difluorophenyl)-2-(4-methyl-1,4'-bipiperidin-1'-yl)-7-oxo-7,8-dihydropyrido[2,3-d]pyrimidin-4-yl]-4-methyl-N-(2,2,2-trifluoroethyl)benzamide

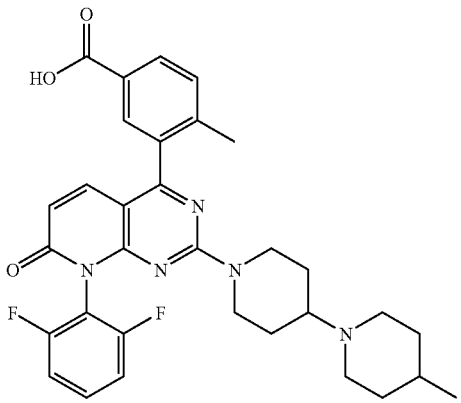

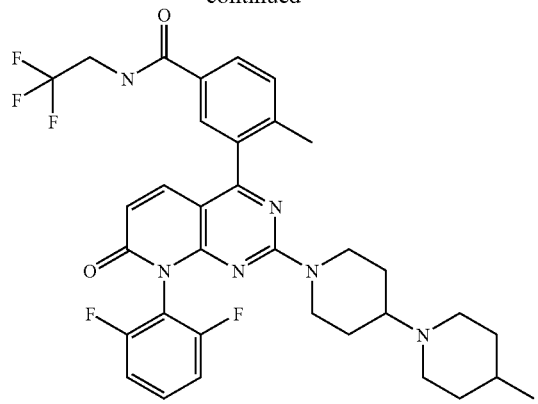

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and 2,2,2-trifluoroethanamine (6.56 uL, 0.0825 mmol). The mixture was stirred at rt overnight. Separation by HPLC with TFA, followed by neutralization with SPE amine cartridge afforded the title compound (24.6 mg, 68%). LC-MS m/z 655 (M+H)+.

Example 173

3-[8-(2,6-difluorophenyl)-2-(4-methyl-1,4'-bipiperidin-1'-yl)-7-oxo-7,8-dihydropyrido[2,3-d]pyrimidin-4-yl]-N-ethyl-4-methylbenzamide

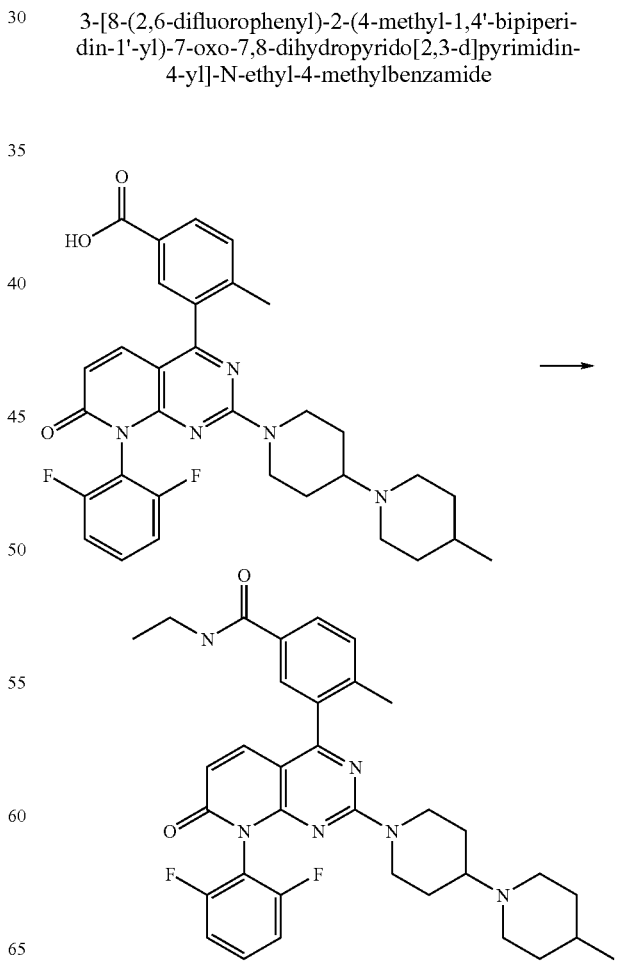

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and ethylamine (41.3 uL, 0.0825 mmol, 2M soln in THF). The mixture was stirred at rt overnight. Separation by HPLC with TFA, followed by neutralization with SPE amine cartridge afforded the title compound (26.2 mg, 78%). LC-MS m/z 601 (M+H)$^+$.

Example 174

3-[8-(2,6-difluorophenyl)-2-(4-methyl-1,4'-bipiperidin-1'-yl)-7-oxo-7,8-dihydropyrido[2,3-d]pyrimidin-4-yl]N-(4-fluorophenyl)-4-methylbenzamide

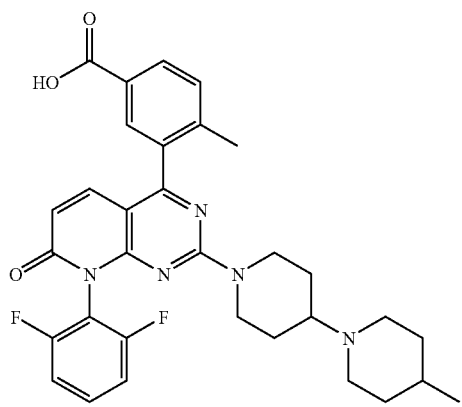

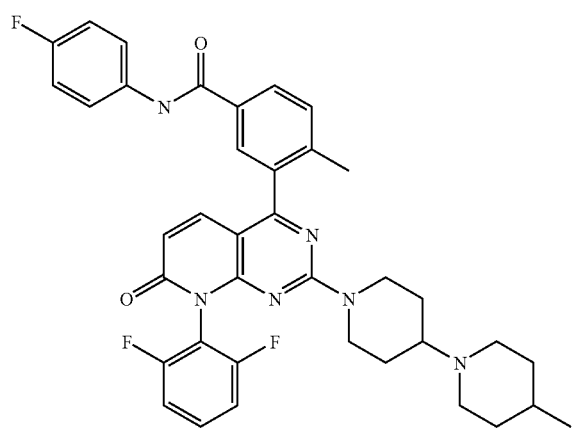

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and 4-fluoroaniline (7.92 uL, 0.0825 mmol). The mixture was stirred at rt overnight. Separation by HPLC with TFA, followed by neutralization with SPE amine cartridge afforded the title compound (26.4 mg, 72%). LC-MS m/z 667 (M+H)$^+$.

Example 175

N-cyclobutyl-3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzamide

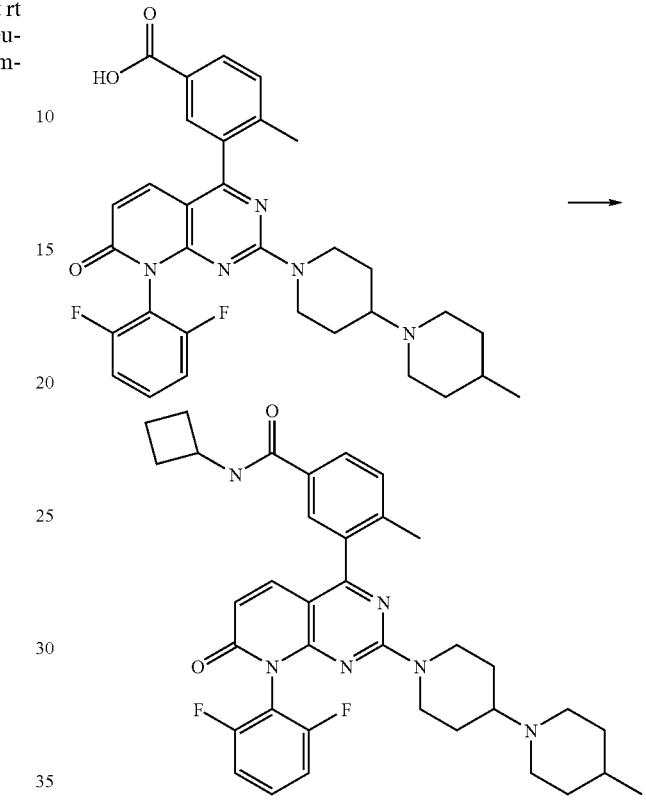

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and cyclobutanamine (7.04 uL, 0.0825 mmol). The mixture was stirred at rt overnight. Separation by HPLC with TFA, followed by neutralization with SPE amine cartridge afforded the title compound (24.8 mg, 72%). LC-MS m/z 627 (M+H)$^+$.

Example 176

N-(cyclopropylmethyl)-3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzamide

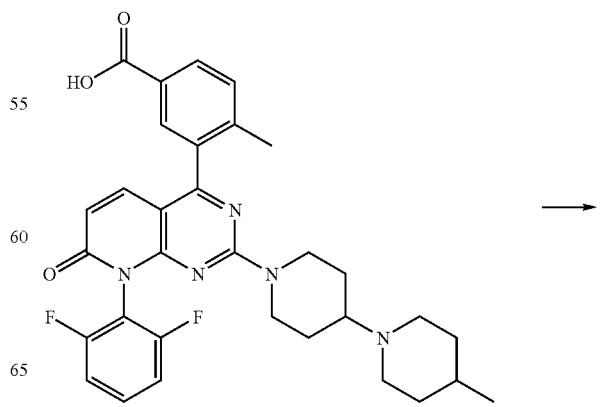

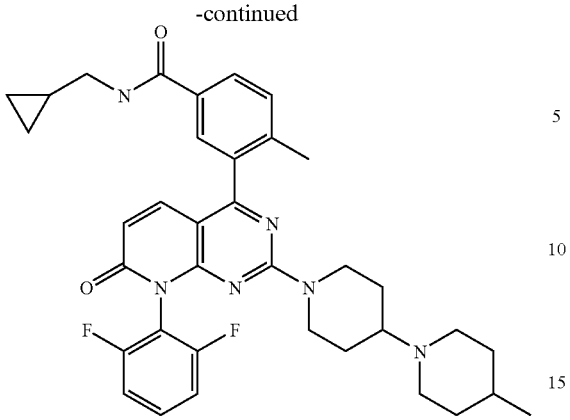

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and 1-cyclopropylmethanamine (7.15 uL, 0.0825 mmol). The mixture was stirred at rt overnight. Separation by HPLC with TFA, followed by neutralization with SPE amine cartridge afforded the title compound (6.2 mg, 18%). LC-MS m/z 627 (M+H)$^+$.

Example 177

3-[8-(2,6-difluorophenyl-2-(4-methyl-1,4'-bipiperidin-1'-yl)-7-oxo-7,8-dihydropyrido[2,3-d]pyrimidin-4-yl]-N-(2-fluoroethyl)-4-methylbenzamide To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and 2-fluoroethylamine hydrochloride (8.09 mg, 0.0825 mmol). The mixture was stirred at rt overnight. Separation by HPLC with TFA, followed by neutralization with SPE amine cartridge afforded the title compound (11.1 mg, 33%). LC-MS m/z 619 (M+H)$^+$.

Example 178

N-cyclopropyl-3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzamide

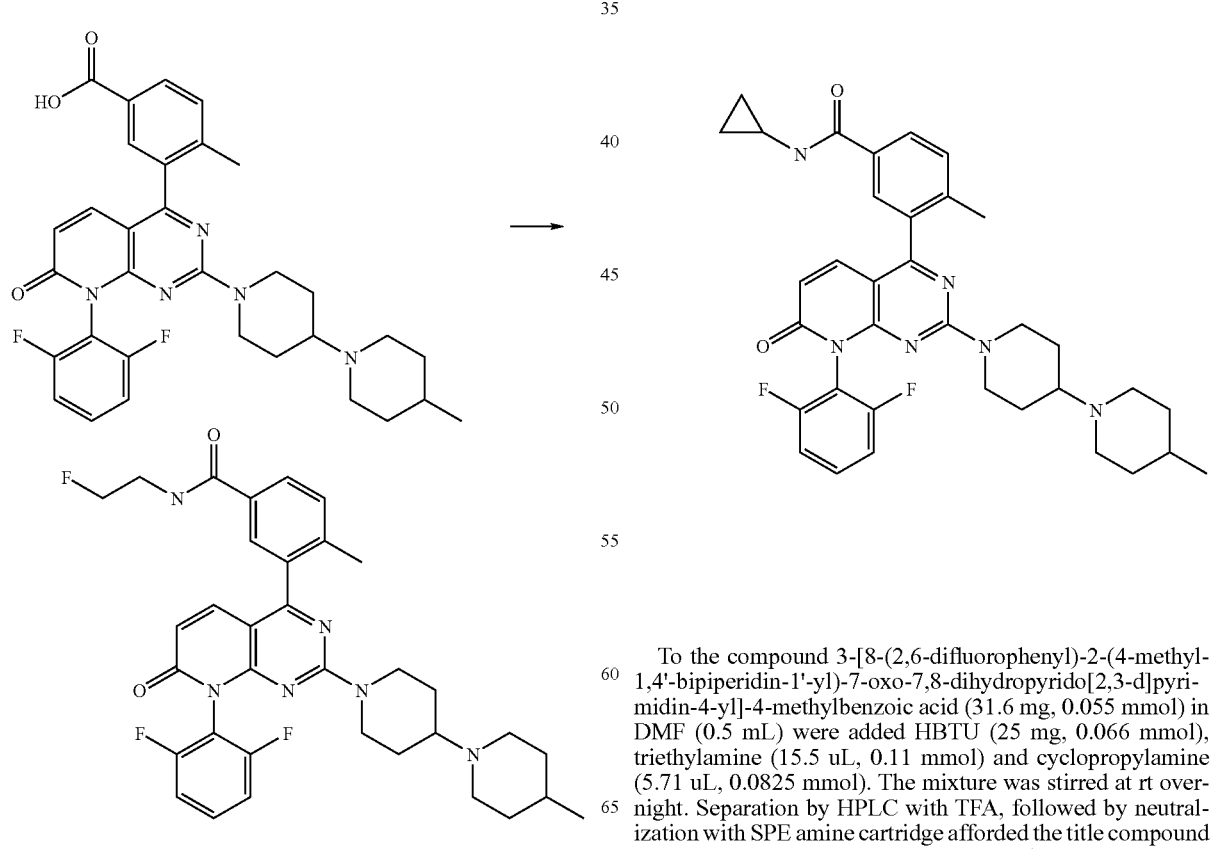

To the compound 3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid (31.6 mg, 0.055 mmol) in DMF (0.5 mL) were added HBTU (25 mg, 0.066 mmol), triethylamine (15.5 uL, 0.11 mmol) and cyclopropylamine (5.71 uL, 0.0825 mmol). The mixture was stirred at rt overnight. Separation by HPLC with TFA, followed by neutralization with SPE amine cartridge afforded the title compound (13.8 mg, 41%). LC-MS m/z 613 (M+H)$^+$.

Example 179

3-[2-{[3-(diethylamino)propyl]amino}-8-(2,6-difluorophenyl)-7-oxo-7,8-dihydropyrido[2,3-d]pyrimidin-4-yl]-5-fluoro-4-methyl-N-(1-methylethyl)benzamide 179a) 1,1-dimethylethyl 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoate, trifluoroacetate

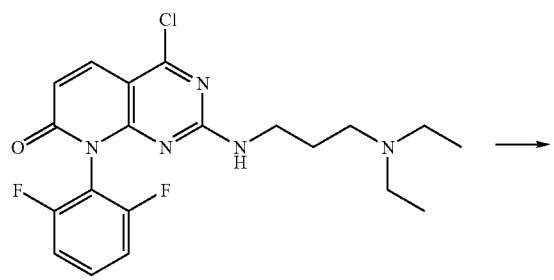

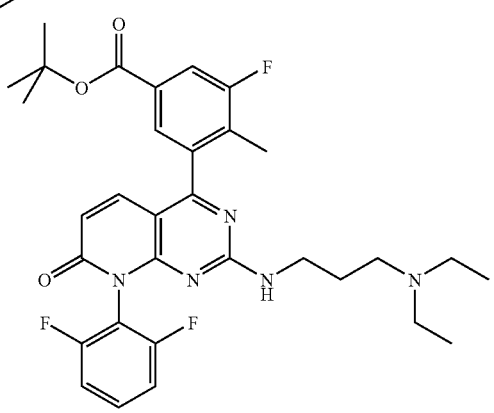

To the compound 4-chloro-2-{[3-(diethylamino)propyl]amino}-8-(2,6-difluorophenyl)pyrido[2,3-d]pyrimidin-7(8H)-one (600 mg, 1.422 mmol) in dioxane (15 mL) and water (5 mL) were added 1,1-dimethylethyl 3-fluoro-4-methyl-5-(4,4,5,5-tetramethyl-1,3,2-dioxaborolan-2-yl)benzoate (542 mg, 2.132 mol), potassium carbonate (590 mg, 4.26 mmol) and tetrakis(triphenylphosphine)-palladium(0) (82 mg, 0.071 mmol). The mixture was heated with microwave at 150° C. for 15 minutes. The mixture was filtered. Separation by HPLC with TFA afforded the crude title compound.

179b) 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid trifluoroacetate

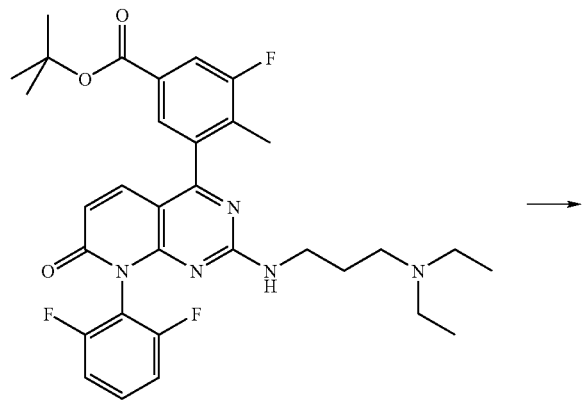

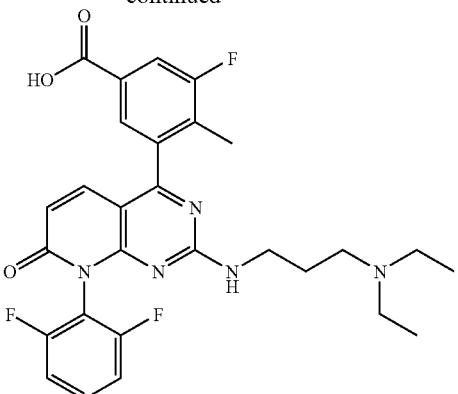

To the crude compound 1,1-dimethylethyl 3-[2-{[3-(diethylamino)-propyl]amino}-8-(2,6-difluorophenyl)-7-oxo-7,8-dihydropyrido[2,3-d]pyrimidin-4-yl]-5-fluoro-4-methylbenzoate trifluoroacetate in dichloromethane (1.5 mL, 23.3 mmol) were added TFA (0.703 mL, 9.5 mmol) and triethylsilane (0.281 mL, 1.82 mmol). The mixture was stirred at rt overnight. Separation by HPLC with TFA afforded the title compound (301 mg, 40%, 2 steps yield). LC-MS m/z 540 (M+H)+.

179c) 3-[2-{[3-(diethylamino)propyl]amino}-8-(2,6-difluorophenyl)-7-oxo-7,8-dihydropyrido[2,3-d]pyrimidin-4-yl]-5-fluoro-4-methyl-N-(1-methylethyl)benzamide

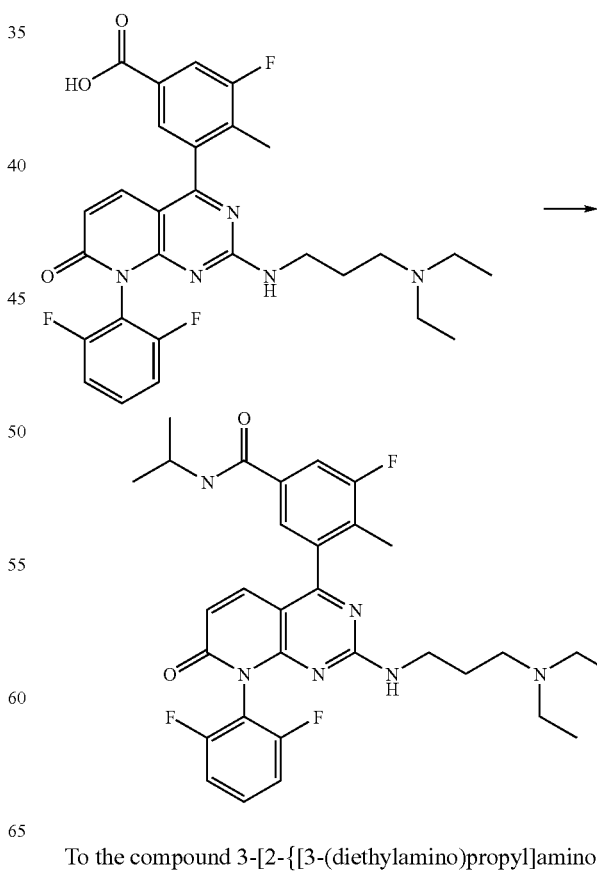

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid trifluoroacetate (30 mg, 0.055 mmol) in DMF (0.5 mL) were added HBTU (25 mg, 0.066 mmol), triethylamine (15.5 uL, 0.11 mmol) and isopropylamine (7.03 uL, 0.0825 mmol). The mixture was stirred at rt overnight. Separation by HPLC with TFA, followed by neutralization with SPE amine cartridge afforded the title compound (19.3 mg, 60%). LC-MS m/z 581 (M+H)$^+$.

Example 180

3-[2-{[3-(diethylamino)propyl]amino}-8-(2,6-difluorophenyl)-7-oxo-7,8-dihydropyrido[2,3-d]pyrimidin-4-yl]-fluoro-N,4-dimethylbenzamide

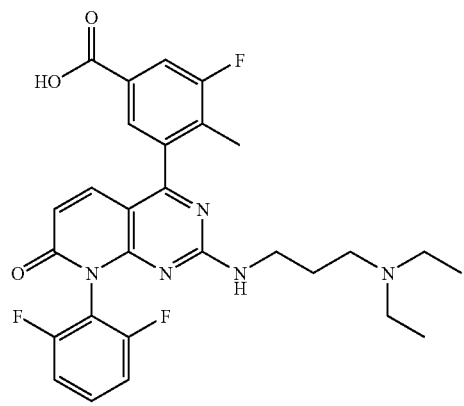

Example 181

3-[2-{[3-(diethylamino)propyl]amino}-8-(2,6-difluorophenyl)-7-oxo-7,8-dihydropyrido[2,3-d]-pyrimidin-4-yl]-5-fluoro-4-methyl-N-propylbenzamide

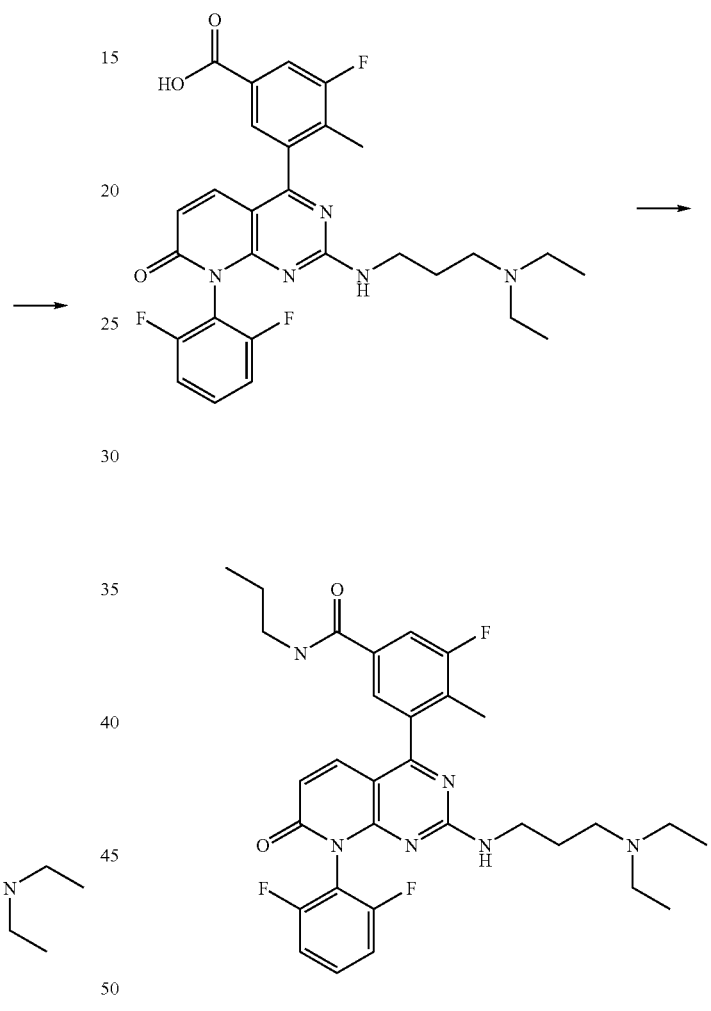

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid (30 mg, 0.055 mmol) in DMF (0.5 mL) were added HBTU (25 mg, 0.066 mmol), triethylamine (15.5 uL, 0.11 mmol) and methylamine (41.5 uL, 0.0825 mmol, 2M soln in THF). The mixture was stirred at rt overnight. Separation by HPLC with TFA, followed by neutralization with SPE amine cartridge afforded the title compound (9.6 mg, 31.5%). LC-MS m/z 553 (M+H)$^+$.

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid (30 mg, 0.055 mmol) in DMF (0.5 mL) were added HBTU (25 mg, 0.066 mmol), triethylamine (15.5 uL, 0.11 mmol) and propylamine (6.78 uL, 0.0825 mmol). The mixture was stirred at rt overnight. Separation by HPLC with TFA, followed by neutralization with SPE amine cartridge afforded the title compound (18.7 mg, 58%). LC-MS m/z 581 (M+H)$^+$.

Example 182

3-[2-{[3-(diethylamino)propyl]amino}-8-(2,6-difluorophenyl)-7-oxo-7,8-dihydropyrido[2,3-d]pyrimidin-4-yl]-5-fluoro-N-(4-fluorophenyl)-4-methylbenzamide

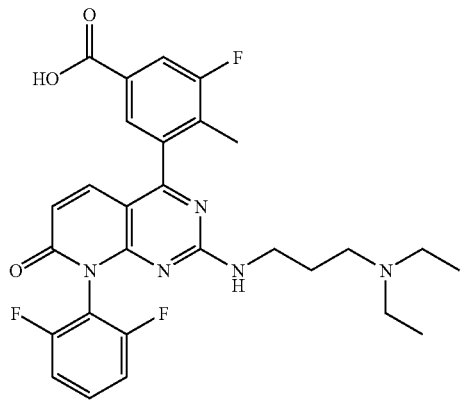

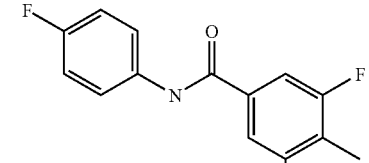

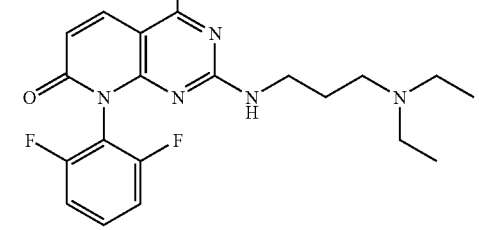

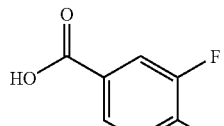

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid (30 mg, 0.055 mmol) in DMF (0.5 mL) were added HBTU (25 mg, 0.066 mmol), triethylamine (15.5 uL, 0.11 mmol) and 4-fluoroaniline (7.92 uL, 0.0825 mmol). The mixture was stirred at rt overnight. Separation by HPLC with TFA, followed by neutralization with SPE amine cartridge afforded the title compound (20.1 mg, 58%). LC-MS m/z 633 (M+H)⁺.

Example 183

3-[2-{[3-(diethylamino)propyl]amino}-8-(2,6-difluorophenyl)-7-oxo-7,8-dihydropyrido[2,3-d]pyrimidin-4-yl]-5-fluoro-4-methyl-N-1,3-thiazol-2-ylbenzamide

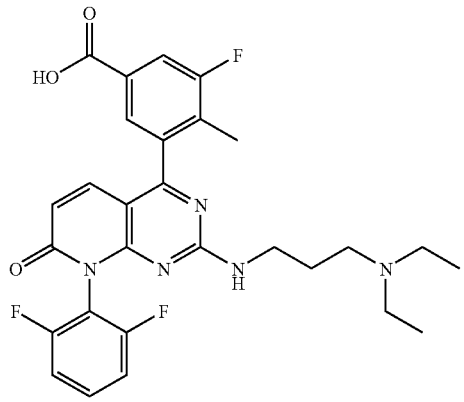

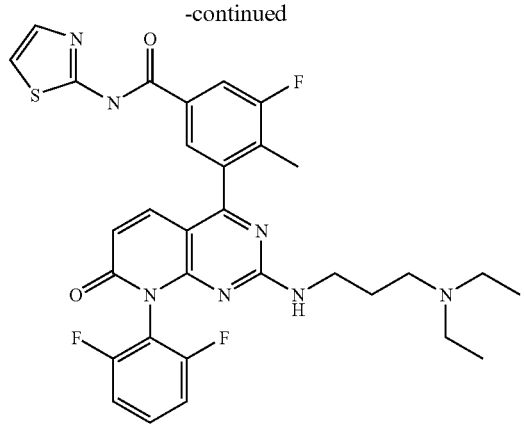

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid (30 mg, 0.055 mmol) in DMF (0.5 mL) were added HBTU (25 mg, 0.066 mmol), triethylamine (15.5 uL, 0.11 mmol) and 2-aminothiozole (8.26 mg, 0.0825 mmol). The mixture was stirred at rt overnight. Separation by HPLC with TFA, followed by neutralization with SPE amine cartridge afforded the title compound (15.6 mg, 46%). LC-MS m/z 622 (M+H)⁺.

Example 184

3-[2-{[3-(diethylamino)propyl]amino}-8-(2,6-difluorophenyl)-7-oxo-7,8-dihydropyrido[2,3-d]pyrimidin-4-yl]-5-fluoro-4-methyl-N-phenylbenzamide

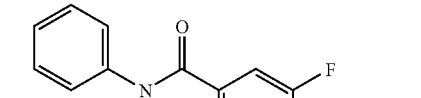

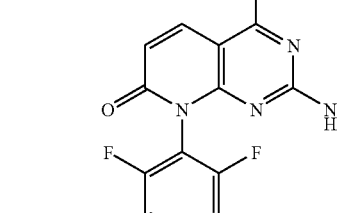

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid (30 mg, 0.055 mmol) in DMF (0.5 mL) were added HBTU (25 mg, 0.066 mmol), triethylamine (15.5 uL, 0.11 mmol) and aniline (7.51 uL, 0.0825 mmol). The mixture was stirred at rt overnight. Separation by HPLC with TFA, followed by neutralization with SPE amine cartridge afforded the title compound (14.1 mg, 42%). LC-MS m/z 615 (M+H)$^+$.

Example 185

N-cyclopropyl-3-[2-{[3-(diethylamino)propyl]amino}-8-(2,6-difluorophenyl)-7-oxo-7,8-dihydropyrido[2,3-d]-pyrimidin-4-yl]-5-fluoro-4-methylbenzamide

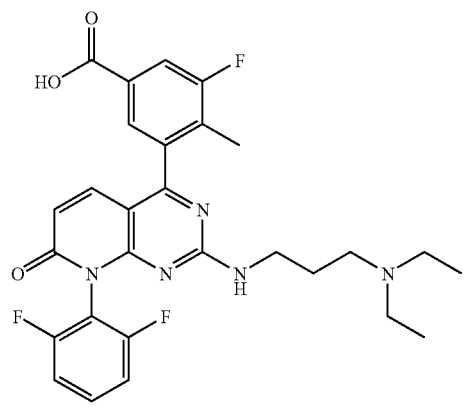

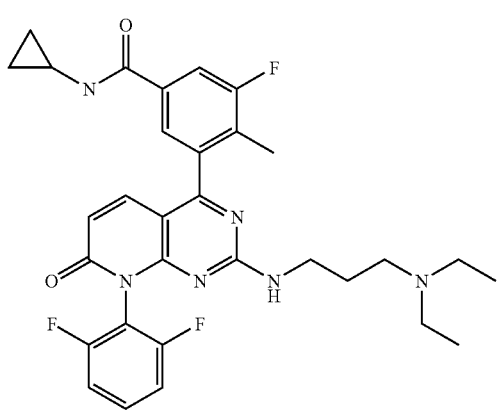

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid (30 mg, 0.055 mmol) in DMF (0.5 mL) were added HBTU (25 mg, 0.066 mmol), triethylamine (15.5 uL, 0.11 mmol) and cyclopropylamine (5.71 uL, 0.0825 mmol). The mixture was stirred at rt overnight. Separation by HPLC with TFA, followed by neutralization with SPE amine cartridge afforded the title compound (20 mg, 60%). LC-MS m/z 579 (M+H)$^+$.

Example 186

N-cyclopentyl-3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzamide

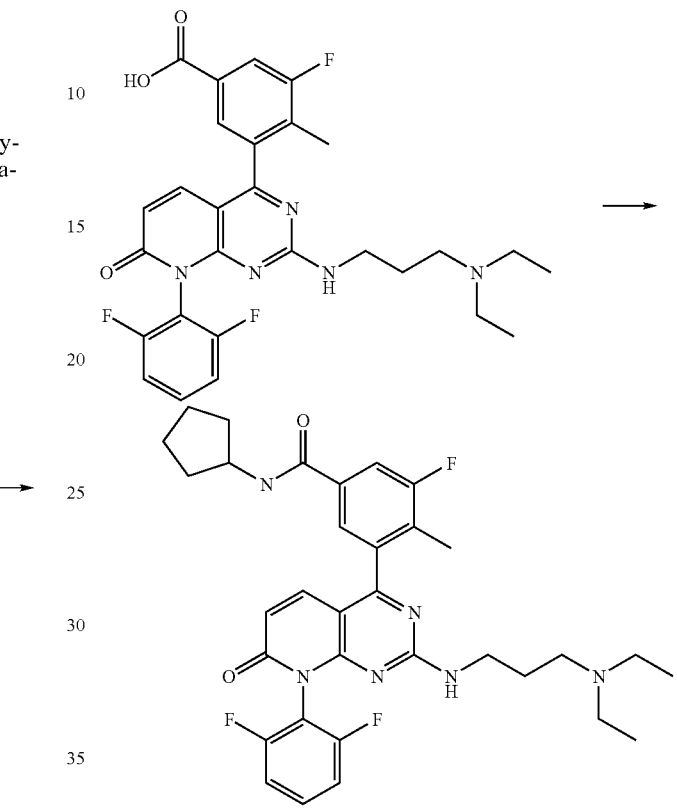

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid (30 mg, 0.055 mmol) in DMF (0.5 mL) were added HBTU (25 mg, 0.066 mmol), triethylamine (15.5 uL, 0.11 mmol) and cyclopentanamine (8.15 uL, 0.0825 mmol). The mixture was stirred at rt overnight. Separation by HPLC with TFA, followed by neutralization with SPE amine cartridge afforded the title compound (18.2 mg, 56%). LC-MS m/z 607 (M+H)$^+$.

Example 187

3-[2-{[3-(diethylamino)propyl]amino}-8-(2,6-difluorophenyl)-7-oxo-7,8-dihydropyrido[2,3-d]pyrimidin-4-yl]-N-(1,1-dimethylethyl)-5-fluoro-4-methylbenzamide

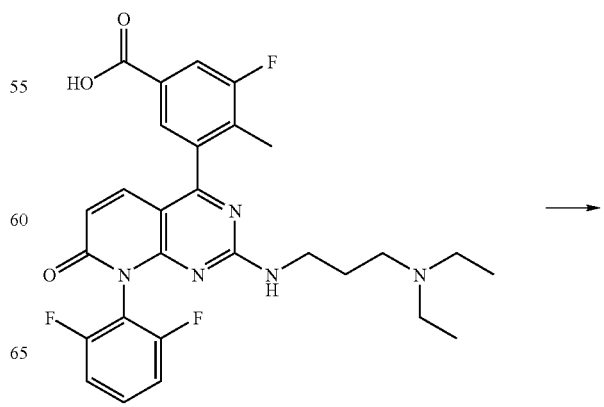

263

-continued

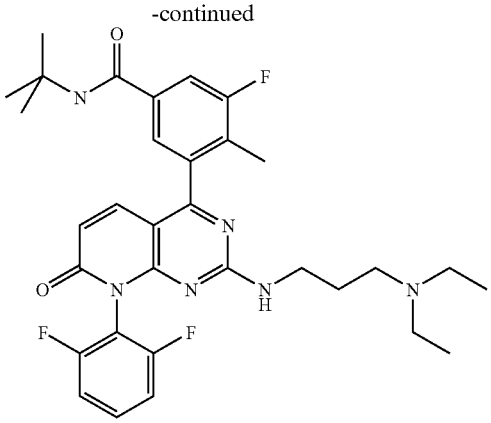

To the compound 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoic acid (30 mg, 0.055 mmol) in DMF (0.5 mL) were added HBTU (25 mg, 0.066 mmol), triethylamine (15.5 uL, 0.11 mmol) and t-butylamine (8.71 uL, 0.0825 mmol). The mixture was stirred at rt overnight. Separation by HPLC with TFA, followed by neutralization with SPE amine cartridge afforded the title compound (14.8 mg, 46%). LC-MS m/z 595 (M+H)$^+$.

Example 188

4-[2-{[3-(diethylamino)propyl]amino}-8-(2,6-difluorophenyl)-7-oxo-7,8-dihydropyrido[2,3-d]pyrimidin-4-yl]-N-propylbenzamide 188a) 4-[2-{[3-(diethylamino)propyl]amino}-8-(2,6-difluorophenyl)-7-oxo-7,8-dihydropyrido[2,3-d]pyrimidin-4-yl]benzoic acid

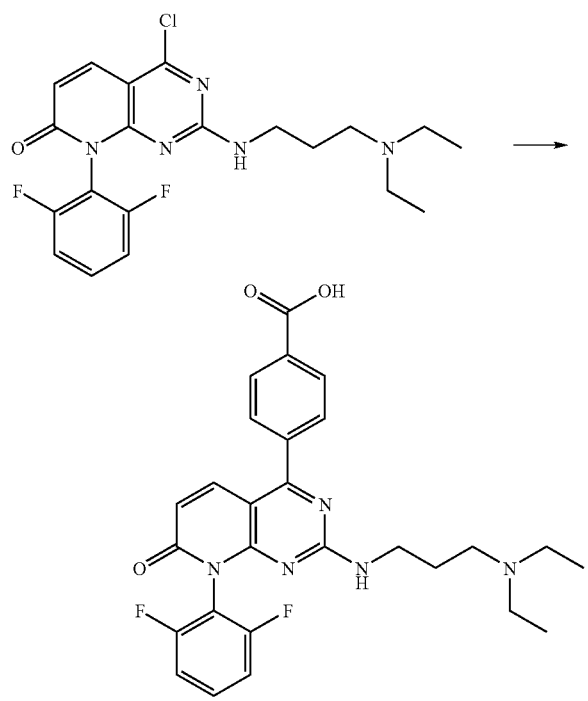

264

To the compound 4-chloro-2-{[3-(diethylamino)propyl]amino}-8-(2,6-difluorophenyl)pyrido[2,3-d]pyrimidin-7(8H)-one (168.75 mg, 0.40 mmol) in dioxane (12 mL) and water (4 mL) were added 4-(4,4,5,5-tetramethyl-1,3,2-dioxaborolan-2-yl)benzoic acid (148.85 mg, 0.60 mol), potassium carbonate (208 mg, 1.20 mmol) and tetrakis(triphenylphosphine)palladium(0) (23 mg, 0.02 mmol). The mixture was heated with microwave at 150° C. for 15 min. The mixture was concentrated. It was mixed with DMSO (0.75 mL) and water (0.25 mL). Separation by HPLC afforded the title compound (147 mg, 72%). LC-MS m/z 508 (M+H)$^+$.

188b) 4-[2-{[3-(diethylamino)propyl]amino}-8-(2,6-difluorophenyl)-7-oxo-7,8-dihydropyrido[2,3-d]pyrimidin-4-yl]-N-propylbenzamide

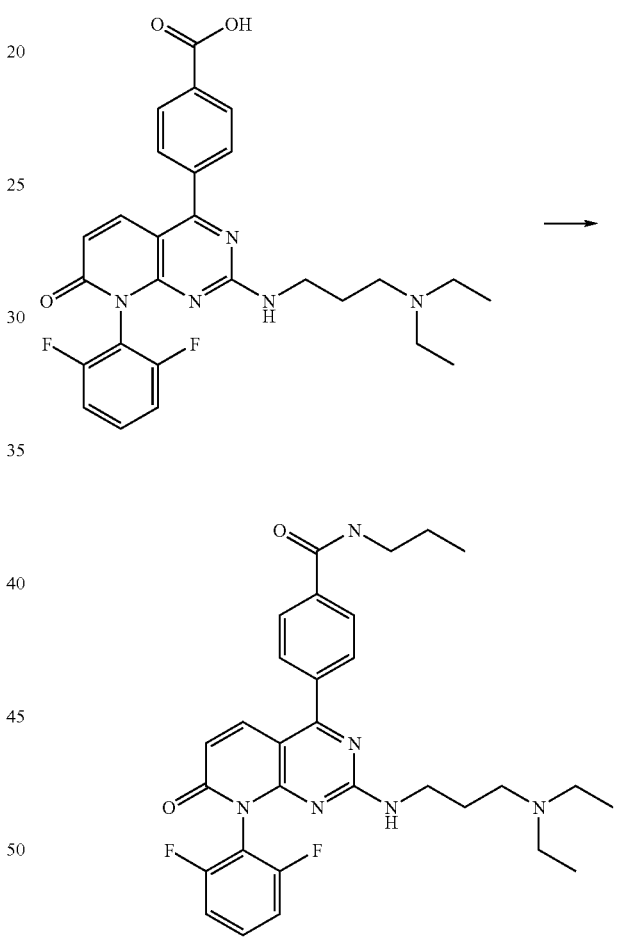

To the compound 4-[2-{[3-(diethylamino)propyl]amino}-8-(2,6-difluorophenyl)-7-oxo-7,8-dihydropyrido[2,3-d]pyrimidin-4-yl]benzoic acid (28 mg, 0.055 mmol) in DMF (0.5 mL) were added HBTU (25 mg, 0.066 mmol), triethylamine (15.5 uL, 0.11 mmol) and propylamine (6.78 uL, 0.0825 mmol). The mixture was stirred at rt overnight. Separation by HPLC with TFA, followed by neutralization with SPE amine cartridge afforded the title compound (16.1 mg, 53%). LC-MS m/z 549 (M+H)$^+$.

Example 189

4-[2-{[3-(diethylamino)propyl]amino}-8-(2,6-difluorophenyl)-7-oxo-7,8-dihydropyrido[2,3-d]pyrimidin-4-yl]-N-(1-methylethyl)benzamide

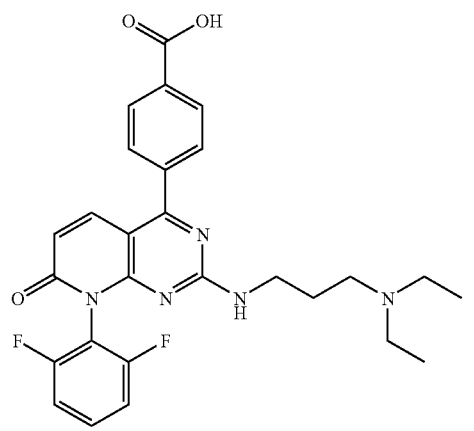

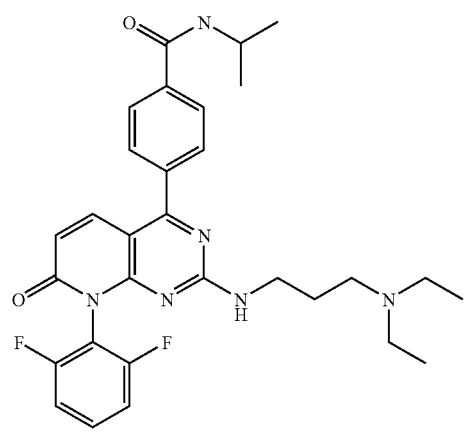

To the compound 4-[2-{[3-(diethylamino)propyl]amino}-8-(2,6-difluorophenyl)-7-oxo-7,8-dihydropyrido[2,3-d]pyrimidin-4-yl]benzoic acid (28 mg, 0.055 mmol) in DMF (0.5 mL) were added HBTU (25 mg, 0.066 mmol), triethylamine (15.5 uL, 0.11 mmol) and isopropylamine (7.03 uL, 0.0825 mmol). The mixture was stirred at rt overnight. Separation by HPLC with TFA, followed by neutralization with SPE amine cartridge afforded the title compound (16.1 mg, 53%). LC-MS m/z 549 (M+H)$^+$.

Example 190

N-cyclopropyl-4-[2-{[3-(diethylamino)propyl]amino}-8-(2,6-difluorophenyl)-7-oxo-7,8-dihydropyrido[2,3-d]pyrimidin-4-yl]benzamide

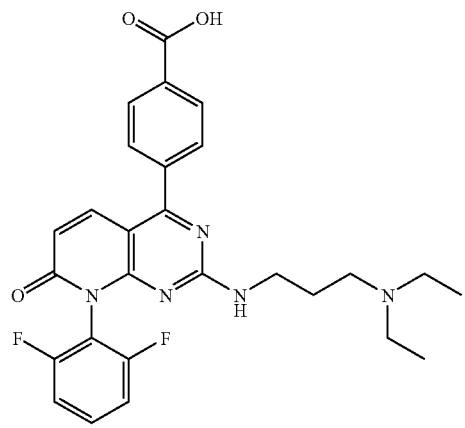

-continued

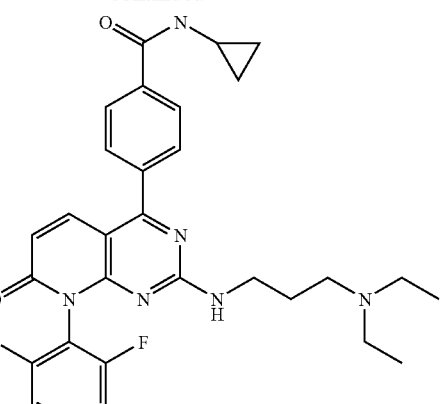

To the compound 4-[2-{[3-(diethylamino)propyl]amino}-8-(2,6-difluorophenyl)-7-oxo-7,8-dihydropyrido[2,3-d]pyrimidin-4-yl]benzoic acid (28 mg, 0.055 mmol) in DMF (0.5 mL) were added HBTU (25 mg, 0.066 mmol), triethylamine (15.5 uL, 0.11 mmol) and cyclopropylamine (5.71 uL, 0.0825 mmol). The mixture was stirred at rt overnight. Separation by HPLC with TFA, followed by neutralization with SPE amine cartridge afforded the title compound (17.8 mg, 59%). LC-MS m/z 547 (M+H)$^+$.

Example 191

4-[2-{[3-(diethylamino)propyl]amino}-8-(2,6-difluorophenyl)-7-oxo-7,8-dihydropyrido[2,3-d]pyrimidin-4-yl]-N-(4-fluorophenyl)benzamide

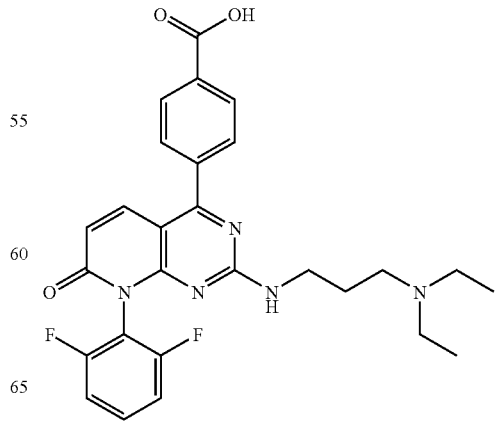

-continued

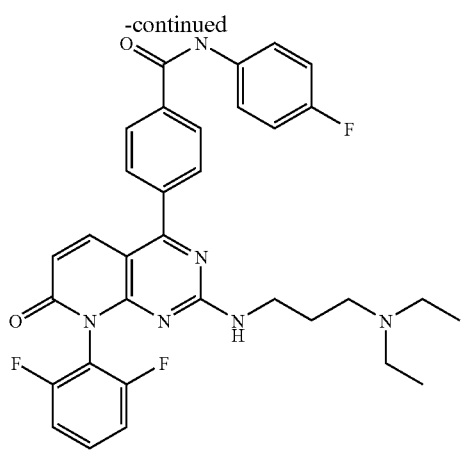

To the compound 4-[2-{[3-(diethylamino)propyl]amino}-8-(2,6-difluorophenyl)-7-oxo-7,8-dihydropyrido[2,3-d]pyrimidin-4-yl]benzoic acid (28 mg, 0.055 mmol) in DMF (0.5 mL) were added HBTU (25 mg, 0.066 mmol), triethylamine (15.5 uL, 0.11 mmol) and 4-fluoroaniline (7.92 uL, 0.0825 mmol). The mixture was stirred at rt overnight. Separation by HPLC with TFA, followed by neutralization with SPE amine cartridge afforded the title compound (15.8 mg, 48%). LC-MS m/z 601 (M+H)$^+$.

Example 192

4-[2-{[3-(diethylamino)propyl]amino}-8-(2,6-difluorophenyl)-7-oxo-7,8-dihydropyrido[2,3-d]pyrimidin-4-yl]-N-1,3-thiazol-2-ylbenzamide

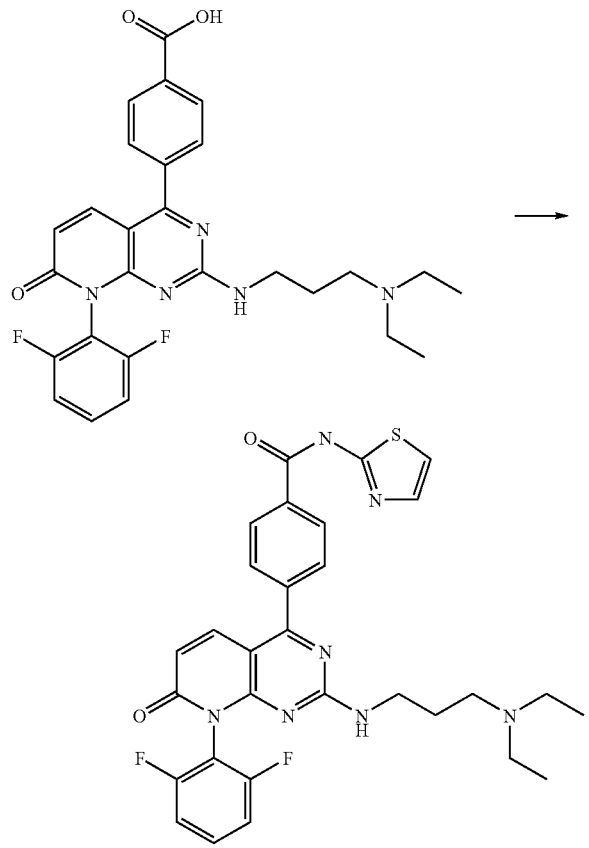

To the compound 4-[2-{[3-(diethylamino)propyl]amino}-8-(2,6-difluorophenyl)-7-oxo-7,8-dihydropyrido[2,3-d]pyrimidin-4-yl]benzoic acid (28 mg, 0.055 mmol) in DMF (0.5 mL) were added HBTU (25 mg, 0.066 mmol), triethylamine (15.5 uL, 0.11 mmol) and 2-aminothiazole (8.26 mg, 0.0825 mmol). The mixture was stirred at rt overnight. Separation by HPLC with TFA, followed by neutralization with SPE amine cartridge afforded the title compound (5.8 mg, 18%). LC-MS m/z 590 (M+H)$^+$.

Example 193

3-[2-{[3-(diethylamino)propyl]amino}-8-(2,6-difluorophenyl)-7-oxo-7,8-dihydropyrido[2,3-d]pyrimidin-4-yl]-N-methylbenzamide 193a) 3-[2-{[3-(diethylamino)propyl]amino}-8-(2,6-difluorophenyl)-7-oxo-7,8-dihydropyrido[2,3-d]pyrimidin-4-yl]benzoic acid (GSK1120344A)

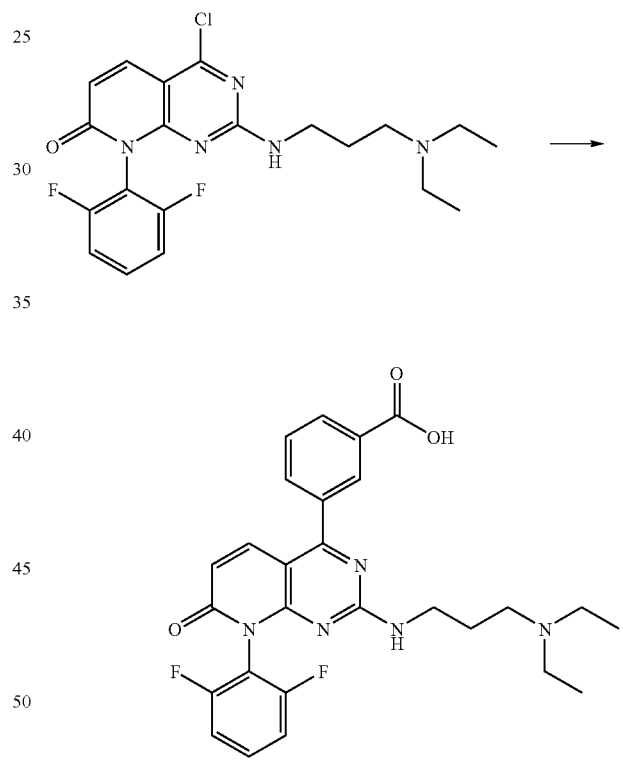

To the compound 4-chloro-2-{[3-(diethylamino)propyl]amino}-8-(2,6-difluorophenyl)pyrido[2,3-d]pyrimidin-7(8H)-one (210.5 mg, 0.50 mmol) in dioxane (15 mL) and water (5 mL) were added 3-(4,4,5,5-tetramethyl-1,3,2-dioxaborolan-2-yl)benzoic acid (125 mg, 0.75 mol), potassium carbonate (210 mg, 1.20 mmol) and tetrakis(triphenylphosphine)palladium(0) (29 mg, 0.025 mmol). The mixture was heated with microwave at 150° C. for 15 min. The mixture was concentrated, then mixed with DMSO (0.75 mL) and water (0.25 mL). Separation by HPLC afforded the title compound (467 mg, 32%). LC-MS m/z 508 (M+H)$^+$.

193b) 3-[2-{[3-(diethylamino)propyl]amino}-8-(2,6-difluorophenyl)-7-oxo-7,8-dihydropyrido[2,3-d]pyrimidin-4-yl]-N-methylbenzamide

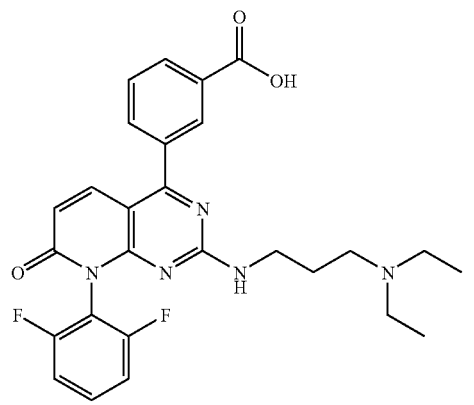

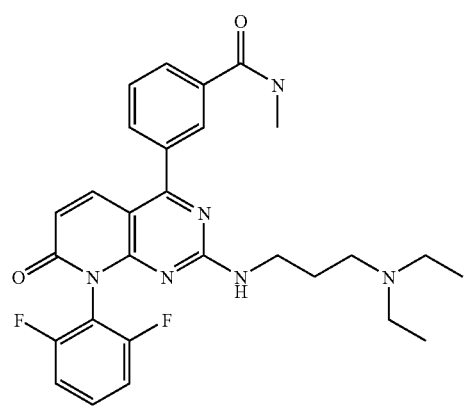

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and methylamine (45 uL, 0.09 mmol, 2M soln in THF). The mixture was stirred at rt overnight. Separation by HPLC with TFA, followed by neutralization with SPE amine cartridge afforded the title compound (9.6 mg, 31%). LC-MS m/z 521 (M+H)+.

Example 194

3-[2-{[3-(diethylamino)propyl]amino}-8-(2,6-difluorophenyl)-7-oxo-7,8-dihydropyrido[2,3-d]pyrimidin-4-yl]-N-propylbenzamide

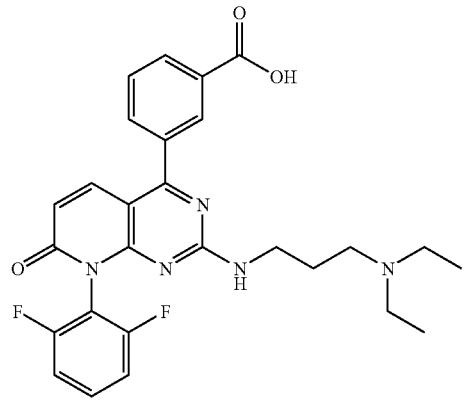

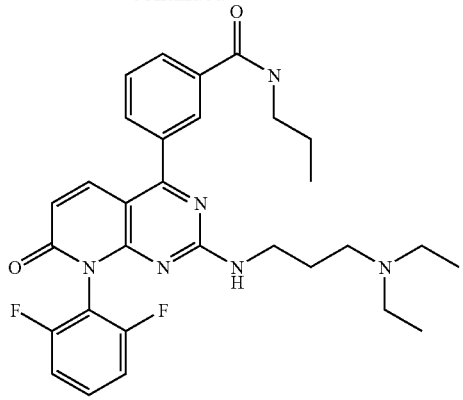

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and propylamine (7.40 uL, 0.09 mmol). The mixture was stirred at rt overnight. Separation by HPLC with TFA, followed by neutralization with SPE amine cartridge afforded the title compound (20.8 mg, 63%). LC-MS m/z 549 (M+H)+.

Example 195

3-[2-{[3-(diethylamino)propyl]amino}-8-(2,6-difluorophenyl)-7-oxo-7,8-dihydropyrido[2,3-d]pyrimidin-4-yl]-N-(1-methylethyl)benzamide

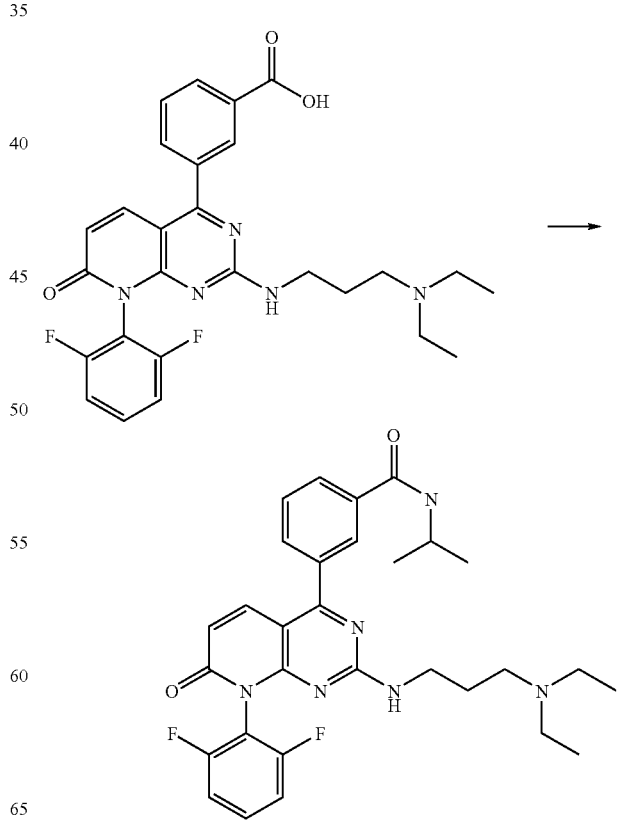

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and isopropylamine (7.67 uL, 0.09 mmol). The mixture was stirred at rt overnight. Separation by HPLC with TFA, followed by neutralization with SPE amine cartridge afforded the title compound (20.5 mg, 62%). LC-MS m/z 549 (M+H)+.

Example 196

3-[2-{[3-(diethylamino)propyl]amino}-8-(2,6-difluorophenyl)-7-oxo-7,8-dihydropyrido[2,3-d]pyrimidin-4-yl]-N-(4-fluorophenyl)benzamide

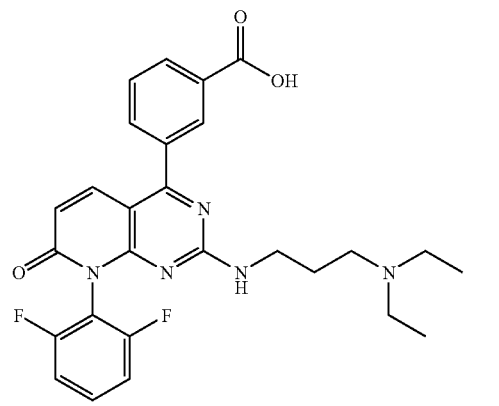

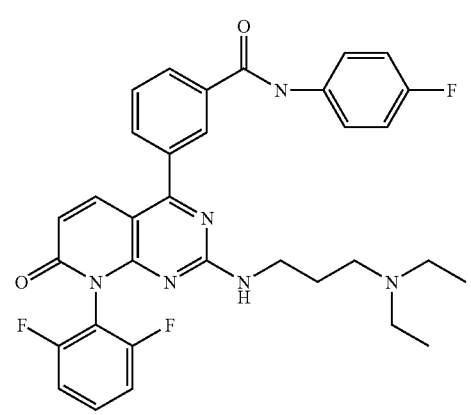

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and 4-fluoroaniline (8.64 uL, 0.09 mmol). The mixture was stirred at rt overnight. Separation by HPLC with TFA, followed by neutralization with SPE amine cartridge afforded the title compound (20 mg, 55.5%). LC-MS m/z 601 (M+H)+.

Example 197

3-[2-{[3-(diethylamino)propyl]amino}-8-(2,6-difluorophenyl)-7-oxo-7,8-dihydropyrido[2,3-d]pyrimidin-4-yl]-N-1,3-thiazol-2-ylbenzamide

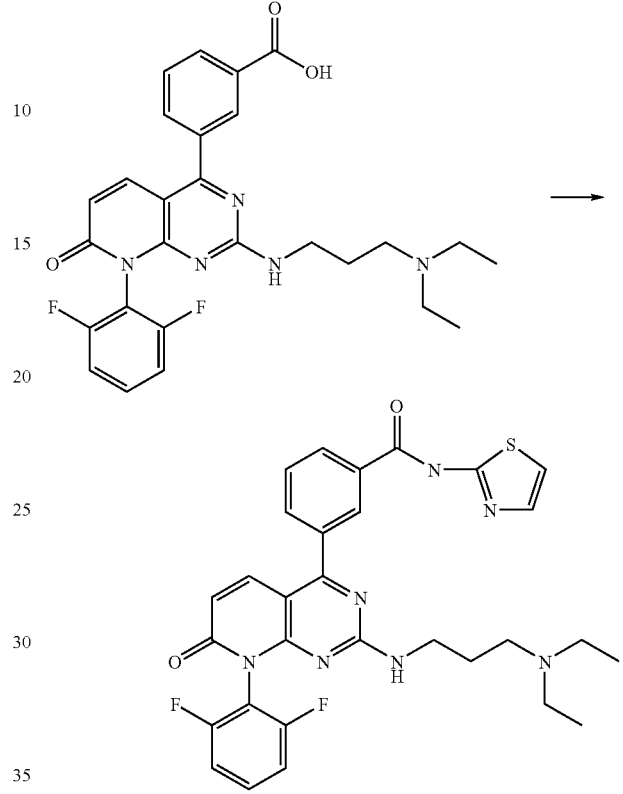

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and 2-aminothiazole (9.01 uL, 0.09 mmol). The mixture was stirred at rt overnight. Separation by HPLC with TFA, followed by neutralization with SPE amine cartridge afforded the title compound (20.5 mg, 58%). LC-MS m/z 590 (M+H)+.

Example 198

3-[2-{[3-(diethylamino)propyl]amino}-8-(2,6-difluorophenyl)-7-oxo-7,8-dihydropyrido[2,3-d]pyrimidin-4-yl]-N-phenylbenzamide

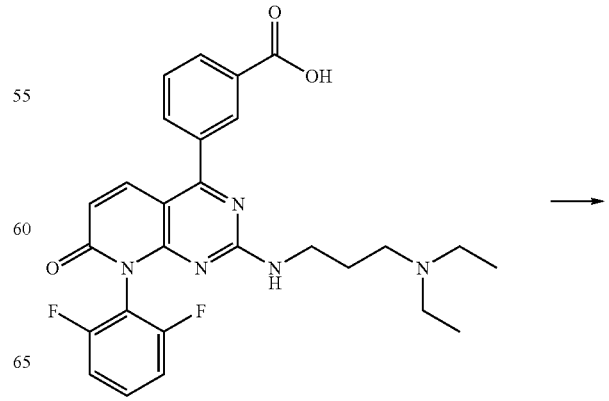

273

-continued

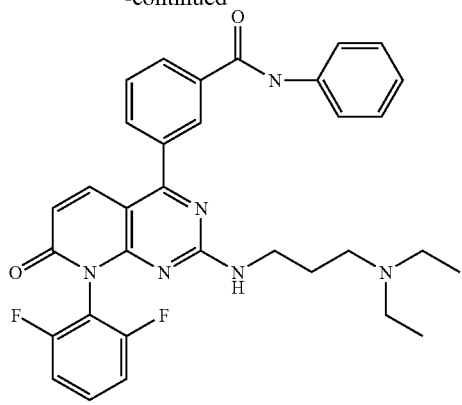

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and aniline (8.21 uL, 0.09 mmol). The mixture was stirred at rt overnight. Separation by HPLC with TFA, followed by neutralization with SPE amine cartridge afforded the title compound (17.2 mg, 49%). LC-MS m/z 583 (M+H)$^+$.

Example 199

3-[2-{[3-(diethylamino)propyl]amino}-8-(2,6-difluorophenyl)-7-oxo-7,8-dihydropyrido[2,3-d]pyrimidin-4-yl]-N-(1,1-dimethylethyl)benzamide

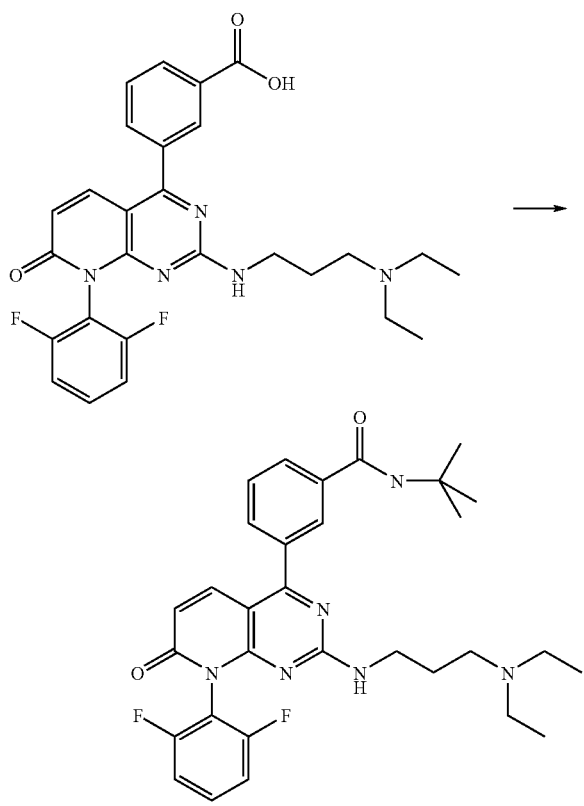

274

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and t-butylamine (9.54 uL, 0.09 mmol). The mixture was stirred at rt overnight. Separation by HPLC with TFA, followed by neutralization with SPE amine cartridge afforded the title compound (17.4 mg, 52%). LC-MS m/z 563 (M+H)$^+$.

Example 200

N-cyclopentyl-3-[2-{[3-(diethylamino)propyl]amino}-8-(2,6-difluorophenyl)-7-oxo-7,8-dihydropyrido[2,3-d]pyrimidin-4-yl]benzamide

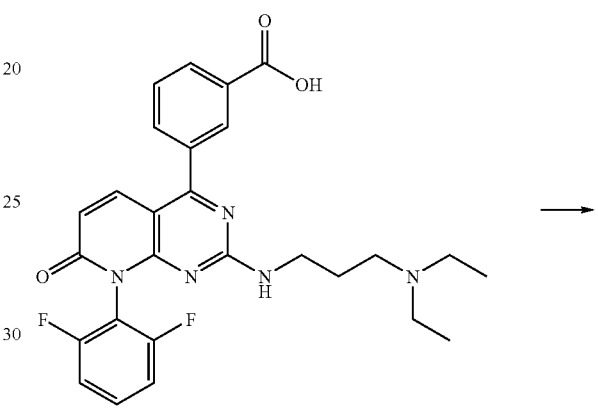

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and cyclopentanamine (8.91 uL, 0.09 mmol). The mixture was stirred at rt overnight. Separation by HPLC with TFA, followed by neutralization with SPE amine cartridge afforded the title compound (6.0 mg, 17%). LC-MS m/z 575 (M+H)$^+$.

Example 201

N-cyclopropyl-3-[2-{[3-(diethylamino)propyl]amino}-8-(2,6-difluorophenyl)-7-oxo-7,8-dihydropyrido[2,3-d]-pyrimidin-4-yl]benzamide

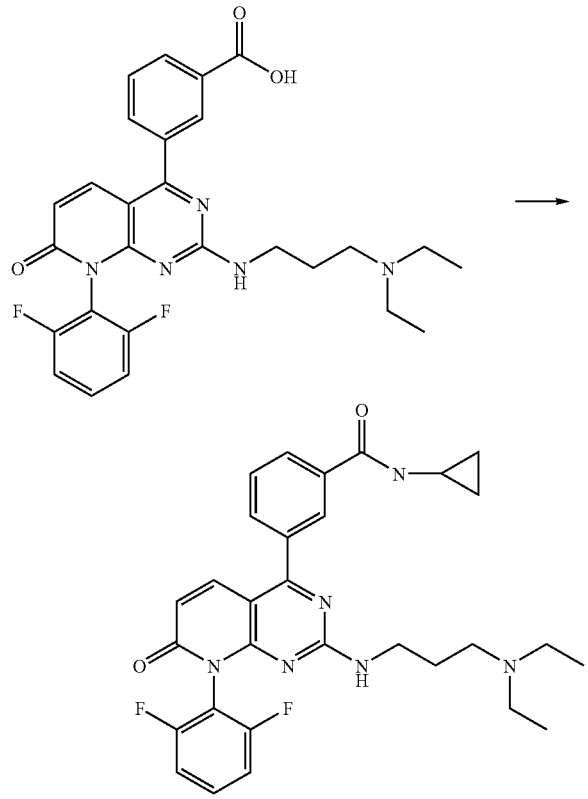

To the compound 3-[2-{[3-(diethylamino)propyl]amino}-8-(2,6-difluorophenyl)-7-oxo-7,8-dihydropyrido[2,3-d]pyrimidin-4-yl]benzoic acid (30 mg, 0.06 mmol) in DMF (0.5 mL) were added HBTU (27 mg, 0.072 mmol), triethylamine (16.9 uL, 0.12 mmol) and cyclopropylamine (6.24 uL, 0.09 mmol). The mixture was stirred at rt overnight. Separation by HPLC with TFA, followed by neutralization with SPE amine cartridge afforded the title compound (15 mg, 46.6%). LC-MS m/z 547 (M+H)$^+$.

Example 202

1,1-dimethylethyl (2-{[8-(2,6-difluorophenyl)-4-(2-methyl-5 {[(2-phenylethyl)amino]carbonyl}phenyl)-7-oxo-7,8-dihydropyrido[2,3-d]pyrimidin-2-yl]amino}ethyl)methylcarbamate 202a) 3-[8-(2,6-difluorophenyl)-2-(methylsulfinyl)-7-oxo-7,8-dihydropyrido[2,3-d]pyrimidin-4-yl]-4-methyl-N-(2-phenylethyl)benzamide

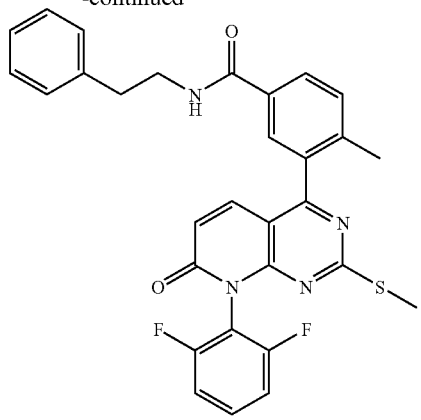

To the solution of 3-[8-(2,6-difluorophenyl)-2-(methylthio)-7-oxo-7,8-dihydropyrido[2,3-d]pyrimidin-4-yl]-4-methylbenzoic acid (220 mg, 0.50 mmol) in dichloromethane (5 mL) was added (2-phenylethyl)amine (69.1 µL, 0.55 mmol), EDC (105 mg, 0.55 mmol), HOBt (6.8 mg, 0.05 mmol) and Et$_3$N (281 mL, 2.0 mmol). The reaction mixture was stirred at room temperature for 20 hours. Then was quenched with H$_2$O, extracted with DCM, dried over Na$_2$SO$_4$, filtered, concentrated and applied to flash chromatography to afford the titled compound 202 mg (74%).

202b) 3-[8-(2,6-difluorophenyl)-2-(methylsulfinyl)-7-oxo-7,8-dihydropyrido[2,3-d]pyrimidin-4-yl]-4-methyl-N-(2-phenylethyl)benzamide

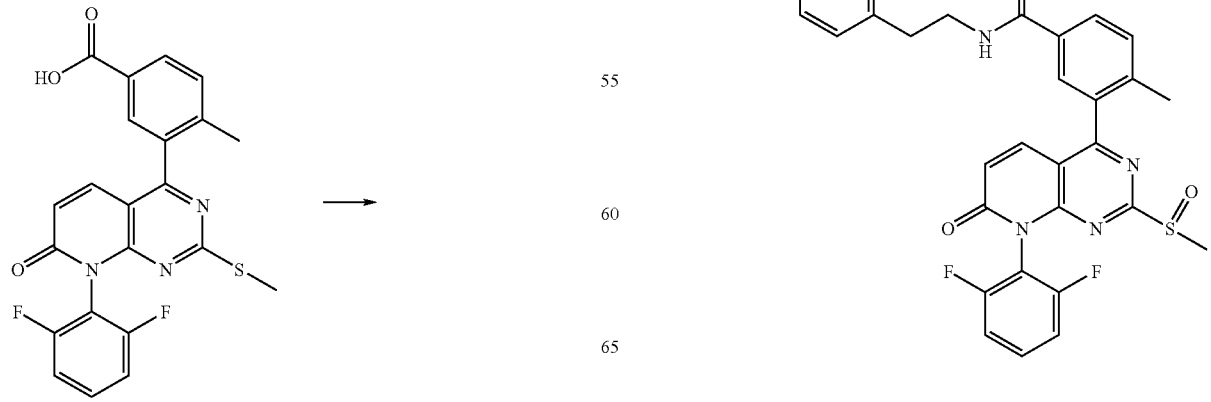

To the solution of 3-[8-(2,6-difluorophenyl)-2-(methylthio)-7-oxo-7,8-dihydropyrido[2,3-d]pyrimidin-4-yl]-4-methyl-N-(2-phenylethyl)benzamide (200 mg, 0.369 mmol) in dichloromethane (7 mL) was added m-CPBA (86.1 mg, 0.553 mmol). The reaction mixture was stirred at room temperature for 10 minutes. Then the reaction mixture was applied to flash chromatography to afford the titled compound 157 mg (76%).

202c) 1,1-dimethylethyl (2-{[8-(2,6-difluorophenyl)-4-(2-methyl-5-{[(2-phenylethyl)amino]carbonyl}phenyl)-7-oxo-7,8-dihydropyrido[2,3-d]pyrimidin-2-yl]amino}ethyl)methylcarbamate

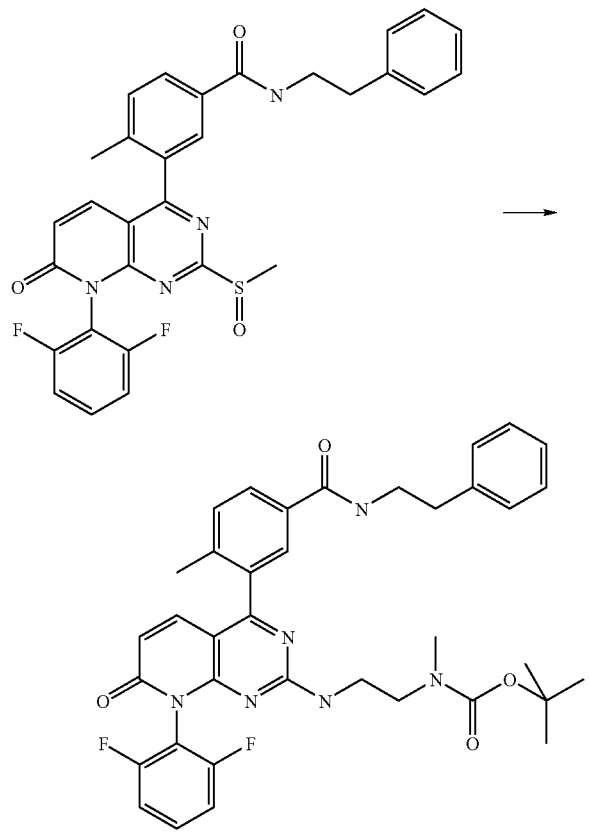

To the solution of 3-[8-(2,6-difluorophenyl)-2-(methylsulfinyl)-7-oxo-7,8-dihydropyrido[2,3-d]pyrimidin-4-yl]-4-methyl-N-(2-phenylethyl)benzamide (156 mg, 0.28 mmol) in dichloromethane (11 mL) was added 1,1-dimethylethyl (2-aminoethyl)methylcarbamate (75 µL, 0.42 mmol) and triethylamine (78.7 µL, 0.56 mmol). The reaction mixture was stirred at room temperature for 16 hours then applied to the flash chromatograph to afford the titled compound 147 mg (79%). LC-MS m/z 669 (M+H)$^+$; $^1$H-NMR (MeOD) 1.30 (m, 9H), 2.31 (m, 3H), 2.65 (m, 2H), 2.76 (m, 1H), 2.92 (m, 2H), 3.22 (m, 2H), 3.45 (m, 1H), 3.60 (m, 2H), 6.35 (m, 1H), 7.19 (m, 2H), 7.26 (m, 5H), 7.43 (m, 1H), 7.49 (m, 1H), 7.60 (m, 1H), 7.74 (m, 1H), 7.97 (m, 1H).

Methods of Treatment

The compounds of Formula (I) and (Ia), (II) and (IIa), (III) and (IIIa), (IV) and (IVa), (V) and (Va), (VIa-VIi), (VIII), (VIIIa), (IX), (IXa), (A), (A1), (B), and (B1) or a pharmaceutically acceptable salt, solvate, or physiologically functional derivative thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

For purposes herein, compounds of Formula (I) and (Ia), (II) and (IIa), (III) and (IIIa), (IV) and (IVa), (V) and (Va), (VIa-VIi), (VIII), (VIIIa), (IX), (IXa), (A), (A1), (B), and (B1) will all be referred to as compounds of Formula (I) herein unless otherwise indicated.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostaglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, gout, traumatic arthritis, rubella arthritis and acute synovitis. Recent evidence also links IL-1 activity to diabetes, pancreatic B cell diseases and Alzheimer's disease.

Use of a CSAID inhibitor compound for the treatment of CSBP mediated disease states, can include, but not be limited to neurodegenerative diseases, such as Alzheimer's disease (as noted above), Parkinson's disease and multiple sclerosis, etc.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, chronic pulmonary inflammatory disease and chronic obstructive pulmonary disease, silicosis, pulmonary sarcoisosis, bone resorption diseases, such as osteoporosis, cardiac, brain and renal reperfusion injury, graft vs. host reaction, allograft rejections, fever and myalgias due to infection, such as influenza, brain infections including encephalitis (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al. (1998), Clin. Infec. Dis., Vol. 26, p 840; Teren et al. (1997), Am. J. Respir. Crit. Care Med., Vol. 155, p 1362; Grunberg et al. (1997), Am. J. Respir. Crit. Care Med. Vol. 156, p 609 and Zhu et al, J Clin. Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac, brain and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A member of the MAP kinase family, alternatively termed CSBP, p38, or RK, has been identified independently by several laboratories. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I) have been determined to be potent and selective inhibitors of CSBP/p38/RK kinase activity. It has been found that some of the compounds of Formula I exhibit reversible time-dependent inhibition of the p38 kinase due to the kinetics of slow binding and/or slow dissociation, resulting in an improved apparent IC50 when a compound has been preincubated with the enzyme or with cells. This slow, tight binding property may contribute to enhanced potency of such compounds both in vitro and in vivo.

These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, coronary arterial bypass grafting (CABG) surgery, chronic renal failure, angiogenesis & related processes, such as cancer, thrombosis, glomerulonephritis, diabetes and pancreatic β cells, multiple sclerosis, muscle degeneration, eczema, psoriasis, sunburn, and conjunctivitis are also included.

The CSBP inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406-1412; Badger, et al., (1989) *Circ. Shock* 27, 51-61; Votta et al., (1994) in vitro. *Bone* 15, 533-538; Lee et al., (1993). B *Ann. N.Y. Acad. Sci.* 696, 149-170.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I), or a pharmaceutically acceptable salt thereof, and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

In one embodiment of the present invention, the agents of the present invention are delivered via oral inhalation or intranasal administration. Appropriate dosage forms for such administration, such as an aerosol formulation or a metered dose inhaler, may be prepared by conventional techniques.

For administration by inhalation the compounds may be delivered in the form of an aerosol spray presentation from pressurized packs or a nebulizer, with the use of a suitable propellant, e.g. dichlorodifluoromethane, trichlorofluoromethane, dichlorotetrafluoroethane, a hydrofluoroalkane such as tetrafluoroethane or heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Dry powder compositions for topical delivery to the lung by inhalation may, for example, be presented in capsules and cartridges of for example gelatine or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di or poly-saccharides (e.g. lactose or starch). Use of lactose is preferred.

Each capsule or cartridge may generally contain between 20 μg-10 mg of the compound of formula (I) or (Ia) optionally in combination with another therapeutically active ingredient. Alternatively, the compound of the invention may be presented without excipients.

Suitably, the packing/medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant an inhaler having a reservoir form pack suitable for comprising multiple (un-metered doses) of medicament in dry powder form and including means for metering medicament dose from the reservoir to a delivery position. The metering means may for example comprise a metering cup, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

In the case of multi-dose delivery, the formulation can be pre-metered (e.g. as in Diskus, see GB 2242134, U.S. Pat. Nos. 6,632,666, 5,860,419, 5,873,360 and 5,590,645 or Diskhaler, see GB 2178965, 2129691 and 2169265, U.S. Pat. Nos. 4,778,054, 4,811,731, 5,035,237, the disclosures of which are hereby incorporated by reference) or metered in use (e.g. as in Turbuhaler, see EP 69715 or in the devices described in U.S. Pat. No. 6,321,747 the disclosures of which are hereby incorporated by reference). An example of a unit-dose device is Rotahaler (see GB 2064336 and U.S. Pat. No. 4,353,656, the disclosures of which are hereby incorporated by reference).

The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) or (Ia) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament there from.

In one aspect, the multi-dose blister pack comprises plural blisters arranged in generally circular fashion on a disc-form blister pack. In another aspect, the multi-dose blister pack is elongate in form, for example comprising a strip or a tape.

In one aspect, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Where the medicament container is an aerosol container, the valve typically comprises a valve body having an inlet port through which a medicament aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 μl, such as 25 μl, 50 μl or 63 μl. Suitably, the valve body defines a metering chamber for metering an amount of medicament formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of medicament formulation into the metering chamber.

The valve may also comprise a 'free flow aerosol valve' having a chamber and a valve stem extending into the chamber and movable relative to the chamber between dispensing and non-dispensing positions. The valve stem has a configuration and the chamber has an internal configuration such that a metered volume is defined there between and such that during movement between is non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation. A valve of this type is described in U.S. Pat. No. 5,772,085. Additionally, intra-nasal delivery of the present compounds is effective.

To formulate an effective pharmaceutical nasal composition, the medicament must be delivered readily to all portions of the nasal cavities (the target tissues) where it performs its pharmacological function. Additionally, the medicament should remain in contact with the target tissues for relatively long periods of time. The longer the medicament remains in contact with the target tissues, the medicament must be capable of resisting those forces in the nasal passages that function to remove particles from the nose. Such forces, referred to as 'mucociliary clearance', are recognised as being extremely effective in removing particles from the nose in a rapid manner, for example, within 10-30 minutes from the time the particles enter the nose.

Other desired characteristics of a nasal composition are that it must not contain ingredients which cause the user discomfort, that it has satisfactory stability and shelf-life properties, and that it does not include constituents that are considered to be detrimental to the environment, for example ozone depletors.

A suitable dosing regime for the formulation of the present invention when administered to the nose would be for the patient to inhale deeply subsequent to the nasal cavity being cleared. During inhalation the formulation would be applied to one nostril while the other is manually compressed. This procedure would then be repeated for the other nostril.

One means for applying the formulation of the present invention to the nasal passages is by use of a pre-compression pump. Most preferably, the pre-compression pump will be a VP7 model manufactured by Valois SA. Such a pump is beneficial as it will ensure that the formulation is not released until a sufficient force has been applied, otherwise smaller doses may be applied. Another advantage of the pre-compression pump is that atomisation of the spray is ensured as it will not release the formulation until the threshold pressure for effectively atomising the spray has been achieved. Typically, the VP7 model may be used with a bottle capable of holding 10-50 ml of a formulation. Each spray will typically deliver 50-100 μl of such a formulation; therefore, the VP7 model is capable of providing at least 100 metered doses.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of Formula (I) or (Ia) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants, e.g., oleic acid or lecithin and cosolvents, e.g. ethanol. Pressurised formulations will generally be retained in a canister (e.g. an aluminium canister) closed with a valve (e.g. a metering valve) and fitted into an actuator provided with a mouthpiece. Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means e.g., by micronization. The desired fraction may be separated out by air classification or sieving. Suitably, the particles will be crystalline in form. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulization may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Suitably, administration by inhalation may preferably target the organ of interest for respiratory diseases, i.e. the lung, and in doing so may reduce the efficacious dose needed to be delivered to the patient. In addition, administration by inhalation may reduce the systemic exposure of the compound thus avoiding effects of the compound outside the lung.

For all methods of use disclosed herein for the compounds of Formula (I), the daily oral dosage regimen will preferably be from about 0.05 to about 80 mg/kg of total body weight, preferably from about 0.1 to 30 mg/kg, more preferably from about 0.5 mg to 15 mg/kg, administered in one or more daily doses. The daily parenteral dosage regimen about 0.1 to about 80 mg/kg of total body weight, preferably from about 0.2 to about 30 mg/kg, and more preferably from about 0.5 mg to 15 mg/kg, administered in one or more daily doses. The daily topical dosage regimen will preferably be from 0.01 mg to 150 mg, administered one to four times daily. The daily inhalation dosage regimen will be from about 0.05 microgram/kg to about 1 mg/kg per day, preferably from about 0.2 microgram/kg to about 20 microgram/kg, administered in one or more daily doses. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of CSBP/p38 or cytokine inhibition or production. In particular, CSBP/p38 mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

Another aspect of the present invention is a method of treating the common cold or respiratory viral infection caused by human rhinovirus (HRV), other enteroviruses, coronavirus, influenza virus, parainfluenza virus, respiratory syncytial virus, or adenovirus in a human in need thereof which method comprises administering to said human an effective amount of a CBSP/p38 inhibitor.

Another aspect of the present invention is a method of treating, including prophylaxis of influenza induced pneumonia in a human in need thereof which method comprises administering to said human an effective amount of a CBSP/p38 inhibitor.

The present invention also relates to the use of the CSBP/p38 kinase inhibitor for the treatment, including prophylaxis, of inflammation associated with a viral infection of a human rhinovirus (HRV), other enteroviruses, coronavirus, influenza virus, parainfluenza virus, respiratory syncytial virus, or adenovirus.

In particular, the present invention is directed to the treatment of a viral infection in a human, which is caused by the human rhinovirus (HRV), other enteroviruses, coronavirus, influenza virus, parainfluenza virus, respiratory syncytial virus, or an adenovirus. In particular the invention is directed to respiratory viral infections that exacerbate asthma (induced by such infections), chronic bronchitis, chronic obstructive pulmonary disease, otitis media, and sinusitis. While inhibiting IL-8 or other cytokines may be beneficial in treating a rhinovirus may be known, the use of an inhibitor of the p38 kinase for treating HRV or other respiratory viral infections causing the common cold is believed novel.

It should be noted that the respiratory viral infection treated herein may also be associated with a secondary bacterial infection, such as otitis media, sinusitis, or pneumonia.

For use herein treatment may include prophylaxis for use in a treatment group susceptible to such infections. It may also include reducing the symptoms of, ameliorating the symptoms of, reducing the severity of, reducing the incidence of, or any other change in the condition of the patient, which improves the therapeutic outcome.

It should be noted that the treatment herein is not directed to the elimination or treatment of the viral organism itself but is directed to treatment of the respiratory viral infection that exacerbates other diseases or symptoms of disease, such as asthma (induced by such infections), chronic bronchitis, chronic obstructive pulmonary disease, otitis media, and sinusitis.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, $\beta_2$-adrenoreceptor agonist, an antiinfective agent (e.g. an antibiotic or an antiviral), or an antihistamine. One aspect of the present invention are combinations comprising a compound of Formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

One suitable combination of the present invention comprises of compound of the invention together with a $\beta_2$-adrenoreceptor agonist.

Examples of $\beta_2$-adrenoreceptor agonists include salmeterol (which may be a racemate or a single enantiomer, such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 24 hour period, such as salmeterol or formoterol.

Suitable long acting $\beta_2$-adrenoreceptor agonists include those described in WO02/66422A, WO02/270490, WO02/076933, WO03/024439, WO03/072539, WO 03/091204, WO04/016578, WO04/022547, WO04/037807, WO04/037773, WO04/037768, WO04/039762, WO04/039766, WO01/42193 and WO03/042160, whose disclosures are incorporated by reference herein.

Preferred long-acting $\beta_2$-adrenoreceptor agonists are:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]foramide, and
N-2-{2-[4-(3-phenyl-4-methoxyphenyl)aminophenyl] ethyl}-2-hydroxy-2-(8-hydroxy-2(1H)-quinolinon-5-yl) ethylamine.

Suitable anti-inflammatory agents include corticosteroids. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-17β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-17α-(1-methylcylopropylcarbonyl)oxy-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethylcyclopropylcarbonyl)oxy-androsta-1,4-diene-17β-carboxylic acid cyanomethyl ester, beclomethasone esters (such as the 17-propionate ester or the 17,21-dipropionate ester), budesonide, flunisolide, mometasone esters (such as the furoate ester), triamcinolone acetonide, rofleponide, ciclesonide, (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Non-steroidal compounds having glucocorticoid agonism that may possess selectivity for transrepression over transactivation and that may be useful in combination therapy include those covered in the following patents: WO03/082827, WO1/10143, WO98/54159, WO04/005229, WO04/009016, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277.

Suitable anti-inflammatory agents include non-steroidal anti-inflammatory drugs (NSAID's).

Suitable NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example, montelukast), iNOS inhibitors, tryptase and elastase inhibitors, beta-2 integrin antagonists and adenosine receptor agonists or antagonists (for example, adenosine 2a agonists), cytokine antagonists (for example, chemokine antagonists, such as a CCR3 antagonist) or inhibitors of cytokine synthesis, or 5-lipoxygenase inhibitors. Suitable other $\beta_2$-adrenoreceptor agonists include salmeterol (for example, as the xinafoate), salbutamol (for example, as the sulphate or the free base), formoterol (for example, as the fumarate), fenoterol or terbutaline and salts thereof. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722.

Another embodiment of the invention is the use of the compound of a Formula (1) or (Ia) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for another description of said assay. In one embodiment, PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 µM[$^3$H]-cAMP as the substrate.

Suitable PDE compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]; these are examples of compounds which bind preferentially to the low affinity binding site and which have an $IC_{50}$ ratio of 0.1 or greater.

Other compounds of interest include: Compounds set out in U.S. Pat. No. 5,552,438 issued 3 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms; AWD-12-281 from elbion (Hofgen, N. et al. 15th EFMC Int. Symp. Med. Chem. (September 6-10, Edinburgh) 1998, Abst. P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585. Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to with:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0; Homatropine—CAS-87-00-3, hydrobromide salt—CAS-51-56-9, methylbromide salt—CAS-80-49-9; Hyoscyamine (d, l)—CAS-101-31-5, hydrobromide salt—CAS-306-03-6 and sulfate salt—CAS-6835-16-1; and Scopolamine—CAS-51-34-3, hydrobromide salt—CAS-6533-68-2, methylbromide salt—CAS-155-41-9.

Suitable anticholinergics for use herein include, but are not limited to, ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO 01/04118, the disclosure of which is hereby incorporated by reference.

Other suitable anticholinergic agents include compounds of formula (XXI), which are disclosed in U.S. patent application 60/487981:

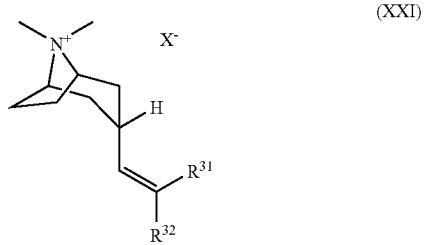

(XXI)

in which the preferred orientation of the alkyl chain attached to the tropane ring is endo;

$R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom.

$X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further suitable anticholinergic agents include compounds of formula (XXII) or (XXIII), which are disclosed in U.S. patent application 60/511009:

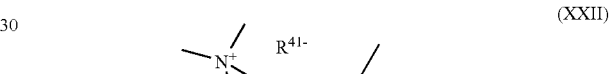

(XXII)

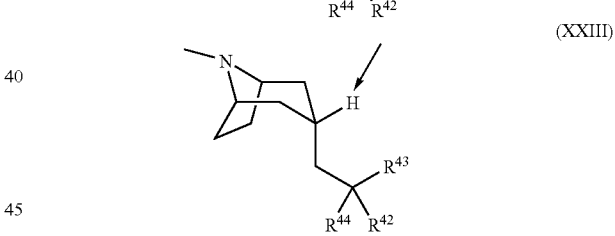

(XXIII)

wherein:
the H atom indicated is in the exo position;
$R^{41}$ represents an anion associated with the positive charge of the N atom. $R^{41}$ may be, but is not limited to, chloride, bromide, iodide, sulfate, benzene sulfonate and toluene sulfonate;
$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;
$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —$CN$, —CF$_3$, —CH$_2$O(CO)R$^{46}$, —CO$_2$R$^{47}$, —CH$_2$NH$_2$, —CH$_2$N(R$^{47}$)SO$_2$R$^{45}$, —SO$_2$N(R$^{47}$)(R$^{48}$), —CON(R$^{47}$)(R$^{48}$), —CH$_2$N(R$^{48}$)CO(R$^{46}$), —CH$_2$N(R$^{48}$)SO$_2$(R$^{46}$), —CH$_2$N(R$^{48}$)CO$_2$(R$^{45}$), —CH$_2$N(R$^{48}$)CONH(R$^{47}$);

R$^{45}$ is selected from the group consisting of (C$_1$-C$_6$)alkyl, (C$_1$-C$_6$)alkyl(C$_3$-C$_{12}$)cycloalkyl, (C$_1$-C$_6$)alkyl(C$_3$-C$_7$)heterocycloalkyl, (C$_1$-C$_6$)alkyl-aryl, (C$_1$-C$_6$)alkyl-heteroaryl;

R$^{46}$ is selected from the group consisting of (C$_1$-C$_6$)alkyl, (C$_3$-C$_{12}$)cycloalkyl, (C$_3$-C$_7$)heterocycloalkyl, (C$_1$-C$_6$)alkyl(C$_3$-C$_{12}$)cycloalkyl, (C$_1$-C$_6$)alkyl(C$_3$-C$_7$)heterocycloalkyl, aryl, heteroaryl, (C$_1$-C$_6$)alkyl-aryl, (C$_1$-C$_6$)alkyl-heteroaryl;

R$^{47}$ and R$^{48}$ are, independently, selected from the group consisting of H, (C$_1$-C$_6$)alkyl, (C$_3$-C$_{12}$)cycloalkyl, (C$_3$-C$_7$)heterocycloalkyl, (C$_1$-C$_6$)alkyl(C$_3$-C$_{12}$)cycloalkyl, (C$_1$-C$_6$)alkyl(C$_3$-C$_7$)heterocycloalkyl, (C$_1$-C$_6$)alkyl-aryl, and (C$_1$-C$_6$)alkyl-heteroaryl.

Representative examples included are:
(Endo)-3-(2-methoxy-2,2-di-thiophen-2-yl-ethyl)-8,8-dimethyl-8-azonia-bicyclo[3.2.1]octane iodide;
3-((Endo)-8-methyl-8-aza-bicyclo[3.2.1]oct-3-yl)-2,2-diphenyl-propionitrile;
(Endo)-8-methyl-3-(2,2,2-triphenyl-ethyl)-8-aza-bicyclo[3.2.1]octane;
3-((Endo)-8-methyl-8-aza-bicyclo[3.2.1]oct-3-yl)-2,2-diphenyl-propionamide;
3-((Endo)-8-methyl-8-aza-bicyclo[3.2.1]oct-3-yl)-2,2-diphenyl-propionic acid;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
3-((Endo)-8-methyl-8-aza-bicyclo[3.2.1]oct-3-yl)-2,2-diphenyl-propan-1-ol;
N-Benzyl-3-((endo)-8-methyl-8-aza-bicyclo[3.2.1]oct-3-yl)-2,2-diphenyl-propionamide;
(Endo)-3-(2-carbamoyl-2,2-diphenyl-ethyl)-8,8-dimethyl-8-azonia-bicyclo[3.2.1]octane iodide;
1-Benzyl-3-[3-((endo)-8-methyl-8-aza-bicyclo[3.2.1]oct-3-yl)-2,2-diphenyl-propyl]urea;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-di-thiophen-2-yl-propionitrile;
(Endo)-3-(2-cyano-2,2-di-thiophen-2-yl-ethyl)-8,8-dimethyl-8-azonia-bicyclo[3.2.1]octane iodide;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-methanesulfonamide; and/or
(Endo)-3-{2,2-diphenyl-3-[(1-phenyl-methanoyl)-amino]-propyl}-8,8-dimethyl-8-azonia-bicyclo[3.2.1]octane bromide.

Preferred compounds useful in the present invention include:
(Endo)-3-(2-methoxy-2,2-di-thiophen-2-yl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
(Endo)-3-(2-carbamoyl-2,2-diphenyl-ethyl)-8,8-dimethyl-8-azonia-bicyclo[3.2.1]octane iodide;
(Endo)-3-(2-cyano-2,2-di-thiophen-2-yl-ethyl)-8,8-dimethyl-8-azonia-bicyclo[3.2.1]octane iodide; and/or
(Endo)-3-{2,2-diphenyl-3-[(1-phenyl-methanoyl)-amino]-propyl}-8,8-dimethyl-8-azonia-bicyclo[3.2.1]octane bromide.

Suitable antihistamines (also referred to as H$_1$-receptor antagonists) include any one or more of the numerous antagonists known which inhibit H$_1$-receptors, and are safe for human use. All are reversible, competitive inhibitors of the interaction of histamine with H$_1$-receptors. The majority of these inhibitors, mostly first generation antagonists, have a core structure, which can be represented by the following formula:

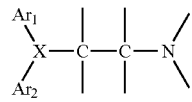

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.
Ethylenediamines: pyrilamine maleate, tripelennamine HCl, and tripelennamine citrate.
Alkylamines: chloropheniramine and its salts such as the maleate salt, and acrivastine.
Piperazines: hydroxyzine HCl, hydroxyzine pamoate, cyclizine HCl, cyclizine lactate, meclizine HCl, and cetirizine HCl.
Piperidines: Astemizole, levocabastine HCl, loratadine or its descarboethoxy analogue, and terfenadine and fexofenadine hydrochloride or another pharmaceutically acceptable salt.

Azelastine hydrochloride is yet another H$_1$ receptor antagonist which may be used in combination with a PDE4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

The invention will now be described by reference to the following biological examples which are merely illustrative and are not to be construed as a limitation of the scope of the present invention.

BIOLOGICAL EXAMPLES

The cytokine-inhibiting effects of compounds of the present invention may be determined by the following in vitro assays:

Assays for Interleukin-1 (IL-1beta), Interleukin-8 (IL-8), and Tumour Necrosis Factor (TNFalpha) are well known in the art, and may be found in a number of publications, and patents. Representative suitable assays for use herein are described in Adams et al., U.S. Pat. No. 5,593,992, whose disclosure is incorporated by reference in its entirety.

It is recognized that the respective assays herein may have been run multiple times for particular compounds of Formula (I) or (Ia), etc. as described herein. The determination of activity, as reported in these assays, will be based upon a mean or median of these values.

Interleukin-1 (IL-1)

Human peripheral blood monocytes are isolated and purified from either fresh blood preparations from volunteer donors, or from blood bank buffy coats, according to the procedure of Colotta et al, J Immunol, 132, 936 (1984), or another suitable procedure such as positive selection using MACS CD14+ beads. These monocytes ($1 \times 10^6$) are plated in 24, 48, 96 or 384-well plates at a concentration of 1-2 million/ml per well. The cells are allowed to adhere for 2 hours, after which time non-adherent cells can be removed by gentle washing. Test compounds are then added to the cells for 1 h before the addition of lipopolysaccharide (50-200 ng/ml), and the cultures are incubated at 37° C. for an additional 24 h. At the end of this period, culture supernatants are removed and clarified of cells and all debris. IL-1beta levels in the cell-free supernatant are then determined by enzyme-linked immunoassay (ELISA) or other antibody based procedure.

In Vivo TNF Assay:

(1) Griswold et al., *Drugs Under Exp. and Clinical Res.*, XIX (6), 243-248 (1993); or (2) Boehm, et al., *Journal Of Medicinal Chemistry* 39, 3929-3937 (1996) whose disclosures are incorporated by reference herein in their entirety.

LPS-Induced TNFα Production in Mice and Rats

In order to evaluate in vivo inhibition of LPS-induced TNFα production in rodents, both mice or rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055-B5, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-B5, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, Olivera et al., Circ. Shock, 37, 301-306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat antirabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes or multiwell plates containing compounds and LPS in 0.2-0.4 mL volumes and the tubes incubated at 37 C. In some studies, compound was incubated with blood for up to 30 min prior to addition of LPS. Following a 4 hour incubation, the tubes or plates were centrifuged to remove cells and plasma was withdrawn and frozen at −80 C.

Cytokine measurement: IL-1beta and/or TNFalpha were quantified using a standardized ELISA, or similar technology. Concentrations of IL-1beta or TNFalpha were determined from standard curves of the appropriate cytokine and IC50 values for test compound (concentration that inhibited 50% of LPS-stimulated cytokine production) were calculated by linear regression analysis.

Results

Compounds would be considered active in this assay if they demonstrated an IC50 of less than 10 uM up to about an IC50 of less than 0.0001 uM.

Representative compounds of Formula (I) and (Ia) as described in Examples 3, 4, 21(c), 22, 24, 25, 27, 29, 30, 31(e), 32, 35, 37(b), 38, 40, 44, 46, 47, 54, 56(d), 57-66, 68-78, 79(c), 82, 87, 99, 101-105, 107, 109, 118(b), 122-125, 128, and 129 were tested in the above assay and found active. Compounds of Examples 93, 97(b), and 100 demonstrated an IC50 of greater than 1.0 uM in this assay. While these compounds were found to be inhibit greater than 50% at a 1 uM of TNF-alpha, some of these would be expected upon retesting with increasing concentrations to reach 50% inhibition.

CSBP/p38 Kinase Assay:

This assay measures the CSBP/p38-catalyzed transfer of $^{32}P$ from [a-$^{32}P$]ATP to threonine residue in an epidermal growth factor receptor (EGFR)-derived peptide (T669) with the following sequence: KRELVEPLTPSGEAPNQALLR (residues 661-681). (See Gallagher et al., "Regulation of Stress Induced Cytokine Production by Pyridinyl Imidazoles: Inhibition of CSBP Kinase", BioOrganic & Medicinal Chemistry, 1997, 5, 49-64).

Reactions were carried in round bottom 96 well plate (from Corning) in a 30 ml volume. Reactions contained (in final concentration): 25 mM Hepes, pH 7.5; 8 mM $MgCl_2$; 0.17 mM ATP (the $Km_{[ATP]}$ of p38 (see Lee et al., Nature 300, n72 pg. 639-746 (December 1994)); 2.5 uCi of [g-32P]ATP; 0.2 mM sodium orthovanadate; 1 mM DTT; 0.1% BSA; 10% glycerol; 0.67 mM T669 peptide; and 2-4 nM of yeast-expressed, activated and purified p38. Reactions were initiated by the addition of [gamma-32P]Mg/ATP, and incubated for 25 min. at 37° C. Inhibitors (dissolved in DMSO) were incubated with the reaction mixture on ice for 30 minutes prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter.

Under these conditions, the specific activity of p38 was 400-450 pmol/pmol enzyme, and the activity was linear for up to 2 hours of incubation. The kinase activity values were obtained after subtracting values generated in the absence of substrate which were 10-15% of total values.

Fluorescence Anisotropy Kinase Binding Assay—Standard Volume

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10× $K_i$) of a potent inhibitor the anisotropy of the unbound fluorescent ligand is measurably different from the bound value.

The concentration of kinase enzyme should preferably be $\geq 2 \times K_f$. The concentration of fluorescent ligand required will depend on the instrumentation used, and the fluorescent and physicochemical properties. The concentration used must be lower than the concentration of kinase enzyme, and preferably less than half the kinase enzyme concentration.

The fluorescent ligand is the following compound:

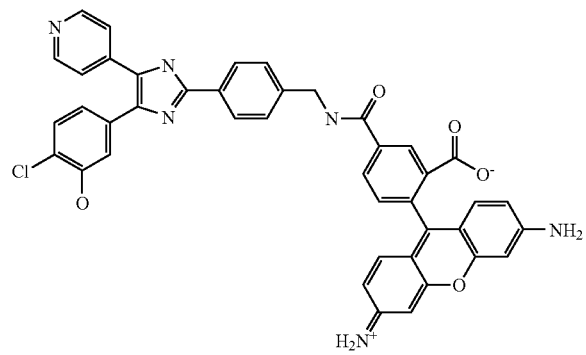

which is derived from 5-[2-(4-aminomethylphenyl)-5-pyridin-4-yl-1H-imidazol-4-yl]-2-chlorophenol and rhodamine green.

Recombinant human p38a was expressed as a GST-tagged protein. To activate this protein, 3.5 μM unactivated p38α was incubated in 50 mM Tris-HCl pH 7.5, 0.1 mM EGTA, 0.1% 2-mercaptoethanol, 0.1 mM sodium vanadate, 10 mM MgAc, 0.1 mM ATP with 200 nM MBP-MKK6 DD at 30 degrees for 30 mins. Following activation p38α was re-purified and the activity assessed using a standard filter-binding assay.

Protocol: All components are dissolved in buffer of composition 62.5 mM HEPES, pH 7.5, 1.25 mM CHAPS, 1 mM DTT, 12.5 mM MgCl$_2$ with final concentrations of 12 nM p38α and 5 nM fluorescent ligand. 30 μl of this reaction mixture is added to wells containing 1 μl of various concentrations of test compound (0.28 nM-16.6 μM final) or DMSO vehicle (3% final) in NUNC 384 well black microtitre plate and equilibrated for 30-60 mins at room temperature. Fluorescence anisotropy is read in Molecular Devices Acquest (excitation 485 nm/emission 535 nm).

Definitions: Ki=dissociation constant for inhibitor binding
Kf=dissociation constant for fluorescent ligand binding Fluorescence Anisotropy Kinase Binding Low Volume Assay The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme should preferably be 2×Kf. The concentration of fluorescent ligand required will depend on the instrumentation used, and the fluorescent and physicochemical properties. The concentration used must be lower than the concentration of kinase enzyme, and preferably less than half the kinase enzyme concentration.

The fluorescent ligand is the following compound:

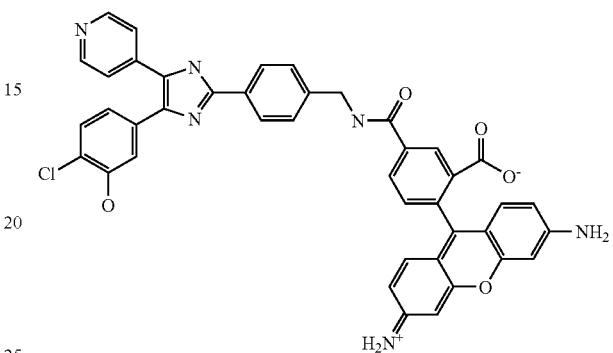

which is derived from 5-[2-(4-aminomethylphenyl)-5-pyridin-4-yl-1H-imidazol-4-yl]-2-chlorophenol and rhodamine green.

Recombinant human p38α was expressed as a GST-tagged protein. To activate this protein, 3.5 μM unactivated p38α was incubated in 50 mM Tris-HCl pH 7.5, 0.1 mM EGTA, 0.1% 2-mercaptoethanol, 0.1 mM sodium vanadate, 10 mM MgAc, 0.1 mM ATP with 200 nM MBP-MKK6 DD at 30 degrees for 30 mins. Following activation p38α was re-purified and the activity assessed using a standard filter-binding assay.

Protocol: All components are dissolved in buffer of composition 62.5 mM HEPES, pH 7.5, 1.25 mM CHAPS, 1 mM DTT, 12.5 mM MgCl$_2$ with final concentrations of 12 nM p38α and 5 nM fluorescent ligand. 30 μl of this reaction mixture is added to wells containing 0.1 μl of various concentrations of test compound (0.02 nM-25 μM final) or DMSO vehicle (1.7% final) in Greiner low volume 384 well black microtitre plate and equilibrated for 30-60 mins at room temperature. Fluorescence anisotropy is read in Molecular Devices Acquest (excitation 485 nm/emission 535 nm).

Definitions: Ki=dissociation constant for inhibitor binding
Kf=dissociation constant for fluorescent ligand binding It is noted that there are two assay formats shown above for the Fluorescence anisotropy kinase binding assay. The only difference between these two assays is the volume used and the plate type. It has been demonstrated that there is no difference in potency between the two formats, and that the assays are considered to be equivalent. The results described herein may have been performed in either assay format and are not differentiated as to which.

Results

Compounds are considered active in this assay if they demonstrate a pIC50 of greater than 4.6 up to about a pIC50 of 9.0. Representative compounds of Formula (I) and (Ia) as described in Examples 1(d), 2(b), 3 to 6, 7(c), 7(d), 8, 11, 12c, 13, 17, 18e, 19(a), 19(c), 20, 21(a), 21(c), 22 to 20, 31(e), 32, 34, 35, 36, 37a, 37b, 38 to 55, 56(d), 57 to 61 to 78, 79(c), 80(a), 80(b), 81 to 95, 97(b), 98 to 112, 113(b), 114(b), 115, 116b, 116(c), 117, 118a, 118b, 119 to 121, and 202c were tested in the above assay and demonstrated pIC$_{50}$ values of between 5.1 and 8.4.

The compounds of Example 1(a), Example 9, Example 96(d) and Example 114b did not demonstrate an IC50 at a concentration of less than 16 uM resulting in a pIC50 of less than 4.8 in this assay.

TR-FRET Assay

Time-Resolved Fluorescence Resonance Energy Transfer Kinase Standard Assay

Recombinant human p38α was expressed as a His-tagged protein. To activate this protein, 3 μM unactivated p38α was incubated in 200 mM Hepes pH 7.4, 625 mM NaCl, 1 mM DTT with 27 nM active MKK6 (Upstate), 1 mM ATP and 10 mM $MgCl_2$ The activity of the MKK6-activated p38α was assessed using a time-resolved fluorescence resonance energy transfer (TR-FRET) assay.

Biotinylated-GST-ATF2 (residues 19-96, 400 nM final), ATP (125M final) and MgCl2 (5 mM final) in assay buffer (40 mM HEPES pH 7.4, 1 mM DTT) were added to wells containing 1 ul of various concentrations of compound or DMSO vehicle (3% final) in NUNC 384 well black plate. The reaction was initiated by the addition of MKK6-activated p38 (100 pM final) to give a total volume of 30 ul. The reaction was incubated for 120 minutes at room temperature, then terminated by the addition of 15 μl of 100 mM EDTA pH 7.4. Detection reagent (15 μl) in buffer (100 mM HEPES pH 7.4, 150 mM NaCl, 0.1% w/v BSA, 1 mM DTT) containing antiphospho-threonine-ATF2-71 polyclonal antibody (Cell Signalling Technology, Beverly Mass., USA) labelled with W-1024 europium chelate (Wallac OY, Turku, Finland), and APC-labelled streptavidin (Prozyme, San Leandro, Calif., USA) was added and the reaction was further incubated for 60 minutes at room temperature. The degree of phosphorylation of GST-ATF2 was measured using a Packard Discovery plate reader (Perkin-Elmer Life Sciences, Pangbourne, UK) as a ratio of specific 665 nm energy transfer signal to reference europium 620 nm signal.

Time-Resolved Fluorescence Resonance Energy Transfer Kinase Low Volume Assay

Recombinant human p38α was expressed as a His-tagged protein. To activate this protein, 3 μM unactivated p38α was incubated in 200 mM Hepes pH7.4, 625 mM NaCl, 1 mM DTT with 27 nM active MKK6 (Upstate), 1 mM ATP and 10 mM $MgCl_2$ The activity of the MKK6-activated p38α was assessed using a time-resolved fluorescence resonance energy transfer (TR-FRET) assay.

Biotinylated-GST-ATF2 (residues 19-96, 400 nM final), ATP (125 μM final) and $MgCl_2$ (5 nM final) in assay buffer (40 mM HEPES pH 7.4, 1 mM DTT) were added to wells containing 0.1 μl of various concentrations of compound or DMSO vehicle (1.7% final) in Greiner low volume 384 well black plate. The reaction was initiated by the addition of MKK6-activated p38α (100 pM final) to give a total volume of 6 μl. The reaction was incubated for 120 minutes at room temperature, then terminated by the addition of 3 μl of detection reagent in buffer (100 mM HEPES pH 7.4, 150 mM NaCl, 0.1% w/v BSA, 1 mM DTT, 100 mM EDTA) containing antiphosphothreonine-ATF2-71 polyclonal antibody (Cell Signalling Technology, Beverly Mass., USA) labelled with W-1024 europium chelate (Wallac OY, Turku, Finland), and APC-labelled streptavidin (Prozyme, San Leandro, Calif., USA). The reaction was further incubated for 60 minutes at room temperature. The degree of phosphorylation of GST-ATF2 was measured using a BMG Rubystar plate reader (BMG, UK) as a ratio of specific 665 nm energy transfer signal to reference europium 620 nm signal.

It is noted that there are two assay formats shown above for the Time-resolved fluorescence resonance energy transfer kinase assay. The only difference between these two assays is the volume used and the plate type. It has been demonstrated that there is no difference in potency between the two formats, and that the assays are considered to be equivalent. The results described herein may have been performed in either assay format and are not differentiated as to which.

Results

Compounds are considered active in this assay if they demonstrate a pIC50 of greater than 4.6 up to about a pIC50 of greater than 10.0.

Representative compounds of Formula (I) and (Ia) were tested in this assay, and as described in Examples 9, 10, 15, 18(e), 31(e), 34, 36, 56(d), 57, 60 to 62, 66, 74, 78, 79(c), 98 to 107, 109, 112, 113(b), 114(b), 117, 118(a), 118(b), 119 to 149, 150(d), 151 to 156, 158 to 160, 162, 163(b), 163(c), 164 to 178, 179(b), 179(c), 180 to 187, 188(b), 189 to 192, 193(a), 193(b), 194 to 201 are active in this assay.

Example 97(b), and Example 115 upon multiple runs provided a broad range of data, ranging from 7.4 to less than 4.6 of a pIC50 in this assay. Example 188(a) did not demonstrate an IC50 at a concentration of less than 16 uM resulting in a pIC50 of less than 4.8 in this assay.

For purposes herein the HTRF assay and the Fluorescence anisotropy kinase binding assay:

| $pIC_{50}$ | $IC_{50}$ (nM) | $IC_{50}$ (uM) |
|---|---|---|
| 4.00 | 100,000.0 | 100 |
| 5.00 | 100,000.0 | 10 |
| 6.00 | 1,000.0 | 1 |
| 7.00 | 100.0 | 0.1 |
| 8.00 | 10.0 | 0.01 |
| 9.00 | 1.0 | 0.001 |
| 10.00 | 0.1 | 0.0001 |

TNF-Stimulated IL-8 Production from Human Neutrophils

The effect of test compounds on TNF-stimulated IL8 production by human neutrophils is measured as follows. Neutrophils are prepared from blood obtained from consenting donors, using standard methods. Blood is collected in heparinized syringes and layered over histopaque (30 ml/20 ml). Following centrifugation, the red cell pellet is resuspended in PBS and purified over a dextran gradient. Red blood cells are lysed with water for 40 sec, remaining granulocytes collected by centrifugation and resuspended at $1.5 \times 10^6$ cells/ml. Cells are added (0.5-1 ml) to 48 well plates already containing compound at 1000× final concentration in neat DMSO or 10% DMSO in RPMI1640 with 10% FBS. TNF (final concentration 100 ng/ml) is used as the stimulus. Cells incubated for approximately 20 hrs at 37° C., 5% CO2. Levels of IL-8 in the cell free supernatant are determined by sandwich ELISA, and inhibition relative to a control with DMPO but no compound is calculated.

Results

Compounds would be considered active in this assay if they demonstrated an IC50 of less than 10 uM up to about an IC50 of less than 0.0001 uM, and were screened at concentrations up to 100 nM.

Representative compounds of Formula (I) and (Ia) as described in Examples 2(b), 3, 5, 6, 8, 13, 18(e), 21(c), 22-26, 28-30, 31(e), 32-36, 37(a) and (b), 38-47, 54, 56(d), 57-66, 68-78, 79(c), 80(b), 81-85, 87, 95, 99-105, 107, 109, 112, 113(b), 114(b), 115, 117, 118(b), 119, 122-129, 132-145, 147-149, 150(d), 151, 158-160, 162, 163(c), 164-170, 172-178, 179(c), 180-187, 193(b), and 194-201 were tested in the above assay and found active.

Compounds of Examples 1(a), 7(c) and (d), 9-11, 12(c), 14(c), 15-17, 51-53, 80(a), 110, 111, 116(b), 118(a), 146, 152-157, 163(b), 171, 170(b), 188(a) and (b), 193(a), 189, and 191-192 demonstrated an IC50 of greater than 0.1 uM in this assay. Compounds of Examples 130 and 131 demonstrated an IC50 of greater than 0.01 uM in this assay. Example 190 demonstrated an IC50 of greater than 0.03 uM in this assay. These later compounds were screened at a different top concentration than the above grouping. While these compounds were not found to inhibit the production of IL-8 at greater than 50% at a 100 nM, some of these would be expected upon retesting with increasing concentrations to reach 50% inhibition.

Compounds of Examples 202(c) upon multiple runs provided a broad range of data, ranging from an IC50 of 0.01 uM to an IC50 of greater than 0.1 uM in this assay. Example 120 upon multiple runs provided a broad range of data, ranging from an IC50 of greater than 0.001 uM to greater than 0.1 uM in this assay.

Rat LPS Neutrophilia Model

The effect of compounds on the influx of neutrophils to the lung in LPS-challenged rats is evaluated as follows. The test compound is suspended in one of the following solutions: 0.5% tween 80/PBS, 0.5% tween 80/saline, 10% EtOH/saline (with pH adjusted to 2.0, or 8.0 with HCl, or unadjusted), Saline @ pH 2.0, 6.5 or 8.0, 0.5% Tragacanth, 1% DMSO/20% Encapsin/Saline, or acidified 5% Tragacanth. The suspension process may be aided by the use of a glass homogenizer. For intratracheal administration, the animals are anesthetized with inhaled isoflurane and placed in a supine position, the trachea is intubated with a steel gavage needle (1.5 inch, 22 gauge, small ball) or a Penn-Century Microsprayer Aerosolizer (model IA-IB) and 200 ul of dosing solution is delivered. The animals are visually monitored during the recovery process, which typically occurs within two minutes. It is noted that the test compounds may be alternatively administered via the microsprayer in a dry powder blend with a suitable excipient, such as lactose.

Rats treated with compound or vehicle (15 min-24 hours pretreatment) are exposed to an LPS aerosol (100 ug/ml) for 15 min. Four hours later the rats are euthanized with pentobarbital (100 mg/kg, i.p.) and the airways are lavaged with 5 washes of 5 ml of phosphate buffered saline. The harvested cells are stained (Diffquick) and counted to determine total and differential cell data. In a typical study, macrophages represent 40-70% of the total cells, and polymorphonuclear cells 30-60% of the total cells. Inhibition of neutrophil levels relative to no compound controls is calculated based on the differential counts.

The assay has varying conditions, such as concentration, pretreat time, form of the compound (crystalline, amorphous, salts, micronised), and a wet or dry application of the compound.

The data is obtained as % inhibition using a particular concentration and pretreat time. While a number of the compounds were found to be statistically nonsignificant (p>0.05), it is expected that upon retesting with either increasing concentrations, and/or a change in pretreat time that some of them may reach statistical significance (p<0.05).

Representative compounds of the invention have been tested in this assay.

Compounds of Examples 4, 22, 27, 29, 31(e), 34, 44, 56(d), 57, 58, 59, 60, 61, 66, 68, 69, 72, 73, 77, 78, 79(c), 101, 103, 104, 105, 107, 109, 117, 119, 124, 133, 137, 160, 166, 167, and 173 were found to have statistically significant inhibition of neutrophilia in at least one of the range of conditions tested in this assay.

Compounds of Examples 23, 24, 25, 28, 32, 67, 70, 71, 76, 95, 99, 100, 102, 112, 113(b), 115, 118(b), 120, 122, 125, 129, 130, 132, 134, 138, 147, 162, 163(c), 169, 178, 181, and 185 were found to have statistically nonsignificant inhibition of neutrophilia in at least one of the range of conditions tested in this assay.

Compounds of Examples 120, 128, 135, 149, 168, 172, 174, and 175 were found to be inactive in this assay.

TNF-α in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 whose disclosure is incorporated herein by reference.

CNS Injury Model for IL-b mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

Rhinovirus/Influenza Assay:

Cell lines, rhinovirus serotype 39, and influenza virus A/PR/8/34 were purchased from American Type Culture Collection (ATCC). BEAS-2B cells were cultured according to instructions provided by ATCC using BEGM (bronchial epithelial growth media) purchased from Clonetics Corp. HELA cell cultures, used for detection and titration of virus, were maintained in Eagle's minimum essential media containing 10% fetal calf serum, 2 mM l-glutamine, and 10 mM HEPES buffer (MEM).

A modification of the method reported by Subauste et al., Supra, for in vitro infection of human bronchial epithelial cells with rhinovirus was used in these studies. BEAS-2B cells ($2\times10^5$/well) were cultured in collagen-coated wells for 24 hours prior to infection with rhinovirus. Rhinovirus serotype 39 was added to cell cultures for one hour incubation at 34° C. after which inoculum was replaced with fresh media and cultures were incubated for an additional 72 hours at 34° C. Supernatants collected at 72 hours post-infection were assayed for cytokine protein concentration by ELISA using commercially available kits (R&D Systems). Virus yield was also determined from culture supernatants using a microtitration assay in HELA cell cultures (Subauste et al., supra 1995). In cultures treated with p38 kinase inhibitors, drug was added 30 minutes prior to infection. Stocks of compounds were prepared in DMSO (10 mM drug) and stored at −20° C.

For detection of p38 kinase, cultures were incubated in basal media without growth factors and additives to reduce endogenous levels of activated p38 kinase. Cells were harvested at various time points after addition of rhinovirus. Detection of tyrosine phosphorylated p38 kinase by immunoblot was analyzed by a commercially available kit and was performed according to the manufacturer's instructions (PhosphoPlus p38 MAPK Antibody Kit: New England BioLabs Inc.).

In some experiments, BEAS-2B cells were infected with influenza virus (strain A/PR/8/34) in place of rhinovirus. Culture supernatant was harvested 48 and 72 hour post-infection and tested by ELISA for cytokine as described above.

Cells and Virus: Influenza A/PR/8/34 sub type H1N1 (VR-95 American Type Culture Collection, Rockville, Md.) was grown in the allantoic cavity of 10 day old chicken eggs. Following incubation at 37° C., and refrigeration for 2½ hours at 4° C., allantoic fluid was harvested, pooled, and centrifuged (1,000 rcf; 15 min; 4° C.) to remove cells. Supernatent was aliquoted and stored at −70° C. The titer of the stock culture of virus was $1.0 \times 10^{10}$ Tissue Culture Infective Dose/ml ($TCID_{50}$)

Inoculation Procedure: Four-six week old female Balb/cAnNcrlBr mice were obtained from Charles River, Raleigh, N.C. Animals were infected intranasally. Mice were anesthetized by intraperitoneal injection of Ketamine (40 mg/kg; Fort Dodge Labs, Fort Dodge, Iowa) and Xylazine (5 mg/kg; Miles, Shawnee Mission, Kans.) and then inoculated with 100 TCID50 of PR8 diluted in PBS in 20 ul. Animals were observed daily for signs of infection. All animal studies were approved by SmithKline Beecham Pharmaceuticals Institutional Animal Care and Use Committee.

Virus Titration: At various times post infection, animals were sacrificed and lungs were aseptically harvested. Tissues were homogenized, in vials containing 1 micron glass beads (Biospec Products, Bartlesville, Okla.) and 1 ml. of Eagles minimal essential medium. Cell debris was cleared by centrifugation at 1,000 rcf for 15 minutes at 4° C., and supernatants were serially diluted on Madin-Darby canine kidney (MDCK) cells. After 5 days of incubation at 37° C. (5% $CO_2$), 50 µl of 0.5% chick red blood cells were added per well, and agglutination was read after 1 hour at room temperature. The virus titer is expressed as 50% tissue culture infective dose ($TCID_{50}$) calculated by logistic regression.

ELISA: Cytokine levels were measured by quantitative ELISA using commercially available kits. Ear samples were homogenized using a tissue minser in PBS. Cell debris was cleared by centrifugation at 14,000 rpm for 5 minutes. The cytokine concentrations and thresholds were determined as described by the manufacturer; IL-6, IFN-γ, and KC (R&D Systems, Minneapolis, Minn.).

Myeloperoxidase Assay: Myeloperoxidase (MPO) activity was determined kinetically as described by Bradley et al. (1982). Briefly, rabbit cornea were homogenized in Hexadecyl Trimethyl-Ammonium Bromide (HTAB) (Sigma Chemical Co. St. Louis, Mo.) which was dissolved in 0.5 m Potassium phosphate buffer (J.T. Baker Scientific, Phillipsburg, N.J.). Following homogenization, the samples were subjected to freeze-thaw-sonication (Cole-Parmer 8853, Cole-Parmer, Vernon Hills, Ill.) 3 times. Suspensions were then cleared by centrifugation at 12,500×g for 15 minutes at 4° C. MPO enzymatic activity was determined by colormetric change in absorbance during a reaction of O-Dianisidine dihydrochloride (ODI) 0.175 mg/ml (Sigma Chemical Co. St. Louis, Mo.) with 0.0002% Hydrogen peroxide (Sigma Chemical Co. St. Louis, Mo.). Measurements were performed by using a Beckman Du 640 Spectrophotometer (Fullerton, Calif.) fitted with a temperature control device. 50 ul of material to be assayed was added to 950 ul of ODI and change in absorbance was measured at a wave length of 460 nm for 2 minutes at 25° C.

Whole Body Pletdiysomographzy: Influenza virus infected mice were placed into a whole body plethysomograph box with an internal volume of approximately 350-ml. A bias airflow of one 1/min was applied to the box and flow changes were measured and recorded with a Buxco XA data acquisition and respiratory analysis system (Buxco Electronics, Sharon, Conn.). Animals were allowed to acclimate to the plethysmograph box for 2 min. before airflow data was recorded. Airway measurements were calculated as Penh (enhanced pause). Penh has previously been shown as an index of airway obstruction and correlates with increased intrapleural pressure. The algorithm for Penh calculation is as follows: Penh=[(expiratory time/relaxation time)−1]×(peak expiratory flow/peak inspiratory flow) where relaxation time is the amount of time required for 70% of the tidal volume to be expired.

Determination of Arterial Oxygen Saturation. A Nonin veterinary hand held pulse oximeter 8500V with lingual sensor (Nonin Medical, Inc., Plymouth Minn.) was used to determine daily arterial oxygen saturation % SpO2 as described (Sidwell et al. 1992 Antimicrobial Agents and Chemotherapy 36:473-476).

Additional data and assay modifications may be found in PCT/US00/25386, (WO 01/19322) filed 15 Sep. 2000, whose disclosure is incorporated herein by reference in its entirety.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound of the formula:

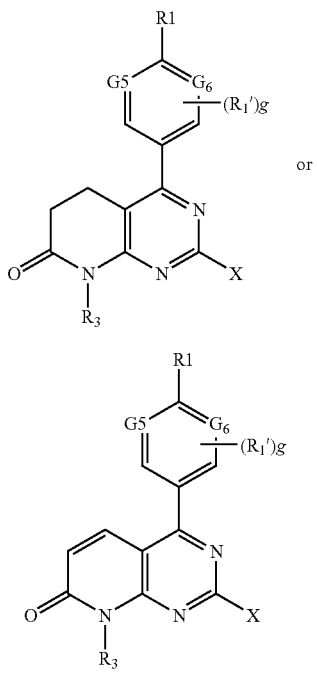

wherein $G_5$ and $G_6$ are independently selected from nitrogen or CH, provided that only one of G5 or G6 is nitrogen and the other is CH;

$R_1$ is $C(Z)N(R_{10'})(CR_{10}R_{20})_v R_b$, $C(Z)O(CR_{10}R_{20})_v R_b$, $N(R_{10'})C(Z)(CR_{10}R_{20})_v R_b$, $N(R_{10'})C(Z)N(R_{10'})(CR_{10}R_{20})_v R_b$, or $N(R_{10'})OC(Z)(CR_{10}R_{20})_v R_b$;

$R_{1'}$ is independently selected at each occurrence from halogen, $C_{1-4}$ alkyl, halo-substituted-$C_{1-4}$ alkyl, cyano, nitro, $(CR_{10}R_{20})_v NR_q R_{q'}$, $(CR_{10}R_{20})_v C(O)R_{12}$, $SR_5$, $S(O)R_5$, $S(O)_2 R_5$, or $(CR_{10}R_{20})_v OR_{13}$;

$R_b$ is hydrogen, $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic, or heterocyclyl$C_{1-10}$ alkyl moiety, which moieties, excluding hydrogen, may all be optionally substituted;

X is $R_2$, $OR_{2'}$, $S(O)_m R_{2'}$, $(CH_2)_n N(R_{10'}) S(O)_m R_{2'}$, $(CH_2)_n N(R_{10'}) C(O) R_{2'}$, $(CH_2)_n NR_4 R_{14}$, $(CH_2)_n N(R_{2'}) (R_{2''})$, or $N(R_{10'})R_h NH—C(=N—CN)NR_q R_{q'}$;

$X_1$ is $N(R_{11})$, O, $S(O)_m$, or $CR_{10}R_{20}$;

$R_h$ is selected from an optionally substituted $C_{1-10}$ alkyl, $—CH_2—C(O)—CH_2—$, $—CH_2—CH_2—O—CH_2—CH_2—$, $—CH_2—C(O)N(R_{10'})CH_2—CH_2—$, $—CH_2—$ $N(R_{10'})C(O)CH_2—$, $—CH_2—CH(OR_{10'})—CH_2—$, $—CH_2—C(O)O—CH_2—CH_2—$, or $—CH_2—CH_2—O—C(O)CH_2—$;

$R_q$ and $R_{q'}$ are independently selected at each occurrence from hydrogen, $C_{1-10}$ alkyl, $C_{3-7}$ cycloalkyl, $C_{3-7}$ cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted, or $R_q$ and $R_{q'}$ together with the nitrogen to which they are attached form an optionally substituted heterocyclic ring of 5 to 7 members, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkyl $C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_q X_1 (CR_{10}R_{20})_q C(A_1)(A_2)(A_3)$, or $(CR_{10}R_{20})_q C(A_1)(A_2)(A_3)$;

$R_{2'}$ is hydrogen, $C_{1-10}$ alkyl, $C_{3-7}$ cycloalkyl, $C_{3-7}$ cycloalkyl $C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkyl $C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally substituted; or wherein $R_{2''}$ is the moiety $(CR_{10}R_{20})_r X_1 (CR_{10}R_{20})_q C(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_4$ and $R_{14}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{4'}$ and $R_{14'}$ are each independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$;

$R_5$ is independently selected at each occurrence from hydrogen, $C_{1-4}$ alkyl, $C_{2-4}$ alkenyl, $C_{2-4}$ alkynyl or $NR_{4'}R_{14'}$, excluding the moieties $SR_5$ being $SNR_{4'}R_{14'}$, $S(O)_2R_5$ being $SO_2H$ and $S(O)R_5$ being SOH;

$R_{9'}$ is independently selected at each occurrence from hydrogen, or $C_{1-4}$ alkyl;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted;

$R_d$ and $R_{d'}$ are each independently selected from hydrogen, $C_{1-4}$ alkyl, $C_{3-6}$ cycloalkyl, $C_{3-6}$ cycloalkyl$C_{1-4}$alkyl moiety, and wherein each of these moieties, excluding hydrogen, may be optionally substituted; or $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$;

g is 0 or an integer having a value of 1, 2, or 3;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6;

v is 0 or an integer having a value of 1 or 2;

v' is independently selected at each occurrence from 0 or an integer having a value of 1 or 2;

Z is independently selected at each occurrence from oxygen or sulfur; and a pharmaceutically acceptable salt thereof.

2. A pharmaceutical composition comprising an effective amount of a compound, or pharmaceutically acceptable salt, solvate or physiologically functional derivative thereof according to claim 1, in admixture with one or more pharmaceutically acceptable carriers, diluents or excipients.

3. The compound according to claim 1 which is Formula (V), and a pharmaceutically acceptable salt thereof.

4. The compound according to claim 1 wherein $R_1$ is $C(Z)N(R_{10'})(CR_{10}R_{20})_{v'}R_b$ or $N(R_{10'})C(Z)(CR_{10}R_{20})_{v'}R_b$.

5. The compound according to claim 4 wherein $R_b$ is selected from an optionally substituted alkyl, optionally substituted heteroaryl, optionally substituted aryl, optionally substituted aryl $C_{1-10}$ alkyl, or an optionally substituted $C_{3-7}$ cycloalkyl $C_{1-10}$ alkyl.

6. The compound according to claim 5 wherein $R_b$ is propyl, isopropyl, thiazolyl, phenyl, or 4-F phenyl.

7. The compound according to claim 1 wherein $R_{1'}$ is independently selected at each occurrence from halogen, $C_{1-4}$ alkyl, or halo-substituted-$C_{1-4}$ alkyl.

8. The compound according to claim 7 wherein $R_{1'}$ is independently selected at each occurrence from fluorine, methyl, or $CF_3$.

9. The compound according to claim 1 wherein X is $S(O)_m R_2$.

10. The compound according to claim 1 wherein X is $(CH_2)_n NR_4 R_{14}$, or $(CH_2)_n N(R_{2'})(R_{2''})$.

11. The compound according to claim 10 wherein the $R_4$ and $R_{14}$ moieties, are optionally substituted, 1 to 4 times, independently at each occurrence, by halogen; hydroxy; hydroxy substituted $C_{1-10}$alkyl; $C_{1-10}$ alkoxy; halosubstituted $C_{1-10}$ alkoxy; $C_{1-10}$ alkyl; halosubstituted $C_{1-4}$ alkyl; $SR_5$; $S(O)R_5$; $S(O)_2R_5$; $C(O)R_j$; $C(O)OR_j$; $C(O)NR_4 R_{14'}$; $NR_4 C(O)C_{1-10}$alkyl; $NR_4 C(O)$aryl; $NR_4 R_{14'}$; cyano, nitro, $C_{1-10}$ alkyl, $C_{3-7}$cycloalkyl, or $C_{3-7}$cycloalkyl $C_{1-10}$ alkyl; halosubstituted $C_{1-10}$ alkyl; an unsubstituted or substituted aryl, or aryl$C_{1-4}$ alkyl; an unsubstituted or substituted heteroaryl or hetero $C_{1-4}$ alkyl; an unsubstituted or substituted heterocyclic or heterocyclic $C_{1-4}$ alkyl, and wherein these aryl, heteroaryl or heterocyclic containing moieties are substituted one to two times independently at each occurrence by halogen; $C_{1-4}$ alkyl, hydroxy; hydroxy substituted $C_{1-4}$ alkyl; $C_{1-4}$ alkoxy; $S(O)_m$alkyl; amino, mono & di-substituted $C_{1-4}$ alkyl amino, or $CF_3$; and wherein $R_j$ is independently selected at each occurrence from hydrogen, $C_{1-4}$alkyl, aryl, aryl $C_{1-4}$alkyl, heteroaryl, heteroaryl $C_{1-4}$alkyl, heterocyclic, or a heterocyclic $C_{1-4}$alkyl moiety, and wherein these moieties, excluding hydrogen, may be optionally substituted.

12. The compound according to claim 11 wherein $R_4$ and $R_{14}$ are independently selected from hydrogen, optionally substituted $C_{1-10}$ alkyl, optionally substituted aryl, optionally substituted aryl-$C_{1-4}$ alkyl, optionally substituted heterocyclic, optionally substituted heterocyclic $C_{1-4}$ alkyl, optionally substituted heteroaryl or optionally substituted heteroaryl $C_{1-4}$ alkyl.

13. The compound according to claim 12 wherein the $C_{1-10}$ alkyl is substituted one or more times, independently at each occurrence with $NR_4 R_{14'}$; halogen, hydroxy, alkoxy, $C(O)NR_4 R_{14'}$; or $NR_4 C(O)C_{1-10}$alkyl.

14. The compound according to claim 11 wherein X is $(CH_2)_n NR_4 R_{14}$; one of $R_4$ and $R_{14}$ is an optionally substituted heteroaryl $C_{1-4}$ alkyl, and the heteroaryl moiety is selected from thienyl, pyrrolyl, oxazolyl, thiazolyl, isoxazolyl, isothiazolyl, imidazolyl, pyrazolyl, triazolyl, pyridazinyl, pyrimidinyl, pyrazinyl, benzoxazolyl, benzimidazolyl, and benzothiazolyl; or one of $R_4$ and $R_{14}$ is an optionally substituted heterocyclic or heterocyclic $C_{1-4}$ alkyl moiety selected from tetrahydropyrrole, tetrahydropyran, tetrahydrofuran, pyrrolinyl, pyrrolidinyl, imidazolinyl, imidazolidinyl, indolinyl, pyrazolinyl, pyrazolidinyl, piperidinyl, piperazinyl, and morpholino, tetrahydropyrrole $C_{1-4}$ alkyl, tetrahydropyran $C_{1-4}$ alkyl, tetrahydrofuran $C_{1-4}$ alkyl, pyrrolinyl $C_{1-4}$ alkyl, pyrrolidinyl $C_{1-4}$ alkyl, imidazolinyl $C_{1-4}$ alkyl, imidazolidinyl $C_{1-4}$ alkyl, indolinyl $C_{1-4}$ alkyl, pyrazolinyl $C_{1-4}$ alkyl, pyrazolidinyl $C_{1-4}$ alkyl, piperidinyl $C_{1-4}$ alkyl, piperazinyl $C_{1-4}$ alkyl, and morpholino $C_{1-4}$ alkyl.

15. The compound according to claim 11 wherein X is $(CH_2)_nNR_4R_{14}$ and $R_4$ and $R_{14}$ together with the nitrogen cyclize to form an optionally substituted ring selected from pyrrolidine, piperidine, piperazine, and morpholine.

16. The compound according to claim 11 wherein X is 1,4'-bipiperin-1'yl or 4-methyl-1,4'-bipiperin-1'yl.

17. The compound according to claim 1 wherein the $R_{2'}$ moieties, excluding hydrogen, are optionally substituted 1 to 4 times, independently, by $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl $C_{1-10}$ alkyl, halogen, —C(O), cyano, nitro, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_eR_{e'}$, $(CR_{10}R_{20})_nNR_eR_{e'}C_{1-4}$-alkylN-$R_eR_{e'}$, $(CR_{10}R_{20})_nCN$, $(CR_{10}R_{20})_nS(O)_2NR_eR_{e'}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_eR_{e'}$, $(CR_{10}R_{20})_nN(R_{10'})C(Z)R_6$, $(CR_{10}R_{20})_nN(R_{10'})C(=N(R_{10'}))NR_eR_{e'}$, $(CR_{10}R_{20})_nC(=NOR_6)NR_eR_{e'}$, $(CR_{10}R_{20})_nOC(Z)NR_eR_{e'}$, $(CR_{10}R_{20})_nN(R_{10'})C(Z)NR_eR_{e'}$, or $(CR_{10}R_{20})_nN(R_{10'})C(Z)OR_7$; and wherein $R_e$ are $R_{e'}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heteroaryl or a heteroaryl $C_{1-4}$ alkyl moiety, which moieties, excluding hydrogen may be optionally substituted; or $R_e$ and $R_{e'}$ together with the nitrogen which they are attached form an optionally substituted heterocyclic ring of 4 to 7 members, which ring optionally contains an additional heteroatom selected from oxygen, sulfur or $NR_9$;

$R_6$ is independently selected at each occurrence from hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein each of these moieties, excluding hydrogen are optionally substituted;

$R_7$ is independently selected at each occurrence from $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl moiety, and wherein each of these moieties may be optionally substituted; and n is independently selected at each occurrence from 0 or an integer having a value of 1 to 10.

18. The compound according to claim 17 wherein X is $(CH_2)_nN(R_{2'})(R_{2''})$; $R_2$ is an optionally substituted $C_{1-10}$ alkyl moiety, and the alkyl is substituted by $(CR_{10}R_{20})_nNR_eR_{e'}$ or $(CR_{10}R_{20})_nNR_eR_{e'}C_{1-4}$-alkyl $NR_eR_{e'}$.

19. The compound according to claim 18 wherein $R_e$ are $R_{e'}$ are independently selected at each occurrence from hydrogen, or $C_{1-4}$ alkyl.

20. The compound according to claim 10 wherein X moiety is 3-(diethylamino)propylamino, 3-(dimethylamino)propyl(methyl)amino, 3-(dimethylamino)propyl(methyl)amino, 2-(dimethylamino)ethylamino, 1-methylethyl)amino-propylamino, (1,1-dimethylethyl)aminopropylamino, (1-methylethyl)aminoethylamino, 2-(methylamino)ethylamino, 2-aminoethyl(methyl)amino, or a 2-(dimethylamino)ethyl(methyl)amino.

21. The compound according to claim 1 wherein $R_2$ is optionally substituted one or more times, independently at each occurrence, with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl$C_{1-10}$ alkyl, halogen, —C(O), cyano, nitro, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_eR_{e'}$, $(CR_{10}R_{20})_nNR_eR_{e'}C_{1-4}$alkyl $NR_eR_{e'}$, $(CR_{10}R_{20})_nCN$, $(CR_{10}R_{20})_nS(O)_2NR_eR_{e'}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_eR_{e'}$, $(CR_{10}R_{20})_nN(R_{10'})C(Z)R_6$, $(CR_{10}R_{20})_nN(R_{10'})C(=N(R_{10'}))NR_eR_{e'}$, $(CR_{10}R_{20})_nC(=NOR_6)NR_eR_{e'}$, $(CR_{10}R_{20})_nOC(Z)NR_eR_{e'}$, $(CR_{10}R_{20})_nN(R_{10'})C(Z)NR_eR_{e'}$, or $(CR_{10}R_{20})_nN(R_{10'})C(Z)OR_7$; and wherein $R_e$ are $R_{e'}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heteroaryl or a heteroaryl $C_{1-4}$ alkyl moiety, which moieties, excluding hydrogen may be optionally substituted; or $R_e$ and $R_{e'}$ together with the nitrogen which they are attached form an optionally substituted heterocyclic ring of 4 to 7 members, which ring optionally contains an additional heteroatom selected from oxygen, sulfur or $NR_9$;

$R_6$ is independently selected at each occurrence from hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein each of these moieties, excluding hydrogen are optionally substituted;

$R_7$ is independently selected at each occurrence from $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl moiety, and wherein each of these moieties may be optionally substituted; and n is independently selected at each occurrence from 0 or an integer having a value of 1 to 10.

22. The compound according to claim 21 wherein $R_2$ is a $C_{1-10}$ alkyl optionally substituted by $(CR_{10}R_{20})_nC(Z)OR_6$, $(CR_{10}R_{20})_nOR_6$, or $(CR_{10}R_{20})_nNR_4R_{14}$.

23. The compound according to claim 1 wherein $R_2$ is the $(CR_{10}R_{20})_{q'}X_1(CR_{10}R_{20})_qC(A_1)(A_2)(A_3)$, or $(CR_{10}R_{20})_qC(A_1)(A_2)(A_3)$, and $X_1$ is oxygen or $N(R_{10})$.

24. The compound according to claim 23 wherein $R_2$ is $(CR_{10}R_{20})_{q'}X_1(CR_{10}R_{20})_qC(A_1)(A_2)(A_3)$, at least one of $A_1$, $A_2$ or $A_3$ is substituted by $(CR_{10}R_{20})_nOR_6$, q is 0 or 1, and q' is 0.

25. The compound according to claim 1 wherein $R_3$ is an optionally substituted $C_{1-10}$ alkyl, $C_{3-7}$ cycloalkyl, $C_{3-7}$ cycloalkylalkyl, or aryl.

26. The compound according to claim 25 wherein $R_3$ is optionally substituted one or more times, independently at each occurrence, with wherein these moieties are all optionally substituted one or more times, independently at each occurrence, by hydrogen, halogen, nitro, $C_{1-10}$ alkyl, halo-substituted $C_{1-10}$ alkyl, $C_{2-10}$ alkenyl, $C_{2-10}$alkynyl, $C_{3-7}$cycloalkyl, $C_{3-7}$cycloalkyl$C_{1-10}$ alkyl, $C_{5-7}$cycloalkenyl, $C_{5-7}$cycloalkenyl$C_{1-10}$ alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_{16}R_{26}$, $(CR_{10}R_{20})_nCN$, $(CR_{10}R_{20})_nS(O)_2NR_{16}R_{26}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_{16}R_{26}$, $(CR_{10}R_{20})_nN(R_{10'})C(Z)R_6$, $(CR_{10}R_{20})_nN(R_{10'})C(=N(R_{10'}))NR_{16}R_{26}$, $(CR_{10}R_{20})_nOC(Z)NR_{16}R_{26}$, $(CR_{10}R_{20})_nN(R_{10'})C(Z)NR_{16}R_{26}$, or $(CR_{10}R_{20})_nN(R_{10'})C(Z)OR_7$; and wherein $R_{16}$ and $R_{26}$ are each independently selected at each occurrence from hydrogen, or $C_{1-4}$ alkyl; or the $R_{16}$ and $R_{26}$ together with the nitrogen which they are attached form an unsubstituted or substituted heterocyclic ring of 4 to 7 members, which ring optionally contains an additional heteroatom selected from oxygen, sulfur or $NR_{9'}$, $R_7$ is independently selected at each occurrence from $C_{1-6}$alkyl, aryl, aryl$C_{1-6}$alkyl, heterocyclic, heterocyclylC$_{1-6}$ alkyl, heteroaryl, or heteroarylC$_{1-6}$alkyl moiety, and wherein each of these moieties may be optionally substituted; and n is 0 or an integer having a value of 1 to 10.

27. The compound according to claim 26 wherein the R$_3$ optional substituent is independently selected at each occurrence from halogen, C$_{1-10}$ alkyl, (CR$_{10}$R$_{20}$)$_n$OR$_6$, (CR$_{10}$R$_{20}$)$_n$NR$_{16}$R$_{26}$, or halo-substituted C$_{1-10}$ alkyl.

28. The compound according to claim 26 wherein R$_3$ is a phenyl substituted one or more times by independently at each occurrence by fluorine, chlorine, hydroxy, methoxy, amino, methyl, or trifluoromethyl.

29. The compound according to claim 1 wherein R$_3$ is a 2,6-difluorophenyl.

30. The compound according to claim 1 wherein R$_3$ is an aryl ring substituted 1 to 4 times, independently at each occurrence by halogen, C$_{1-10}$ alkyl, (CR$_{10}$R$_{20}$)$_n$OR$_6$, (CR$_{10}$R$_{20}$)$_n$NR$_{16}$R$_{26}$, or halo-substituted C$_{1-10}$ alkyl; R$_{1'}$ is independently selected at each occurrence from halogen, C$_{1-4}$ alkyl, or halo-substituted-C$_{1-4}$ alkyl; g is 0, or 1; R$_1$ is C(Z)N (R$_{10'}$)(CR$_{10}$R$_{20}$)$_v$R$_b$; v is 0; R$_b$ is thiazolyl; Z is oxygen, R$_{10'}$ is hydrogen; X is (CH$_2$)$_n$NR$_4$R$_{14}$; one of R$_4$ and R$_{14}$ is an optionally substituted heteroaryl C$_{1-4}$ alkyl, and the other of R$_4$ and R$_{14}$ is hydrogen.

31. A pharmaceutical composition comprising an effective amount of a compound, or pharmaceutically acceptable salt, solvate or physiologically functional derivative, according to claim 1, in admixture with one or more pharmaceutically acceptable carriers, diluents or excipients, for administration by intravenous, intramuscular, subcutaneous, intranasal, oral inhalation, intrarectal, intravaginal or intraperitoneal means.

* * * * *